United States Patent
Allen et al.

(10) Patent No.: US 10,246,429 B2
(45) Date of Patent: Apr. 2, 2019

(54) VINYL FLUORIDE CYCLOPROPYL FUSED THIAZIN-2-AMINE COMPOUNDS AS BETA-SECRETASE INHIBITORS AND METHODS OF USE

(71) Applicant: AMGEN INC., Thousand Oaks, CA (US)

(72) Inventors: Jennifer R. Allen, Newbury Park, CA (US); Albert Amegadzie, Moorpark, CA (US); Matthew P. Bourbeau, Woodland Hills, CA (US); James A. Brown, Moorpark, CA (US); Ning Chen, Thousand Oaks, CA (US); Michael J. Frohn, Thousand Oaks, CA (US); Longbin Liu, Thousand Oaks, CA (US); Qingyian Liu, Camarillo, CA (US); Liping H. Pettus, Thousand Oaks, CA (US); Wenyuan Qian, Thousand Oaks, CA (US); Corey M. Reeves, Sherman Oaks, CA (US); Aaron C. Siegmund, Ventura, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/749,895

(22) PCT Filed: Aug. 4, 2016

(86) PCT No.: PCT/US2016/045650
§ 371 (c)(1),
(2) Date: Feb. 2, 2018

(87) PCT Pub. No.: WO2017/024180
PCT Pub. Date: Feb. 9, 2017

(65) Prior Publication Data
US 2018/0222876 A1    Aug. 9, 2018

Related U.S. Application Data

(60) Provisional application No. 62/202,018, filed on Aug. 6, 2015.

(51) Int. Cl.

| | | |
|---|---|---|
| C07D 417/10 | (2006.01) |
| C07D 279/08 | (2006.01) |
| C07D 417/14 | (2006.01) |
| C07D 471/04 | (2006.01) |
| C07D 491/056 | (2006.01) |
| A61P 25/28 | (2006.01) |
| A61P 25/00 | (2006.01) |
| A61P 25/16 | (2006.01) |
| C07D 491/08 | (2006.01) |
| C07D 491/107 | (2006.01) |
| C07D 498/10 | (2006.01) |
| C07F 7/08 | (2006.01) |

(52) U.S. Cl.
CPC ............ *C07D 279/08* (2013.01); *A61P 25/00* (2018.01); *A61P 25/16* (2018.01); *A61P 25/28* (2018.01); *C07D 417/10* (2013.01); *C07D 417/14* (2013.01); *C07D 471/04* (2013.01); *C07D 491/056* (2013.01); *C07D 491/08* (2013.01); *C07D 491/107* (2013.01); *C07D 498/10* (2013.01); *C07F 7/0812* (2013.01)

(58) Field of Classification Search
CPC .. C07D 471/04; C07D 417/14; C07D 417/12; C07D 513/10
USPC ................. 544/65; 514/218.18, 224.2, 224.5
See application file for complete search history.

(56) References Cited

U.S. PATENT DOCUMENTS

| 5,441,870 A | 8/1995 | Seubert et al. |
| 5,712,130 A | 1/1998 | Hajko et al. |
| (Continued) |

FOREIGN PATENT DOCUMENTS

| EP | 2 703 401 A1 | 3/2014 |
| EP | 1 942 105 B1 | 4/2014 |
| (Continued) |

OTHER PUBLICATIONS

Aisen, P.S., "Alzheimer's disease therapeutic research: the patch forward," *Alzheimer 's Research & Therapy* 1:2 (2009), pp. 1-6.
(Continued)

*Primary Examiner* — Kahsay Habte
(74) *Attorney, Agent, or Firm* — Markus Bergauer

(57) ABSTRACT

The present invention provides a new class of compounds useful for the modulation of beta-secretase enzyme (BACE) activity. The compounds have a general Formula I: wherein variables $A^4$, $A^5$, $A^6$, $A^7$, and each of $R^a$, $R^b$, $R^1$, $R^2$, $R^3$, $R^8$ $R^9$ and $R^{10}$ of Formula I, independently, are defined herein. The invention also provides pharmaceutical compositions comprising the compounds, and uses of the compounds and compositions for treatment of disorders and/or conditions related to Aβ plaque formation and deposition, resulting from the biological activity of BACE. Such BACE mediated disorders include, for example, Alzheimer's Disease, cognitive deficits, cognitive impairments, schizophrenia and other central nervous system conditions.

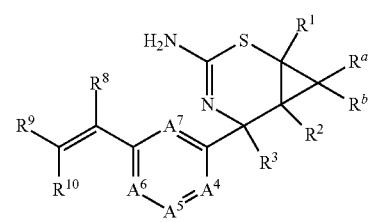

54 Claims, No Drawings

(56) References Cited

U.S. PATENT DOCUMENTS

| | | | |
|---|---|---|---|
| 5,942,400 | A | 8/1999 | Anderson et al. |
| 9,550,762 | B2 | 1/2017 | Allen et al. |
| 2009/0082560 | A1 | 3/2009 | Kobayashi et al. |
| 2009/0209755 | A1 | 8/2009 | Suzuki et al. |
| 2010/0075957 | A1 | 3/2010 | Tamura et al. |
| 2010/0160290 | A1 | 6/2010 | Kobayashi et al. |
| 2011/0152253 | A1 | 6/2011 | Motoki et al. |
| 2012/0238557 | A1 | 9/2012 | Masui et al. |
| 2012/0245154 | A1 | 9/2012 | Anan et al. |
| 2012/0245157 | A1 | 9/2012 | Masui et al. |
| 2017/0267673 | A1 | 9/2017 | Allen et al. |

FOREIGN PATENT DOCUMENTS

| | | |
|---|---|---|
| WO | 2000/017369 A2 | 3/2000 |
| WO | 2009/134617 A1 | 11/2009 |
| WO | 2009/151098 A1 | 12/2009 |
| WO | 2010/013302 A1 | 2/2010 |
| WO | 2010/013794 A1 | 2/2010 |
| WO | 2011/005738 A1 | 1/2011 |
| WO | 2011/029803 A1 | 3/2011 |
| WO | 2011/069934 A1 | 6/2011 |
| WO | 2012/138734 A1 | 10/2012 |
| WO | 2012/139425 A1 | 10/2012 |
| WO | 2012/147762 A1 | 11/2012 |
| WO | 2012/162330 A1 | 11/2012 |
| WO | 2012/162334 A1 | 11/2012 |
| WO | 2013/004676 A1 | 1/2013 |
| WO | 2013/028670 A1 | 2/2013 |
| WO | 2013/030713 A1 | 3/2013 |
| WO | 2013/164730 A1 | 11/2013 |
| WO | 2013/182638 A1 | 12/2013 |
| WO | 2014/013076 A1 | 1/2014 |
| WO | 2014/045162 A1 | 3/2014 |
| WO | 2014/062549 A1 | 4/2014 |
| WO | 2014/062553 A1 | 4/2014 |
| WO | 2014/065434 A1 | 5/2014 |
| WO | 2014/066132 A1 | 5/2014 |
| WO | 2014/093190 A1 | 6/2014 |
| WO | 2014/097038 A1 | 6/2014 |
| WO | 2014/098831 A1 | 6/2014 |
| WO | 2014/099788 A9 | 6/2014 |
| WO | 2014/099794 A1 | 6/2014 |
| WO | 2016/022724 A1 | 2/2016 |
| WO | 2017/024180 A1 | 2/2017 |

OTHER PUBLICATIONS

Alzforum Networking for a Cure, "Barcelona: Out of Left Field—Hit to the Eye Kills BACE Inhibitor," pp. 1-7 (Mar. 31, 2011); access online: www.alzforum.org/news/conference-coverage/barcelona-out-left-field-hit-eye-kills-bace-inhibitor (last accessed Dec. 16, 2015).

Best, J.D. et al., "Quantitative Measurement of Changes in Amyloid -β(40) in the Rat Brain and Cerebrospinal Fluid Following Treatment with the γ-Secretase Inhibitor LY-411575 [$N^2$-[(2S)-2-(3,5-Difluorophenyl)-2-hydroxyethanoyl]-$N^1$-[(7S)-5-methyl-6-oxo-6,7-dihydro-5H-dibenzo[b,d]azepin-7-yl]-alaninamide]," *Journal of Pharmacology and Experimental Therapeutics* 313(2):902-908 (2005).

Citron, M., "β-Secretase inhibition for the treatment of Alzheimer's disease—promise and challenge," *TRENDS in Pharmacological Sciences* 25(2):92-97 (2004).

Cole, S.L. and Vassar, R., "The Alzheimer's disease β-secretase enzyme, BACE1," *Molecular Neurodegeneration* 2(22):1-25 (2007).

De Meyer, G. et al., "Diagnosis-Independent Alzheimer Disease Biomarker Signature in Cognitively Normal Elderly People," *Arch. Neurol.* 67(8):949-956 (2010).

Dovey, H.F. et al., "Functional gamma-secretasae inhibitors reduce beta-amyloid peptide levels in brain," *Journal of Neurochemistry* 76:173-181 (2001).

Follo, C. et al., "Knock-Down of Cathepsin D Affects the Retinal Pigment Epithelium, Impairs Swim-Bladder Ontogenesis and Causes Premature Death in Zebrafish," *PLoS One* 6(7):e21908, pp. 1-13 (2011).

Games, D. et al., "Alzheimer-type neuropathology in transgenic mice overexpressing V717F β-amyloid precursor protein," *Nature* 373:523-527 (1995).

Götz, J. et al., "Transgenic animal models of Alzheimer's disease and related disorders: histopathology, behavior and therapy," *Molecular Psychiatry* 9:664-683 (2004).

Gulnik, S.V. et al. "Design of sensitive fluorogenic substrates for human cathespin D," *FEBS Letters* 413:379-384 (1997).

Harris, J.A. et al, "Transsynaptic Progression of Amyloid-β-Induced Neuronal Dysfunction within the Entorhinal-Hippocampal Network," *Neuron* 68:428-441 (2010).

Henley, D.B. et al., "Development of semagacestat (LY450139), a functional γ-secretase inhibitor, for the treatment of Alzheimer's disease," *Expert Opin. Pharmacother.* 10(10):1657-1664 (2009).

Hsia, A.Y. et al., "Plaque-independent disruption of neural circuits in Alzheimer's disease mouse models," *Proc. Natl. Acad. Sci. USA* 96:3228-3233 (1999).

Hsiao, K. et al., "Correlative Memory Deficits, Aβ Elevation, and Amyloid Plaques in Transgenic Mice," *Science* 274:99-102 (1996).

International Preliminary Report on Patentability and Written Opinion for International Patent Application No. PCT/US2016/045650, dated Feb. 6, 2018, pp. 1-7.

International Search Report for International Patent Application No. PCT/US2016/045650, dated Oct. 10, 2016, pp. 1-3.

Joachim, C.L. and Selkoe, D.J., "The Seminal Role of β-Amyloid in the Pathogenesis of Alzheimer Disease," *Alzheimer Disease and Associated Disorders* 6(1):7-34 (1992).

Koike, M. et al., "Involvement of two different cell death pathways in retinal atrophy of cathepsin D-deficient mice," *Molecular and Cellular Neuroscience* 22:146-161 (2003).

Luo, Y. et al., "Mice deficient in BACE1, the Alzheimer's β-secretase, have normal phenotype and abolished β-amyloid generation," *Nature Neuroscience* 4:231-232 (2001).

May, P.C. et al., "Robust Central Reduction of Amyloid-β in Humans with an Orally Available, Non-Peptidic β-Secretase Inhibitor," *Journal of Neuroscience* 31(46):16507-16516 (2011).

Palop, J.J. and Mucke, L., "Amyloid-β-induced neuronal in Alzheimer's disease: from synapses toward neural networks," *Nature Neuroscience* 13(7):812-818 (2010).

Sabbagh, M.N. et al., "β-Amyloid and Treatment Opportunities for Alzheimer's Disease," *Alzheimer's Disease Review* 3:1-19 (1997).

Selkoe, D.J., "Soluble oligomers of the amyloid β-protein impair synaptic plasticity and behavior," *Behavioural Brain Research* 192:106-113 (2008).

Selkoe, D.J., "The Molecular Pathology of Alzheimer's Disease," *Neuron* 6:487-498 (1991).

Seubert, P. et al., "Isolation and quantification of soluble Alzheimer's β-peptide from biological fluids," *Nature* 359:325-327 (1992).

Shacka, J.J. and Roth, K.A., "Cathepsin D Deficiency and NCL/Batten Disease: There's More to Death than Apoptosis," *Autophagy*, 3(5):474-476 (2007).

Shankar, G.M. et al., "Amyloid-β protein dimers isolated directly from Alzheimer's brains impair synaptic plasticity and memory," *Nature Medicine* 14(8):837-842 (2008).

Siemers, E.R. et al., "Effects of a γ-secretase inhibitor in a randomized study of patients with Alzheimer's disease," *Neurology* 66:602-604 (2006).

Siemers, E.R. et al., "Safety, Tolerability, and Effects on Plasma and Cerebrospinal Fluid Amyloid-β After Inhibition of γ-Secretase," *Clin. Neuropharmacol.* 30(6):317-325 (2007).

Sinha, S. et al., "Purification and cloning of amyloid precursor protein β-secretase from human brain," *Nature* 402:537-540 (1999).

Tanzi, R.E. and Bertram, L., "Twenty Years of the Alzheimer's Disease Amyloid Hypothesis: A Genetic Perspective," *Cell* 120(4):545-555 (2005).

Vassar, R. and Yan, R., "Targeting the β secretase BACE1 for Alzheimer's disease therapy," *Lancet Neurology* 13:319-329 (2014).

Vassar, R. et al, "The β-Secretase Enzyme BACE in Health and Alzheimer's Disease: Regulation, Cell Biology, Function, and Therapeutic Potential," *Journal of Neuroscience* 29(41):12787-12794 (2009).

(56) References Cited

OTHER PUBLICATIONS

Walsh, D.M. and Selkoe, D.J., "Deciphering the Molecular Basis of Memory Failure in Alzheimer's Disease," *Neuron* 44(1):181-193 (2004).

Yasuda, Y. et al., "Characterization of New Fluorogenic Substrates for the Rapid and Sensitive Assay of Cathepsin E and Cathepsin D," *J. Biochem.* 125(6):1137-1143 (1999).

VINYL FLUORIDE CYCLOPROPYL FUSED THIAZIN-2-AMINE COMPOUNDS AS BETA-SECRETASE INHIBITORS AND METHODS OF USE

This application is a national stage application under 35 U.S.C. § 371 of International Application No. PCT/US2016/045650, having an international filing date of Aug. 4, 2016, which claims the benefit of U.S. Provisional Patent Application No. 62/202,018, filed on Aug. 6, 2015.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and associated central nervous system (CNS) disorders.

BACKGROUND OF THE INVENTION

Alzheimer's disease (AD) affects greater than 12 million aging people worldwide, and importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (Aβ), or Aβ fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. Vassar & Yan, Lancet *Neurology*, 13:319-329 (2014). The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of Aβ plays a seminal role in the pathogenesis of AD and can precede cognitive symptoms by years or even decades. Selkoe, *Neuron*, 6:487 (1991). Release of Aβ from neuronal cells grown in culture and the presence of Aβ in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that Aβ formation is a causative precursor or factor in the development of AD. More specifically, deposition of Aβ in areas of the brain responsible for cognitive factors is believed to be a major factor in the development of AD. Beta amyloid plaques are primarily composed of Aβ. Aβ is derived from the proteolytic cleavage of a large transmembrane amyloid precursor protein (APP), and is a peptide comprised of about 39-42 amino acid residues. Beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the dimeric, soluble form of the peptide is a causative agent in the development of Alzheimer's and is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of Aβ. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the Aβ. APP has also found to be cleaved by alpha-secretase to produce alpha-sAPP, a secreted form of APP that does not result in beta-amyloid plaque formation. This alternate pathway precludes the formation of Aβ. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p 510) and PCT application WO 2000/17369. It has been proposed that Aβ accumulates as a result of APP processing by BACE. Moreover, in vivo processing of APP at the beta secretase cleavage site is thought to be a rate-limiting step in Aβ production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of β-amyloid or Aβ. BACE knockout mice do not produce beta-amyloid and are free from Alzheimer's associated pathologies including neuronal loss and certain memory deficits. Cole, S. L., Vasser, R.,

*Molecular Degeneration* 2:22, 2007. When crossed with transgenic mice that over express APP, the progeny of BACE deficient mice show reduced amounts of Aβ in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of Aβ in the brain should provide a therapeutic method for treating AD and other beta amyloid or plaque related disorders.

Consequently, the approach of regulating or reducing the formation of Aβ formation and deposition as a potential treatment for AD has received tremendous attention, support and commitment from both researchers and investors alike. A small molecule gamma-secretase inhibitor, LY450139 ("Semagacestat"), an Aβ lowering agent, advanced to phase III clinical trials for the treatment of Alzheimer's Disease. The pharmacokinetics of semagacestat in plasma, as well as the plasma and cerebral spinal fluid (CSF) Aβ levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother*. (2009), 10 (10); *Clin. Neuropharmacol*. 2007; 30 (pgs 317-325); and *Neurology*, 2006, 66 (pgs 602-624)).

Additional approaches have been taken in attempts to treat AD and plaque-related disorders. One such approach to reduce the formation of plaque deposits in the brain involves the inhibition of and, therefore, the reduction of BACE activity. Vassar & Yan, *Lancet Neurology*, 13:319-329 (2014). For example, each of the following patent publications: WO 14/098831, WO 14/099794, WO 14/099788, WO 14/097038, WO 14/093190, WO 14/066132, WO 14/65434, WO 14/062553, WO 14/062549, WO 14/013076, WO13/ 182638, WO13/164730, WO13/030713, WO 13/028670, WO13/004676, WO2012162334, WO12/162330, WO12/ 147762, WO2013139425, WO2012138734, US20120245157, US20120245154, US20120238557, US2009082560, US2010160290, US2010075957, WO2009151098, WO2011029803, WO2014045162, WO201105738, WO2009134617, WO201013794, WO201013302, US20110152253, US2009209755, EP 2703401 (equivalent of WO2012146762) and EP01942105 describe inhibitors of BACE, useful for treating AD and other beta-secretase mediated disorders. For Example, US20120245154 describes "Substituted Aminothiazine Derivative" as BACE inhibitors for the treatment of neurological disorders of the general formula:

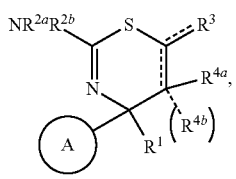

while EP2703401 describes "Pyridine Derivative and BACE1 Inhibitor Containing Same" and discloses compounds of the general formula:

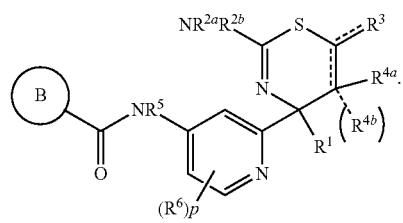

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the multi-pathophysiological roles of CatD in tissue homeostasis and organ development.

Inhibition of protein CatD has been implicated in undesirable side effects. For instance, the inhibition of CatD is believed to be linked to adverse retinal development and retinal atrophy. Particularly, in mice it was found that CatD is essential for the metabolic maintenance of retinal photoreceptor cells and that its deficiency induces apoptosis of the cells, while the loss of inner nuclear layer (INL) neurons is mediated by nitric oxide release from microglial cells. However, in the very same mice, it was also found that no atrophic change was detected in the retina of mice deficient in cathepsin B or L. *Mol. Cell. Neurosci*, 2003, February 22(2):146-161. Further, Animal models of CatD deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the proapoptotic molecule Bax prevents apoptotic markers but not neuronal cell death and neurodegeneration induced by CatD deficiency, which suggests that alterations in the macroautophagy-lysosomal degradation pathway can mediate neuronal cell death in NCL/Batten Disease in the absence of apoptosis. *Autophagy*, 2007, September-October; 3(5):474-476. Finally, an adverse effect of the inhibition of CatD is evident from the data presented in *PLoS One*, 2011; 6(7): e21908, published Jul. 1, 2011. The authors of the PLoS One paper found that knock-down of CatD affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyperpigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human BACE-mediated Alzheimer's Disease clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Ph I dosing trial was terminated and people brought in for eye assessments did not show any abnormalities. (Alzheimer's Research Forum News, Mar. 31, 2011 reporting on Martin Citron's presentation at the AD/PD Conference 3-2011 in Barcelona, Spain).

Hence, it is desirable to provide compounds which modulate the activity of and are reasonably selective for BACE, while not suffering from undesirable side effects possibly due to intervention with or the reduction and/or direct or indirect inhibition of the expression and/or function of other proteins or biological pathways.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of Aβ and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, hydrates, solvates and pharmaceutically acceptable salts thereof, are generally defined by Formula I

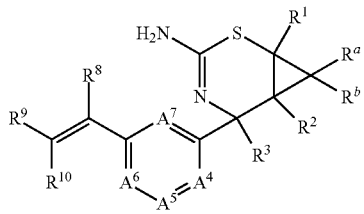

I wherein each of $A^4$, $A^5$, $A^6$, $A^7$, $R^a$, $R^b$, $R^1$, $R^2$, $R^3$, $R^8$, $R^9$, and $R^{10}$ of Formula I are defined below. The invention also provides procedures for making compounds of Formula I, and sub-Formulas thereof, as well as intermediates useful in such procedures.

The invention further provides pharmaceutical compositions comprising compounds of the invention, and uses of these compositions in the treatment of beta secretase mediated diseases. For example, and in one embodiment, the invention provides a pharmaceutical composition comprising a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In a first embodiment of the invention, there are provided compounds, including stereoisomers, tautomers, hydrates, solvates and pharmaceutically acceptable salts thereof, which are generally defined by Formula I:

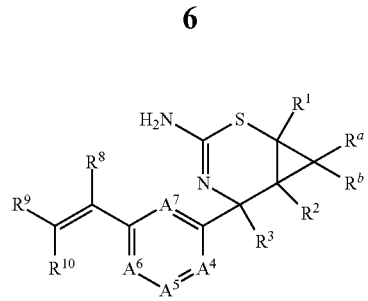

I wherein
$A^4$ is $CR^4$ or N;
$A^5$ is $CR^5$ or N;
$A^6$ is $CR^6$ or N;
$A^7$ is $CR^7$ or N, provided that no more than two of $A^4$, $A^5$, $A^6$ and $A^7$ are N;
each of $R^a$ and $R^b$, independently, is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$-alkenyl, $C_{2-4}$-alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents independently selected from F, oxo or OH;
$R^1$ is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)NH_2$, —$CH$=$CHC(O)NH_2$, —$CH$=$CHC(O)NHC_{1-6}$-alkyl, —$CH$=$CHC(O)N(C_{1-6}$-alkyl$)_2$, —$CH$=$CHC(O)NHC_{1-6}$-alkyl-$OC_{1-6}$-alkyl, —$CH$=$CHC(O)$-heterocyclyl, —$CH$=$C(CH_3)C(O)$-heterocyclyl, —$CH$=$CHC(O)_2H$, —$CH$=$CHC(O)OC_{1-6}$-alkyl, —$CH$=$CHCH_2OH$, $C_{1-6}$-alkyl-$C(O)NHC_{1-6}$-alkyl, $C_{1-6}$-alkyl-$C(O)N(C_{1-6}$-alkyl$)_2$, —$C(O)C_{1-6}$-alkyl, —$C(O)C_{2-6}$-alkenyl, —$C(O)OH$, —$C(O)OC_{1-6}$-alkyl, —$C(O)NHC_{1-6}$-alkyl, —$C(O)N(C_{1-6}$-alkyl$)_2$, —$C(O)NHC_{3-6}$-cycloalkyl, —$C(O)NH$-aryl, —$C(O)NH$-heterocyclyl, —$C(O)NHOC_{1-6}$-alkyl, —$C(O)N(C_{1-6}$-alkyl)$OC_{1-6}$-alkyl, —$C(O)$-heterocyclyl, —$CH_2$-heteroaryl, or heteroaryl, wherein the heterocyclyl groups of the —$CH$=$CHC(O)$-heterocyclyl, —$CH$=$C(CH_3)C(O)$-heterocyclyl, —$C(O)$-heterocyclyl, and —$C(O)NH$-heterocyclyl groups are fully or partially saturated 3-, 4-, 5-, 6- or 7-membered monocyclic rings or 6-, 7-, 8-, 9-, or 10-membered bicyclic rings that include 1 heteroatom selected from N, O, or S if the ring is a 3-membered ring, that include 1 or 2 heteroatoms independently selected from N, O, or S if the ring is a 4- or 5-membered ring, and include 1, 2, or 3 heteroatoms independently selected from N, O, or S if the ring is a 6-, 7-, 8-, 9-, or 10-membered ring, wherein the heteroaryl groups of the —$CH_2$-heteroaryl and heteroaryl groups is a 5- or 6-membered ring that includes 1, 2, 3, or 4 heteroatoms independently selected from N, O, or S, wherein the aryl group of the —$C(O)NH$-aryl group is a phenyl or naphthyl group, wherein each of the $C_{1-6}$-alkyl, $C_{2-4}$-alkenyl, $C_{2-4}$-alkynyl, and $C_{1-6}$-alkyl and $C_{2-6}$-alkynyl portions of —$CH_2OC_{1-6}$-alkyl, —$OC_{1-6}$-alkyl, —$S(O)_oC_{1-6}$-alkyl, —$NHC_{1-6}$-alkyl, $C(O)C_{1-6}$-alkyl, —$C(O)C_{2-6}$-alkenyl, —$CH$=$CHC(O)NHC_{1-6}$-alkyl, —$C(O)NHC_{1-6}$-alkyl, —$C(O)N(C_{1-6}$-alkyl$)_2$, and $C_{1-6}$-alkyl-$C(O)NHC_{1-6}$-alkyl groups is optionally substituted with 1-4 substituents independently selected from F, CN, oxo or OH, and further wherein each of the heterocyclyl groups of the —$CH$=$CHC(O)$-heterocyclyl, —$CH$=$C(CH_3)C(O)$-heterocyclyl, —$C(O)$heterocyclyl, and, —$C(O)NH$-heterocyclyl groups is optionally substituted with 1-4 substituents independently selected from methyl, F, OH, oxo, —CN, OCH$_3$, —CH$_2$OC$_{1-6}$-alkyl, —C(O)C$_{1-6}$-alkyl, —C(O)OC$_{1-6}$-alkyl, —CH$_2$OH, —NH$_2$, —NHC$_{1-6}$-alkyl, —N(C$_{1-6}$-alkyl)$_2$, —CF$_3$, phenyl, or —CH$_2$—C$_{3-6}$-cycloalkyl and further wherein each of the heteroaryl groups of the —CH$_2$-heteroaryl and heteroaryl groups and the aryl group of the —C(O)NH-aryl group is optionally substituted with 1-3 substituents independently selected from halo, methyl, or OH;

R$^2$ is H, F, Cl, C$_{1-6}$-alkyl, C$_{2-4}$-alkenyl, C$_{2-4}$-alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl, —C(O)NH$_2$, —CH═CHC(O)NHC$_{1-6}$-alkyl, —CH═CHC(O)$_2$H, —CH═CHCH$_2$OH, C$_{1-6}$-alkyl-C(O)NHC$_{1-6}$-alkyl, —C(O)C$_{1-6}$-alkyl or —C(O)C$_{2-6}$-alkenyl, wherein each of the C$_{1-6}$-alkyl, C$_{2-4}$-alkenyl, C$_{2-4}$-alkynyl, and C$_{1-6}$-alkyl and C$_{2-6}$-alkynyl portion of —CH$_2$OC$_{1-6}$-alkyl, —OC$_{1-6}$-alkyl, —S(O)$_o$C$_{1-6}$-alkyl, —NHC$_{1-6}$-alkyl, C(O)C$_{1-6}$-alkyl, —C(O)C$_{2-6}$-alkenyl, —CH═CHC(O)NHC$_{1-6}$-alkyl and C$_{1-6}$-alkyl-C(O) NHC$_{1-6}$-alkyl, is optionally substituted with 1-4 substituents independently selected from F, CN, oxo or OH;

R$^3$ is C$_{1-4}$-alkyl, CH$_2$OC$_{1-4}$-alkyl, CH$_2$OH, C$_{1-4}$haloalkyl or cyclopropyl, wherein each of the C$_{1-4}$-alkyl, CH$_2$OC$_{1-4}$-alkyl, C$_{1-4}$-haloalkyl and cyclopropyl is optionally substituted with 1-4 F atoms;

each of R$^4$, R$^5$, R$^6$ and R$^7$, independently, is H, halo, haloalkyl, haloalkoxy, C$_{1-4}$-alkyl, CN, OH, OC$_{1-4}$-alkyl, S(O)$_o$C$_{1-4}$-alkyl, NHC$_{1-4}$-alkyl, C(O)C$_{1-4}$-alkyl, C(O) OC$_{1-4}$-alkyl, or CH$_2$OH;

R$^8$ is selected from H, F, Cl, or C$_{1-3}$-alkyl;

one of R$^9$ and R$^{10}$ is selected from F or H and the other of R$^9$ and R$^{10}$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of R$^{11}$;

each R$^{11}$, independently, is H, halo, haloalkyl, CN, OH, NO$_2$, NH$_2$, SF$_5$, acetyl, —C(O)NHC$_{1-6}$-alkyl, —OCH$_2$C(O) NHC$_{1-6}$-alkyl, —OCH$_2$C(O)N(C$_{1-6}$-alkyl)$_2$, —OCH$_2$CH$_2$-pyrrolidinonyl, oxo, cyclopropylmethoxy, 2-propynyloxy, 2-butynyloxy, 2-pentyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, morpholinyl, pyrazolyl, isoxazolyl, dihydropyranyl, pyrrolyl, pyrrolidinyl, piperazinyl, oxetan-3-yl, imidazo-pyridinyl, dioxolyl, or —OCH$_2$-heteroaryl, wherein the heteroaryl group of the —OCH$_2$-heteroaryl group is a 5- or 6-membered ring that includes 1, 2, 3, or 4 heteroatoms selected from N, O, or S, and further wherein each of the cyclopropylmethoxy, 2-propynyloxy, 2-butynyloxy, 2-pentyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, morpholinyl, pyrazolyl, isoxazolyl, dihydropyranyl, pyrrolidinyl, oxetan-3-yl, dioxolyl, or —OCH$_2$-heteroaryl is optionally substituted independently with 1-5 substituents of F, Cl, Br, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, trimethylsilyl, cyclopentyl, cyclohexyl, C$_{1-3}$alkylamino-, C$_{1-3}$dialkylamino, C$_{1-3}$thioalkoxyl, oxazolyl, isoxazolyl, thiazolyl, isothiazolyl, thiadiazolyl, thienyl, furyl, pyrrolyl, tetrahydropyranyl, pyrrolidinyl or oxetan-3yl; and the subscript o is selected from 0, 1, or 2.

In some embodiments of the first embodiment, at least one of R$^8$, R$^9$, and R$^{10}$ is —F. In some such embodiments, at least one of R$^9$ and R$^{10}$ is —F.

In a second embodiment, the invention provides the compound according to embodiment 1, or the stereoisomer, tautomer, hydrate, solvate or the pharmaceutically acceptable salt thereof, wherein the compound of Formula I is a compound of Formula IA

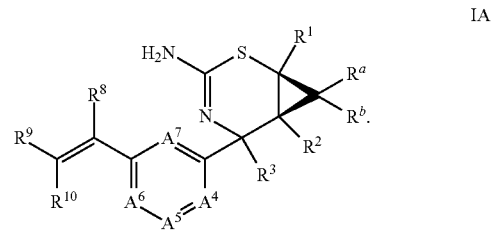

IA

In a third embodiment, the invention provides the compound according to embodiment 1, or the stereoisomer, tautomer, hydrate, solvate or the pharmaceutically acceptable salt thereof, wherein the compound of Formula I is a compound of Formula IB

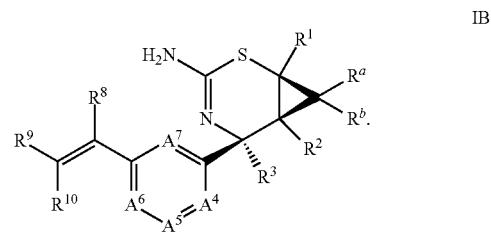

IB

In a fourth embodiment, the invention provides the compound according to any one of embodiments 1-3, the stereoisomer, tautomer, hydrate, solvate or the pharmaceutically acceptable salt thereof, wherein R$^a$ and R$^b$ are both —H.

In a fifth embodiment, the invention provides the compound according to any one of embodiments 1-4, the stereoisomer, tautomer, hydrate, solvate or the pharmaceutically acceptable salt thereof, wherein R$^2$ is —H.

In a sixth embodiment, the invention provides the compound according to any one of embodiments 1-5, the stereoisomer, tautomer, hydrate, solvate or the pharmaceutically acceptable salt thereof, wherein A$^6$ is CR$^6$ and R$^6$ is —H.

In a seventh embodiment, the invention provides the compound according to any one of embodiments 1-6, the stereoisomer, tautomer, hydrate, solvate or the pharmaceutically acceptable salt thereof, wherein A$^7$ is CR$^7$ and R$^7$ is —H.

In an eighth embodiment, the invention provides the compound according to any one of embodiments 1-7, the stereoisomer, tautomer, hydrate, solvate or the pharmaceutically acceptable salt thereof, wherein A$^4$ is CR$^4$.

In a ninth embodiment, the invention provides the compound according to embodiment 8, the stereoisomer, tautomer, hydrate, solvate or the pharmaceutically acceptable salt thereof, wherein R$^4$ is —H.

In some embodiments, the invention provides the compound according to embodiment 8, the stereoisomer, tautomer, hydrate, solvate or the pharmaceutically acceptable salt thereof, wherein $R^4$ is —F.

In a tenth embodiment, the invention provides the compound according to embodiment 8, the stereoisomer, tautomer, hydrate, solvate or the pharmaceutically acceptable salt thereof, wherein $R^4$ is —OCH$_3$ or —F.

In an eleventh embodiment, the invention provides the compound according to embodiment 8, the stereoisomer, tautomer, hydrate, solvate or the pharmaceutically acceptable salt thereof, wherein $R^4$ is —OCH$_3$.

In a twelfth embodiment, the invention provides the compound according to any one of embodiments 1-11, the stereoisomer, tautomer, hydrate, solvate or the pharmaceutically acceptable salt thereof, wherein $R^8$ is —H.

In a thirteenth embodiment, the invention provides the compound according to any one of embodiments 1-12, the stereoisomer, tautomer, hydrate, solvate or the pharmaceutically acceptable salt thereof, wherein $R^8$ is —F.

In a fourteenth embodiment, the invention provides the compound according to any one of embodiments 1-13, the stereoisomer, tautomer, hydrate, solvate or the pharmaceutically acceptable salt thereof, wherein $R^3$ is selected from $C_{1-4}$-alkyl or $C_{1-4}$-haloalkyl.

In a fifteenth embodiment, the invention provides the compound according to any one of embodiments 1-14, the stereoisomer, tautomer, hydrate, solvate or the pharmaceutically acceptable salt thereof, wherein $R^3$ is selected from —CH$_3$ or —CH$_2$F.

In a sixteenth embodiment, the invention provides the compound according to any one of embodiments 1-15, the stereoisomer, tautomer, hydrate, solvate or the pharmaceutically acceptable salt thereof, wherein $A^5$ is CR$^5$.

In a seventeenth embodiment, the invention provides the compound according to embodiment 16, the stereoisomer, tautomer, hydrate, solvate or the pharmaceutically acceptable salt thereof, wherein $R^5$ is —H.

In an eighteenth embodiment, the invention provides the compound according to any one of embodiments 1-15, the stereoisomer, tautomer, hydrate, solvate or the pharmaceutically acceptable salt thereof, wherein $A^5$ is N.

In an nineteenth embodiment, the invention provides the compound according to any one of embodiments 1-18, the stereoisomer, tautomer, hydrate, solvate or the pharmaceutically acceptable salt thereof, wherein one of $R^9$ and $R^{10}$ is —F.

In an twentieth embodiment, the invention provides the compound according to any one of embodiments 1-19, the stereoisomer, tautomer, hydrate, solvate or the pharmaceutically acceptable salt thereof, wherein $R^1$ is selected from substituted or unsubstituted $C_{1-6}$-alkyl, substituted or unsubstituted —CH$_2$OC$_{1-6}$-alkyl, substituted or unsubstituted —C(O)OC$_{1-6}$-alkyl, substituted or unsubstituted —C(=O)NHC$_{1-6}$-alkyl, substituted or unsubstituted —C(=O)N(C$_{1-6}$-alkyl)$_2$, substituted or unsubstituted —C(=O)NHC$_{3-6}$-cycloalkyl, substituted or unsubstituted —C(=O)NH-aryl, or substituted or unsubstituted —C(=O)NH-heterocyclyl.

In an alternative twentieth embodiment, the invention provides the compound according to any one of embodiments 1-19, the stereoisomer, tautomer, hydrate, solvate or the pharmaceutically acceptable salt thereof, wherein $R^1$ is selected from substituted or unsubstituted —CH$_2$OC$_{1-6}$-alkyl, substituted or unsubstituted —S(O)$_o$C$_{1-6}$-alkyl, —C(O)NH$_2$, substituted or unsubstituted —C(O)C$_{1-6}$-alkyl, substituted or unsubstituted —C(=O)NHC$_{1-6}$-alkyl, substituted or unsubstituted —C(=O)N(C$_{1-6}$-alkyl)$_2$, substituted or unsubstituted —C(O)-heterocyclyl.

In a twenty-first embodiment, the invention provides the compound according to any one of embodiments 1-19, the stereoisomer, tautomer, hydrate, solvate or the pharmaceutically acceptable salt thereof, wherein $R^1$ is selected from

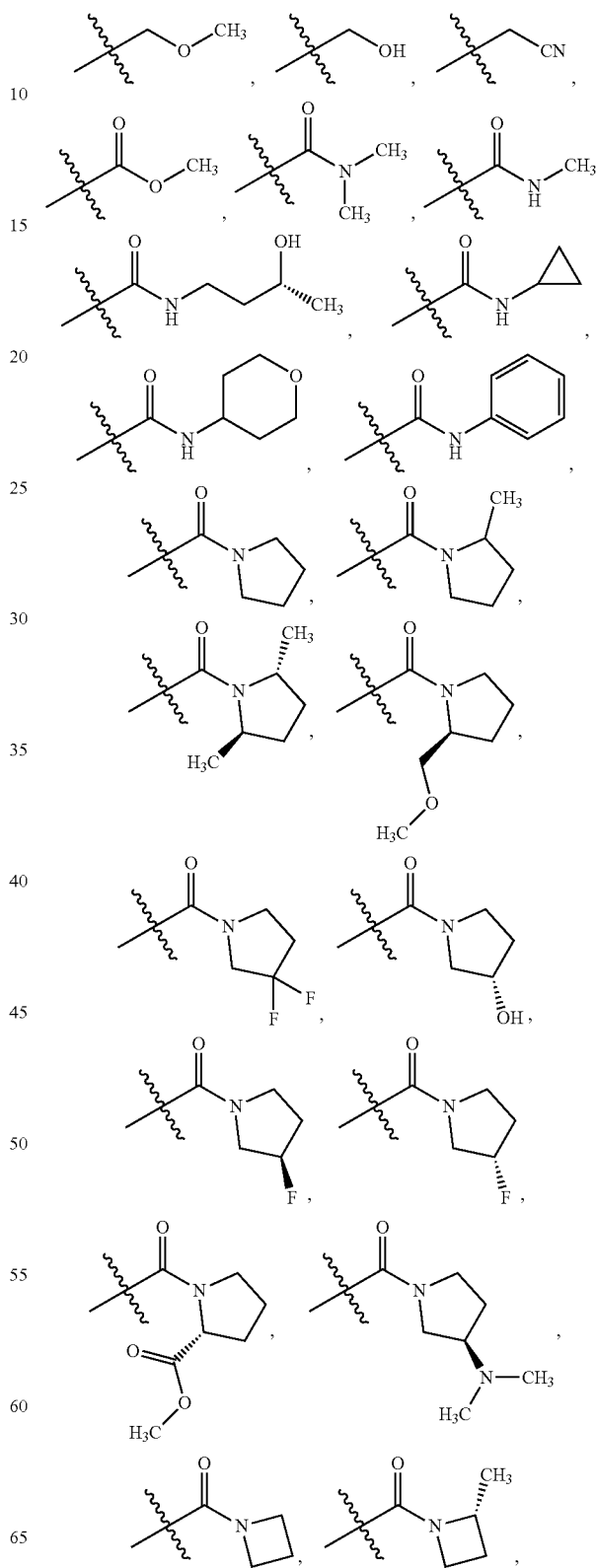

-continued
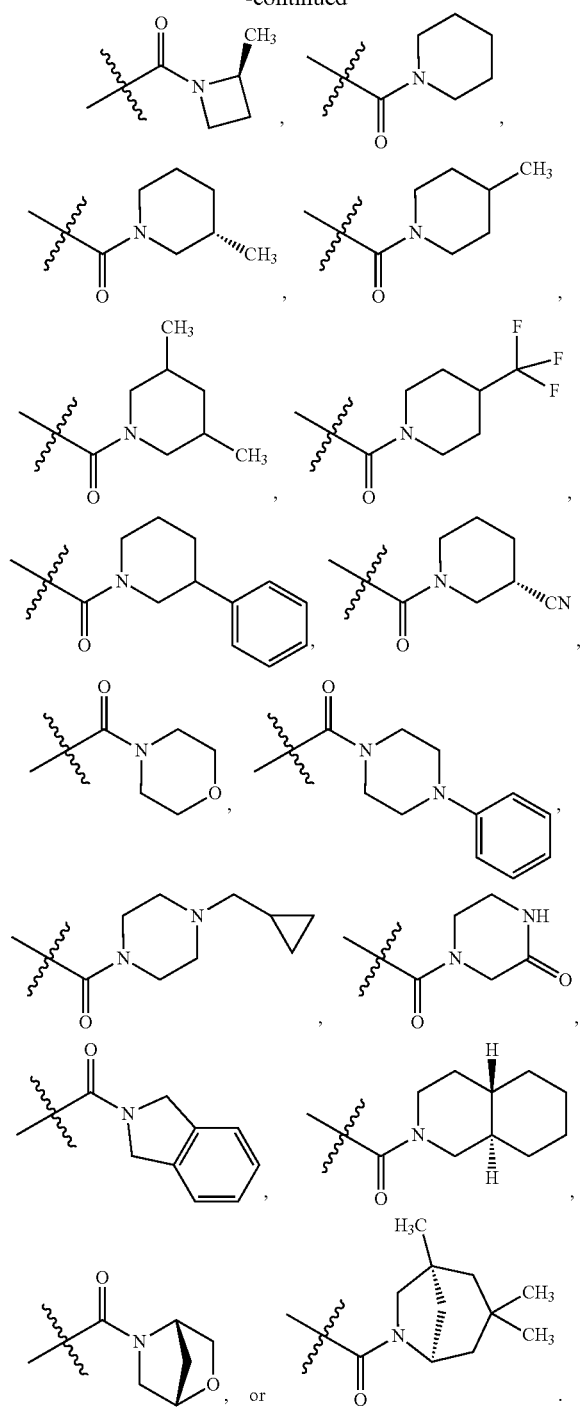
In an alternative twenty-first embodiment, the invention provides the compound according to any one of embodiments 1-19, the stereoisomer, tautomer, hydrate, solvate or the pharmaceutically acceptable salt thereof, wherein $R^1$ is selected from
-continued
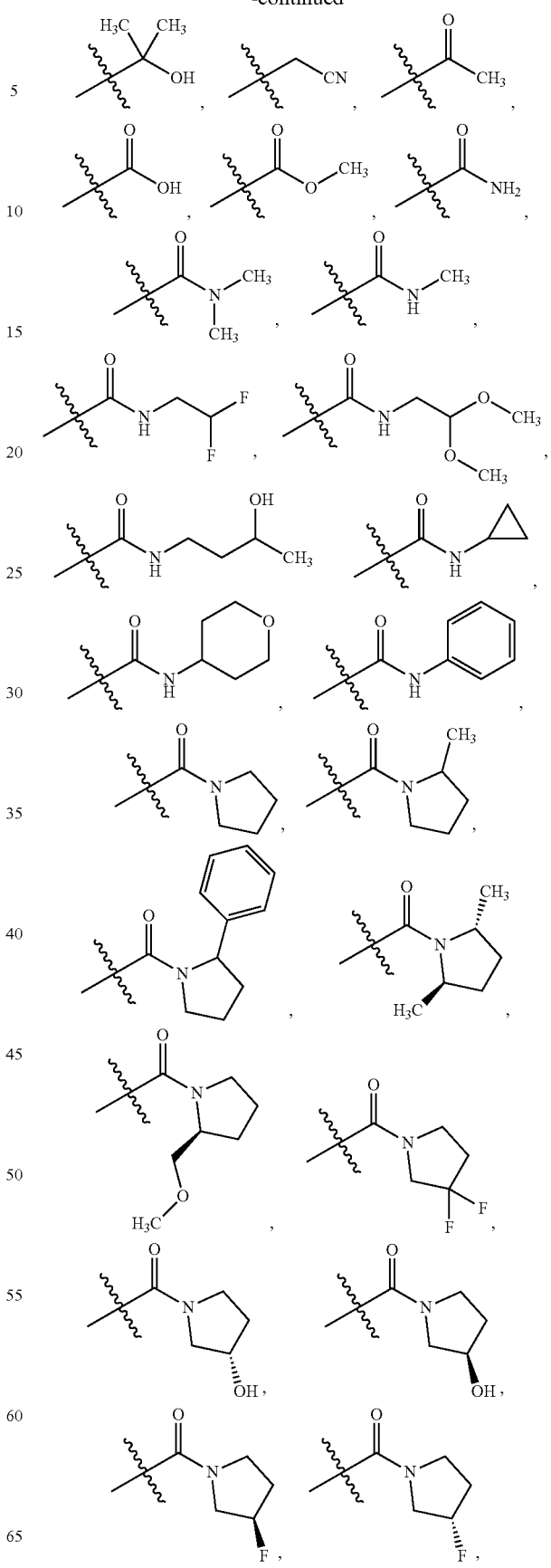

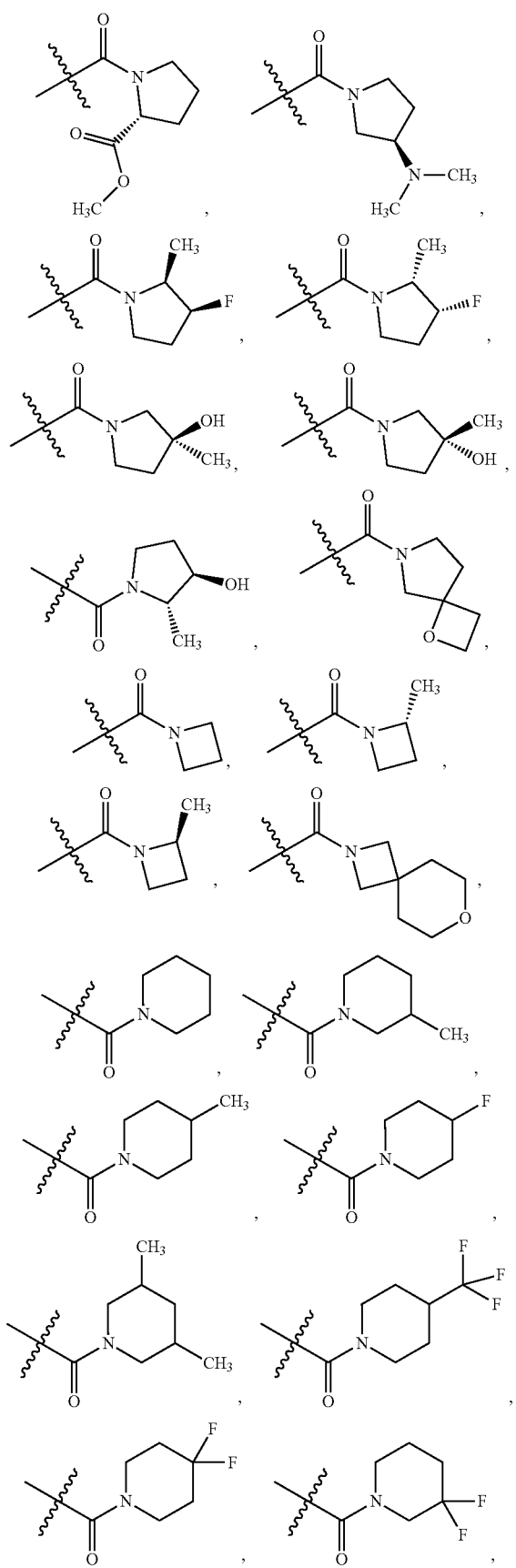
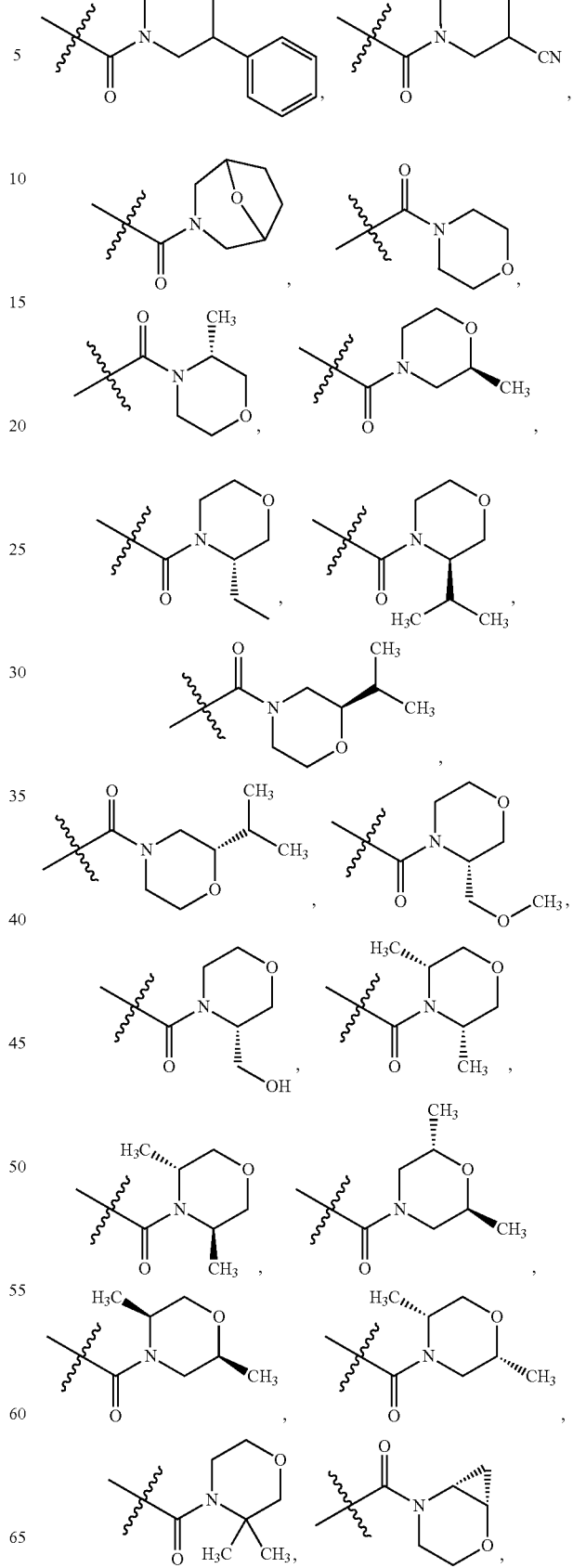

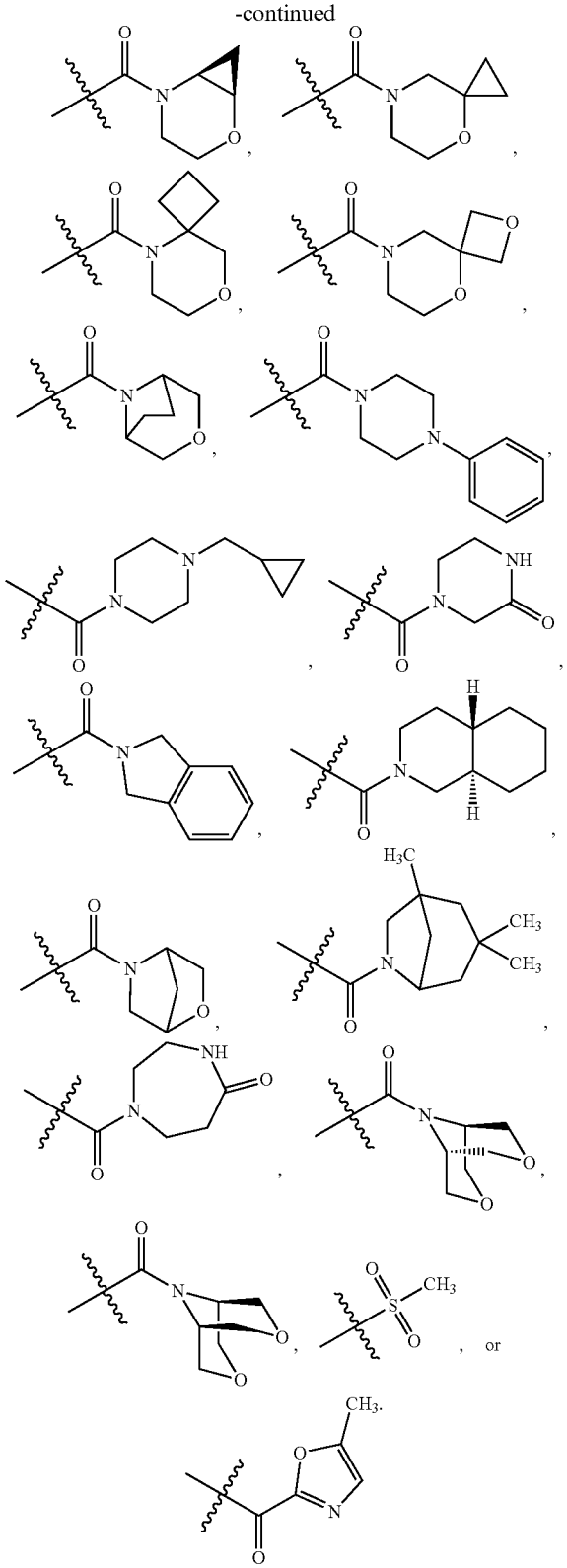
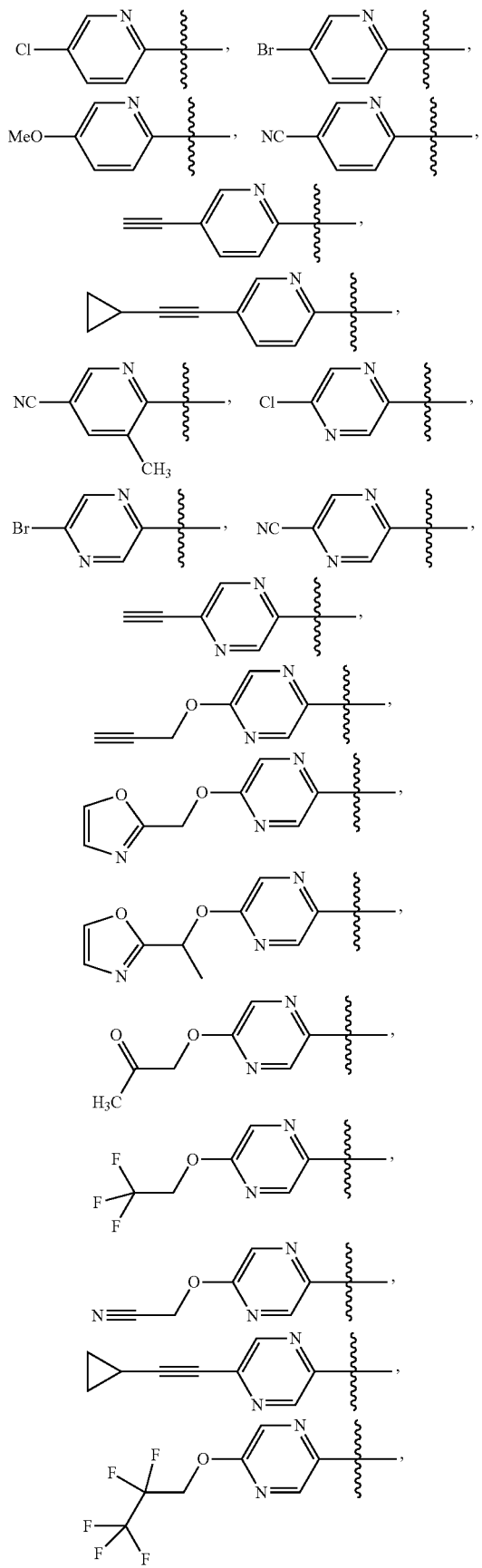
In a twenty-second embodiment, the invention provides the compound according to any one of embodiments 1-21, the stereoisomer, tautomer, hydrate, solvate or the pharmaceutically acceptable salt thereof, wherein one of $R^9$ and $R^{10}$ is —F and the other of $R^9$ and $R^{10}$ is selected from

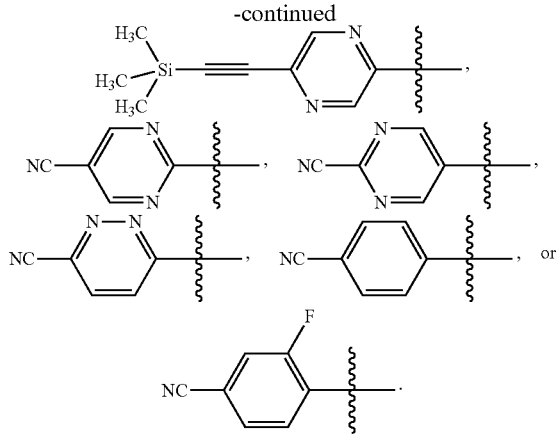
In an alternative twenty-second embodiment, the invention provides the compound according to any one of embodiments 1-21, the stereoisomer, tautomer, hydrate, solvate or the pharmaceutically acceptable salt thereof, wherein one of $R^9$ and $R^{10}$ is —F and the other of $R^9$ and $R^{10}$ is selected from
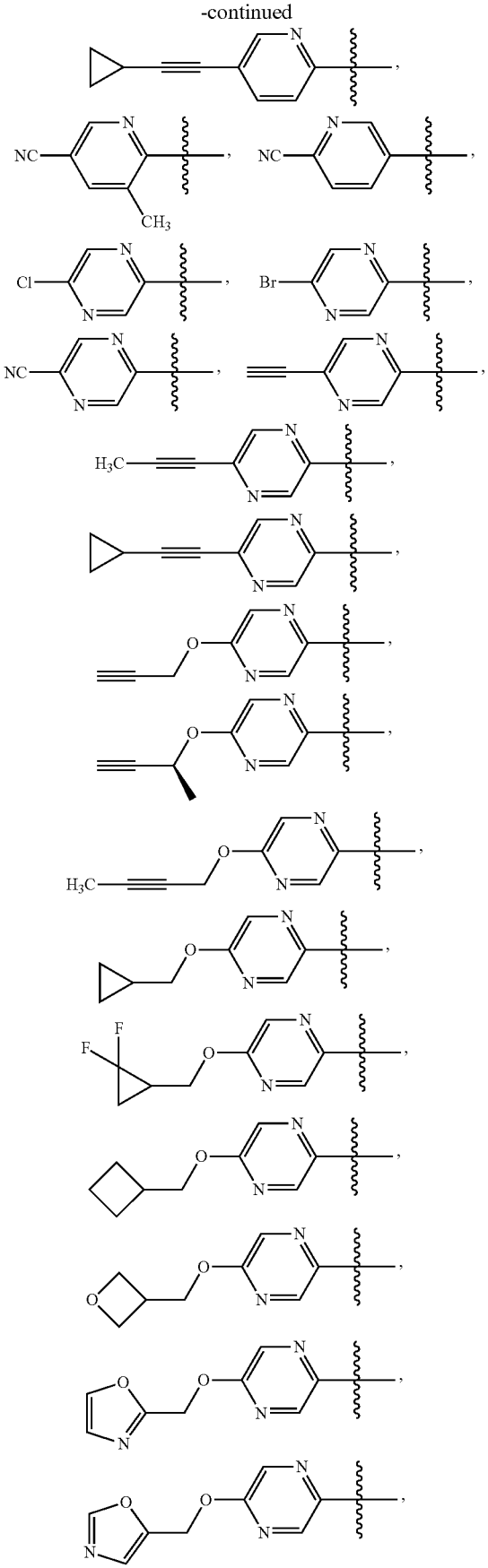

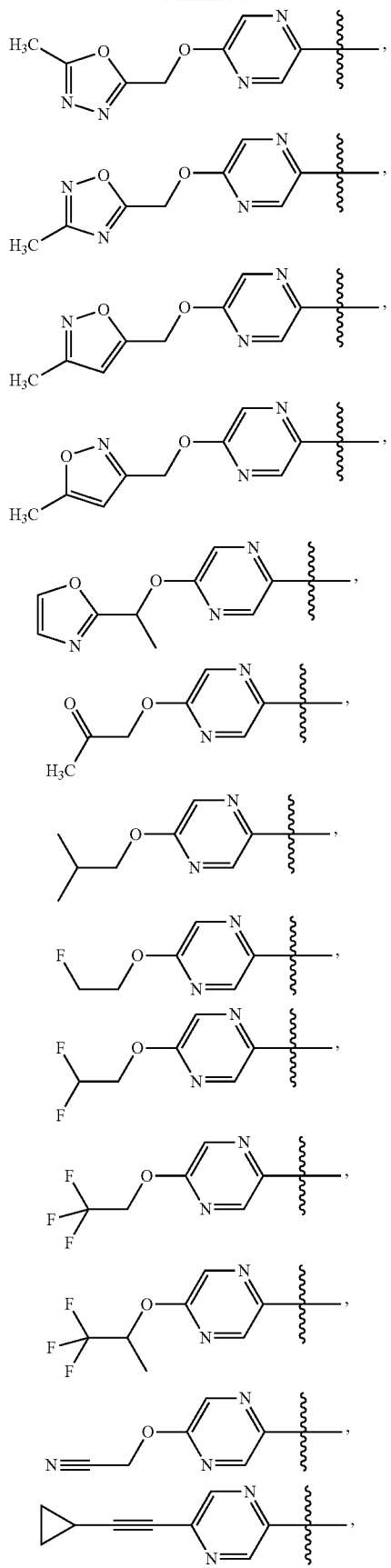
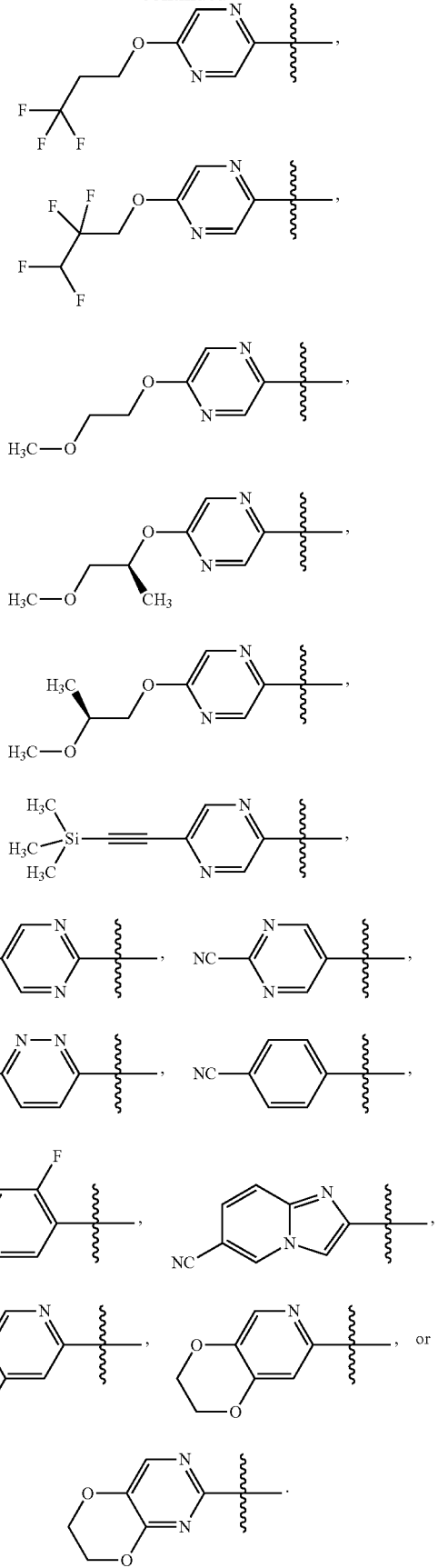

In a twenty-third embodiment, the invention provides the compound according to embodiment 22, the stereoisomer, tautomer, hydrate, solvate or the pharmaceutically acceptable salt thereof, wherein $R^{10}$ is —F.

In a twenty-fourth embodiment, the invention provides the compound according to any one of embodiments 1-21, the stereoisomer, tautomer, hydrate, solvate or the pharmaceutically acceptable salt thereof, wherein one of $R^9$ and $R^{10}$ is —F and the other of $R^9$ and $R^{10}$ is selected from a substituted or unsubstituted pyridinyl, a substituted or unsubstituted pyrazinyl, a substituted or unsubstituted pyrimidinyl, a substituted or unsubstituted pyridazinyl, or a substituted or unsubstituted phenyl group.

In an alternative twenty-fourth embodiment, the invention provides the compound according to any one of embodiments 1-21, the stereoisomer, tautomer, hydrate, solvate or the pharmaceutically acceptable salt thereof, wherein one of $R^9$ and $R^{10}$ is —F and the other of $R^9$ and $R^{10}$ is selected from a substituted or unsubstituted thienyl, a substituted or unsubstituted thiazolyl, a substituted or unsubstituted pyridinyl, a substituted or unsubstituted pyrazinyl, a substituted or unsubstituted pyrimidinyl, a substituted or unsubstituted pyridazinyl, a substituted or unsubstituted phenyl, a substituted or unsubstituted imidazo[1,2-a]pyridinyl, a substituted or unsubstituted pyrido[3,4-b]pyrazinyl, a substituted or unsubstituted 2,3-dihydro-[1,4]dioxino[2,3-c]pyridinyl, or a substituted or unsubstituted 6,7-dihydro-[1,4]dioxino[2,3-d]pyrimidinyl group.

In a twenty-fifth embodiment, the invention provides the compound according to embodiment 24, the stereoisomer, tautomer, hydrate, solvate or the pharmaceutically acceptable salt thereof, wherein the substituted pyridinyl, substituted pyrazinyl, substituted pyrimidinyl, substituted pyridazinyl, or substituted phenyl of the $R^9$ or $R^{10}$ groups are independently substituted with 1-3 substituents selected from —Cl, —Br, —F, —CN, —CH$_3$, —C≡CH, —C≡C-cyclopropyl, —OCH$_3$, —OCH$_2$—C≡CH, —OCH$_2$-oxazolyl, —OCH(CH$_3$)-oxazolyl, —OCH$_2$C(=O)CH$_3$, —OCH$_2$CF$_3$, —OCH$_2$CN, or —OCH$_2$CF$_2$CF$_3$.

In an alternative twenty-fifth embodiment, the invention provides the compound according to embodiment 24, the stereoisomer, tautomer, hydrate, solvate or the pharmaceutically acceptable salt thereof, wherein the substituted or unsubstituted thienyl, substituted or unsubstituted thiazolyl, substituted or unsubstituted pyridinyl, substituted or unsubstituted pyrazinyl, substituted or unsubstituted pyrimidinyl, substituted or unsubstituted pyridazinyl, substituted or unsubstituted phenyl, substituted or unsubstituted imidazo[1,2-a]pyridinyl, substituted or unsubstituted pyrido[3,4-b]pyrazinyl, substituted or unsubstituted 2,3-dihydro-[1,4]dioxino[2,3-c]pyridinyl, or substituted or unsubstituted 6,7-dihydro-[1,4]dioxino[2,3-d]pyrimidinyl of the $R^9$ or $R^{10}$ groups are independently substituted with 1-3 substituents selected from —Cl, —Br, —F, —CN, cyclopropylmethoxy, 2-propynyloxy, 2-butynyloxy, C$_{1-6}$-alkyl, C$_{2-6}$-alkynyl, C$_{1-6}$-alkoxy, oxetan-3-yl, —O—CH$_2$-heteroaryl, and further wherein each of the 2-propynyloxy, C$_{1-6}$-alkyl, C$_{2-6}$-alkynyl, C$_{1-6}$-alkoxy or —O—CH$_2$-heteroaryl is optionally substituted independently with 1-5 substituents of F, CN, OH, oxo, methyl, cyclopropyl, cyclobutyl, trimethylsilyl, or oxetanyl.

In a twenty-sixth embodiment, the invention provides the compound according to embodiment 24 or embodiment 25, the stereoisomer, tautomer, hydrate, solvate or the pharmaceutically acceptable salt thereof, wherein $R^{10}$ is —F.

In a twenty-seventh embodiment, the invention provides the compound according to embodiment 1, or the stereoisomer, tautomer, hydrate, solvate or the pharmaceutically acceptable salt thereof, wherein the compound of Formula I is a compound of Formula IC

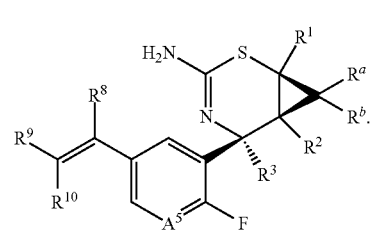

IC wherein
$A^5$ is CR$^5$ or N;
$R^a$ is —H;
$R^b$ is —H;
$R^2$ is —H;
$R^3$ is selected from C$_{1-4}$-alkyl or C$_{1-4}$-haloalkyl; and
$R^8$ is —H.

In a twenty-eighth embodiment, the invention provides the compound according to embodiment 1, or the stereoisomer, tautomer, hydrate, solvate or the pharmaceutically acceptable salt thereof, wherein the compound of Formula I is a compound of Formula ID

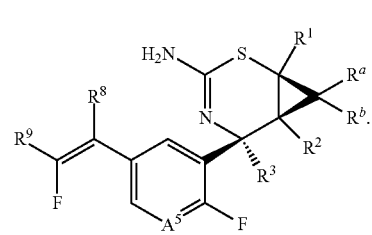

ID wherein
$A^5$ is CR$^5$ or N;
$R^a$ is —H;
$R^b$ is —H;
$R^2$ is —H;
$R^3$ is selected from C$_{1-4}$-alkyl or C$_{1-4}$-haloalkyl; and
$R^8$ is —H.

In a twenty-ninth embodiment, the invention provides the compound according to embodiment 1, or the stereoisomer, tautomer, hydrate, solvate or the pharmaceutically acceptable salt thereof, wherein the compound of Formula I is a compound of Formula IE

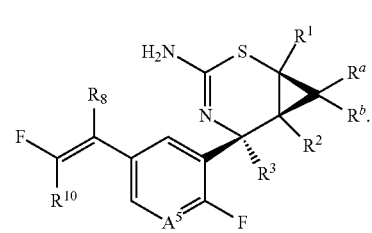

IE wherein
$A^5$ is CR$^5$ or N;
$R^a$ is —H;

$R^b$ is —H;

$R^2$ is —H;

$R^3$ is selected from $C_{1-4}$-alkyl or $C_{1-4}$-haloalkyl; and $R^8$ is —H.

In a thirtieth embodiment, the invention provides the compound according to any one of embodiments 27-29, the stereoisomer, tautomer, hydrate, solvate or the pharmaceutically acceptable salt thereof, wherein $R^1$ is selected from substituted or unsubstituted $C_{1-6}$-alkyl, substituted or unsubstituted —$CH_2OC_{1-6}$-alkyl, substituted or unsubstituted —C(O)O$C_{1-6}$-alkyl, substituted or unsubstituted —C(=O)NH$C_{1-6}$-alkyl, substituted or unsubstituted —C(=O)N($C_{1-6}$-alkyl)$_2$, substituted or unsubstituted —C(=O)NH$C_{3-6}$-cycloalkyl, substituted or unsubstituted —C(=O)NH-aryl, or substituted or unsubstituted —C(=O)NH-heterocyclyl.

In an alternative thirtieth embodiment, the invention provides the compound according to any one of embodiments 27-29, the stereoisomer, tautomer, hydrate, solvate or the pharmaceutically acceptable salt thereof, wherein $R^1$ is selected from substituted or unsubstituted —$CH_2OC_{1-6}$-alkyl, substituted or unsubstituted —S(O)$_o$$C_{1-6}$-alkyl, —C(O)NH$_2$, substituted or unsubstituted —C(O)$C_{1-6}$-alkyl, substituted or unsubstituted —C(=O)NH$C_{1-6}$-alkyl, substituted or unsubstituted —C(=O)N($C_{1-6}$-alkyl)$_2$, substituted or unsubstituted —C(O)-heterocyclyl.

In a thirty-first embodiment, the invention provides the compound according to any one of embodiments 27-29, the stereoisomer, tautomer, hydrate, solvate or the pharmaceutically acceptable salt thereof, wherein $R^1$ is selected from

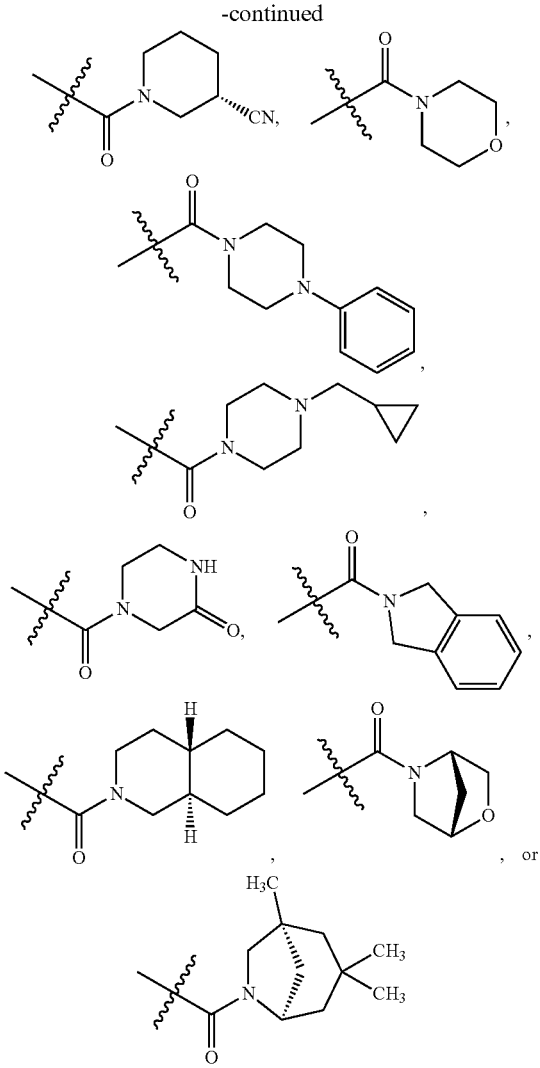
In an alternative thirty-first embodiment, the invention provides the compound according to any one of embodiments 27-29, the stereoisomer, tautomer, hydrate, solvate or the pharmaceutically acceptable salt thereof, wherein $R^1$ is selected from
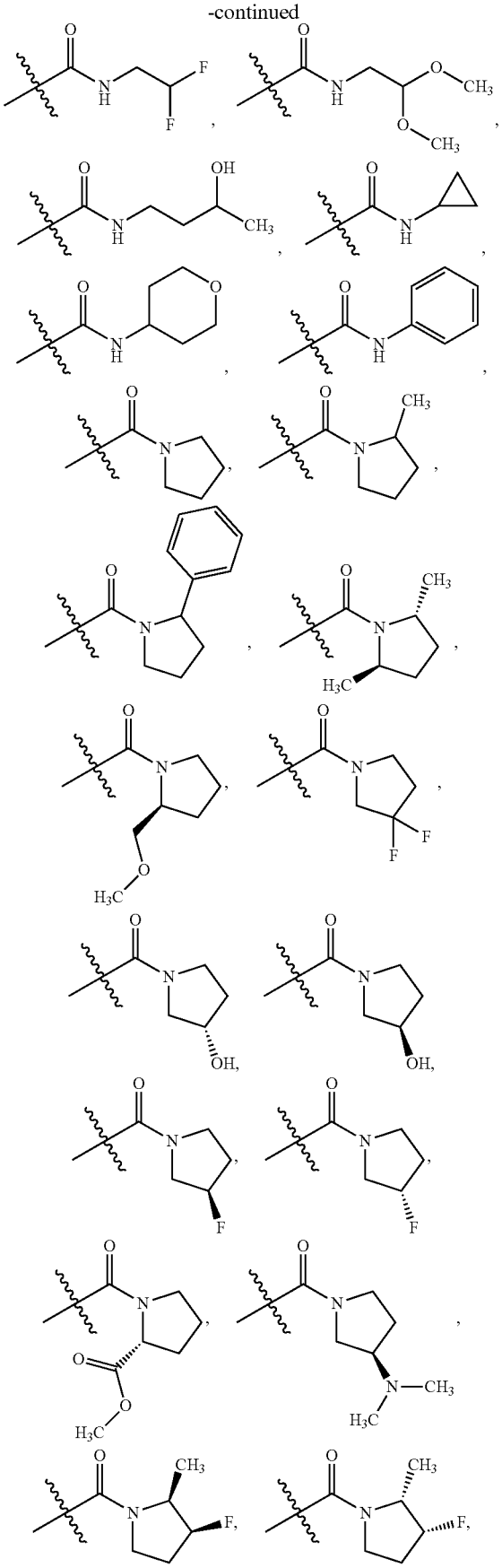

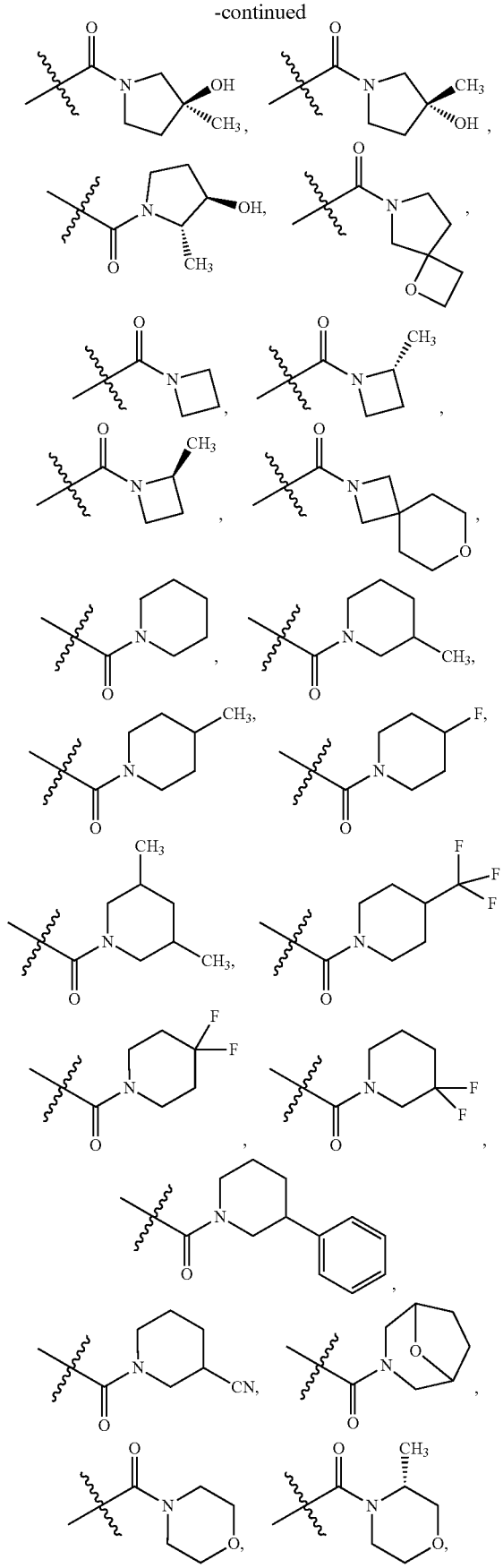
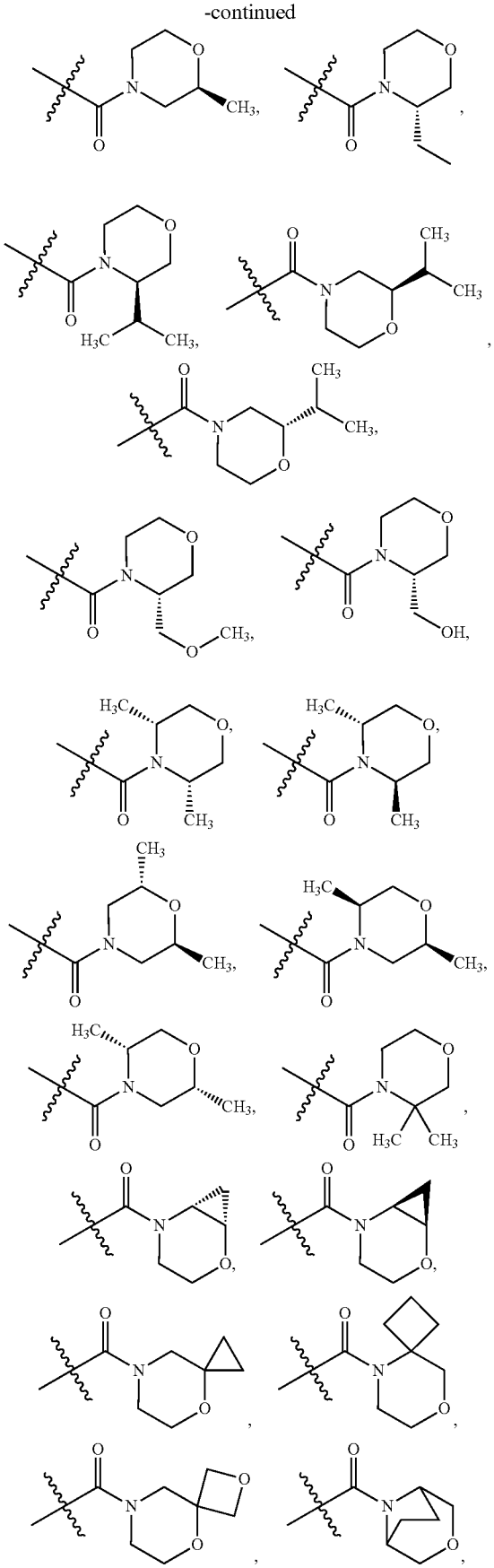

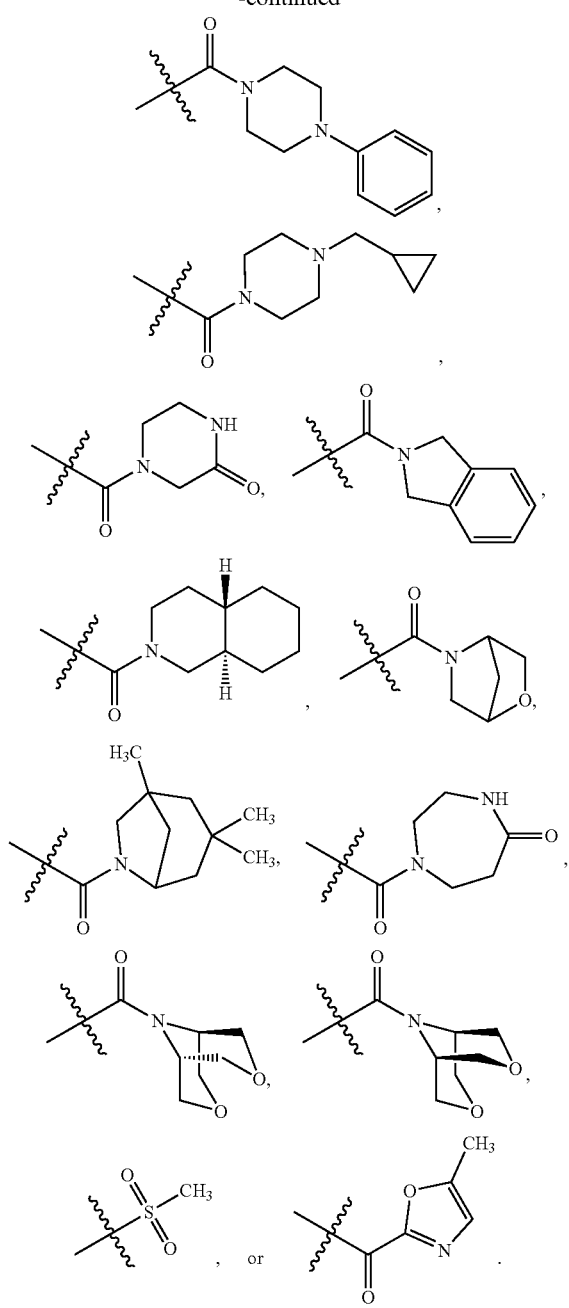
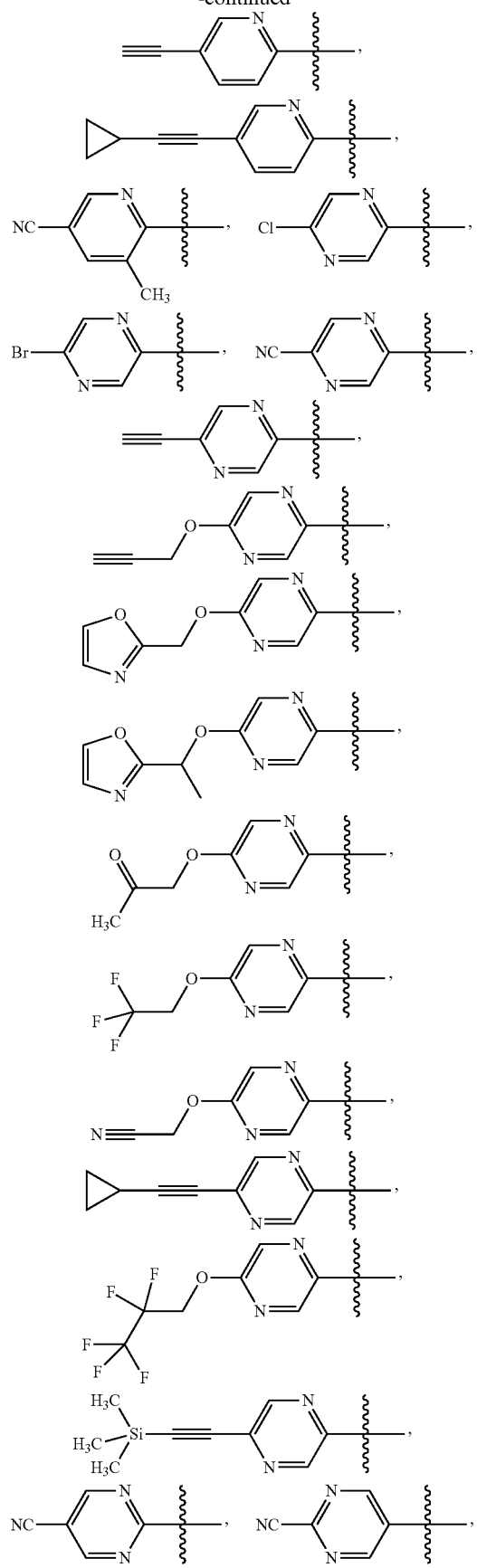
In a thirty-second embodiment, the invention provides the compound according to any one of embodiments 27-31, the stereoisomer, tautomer, hydrate, solvate or the pharmaceutically acceptable salt thereof, wherein one of $R^9$ or $R^{10}$ is selected from
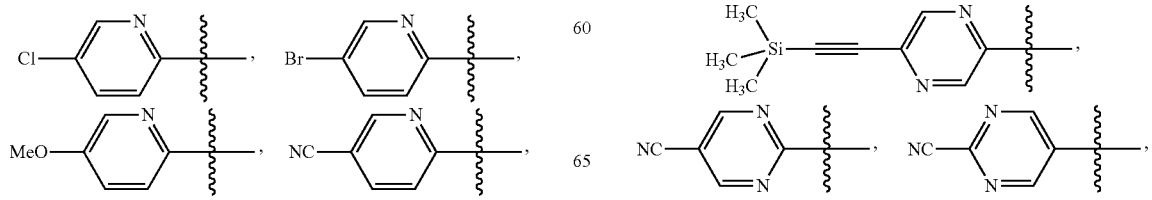

-continued
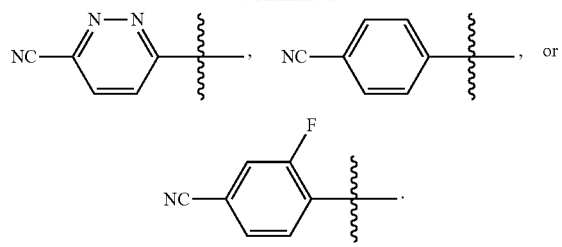
In an alternative thirty-second embodiment, the invention provides the compound according to any one of embodiments 27-31, the stereoisomer, tautomer, hydrate, solvate or the pharmaceutically acceptable salt thereof, wherein one of $R^9$ or $R^{10}$ is selected from
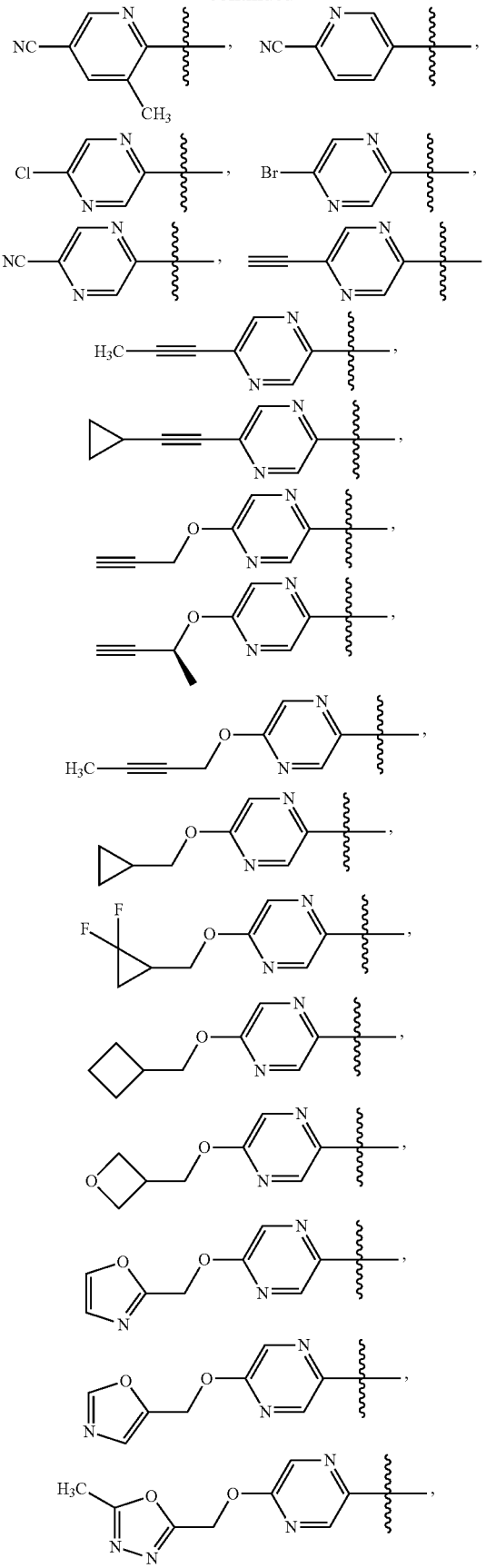

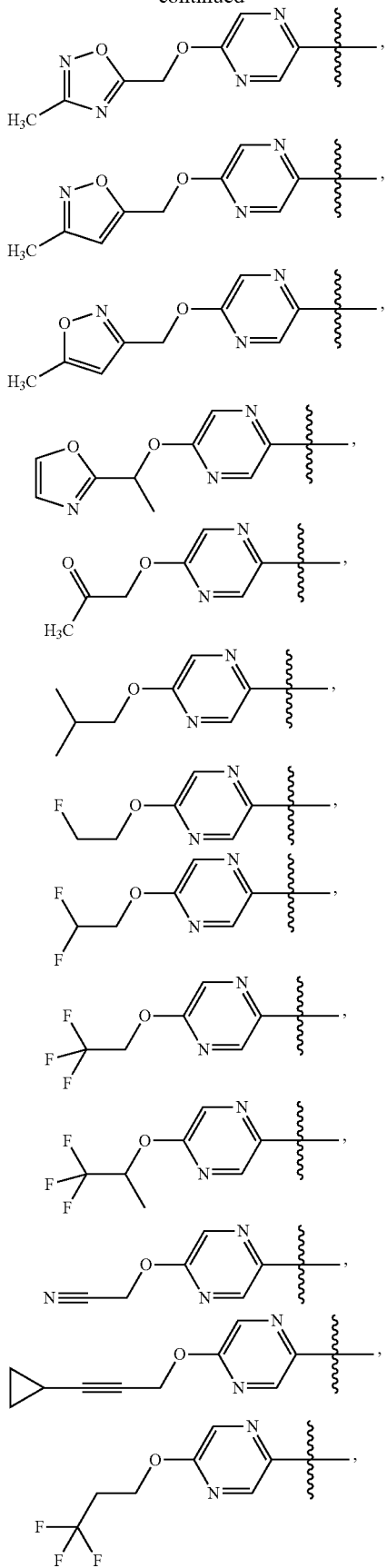

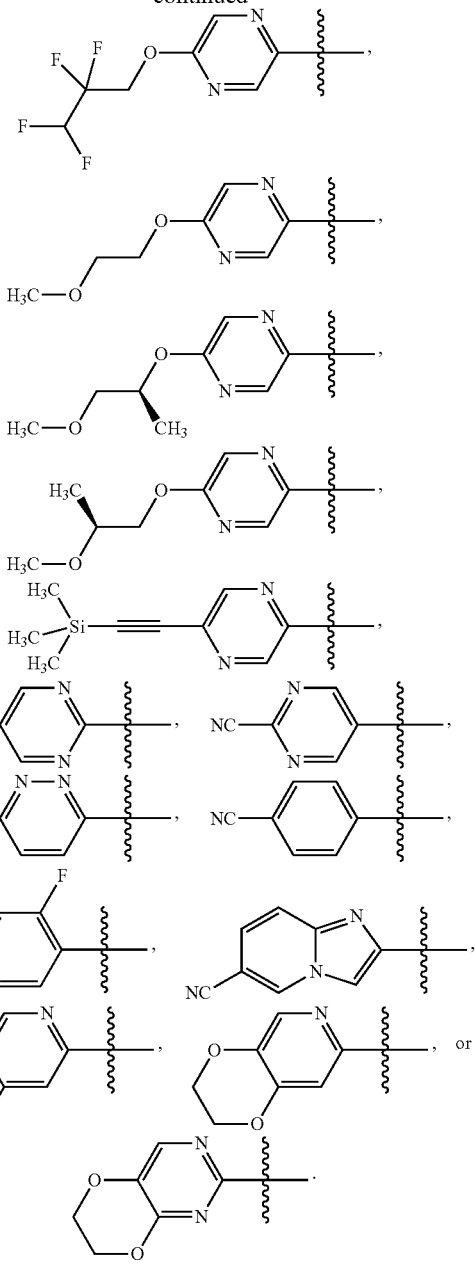

In a thirty-third embodiment, the invention provides the compound according to any one of embodiments 27-31, the stereoisomer, tautomer, hydrate, solvate or the pharmaceutically acceptable salt thereof, wherein one of $R^9$ and $R^{10}$ is selected from a substituted or unsubstituted pyridinyl, a substituted or unsubstituted pyrazinyl, a substituted or unsubstituted pyrimidinyl, a substituted or unsubstituted pyridazinyl, or a substituted or unsubstituted phenyl group.

In an alternative thirty-third embodiment, the invention provides the compound according to any one of embodiments 27-31, the stereoisomer, tautomer, hydrate, solvate or the pharmaceutically acceptable salt thereof, wherein one of $R^9$ and $R^{10}$ is selected from a substituted or unsubstituted thienyl, a substituted or unsubstituted thiazolyl, a substituted or unsubstituted pyridinyl, a substituted or unsubstituted pyrazinyl, a substituted or unsubstituted pyrimidinyl, a substituted or unsubstituted pyridazinyl, a substituted or unsubstituted phenyl, a substituted or unsubstituted imidazo[1,2-a]pyridinyl, a substituted or unsubstituted pyrido[3,4-b]pyrazinyl, a substituted or unsubstituted 2,3-dihydro-[1,4]dioxino[2,3-c]pyridinyl, or a substituted or unsubstituted 6,7-dihydro-[1,4]dioxino[2,3-d]pyrimidinyl group.

In a thirty-fourth embodiment, the invention provides the compound according to embodiment 33, the stereoisomer, tautomer, hydrate, solvate or the pharmaceutically acceptable salt thereof, wherein the substituted pyridinyl, substituted pyrazinyl, substituted pyrimidinyl, substituted pyridazinyl, or substituted phenyl of the $R^9$ or $R^{10}$ groups are independently substituted with 1-3 substituents selected from —Cl, —Br, —F, —CN, —CH$_3$, —C≡CH, —C≡C-cyclopropyl, —OCH$_3$, —OCH$_2$—C≡CH, —OCH$_2$-oxazolyl, —OCH(CH$_3$)-oxazolyl, —OCH$_2$C(=O)CH$_3$, —OCH$_2$CF$_3$, —OCH$_2$CN, or —OCH$_2$CF$_2$CF$_3$.

In an alternative thirty-fourth embodiment, the invention provides the compound according to embodiment 33, the stereoisomer, tautomer, hydrate, solvate or the pharmaceutically acceptable salt thereof, wherein the substituted or unsubstituted thienyl, substituted or unsubstituted thiazolyl, substituted or unsubstituted pyridinyl, substituted or unsubstituted pyrazinyl, substituted or unsubstituted pyrimidinyl, substituted or unsubstituted pyridazinyl, substituted or unsubstituted phenyl, substituted or unsubstituted imidazo[1,2-a]pyridinyl, substituted or unsubstituted pyrido[3,4-b]pyrazinyl, substituted or unsubstituted 2,3-dihydro-[1,4]dioxino[2,3-c]pyridinyl, or substituted or unsubstituted 6,7-dihydro-[1,4]dioxino[2,3-d]pyrimidinyl of the $R^9$ or $R^{10}$ groups are independently substituted with 1-3 substituents selected from —Cl, —Br, —F, —CN, cyclopropylmethoxy, 2-propynyloxy, 2-butynyloxy, $C_{1-6}$-alkyl, $C_{2-6}$-alkynyl, $C_{1-6}$-alkoxy, oxetan-3-yl, —O—CH$_2$-heteroaryl, and further wherein each of the 2-propynyloxy, $C_{1-6}$-alkyl, $C_{2-6}$-alkynyl, $C_{1-6}$-alkoxy or —O—CH$_2$-heteroaryl is optionally substituted independently with 1-5 substituents of F, CN, OH, oxo, methyl, cyclopropyl, cyclobutyl, trimethylsilyl, or oxetanyl.

In a thirty-fifth embodiment, the invention provides the compound of embodiment 1, or a pharmaceutically acceptable salt thereof, selected from (1S,5S,6S)-5-(5-((Z)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine;

(1S,5S,6S)-5-(5-((E)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine;

(1S,5S,6S)-3-amino-5-(5-((Z)-2-(5-chloropyridin-2-yl)-2-fluorovinyl)-2-fluorophenyl)-N,N,5-trimethyl-2-thia-4-azabicyclo[4.1.0]hept-3-ene-1-carboxamide;

((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(pyrrolidin-1-yl)methanone;

((1S,5S,6S)-3-amino-5-(2-fluoro-5-((Z)-2-fluoro-2-(5-methoxypyridin-2-yl)vinyl)phenyl)-5-methyl-2-thia-4-azabicyclo[4.1.0]hept-3-en-1-yl)(pyrrolidin-1-yl)methanone;

(1S,5S,6S)-methyl 3-amino-5-(5-((Z)-2-(5-bromopyridin-2-yl)-2-fluorovinyl)-2-fluorophenyl)-5-methyl-2-thia-4-azabicyclo[4.1.0]hept-3-ene-1-carboxylate;

(1S,5S,6S)-3-amino-5-(5-((Z)-2-(5-cyanopyridin-2-yl)-2-fluorovinyl)-2-fluorophenyl)-N,N,5-trimethyl-2-thia-4-azabicyclo[4.1.0]hept-3-ene-1-carboxamide;

6-((Z)-2-(3-((1S,5S,6S)-3-amino-5-methyl-1-(pyrrolidine-1-carbonyl)-2-thia-4-azabicyclo[4.1.0]hept-3-en-5-yl)-4-fluorophenyl)-1-fluorovinyl)nicotinonitrile;

(1S,5S,6S)-3-amino-5-(5-((Z)-2-(5-bromopyridin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-(cyclopropylethynyl)pyridin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-ethynylpyridin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-methyl 3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylate;

((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(azetidin-1-yl)methanone;

((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)methanol;

2-((1R,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)acetonitrile;

(1S,5S,6S)-3-amino-5-(5-((Z)-2-(5-chloropyridin-2-yl)-2-fluorovinyl)-2-fluorophenyl)-N-(3-hydroxybutyl)-5-methyl-2-thia-4-azabicyclo[4.1.0]hept-3-ene-1-carboxamide;

((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(2-methylazetidin-1-yl)methanone;

((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((S)-2-(methoxymethyl)pyrrolidin-1-yl)methanone;

(1S,5S,6S)-3-amino-5-(5-((Z)-2-(5-chloropyridin-2-yl)-2-fluorovinyl)-2-fluorophenyl)-5-methyl-N-phenyl-2-thia-4-azabicyclo[4.1.0]hept-3-ene-1-carboxamide;

((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((S)-2-methylazetidin-1-yl)methanone;

((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((R)-2-methylazetidin-1-yl)methanone;

(1S,5S,6S)-3-amino-5-(5-((Z)-2-(5-cyanopyridin-2-yl)-2-fluorovinyl)-2-fluorophenyl)-N-cyclopropyl-5-methyl-2-thia-4-azabicyclo[4.1.0]hept-3-ene-1-carboxamide;

6-((Z)-2-(3-((1S,5S,6S)-3-amino-1-(3,3-difluoropyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(azetidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-hydroxypyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-3-fluoropyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-fluoropyrrolidine-1-carbonyl)-5-methyl-2-thia-4-azabicyclo[4.1.0]hept-3-en-5-yl)-4-fluorophenyl)-1-fluorovinyl)nicotinonitrile;

(1S,5S,6S)-3-amino-5-(5-((Z)-2-(5-cyanopyridin-2-yl)-2-fluorovinyl)-2-fluorophenyl)-5-methyl-N-(tetrahydro-2H-pyran-4-yl)-2-thia-4-azabicyclo[4.1.0]hept-3-ene-1-carboxamide;

6-((Z)-2-(3-((1S,5S,6S)-3-amino-1-(isoindoline-2-carbonyl)-5-methyl-2-thia-4-azabicyclo[4.1.0]hept-3-en-5-yl)-4-fluorophenyl)-1-fluorovinyl)nicotinonitrile;

(R)-methyl 1-((1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carbonyl)pyrrolidine-2-carboxylate;

6-((Z)-2-(3-((1S,5S,6S)-3-amino-5-methyl-1-(4-phenylpiperazine-1-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((1S,4S)-2-oxa-5-azabicyclo[2.2.1]heptane-5-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2R,5R)-2,5-dimethylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-3-(dimethylamino)pyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((4aS,8aR)-decahydroisoquinoline-2-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(1,3,3-trimethyl-6-azabicyclo[3.2.1]octane-6-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(3,5-dimethylpiperidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(2-methylpyrrolidine-1-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(4-(trifluoromethyl)piperidine-1-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(3-phenylpiperidine-1-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(4-(cyclopropylmethyl)piperazine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(5-oxo-1,4-diazepane-1-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(3-cyanopiperidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(3-oxopiperazine-1-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(3-methylpiperidine-1-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(piperidine-1-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(4-methylpiperidine-1-carbonyl)-2-thia-4-azabicyclo[4.1.0]hept-3-en-5-yl)-4-fluorophenyl)-1-fluorovinyl)nicotinonitrile;

(1S,5S,6S)-methyl 3-amino-5-(5-((Z)-2-(5-bromopyrazin-2-yl)-2-fluorovinyl)-2-fluorophenyl)-5-methyl-2-thia-4-azabicyclo[4.1.0]hept-3-ene-1-carboxylate;

(1S,5S,6S)-methyl 3-amino-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate;

(1S,5S,6S)-methyl 3-amino-5-(2-fluoro-5-((Z)-2-fluoro-2-(5-(oxazol-2-ylmethoxy)pyrazin-2-yl)vinyl)phenyl)-5-methyl-2-thia-4-azabicyclo[4.1.0]hept-3-ene-1-carboxylate;

(1S,5S,6S)-3-amino-5-(2-fluoro-5-((Z)-2-fluoro-2-(5-(prop-2-yn-1-yloxy)pyrazin-2-yl)vinyl)phenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(2-oxopropoxy)pyrazin-2-yl)vinyl)phenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(prop-2-yn-1-yloxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(oxazol-2-ylmethoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(2,2,2-trifluoroethoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(-1-(oxazol-2-yl)ethoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-(cyanomethoxy)pyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-(cyclopropylethynyl)pyrazin-2-yl)-2-fluorovinyl)-2-fluorophenyl)-N,N,5-trimethyl-2-thia-4-azabicyclo[4.1.0]hept-3-ene-1-carboxamide;

6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)-5-methylnicotinonitrile;

(1S,5S,6S)-3-amino-5-(2-fluoro-5-((Z)-2-fluoro-2-(5-(2,2,3,3-tetrafluoropropoxy)pyrazin-2-yl)vinyl)phenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(oxazol-2-ylmethoxy)pyrazin-2-yl)vinyl)phenyl)-N,5-dimethyl-2-thia-4-azabicyclo[4.1.0]hept-3-ene-1-carboxamide;

(1S,5S,6S)-3-amino-5-(5-((Z)-2-(5-bromopyrazin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(prop-1-yn-1-yl)pyrazin-2-yl)vinyl)phenyl)-N,5-dimethyl-2-thia-4-azabicyclo[4.1.0]hept-3-ene-1-carboxamide;

(1S,5S,6S)-3-amino-5-(5-((Z)-2-(5-(cyclopropylethynyl)pyrazin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-((trimethylsilyl) ethynyl)pyrazin-2-yl)vinyl)phenyl)-N,5-dimethyl-2-thia-4-azabicyclo[4.1.0]hept-3-ene-1-carboxamide;

(1S,5S,6S)-3-amino-5-(5-((Z)-2-(5-ethynylpyrazin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(5-((Z)-2-(4-cyanophenyl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-cyanopyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-cyanopyrimidin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(6-cyanopyridin-3-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(4-cyano-2-fluorophenyl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(2-cyanopyrimidin-5-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(6-cyanopyridazin-3-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-chloropyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-methyl 3-amino-5-(5-((Z)-2-(5-chloropyridin-2-yl)-2-fluorovinyl)-2-fluoropyridin-3-yl)-5-methyl-2-thia-4-azabicyclo[4.1.0]hept-3-ene-1-carboxylate;

(1S,5S,6S)-methyl 3-amino-5-(5-((E)-2-(5-chloropyridin-2-yl)-2-fluorovinyl)-2-fluoropyridin-3-yl)-5-methyl-2-thia-4-azabicyclo[4.1.0]hept-3-ene-1-carboxylate;

(1S,5S,6S)-3-amino-5-(5-((Z)-2-(5-chloropyridin-2-yl)-2-fluorovinyl)-2-fluoropyridin-3-yl)-N,N,5-trimethyl-2-thia-4-azabicyclo[4.1.0]hept-3-ene-1-carboxamide;

(1S,5S,6S)-3-amino-5-(5-((E)-2-(5-chloropyridin-2-yl)-2-fluorovinyl)-2-fluoropyridin-3-yl)-N,N,5-trimethyl-2-thia-4-azabicyclo[4.1.0]hept-3-ene-1-carboxamide;

(1S,5S,6S)-3-amino-5-(5-((Z)-2-(5-cyanopyridin-2-yl)-2-fluorovinyl)-2-fluoropyridin-3-yl)-N,N,5-trimethyl-2-thia-4-azabicyclo[4.1.0]hept-3-ene-1-carboxamide;

6-((Z)-2-(5-((1S,5S,6S)-3-amino-1-((R)-3-fluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile;

6-((Z)-2-(5-((1S,5S,6S)-3-amino-1-((S)-3-fluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile;

6-((Z)-2-(5-((1S,5S,6S)-3-amino-5-methyl-1-(morpholine-4-carbonyl)-2-thia-4-azabicyclo[4.1.0]hept-3-en-5-yl)-6-fluoropyridin-3-yl)-1-fluorovinyl)nicotinonitrile;

6-((Z)-2-(5-((1S,5S,6S)-3-amino-1-((R)-3-fluoropyrrolidine-1-carbonyl)-5-methyl-2-thia-4-azabicyclo[4.1.0]hept-3-en-5-yl)-6-methoxypyridin-3-yl)-1-fluorovinyl)nicotinonitrile;

(1S,5S,6S)-3-amino-5-(5-((Z)-2-(5-chloropyridin-2-yl)-1-fluorovinyl)-2-fluorophenyl)-N,N,5-trimethyl-2-thia-4-azabicyclo[4.1.0]hept-3-ene-1-carboxamide; or (1S,5S,6S)-3-amino-5-(5-((Z)-2-(4-cyanophenyl)-1-fluorovinyl)-2-fluorophenyl)-N,N,5-trimethyl-2-thia-4-azabicyclo[4.1.0]hept-3-ene-1-carboxamide.

In some embodiments, the invention provides any of the specific compounds of the thirty-fifth embodiment or a pharmaceutically acceptable salt thereof.

In a thirty-sixth embodiment, the invention provides the compound of embodiment 1, or a pharmaceutically acceptable salt thereof, selected from 5-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)pyrazine-2-carbonitrile;

5-((Z)-2-(3-((1S,5S,6S)-3-amino-5-methyl-1-(piperidine-1-carbonyl)-2-thia-4-azabicyclo[4.1.0]hept-3-en-5-yl)-4-fluorophenyl)-1-fluorovinyl)pyrazine-2-carbonitrile;

5-((Z)-2-(3-((1S,5S,6S)-3-amino-1-((S)-3-fluoropyrrolidine-1-carbonyl)-5-methyl-2-thia-4-azabicyclo[4.1.0]hept-3-en-5-yl)-4-fluorophenyl)-1-fluorovinyl)pyrazine-2-carbonitrile;

5-((Z)-2-(3-((1S,5S,6S)-3-amino-1-((R)-3-fluoropyrrolidine-1-carbonyl)-5-methyl-2-thia-4-azabicyclo[4.1.0]hept-3-en-5-yl)-4-fluorophenyl)-1-fluorovinyl)pyrazine-2-carbonitrile;

5-((Z)-2-(3-((1S,5S,6S)-3-amino-5-methyl-1-(pyrrolidine-1-carbonyl)-2-thia-4-azabicyclo[4.1.0]hept-3-en-5-yl)-4-fluorophenyl)-1-fluorovinyl)pyrazine-2-carbonitrile;

(1S,5S,6S)-3-amino-5-(5-((Z)-2-(5-ethynylpyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(2-methoxyethoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(5-((Z)-2-(5-(cyclopropylmethoxy)pyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(oxetan-3-ylmethoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(5-((Z)-2-(5-(2,2-difluoroethoxy)pyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(((S)-1-methoxypropan-2-yl)oxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(5-((Z)-2-(5-((2,2-difluorocyclopropyl)methoxy)pyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-((5-methyl-1,3,4-oxadiazol-2-yl)methoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-((3-methyl-1,2,4-oxadiazol-5-yl)methoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-((3-methylisoxazol-5-yl)methoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(5-((Z)-2-(5-cyanothiazol-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-cyanothiophen-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(4-cyanophenyl)-1-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-cyanopyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(5-((Z)-2-(5-cyanopyrazin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(trifluoromethyl)pyridin-2-yl)vinyl)phenyl)-N,5-dimethyl-2-thia-4-azabicyclo[4.1.0]hept-3-ene-1-carboxamide;

(1S,5S,6S)-3-amino-5-(5-((Z)-2-(5-cyano-3-methylpyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(oxazol-5-ylmethoxy)pyrazin-2-yl)vinyl)phenyl)-N,5-dimethyl-2-thia-4-azabicyclo[4.1.0]hept-3-ene-1-carboxamide;

(1R,5S,6S)-5-(2-fluoro-5-((Z)-2-fluoro-2-(5-(prop-2-yn-1-yloxy)pyrazin-2-yl)vinyl)phenyl)-5-methyl-1-(methylsulfonyl)-2-thia-4-azabicyclo[4.1.0]hept-3-en-3-amine;

(1R,5S,6S)-5-(2-fluoro-5-((Z)-2-fluoro-2-(5-((5-methyl-1,3,4-oxadiazol-2-yl)methoxy)pyrazin-2-yl)vinyl)phenyl)-5-methyl-1-(methylsulfonyl)-2-thia-4-azabicyclo[4.1.0]hept-3-en-3-amine;

(1R,5S,6S)-5-(2-fluoro-5-((Z)-2-fluoro-2-(5-(2,2,2-trifluoroethoxy)pyrazin-2-yl)vinyl)phenyl)-5-methyl-1-(methylsulfonyl)-2-thia-4-azabicyclo[4.1.0]hept-3-en-3-amine;

(1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-amine;

(1R,5S,6S)-5-(5-((Z)-2-(5-(but-2-yn-1-yloxy)pyrazin-2-yl)-2-fluorovinyl)-2-fluorophenyl)-5-methyl-1-(methylsulfonyl)-2-thia-4-azabicyclo[4.1.0]hept-3-en-3-amine;

(1R,5S,6S)-5-(5-((Z)-2-(5-((S)-but-3-yn-2-yloxy)pyrazin-2-yl)-2-fluorovinyl)-2-fluorophenyl)-5-methyl-1-(methylsulfonyl)-2-thia-4-azabicyclo[4.1.0]hept-3-en-3-amine;

6-((Z)-2-(3-((1R,5S,6S)-3-amino-5-methyl-1-(methylsulfonyl)-2-thia-4-azabicyclo[4.1.0]hept-3-en-5-yl)-4-fluorophenyl)-1-fluorovinyl)nicotinonitrile;

1-((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)ethanone;

1-((1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-en-1-yl)ethanone;

1-((1S,5S,6S)-3-amino-5-(2-fluoro-5-((Z)-2-fluoro-2-(5-(2,2,2-trifluoroethoxy)pyrazin-2-yl)vinyl)phenyl)-5-methyl-2-thia-4-azabicyclo[4.1.0]hept-3-en-1-yl)ethanone;

1-((1S,5S,6S)-3-amino-5-(5-((Z)-2-(5-((S)-but-3-yn-2-yloxy)pyrazin-2-yl)-2-fluorovinyl)-2-fluorophenyl)-5-methyl-2-thia-4-azabicyclo[4.1.0]hept-3-en-1-yl)ethanone;

6-((Z)-2-(3-((1S,5S,6S)-1-acetyl-3-amino-5-methyl-2-thia-4-azabicyclo[4.1.0]hept-3-en-5-yl)-4-fluorophenyl)-1-fluorovinyl)nicotinonitrile;

(1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxamide;

(1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carbonitrile;

(1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-ene-1-carboxamide;

(1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxamide;

(1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxamide;

(1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-ene-1-carbonitrile;

(1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carbonitrile;

(1S,5S,6S)-3-amino-5-(5-((Z)-2-(6-cyanoimidazo[1,2-a]pyridin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(pyrido[3,4-b]pyrazin-7-yl)vinyl)phenyl)-N,N,5-trimethyl-2-thia-4-azabicyclo[4.1.0]hept-3-ene-1-carboxamide;

(1S,5S,6S)-methyl 3-amino-5-(5-((Z)-2-(5-chloropyridin-2-yl)-2-fluorovinyl)-2,3-difluorophenyl)-5-methyl-2-thia-4-azabicyclo[4.1.0]hept-3-ene-1-carboxylate;

(1S,5S,6S)-3-amino-5-(5-((Z)-2-(2,3-dihydro-[1,4]dioxino[2,3-c]pyridin-7-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(5-((Z)-2-(6,7-dihydro-[1,4]dioxino[2,3-d]pyrimidin-2-yl)-2-fluorovinyl)-2-fluorophenyl)-N,N,5-trimethyl-2-thia-4-azabicyclo[4.1.0]hept-3-ene-1-carboxamide;

6-((Z)-2-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-1-fluorovinyl)nicotinonitrile;

((1S,5S,6R)-3-amino-5-(5-((Z)-2-(5-chloropyrazin-2-yl)-2-fluorovinyl)-2-fluorophenyl)-7,7-difluoro-5-methyl-2-thia-4-azabicyclo[4.1.0]hept-3-en-1-yl)methanol;

((1S,5S,6R)-3-amino-7,7-difluoro-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)methanol;

5-((Z)-2-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-1-fluorovinyl)pyrazine-2-carbonitrile;

((1S,5S,6R)-3-amino-5-(5-((Z)-2-(5-chloropyridin-2-yl)-2-fluorovinyl)-2-fluorophenyl)-7,7-difluoro-5-methyl-2-thia-4-azabicyclo[4.1.0]hept-3-en-1-yl)methanol;

(1S,5S,6R)-methyl 3-amino-5-(5-((Z)-2-(5-cyanopyridin-2-yl)-2-fluorovinyl)-2-fluorophenyl)-7,7-difluoro-5-methyl-2-thia-4-azabicyclo[4.1.0]hept-3-ene-1-carboxylate;

6-((Z)-2-(3-((1S,5S,6R)-3-amino-7,7-difluoro-1-(2-hydroxypropan-2-yl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6R)-3-amino-7,7-difluoro-1-(methoxymethyl)-5-methyl-2-thia-4-azabicyclo[4.1.0]hept-3-en-5-yl)-4-fluorophenyl)-1-fluorovinyl)nicotinonitrile;

6-((Z)-2-(5-((1S,5S,6S)-3-amino-1-(3,3-difluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile;

6-((Z)-2-(5-((1S,5S,6S)-3-amino-1-(4,4-difluoropiperidine-1-carbonyl)-5-methyl-2-thia-4-azabicyclo[4.1.0]hept-3-en-5-yl)-6-fluoropyridin-3-yl)-1-fluorovinyl)nicotinonitrile;

(1S,5S,6S)-5-(5-((Z)-2-(5-chloropyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(prop-2-yn-1-yloxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(5-((Z)-2-(5-(but-2-yn-1-yloxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(5-((Z)-2-(5-((S)-but-3-yn-2-yloxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-((S)-2-methoxypropoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(5-((Z)-2-(5-(2,2-difluoroethoxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(2,2,2-trifluoroethoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(3,3,3-trifluoropropoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(2-fluoroethoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(5-((Z)-2-(5-(cyclopropylmethoxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(5-((Z)-2-(5-(cyclobutylmethoxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(oxetan-3-ylmethoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-isobutoxypyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-((5-methylisoxazol-3-yl)methoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-((3-methylisoxazol-5-yl)methoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-((1,1,1-trifluoropropan-2-yl)oxy)pyrazin-2-yl)vinyl)phenyl)-1-(methoxymethyl)-5-methyl-2-thia-4-azabicyclo[4.1.0]hept-3-en-3-amine;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((1R,5R)-3,7-dioxa-9-azabicyclo[3.3.1]nonan-9-yl)methanone;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((S)-3-fluoropyrrolidin-1-yl)methanone;

(1S,5S,6S)-3-amino-5-(5-((Z)-2-(5-cyanopyridin-2-yl)-2-fluorovinyl)-2-fluoropyridin-3-yl)-N-(2,2-difluoroethyl)-5-methyl-2-thia-4-azabicyclo[4.1.0]hept-3-ene-1-carboxamide;

(1S,5S,6S)-3-amino-5-(2-fluoro-5-((Z)-2-fluoro-2-(5-(2,2,2-trifluoroethoxy)pyrazin-2-yl)vinyl)pyridin-3-yl)-N,N,5-trimethyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((R)-3-methylmorpholino)methanone;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((1R,5R)-3,7-dioxa-9-azabicyclo[3.3.1]nonan-9-yl)methanone;

(1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid;

(1S,5S,6S)-5-(5-((Z)-2-(5-chloropyridin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-3-amino-5-(2-fluoro-5-((Z)-2-fluoro-2-(5-(prop-2-yn-1-yloxy)pyrazin-2-yl)vinyl)pyridin-3-yl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(2-oxopropoxy)pyrazin-2-yl)vinyl)pyridin-3-yl)-N,N,5-trimethyl-2-thia-4-azabicyclo[4.1.0]hept-3-ene-1-carboxamide;

(1S,5S,6S)-3-amino-5-(5-((Z)-2-(5-(but-2-yn-1-yloxy)pyrazin-2-yl)-2-fluorovinyl)-2-fluoropyridin-3-yl)-N,N,5-trimethyl-2-thia-4-azabicyclo[4.1.0]hept-3-ene-1-carboxamide;

6-((Z)-2-(5-((1S,5S,6S)-3-amino-5-methyl-1-((R)-3-methylmorpholine-4-carbonyl)-2-thia-4-azabicyclo[4.1.0]hept-3-en-5-yl)-6-fluoropyridin-3-yl)-1-fluorovinyl)nicotinonitrile;

(1S,5S,6S)-3-amino-5-(2-fluoro-5-((Z)-2-fluoro-2-(5-(2,2,3,3-tetrafluoropropoxy)pyrazin-2-yl)vinyl)pyridin-3-yl)-N,N,5-trimethyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)(morpholino)methanone;

6-((Z)-2-(3-((1S,5S,6S)-3-amino-1-(methoxymethyl)-5-methyl-2-thia-4-azabicyclo[4.1.0]hept-3-en-5-yl)-4-fluorophenyl)-1-fluorovinyl)nicotinonitrile;

(1S,5S,6S)-methyl 3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylate methanone;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((R)-3-fluoropyrrolidin-1-yl)methanone;

(1S,5S,6S)-3-amino-5-(5-((Z)-2-(5-cyanopyrazin-2-yl)-2-fluorovinyl)-2-fluoropyridin-3-yl)-N,N,5-trimethyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((R)-3-fluoropyrrolidin-1-yl)methanone;

6-((Z)-2-(5-((1S,5S,6S)-3-amino-1-((1R,5R)-3,7-dioxa-9-azabicyclo[3.3.1]nonane-9-carbonyl)-5-methyl-2-thia-4-azabicyclo[4.1.0]hept-3-en-5-yl)-6-fluoropyridin-3-yl)-1-fluorovinyl)nicotinonitrile;

5-((Z)-2-(3-((1S,5S,6S)-3-amino-1-(methoxymethyl)-5-methyl-2-thia-4-azabicyclo[4.1.0]hept-3-en-5-yl)-4-fluorophenyl)-1-fluorovinyl)pyrazine-2-carbonitrile;

(1S,5S,6S)-3-amino-N-(2,2-difluoroethyl)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)(morpholino)methanone;

(1S,5S,6S)-3-amino-N-(2,2-difluoroethyl)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((S)-3-fluoropyrrolidin-1-yl)methanone;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((R)-3-methylmorpholino)methanone;

(1S,5S,6S)-5-(5-((Z)-2-(2,3-dihydro-[1,4]dioxino[2,3-c]pyridin-7-yl)-2-fluorovinyl)-2-fluorophenyl)-1-(methoxymethyl)-5-methyl-2-thia-4-azabicyclo[4.1.0]hept-3-en-3-amine;

6-((Z)-2-(3-((1S,5S,6S)-3-amino-1-((2S,3S)-3-fluoro-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2R,3R)-3-fluoro-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(2,5-dioxa-8-azaspiro[3.5]nonane-8-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-hydroxy-3-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-3-hydroxy-3-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((1S,6R)-2-oxa-5-azabicyclo[4.1.0]heptane-5-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((1R,6S)-2-oxa-5-azabicyclo[4.1.0]heptane-5-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((3S,5R)-3,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((3R,5R)-3,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(3-oxa-8-azabicyclo[3.2.1]octane-8-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-2-isopropylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-2-isopropylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(4-oxa-7-azaspiro[2.5]octane-7-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(4-oxa-7-azaspiro[2.5]octane-7-6-((Z)-2-(3-((1S,5S,6S)-3-amino-1-(8-oxa-3-azabicyclo[3.2.1]octane-3-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(7-oxa-2-azaspiro[3.5]nonane-2-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-((S)-2-methylmorpholine-4-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-3-isopropylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2S,6S)-2,6-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(3,3-difluoropiperidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(4,4-difluoropiperidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(4-fluoropiperidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(1-oxa-6-azaspiro[3.4]octane-6-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-(methoxymethyl)morpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2S,5S)-2,5-dimethyl-morpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2R,5R)-2,5-dimethyl-morpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(8-oxa-5-azaspiro[3.5]nonane-5-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(3,3-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-3-hydroxypyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-ethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-ethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2S,3R)-3-hydroxy-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(2-phenylpyrrolidine-1-carbonyl)-2-thia-4-azabicyclo[4.1.0]hept-3-en-5-yl)-4-fluorophenyl)-1-fluorovinyl)nicotinonitrile;

((1S,5S,6S)-3-amino-5-(5-((Z)-2-(5-bromopyridin-2-yl)-2-fluorovinyl)-2-fluorophenyl)-5-methyl-2-thia-4-azabicyclo[4.1.0]hept-3-en-1-yl) (morpholino)methanone;

((1S,5S,6S)-3-amino-5-(2-fluoro-5-((Z)-2-fluoro-2-(pyridin-2-yl)vinyl)phenyl)-5-methyl-2-thia-4-azabicyclo[4.1.0]hept-3-en-1-yl)(morpholino)methanone;

((1S,5S,6S)-3-amino-5-(2-fluoro-5-((Z)-2-fluoro-2-(5-(oxetan-3-yl)pyridin-2-yl)vinyl)phenyl)-5-methyl-2-thia-4-azabicyclo[4.1.0]hept-3-en-1-yl)(morpholino)methanone;

(1S,5S,6S)-3-amino-5-(5-((Z)-2-(5-cyanopyridin-2-yl)-2-fluorovinyl)-2-fluorophenyl)-N-(2,2-dimethoxyethyl)-5-methyl-2-thia-4-azabicyclo[4.1.0]hept-3-ene-1-carboxamide;

6-((Z)-2-(3-((1S,5S,6S)-3-amino-5-methyl-1-(5-methyloxazol-2-yl)-2-thia-4-azabicyclo[4.1.0]hept-3-en-5-yl)-4-fluorophenyl)-1-fluorovinyl)nicotinonitrile;

(1S,5S,6S)-5-(2-fluoro-5-((Z)-2-fluoro-2-(5-(prop-2-yn-1-yloxy)pyrazin-2-yl)vinyl)phenyl)-5-methyl-1-(5-methyloxazol-2-yl)-2-thia-4-azabicyclo[4.1.0]hept-3-en-3-amine;

6-((E)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)nicotinonitrile;

((1S,5S,6S)-3-amino-5-(5-((Z)-2-(5-ethynylpyridin-2-yl)-2-fluorovinyl)-2-fluorophenyl)-5-methyl-2-thia-4-azabicyclo[4.1.0]hept-3-en-1-yl) (morpholino)methanone;

((1S,5S,6S)-3-amino-5-(2-fluoro-5-((Z)-2-fluoro-2-(5-((trimethylsilyl)ethynyl)pyrazin-2-yl)vinyl)phenyl)-5-methyl-2-thia-4-azabicyclo[4.1.0]hept-3-en-1-yl)(morpholino)methanone;

((1S,5S,6S)-3-amino-5-(5-((Z)-2-(5-ethynylpyrazin-2-yl)-2-fluorovinyl)-2-fluorophenyl)-5-methyl-2-thia-4-azabicyclo[4.1.0]hept-3-en-1-yl) (morpholino)methanone;

(1S,5S,6S)-3-amino-5-(5-((Z)-2-(5-chloropyrazin-2-yl)-2-fluorovinyl)-2-fluorophenyl)-N,5-dimethyl-2-thia-4-azabicyclo[4.1.0]hept-3-ene-1-carboxamide;

((1S,5S,6S)-3-amino-5-(5-((Z)-2-(5-(cyclopropylethynyl)pyrazin-2-yl)-2-fluorovinyl)-2-fluorophenyl)-5-methyl-2-thia-4-azabicyclo[4.1.0]hept-3-en-1-yl)(morpholino)methanone;

((1S,5S,6S)-3-amino-5-(2-fluoro-5-((Z)-2-fluoro-2-(5-((trimethylsilyl)ethynyl)pyridin-2-yl)vinyl)phenyl)-5-methyl-2-thia-4-azabicyclo[4.1.0]hept-3-en-1-yl)(morpholino)methanone;

(1S,5S,6S)-3-amino-5-(5-((Z)-2-(5-bromopyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(5-((E)-2-(5-bromopyridin-2-yl)-2-fluorovinyl)-2-fluorophenyl)-N,5-dimethyl-2-thia-4-azabicyclo[4.1.0]hept-3-ene-1-carboxamide;

((1S,5S,6S)-3-amino-5-(5-((Z)-2-(5-(cyclopropylethynyl)pyridin-2-yl)-2-fluorovinyl)-2-fluorophenyl)-5-methyl-2-thia-4-azabicyclo[4.1.0]hept-3-en-1-yl)(morpholino)methanone;

(1S,5S,6S)-3-amino-5-(5-((Z)-2-(5-(cyclopropylethynyl)pyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(5-((Z)-2-(5-(3,3-dimethylbut-1-yn-1-yl)pyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(pent-1-yn-1-yl)pyridin-2-yl)vinyl)phenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(3-hydroxyprop-1-yn-1-yl)pyrazin-2-yl)vinyl)phenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(3-fluoroprop-1-yn-1-yl)pyrazin-2-yl)vinyl)phenyl)-N,5-dimethyl-2-thia-4-azabicyclo[4.1.0]hept-3-ene-1-carboxamide; or (1S,5S,6S)-3-Amino-5-(2-fluoro-5-((Z)-2-fluoro-2-(5-(trifluoromethoxy)pyridin-2-yl)vinyl)phenyl)-N,5-dimethyl-2-thia-4-azabicyclo[4.1.0]hept-3-ene-1-carboxamide.

In some embodiments, the invention provides any of the specific compounds of the thirty-sixth embodiment or a pharmaceutically acceptable salt thereof.

In a thirty-seventh embodiment, the invention provides a compound, or a pharmaceutically acceptable salt thereof, selected from (1S,5S,6S)-3-amino-5-(2-fluoro-5-((E)-2-fluoro-2-iodovinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-4-phenyl-but-1-en-3-yn-1-yl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluorovinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoropent-1-en-3-yn-1-yl)phenyl)-N,N,5-trimethyl-2-thia-4-azabicyclo[4.1.0]hept-3-ene-1-carboxamide;

(1S,5S,6S)-5-(2-fluoro-5-((Z)-2-fluoro-2-(5-(oxetan-2-ylmethoxy)pyrazin-2-yl)vinyl)phenyl)-1-(methoxymethyl)-5-methyl-2-thia-4-azabicyclo[4.1.0]hept-3-en-3-amine (1S,5S,6S)-5-(5-((Z)-2-(5-((3,3-difluorocyclobutyl)
methoxy)pyrazin-2-yl)-2-fluorovinyl)-2-fluorophenyl)-1-
(methoxymethyl)-5-methyl-2-thia-4-azabicyclo[4.1.0]
hept-3-en-3-amine
6-((Z)-2-(3-((1S,5S,6S)-3-amino-5-methyl-1-(4-methyl-4,
5-dihydrooxazol-2-yl)-2-thia-4-azabicyclo[4.1.0]hept-3-
en-5-yl)-4-fluorophenyl)-1-fluorovinyl)nicotinonitrile;
6-((Z)-2-(3-((1S,5S,6S)-3-amino-5-methyl-1-((R)-5-
methyl-4,5-dihydrooxazol-2-yl)-2-thia-4-azabicyclo
[4.1.0]hept-3-en-5-yl)-4-fluorophenyl)-1-fluorovinyl)
nicotinonitrile;
3-(5-((Z)-2-(3-((1S,5S,6S)-3-amino-5-methyl-1-(morpho-
line-4-carbonyl)-2-thia-4-azabicyclo[4.1.0]hept-3-en-5-
yl)-4-fluorophenyl)-1-fluorovinyl)pyrazin-2-yl)oxazoli-
din-2-one;
((1S,5S,6S)-3-amino-5-(5-((Z)-2-(5-(azetidin-1-yl)pyrazin-
2-yl)-2-fluorovinyl)-2-fluorophenyl)-5-methyl-2-thia-4-
azabicyclo[4.1.0]hept-3-en-1-yl)(morpholino)metha-
none; or
(1S,5S,6S)-3-amino-5-(2-fluoro-5-((Z)-2-fluoro-2-(5-((3-
methyloxetan-3-yl)ethynyl)pyridin-2-yl)vinyl)phenyl)-N,
5-dimethyl-2-thia-4-azabicyclo[4.1.0]hept-3-ene-1-car-
boxamide.

In some embodiments, the invention provides any of the specific compounds of the thirty-seventh embodiment or a pharmaceutically acceptable salt thereof.

In a thirty-eighth embodiment, the invention provides the compound of embodiment 1, or a pharmaceutically acceptable salt thereof, selected from

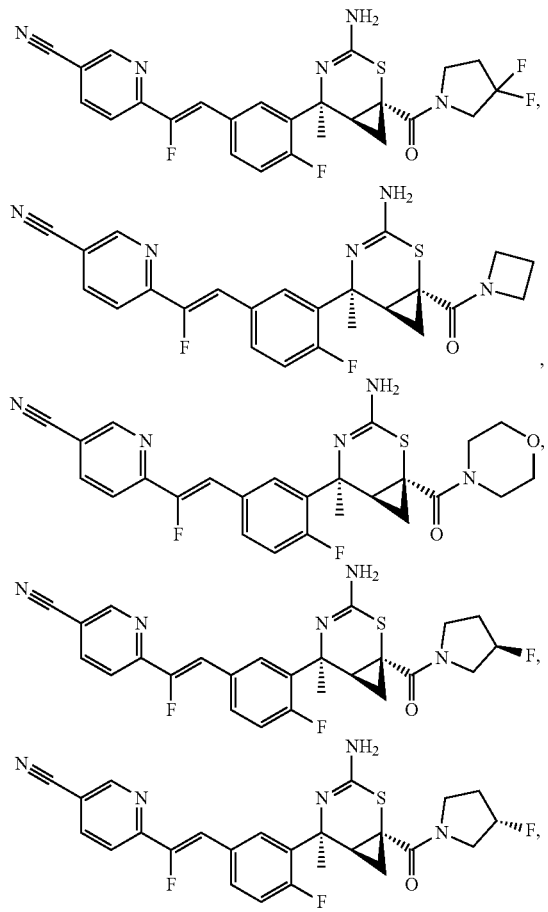

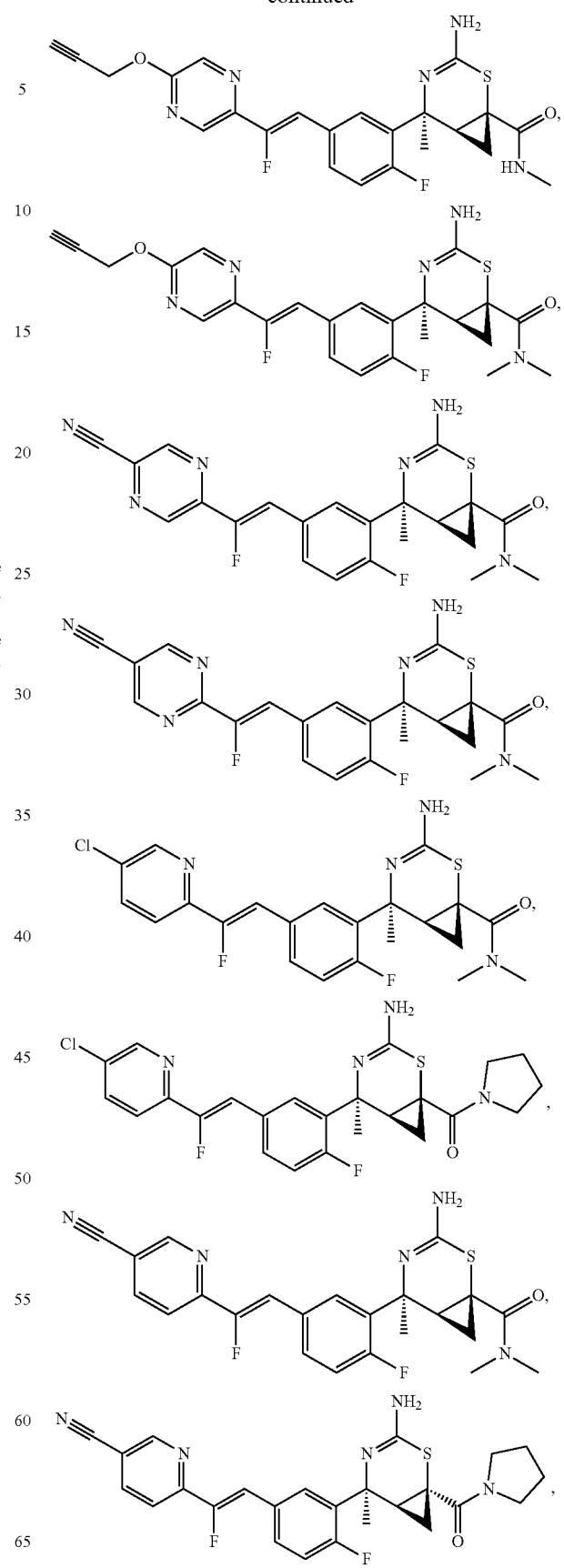

-continued
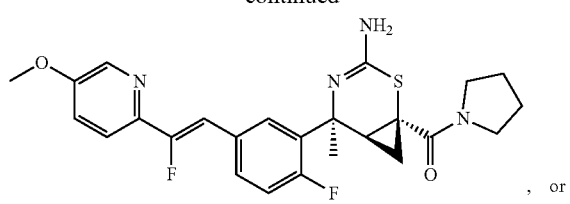
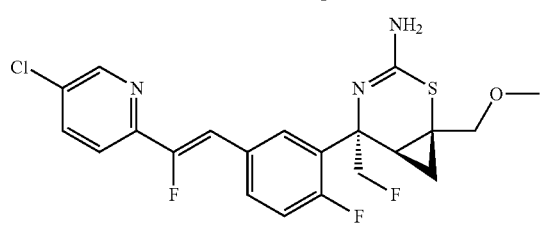
In a thirty-ninth embodiment, the invention provides the compound of embodiment 1, or a pharmaceutically acceptable salt thereof, selected from
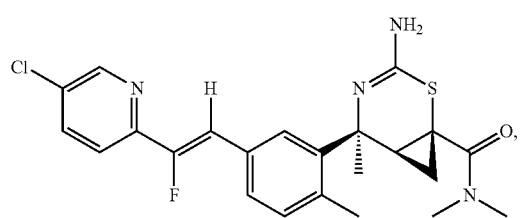
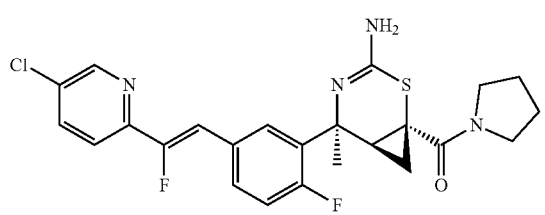
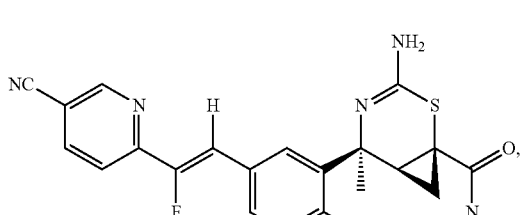
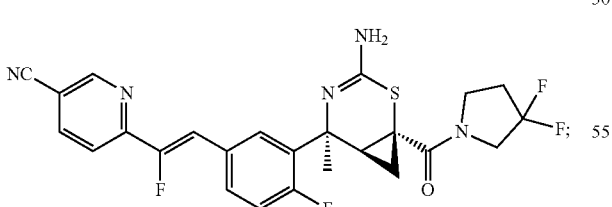
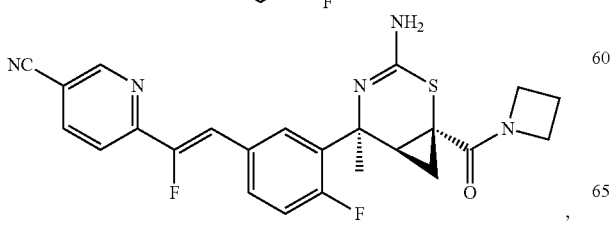
-continued
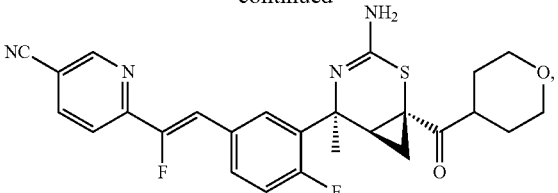
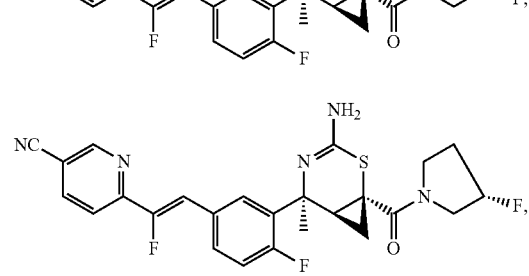
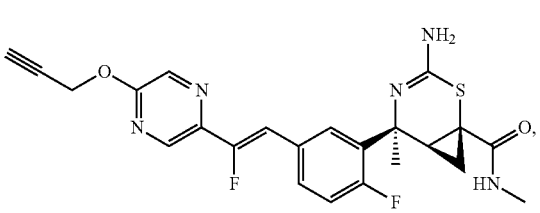
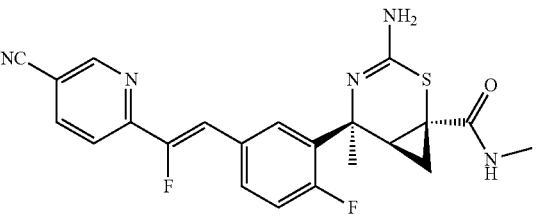
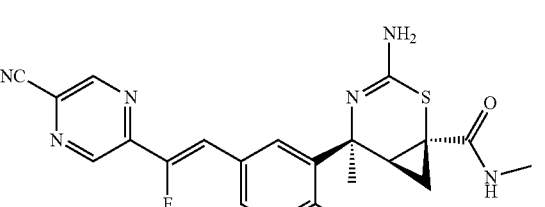
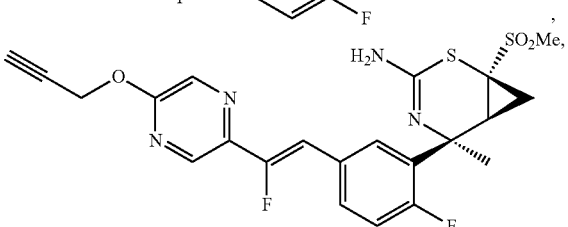
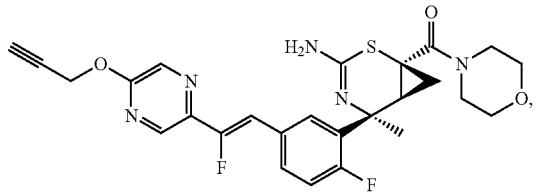

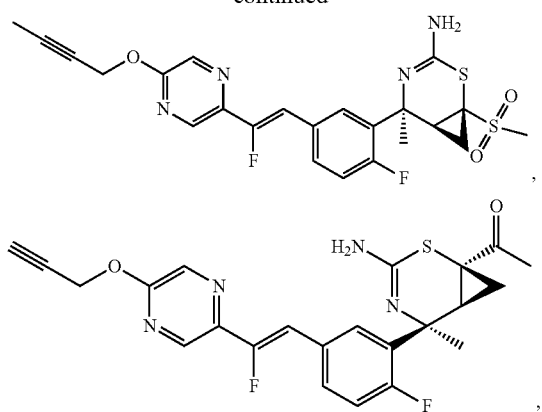

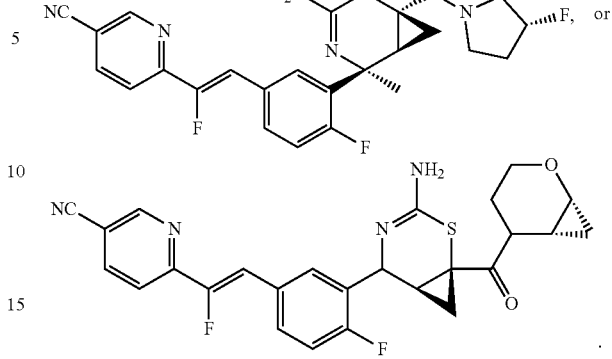

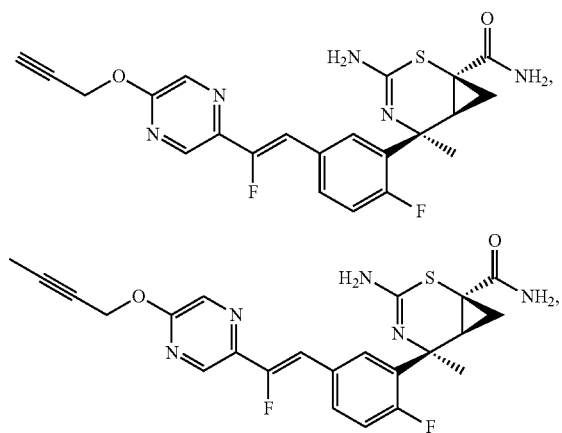

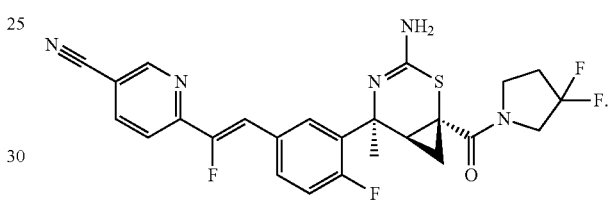

In a fortieth embodiment, the invention provides the compound of embodiment 1, or pharmaceutically acceptable salt thereof, wherein the compound is a compound of formula

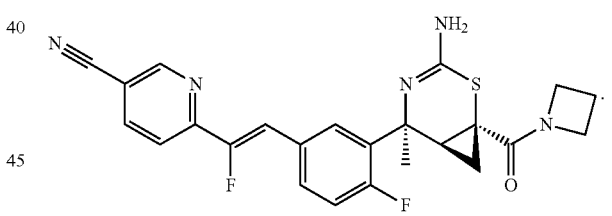

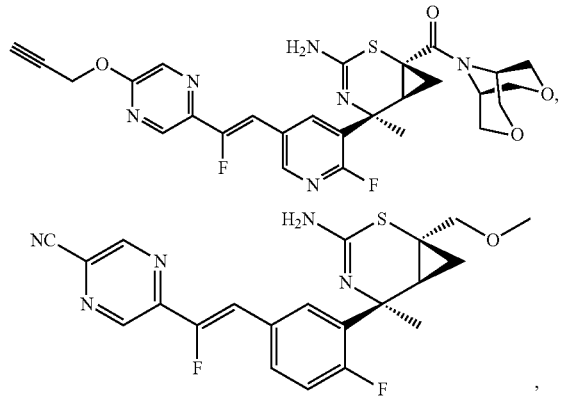

In a forty-first embodiment, the invention provides the compound of embodiment 1, or pharmaceutically acceptable salt thereof, wherein the compound is a compound of formula

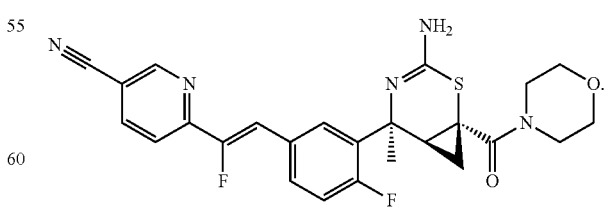

In a forty-second embodiment, the invention provides the compound of embodiment 1, or pharmaceutically acceptable salt thereof, wherein the compound is a compound of formula

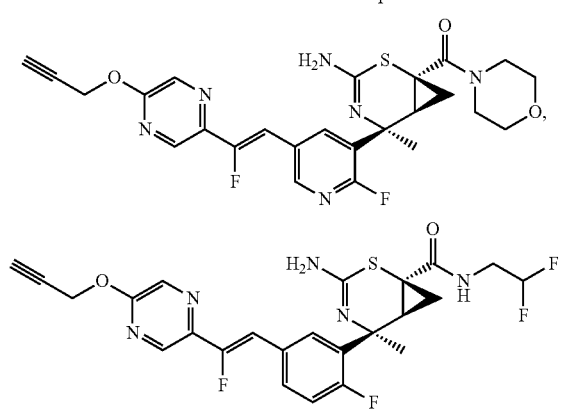

In a forty-third embodiment, the invention provides the compound of embodiment 1, or pharmaceutically acceptable salt thereof, wherein the compound is a compound of formula

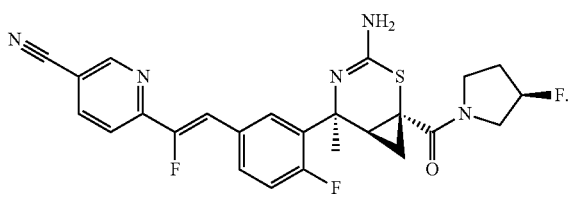

In a forty-fourth embodiment, the invention provides the compound of embodiment 1, or pharmaceutically acceptable salt thereof, wherein the compound is a compound of formula

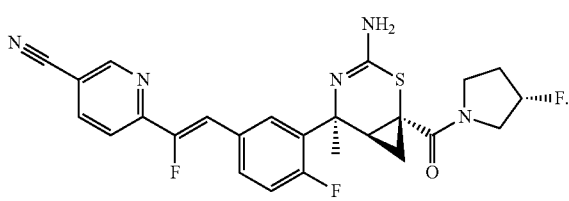 [SMILES: C[C@]1(c2cc(/C=C(\F)c3ccc(C#N)cn3)ccc2F)N=C(N)S[C@@]2(C(=O)N3CCC(F)(F)C3)C[C@H]21]

In a forty-fifth embodiment, the invention provides the compound of embodiment 1, or pharmaceutically acceptable salt thereof, wherein the compound is a compound of formula

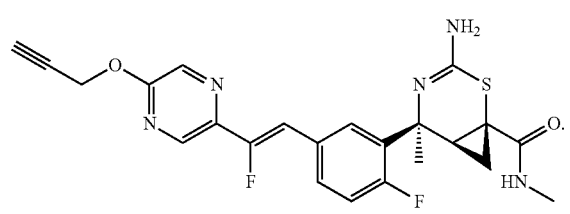 [SMILES: C#CCOc1cnc(/C(F)=C/c2ccc(F)c([C@@]3(C)N=C(N)S[C@@]4(C(=O)NC)C[C@H]43)c2)cn1]

In a forty-sixth embodiment, the invention provides the compound of embodiment 1, or pharmaceutically acceptable salt thereof, wherein the compound is a compound of formula

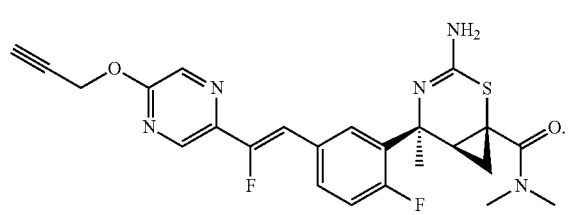 [SMILES: C#CCOc1cnc(/C(F)=C/c2ccc(F)c([C@@]3(C)N=C(N)S[C@@]4(C(=O)N(C)C)C[C@H]43)c2)cn1]

In a forty-seventh embodiment, the invention provides the compound of embodiment 1, or pharmaceutically acceptable salt thereof, wherein the compound is a compound of formula

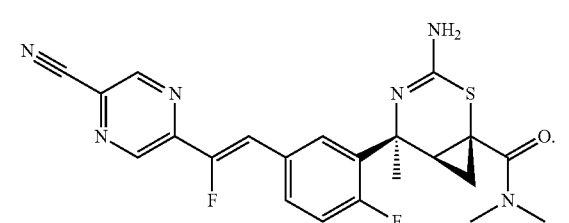

In a forty-eighth embodiment, the invention provides the compound of embodiment 1, or pharmaceutically acceptable salt thereof, wherein the compound is a compound of formula

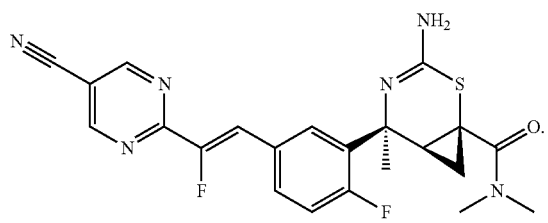 [SMILES: CN(C)C(=O)[C@]12C[C@H]1[C@@](C)(c1cc(/C=C(\F)c3ncc(C#N)cn3)ccc1F)N=C(N)S2]

In a forty-ninth embodiment, the invention provides the compound of embodiment 1, or pharmaceutically acceptable salt thereof, wherein the compound is a compound of formula

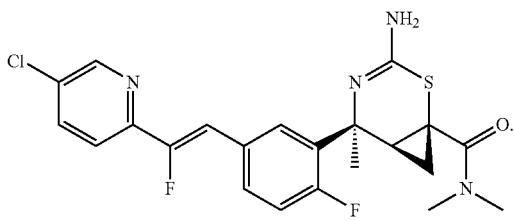 [SMILES: CN(C)C(=O)[C@]12C[C@H]1[C@@](C)(c1cc(/C=C(\F)c3ccc(Cl)cn3)ccc1F)N=C(N)S2]

In a fiftieth embodiment, the invention provides the compound of embodiment 1, or pharmaceutically acceptable salt thereof, wherein the compound is a compound of formula

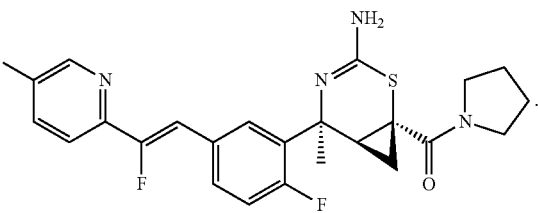

In a fifty-first embodiment, the invention provides the compound of embodiment 1, or or pharmaceutically acceptable salt thereof, wherein the compound is a compound of formula

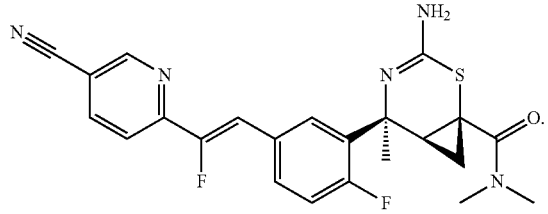 [SMILES: CN(C)C(=O)[C@]12C[C@H]1[C@@](C)(c1cc(/C=C(\F)c3ccc(C#N)cn3)ccc1F)N=C(N)S2]

In a fifty-second embodiment, the invention provides the compound of embodiment 1, or pharmaceutically acceptable salt thereof, wherein the compound is a compound of formula

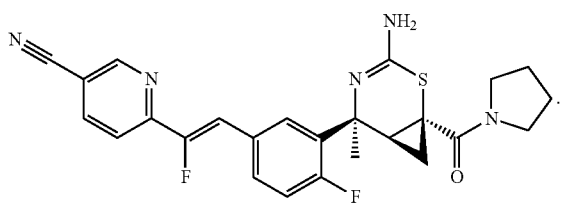 [SMILES: C[C@]1(c2cc(/C=C(\F)c3ccc(C#N)cn3)ccc2F)N=C(N)S[C@@]2(C(=O)N3CCCC3)C[C@H]21]

In a fifty-third embodiment, the invention provides the compound of embodiment 1, or pharmaceutically acceptable salt thereof, wherein the compound is a compound of formula

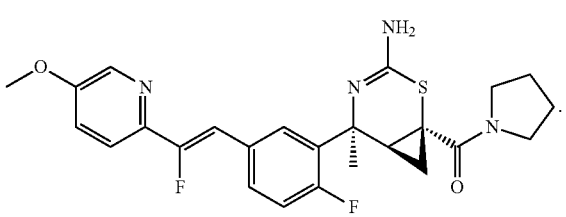 [SMILES: COc1ccc(/C(F)=C/c2ccc(F)c([C@@]3(C)N=C(N)S[C@@]4(C(=O)N5CCCC5)C[C@H]43)c2)nc1]

In a fifty-fourth embodiment, the invention provides the compound of embodiment 1, or pharmaceutically acceptable salt thereof, wherein the compound is a compound of formula

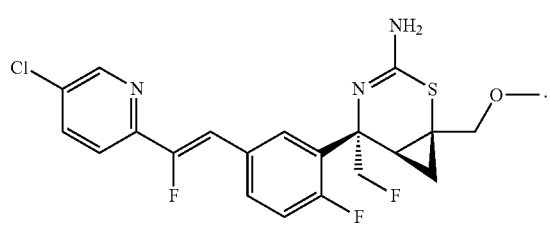 [SMILES: COC[C@]12C[C@H]1[C@@](CF)(c1cc(/C=C(\F)c3ccc(Cl)cn3)ccc1F)N=C(N)S2]

In a fifty-fifth embodiment, the invention provides the compound of embodiment 1, or pharmaceutically acceptable salt thereof, wherein the compound is a compound of formula

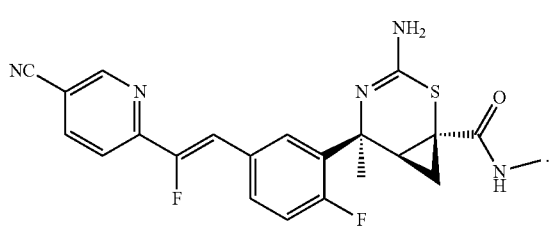 [SMILES: CNC(=O)[C@]12C[C@H]1[C@@](C)(c1cc(/C=C(\F)c3ccc(C#N)cn3)ccc1F)N=C(N)S2]

In a fifty-sixth embodiment, the invention provides the compound of embodiment 1, or pharmaceutically acceptable salt thereof, wherein the compound is a compound of formula

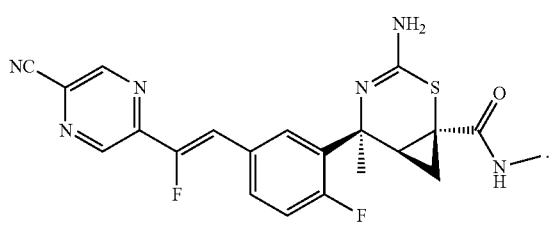 [SMILES: CNC(=O)[C@]12C[C@H]1[C@@](C)(c1cc(/C=C(\F)c3cnc(C#N)cn3)ccc1F)N=C(N)S2]

In a fifty-seventh embodiment, the invention provides the compound of embodiment 1, or pharmaceutically acceptable salt thereof, wherein the compound is a compound of formula

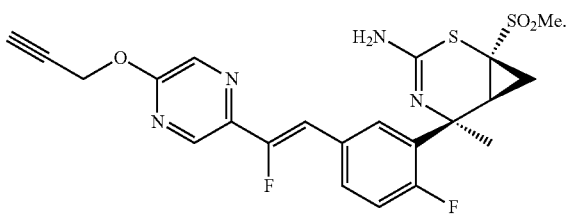 [SMILES: C#CCOc1cnc(/C(F)=C/c2ccc(F)c([C@@]3(C)N=C(N)S[C@@]4(S(C)(=O)=O)C[C@H]43)c2)cn1]

In a fifty-eighth embodiment, the invention provides the compound of embodiment 1, or pharmaceutically acceptable salt thereof, wherein the compound is a compound of formula

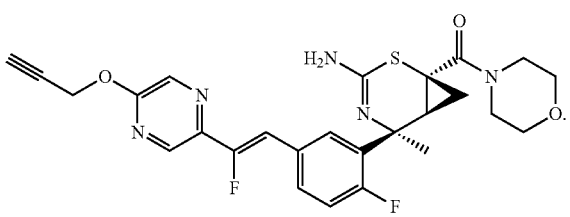 [SMILES: C#CCOc1cnc(/C(F)=C/c2ccc(F)c([C@@]3(C)N=C(N)S[C@@]4(C(=O)N5CCOCC5)C[C@H]43)c2)cn1]

In a fifty-ninth embodiment, the invention provides the compound of embodiment 1, or pharmaceutically acceptable salt thereof, wherein the compound is a compound of formula

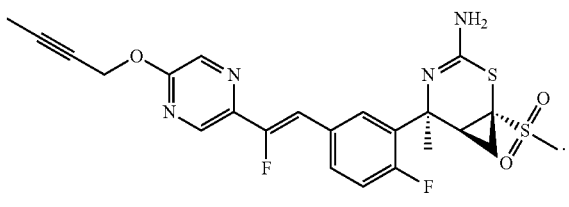 [SMILES: CC#CCOc1cnc(/C(F)=C/c2ccc(F)c([C@@]3(C)N=C(N)S[C@@]4(S(C)(=O)=O)C[C@H]43)c2)cn1 ; "."]

In a sixtieth embodiment, the invention provides the compound of embodiment 1, or pharmaceutically acceptable salt thereof, wherein the compound is a compound of formula

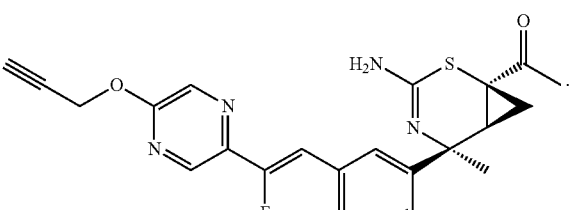

In a sixty-first embodiment, the invention provides the compound of embodiment 1, or pharmaceutically acceptable salt thereof, wherein the compound is a compound of formula

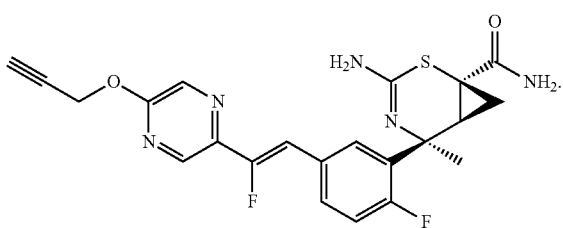 [SMILES: C#CCOc1cnc(/C(F)=C/c2ccc(F)c([C@@]3(C)N=C(N)S[C@@]4(C(N)=O)C[C@H]43)c2)cn1]

In a sixty-second embodiment, the invention provides the compound of embodiment 1, or pharmaceutically acceptable salt thereof, wherein the compound is a compound of formula

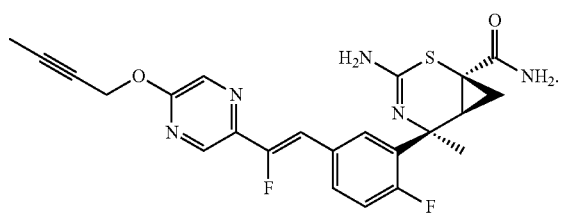 [SMILES: CC#CCOc1cnc(/C(F)=C/c2ccc(F)c([C@@]3(C)N=C(N)S[C@@]4(C(N)=O)C[C@H]43)c2)cn1]

In a sixty-third embodiment, the invention provides the compound of embodiment 1, or pharmaceutically acceptable salt thereof, wherein the compound is a compound of formula

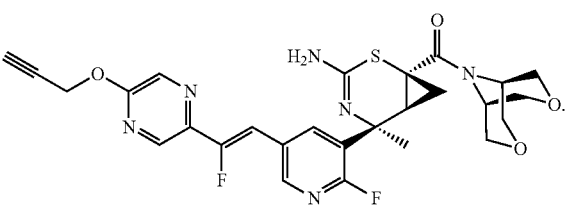 [SMILES: C#CCOc1cnc(/C(F)=C/c2cnc(F)c([C@@]3(C)N=C(N)S[C@@]4(C(=O)N5[C@H]6COC[C@H]5COC6)C[C@H]43)c2)cn1]

In a sixty-fourth embodiment, the invention provides the compound of embodiment 1, or pharmaceutically acceptable salt thereof, wherein the compound is a compound of formula

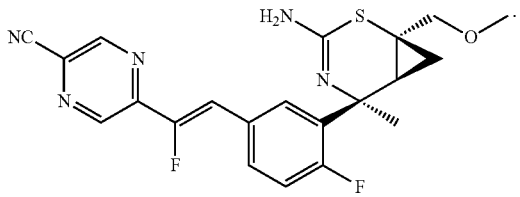 [SMILES: COC[C@]12C[C@H]1[C@@](C)(c1cc(/C=C(\F)c3cnc(C#N)cn3)ccc1F)N=C(N)S2 ; "."]

In a sixty-fifth embodiment, the invention provides the compound of embodiment 1, or pharmaceutically acceptable salt thereof, wherein the compound is a compound of formula

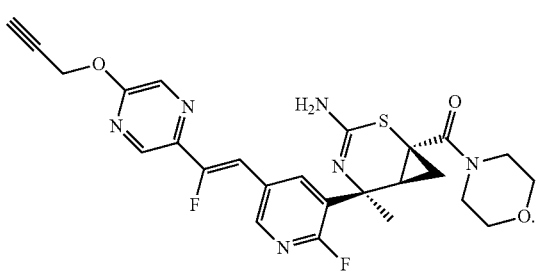 [SMILES: C#CCOc1cnc(/C(F)=C/c2cnc(F)c([C@@]3(C)N=C(N)S[C@@]4(C(=O)N5CCOCC5)C[C@H]43)c2)cn1]

In a sixty-sixth embodiment, the invention provides the compound of embodiment 1, or pharmaceutically acceptable salt thereof, wherein the compound is a compound of formula

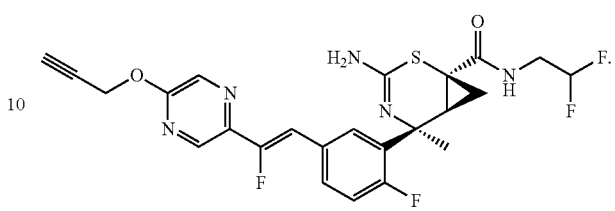

In a sixty-seventh embodiment, the invention provides the compound of embodiment 1, or pharmaceutically acceptable salt thereof, wherein the compound is a compound of formula

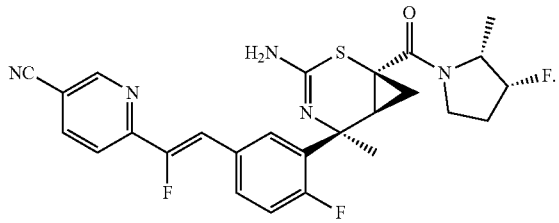 [SMILES: C[C@@H]1[C@H](F)CCN1C(=O)[C@]12C[C@H]1[C@@](C)(c1cc(/C=C(\F)c3ccc(C#N)cn3)ccc1F)N=C(N)S2]

In a sixty-eighth embodiment, the invention provides the compound of embodiment 1, or pharmaceutically acceptable salt thereof, wherein the compound is a compound of formula

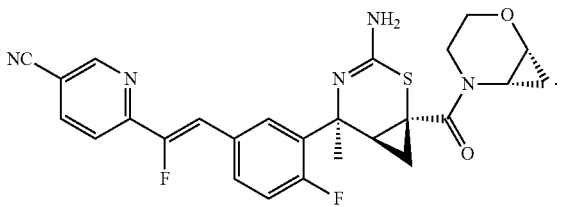 [SMILES: C[C@]1(c2cc(/C=C(\F)c3ccc(C#N)cn3)ccc2F)N=C(N)S[C@@]2(C(=O)N3CCO[C@@H]4C[C@@H]43)C[C@H]21 ; "."]

In a sixty-ninth embodiment, the invention provides a pharmaceutical composition comprising the compound according to any of embodiments 1-68 and a pharmaceutically acceptable excipient.

In a seventieth embodiment, the invention provides a compound according to any one of embodiments 1-68 or the pharmaceutical composition according to embodiment 69 for reducing beta amyloid peptide levels in the cerebral spinal fluid of a subject.

In a seventy-first embodiment, the invention provides a compound according to any one of embodiments 1-68 or the pharmaceutical composition according to embodiment 69 for treating Alzheimer's disease, cognitive impairment or a combination thereof in a subject.

In a seventy-second embodiment, the invention provides a compound according to any one of embodiments 1-68 or the pharmaceutical composition according to embodiment 69 for treating a neurological disorder selected from mild cognitive impairment, Down's syndrome, Hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease or a combination thereof in a subject.

In a seventh-third embodiment, the invention provides a compound according to any one of embodiments 1-68 or the pharmaceutical composition according to embodiment 69 for reducing formation of plaque on the brain of a subject.

In a seventy-fourth embodiment, the invention provides a use of a compound according to any one of embodiments 1-68 or the pharmaceutical composition according to embodiment 69 for reducing beta amyloid peptide levels in the cerebral spinal fluid of a subject.

In a seventy-fifth embodiment, the invention provides a use of a compound according to any one of embodiments 1-68 or the pharmaceutical composition according to embodiment 69 for treating Alzheimer's disease, cognitive impairment or a combination thereof in a subject.

In a seventh-sixth embodiment, the invention provides a use of a compound according to any one of embodiments 1-68 or the pharmaceutical composition according to embodiment 69 for the treatment of a neurological disorder selected from mild cognitive impairment, Down's syndrome, Hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease or a combination thereof in a subject.

In a seventy-eighth embodiment, the invention provides a use of a compound according to any one of embodiments 1-68 or the pharmaceutical composition according to embodiment 69 for the reduction of formation of plaque on the brain of a subject.

In a sixty-first embodiment, the invention provides a method of reducing beta amyloid peptide levels in the cerebral spinal fluid of a subject, the method comprising administering to the subject a therapeutically effective amount of a compound according to any one of embodiments 1-68 or the pharmaceutical composition according to embodiment 69.

In a seventy-ninth embodiment, the invention provides a method of treating Alzheimer's disease, cognitive impairment or a combination thereof in a subject, the method comprising administering to the subject a therapeutically effective amount of a compound according to any one of embodiments 1-68 or the pharmaceutical composition according to embodiment 69.

In a eightieth embodiment, the invention provides a method of treating a neurological disorder selected from mild cognitive impairment, Down's syndrome, Hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease or a combination thereof in a subject, the method comprising administering to the subject a therapeutically effective amount of a compound according to any one of embodiments 1-68 or the pharmaceutical composition according to embodiment 69.

In an eighty-first embodiment, the invention provides a method of reducing the formation of plaque on the brain of a subject, the method comprising administering to the subject a therapeutically effective amount of a compound according to any one of embodiments 1-68 or the pharmaceutical composition according to embodiment 69.

DEFINITIONS

The following definitions should assist in understanding the metes and bounds of the invention.

The term "comprising" is meant to be open ended, i.e., all encompassing and non-limiting. It may be used herein synonymously with "having." Comprising is intended to include each and every indicated or recited component or element(s) while not excluding any other components or elements.

The compounds of the invention may contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T). However, in certain deuterated compounds, if a structure is drawn showing D groups, then this site is enriched with respect to D. Non-limiting examples of other isotopes include $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Deuterated ($^2H$), tritiated ($^3H$), and $^{14}C$, isotopes are used in some embodiments due to their ease of preparation and detection. Further, substitution with heavier isotopes such as deuterium can afford certain therapeutic advantages resulting from greater metabolic stability, for example increased in vivo half-life or reduced dosage requirements and, hence, may be used in some embodiments. Isotopically labeled compounds of this invention can generally be prepared by substituting a readily available isotopically labeled reagent for a non-isotopically labeled reagent.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl"

and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$alkoxyl" or "—$OC_{\alpha-\beta}$alkyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy, tert-butoxy and neopentoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated. Thus, the term "aryl" embraces aromatic radicals such as phenyl, naphthyl, indenyl, tetrahydronaphthyl, anthracenyl, indanyl, and the like.

The term "$C_{\alpha-\beta}$-cycloalkyl", also referred to herein as "carbocyclic", when used alone or in combination, denotes a partially or fully saturated ring radical having a number of carbon atoms in the range from $\alpha$ and $\beta$. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substituents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, aza-quinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner or in bicyclic systems such as 2-oxa-5-azabicyclo[2.2.1]heptanyl or 6-azabicyclo[3.2.1]octanyl, formed from carbon atoms and including one or more heteroatoms selected from N, O or S. The Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydroisoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 6-azabicyclo[3.2.1]octanyl, 2-oxa-5-azabicyclo[2.2.1]heptanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. In some embodiments, alkylamino radicals are "lower alkylamino" radicals having one to six carbon atoms. In still other embodiments, lower alkylamino radicals have one to three carbon atoms. Examples of such lower alkylamino radicals include N-methylamino, and N-ethylamino, N-propylamino, N-isopropylamino and the like.

The term "dialkylamino" includes "N, N-dialkylamino" where amino radicals are independently substituted with two alkyl radicals. In some embodiments, alkylamino radicals are "lower alkylamino" radicals having one to six carbon atoms. In yet other embodiments, lower alkylamino radicals have one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "Formula I" includes any sub formulas, such as Formulas IA, IB, IC, ID, and IE.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, and in some embodiments greater than about 90% by weight of one stereoisomer of the compound and less than about 10% by weight of the other stereoisomers of the compound. In still other embodiments a stereomerically pure compound comprises greater than about 95% by weight of one stereoisomer of the compound and less than about 5% by weight of the other stereoisomers of the compound, and in other embodiments greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

The present invention also includes tautomeric forms of compounds of the invention. For example, the invention comprises compounds of Formula I as well as their tautomers, as shown:

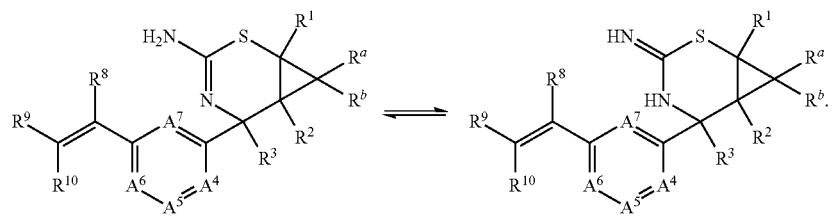

Similarly, tautomers of any of the compounds are also included in the invention.

The term "pharmaceutically-acceptable" when used with reference to a compound of any of the embodiments is intended to refer to a form of the compound that is safe for administration.

Included in the compounds of any of the embodiments unless specified to the contrary are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of the compounds may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, 3-hydroxybutyric, salicylic, galactaric and galacturonic acid. Suitable pharmaceutically-acceptable base addition salts of compounds of Formulas I, IA, IB, IC, ID, and IE include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I, IA, IB, IC, ID, and IE.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The compound(s) of any of the embodiments may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether, reducing the severity of symptoms, delaying the onset of symptoms, or delaying the onset of a pre-clinically evident stage of disorders in individuals.

The phrase "therapeutically effective amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. Thus, "therapeutically effective amount" is not limited to a single capsule or tablet, but may include more than one capsule or tablet, which is the dose prescribed by a qualified physician or medical care giver to the subject.

General Synthetic Procedures

The present invention further comprises procedures for the preparation of compounds of the various embodiments. The compounds of the invention can be synthesized according to the procedures described in the following Schemes and procedures. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:

ACN, MeCN—acetonitrile
AcOH—acetic acid
AIBN—azobisisobutyronitrile
AmPhos/PdAmPhos—Bis(di-tert-butyl(4-dimethyl aminophenyl)phosphine) dichloropalladium(II)
Aq., aq.—aqueous
Boc—tert-butoxycarbonyl
BOP—benzotriazol-1-yl-oxy Hexafluorophosphate
(Bpin)$_2$—(Bispinacolato)diboron
BuLi—Butyllithium
CDI—Carbonyldiimidazole
COMU (1-cyano-2-ethoxy-2-oxoethylidenaminooxy) dimethylaminomorpholinocarbenium hexafluorophosphate
Cs$_2$CO$_3$—cesium carbonate
DAST—diethylaminosulfur trifluoride
DCC—dicyclohexylcarbodiimide
DCM—dichloromethane, methylene chloride
DEA—diethylamine
DEAD—diethylazodicarboxylate
Deoxofluor—bis(2-methoxyethyl)aminosulfur trifluoride
DIC—1,3-diisopropylcarbodiimide
DIEA, DIPEA—diisopropylethylamine
DMA N,N-dimethylacetamide
DME—dimethoxyethane
DMF—dimethylformamide
DMAP—4-dimethylaminopyridine
DMSO—dimethylsulfoxide
Dppf—(1,1-bisdiphenylphosphinoferrocene)

EDC, EDCI—1-(3-dimethylaminopropyl)-3-ethylcarbodiimide
Et$_2$O—diethyl ether
EtOAc—ethyl acetate
EtOH—ethanol
g, gm—gram
Ghosez's rgt—1-Chloro-N,N,2-trimethylpropenylamine
h, hr—hour
HATU—O-(7-azabenzotriazol-1-yl)-N,N,N',N'-tetramethyluroniumhexafluorophosphate
HOBt—1-hydroxybenzotriazole hydrate
HOAc—acetic acid
HPLC—high pressure liquid chromatography
IPA, iPrOH—isopropyl alcohol
KOAc—potassium acetate
KOtBu—potassium tert-butoxide
LG—leaving group
LDA—Lithium diisopropylamide
LiBH$_4$—Lithium borohydride
LiHMDS—Lithium bis(trimethylsilyl)amide
mCPBA 3-chloroperbenzoic acid
MS—mass spectrum
MeOH—methanol
MeNH$_2$—methylamine
Me$_2$NH—dimethylamine
Me$_3$SOI—trimethylsulfoxonium iodide
MeI—iodomethane
MsCl—methanesulfonyl chloride
NaBH$_4$—sodium borohydride
Na$_2$CO$_3$—sodium carbonate
NaHCO$_3$—sodium bicarbonate
NaIO$_4$—sodium periodate
NaOH—sodium hydroxide
NFSI—N-fluorobenzenesulfonimide
NMO—N-methylmorpholine N-oxide
OsO$_4$—Osmium tetroxide
P(t-Bu)$_3$—tri(tert-butyl)phosphine
Ph$_3$P—triphenylphosphine
Pd/C—palladium on carbon
Pd(PPh$_3$)$_4$—palladium(0)triphenylphosphine tetrakis
Pd(dppf)Cl$_2$—palladium(1,1-bisdiphenylphosphinoferrocene) II chloride
Pd(PhCN)$_2$Cl$_2$—palladium di-cyanophenyl dichloride
Pd(OAc)$_2$—palladium acetate
Pd$_2$(dba)$_3$—tris(dibenzylideneacetone) dipalladium
PTSA/TsOH—4-toluenesulfonic acid
PyBop—benzotriazol-1-yl-oxy-tripyrrolidino-phosphonium hexafluorophosphate
RT, r.t.—room temperature
RBF, rbf—round bottom flask
SEM—2-(Trimethylsilyl)ethoxymethyl
SEMCl—2-(Trimethylsilyl)ethoxymethyl chloride
SnBu$_3$—Tributyltin
SFC—Supercritical fluid chromatography
SOCl$_2$—thionyl chloride
S-Phos—2-Dicyclohexylphosphino-2',6'-dimethoxybiphenyl
Tf$_2$O—triflic anhydride
T$_3$P/T3P—Propylphosphonic anhydride
TLC, tlc—thin layer chromatography
TBAF—Tetrabutylammonium fluoride
TBTU—O-benzotriazol-1-yl-N,N,N,N'-tetramethyluronium tetrafluoroborate
TEA, Et$_3$N—triethylamine
Ti(OEt)$_4$—titanium tetraethoxide
TMS—trimethylsilyl
TFA—trifluoroacetic acid
TFAA—trifluoroacetic anhydride
THF—tetrahydrofuran
TsCl—4-toluenesulfonyl chloride
UV—ultraviolet light
X-Phos—2-Dicyclohexylphosphino-2',4',6'-triisopropylbiphenyl

GENERAL SYNTHETIC SCHEMES AND EXAMPLES

The general synthetic schemes, starting materials, synthetic intermediates and compounds (examples) representative of the invention, i.e., compounds of Formulas I, IA, IB, IC, ID, and IE, should assist in a better understanding and appreciation of the scope of the present invention and of the various methods which may be used to synthesize compounds of Formulas IA, IB, IC, ID, and IE. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through either a Biotage or Isco brand silica gel column (pre-packed or individually packed with SiO$_2$) and eluting the product off the column with a solvent gradient as indicated. For example a description of (330 g SiO$_2$, 0-40% EtOAc/Hexane) means the product was obtained by elution from the column packed with 330 gms of silica, with a solvent gradient of 0% to 40% EtOAc in Hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 mL/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all 1H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 11.0 software, available in Chem Office, or (2) by the ISIS database software (Advanced Chemistry Design Labs or ACD software).

71

Preparation of (1S,5S,6S)-methyl 3-((tert-butoxycarbonyl)((2-(trimethylsilyl)ethoxy)methyl)amino)-5-(2-fluoro-5-formylphenyl)-5-methyl-2-thia-4-azabicyclo[4.1.0]hept-3-ene-1-carboxylate (Intermediate 1)

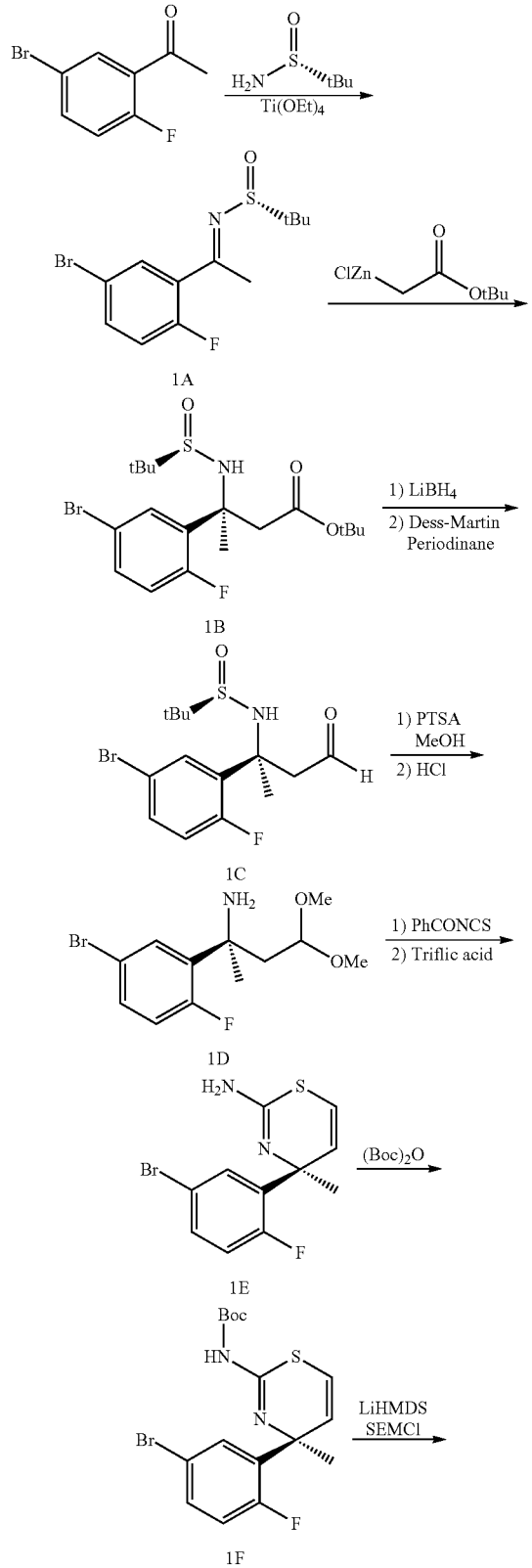

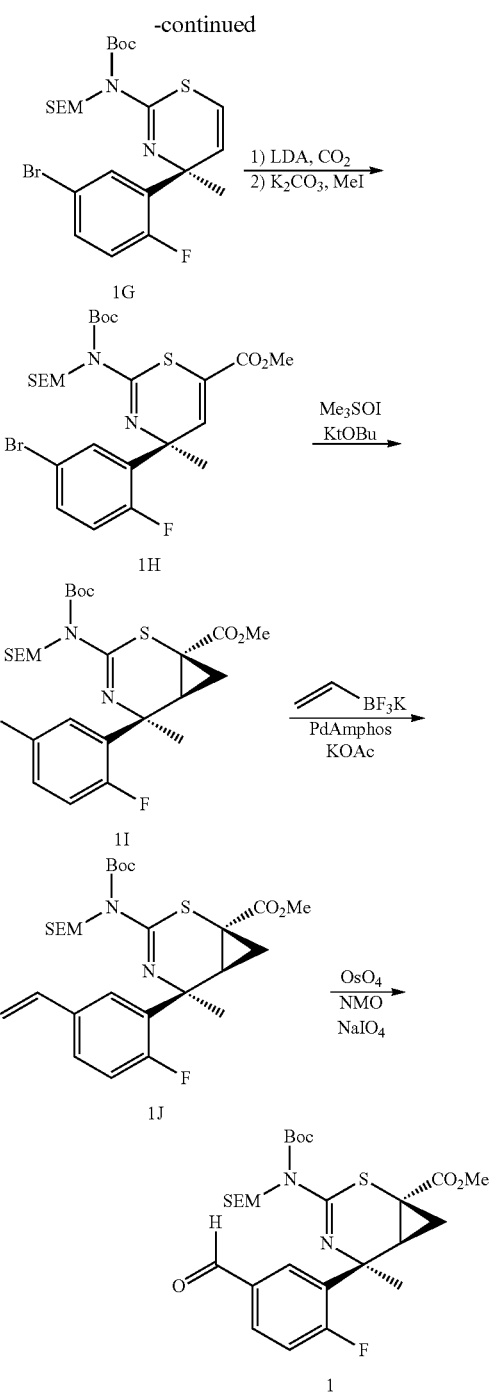

Preparation of (R,E)-N-(1-(5-bromo-2-fluorophenyl)ethylidene)-2-methylpropane-2-sulfinamide (1A)

Titanium (iv) ethoxide (227 mL, 1100 mmol) was added to 1-(5-bromo-2-fluorophenyl)-1-ethanone (95 g, 440 mmol), (R)-(+)-2-methyl-2-propanesulfinamide (106 g, 877 mmol) in 2-methyltetrahydrofuran (800 mL) at room temperature. The reaction was heated to 70° C. for 14 hours. The reaction was allowed to cool and was concentrated in vacuo to half the volume and then diluted with 200 mL of EtOAc. The resulting solution was slowly poured into an Erlenmeyer flask with water (~3 L) with vigorous stirring. After the addition, the mixture was filtered through a pad of Celite® filter aid and the filter cake was washed with EtOAc. The layers were separated and the aqueous layer was extracted with EtOAc. The combined organic extracts were washed with water, saturated aqueous sodium chloride, and dried over sodium sulfate. The solution was filtered and concentrated in vacuo to give the material as an orange solid residue. The residue was purified by dissolving in DCM and filtering through a pad of silica gel by eluting with 1:9 EtOAc in hexane, to provide (R,E)-N-(1-(5-bromo-2-fluorophenyl)ethylidene)-2-methylpropane-2-sulfinamide (1A) (136 g, 425 mmol, 97% yield) as an orange solid. MS m/z=320/322 [M+H]$^+$. $^1$H NMR (400 MHz, CDCl$_3$) δ 7.77 (d, J=4.50 Hz, 1H), 7.53 (td, J=3.79, 7.48 Hz, 1H), 7.02 (dd, J=8.90, 10.47 Hz, 1H), 2.76 (d, J=3.13 Hz, 3H), 1.33 (s, 9H).

Preparation of (S)-tert-butyl 3-(5-bromo-2-fluorophenyl)-3-((R)-1,1-dimethylethylsulfinamido)butanoate (1B)

(R,E)-N-(1-(5-Bromo-2-fluorophenyl)ethylidene)-2-methylpropane-2-sulfinamide (1A) (5.00 g, 15.6 mmol) was taken up in 75 mL of THF and chilled to 0° C. 2-tert-Butoxy-2-oxoethylzinc chloride 0.5M in diethyl ether (78 mL, 39 mmol) was added to the mixture dropwise via addition funnel over ~30 minutes. After 30 minutes of additional stirring, the reaction was quenched by slow addition of 100 mL of aq. NH$_4$Cl. The mixture was diluted with 100 mL of water and extracted twice with 100 mL of EtOAc. The combined organic extracts were washed with 100 mL of brine and dried over MgSO$_4$. Filtration and concentration under reduced pressure, followed by flash chromatography on silica gel (80 g Grace column, elute with 5% to 50% EtOAc/heptane gradient) afforded (S)-tert-butyl 3-(5-bromo-2-fluorophenyl)-3-((R)-1,1-dimethylethylsulfinamido)butanoate (1B) (6.6 g, 96% yield) as a yellow oil. MS m/z=436/438 [M+H]$^+$. $^1$H NMR (400 MHz, CDCl$_3$) δ 7.63 (dd, J=2.54, 7.24 Hz, 1H), 7.36 (ddd, J=2.54, 4.11, 8.61 Hz, 1H), 6.91 (dd, J=8.71, 11.84 Hz, 1H), 5.43 (s, 1H), 3.21 (dd, J=1.37, 15.85 Hz, 1H), 3.02 (dd, J=1.56, 15.85 Hz, 1H), 1.82 (s, 3H), 1.31 (s, 18H).

Preparation of (R)—N—((S)-2-(5-bromo-2-fluorophenyl)-4-oxobutan-2-yl)-2-methylpropane-2-sulfinamide (1C)

A 3-neck 3 L round bottom flask was charged with a solution of (S)-tert-butyl 3-(5-bromo-2-fluorophenyl)-3-((R)-1,1-dimethylethylsulfinamido)butanoate (1B) (64.9 g, 149 mmol) in THF (400 mL). The flask was equipped with an overhead stirrer, a 250 mL addition funnel, and a Y-Joint equipped with a thermocouple temperature probe (JKem) and a septum. The addition funnel was charged with LiBH$_4$, 2.0M in THF (186 mL, 372 mmol) via cannula. The LiBH$_4$ was added to the stirring solution at room temperature. The addition funnel was removed and replaced with a 125 mL addition funnel charged with MeOH (30.1 mL, 744 mmol). The rubber septum on the Y-joint was removed to allow for proper ventilation during the reaction. The MeOH was added dropwise to the stirring solution at room temperature via addition funnel. Evolution of gas was observed. The internal temperature of the reaction rose to 47.5° C. over the course of the reaction and then began to subside. Upon reaching an internal temperature of 26° C., a 250 mL addition funnel was attached to the reaction flask and charged with an additional portion of LiBH$_4$, 2.0M in THF (186 mL, 372 mmol) via cannula. The LiBH$_4$ was added to the reaction. The addition funnel was removed and replaced with a 125 mL addition funnel charged with MeOH (30.1 mL, 744 mmol). The MeOH was added dropwise to the stirring solution. Evolution of gas was observed and the internal temperature increased to 35° C. and then subsided. The flask was placed in an ice/water bath and carefully quenched with saturated aq. NH$_4$Cl. The reaction was diluted with water and EtOAc and stirred for 18 h. The solids were filtered off and washed with EtOAc. The filtrate was transferred to a separatory funnel. The organic layer was separated, washed with brine, dried over MgSO$_4$ and concentrated under reduced pressure to afford (R)—N—((S)-2-(5-bromo-2-fluorophenyl)-4-hydroxybutan-2-yl)-2-methylpropane-2-sulfinamide (50.9 g, 93% yield) as a white solid.

(R)—N—((S)-2-(5-bromo-2-fluorophenyl)-4-hydroxybutan-2-yl)-2-methylpropane-2-sulfinamide (5.5 g, 15 mmol) was taken up in 100 mL of DCM. Dess-Martin periodinane (6.37 g, 15.0 mmol) was added. After 30 minutes, the reaction was quenched with 50 mL of aq. Na$_2$S$_2$O$_3$ and 50 mL of aq. NaHCO$_3$. The mixture was stirred for 10 min, them partitioned. The aqueous portion was extracted with 100 mL of DCM and the combined organic extracts were dried over MgSO$_4$. Filtration and concentration under reduced pressure, followed by flash chromatography on silica gel (80 g Grace column, elute with 10% to 60% EtOAc/hexanes gradient) afforded (R)—N—((S)-2-(5-bromo-2-fluorophenyl)-4-oxobutan-2-yl)-2-methylpropane-2-sulfinamide (1C) (3.3 g, 60% yield) as a clear oil. MS m/z=364/366 [M+H]$^+$. $^1$H NMR (400 MHz, CDCl$_3$) δ 9.56-9.82 (m, 1H), 7.63 (dd, J=2.45, 7.34 Hz, 1H), 7.37 (ddd, J=2.54, 4.21, 8.71 Hz, 1H), 6.91 (dd, J=8.61, 12.13 Hz, 1H), 4.87 (s, 1H), 3.61 (d, J=18.78 Hz, 1H), 3.28-3.43 (m, 1H), 1.78 (s, 3H), 1.29 (s, 9H).

Preparation of (S)-2-(5-bromo-2-fluorophenyl)-4,4-dimethoxybutan-2-amine (1D)

(R)—N—((S)-2-(5-bromo-2-fluorophenyl)-4-oxobutan-2-yl)-2-methylpropane-2-sulfinamide (1C) (3.3 g, 9.1 mmol) was taken up in 50 mL of MeOH. p-Toluenesulfonic acid monohydrate (0.086 g, 0.45 mmol) was added, and the mixture was heated to 75° C. After 30 minutes, the mixture was cooled to room temperature and hydrogen chloride, 4M in 1,4-dioxane (3.40 mL, 13.6 mmol) was added. After 1 h, the solvent was removed under reduced pressure. The residue was partitioned between 50 mL of 9:1 chloroform:IPA and 50 mL of aq. NaHCO$_3$. The aqueous portion was extracted with 50 mL of 9:1 chloroform:IPA. The combined organic extracts were dried over MgSO$_4$. Filtration and concentration under reduced pressure afforded (S)-2-(5-bromo-2-fluorophenyl)-4,4-dimethoxybutan-2-amine (1D) (2.7 g, 97% yield) as a yellow oil. The product was carried on without additional purification.

Preparation of (S)-4-(5-bromo-2-fluorophenyl)-4-methyl-4H-1,3-thiazin-2-amine (1E)

(S)-2-(5-Bromo-2-fluorophenyl)-4,4-dimethoxybutan-2-amine (1D) (2.7 g, 8.8 mmol) was taken up in 50 mL of acetone. Benzoyl isothiocyanate (1.2 mL, 8.8 mmol) was added. After 30 minutes, the solvent was removed under reduced pressure. The residue was taken up in sulfuric acid (7.0 mL, 130 mmol) and heated to 50° C. for 18 hours. The mixture was cooled to room temperature and poured into a 500 mL Erlenmeyer flash ~½ full of ice. The mixture was basified with 10N aq. NaOH and the resulting mixture was extracted twice with 150 mL of DCM. The combined organic extracts were dried over MgSO$_4$. Filtration and concentration under reduced pressure, followed by flash chromatography on silica gel (40 g Grace column, elute with 5% to 60% EtOAc/heptane gradient) afforded (S)-4-(5-bromo-2-fluorophenyl)-4-methyl-4H-1,3-thiazin-2-amine (1.5 g, 51% yield) as a brown oil. MS m/z=299/301 [M+H]$^+$. $^1$H NMR (400 MHz, CDCl$_3$) δ 7.54-7.65 (m, 1H), 7.32 (ddd, J=2.64, 4.25, 8.56 Hz, 1H), 6.91 (dd, J=8.61, 11.15 Hz, 1H), 6.20-6.36 (m, 2H), 1.65-1.72 (m, 3H).

Preparation of (S)-tert-butyl (4-(5-bromo-2-fluorophenyl)-4-methyl-4H-1,3-thiazin-2-yl)carbamate (1F)

Di-tert-butyl dicarbonate (16.45 mL, 71.6 mmol) was added to a stirred solution of (S)-4-(5-bromo-2-fluorophenyl)-4-methyl-4H-1,3-thiazin-2-amine (1E) (17.2 g, 57.3 mmol) in THF (200 mL) in a 3-neck flask equipped with an internal thermometer. The reaction mixture was heated to 50° C. and stirred for 17 hrs. The reaction mixture was cooled to room temperature and concentrated. The resulting residue was purified via silica gel flash column chromatography eluting with 0 to 40% EtOAc in heptane to yield (S)-tert-butyl (4-(5-bromo-2-fluorophenyl)-4-methyl-4H-1,3-thiazin-2-yl)carbamate (1F) (21.9 g, 95% yield) as a yellow oil. MS m/z=401/403 [M+H]$^+$. $^1$H NMR (400 MHz, CDCl$_3$) δ 7.45-7.61 (m, 1H), 7.33-7.41 (m, 1H), 6.95 (dd, J=8.71, 11.25 Hz, 1H), 6.26 (d, J=9.59 Hz, 1H), 6.13 (dd, J=2.74, 9.59 Hz, 1H), 1.72 (br. s., 3H), 1.53 (s, 9H).

Preparation of (S)-tert-butyl (4-(5-bromo-2-fluorophenyl)-4-methyl-4H-1,3-thiazin-2-yl)((2-(trimethylsilyl)ethoxy)methyl)carbamate (1G)

(S)-tert-Butyl (4-(5-bromo-2-fluorophenyl)-4-methyl-4H-1,3-thiazin-2-yl)carbamate (21.9 g, 54.5 mmol) and THF (200 mL) were added to a 3-neck flask with internal thermometer. The mixture was cooled to −10° C. before lithium bis(trimethylsilyl)amide (1.0M solution in THF (59.9 mL, 59.9 mmol)) was added slowly over 15 min via cannula (internal temperature never exceeded −8° C.). The mixture was stirred at −10° C. for 20 minutes before 2-(trimethylsilyl)ethoxymethyl chloride (10.6 mL, 59.9 mmol) in THF (10 mL) was added slowly via syringe over 5 min (internal temperature never exceeded −8° C.). The reaction mixture was stirred at −10° C. for another 5 minutes before being allowed to warm to room temperature over the course of 1 hour. The reaction mixture was stirred for another 1.5 hours. The reaction mixture was quenched with saturated NH$_4$Cl and extracted with EtOAc. The organic layer was separated, washed with brine, dried over MgSO$_4$, filtered, and concentrated. The resulting residue was purified via silica gel flash column chromatography eluting with 0 to 20% EtOAc in heptane to yield (S)-tert-butyl (4-(5-bromo-2-fluorophenyl)-4-methyl-4H-1,3-thiazin-2-yl)((2-(trimethylsilyl)ethoxy)methyl)carbamate (1G) (25.4 g, 88% yield) as a yellow oil. MS m/z=531/533 [M+H]$^+$. $^1$H NMR (400 MHz, CDCl$_3$) δ 7.73 (dd, J=2.54, 7.04 Hz, 1H), 7.31-7.39 (m, 1H), 6.86-7.03 (m, 1H), 6.30 (s, 1H), 6.05 (dd, J=3.52, 9.39 Hz, 1H), 5.28-5.36 (m, 1H), 5.15-5.25 (m, 1H), 3.64-3.77 (m, 2H), 1.68 (d, J=0.98 Hz, 3H), 1.54 (s, 9H), 0.94-1.01 (m, 2H), 0.00 (s, 9H).

Preparation of (S)-methyl 4-(5-bromo-2-fluorophenyl)-2-((tert-butoxycarbonyl)((2-(trimethylsilyl)ethoxy)methyl)amino)-4-methyl-4H-1,3-thiazine-6-carboxylate (1H)

To a stirring solution of (S)-tert-butyl (4-(5-bromo-2-fluorophenyl)-4-methyl-4H-1,3-thiazin-2-yl)((2-(trimethylsilyl)ethoxy)methyl)carbamate (1G) (15.0 g, 28.2 mmol) in THF (100 mL) at −78° C. was added lithium diisopropylamide (14.1 mL of 2M in THF, 28.2 mmol) at a rate that the reaction temperature did not exceed −65° C. The light orange solution was stirred for 20 min at −78° C. The reaction was then exposed to carbon dioxide (g), first as a stream above the level of the solvent for 2 min, followed by the gas bubbled through the solvent for 2 min. The reaction was then slowly quenched with saturated NH$_4$Cl (25 mL). Once the suspension reached r.t., both EtOAc (200 mL) and water (25 mL) were added. The organic layer was separated and the aqueous layer was extracted with EtOAc (1×). The combined organic extracts were then dried over MgSO$_4$ and concentrated under reduced pressure to afford (S)-4-(5-bromo-2-fluorophenyl)-2-((tert-butoxycarbonyl)((2-(trimethylsilyl)ethoxy)methyl)amino)-4-methyl-4H-1,3-thiazine-6-carboxylic acid as a thick oil. MS m/z=575/577 [M+H]$^+$.

The resulting thick oil was dissolved in DMF (100 mL) and treated with potassium carbonate (7.8 g, 56 mmol) followed by iodomethane (3.5 mL, 56 mmol) at room temperature. The mixture was then stirred for 3 d at rt. The reaction mixture was diluted with 100 mL of EtOAc, and then water (50 mL) was added. The resulting biphasic mixture was separated and the aqueous layer was extracted with EtOAc (1×). The combined extracts were washed with water (2×), dried (MgSO$_4$), filtered, and concentrated in vacuo to give an oil. The oil thus obtained was loaded on a silica gel column and eluted with a gradient of 0-10% EtOAc in hexanes to afford (S)-methyl 4-(5-bromo-2-fluorophenyl)-2-((tert-butoxycarbonyl)((2-(trimethylsilyl)ethoxy)methyl)amino)-4-methyl-4H-1,3-thiazine-6-carboxylate (1H) (15 g, 46% yield) as a yellow viscous oil. MS m/z=589/591 [M+H]$^+$. $^1$H NMR (CDCl$_3$) δ: 7.73 (dd, J=7.0, 2.5 Hz, 1H), 7.39 (ddd, J=8.7, 4.3, 2.5 Hz, 1H), 7.11 (d, J=3.1 Hz, 1H), 6.97 (dd, J=11.3, 8.6 Hz, 1H), 5.34 (d, J=10.4 Hz, 1H), 5.21 (d, J=10.4 Hz, 1H), 3.83 (s, 3H), 3.58-3.73 (m, 2H), 1.71 (s, 3H), 1.56 (s, 9H), 0.87-1.08 (m, 2H), 0.00 (s, 9H).

Preparation of (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (1I)

Corey-Chaykovsky Reagent [~0.25M in DMSO]: To a stirring solution of trimethylsulfoxonium iodide (12.46 g, 56.60 mmol) in DMSO (200 mL) at r.t. was added potassium tert-butoxide (6.35 g, 56.6 mmol) in one portion. The solution was stirred for 1 hour and then used in the reaction outlined below.

To a stirring solution of (S)-methyl 4-(5-bromo-2-fluorophenyl)-2-((tert-butoxycarbonyl)((2-(trimethylsilyl)ethoxy)methyl)amino)-4-methyl-4H-1,3-thiazine-6-carboxylate (1H, 26.7 g, 45.3 mmol) in THF (200 mL) at r.t. was added freshly prepared Corey-Chaykovsky Reagent (56.60 mmol) via a syringe dropwise. The reaction mixture was stirred at room temperature for 1 hour and then quenched with sat. NH$_4$Cl (300 mL) dropwise (exothermic!). The mixture was extracted with of EtOAc (2×300 mL). The combined organic extracts were then washed with water (2×30 mL) followed by brine (30 mL), dried over MgSO$_4$, and concentrated under reduced pressure. The resulting oil was purified by silica gel chromatography (0-20% EtOAc in hexanes) to give compound 11 (24.0 g, 88% yield) as a light yellow oil. MS m/z=603/605 [M+H]$^+$. $^1$H NMR (300 MHz, CDCl$_3$) δ 7.77 (dd, J=2.63, 7.02 Hz, 1H), 7.35 (ddd, J=2.63, 4.24, 8.62 Hz, 1H), 6.95 (dd, J=8.62, 11.55 Hz, 1H), 5.25 (d, J=10.52 Hz, 1H), 5.00 (d, J=10.52 Hz, 1H), 3.78 (s, 3H), 3.61-3.72

(m, 2H), 2.63 (ddd, J=1.39, 7.86, 9.61 Hz, 1H), 1.72 (d, J=1.17 Hz, 3H), 1.51 (s, 9H), 1.46 (dd, J=5.19, 9.87 Hz, 1H), 1.17 (dd, J=5.33, 7.53 Hz, 1H), 0.88-1.03 (m, 2H), 0.00 (s, 9H).

Preparation of (1S,5S,6S)-methyl 3-((tert-butoxycarbonyl)((2-(trimethylsilyl)ethoxy)methyl)amino)-5-(2-fluoro-5-vinylphenyl)-5-methyl-2-thia-4-azabicyclo[4.1.0]hept-3-ene-1-carboxylate (1J)

Potassium acetate (11.7 g, 120 mmol), 1,1-bis[di-t-butyl-p-methylaminophenyl]palladium(ii) chloride (1.41 g, 1.99 mmol), potassium vinyltrifluoroborate (6.94 g, 51.8 mmol) and (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (1I) (24.0 g, 39.8 mmol) were charged into a 500 mL RBF. The mixture was placed under nitrogen atmosphere and then MeCN (150 mL) and water (50 mL) were added. The mixture was heated to 75° C. for 2.5 h and then cooled to room temperature. EtOAc (200 mL) was added, and the mixture was washed with saturated NaHCO$_3$ (50 mL), brine (50 mL), dried over MgSO$_4$ and concentrated under reduced pressure. The residue was purified by flash chromatography on silica gel using EtOAc in heptane (5% to 30%) as eluent to give (1S,5S,6S)-methyl 3-((tert-butoxycarbonyl)((2-(trimethylsilyl)ethoxy)methyl)amino)-5-(2-fluoro-5-vinylphenyl)-5-methyl-2-thia-4-azabicyclo[4.1.0]hept-3-ene-1-carboxylate (1J) (16.7 g, 76% yield) as yellow oil. MS m/z=551 [M+H]$^+$.

Preparation of (1S,5S,6S)-methyl 3-((tert-butoxycarbonyl)((2-(trimethylsilyl)ethoxy)methyl)amino)-5-(2-fluoro-5-formylphenyl)-5-methyl-2-thia-4-azabicyclo[4.1.0]hept-3-ene-1-carboxylate (1)

To a mixture of (1S,5S,6S)-methyl 3-((tert-butoxycarbonyl)((2-(trimethylsilyl)ethoxy)methyl)amino)-5-(2-fluoro-5-vinylphenyl)-5-methyl-2-thia-4-azabicyclo[4.1.0]hept-3-ene-1-carboxylate (1J) (16.7 g, 30.3 mmol) in THF (120 mL) and water (80 mL) was added 4-methylmorpholine-4-oxide (5.33 g, 45.5 mmol) followed by osmium tetroxide (2.5 wt. %, solution in 2-methyl-2-propanol (3.22 mL, 0.303 mmol)). The mixture was stirred for 4 h before sodium (meta)periodate (19.5 mL, 91.0 mmol) was added resulting in a slurry and exotherm (mild). After 30 minutes, the mixture was diluted with EtOAc (250 mL). The organic layer was washed with saturated Na$_2$S$_2$O$_3$ (5×30 mL), brine (20 mL), dried over Na$_2$SO$_4$, and concentrated. The resulting oil was purified by silica gel chromatography (10 to 50% EtOAc/hexane gradient) to afford (1S,5S,6S)-methyl 3-((tert-butoxycarbonyl)((2-(trimethylsilyl)ethoxy)methyl)amino)-5-(2-fluoro-5-formylphenyl)-5-methyl-2-thia-4-azabicyclo[4.1.0]hept-3-ene-1-carboxylate (1) (15.0 g, 90% yield) as a light yellow glass. MS m/z=553 [M+H]$^+$. $^1$H NMR (400 MHz, CDCl$_3$) δ 9.83-10.06 (m, 1H), 8.24 (dd, J=2.05, 7.73 Hz, 1H), 7.86 (ddd, J=2.15, 4.84, 8.26 Hz, 1H), 7.20-7.27 (m, 1H), 5.33 (d, J=10.56 Hz, 1H), 5.29-5.42 (m, 1H), 5.07 (d, J=10.56 Hz, 1H), 3.81 (s, 3H), 3.62-3.73 (m, 2H), 2.67 (t, J=8.71 Hz, 1H), 1.79 (s, 3H), 1.54 (s, 9H), 1.49 (dd, J=5.18, 9.88 Hz, 1H), 1.22 (dd, J=5.28, 7.43 Hz, 1H), 0.87-1.00 (m, 2H), 0.01 (s, 9H).

Preparation of tert-butyl ((1S,5S,6S)-5-(2-fluoro-5-formylphenyl)-5-(fluoromethyl)-1-(methoxymethyl)-2-thia-4-azabicyclo[4.1.0]hept-3-en-3-yl)((2-(trimethylsilyl)ethoxy)methyl)carbamate (Intermediate 2)

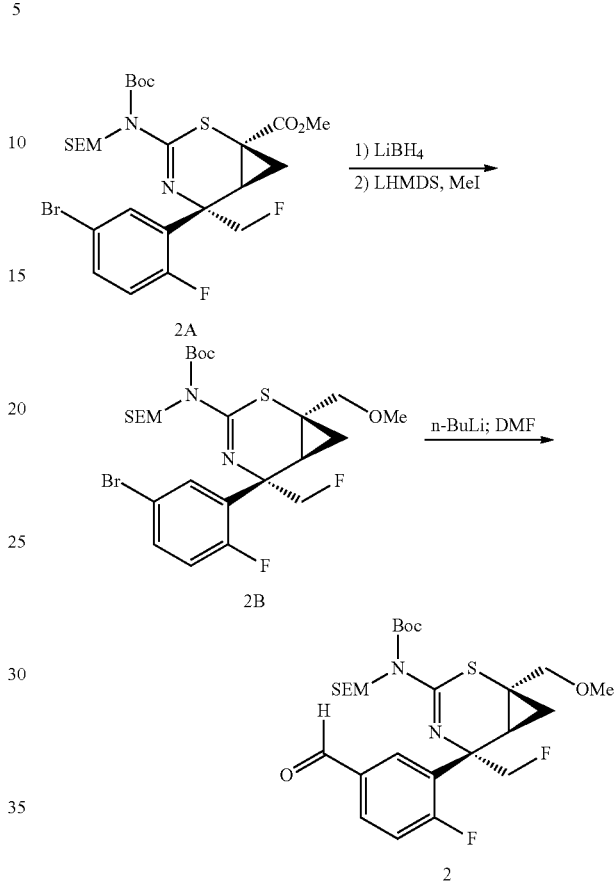

Preparation of (1S,5S,6S)-methyl 5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-ene-1-carboxylate (2A)

This compound was prepared using the chemical procedures similar to that described for intermediate 1I.

Preparation of tert-butyl ((1S,5S,6S)-5-(5-bromo-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (2B)

MeOH (0.78 mL, 19 mmol) was added to a solution of (1S,5S,6S)-methyl 5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-ene-1-carboxylate (2A) (1.5 g, 2.4 mmol) and LiBH$_4$ (2M in THF) (2.41 mL, 4.82 mmol) in THF (15 mL) at room temperature, and the mixture was stirred for 2 hours. Saturated aqueous ammonium chloride solution was added and the product was extracted into EtOAc (3×). The combined extracts were dried over anhydrous MgSO$_4$, filtered, and concentrated in vacuo to give an oil. The oil was dissolved in THF (6 mL) and LHMDS (1.0M solution in THF, 3.6 mL, 3.6 mmol) was added. The mixture was stirred for 30 minutes and then iodomethane (0.23 mL, 3.6 mmol) was added dropwise. The mixture was stirred for 20 hours, then saturated aqueous ammonium chloride solution was added. The product was extracted into EtOAc (3×). The combined organic layers were dried over anhydrous MgSO₄, filtered, and concentrated in vacuo to give an oil. The oil was purified by silica gel chromatography (0 to 40% EtOAc/heptane gradient) to give tert-butyl ((1S,5S,6S)-5-(5-bromo-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (2B) (0.98 g, 67% yield) as a colorless oil. MS m/z=607 [M+H]⁺. ¹H NMR (400 MHz, CDCl₃) δ ppm 7.83 (d, J=6.46 Hz, 1H) 7.39 (br. s., 1H) 6.96 (t, J=10.47 Hz, 1H) 5.29 (d, J=10.56 Hz, 1H) 5.03 (d, J=10.56 Hz, 1H) 4.62-4.95 (m, 2H) 3.62-3.71 (m, 3H) 3.49 (d, J=5.09 Hz, 1H) 3.38 (s, 3H) 1.87 (t, J=8.22 Hz, 1H) 1.52 (s, 9H) 0.88-1.07 (m, 3H) 0.77 (t, J=6.26 Hz, 1H) 0.00 (s, 9H).

Preparation of tert-butyl ((1S,5S,6S)-5-(2-fluoro-5-formylphenyl)-5-(fluoromethyl)-1-(methoxymethyl)-2-thia-4-azabicyclo[4.1.0]hept-3-en-3-yl)((2-(trimethylsilyl)ethoxy)methyl)carbamate (2)

n-Butyllithium (2.5M in hexanes) (0.24 mL, 0.60 mmol) was added to a −78° C. solution of tert-butyl ((1S,5S,6S)-5-(5-bromo-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (2B) (0.33 g, 0.54 mmol) in THF (2 mL) under argon. The resulting light yellow solution was stirred for 15 minutes before DMF (0.030 mL, 0.39 mmol) was added. The mixture was warmed to room temperature and stirred for 1 hour and then saturated aqueous ammonium chloride solution was added. The product was extracted into EtOAc (3×) and the combined extracts were dried over anhydrous MgSO₄, filtered, and concentrated in vacuo to give an oil. The oil was purified by silica gel chromatography (0 to 40% EtOAc/heptane gradient) to give tert-butyl ((1S,5S,6S)-5-(2-fluoro-5-formylphenyl)-5-(fluoromethyl)-1-(methoxymethyl)-2-thia-4-azabicyclo[4.1.0]hept-3-en-3-yl)((2-(trimethylsilyl)ethoxy)methyl)carbamate (2) (0.13 g, 43% yield) as a colorless oil. MS m/z=557 [M+H]⁺.

Preparation of tert-butyl ((1S,5S,6S)-1-(dimethylcarbamoyl)-5-(2-fluoro-5-formylphenyl)-5-methyl-2-thia-4-azabicyclo[4.1.0]hept-3-en-3-yl)((2-(trimethylsilyl)ethoxy)methyl)carbamate (Intermediate 3)

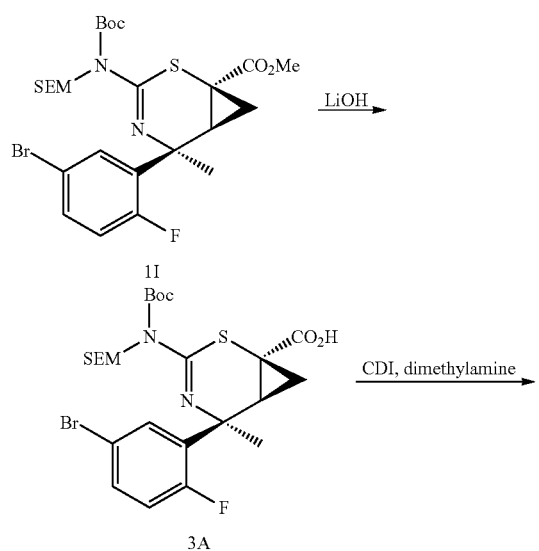

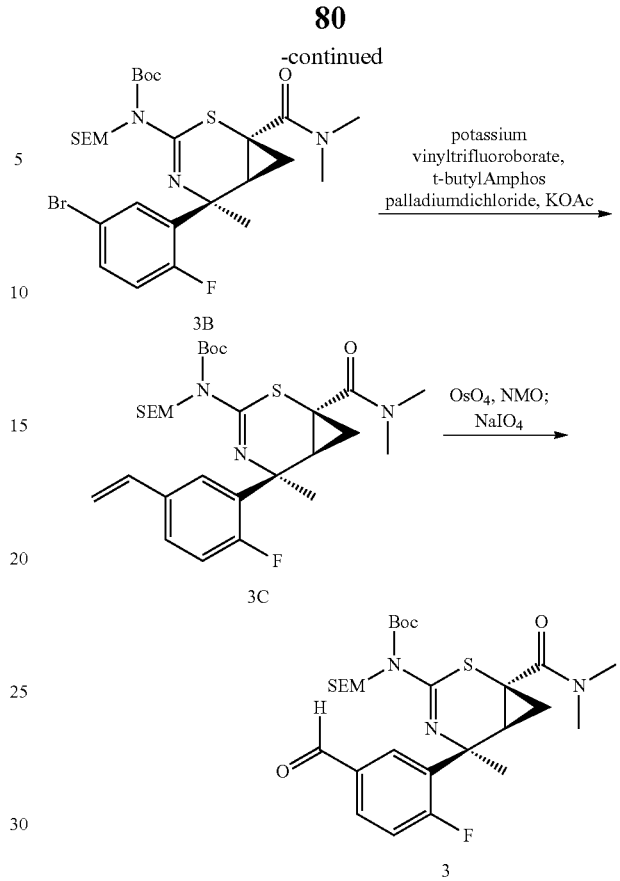

Preparation of (1S,5S,6S)-5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (3A)

A solution of lithium hydroxide monohydrate (2.05 g, 48.9 mmol) in water (40 mL) was added to a stirred solution of (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (11) (5.90 g, 9.77 mmol) in THF (60 mL) and MeOH (40 mL). The reaction mixture was stirred at room temperature for 1.5 hours. The reaction mixture was partitioned between EtOAc and 1M aqueous HCl. The organic layer was separated, washed with saturated aqueous ammonium chloride solution, dried over anhydrous MgSO₄, filtered, and concentrated in vacuo to give (1S,5S,6S)-5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (3A) (6.40 g, 111% yield) as an oil. MS m/z=589 [M+H]⁺. ¹H NMR (400 MHz, CDCl₃) δ ppm 7.77 (d, J=6.53 Hz, 1H) 7.33-7.38 (m, 1H) 6.96 (dd, J=11.74, 8.61 Hz, 1H) 5.26 (d, J=10.56 Hz, 1H) 5.01 (d, J=10.56 Hz, 1H) 3.61-3.70 (m, 2H) 2.69 (t, J=8.41 Hz, 1H) 1.69-1.78 (m, 3H) 1.52 (m, 10H) 1.17-1.29 (m, 1H) 0.93-1.00 (m, 2H) −0.02-0.02 (m, 9H).

Preparation of tert-butyl ((1S,5S,6S)-5-(5-bromo-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (3B)

To a stirring solution of (1S,5S,6S)-5-(5-bromo-2-fluorophenyl)-3-((tert-butoxycarbonyl)((2-(trimethylsilyl)ethoxy)

methyl)amino)-5-methyl-2-thia-4-azabicyclo[4.1.0]hept-3-ene-1-carboxylic acid (3A) (2.5 g, 4.2 mmol) in THF (20 mL) at 20° C. was added CDI (1.03 g, 6.36 mmol) in one portion. The solution was stirred for 1 hour at 20° C. The solution was chilled to 0° C. and dimethylamine (2N in THF, 10.6 mL, 21.2 mmol) was added. The solution was stirred for 1 hour and then the reaction was partitioned between EtOAc (30 mL) and 1M HCl (30 mL). The organic layer was washed with saturated aqueous sodium chloride solution, dried over anhydrous MgSO$_4$, filtered and concentrated in vacuo to give tert-butyl ((1S,5S,6S)-5-(5-bromo-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (3B) (2.50 g, 96% yield) as a light yellow oil. MS m/z=616 [M+H]$^+$. $^1$H NMR (400 MHz, CDCl$_3$) δ ppm 7.73 (d, J=6.80 Hz, 1H) 7.34 (ddd, J=8.61, 4.11, 2.74 Hz, 1H) 6.94 (dd, J=11.54, 8.61 Hz, 1H), 5.28 (d, J=10.37 Hz, 1H) 5.02 (d, J=10.37 Hz, 1H) 3.62-3.72 (m, 2H) 3.08 (br. s, 6H) 2.45 (ddd, J=9.54, 7.48, 1.56 Hz, 1H) 1.81 (s, 3H) 1.51 (s, 9H) 1.18-1.23 (m, 1H) 0.93-1.03 (m, 3H) 0.00 (s, 9H).

Preparation of tert-butyl ((1S,5S,6S)-1-(dimethylcarbamoyl)-5-(2-fluoro-5-vinylphenyl)-5-methyl-2-thia-4-azabicyclo[4.1.0]hept-3-en-3-yl)((2-(trimethylsilyl)ethoxy)methyl)carbamate (3C)

1,1-Bis[di-t-butyl-p-methylaminophenyl]palladium(II) chloride (0.087 g, 0.12 mmol) was added to a suspension of tert-butyl ((1S,5S,6S)-5-(5-bromo-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (3B) (1.51 g, 2.45 mmol), potassium vinyltrifluoroborate (0.43 g, 3.2 mmol), and potassium acetate (0.72 g, 7.4 mmol) in 3:1 CH$_3$CN/H$_2$O (10 mL) under argon atmosphere. The mixture was degassed and backfilled with argon, heated to 75° C. for 3 hours, and then cooled to room temperature. EtOAc was added and the mixture was washed with 10 mL of water and 10 mL of saturated aqueous sodium chloride solution and then dried over anhydrous MgSO$_4$. Filtration and concentration under reduced pressure, followed by flash chromatography on silica gel (0% to 50% EtOAc/heptane gradient) gave tert-butyl ((1S,5S,6S)-1-(dimethylcarbamoyl)-5-(2-fluoro-5-vinylphenyl)-5-methyl-2-thia-4-azabicyclo[4.1.0]hept-3-en-3-yl)((2-(trimethylsilyl)ethoxy)methyl)carbamate (3C) (0.87 g, 63% yield) as an oil. MS m/z=564 [M+H]$^+$. $^1$H NMR (400 MHz, CDCl$_3$) δ ppm 7.65 (d, J=7.43 Hz, 1H) 7.28-7.33 (m, 1H) 6.99-7.05 (m, 1H) 6.68 (dd, J=17.51, 10.86 Hz, 1H) 5.70 (d, J=17.80 Hz, 1H) 5.35 (d, J=10.37 Hz, 1H) 5.20 (d, J=10.76 Hz, 1H) 5.07 (d, J=10.56 Hz, 1H) 3.67 (t, J=8.31 Hz, 2H) 3.07 (br. s, 6H) 2.46 (t, J=8.61 Hz, 1H) 1.85 (s, 3H) 1.52 (s, 9H) 1.19-1.25 (m, 1H) 0.99-1.06 (m, 1H) 0.91-0.98 (m, 2H) 0.00 (s, 9H).

Preparation of tert-butyl ((1S,5S,6S)-1-(dimethylcarbamoyl)-5-(2-fluoro-5-formylphenyl)-5-methyl-2-thia-4-azabicyclo[4.1.0]hept-3-en-3-yl)((2-(trimethylsilyl)ethoxy)methyl)carbamate (3)

To tert-butyl ((1S,5S,6S)-1-(dimethylcarbamoyl)-5-(2-fluoro-5-vinylphenyl)-5-methyl-2-thia-4-azabicyclo[4.1.0]hept-3-en-3-yl)((2-(trimethylsilyl)ethoxy)methyl)carbamate (3C) (0.87 g, 1.6 mmol) in THF (7.5 mL) and water (7.5 mL) was added 4-methylmorpholine-4-oxide (0.27 g, 2.3 mmol) and OsO$_4$ (2.5 wt. %, solution in 2-methyl-2-propanol, 0.16 mL, 0.016 mmol). The mixture was stirred for 15 min, and then sodium (meta)periodate (1.0 g, 4.7 mmol) was added and the mixture was stirred at room temperature for 2 hours. The resulting suspension was diluted with EtOAc. The organic layer washed with saturated sodium thiosulfate solution, saturated sodium chloride solution, and dried over anhydrous sodium sulfate. After filtration and concentration in vacuo, the resulting oil was purified by silica gel chromatography (30 to 100% EtOAc/hexane gradient) to give tert-butyl ((1S,5S,6S)-1-(dimethylcarbamoyl)-5-(2-fluoro-5-formylphenyl)-5-methyl-2-thia-4-azabicyclo[4.1.0]hept-3-en-3-yl)((2-(trimethylsilyl)ethoxy)methyl)carbamate (3) (0.70 g, 80% yield) as a colorless glass. MS m/z=566 [M+H]$^+$. $^1$H NMR (400 MHz, CDCl$_3$) δ ppm 9.97 (s, 1H) 8.20 (dd, J=7.26, 2.15 Hz, 1H) 7.84 (ddd, J=5.76 Hz, 1H) 7.22 (dd, J=11.54, 8.22 Hz, 1H) 5.36 (d, J=10.56 Hz, 1H) 5.09 (d, J=10.37 Hz, 1H) 3.69 (t, J=8.31 Hz, 2H) 2.89-3.40 (m, 6H) 2.49 (ddd, J=9.54, 7.38, 1.66 Hz, 1H) 1.85-1.90 (m, 3H) 1.53 (s, 9H) 1.22 (dd, J=9.78, 5.67 Hz, 1H) 1.02-1.07 (m, 1H) 0.91-0.99 (m, 2H) 0.00 (s, 9H).

Preparation of tert-butyl ((1S,5S,6S)-5-(2-fluoro-5-formylphenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (Intermediate 4)

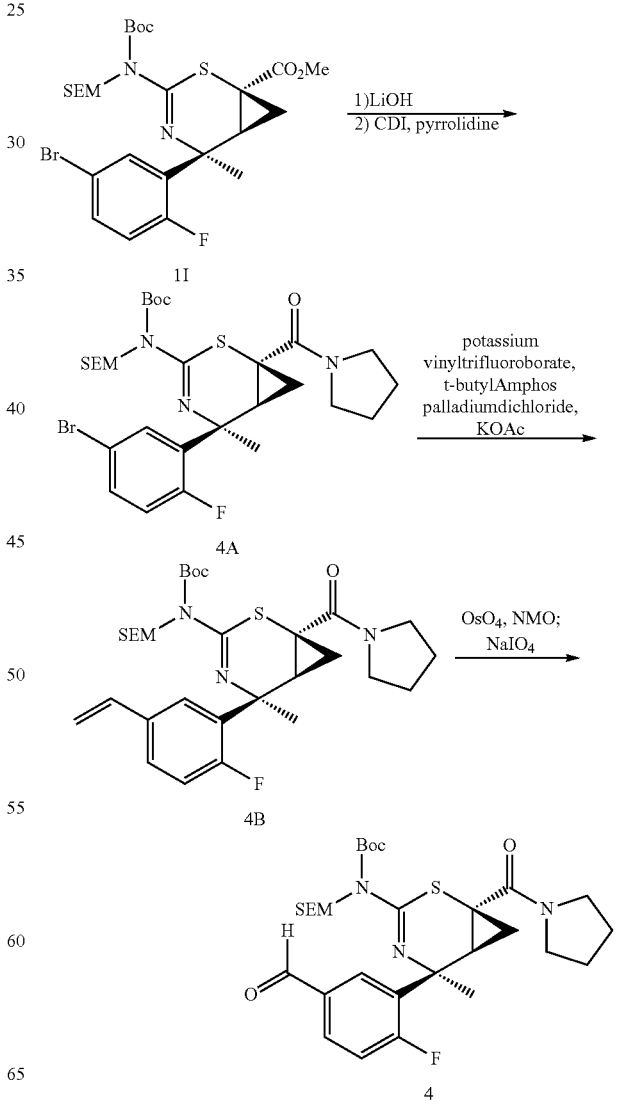

Preparation of tert-butyl ((1S,5S,6S)-5-(5-bromo-2-fluorophenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (4A)

To a stirring solution of (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (11) (5.02 g, 8.32 mmol) in THF (50 mL) and MeOH (33 mL) at 20° C. was added a solution of lithium hydroxide monohydrate (1.75 g, 41.6 mmol) in water (30 mL). The reaction was stirred for 45 min at room temperature and then EtOAc (75 mL) and 1M HCl (75 mL) were added. The layers were separated, and the organic layer was washed with saturated aqueous sodium chloride solution (50 mL), dried over anhydrous MgSO$_4$, filtered, then concentrated in vacuo to give a colorless oil. The oil was dissolved in THF (30 mL), and 1,1'-carbonyldiimidazole (2.02 g, 12.5 mmol) was added in one portion. The solution was stirred for 1 hour, then cooled to 0° C. Pyrrolidine (2.09 mL, 25.0 mmol) was added and the solution was stirred for 1 hour. The reaction was then partitioned between EtOAc (30 mL) and 1M HCl (30 mL). The organic layer was washed with saturated aqueous sodium chloride solution (25 mL), dried over anhydrous MgSO$_4$, filtered, and concentrated under reduced pressure to give tert-butyl ((1S,5S,6S)-5-(5-bromo-2-fluorophenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (4A) (3.02 g, 57% yield) as a light yellow oil. MS m/z=642 [M+H]$^+$. $^1$H NMR (400 MHz, CDCl$_3$) δ ppm 7.72 (d, J=6.60 Hz, 1H) 7.31-7.37 (m, 1H) 6.94 (dd, J=11.54, 8.61 Hz, 1H) 5.28 (d, J=10.37 Hz, 1H) 5.01 (d, J=10.37 Hz, 1H) 3.58-3.80 (m, 4H) 3.46 (br. s., 2H) 2.40-2.46 (m, 1H) 1.88 (br. s., 4H) 1.80 (s, 3H) 1.51 (s, 9H) 1.21-1.31 (m, 1H) 0.92-1.01 (m, 3H) 0.00 (s, 9H).

Preparation of tert-butyl ((1S,5S,6S)-5-(2-fluoro-5-vinylphenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (4B)

1,1-Bis[di-t-butyl-p-methylaminophenyl]palladium(II) chloride (0.17 g, 0.24 mmol) was added to a suspension of tert-butyl ((1S,5S,6S)-5-(5-bromo-2-fluorophenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (4A) (3.02 g, 4.70 mmol), potassium vinyltrifluoroborate (0.82 g, 6.1 mmol) and potassium acetate (1.38 g, 14.1 mmol) in 3:1 CH$_3$CN/H$_2$O (16 mL) under argon atmosphere. The mixture was degassed and backfilled with argon and then heated to 75° C. for 3 hours and then cooled to room temperature. EtOAc was added and the mixture was washed with 10 mL of water and 10 mL of saturated aqueous sodium chloride solution, then dried over anhydrous MgSO$_4$. Filtration and concentration under reduced pressure, followed by flash chromatography on silica gel (0% to 50% EtOAc/heptane gradient) gave tert-butyl ((1S,5S,6S)-5-(2-fluoro-5-vinylphenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (4B) (2.30 g, 83% yield) as an oil. MS m/z=590 [M+H]$^+$.

Preparation of tert-butyl ((1S,5S,6S)-5-(2-fluoro-5-formylphenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (4)

tert-Butyl ((1S,5S,6S)-5-(2-fluoro-5-vinylphenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (4B) (2.30 g, 3.90 mmol) in THF (15 mL) and water (15 mL) was added 4-methylmorpholine-4-oxide (0.69 g, 5.8 mmol) and osmium tetroxide (2.5 wt. %, solution in 2-methyl-2-propanol, 0.40 mL, 0.039 mmol). The reaction was stirred at room temperature for 15 minutes and then sodium meta-periodate (2.50 g, 11.7 mmol) was added and the cloudy reaction was stirred at r.t. for 2 hours. The mixture was then diluted with EtOAc, and the organic layer was washed with saturated aqueous sodium thiosulfate solution, saturated aqueous sodium chloride solution, and then dried over anhydrous sodium sulfate. The resulting mixture was filtered and the filtrate was concentrated in vacuo to give an oil that was purified by silica gel chromatography (30 to 100% EtOAc/hexane gradient) to give tert-butyl ((1S,5S,6S)-5-(2-fluoro-5-formylphenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (4) as a light yellow oil. MS m/z=592 [M+H]$^+$. $^1$H NMR (400 MHz, CDCl$_3$) δ ppm 9.97 (s, 1H) 8.19 (d, J=7.30 Hz, 1H) 7.84 (ddd, J=5.85 Hz, 1H) 7.22 (dd, J=11.54, 8.41 Hz, 1H) 5.36 (d, J=10.56 Hz, 1H) 5.08 (d, J=10.56 Hz, 1H) 3.76 (br. s, 2H) 3.68 (t, J=8.20 Hz, 2H) 3.48 (br. s., 2H) 2.48 (ddd, J=9.49, 7.34, 1.56 Hz, 1H) 1.95 (br. s, 4H) 1.86 (s, 3H) 1.53 (s, 9H) 1.27 (dd, J=9.98, 5.87 Hz, 1H) 0.88-1.05 (m, 3H) 0.00 (s, 9H).

Preparation of 2-(((5-chloropyridin-2-yl)fluoromethyl)sulfonyl)benzo[d]thiazole (Intermediate 5)

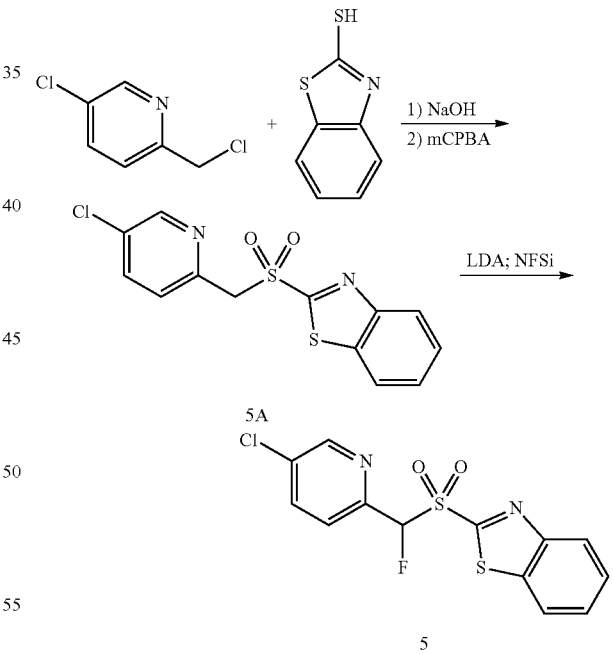

Preparation of 2-(((5-chloropyridin-2-yl)methyl)sulfonyl)benzo[d]thiazole (5A)

Aqueous sodium hydroxide (2M, 5 mL, 10 mmol) was added to a suspension of 2-mercaptobenzothiazole (1.60 g, 9.57 mmol) in MeOH (25 mL), and the mixture was stirred for 2-3 minutes, during which time the suspension became a solution. 5-Chloro-2-(chloromethyl)pyridine (1.17 mL, 9.57 mmol) was added via syringe, and the mixture was stirred for 5 hours at room temperature. The solvent was then removed in vacuo and the resulting solid was dissolved in 1:1 DCM/water. The layers were separated and the aqueous layer was extracted with DCM. The combined extracts were dried over anhydrous MgSO$_4$, filtered, and concentrated in vacuo to give an oil. The oil was purified by silica gel chromatography (0 to 50% EtOAc/heptane gradient) to give a white solid that was taken directly to the next step.

The solid prepared above was then dissolved in DCM (20 mL) and 3-chloroperbenzoic acid (5.36 g, 23.9 mmol) was added. This mixture was stirred for 3 hours at room temperature, during which time a suspension formed. Saturated aqueous sodium bicarbonate solution was added and the mixture was then stirred until the suspension dissipated. The biphasic mixture was separated and the aqueous layer was extracted with DCM (2×). The combined extracts were dried over anhydrous MgSO$_4$, filtered, and concentrated in vacuo to give a white solid that was purified by silica gel chromatography (0 to 50% EtOAc/heptane gradient) to give 2-(((5-chloropyridin-2-yl)methyl)sulfonyl)benzo[d]thiazole (5A) (0.83 g, 27% yield for 2 steps) as a white solid. MS m/z=325 [M+H]$^+$.

Preparation of 2-(((5-chloropyridin-2-yl)fluoromethyl)sulfonyl)benzo[d]thiazole (5)

To a solution of 2-(((5-chloropyridin-2-yl)methyl)sulfonyl)benzo[d]thiazole (5A) (0.76 g, 2.3 mmol) in THF (14 mL) at −78° C. was added LDA (2.0M solution in THF/heptane/ethylbenzene, 1.17 mL, 2.34 mmol) dropwise under N$_2$. The resulting mixture was stirred for 20 minutes and then N-fluorobenzenesulfonimide (0.81 g, 2.6 mmol) was added in one portion. The resulting mixture was stirred at −78° C. for 15 minutes and then was warmed to room temperature and stirred overnight. This mixture was cooled to −78° C. and was then treated with LDA (2.0M solution in THF/heptane/ethylbenzene, 0.60 mL, 1.2 mmol). After 10 minutes, N-fluorobenzenesulfonimide (0.40 g) was added. The cooling bath was removed after 5 minutes. After 30 min the reaction was quenched with AcOH (0.20 mL, 3.5 mmol) and cooled in an ice bath. The slurry was filtered and the solids were washed with cold THF (3×5 mL). The collected solid was air dried on the frit to give 2-(((5-chloropyridin-2-yl)fluoromethyl)sulfonyl)benzo[d]thiazole (5) as a white powder (0.41 g, 51% yield). MS m/z=343 [M+H]$^+$. $^1$H NMR 400 MHz, DMSO-d$_6$) δ ppm 8.72 (d, J=2.35 Hz, 1H) 8.32-8.43 (m, 2H) 8.15 (dd, J=8.41, 2.35 Hz, 1H) 7.68-7.83 (m, 3H) 7.40 (d, J=43.62 Hz, 1H).

Preparation of 2-(((3,5-bis(trifluoromethyl)phenyl)sulfonyl)fluoromethyl)-5-chloropyridine (Intermediate 6)

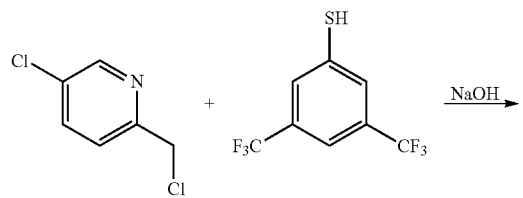

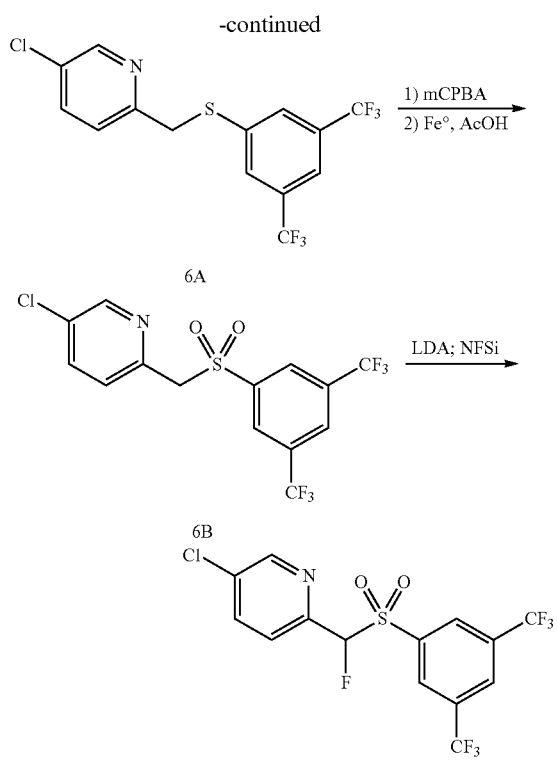

Preparation of 2-(((3,5-bis(trifluoromethyl)phenyl)thio)methyl)-5-chloropyridine (6A)

Sodium hydroxide (2N, aqueous, 5.46 mL, 10.9 mmol) was added dropwise to a solution of 3,5-bis-trifluoromethyl benzenethiol (1.83 mL, 10.9 mmol) in MeOH (3 mL). This mixture was stirred for 5 minutes and then 5-chloro-2-(chloromethyl)pyridine (1.77 g, 10.9 mmol) was added as a solution in MeOH (10 mL). This mixture was stirred 2 hours at r.t. and then it was concentrated to about half volume in vacuo. EtOAc and half saturated aqueous ammonium chloride were added, the layers were separated, and the aqueous layer was extracted with EtOAc (1×). The combined organic layers were dried over anhydrous MgSO$_4$, filtered, and concentrated in vacuo to give 2-(((3,5-bis(trifluoromethyl)phenyl)thio)methyl)-5-chloropyridine (6A) as a solid (4.1 g, 101% yield). MS m/z=372 [M+H]$^+$. $^1$H NMR (400 MHz, CDCl$_3$) δ ppm 8.49 (d, J=2.35 Hz, 1H) 7.75 (s, 2H) 7.61-7.65 (m, 2H) 7.32 (d, J=8.08 Hz, 1H) 4.32 (s, 2H).

Preparation of 2-(((3,5-bis(trifluoromethyl)phenyl)sulfonyl)methyl)-5-chloropyridine (6B)

mCPBA (6.18 g, 27.6 mmol) was added to a solution of 2-(((3,5-bis(trifluoromethyl)phenyl)thio)methyl)-5-chloropyridine (6A) (4.1 g, 11 mmol) in DCM (40 mL) and the mixture was stirred for 2 hours. Saturated aqueous sodium bicarbonate solution and DCM were added and the biphasic mixture was stirred vigorously until all solids went into solution. The layers were separated and the organic layer was washed with saturated aqueous sodium bicarbonate solution, dried over anhydrous MgSO$_4$, filtered, and concentrated in vacuo to give a mixture of 2-(((3,5-bis(trifluoromethyl)phenyl)sulfonyl)methyl)-5-chloropyridine (6B)

and 2-(((3,5-bis(trifluoromethyl)phenyl)sulfonyl)methyl)-5-chloropyridine-N-oxide as a white solid, that was taken directly to the next step without further characterization.

Iron powder (1.55 g, 27.9 mmol) and glacial acetic acid (5.4 mL, 93 mmol) were added to a suspension of 2-(((3,5-bis(trifluoromethyl)phenyl)sulfonyl)methyl)-5-chloropyridine (6B) and 2-(((3,5-bis(trifluoromethyl)phenyl)sulfonyl)methyl)-5-chloropyridine-N-oxide in EtOH (50 mL). This mixture was heated to 75° C. and then the iron was removed by filtering through a pad of Celite® filter aid while still hot. The filtrate was concentrated in vacuo and then suspended in 1:1 EtOAc/heptane (15 mL). After cooling to 0° C. for 1 hour, the suspension was filtered and the collected solid was air dried to give 2-(((3,5-bis(trifluoromethyl)phenyl)sulfonyl)methyl)-5-chloropyridine (6B) (2.9 g, 78% yield for 2 steps) as a white solid. MS m/z=404 [M+H]$^+$. $^1$H NMR (400 MHz, CDCl$_3$) δ ppm 8.31 (d, J=2.35 Hz, 1H) 8.12 (s, 1H) 8.05 (s, 2H) 7.76 (d, J=8.02 Hz, 1H) 7.50 (d, J=8.41 Hz, 1H) 4.58 (s, 2H).

Preparation of 2-(((3,5-bis(trifluoromethyl)phenyl)sulfonyl)fluoromethyl)-5-chloropyridine (6)

LDA (2.0M solution in THF/heptane/ethylbenzene, 3.78 mL, 7.57 mmol) was added dropwise to a −78° C. solution of 2-(((3,5-bis(trifluoromethyl)phenyl)sulfonyl)-methyl)-5-chloropyridine (6B) (2.91 g, 7.21 mmol) in THF (25 mL). This mixture was stirred for 15 minutes before NFSi (2.39 g, 7.57 mmol) was added as a solid. This mixture was stirred at −78° C. for 30 minutes, then at r.t. for 30 minutes. The resulting suspension was partitioned between water and EtOAc. The layers were separated and the organic layer was dried over anhydrous MgSO$_4$, filtered, and concentrated in vacuo to give a solid. The solid was fused to silica gel and the product was purified by silica gel chromatography (0 to 20% EtOAc/heptane gradient) to give 2-(((3,5-bis(trifluoromethyl)phenyl)sulfonyl)fluoromethyl)-5-chloropyridine (6) (2.3 g, 76% yield) as a white solid. MS m/z=422 [M+H]$^+$. $^1$H NMR (400 MHz, CDCl$_3$) δ ppm 8.60-8.66 (m, 1H) 8.34 (s, 2H) 8.23 (s, 1H) 7.84 (d, J=8.30 Hz, 1H) 7.56 (d, J=8.22 Hz, 1H) 6.24 (d, J=45.97 Hz, 1H).

Preparation of 2-((fluoro(5-methoxypyridin-2-yl)methyl)sulfonyl)benzo[d]thiazole (Intermediate 7)

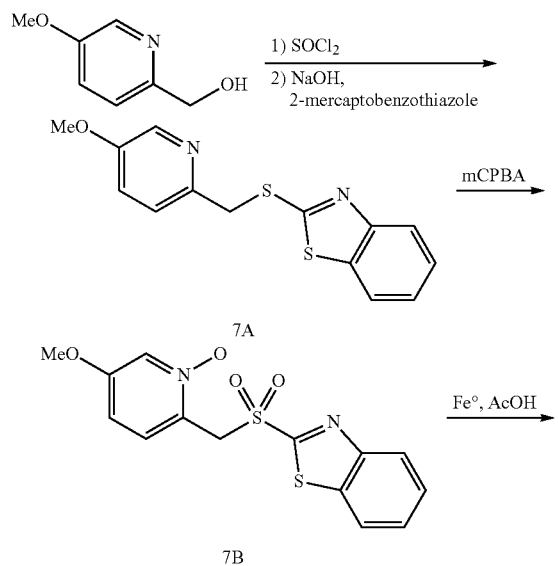

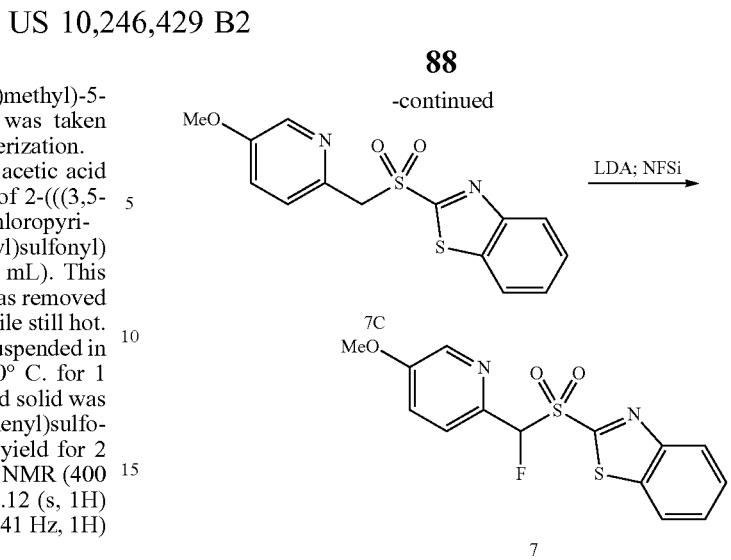

Preparation of 2-(((5-methoxypyridin-2-yl)methyl)thio)benzo[d]thiazole (7A)

Thionyl chloride (2.73 mL, 37.4 mmol) was added as a solution in DCM (50 mL) to an ice cold solution of (5-methoxypyridin-2-yl)methanol (1.07 g, 7.69 mmol) in DCM (50 mL). This mixture was stirred for 1 hour at 0° C., then 5% aqueous sodium bicarbonate solution was added. The layers were separated and the aqueous layer was extracted with DCM (1×). The combined extracts were dried over anhydrous MgSO$_4$, filtered, and concentrated in vacuo to give 2-(chloromethyl)-5-methoxypyridine.

2-Mercaptobenzothiazole (4.81 g, 28.7 mmol) was suspended in MeOH (50 mL) and aqueous sodium hydroxide (2N, 14.4 mL, 28.7 mmol) was added. This mixture was stirred for 2 min and then 2-(chloromethyl)-5-methoxypyridine was added as a solution in MeOH (15 mL). The resulting mixture was stirred overnight at r.t. and then the solvent was removed in vacuo. The resulting solid was dissolved in 1:1 EtOAc/water. The layers were separated, and the aqueous layer was extracted with EtOAc (1×). The combined extracts were dried over anhydrous MgSO$_4$, filtered, and concentrated in vacuo to give an oil. The oil was purified by silica gel chromatography (0 to 50% EtOAc/heptane gradient) to give 2-(((5-methoxypyridin-2-yl)methyl)thio)benzo[d]thiazole (7A) (7.4 g, 90% yield) as a colorless oil. MS m/z=289 [M+H]$^+$. $^1$H NMR (400 MHz, CDCl$_3$) δ ppm 8.26 (d, J=2.93 Hz, 1H) 7.89 (d, J=8.22 Hz, 1H) 7.74 (d, J=8.14 Hz, 1H) 7.46 (d, J=8.61 Hz, 1H) 7.39-7.44 (m, 1H) 7.26-7.32 (m, 1H) 7.14 (dd, J=8.61, 2.93 Hz, 1H) 4.70 (s, 2H) 3.84 (s, 3H).

Preparation of (((5-methoxypyridin-2-yl N-oxide)methyl)thio)benzo[d]thiazole (7B)

3-Chloroperbenzoic acid (15.6 g, 90.0 mmol) was added to a solution of 2-(((5-methoxypyridin-2-yl)methyl)thio)benzo[d]thiazole (7A) (7.44 g, 25.8 mmol) in DCM (100 mL) and the mixture was stirred overnight at room temperature. Saturated aqueous sodium bicarbonate solution (200 mL) and DCM (50 mL) was added and the mixture was stirred vigorously for 1 hour. The layers were separated and the aqueous layer was extracted with DCM (1×). The combined extracts were dried over anhydrous MgSO$_4$, filtered, and concentrated in vacuo to give 7B (8.47 g, 98% yield) as a white solid. MS m/z=337 [M+H]$^+$.

Preparation of 2-(((5-methoxypyridin-2-yl)methyl)sulfonyl)benzo[d]thiazole (7C)

A mixture of 7B (3.0 g, 8.9 mmol), iron powder (1.99 g, 35.7 mmol), and acetic acid (5.15 mL, 89.0 mmol) in EtOH (60 mL) was heated to 80° C. for 30 minutes. The resulting mixture was then filtered through a pad of Celite® filter aid while still hot. The filtrate was concentrated in vacuo, diluted with EtOAc, and washed with saturated aqueous sodium bicarbonate solution. The aqueous layer was then extracted with EtOAc (1×), and the combined extracts were dried over anhydrous MgSO$_4$, filtered, and concentrated in vacuo to give an oil that was fused to silica gel. The silica gel was added to the top of a plug of silica gel on a glass frit, and the product was then filtered through the silica gel using 1:1 heptane/EtOAc. The filtrate was concentrated to give 2-(((5-methoxypyridin-2-yl)methyl)sulfonyl)benzo[d]thiazole (7C) (1.6 g, 57% yield) as a light brown solid. MS m/z=321 [M+H]$^+$. $^1$H NMR (400 MHz, CDCl$_3$) δ ppm 8.25 (d, J=7.93 Hz, 1H) 8.14 (d, J=2.93 Hz, 1H) 7.96 (d, J=8.17 Hz, 1H) 7.64 (td, J=8.00, 0.98 Hz, 1H) 7.58 (td, J=7.00, 1.37 Hz, 1H) 7.39 (d, J=8.26 Hz, 1H) 7.17 (dd, J=8.51, 3.03 Hz, 1H) 4.90 (s, 2H) 3.83 (s, 3H).

Preparation of 2-((fluoro(5-methoxypyridin-2-yl)methyl)sulfonyl)benzo[d]thiazole (7)

LDA (2.0M solution in THF/heptane/ethylbenzene, 1.05 mL, 2.10 mmol) was added over 5 minutes to a solution of 2-(((5-methoxypyridin-2-yl)methyl)sulfonyl)benzo[d]thiazole (7C) (0.64 g, 2.0 mmol) in THF (7 mL) under argon at −78° C. The resulting mixture was stirred for 15 minutes and then N-fluorobenzenesulfonimide (0.66 g, 2.10 mmol) was added as a solid. This mixture was stirred at −78° C. for 15 minutes and then warmed to room temperature and stirred for 30 minutes. The resulting suspension was then cooled to 0° C. and then filtered. The filter cake was washed with cold THF and then suspended in THF (4 mL) and stirred for 15 minutes. Filtration gave 2-((fluoro(5-methoxypyridin-2-yl)methyl)sulfonyl)benzo[d]thiazole (7) (0.45 g, 66% yield) as an off white solid. MS m/z=339 [M+H]$^+$. $^1$H NMR (400 MHz, DMSO-d6) δ ppm 8.30-8.41 (m, 3H) 7.73-7.81 (m, 2H) 7.66 (d, J=8.61 Hz, 1H) 7.56 (dd, J=8.61, 2.93 Hz, 1H) 7.22 (d, J=43.82 Hz, 1H) 3.89 (s, 3H).

Preparation of 2-(((3,5-bis(trifluoromethyl)phenyl)sulfonyl)fluoromethyl)-5-bromopyridine (Intermediate 8)

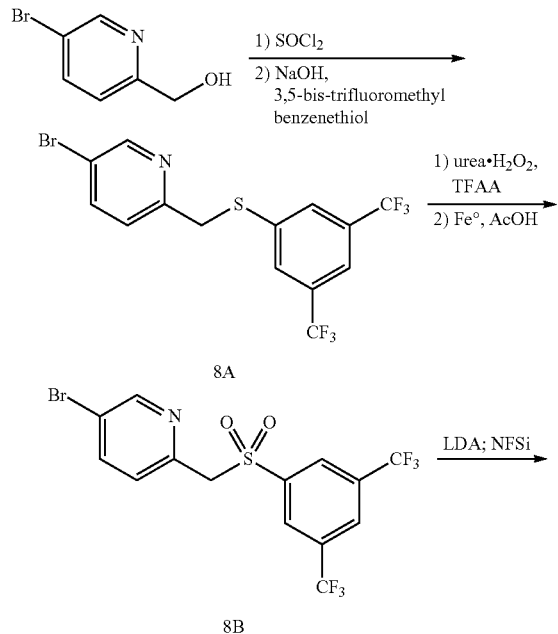

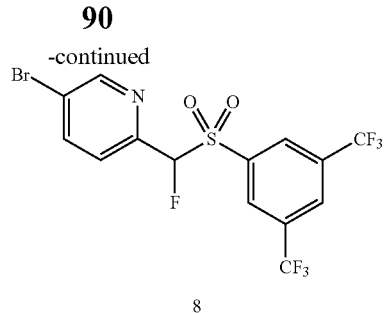

Preparation of 2-(((3,5-bis(trifluoromethyl)phenyl)thio)methyl)-5-bromopyridine (8A)

Methanesulfonyl chloride (5.35 mL, 69.1 mmol) was added dropwise to an ice cold solution of 5-bromo-2-hydroxymethylpyridine (10.0 g, 53.2 mmol) and TEA (11.1 mL, 80.0 mmol) in THF (150 mL). The mixture was stirred for 1 hour. Water was then added and the product was extracted into EtOAc (2×). The combined organic layers were dried over anhydrous MgSO$_4$, filtered, and concentrated in vacuo to give the mesylate as an oil.

3,5-bis-Trifluoromethyl benzenethiol (8.91 mL, 53.2 mmol) was dissolved in MeOH (150 mL). Aqueous sodium hydroxide (2N, 31.9 mL, 63.8 mmol) was added and then the mixture was stirred for 5 minutes. The mesylate was added as a suspension in MeOH (40 mL) and the mixture was stirred for 1 hour at room temperature before the MeOH was removed in vacuo. The resulting residue was partitioned between water and EtOAc, the layers were separated, and the aqueous layer was extracted with EtOAc (1×). The combined extracts were dried over anhydrous MgSO$_4$, filtered, and concentrated in vacuo to give 2-(((3,5-bis(trifluoromethyl)phenyl)thio)methyl)-5-bromopyridine (8A) (22.3 g, 101% yield) as an oil. MS m/z=416 [M+H]$^+$. $^1$H NMR (400 MHz, CDCl$_3$) δ ppm 8.59 (s, 1H) 7.73-7.79 (m, 3H) 7.63 (s, 1H) 7.26 (d, J=8.02 Hz, 1H) 4.29 (s, 2H).

Preparation of 2-(((3,5-bis(trifluoromethyl)phenyl)sulfonyl)methyl)-5-bromopyridine (8B)

A 100 mL 2-necked flask was charged with 2-(((3,5-bis(trifluoromethyl)phenyl)thio)methyl)-5-bromopyridine (8A) (1.8 g, 4.3 mmol), placed under argon atmosphere, and dissolved in CH$_3$CN (20 mL). The mixture was cooled to 4° C. internal temperature using an ice water bath, and then hydrogen peroxide urea adduct (1.02 g, 10.8 mmol) and TFAA (2.27 g, 10.8 mmol) were added. This mixture was stirred with warming to room temperature for 3 hours. In a separate flask, hydrogen peroxide urea adduct (1.0 g) was suspended in CN$_3$CN (20 mL) and TFAA (1 equiv.) was added. This mixture was stirred until all the peroxide complex went into solution (about 30 minutes) and then it was added to the reaction mixture. The reaction was stirred for 1 hour and then transferred to a separatory funnel. EtOAc and saturated aqueous sodium bicarbonate solution were added. The layers were mixed and then separated. The organic layer was washed with saturated aqueous sodium thiosulfate until peroxide test strips tested negative for peroxide. The organic solution was then dried over anhydrous MgSO$_4$, filtered, and then concentrated in vacuo to give a mixture of desired sulfone product and the corresponding N-oxide, which was taken directly to the next step.

A mixture of iron powder (0.96 g, 17 mmol), acetic acid (2.49 mL, 43.1 mmol), and the material generated in the first step in EtOH (25 mL) was heated to 80° C. for 3 hours. The solution was then filtered through a pad of Celite® filter aid while hot and the filtrate was concentrated in vacuo. The residue was partitioned between EtOAc and saturated aqueous sodium bicarbonate solution, the layers were separated, and the organic layer was washed with saturated aqueous sodium bicarbonate solution (2×), dried over anhydrous MgSO$_4$, filtered, and concentrated in vacuo. The resulting solid was recrystallized from 1:1 EtOAc/heptane to give 2-(((3,5-bis(trifluoromethyl)phenyl)sulfonyl)methyl)-5-bromopyridine (8B) (1.11 g, 58% yield for 2 steps) as a white solid. MS m/z=448 [M+H]$^+$. $^1$H NMR (400 MHz, CDCl$_3$) δ ppm 8.61 (s, 1H) 8.54 (d, J=2.15 Hz, 1H) 8.26 (s, 2H) 8.14 (dd, J=8.50, 2.35 Hz, 1H) 7.46 (d, J=8.41 Hz, 1H) 5.14 (s, 2H).

Preparation of 2-(((3,5-bis(trifluoromethyl)phenyl)sulfonyl)fluoromethyl)-5-bromopyridine (8)

LDA (2.0M solution in THF/heptane/ethylbenzene, 4.44 mL, 8.88 mmol) was added dropwise to a solution of 2-(((3,5-bis(trifluoromethyl)phenyl)sulfonyl)methyl)-5-bromopyridine (8B) (3.79 g, 8.46 mmol) in THF (30 mL) at −78° C. This mixture was then stirred for 15 minutes before N-fluorobenzenesulfonimide (2.80 g, 8.88 mmol) was added in one portion. The ice bath was removed and the mixture was allowed to warm to room temperature and stir for 30 minutes. Water was added and the product was extracted into DCM. The resulting solid was recrystallized once from DCM to give 2.0 g product, and then the remaining material was recrystallized from 1:1 EtOAc/heptane to give an additional 0.6 g of product. Together, the recrystallizations gave 2.6 g (65% yield) of 2-(((3,5-bis(trifluoromethyl)phenyl)sulfonyl)fluoromethyl)-5-bromopyridine (8) as a white solid. MS m/z=466 [M+H]$^+$. $^1$H NMR (400 MHz, CDCl$_3$) δ ppm 8.73 (d, J=2.15 Hz, 1H) 8.34 (s, 2H) 8.23 (s, 1H) 7.99 (dd, J=8.16, 2.35 Hz, 1H) 7.50 (d, J=8.22 Hz, 1H) 6.22 (d, J=45.97 Hz, 1H).

Preparation of (1S,5S,6S)-5-(5-((Z)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine (Example 100) and (1S,5S,6S)-5-(5-((E)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine (Example 101)

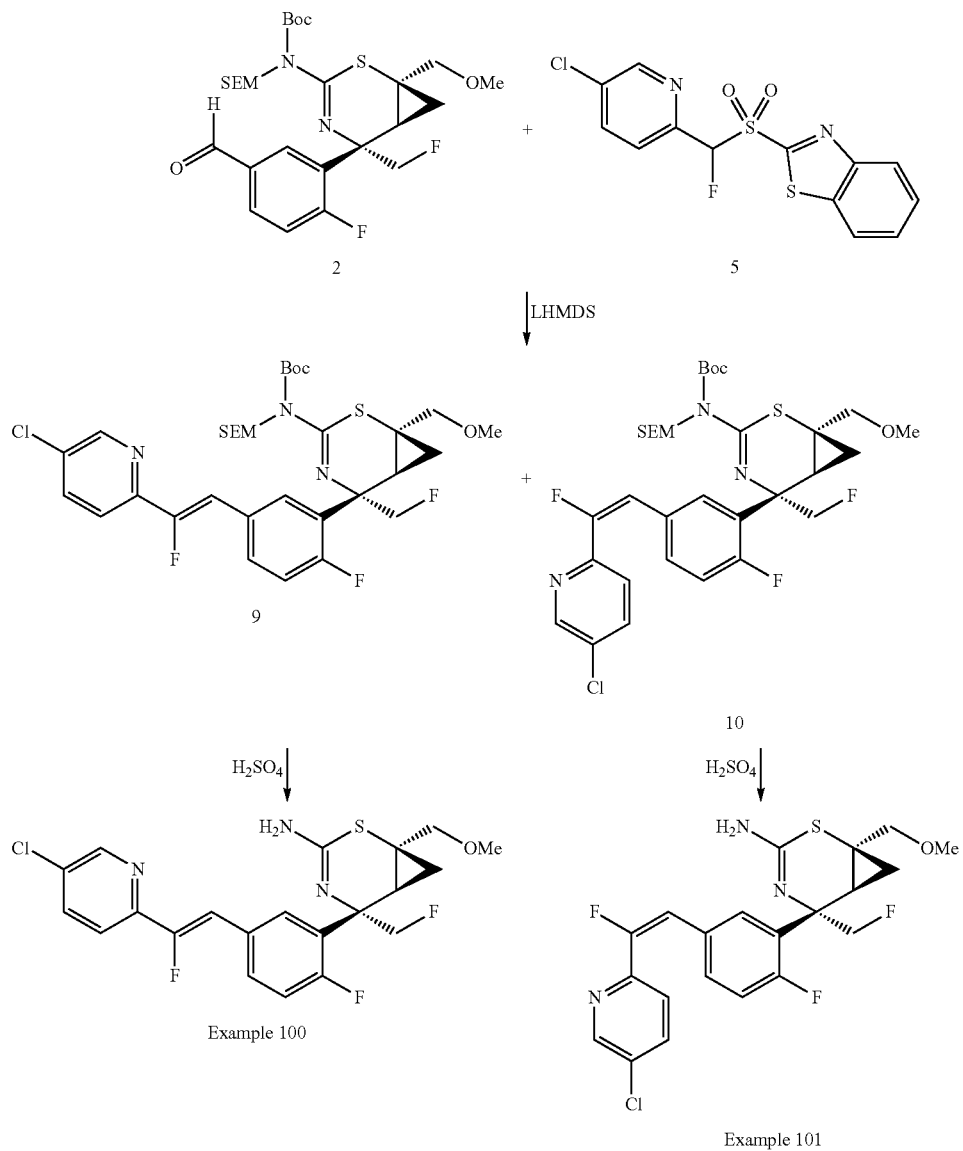

Example 100

Example 101

Preparation of tert-butyl ((1S,5S,6S)-5-(5-((Z)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (9) and tert-butyl ((1S,5S,6S)-5-(5-((E)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (10)

LHMDS (1.0M solution in THF, 0.70 mL, 0.70 mmol) was added to an ice cold solution of 2-(((5-chloropyridin-2-yl)fluoromethyl)sulfonyl)benzo[d]thiazole (5) (104 mg, 0.30 mmol) and tert-butyl ((1S,5S,6S)-5-(2-fluoro-5-formylphenyl)-5-(fluoromethyl)-1-(methoxymethyl)-2-thia-4-azabicyclo[4.1.0]hept-3-en-3-yl)((2-(trimethylsilyl)ethoxy)methyl)carbamate (2) (130 mg, 0.23 mmol) in THF (0.5 mL). The resulting mixture was stirred with warming to r.t. overnight. Saturated aqueous ammonium chloride solution was added, and the product was extracted into EtOAc (3×). The combined organic layers were dried over anhydrous MgSO$_4$, filtered, and concentrated in vacuo to give an oil. The oil was purified by reverse phase HPLC to give tert-butyl ((1S,5S,6S)-5-(5-((Z)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (9) (36 mg, 23% yield) and tert-butyl ((1S,5S,6S)-5-(5-((E)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (10) (22 mg, 14% yield), both as oils.

"Z" Isomer (9):
MS m/z=684 [M+H]$^+$. $^1$H NMR (400 MHz, CDCl$_3$) δ ppm 8.56 (s, 1H) 7.98-8.03 (m, 1H) 7.70-7.78 (m, 2H) 7.57 (dd, J=8.41, 1.17 Hz, 1H) 7.10-7.17 (m, 1H) 7.10 (d, J=39.32 Hz, 1H) 5.36 (d, J=10.76 Hz, 1H) 5.18 (d, J=10.56 Hz, 1H) 4.72-5.04 (m, 2H) 3.68-3.76 (m, 3H) 3.40-3.45 (m, 4H) 1.95 (ddd, J=9.39, 6.94, 2.05 Hz, 1H) 1.56 (s, 9H) 1.08 (dd, J=9.68, 5.77 Hz, 1H) 0.95-1.03 (m, 2H) 0.86 (t, J=6.16 Hz, 1H) 0.00 (s, 9H).

"E" Isomer (10):
MS m/z=684 [M+H]$^+$. $^1$H NMR (400 MHz, CDCl$_3$) δ ppm 8.49-8.54 (m, 1H) 7.63 (dd, J=8.70, 2.25 Hz, 2H) 7.37 (d, J=8.61 Hz, 1H) 7.23-7.30 (m, 1H) 6.97 (dd, J=11.93, 8.41 Hz, 1H) 6.64 (d, J=23.08 Hz, 1H) 5.18 (d, J=10.56 Hz, 1H) 4.65-4.99 (m, 3H) 3.56-3.71 (m, 3H) 3.33-3.45 (m, 4H) 1.83-1.89 (m, 1H) 1.52 (s, 9H) 0.85-1.07 (m, 3H) 0.69-0.85 (m, 1H) 0.00 (s, 9H).

Preparation of (1S,5S,6S)-5-(5-((Z)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine (Example 100)

tert-Butyl ((1S,5S,6S)-5-(5-((Z)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (36 mg, 0.053 mmol) was dissolved in concentrated sulfuric acid (0.5 mL). This mixture was stirred for 10 minutes and then pipetted onto a mixture of ice and DCM. The resulting biphasic mixture was then neutralized to pH 7 with solid K$_3$PO$_4$ (2 g), the layers were separated, and the aqueous layer was extracted with DCM (3×). The combined organic layers were dried over anhydrous MgSO$_4$, filtered, and concentrated in vacuo to give an oil. The oil was purified by silica gel chromatography (0 to 40% EtOAc/DCM gradient) to give (1S,5S,6S)-5-(5-((Z)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine (Example 100) (15 mg, 63% yield) as an oil. MS m/z=454 [M+H]$^+$. $^1$H NMR (400 MHz, CDCl$_3$) δ ppm 8.54 (d, J=2.15 Hz, 1H) 7.87 (dd, J=7.82, 2.15 Hz, 1H) 7.66-7.75 (m, 2H) 7.54 (d, J=8.30 Hz, 1H) 6.94-7.17 (m, 2H) 4.30-5.06 (m, 4H) 3.65 (d, J=10.56 Hz, 1H) 3.40 (s, 3H) 3.38 (d, J=10.56 Hz, 1H) 1.78 (t, J=7.63 Hz, 1H) 1.11 (dd, J=9.59, 5.67 Hz, 1H) 0.74 (t, J=6.16 Hz, 1H).

Preparation of (1S,5S,6S)-5-(5-((E)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine (Example 101)

tert-Butyl ((1S,5S,6S)-5-(5-((E)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (22 mg, 0.032 mmol) was dissolved in concentrated sulfuric acid (0.5 mL). This mixture was stirred for 10 minutes and then pipetted onto a mixture of ice and DCM. The mixture was then neutralized to pH=7 with solid K$_3$PO$_4$ (2 g). The resulting biphasic mixture was separated, the aqueous layer was extracted with DCM (3×), and the combined extracts were dried over anhydrous MgSO$_4$, filtered, and concentrated in vacuo to give an oil. The oil was purified by silica gel chromatography (0 to 40% EtOAc/DCM gradient) to give (1S,5S,6S)-5-(5-((E)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine (Example 101) (4 mg, 27% yield) product as an oil. MS m/z=454 [M+H]$^+$. $^1$H NMR (400 MHz, CDCl$_3$) δ ppm 8.52 (d, J=2.54 Hz, 1H) 7.62 (dd, J=8.41, 2.74 Hz, 1H) 7.47 (dd, J=7.63, 2.15 Hz, 1H) 7.34 (d, J=8.41 Hz, 1H) 7.18-7.24 (m, 1H) 6.91-6.98 (m, 1H) 6.61 (d, J=22.69 Hz, 1H) 4.85 (dd, J=8.61, 1.37 Hz, 1H) 4.73 (dd, J=8.61, 0.78 Hz, 1H) 4.68 (d, J=8.61 Hz, 1H) 4.57 (d, J=8.22 Hz, 1H) 3.61 (d, J=10.56 Hz, 1H) 3.38 (s, 3H) 3.33 (d, J=10.56 Hz, 1H) 1.67-1.74 (m, 1H) 1.07 (dd, J=9.59, 5.67 Hz, 1H) 0.59-0.67 (m, 1H).

Preparation of (1S,5S,6S)-3-amino-5-(5-((Z)-2-(5-chloropyridin-2-yl)-2-fluorovinyl)-2-fluorophenyl)-N,N,5-trimethyl-2-thia-4-azabicyclo[4.1.0]hept-3-ene-1-carboxamide (Example 102)

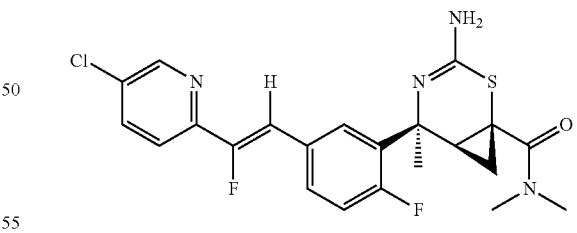

Example 102

(1S,5S,6S)-3-Amino-5-(5-((Z)-2-(5-chloropyridin-2-yl)-2-fluorovinyl)-2-fluorophenyl)-N,N,5-trimethyl-2-thia-4-azabicyclo[4.1.0]hept-3-ene-1-carboxamide (Example 102) was prepared from sulfone 6 and aldehyde 3 in a similar manner to Example 100. MS m/z=463 [M+H]$^+$. $^1$H NMR (400 MHz, CDCl$_3$) δ ppm 8.46-8.59 (m, 1H) 7.69-7.82 (m, 2H) 7.59-7.67 (m, 1H) 7.48-7.57 (m, 1H) 6.96-7.12 (m, 2H) 3.04 (br. s, 6H) 2.22-2.30 (m, 1H) 1.86 (s, 3H) 1.37 (dd, J=9.68, 5.58 Hz, 1H) 0.86 (t, J=6.36 Hz, 1H).

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(pyrrolidin-1-yl)methanone (Example 103)

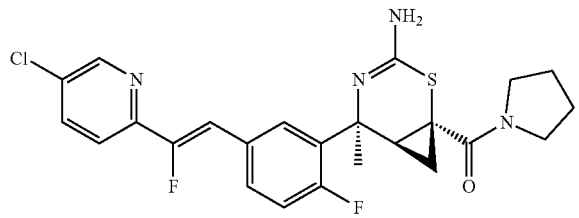 [SMILES: C[C@]1(c2cc(/C=C(\F)c3ccc(Cl)cn3)ccc2F)N=C(N)S[C@@]2(C(=O)N3CCCC3)C[C@H]21]

Example 103

((1S,5S,6S)-3-Amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(pyrrolidin-1-yl)methanone (Example 103) was prepared from sulfone 6 and aldehyde 4 in a similar manner to Example 100. MS m/z=489 [M+H]$^+$. $^1$H NMR (400 MHz, CDCl$_3$) δ ppm 8.54 (d, J=2.15 Hz, 1H) 7.70-7.75 (m, 2H) 7.64 (ddd, J=8.36, 4.55, 2.35 Hz, 1H) 7.55 (d, J=8.41 Hz, 1H) 6.95-7.10 (m, 2H) 3.67 (br. s., 2H) 3.47 (br. s., 2H) 2.22-2.27 (m, 1H) 1.87-1.98 (m, 4H) 1.85-1.87 (m, 3H) 1.43 (dd, J=9.59, 5.67 Hz, 1H) 0.81 (t, J=6.36 Hz, 1H).

Preparation of ((1S,5S,6S)-3-amino-5-(2-fluoro-5-((Z)-2-fluoro-2-(5-methoxypyridin-2-yl)vinyl)phenyl)-5-methyl-2-thia-4-azabicyclo[4.1.0]hept-3-en-1-yl)(pyrrolidin-1-yl)methanone (Example 104)

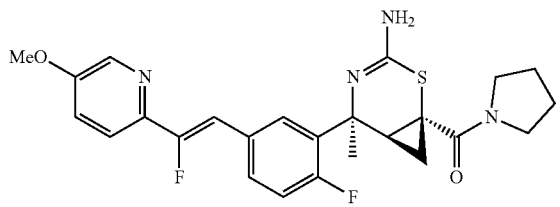 [SMILES: COc1ccc(/C(F)=C/c2ccc(F)c([C@@]3(C)N=C(N)S[C@@]4(C(=O)N5CCCC5)C[C@H]43)c2)nc1]

Example 104

((1S,5S,6S)-3-Amino-5-(2-fluoro-5-((Z)-2-fluoro-2-(5-methoxypyridin-2-yl)vinyl)phenyl)-5-methyl-2-thia-4-azabicyclo[4.1.0]hept-3-en-1-yl)(pyrrolidin-1-yl)methanone (Example 104) was prepared from sulfone 7 and aldehyde 4 in a similar manner to Example 100. MS m/z=485 [M+H]$^+$. $^1$H NMR (400 MHz, CDCl$_3$) δ (400 MHz, CDCl$_3$) ppm 8.29 (d, J=2.74 Hz, 1H) 7.66-7.72 (m, 1H) 7.57-7.63 (m, 1H) 7.51 (dd, J=8.80, 1.56 Hz, 1H) 7.20 (dd, J=8.80, 2.93 Hz, 1H) 7.03 (dd, J=11.93, 8.41 Hz, 1H) 6.84 (d, J=40.10 Hz, 1H) 3.88 (s, 3H) 3.64 (br. s., 2H) 3.46 (br. s., 2H) 2.15-2.28 (m, 1H) 1.83-2.01 (m, 7H) 1.44 (dd, J=9.78, 5.67 Hz, 1H) 0.80 (t, J=6.26 Hz, 1H).

Preparation of (1S,5S,6S)-methyl 3-amino-5-(5-((Z)-2-(5-bromopyridin-2-yl)-2-fluorovinyl)-2-fluorophenyl)-5-methyl-2-thia-4-azabicyclo[4.1.0]hept-3-ene-1-carboxylate (Example 105)

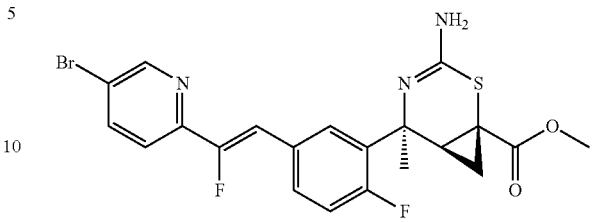

Example 105

(1S,5S,6S)-Methyl 3-amino-5-(5-((Z)-2-(5-bromopyridin-2-yl)-2-fluorovinyl)-2-fluorophenyl)-5-methyl-2-thia-4-azabicyclo[4.1.0]hept-3-ene-1-carboxylate (Example 105) was prepared from sulfone 8 and aldehyde 1 in a similar manner to Example 100. MS m/z=494 [M+H]$^+$. $^1$H NMR (400 MHz, DMSO-d6) δ ppm 8.77 (d, J=2.35 Hz, 1H) 8.19 (dd, J=8.41, 2.35 Hz, 1H) 8.10 (dd, J=7.82, 2.15 Hz, 1H) 7.62-7.70 (m, 2H) 7.26 (dd, J=12.32, 8.61 Hz, 1H) 7.11 (d, J=40.30 Hz, 1H) 6.24 (s, 2H) 3.72 (s, 3H) 2.40 (t, J=8.51 Hz, 1H) 1.60 (s, 3H) 1.43 (dd, J=9.68, 4.99 Hz, 1H) 0.99 (dd, J=7.34, 4.99 Hz, 1H).

Preparation of (1S,5S,6S)-3-amino-5-(5-((Z)-2-(5-cyanopyridin-2-yl)-2-fluorovinyl)-2-fluorophenyl)-N,N,5-trimethyl-2-thia-4-azabicyclo[4.1.0]hept-3-ene-1-carboxamide (Example 106)

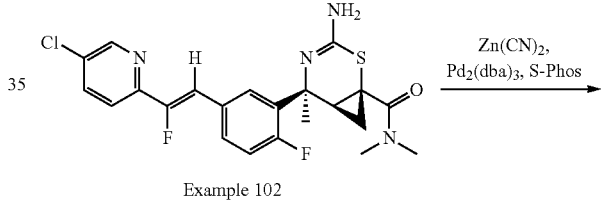

Example 102

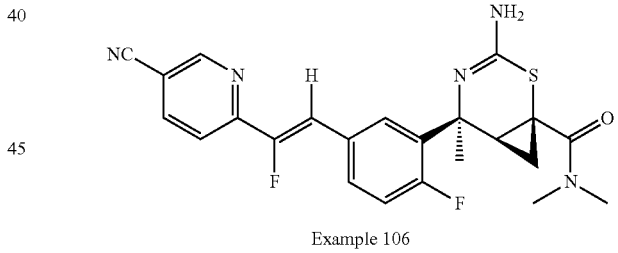

Example 106

A vial was charged with (1S,5S,6S)-3-amino-5-(5-((Z)-2-(5-chloropyridin-2-yl)-2-fluorovinyl)-2-fluorophenyl)-N,N,5-trimethyl-2-thia-4-azabicyclo[4.1.0]hept-3-ene-1-carboxamide (Example 102) (100 mg, 0.22 mmol), S-Phos (18 mg, 0.043 mmol), tris(dibenzylideneacetone)dipalladium (0) (20 mg, 0.022 mmol), and zinc cyanide (0.016 mL, 0.26 mmol). DMF (1.0 mL) and a drop of water were added and the mixture was placed under argon atmosphere. The resulting mixture was then heated to 100° C. for 3 hours. The mixture was then cooled to room temperature, half saturated aqueous sodium bicarbonate and EtOAc were added, the layers were separated, and the organic layer was washed with half saturated aqueous sodium bicarbonate (2×). The organic extracts were dried over anhydrous MgSO$_4$, filtered, and concentrated in vacuo to give a yellow solid. The solid was purified by reversed phase HPLC to give (1S,5S,6S)-3-amino-5-(5-((Z)-2-(5-cyanopyridin-2-yl)-2-fluorovinyl)-2-fluorophenyl)-N,N,5-trimethyl-2-thia-4-azabicyclo[4.1.0]hept-3-ene-1-carboxamide (Example 106) (27 mg, 16% yield) as a white solid. MS m/z=454 [M+H]⁺. ¹H NMR (400 MHz, CDCl₃) δ ppm 8.82 (s, 1H) 8.01 (dd, J=8.31, 1.86 Hz, 1H) 7.61-7.73 (m, 3H) 7.20 (d, J=38.93 Hz, 1H) 7.06-7.14 (m, 1H) 3.05 (br. s., 6H) 2.30-2.38 (m, 1H) 1.95 (s, 3H) 1.50 (dd, J=9.39, 5.87 Hz, 1H) 0.90 (t, J=6.46 Hz, 1H).

Preparation of 6-((Z)-2-(3-((1S,5S,6S)-3-amino-5-methyl-1-(pyrrolidine-1-carbonyl)-2-thia-4-azabicyclo[4.1.0]hept-3-en-5-yl)-4-fluorophenyl)-1-fluorovinyl)nicotinonitrile (Example 107)

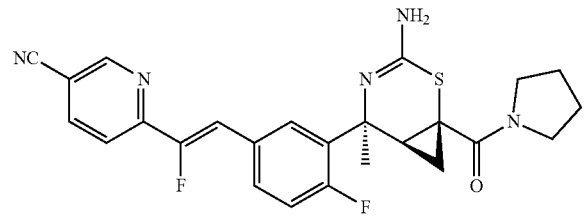 [SMILES: C[C@]1(c2cc(/C=C(\F)c3ccc(C#N)cn3)ccc2F)N=C(N)S[C@@]2(C(=O)N3CCCC3)C[C@H]21]

Example 107

6-((Z)-2-(3-((1S,5S,6S)-3-Amino-5-methyl-1-(pyrrolidine-1-carbonyl)-2-thia-4-azabicyclo[4.1.0]hept-3-en-5-yl)-4-fluorophenyl)-1-fluorovinyl)nicotinonitrile (Example 107) was prepared from Example 103 in a similar manner to Example 106. MS m/z=480 [M+H]⁺. (400 MHz, CDCl₃) δ ppm 8.79-8.83 (m, 1H) 7.97-8.04 (m, 1H) 7.73-7.82 (m, 1H) 7.62-7.71 (m, 2H) 7.21 (d, J=40.30 Hz, 1H) 7.08 (dd, J=11.74, 8.80 Hz, 1H) 3.66 (br. s., 2H) 3.47 (br. s., 2H) 2.25 (ddd, J=9.68, 7.24, 1.08 Hz, 1H) 1.80-1.99 (m, 7H) 1.44 (dd, J=9.78, 5.67 Hz, 1H) 0.80 (t, J=6.36 Hz, 1H).

Preparation of (1S,5S,6S)-3-amino-5-(5-((Z)-2-(5-bromopyridin-2-yl)-2-fluorovinyl)-2-fluorophenyl)-N,N,5-trimethyl-2-thia-4-azabicyclo[4.1.0]hept-3-ene-1-carboxamide (Example 108)

(1S,5S,6S)-3-Amino-5-(5-((Z)-2-(5-bromopyridin-2-yl)-2-fluorovinyl)-2-fluorophenyl)-N,N,5-trimethyl-2-thia-4-azabicyclo[4.1.0]hept-3-ene-1-carboxamide was prepared from sulfone 8 and aldehyde 3 in a similar manner to Example 100.

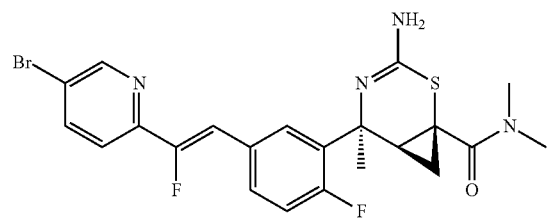

Example 108

Preparation of (1S,5S,6S)-3-amino-5-(5-((Z)-2-(5-(cyclopropylethynyl)pyridin-2-yl)-2-fluorovinyl)-2-fluorophenyl)-N,N,5-trimethyl-2-thia-4-azabicyclo[4.1.0]hept-3-ene-1-carboxamide (Example 109)

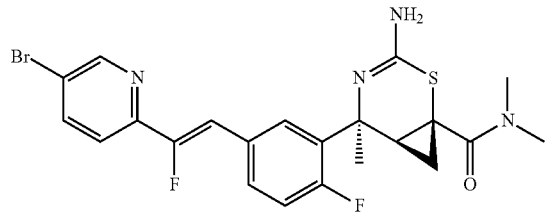 [SMILES: CN(C)C(=O)[C@]12C[C@H]1[C@@](C)(c1cc(/C=C(\F)c3ccc(Br)cn3)ccc1F)N=C(N)S2]

Example 108

| dichlorobis(triphenylphosphine)palladium copper (I) iodide DIEA, cyclopropylacetylene ↓

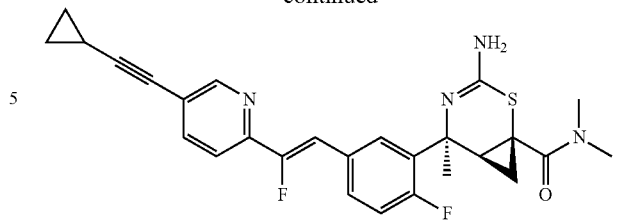

Example 109

A mixture of (1S,5S,6S)-3-amino-5-(5-((Z)-2-(5-bromopyridin-2-yl)-2-fluorovinyl)-2-fluorophenyl)-N,N,5-trimethyl-2-thia-4-azabicyclo[4.1.0]hept-3-ene-1-carboxamide (Example 108) (46 mg, 0.091 mmol), copper(I) iodide (0.31 mL, 9.1 µmol), and Hunig's base (0.16 mL, 0.91 mmol) in DMF (0.5 mL) was sparged with argon for 3 min. Cyclopropylacetylene (38 µL, 0.45 mmol) was added and the mixture was then heated at 60° C. for 2 hours before it was cooled to room temperature. EtOAc was added, and the DMF was removed by washing with water (3×). The organic solution was then dried over anhydrous MgSO₄, filtered, and concentrated in vacuo to give an oil. The oil was purified by silica gel chromatography (0 to 100% EtOAc/EtOH (3:1): heptane gradient) to give (1S,5S,6S)-3-amino-5-(5-((Z)-2-(5-(cyclopropylethynyl)pyridin-2-yl)-2-fluorovinyl)-2-fluorophenyl)-N,N,5-trimethyl-2-thia-4-azabicyclo[4.1.0]hept-3-ene-1-carboxamide (Example 109) (28 mg, 63% yield) as a white solid. MS m/z=493 [M+H]⁺. ¹H NMR (400 MHz, CDCl₃) δ ppm 8.55 (s, 1H) 7.74 (dd, J=7.82, 2.15 Hz, 1H) 7.67 (dd, J=8.02, 1.96 Hz, 1H) 7.60-7.65 (m, 1H) 7.49 (d, J=7.63 Hz, 1H) 6.94-7.10 (m, 2H) 3.06 (br. s., 6H) 2.22-2.29 (m, 1H) 1.82-1.89 (m, 3H) 1.42-1.58 (m, 1H) 1.37 (dd, J=9.78, 5.67 Hz, 1H) 0.81-0.95 (m, 5H).

Preparation of (1S,5S,6S)-3-amino-5-(5-((Z)-2-(5-ethynylpyridin-2-yl)-2-fluorovinyl)-2-fluorophenyl)-N,N,5-trimethyl-2-thia-4-azabicyclo[4.1.0]hept-3-ene-1-carboxamide (Example 110)

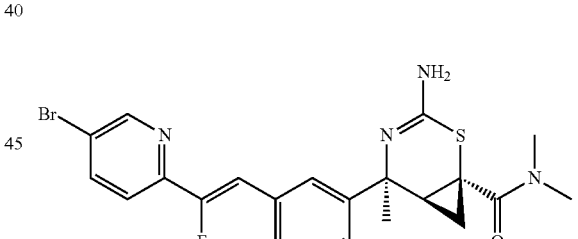

Example 108

1) dichlorobis(triphenylphosphine)palladium copper (I) iodide DIEA, TMSacetylene
2) K₂CO₃
↓

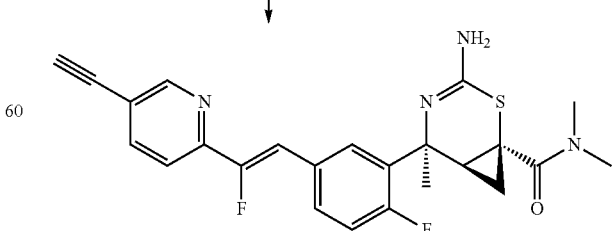

Example 110

A solution of (1S,5S,6S)-3-amino-5-(5-((Z)-2-(5-bromopyridin-2-yl)-2-fluorovinyl)-2-fluorophenyl)-N,N,5-trimethyl-2-thia-4-azabicyclo[4.1.0]hept-3-ene-1-carboxamide (Example 108) (68 mg, 0.134 mmol), dichlorobis(triphenylphosphine)palladium (II) (9.41 mg, 0.013 mmol), copper(I) iodide (2.5 mg, 0.013 mmol), and Hunig's base (0.23 mL, 1.34 mmol) in DMF (0.5 mL) was sparged with argon for 5 min and then (trimethylsilyl)-acetylene (0.095 mL, 0.67 mmol) was added. This mixture was heated to 50° C. for 3 hours, then cooled to room temperature. EtOAc (3 mL) was added and the mixture was washed with water, saturated aqueous sodium chloride solution, dried over anhydrous MgSO$_4$, filtered, and concentrated in vacuo to give an oil. The oil was purified by silica gel chromatography (0 to 100% EtOAc/EtOH (3:1):heptane gradient) to give (1S,5S,6S)-3-amino-5-(2-fluoro-5-((Z)-2-fluoro-2-(5-((trimethylsilyl)ethynyl)pyridin-2-yl)vinyl)phenyl)-N,N,5-trimethyl-2-thia-4-azabicyclo[4.1.0]hept-3-ene-1-carboxamide (49 mg, 70% yield) as an oil. MS m/z=525 [M+H]$^+$.

Potassium carbonate (13 mg, 0.093 mmol) was added to a solution of (1S,5S,6S)-3-amino-5-(2-fluoro-5-((Z)-2-fluoro-2-(5-((trimethylsilyl)ethynyl)pyridin-2-yl)vinyl)phenyl)-N,N,5-trimethyl-2-thia-4-azabicyclo[4.1.0]hept-3-ene-1-carboxamide (49 mg, 0.093 mmol) in MeOH (1 mL) and the mixture was stirred for 1 hour at room temperature. Saturated aqueous ammonium chloride solution was added and the product was extracted into EtOAc (2x). The combined extracts were dried over anhydrous MgSO$_4$, filtered, and concentrated onto silica gel. The product was purified by silica gel chromatography (0 to 100% EtOAc/EtOH (3:1)/heptane gradient for the first column and then 1 to 3% MeOH/DCM gradient for the second column) to give (1S,5S,6S)-3-amino-5-(5-((Z)-2-(5-ethynylpyridin-2-yl)-2-fluorovinyl)-2-fluorophenyl)-N,N,5-trimethyl-2-thia-4-azabicyclo[4.1.0]hept-3-ene-1-carboxamide (Example 110) (18 mg, 43% yield) as a white solid. MS m/z=453 [M+H]$^+$. $^1$H NMR (400 MHz, CDCl$_3$) δ ppm 8.65-8.68 (m, 1H) 7.82 (dd, J=8.22, 1.96 Hz, 1H) 7.75 (dd, J=7.82, 2.15 Hz, 1H) 7.64 (ddd, J=8.41, 4.69, 2.35 Hz, 1H) 7.54 (d, J=7.63 Hz, 1H) 7.00-7.12 (m, 2H) 3.29 (s, 1H) 2.90-3.18 (m, 6H) 2.27 (ddd, J=9.63, 7.29, 1.08 Hz, 1H) 1.85-1.89 (m, 3H) 1.38 (dd, J=9.78, 5.67 Hz, 1H) 0.86 (t, J=6.36 Hz, 1H).

Preparation of (1S,5S,6S)-methyl 3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylate (Example 111)

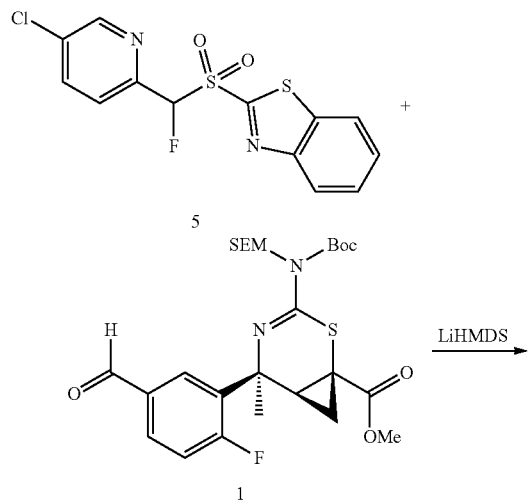

Preparation of (1S,5S,6S)-methyl 3-((tert-butoxycarbonyl)((2-(trimethylsilyl)ethoxy)methyl)amino)-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylate (11)

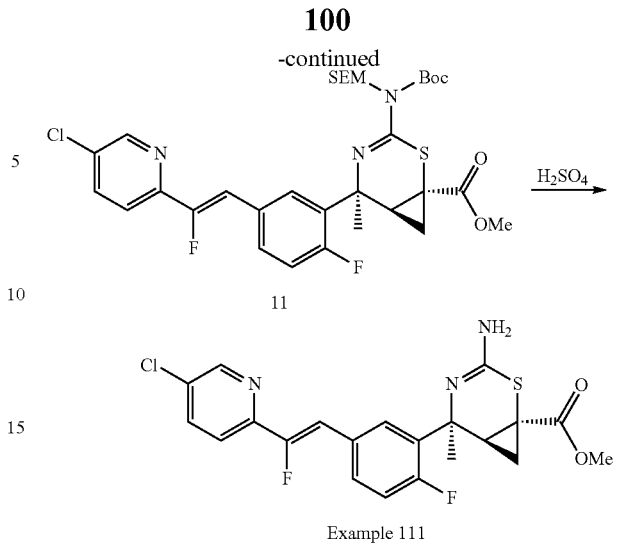

Example 111

To a mixture of (1S,5S,6S)-methyl 3-((tert-butoxycarbonyl)((2-(trimethylsilyl)ethoxy)methyl)amino)-5-(2-fluoro-5-formylphenyl)-5-methyl-2-thia-4-azabicyclo[4.1.0]hept-3-ene-1-carboxylate (1) (170 mg, 0.308 mmol) and 2-(((5-chloropyridin-2-yl)fluoromethyl)sulfonyl)benzo[d]thiazole (5) (170 mg, 0.496 mmol) in 2-Me-THF (3 mL) cooled in an ice bath was added lithium bis(trimethylsilyl)amide, 1.0M solution in THF (600 μL, 0.600 mmol) under N$_2$. The mixture was allowed to warm to room temperature overnight. The mixture was quenched with saturated NH$_4$Cl (5 mL). EtOAc (10 mL) was added, and the organic layer was dried (MgSO$_4$), filtered, and concentrated in vacuo to give an oil. The oil was purified by silica gel chromatography (10 to 30% EtOAc/heptane gradient) to give the product as a clear oil (89 mg, 48% yield). MS m/z=680 [M+H]$^+$. $^1$H NMR (400 MHz, CDCl$_3$) δ 8.54 (d, J=2.35 Hz, 1H), 7.95 (dd, J=2.15, 7.82 Hz, 1H), 7.72 (dd, J=2.45, 8.51 Hz, 1H), 7.65 (ddd, J=2.15, 4.65, 8.46 Hz, 1H), 7.51-7.57 (m, 1H), 7.13 (m, 1H), 7.03 (d, J=40.1 Hz, 1H), 5.27-5.34 (m, 1H), 5.09 (d, J=10.76 Hz, 1H), 3.80 (s, 3H), 3.68 (dd, J=7.73, 8.90 Hz, 2H), 2.67 (dd, J=8.12, 9.29 Hz, 1H), 1.78 (s, 3H), 1.54 (s, 9H), 1.46-1.51 (m, 1H), 1.22-1.29 (m, 1H), 0.96 (dd, J=7.63, 8.80 Hz, 2H), -0.02 (s, 9H). $^{19}$F NMR (376 MHz, CDCl$_3$) δ -111.58 (d, J=1.30 Hz, 1F), -124.13 (d, J=1.95 Hz, 1F).

Preparation of (1S,5S,6S)-methyl 3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylate (Example 111)

A mixture of (1S,5S,6S)-methyl 3-((tert-butoxycarbonyl)((2-(trimethylsilyl)ethoxy)methyl)amino)-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylate (89 mg, 0.13 mmol) and H$_2$SO$_4$ (0.2 mL, 4.0 mmol) was stirred at room temperature for 20 minutes. The orange syrup was quenched with ice (5 g) and neutralized with Na$_2$CO$_3$. The mixture was extracted with EtOAc (15 mL). The organic layer was dried over Na$_2$SO$_4$ and concentrated. The resulting solids were dissolved in DMSO and purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 7 minutes. The product fractions were combined and saturated with Na$_2$CO$_3$. The mixture was extracted with EtOAc (30 mL). The organic layer was washed with saturated NaHCO$_3$ (2×5 mL), brine (5 mL), dried over Na$_2$SO$_4$, filtered, and concentrated. The resulting residue was suspended in MeCN (4 mL) and water (2 mL) and was lyophilized overnight to provide a white foam (60 mg, 100% yield). MS m/z=450 [M+H]$^+$. $^1$H NMR (400 MHz, DMSO-d$_6$) δ 8.70 (d, J=2.35 Hz, 1H), 8.11 (dd, J=2.25, 8.12 Hz, 1H), 8.08 (dd, J=2.45, 8.51 Hz, 1H), 7.72 (d, J=8.02 Hz, 1H), 7.65-7.70 (m, 1H), 7.26 (dd, J=8.51, 12.23 Hz, 1H), 7.11 (d, J=37.17 Hz, 1H), 6.25 (s, 2H), 3.72 (s, 3H), 2.41 (t, J=8.61 Hz, 1H), 1.61 (s, 3H), 1.43 (dd, J=4.89, 9.59 Hz, 1H), 1.00 (dd, J=5.09, 7.43 Hz, 1H). $^{19}$F NMR (376 MHz, DMSO-d$_6$) δ −111.05 (s, 1F), −123.52 (s, 1F).

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(azetidin-1-yl)methanone (Example 112)

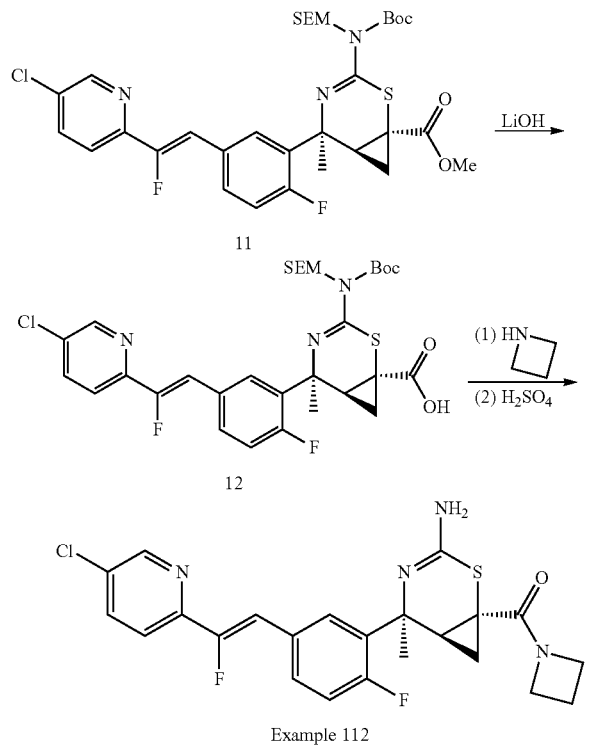

Example 112

Preparation of (1S,5S,6S)-3-((tert-butoxycarbonyl)((2-(trimethylsilyl)ethoxy)methyl)amino)-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylic acid (12)

A mixture of (1S,5S,6S)-methyl 3-((tert-butoxycarbonyl)((2-(trimethylsilyl)ethoxy)methyl)amino)-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylate (11) (250 mg, 0.367 mmol) and lithium hydroxide monohydrate (63 mg, 1.5 mmol) in THF (6 mL) and water (3 mL) was stirred at room temperature. After 1 hour, the mixture was concentrated to ~⅓ volume. HCl (1N) was used to adjust the pH to ~4. The resulting slurry was partitioned between EtOAc (30 mL) and brine (5 mL). The organic layer was dried over Na$_2$SO$_4$, filtered, and concentrated to give a white foam. LCMS indicated the presence of ~13% starting material. This material was used directly in the next steps assuming 100% mass recovery. MS m/z=666 [M+H]$^+$.

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(azetidin-1-yl)methanone (Example 112)

(1S,5S,6S)-3-((tert-Butoxycarbonyl)((2-(trimethylsilyl)ethoxy)methyl)amino)-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylic acid (12) (245 mg, 0.320 mmol) was dissolved in THF (3 mL) followed by the addition of a catalytic amount of 4-dimethylaminopyridine (2.0 mg, 0.016 mmol) and finally 1,1'-carbonyldiimidazole (65 mg, 0.40 mmol). The yellow solution was stirred at 50° C. for 2 hours and was shown by LCMS to be mostly the starting material. One third of this solution was added to a solution of azetidine (47.2 μL, 0.701 mmol) in THF (2 mL). Then HATU (60 mg, 0.16 mmol) was added. The resulting mixture was then stirred at room temperature for 16 hours. The mixture was concentrated to remove most of the volatile organic solvents. The residue was cooled in an ice bath and treated with sulfuric acid (200 μL, 3.75 mmol) dropwise. The resulting material was stirred at room temperature for 30 minutes. Ice (5 mL) was added, and the mixture was neutralized with Na$_2$CO$_3$ until the pH was >10. The mixture was extracted with MeOH-EtOAc (10%, 30 mL). The organic layer was washed with saturated NaHCO$_3$ (2×5 mL), dried over Na$_2$SO$_4$, filtered, and concentrated. The material thus obtained was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 7 minutes. The product fractions were concentrated to half the volume and saturated with Na$_2$CO$_3$. The mixture was extracted with EtOAc (30 mL). The organic layer was washed with saturated NaHCO$_3$ (2×5 mL), brine (5 mL), dried over Na$_2$SO$_4$, filtered, and concentrated. The resulting residue was suspended in MeCN (4 mL) and water (2 mL) and was lyophilized overnight to provide a white foam (22 mg, 14% yield). LCMS (ESI, pos.): calcd for MS m/z=475 [M+H]$^+$. $^1$H NMR (400 MHz, CDCl$_3$) δ 8.51-8.54 (m, 1H), 7.76 (dd, J=2.15, 7.82 Hz, 1H), 7.71 (dd, J=2.45, 8.51 Hz, 1H), 7.63 (ddd, J=2.35, 4.69, 8.41 Hz, 1H), 7.53 (dd, J=1.27, 8.51 Hz, 1H), 7.03-7.11 (m, 1H), 7.02 (d, J=36.39 Hz, 1H), 4.44 (br. s., 2H), 4.12 (q, J=7.24 Hz, 2H), 2.28-2.36 (m, 2H), 2.20-2.27 (m, 1H), 1.79-1.84 (m, 3H), 1.59 (dd, J=5.38, 9.68 Hz, 1H), 0.80 (dd, J=5.87, 6.65 Hz, 1H). $^{19}$F NMR (376 MHz, CDCl$_3$) δ −109.88 (s, 1F), −124.28 (d, J=1.30 Hz, 1F).

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)methanol (113)

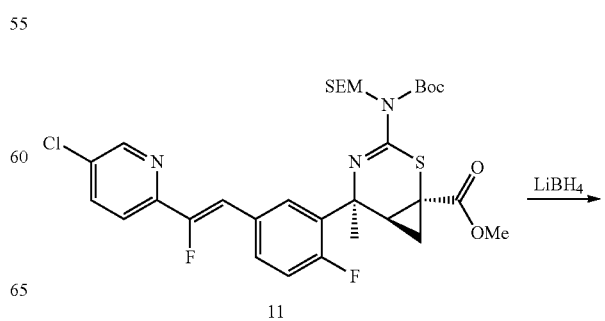

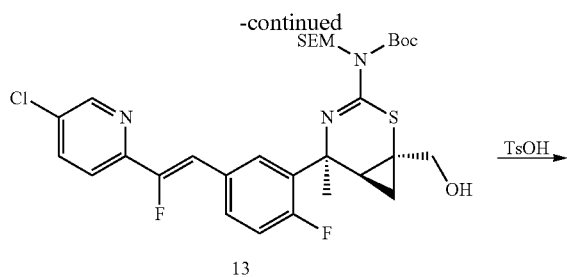

13

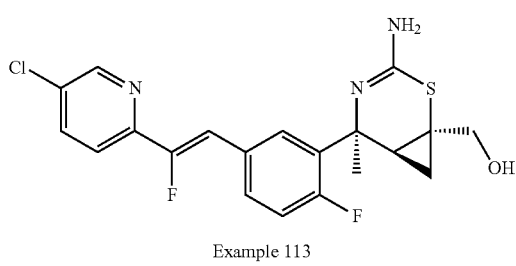

Example 113

Preparation of tert-butyl ((1S,5S,6S)-5-(5-((Z)-2-(5-chloropyridin-2-yl)-2-fluorovinyl)-2-fluorophenyl)-1-(hydroxymethyl)-5-methyl-2-thia-4-azabicyclo[4.1.0]hept-3-en-3-yl)((2-(trimethylsilyl)ethoxy)methyl)carbamate (13)

To a solution of (1S,5S,6S)-methyl 3-((tert-butoxycarbonyl)((2-(trimethylsilyl)ethoxy)methyl)amino)-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylate (11) (350 mg, 0.514 mmol) in THF (5 mL) was added, under N$_2$, lithium borohydride (2M, THF) (0.60 mL, 1.2 mmol) followed by MeOH (0.10 mL, 2.5 mmol). After 1 hour, LCMS indicated the completion of the reduction. The mixture was quenched by the careful addition of saturated NH$_4$Cl solution (0.5 mL). The mixture was diluted with EtOAc (30 mL) and washed with saturated NH$_4$Cl solution (2×50 mL), brine (5 mL), dried over MgSO$_4$ and concentrated to give tert-butyl ((1S,5S,6S)-5-(5-((Z)-2-(5-chloropyridin-2-yl)-2-fluorovinyl)-2-fluorophenyl)-1-(hydroxymethyl)-5-methyl-2-thia-4-azabicyclo[4.1.0]hept-3-en-3-yl)((2-(trimethylsilyl)ethoxy)methyl)carbamate (13) (0.35 g) as a yellow foam. MS m/z=652 [M+H]$^+$.

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)methanol (113)

A mixture of tert-butyl ((1S,5S,6S)-5-(5-((Z)-2-(5-chloropyridin-2-yl)-2-fluorovinyl)-2-fluorophenyl)-1-(hydroxymethyl)-5-methyl-2-thia-4-azabicyclo[4.1.0]hept-3-en-3-yl)((2-(trimethylsilyl)ethoxy)methyl)carbamate (13) (86 mg, 0.13 mmol) and p-toluenesulfonic acid monohydrate (80 mg, 0.42 mmol) in IPA (5 mL) was heated at 85° C. for 1.5 hour. Water (2 mL) was added. Heating was continued for another 2 h. The mixture was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 7 minutes. The product fraction was concentrated to half the volume and treated with Na$_2$CO$_3$ to bring the pH to 12. The mixture was extracted with EtOAc (25 mL). The organic phase was washed with saturated NaHCO$_3$ (2×5 mL), dried over Na$_2$SO$_4$ and concentrated. The foam was taken in MeCN (2 mL) and water (2 mL) and was frozen-lyophilized overnight affording ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)methanol (Example 113) (55 mg, 99% yield) as a white foam (55 mg, 99% yield). MS m/z=422 [M+H]$^+$. $^1$H NMR (400 MHz, CDCl$_3$) δ 8.54 (d, J=2.35 Hz, 1H), 7.84 (d, J=7.28 Hz, 1H), 7.72 (dd, J=2.45, 8.51 Hz, 1H), 7.65 (ddd, J=2.25, 4.60, 8.41 Hz, 1H), 7.55 (dd, J=1.27, 8.51 Hz, 1H), 7.07 (dd, J=8.61, 11.93 Hz, 1H), 6.98-7.11 (d, J=8.61, 39.91 Hz, 1H), 3.69-3.75 (m, 1H), 3.63 (d, J=11.93 Hz, 1H), 1.81 (dd, J=7.14, 9.10 Hz, 1H), 1.77 (s, 3H), 0.88-0.97 (m, 1H), 0.77 (t, J=6.26 Hz, 1H). $^{19}$F NMR (376 MHz, CDCl$_3$) δ −110.67 (br. s., 1F), −124.26 (br. s., 1F).

Preparation of 2-((1R,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)acetonitrile (Example 114)

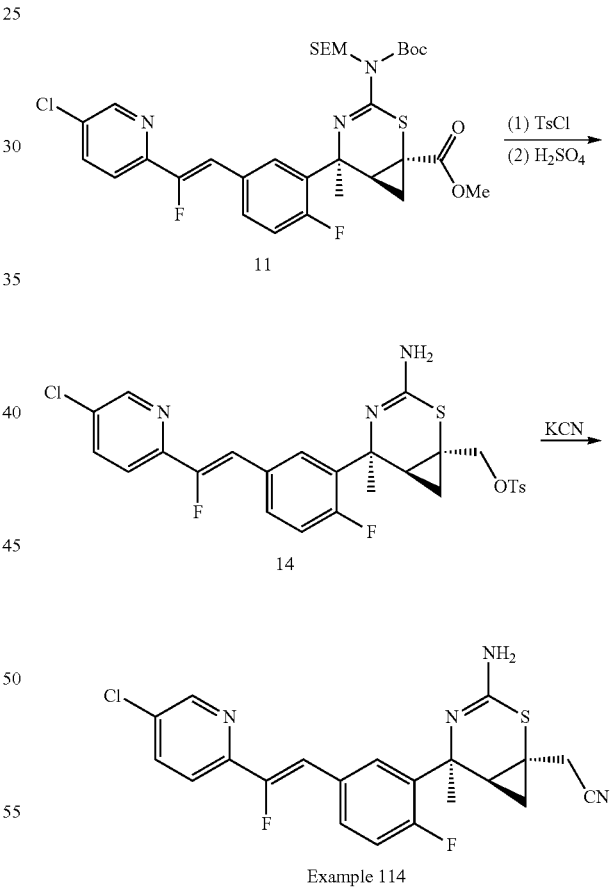

Example 114

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl) methyl 4-methylbenzenesulfonate (14)

A mixture of tert-butyl ((1S,5S,6S)-5-(5-((Z)-2-(5-chloropyridin-2-yl)-2-fluorovinyl)-2-fluorophenyl)-1-(hydroxymethyl)-5-methyl-2-thia-4-azabicyclo[4.1.0]hept-3-en-3-yl)((2-(trimethylsilyl)ethoxy)methyl)carbamate (11) (90 mg, 0.14 mmol), 4-methylbenzene-1-sulfonyl chloride (60 mg, 0.32 mmol) and TEA (50 μL, 0.36 mmol) in DCM (2 mL) was stirred at room temperature for 15 hours. The solvents were removed by a stream of Ar. The residue was then treated with sulfuric acid (0.30 mL, 5.6 mmol). After 10 min, ice (~4 g) was added. The mixture was stirred for 20 minutes. The aqueous layer was decanted. The residue was partitioned between EtOAc (20 mL) and saturated NaHCO$_3$ (10 mL). The organic layer was concentrated. The residue was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 10 minutes. The product fraction was concentrated to half the volume and was treated with Na$_2$CO$_3$ to bring the pH to 12. The mixture was extracted with EtOAc (25 mL). The organic phase was washed with saturated NaHCO$_3$ (2×5 mL), dried over Na$_2$SO$_4$ and concentrated to give ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)methyl 4-methylbenzenesulfonate (14) (39 mg, 49% yield) as a white foam. MS m/z=576 [M+H]$^+$. $^1$H NMR (400 MHz, CDCl$_3$) δ 8.53 (s, 1H), 7.78-7.85 (m, 3H), 7.68-7.74 (m, 1H), 7.61-7.67 (m, 1H), 7.54 (d, J=7.93 Hz, 1H), 7.37 (d, J=8.22 Hz, 2H), 7.01-7.08 (m, 1H), 6.98 (d, J=40.88 Hz, 1H), 4.11 (d, J=0.59 Hz, 1H), 4.05 (d, J=10.95 Hz, 1H), 2.47 (s, 3H), 1.77 (dd, J=7.24, 9.19 Hz, 1H), 1.70 (s, 3H), 0.93-1.01 (m, 1H), 0.80 (t, J=6.46 Hz, 1H). $^{19}$F NMR (376 MHz, CDCl$_3$) δ -110.74 (br. s., 1F), -124.16 (br. s., 1F).

Preparation of 2-((1R,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)acetonitrile (Example 114)

To a mixture of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)methyl 4-methylbenzenesulfonate (14) (33 mg, 0.057 mmol) in DMSO (1 mL) was added potassium cyanide (5.0 mg, 0.077 mmol). The mixture was heated at 50° C. under N$_2$. After 2 hours, the mixture was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 10 min. The product fraction was concentrated to half the volume and was treated with Na$_2$CO$_3$ to bring the pH to 12. The mixture was extracted with EtOAc (25 mL). The organic phase was washed with saturated NaHCO$_3$ (2×5 mL), dried over Na$_2$SO$_4$ and concentrated to give 2-((1R,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)acetonitrile as a white foam (17 mg, 69% yield). MS m/z=431 [M+H]$^+$. $^1$H NMR (400 MHz, CDCl$_3$) δ 8.54 (s, 1H), 7.80 (d, J=7.04 Hz, 1H), 7.72 (dd, J=2.45, 8.51 Hz, 1H), 7.66 (ddd, J=2.35, 4.69, 8.41 Hz, 1H), 7.56 (d, J=7.43 Hz, 1H), 7.04-7.14 (m, 1H), 7.04 (d, J=35.60 Hz, 1H), 2.74-2.83 (m, 1H), 2.63-2.71 (m, 1H), 1.91 (dd, J=6.94, 9.49 Hz, 1H), 1.83 (s, 3H), 1.02-1.13 (m, 1H), 0.88 (t, J=6.55 Hz, 1H). $^{19}$F NMR (376 MHz, CDCl$_3$) δ -110.53 (br. s., 1F), -123.99 (br. s., 1F).

Preparation of (1S,5S,6S)-3-amino-5-(5-((Z)-2-(5-chloropyridin-2-yl)-2-fluorovinyl)-2-fluorophenyl)-N-(3-hydroxybutyl)-5-methyl-2-thia-4-azabicyclo[4.1.0]hept-3-ene-1-carboxamide (Example 115)

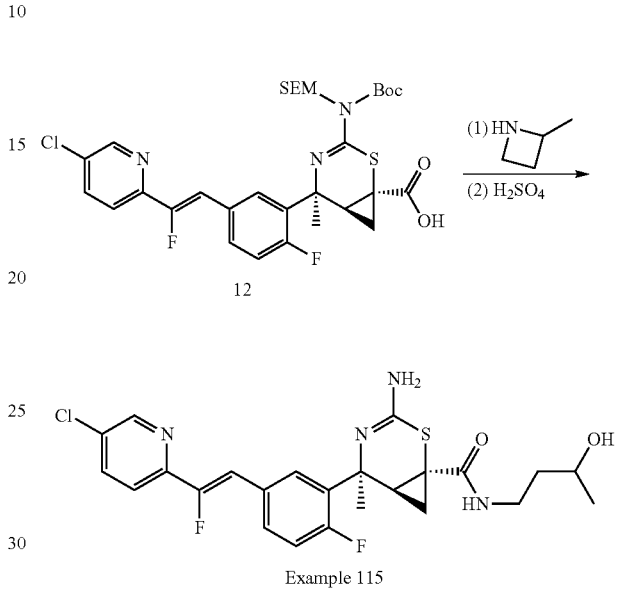

Example 115

The acid 12 (130 mg, 0.185 mmol) (used without further purification) was dissolved in DCM (3 mL) followed by the addition of 2-methylazetidine hydrochloride (50 mg, 0.46 mmol) and 1-(3-dimethylaminopropyl)-3-ethylcarbodiimide HCl salt (97 mg, 0.51 mmol). After 10 minutes, the solvent was removed by a stream of N$_2$ and then under vacuum. The residue was treated with sulfuric acid (300 μL, 5.63 mmol) After 10 minutes, the mixture was quenched with ice (5 mL) and neutralized with solid Na$_2$CO$_3$. The resulting solid was filtered and air dried. The solids were dissolved in DMSO and purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 7 minutes. The product fraction was adjusted to pH ~11 where solids precipitated. The solids were collected on a glass frit and was washed with water (2 mL), and dried under a stream of air to give (1S,5S,6S)-3-amino-5-(5-((Z)-2-(5-chloropyridin-2-yl)-2-fluorovinyl)-2-fluorophenyl)-N-(3-hydroxybutyl)-5-methyl-2-thia-4-azabicyclo[4.1.0]hept-3-ene-1-carboxamide (115) (13 mg, 14% yield) as a white powder. LCMS (ESI, pos.): MS m/z=507 [M+H]$^+$. $^1$H NMR (400 MHz, CDCl$_3$) δ 8.50-8.54 (m, 1H), 7.71 (dd, J=2.45, 8.51 Hz, 1H), 7.58-7.64 (m, 1H), 7.53-7.58 (m, 1H), 7.51 (d, J=8.02 Hz, 1H), 7.11-7.21 (m, 1H), 7.05 (dd, J=8.51, 11.44 Hz, 1H), 6.90-7.02 (m, 1H), 3.84 (ttd, J=3.06, 6.24, 9.38 Hz, 1H), 3.59-3.75 (m, 1H), 3.16-3.29 (m, 1H), 2.16-2.24 (m, 1H), 1.97 (dd, J=4.99, 9.68 Hz, 1H), 1.82 (s, 3H), 1.63-1.72 (m, 1H), 1.47-1.61 (m, 1H), 1.23 (2d, J=6.16 Hz, 3H), 0.76-0.83 (m, 1H). $^{19}$F NMR (376 MHz, CDCl$_3$) δ -108.24 (2s, 1F), -124.18 (s, 1F).

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(2-methylazetidin-1-yl)methanone (Example 116)

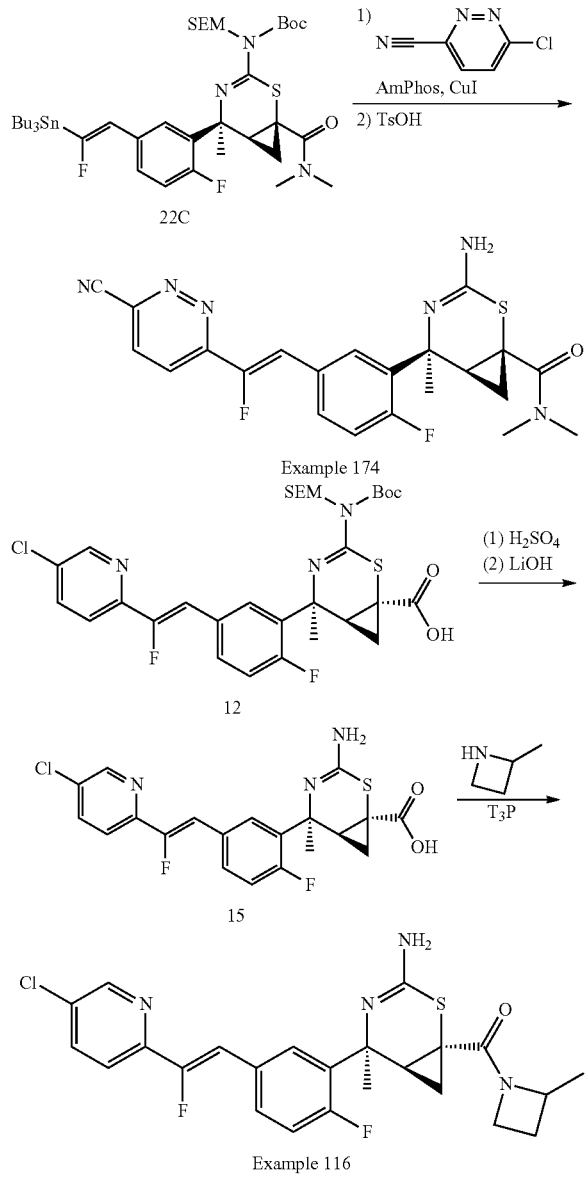

Preparation of (1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylic acid (15)

A mixture of 12 (550 mg, 0.808 mmol) and H₂SO₄ (1.5 mL, 28 mmol) was stirred at room temperature for 20 minutes. The orange syrup was quenched with ice (15 g) followed by NaOH (5N, 12 mL). The mixture was filtered and the solids were suspended in THF-MeOH-water (10-10-5 mL) and were stirred with lithium hydroxide (60 mg, 1.4 mmol). After 2 hours, the mixture was concentrated to remove most of the organic solvents. The pH of the mixture was adjusted to ~2 with HCl (5N). The slurry was filtered and dried on the frit under a stream of air to give (1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylic acid as a brown solid (450 mg, corresponding to 78% purity based on the theoretical yield).

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(2-methylazetidin-1-yl)methanone (Example 116)

The acid 15 (150 mg, 0.268 mmol) was used without further purification and was suspended in DCM (3 mL) followed by the addition of 2-methylazetidine hydrochloride (100 mg, 0.930 mmol), 1-propanephosphonic acid cyclic anhydride (600 µL, 0.943 mmol), and TEA (180 µL, 1.30 mmol) slowly. After 30 minutes, more 1-propanephosphonic acid cyclic anhydride (200 µL, 0.310 mmol) and TEA (90 µL, 0.65 mmol) were added at room temperature. The mixture was heated to 50° C. for 20 minutes. The mixture was quenched with MeOH (1 mL) and was purified by reverse-phase preparative HPLC (Gilson GX281) using a Phenomenex Gemini column, 5 micron, C18, 110 Å, 150×30 mm, 0.1% TFA in CH₃CN/H₂O, gradient 30% to 85% over 12 minutes. The product fractions were concentrated to half the volume and saturated with Na₂CO₃. The slurry was filtered followed by rinsing with water. The residue was dried under a stream of air to give the ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(2-methylazetidin-1-yl)methanone (Example 116) (59 mg, 45% yield) as a white powder. MS m/z=489 [M+H]⁺. ¹H NMR (400 MHz, CDCl₃) δ 8.54 (s, 1H), 7.72 (dd, J=2.35, 8.41 Hz, 2H), 7.64 (dd, J=2.54, 5.48 Hz, 1H), 7.55 (d, J=7.83 Hz, 1H), 7.03-7.12 (m, 1H), 6.98 (d, J=39.52 Hz, 1H), 4.54 (br. s., 1H), 4.13-4.45 (m, 2H), 2.08-2.53 (m, 2H), 1.86-1.94 (m, 1H), 1.85 (s, 3H), 1.75-1.40 (m, 1H), 1.46 (2d, J=6.65 Hz, 3H), 0.72-0.90 (m, 1H). ¹⁹F NMR (376 MHz, CDCl₃) δ −109.53, −109.82 (2s, 1F), −124.14, 124.20 (2s, 1F).

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((S)-2-(methoxymethyl)pyrrolidin-1-yl)methanone (Example 117)

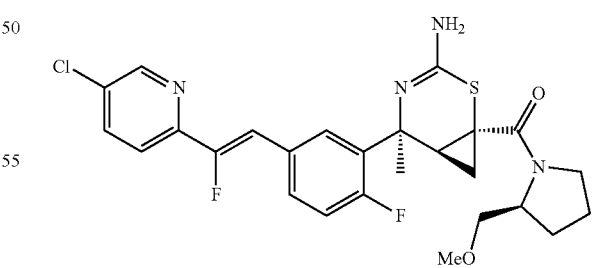

Example 117

The title compound was prepared according to the procedure described for the synthesis of Example 116 using 15 (90 mg, 0.206 mmol) and (S)-(+)-2-(methoxymethyl)pyrrolidine (60 mg, 0.521 mmol) to afford ((1S,5S,6S)-3-amino- 5-(5-((Z)-2-(5-chloropyridin-2-yl)-2-fluorovinyl)-2-fluorophenyl)-5-methyl-2-thia-4-azabicyclo[4.1.0]hept-3-en-1-yl)((S)-2-(methoxymethyl)pyrrolidin-1-yl)methanone (Example 117) (62 mg, 56% yield) as a white sponge. MS m/z=533 [M+H]⁺. ¹H NMR (400 MHz, CDCl₃) δ 8.53 (d, J=2.15 Hz, 1H), 7.70 (dt, J=2.15, 9.29 Hz, 2H), 7.59-7.66 (m, 1H), 7.53 (d, J=8.41 Hz, 1H), 7.06 (t, J=11.0 Hz, 1H) −7.11 (m, 2H), 6.92-7.09 (d, J=40.2 Hz, 1H), 4.21 (br. s., 1H), 3.60-3.79 (m, 2H), 3.48-3.55 (m, 1H), 3.39-3.47 (m, 1H), 3.33 (s, 3H), 2.14 (br. s., 1H), 1.83-2.04 (m, 4H), 1.88 (s, 3H), 1.55 (dd, J=5.97, 9.49 Hz, 1H), 0.77 (t, J=6.16 Hz, 1H). ¹⁹F NMR (376 MHz, CDCl₃) δ −109.58 (br. s., 1F), −124.16 (br. s., 1F).

Preparation of (1S,5S,6S)-3-amino-5-(5-((Z)-2-(5-chloropyridin-2-yl)-2-fluorovinyl)-2-fluorophenyl)-5-methyl-N-phenyl-2-thia-4-azabicyclo[4.1.0]hept-3-ene-1-carboxamide (Example 118)

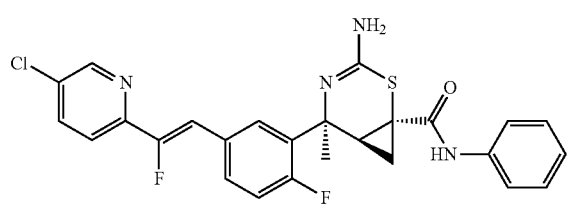 [SMILES: C[C@]1(c2cc(/C=C(\F)c3ccc(Cl)cn3)ccc2F)N=C(N)S[C@@]2(C(=O)Nc3ccccc3)C[C@H]21]

Example 118

The title compound was prepared according to the procedure described for the synthesis of Example 116 using 15 (150 mg, 0.268 mmol) and aniline (40 mg, 0.52 mmol) to afford (1S,5S,6S)-3-amino-5-(5-((Z)-2-(5-chloropyridin-2-yl)-2-fluorovinyl)-2-fluorophenyl)-5-methyl-N-phenyl-2-thia-4-azabicyclo[4.1.0]hept-3-ene-1-carboxamide (56 mg, 41% yield) as a white sponge. MS m/z=511 [M+H]⁺. ¹H NMR (400 MHz, CDCl₃) δ 8.53 (d, J=1.96 Hz, 1H), 8.50 (br. s., 1H), 7.71 (dd, J=2.35, 8.61 Hz, 1H), 7.59-7.65 (m, 1H), 7.53 (t, J=8.41 Hz, 4H), 7.33 (t, J=7.92 Hz, 2H), 7.11-7.16 (m, 1H), 7.08 (dd, J=8.41, 11.35 Hz, 1H), 6.97 (d, J=40.49 Hz, 1H), 2.28-2.37 (m, 1H), 2.16 (dd, J=5.09, 9.59 Hz, 1H), 1.90 (s, 3H), 0.88 (t, J=5.97 Hz, 1H). ¹⁹F NMR (377 MHz, CDCl₃) δ −107.92 (br. s., 1F), −123.93 (br. s., 1F).

Preparation of ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((S)-2-methylazetidin-1-yl)methanone (Example 119) and ((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((R)-2-methylazetidin-1-yl)methanone (Example 120)

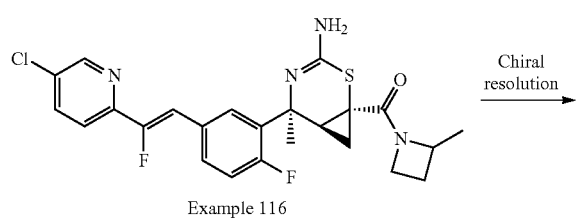

Example 116    Chiral resolution

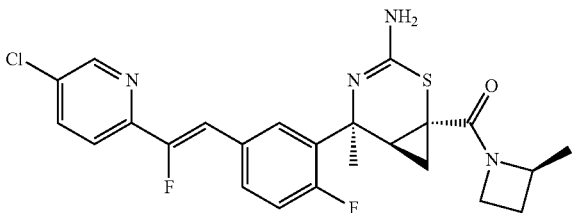

Example 119

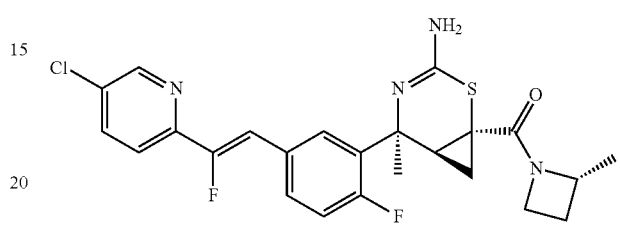

Example 120

A sample of Example 116 (52 mg) was resolved by chiral SFC separation (column: Chiral Technologies IC 21×250 mm, 5 um; mobile phase: 30% EtOH with 20 mM NH₃-70% CO₂; flow rate=70 mL/min, T=40° C.; detection: 220 nm). The first peak was arbitrarily assigned as the (S)-isomer and the second peak was assigned as the (R)-isomer. The product fractions were lyophilized as white foams.

Example 119

((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((S)-2-methylazetidin-1-yl)methanone (27 mg, 52% yield). MS m/z=489 [M+H]⁺. ¹H NMR (400 MHz, CDCl₃) δ 8.53 (s, 1H), 7.69-7.75 (m, 2H), 7.61-7.68 (m, 1H), 7.54 (d, J=8.41 Hz, 1H), 7.02-7.14 (m, 1H), 6.94-7.08 (d, J=37 Hz, 1H), 4.56 (br. s., 1H), 4.42 (br. s., 1H), 4.21 (d, J=5.87 Hz, 1H), 2.45 (td, J=8.85, 17.12 Hz, 1H), 2.07-2.16 (m, 1H), 1.84 (s, 3H), 1.89 (m, 1H), 1.74 (dd, J=5.38, 9.68 Hz, 1H), 1.46 (d, J=6.06 Hz, 3H), 0.75 (t, J=6.26 Hz, 1H). ¹⁹F NMR (377 MHz, CDCl₃) δ −109.82 (br. s., 1F), −124.16 (br. s., 1F).

Example 120

((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((R)-2-methylazetidin-1-yl)methanone (20 mg, 38% yield): MS m/z=489 [M+H]⁺. ¹H NMR (400 MHz, CDCl₃) δ 8.51-8.55 (m, 1H), 7.69-7.79 (m, 2H), 7.60-7.67 (m, 1H), 7.54 (d, J=7.82 Hz, 1H), 7.03-7.13 (m, 1H), 6.97 (d, J=33.65 Hz, 1H), 4.03-4.70 (m, 3H), 2.46 (br. s., 2H), 1.86 (m, 1H), 1.83 (s, 3H), 1.47 (d, J=6.26 Hz, 3H), 1.38 (dd, J=5.38, 9.68 Hz, 1H), 0.86 (t, J=6.16 Hz, 1H). ¹⁹F NMR (377 MHz, CDCl₃) δ −109.58 (br. s., 1F), −124.28 (br. s., 1F).

Preparation (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (16)

Method A.

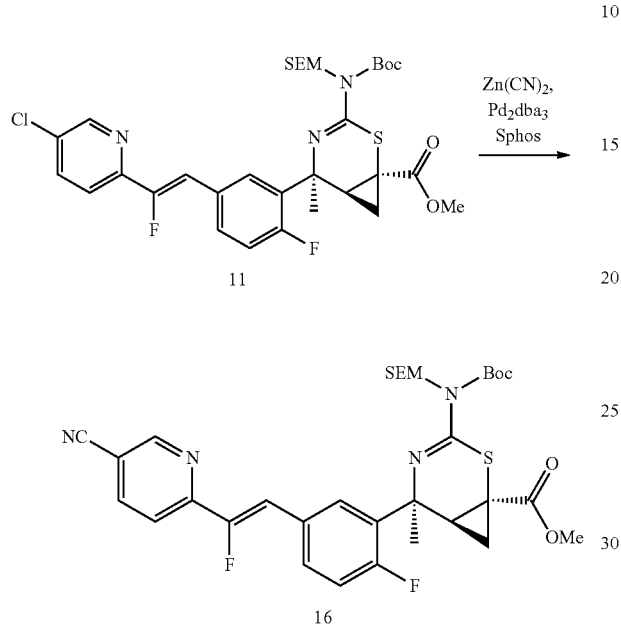

A mixture of dicyclohexyl(2',6'-dimethoxy-[1,1'-biphenyl]-2-yl)phosphine (20 mg, 0.049 mmol) and tris (dibenzylideneacetone) dipalladium (22 mg, 0.024 mmol) in DMA (0.5 mL) was bubbled with Ar for 5 minutes at 50° C. This solution was added to a mixture of zinc cyanide (41 mg, 0.349 mmol) and (1S,5S,6S)-methyl 3-((tert-butoxycarbonyl)((2-(trimethylsilyl)ethoxy)methyl)amino)-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylate (345 mg, 0.507 mmol) in DMA (2.0 mL) under $N_2$. The reaction mixture was heated at 120° C. for 20 hours. The reaction mixture was loaded directly onto a silica cartridge and eluted with 10-40% EtOAc-heptane to give (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (139 mg, 41% yield) as a white foam. MS m/z=671 [M+H]+. $^1$H NMR (400 MHz, CDCl$_3$) δ 8.84 (d, J=1.17 Hz, 1H), 8.02 (ddd, J=2.05, 8.07, 10.22 Hz, 2H), 7.67-7.76 (m, 2H), 7.29 (d, J=38.34 Hz, 1H), 7.15 (dd, J=8.51, 11.83 Hz, 1H), 5.34 (d, J=10.56 Hz, 1H), 5.12 (d, J=10.56 Hz, 1H), 3.82 (s, 3H), 3.66-3.75 (m, 2H), 2.65-2.73 (m, 1H), 1.80 (s, 3H), 1.56 (s, 9H), 1.48-1.54 (m, 1H), 1.23-1.27 (m, 1H), 0.98 (dd, J=7.53, 8.90 Hz, 2H), 0.00 (s, 9H). $^{19}$F NMR (376 MHz, CDCl$_3$) δ −110.10 (d, J=1.95 Hz, 1F), −125.63 (d, J=1.95 Hz, 1F).

Preparation (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (16)

Method B.

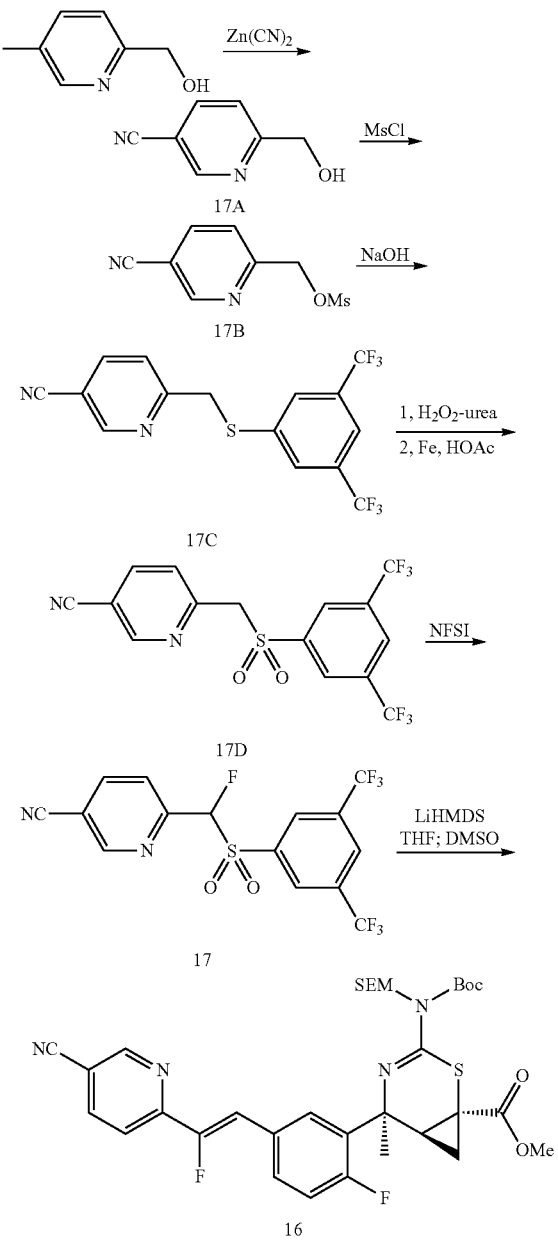

Preparation of 6-(hydroxymethyl)nicotinonitrile (17A)

A mixture of 5-bromo-2-hydroxymethylpyridine (4.90 g, 26.1 mmol), S-phos dicyclohexyl(2',6'-dimethoxy-[1,1'-biphenyl]-2-yl)phosphine (250 mg, 0.609 mmol), zinc cyanide (1.90 g, 16.2 mmol), and tris(dibenzylideneacetone) dipalladium (250 mg, 0.273 mmol) in DMF (5.5 mL) was degassed with a stream of Ar passing through the mixture for 1 minute. The mixture was heated at 80° C. under N₂. After 4.5 hours, a second batch of the catalysts were prepared by mixing S-phos dicyclohexyl(2',6'-dimethoxy-[1,1'-biphenyl]-2-yl)phosphine (250 mg, 0.609 mmol) and tris (dibenzylideneacetone) dipalladium (250 mg, 0.273 mmol) in DMF (2 mL) under N₂. The mixture was stirred at 35° C. for 2 minutes before it was added to the reaction mixture. After an additional 3 hours, water (0.5 mL) was added. The mixture was stirred for 1.5 hours and was allowed to cool to room temperature and was mixed with silica gel. The solvents were removed at 50° C. The solids were purified by chromatography on silica using EtOAc in heptane (20-50%) as eluent to give 6-(hydroxymethyl)nicotinonitrile (17A) as a white powder (1.38 g). MS m/z=135 [M+H]⁺. ¹H NMR (400 MHz, CDCl₃) δ 8.85 (s, 1H), 7.97 (dd, J=1.96, 8.02 Hz, 1H), 7.47 (d, J=8.22 Hz, 1H), 4.86 (s, 2H), 2.61-3.26 (m, 1H).

Preparation of (5-cyanopyridin-2-yl)methyl methanesulfonate (7B)

A solution of 6-(hydroxymethyl)nicotinonitrile (7A) (1.38 g, 10.3 mmol) in DCM (60 mL) was cooled in an ice bath under N₂. TEA (2.0 mL, 14 mmol) was added followed by drop wise addition of methanesulfonyl chloride (0.90 mL, 12 mmol). After 1 hour, saturated NaHCO₃ (30 mL) was added. The layers were separated. The aqueous layer was extracted with DCM (2×10 mL). The combined organic layers were dried over MgSO₄, filtered, and concentrated to give (5-cyanopyridin-2-yl)methyl methanesulfonate (7B) as a light yellow powder (2.1 g, 96% yield). MS m/z=213 [M+H]⁺. ¹H NMR (400 MHz, CDCl₃) δ 8.87 (s, 1H), 8.04 (dd, J=1.86, 8.12 Hz, 1H), 7.64 (d, J=8.22 Hz, 1H), 5.38 (s, 2H), 3.15 (s, 3H).

Preparation of 6-(((3,5-bis(trifluoromethyl)phenyl)thio)methyl)nicotinonitrile (7C)

Step (3) To a solution of 3,5-bis-trifluoromethyl benzenethiol (7B) (2.5 g, 9.9 mmol) in MeOH (15 mL) was added sodium hydroxide 0.5N (2.0 mL, 10 mmol) under N₂. After 10 min, (5-cyanopyridin-2-yl)methyl methanesulfonate (7B) (2.0 g, 9.4 mmol) was added followed by MeOH rinsing (~30 mL). The thick mixture was stirred at room temperature for 15 minutes. EtOAc (120 mL) was then added. The mixture was washed with half-saturated NH₄Cl (50 mL). The aqueous layer was extracted with EtOAc (50 mL). The combined organic layers were dried over Na₂SO₄, filtered, and concentrated to give 6-(((3,5-bis(trifluoromethyl)phenyl)thio)methyl)nicotinonitrile (7C) as a light yellow powder (3.5 g, 100% yield). MS m/z=363 [M+H]⁺. ¹H NMR (400 MHz, CDCl₃) δ 8.79 (d, J=1.56 Hz, 1H), 7.93 (dd, J=2.05, 8.12 Hz, 1H), 7.75 (s, 2H), 7.66 (s, 1H), 7.51 (d, J=8.22 Hz, 1H), 4.38 (s, 2H). ¹⁹F NMR (376 MHz, CDCl₃) δ −63.14 (s, 1F).

Preparation of 6-(((3,5-bis(trifluoromethyl)phenyl)sulfonyl)methyl)nicotinonitrile (7D)

To a slurry of hydrogen peroxide urea adduct (3.0 g, 32 mmol) in ACN (18 mL) cooled at 0° C. was added trifluoroacetic anhydride (4.5 mL, 32 mmol) in 10 portions while the internal temperature was kept ~0-5° C. The mixture was stirred for 0.5 hour. To a suspension of 6-(((3,5-bis(trifluoromethyl)phenyl)thio)methyl)nicotinonitrile (7C) (3.52 g, 9.72 mmol) in ACN (10 mL) cooled in an ice bath was added the hydrogen peroxide urea solution (15 mL, 27 mmol, ~2.7 equiv.) prepared above in small portions. After 10 minutes, the mixture was allowed to stir at room temperature. After 30 minutes, LCMS indicated the completion of the reaction. The mixture was cooled in an ice bath, EtOAc (100 mL) was added and was quenched with saturated NaHCO₃ until the pH of the aqueous layer became basic. Solid Na₂S₂O₃ (1.6 g, 10 mmol) was added followed by NaCl to saturate the aqueous layer. The aqueous layer was extracted with EtOAc (2×30 mL). The combined organic phase was dried over MgSO₄, filtered, and concentrated to give a light yellow solid (4.40 g) as a mixture of pyridine and pyridine N-oxide. This mixture was taken in EtOH (5 mL) under N2. Acetic acid (6.0 mL, 104 mmol) followed by iron (2.0 g, 35.8 mmol) were under. The mixture was heated at 75° C. for 1 hour. The mixture was filtered through a pad of Celite® filter aid and the filtrate was concentrated. The Celite® filter aid pad was rinsed with EtOAc (3×15 mL). The combined washings were washed with NaHCO₃ (2×5 mL), brine (5 mL), dried over Na₂SO₄, and concentrated to give 6-(((3,5-bis(trifluoromethyl)phenyl)sulfonyl)methyl)nicotinonitrile (7D) (3.8 g, 91% overall yield) as a yellow solid. MS m/z=395 [M+H]⁺. ¹H NMR (400 MHz, CDCl₃) δ 8.63 (d, J=1.56 Hz, 1H), 8.03-8.18 (m, 4H), 7.70 (d, J=8.02 Hz, 1H), 4.67 (s, 2H). ¹⁹F NMR (376 MHz, CDCl₃) δ −62.99 (s, 1F).

Preparation of 6-(((3,5-bis(trifluoromethyl)phenyl)sulfonyl)fluoromethyl)-nicotinonitrile (7)

To a solution of 6-(((3,5-bis(trifluoromethyl)phenyl)sulfonyl)methyl)-nicotinonitrile (7D) (1.94 g, 4.92 mmol) in THF (10 mL) cooled in an ice bath was added lithium bis(trimethylsilyl)amide, 1.0M solution in THF (5.5 mL, 5.5 mmol) under N₂. The mixture was stirred at room temperature for 30 minutes before it was cooled in a −78° C. bath. After 10 minutes of cooling, a solution of N-fluorobenzenesulfonimide (NFSI) (1.8 g, 5.7 mmol) in THF (10 mL) was added. The cooling bath was removed. After 30 minutes, EtOAc-heptane (1:1, 100 mL) was added. The mixture was washed with saturated NaHCO₃ (3×30 mL), brine (10 mL), dried over Na₂SO₄, filtered, and concentrated. The residue was purified by chromatography on silica using EtOAc in heptane (20-55%) as eluent to give 6-(((3,5-bis(trifluoromethyl)phenyl)sulfonyl)fluoro-methyl) nicotinonitrile (7) as a white solid. The combined product from three runs with a total of 2.58 g of substrate was 1.62 g (60% yield). MS m/z=413 [M+H]⁺. ¹H NMR (400 MHz, CDCl₃) δ ppm 8.95 (d, J=2.0 Hz, 1H), 8.38 (s, 2H), 8.26 (s, 1H), 8.15 (dd, J=8.2, 2.0 Hz, 1H), 7.78 (d, J=8.2 Hz, 1H), 6.30 (d, J=46.8 Hz, 1H). ¹⁹F NMR (376 MHz, CDCl₃) δ ppm −62.95 (s, 6F), −177.20 (s, 1F).

Preparation (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (16)

To a mixture of (1S,5S,6S)-methyl 3-((tert-butoxycarbonyl)((2-(trimethylsilyl)ethoxy)methyl)amino)-5-(2-fluoro-5-formylphenyl)-5-methyl-2-thia-4-azabicyclo[4.1.0]hept-3-ene-1-carboxylate (1) (2.18 g, 3.94 mmol) and 6-(((3,5-bis(trifluoromethyl)phenyl)sulfonyl)fluoromethyl) nicotinonitrile (7) (1.54 g, 3.74 mmol) in THF (25 mL), cooled in an ice bath, was added lithium bis(trimethylsilyl) amide, 1.0M in THF (4.0 mL, 4.0 mmol) under N₂. After 10 minutes, the ice bath was removed and DMSO (8 mL) was added. The resulting red solution was stirred at room temperature for 5 hours. The mixture was diluted with EtOAc-heptane (1:1, 200 mL) and was washed with saturated NaHCO$_3$ (30 mL) and water (3×15 mL). The aqueous layer was extracted with EtOAc-heptane (1:1, 30 mL). The combined organic phase was washed with brine (15 mL), dried over Na$_2$SO$_4$, filtered, and concentrated. The residue was purified by silica gel chromatography [0%, then 0% to 50% (EtOAc-heptane)/DCM gradient] to give (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (16) (1 µg, 44% yield) as a yellow foam.

Preparation (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (16)

Method C.

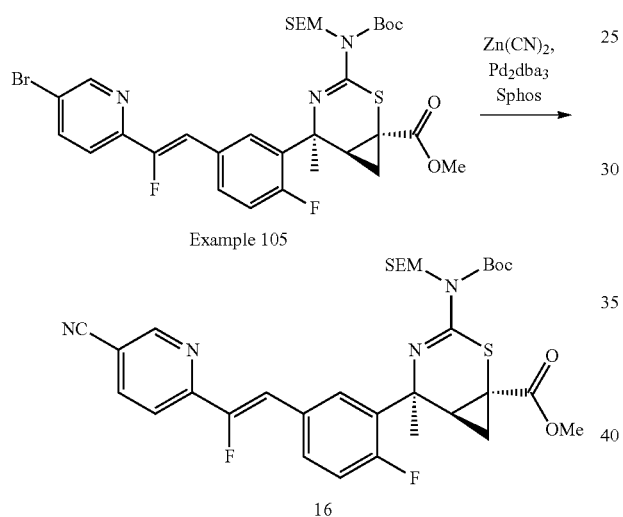

A mixture of 2-(dicyclohexylphosphino)-2',6'-dimethoxy-1,1'-biphenyl (0.244 g, 0.593 mmol) and tris (dibenzylideneacetone) dipalladium (0.272 g, 0.297 mmol) was mixed in DMA (2 mL) and then argon was bubbled through for 5 minutes at 50° C. This solution was added to a mixture of (1S,5S,6S)-methyl 5-(5-((Z)-2-(5-bromopyridin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (Example 105) (4.30 g, 5.93 mmol) and zinc cyanide (0.45 g, 3.8 mmol) in DMA (15 mL) under argon. The mixture was heated to 115° C. for 2 hours and was allowed to cool to room temperature. The mixture was diluted with EtOAc (150 mL), washed with saturated NaHCO$_3$ (3×50 mL), and dried (MgSO$_4$). After filtering and concentrating in vacuo, the resulting oil was purified by silica gel chromatography (10 to 50% EtOAc/heptane gradient) to give (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (16) (3.4 g, 85% yield) as a white solid. MS m/z=671 [M+H]$^+$.

Preparation of (1S,5S,6S)-3-amino-5-(5-((Z)-2-(5-cyanopyridin-2-yl)-2-fluorovinyl)-2-fluorophenyl)-N-cyclopropyl-5-methyl-2-thia-4-azabicyclo[4.1.0]hept-3-ene-1-carboxamide (Example 121)

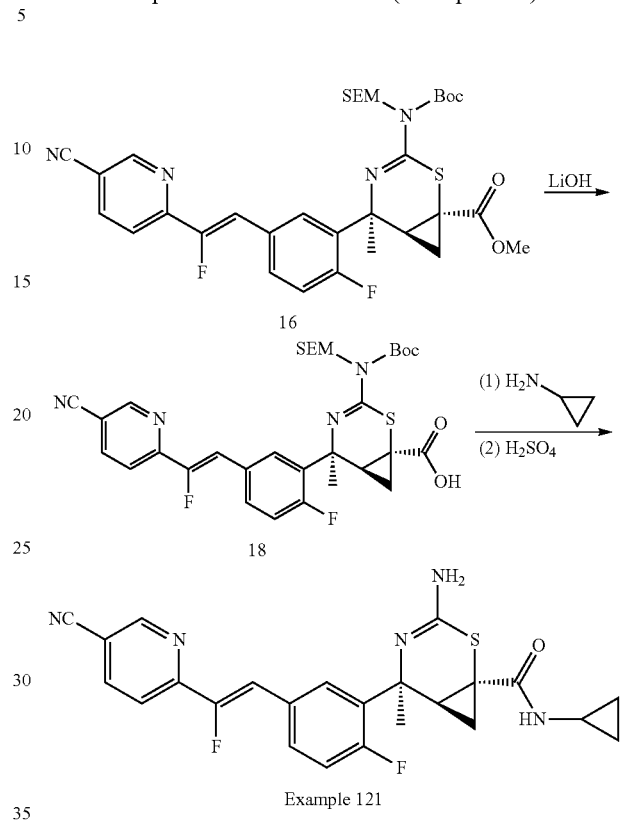

Preparation of (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (18)

To a mixture of (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (16) (139 mg, 0.207 mmol) in THF (5 mL)-water (2.5 mL) was added lithium hydroxide monohydrate (40 mg, 0.95 mmol). The mixture was stirred at room temperature for 1.5 hours. EtOAc (20 mL) was added followed by HCl (1N, 0.9 mL). The mixture was washed with brine (5 mL), dried over Na$_2$SO$_4$, filtered, and concentrated to give (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (18) (0.15 g) as a white foam. This material was used without purification in the next step. MS m/z=657 [M+H]$^+$.

Preparation of (1S,5S,6S)-3-amino-5-(5-((Z)-2-(5-cyanopyridin-2-yl)-2-fluorovinyl)-2-fluorophenyl)-N-cyclopropyl-5-methyl-2-thia-4-azabicyclo[4.1.0]hept-3-ene-1-carboxamide (Example 121)

To a solution of (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (18) (136 mg, 0.207 mmol) in DCM (2 mL) was added cyclopropylamine (0.037 mL, 0.52 mmol) followed by 1-propanephosphonic acid cyclic anhydride, 50 wt. % solution in EtOAc (0.40 mL, 0.63 mmol). The mixture was heated at 50° C. for 1 hour. MeOH (0.5 mL) was then added and the mixture was concentrated under vacuum to give the product as a light yellow syrup. The resulting material was dissolved in IPA (3 mL) and was treated with a solution of sulfuric acid (32.6 µL, 0.612 mmol) in water (2 mL). The mixture was heated at 65° C. for 1 hour. More sulfuric acid (32.6 µL, 0.612 mmol) was added, and the solution was heated for an additional 1 hour. The mixture was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 10 minutes. The product fractions were concentrated to ~½ volume. EtOAc (30 mL) and solid Na$_2$CO$_3$ (1 g) were added. The mixture was shaken in a separatory funnel. The organic layer was washed with saturated NaHCO$_3$, dried over Na$_2$SO$_4$, filtered, and concentrated. The residue was taken up in MeCN (3 mL) and water (2 mL) and lyophilized overnight to give (1S,5S,6S)-3-amino-5-(5-((Z)-2-(5-cyanopyridin-2-yl)-2-fluorovinyl)-2-fluorophenyl)-N-cyclopropyl-5-methyl-2-thia-4-azabicyclo[4.1.0]hept-3-ene-1-carboxamide (Example 121) (72 mg, 75% yield) as a white sponge. MS m/z=466 [M+H]$^+$. $^1$H NMR (400 MHz, CDCl$_3$) δ 8.81 (s, 1H), 8.00 (dd, J=1.96, 8.41 Hz, 1H), 7.60-7.71 (m, 2H), 7.52-7.60 (m, 1H), 7.11-7.23 (m, 1H), 7.09 (dd, J=8.51, 11.44 Hz, 1H), 6.69 (br. s., 1H), 2.74 (qt, J=3.64, 7.05 Hz, 1H), 2.26 (t, J=8.41 Hz, 1H), 2.01 (dd, J=5.09, 9.59 Hz, 1H), 1.86 (s, 3H), 0.74-0.84 (m, 3H), 0.52-0.61 (m, 2H). $^{19}$F NMR (376 MHz, CDCl$_3$) δ −106.66 (br. s., 1F), −125.53 (br. s., 1F).

Preparation of (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (19)

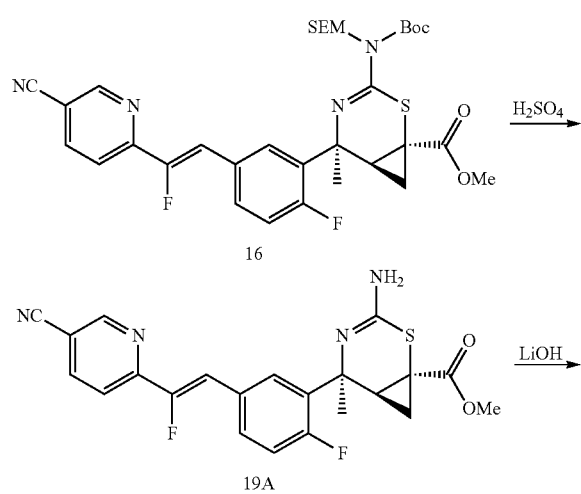

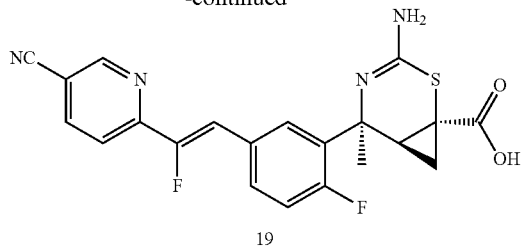

Preparation of (1S,5S,6S)-methyl 3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (19A)

To a solution of (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (1.10 g, 1.64 mmol) in IPA (15 mL) was added water (15 mL) followed by sulfuric acid (0.40 mL, 7.5 mmol). The slurry was heated at 65° C. for 1.5 hours. The mixture was concentrated to half volume. The resulting slurry was quenched with saturated NaHCO$_3$ (50 mL) and was extracted with CHCl$_3$ containing 1% IPA (3×50 mL). The combined organic phases were dried over Na$_2$SO$_4$, filtered, and concentrated. The residue was purified by chromatography on silica using MeOH in DCM (0-5%) as eluent to give (1S,5S,6S)-methyl 3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (19A) (0.55 g, 76% yield) as a white foam. MS m/z=441 [M+H]$^+$. $^1$H NMR (400 MHz, CDCl$_3$) δ ppm 8.83 (d, J=1.0 Hz, 1H), 8.02 (dd, J=8.3, 2.1 Hz, 1H), 7.94-7.99 (m, 1H), 7.67-7.76 (m, 2H), 7.27 (d, J=35.8 Hz, 1H), 7.12 (dd, J=11.8, 8.5 Hz, 1H), 3.80 (s, 3H), 2.57 (dd, J=9.1, 8.1 Hz, 1H), 1.76 (s, 3H), 1.57 (dd, J=9.6, 5.1 Hz, 1H), 1.14 (dd, J=7.4, 5.5 Hz, 1H). $^{19}$F NMR (376 MHz, CDCl$_3$) δ ppm −109.23 (br. s., 1F), −125.67 (br. s., 1F).

Preparation of (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (19)

A mixture of (1S,5S,6S)-methyl 3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylate (19A) (0.55 g, 1.2 mmol) and lithium hydroxide monohydrate (0.073 mL, 2.6 mmol) in THF (10 mL), MeCN (10 mL) and water (10 mL) was stirred at rt. After 1.5 hours, HCl (1N, 2.6 mL, 2.6 mmol) was added. The mixture was concentrated to remove most of the THF. The mixture was suspended in saturated NaHCO$_3$ (20 mL) and was agitated for 5 min. The slurry was filtered on a glass frit and the residue was washed with water (10 mL) and dried by air flowing through. The resulting white powder (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (19) (0.47 g, 88% yield) was shown to be ~94% pure based on LCMS (LCAP@215 and 254 nm). MS m/z=427 [M+H]$^+$.

Preparation of 6-((Z)-2-(3-((1S,5S,6S)-3-amino-1-(3,3-difluoropyrrolidine-1-carbonyl)-5-methyl-2-thia-4-azabicyclo[4.1.0]hept-3-en-5-yl)-4-fluorophenyl)-1-fluorovinyl)nicotinonitrile (Example 122)

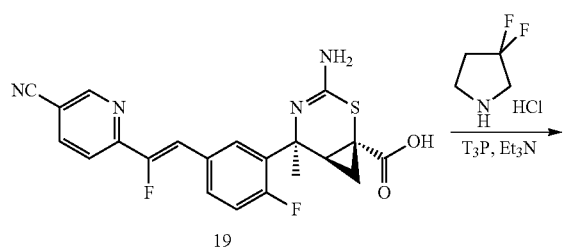

19

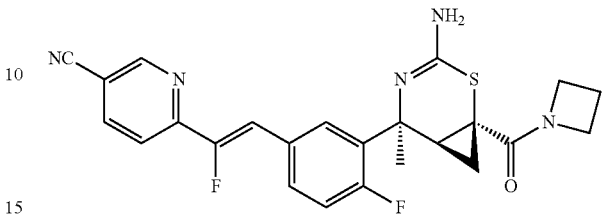

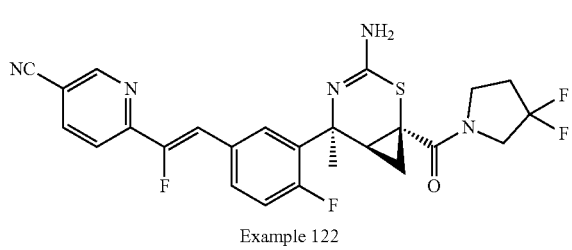

Example 122

To a mixture of (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (19) (0.13 g, 0.17 mmol) and 3,3-difluoropyrrolidine hydrochloride (0.070 g, 0.49 mmol) in DCM (3 mL) was added 1-propanephosphonic acid cyclic anhydride (50% in EtOAc) (0.50 mL, 0.79 mmol) followed by TEA (0.10 mL, 0.72 mmol). The mixture was stirred at 50° C. for 20 minutes. The mixture was diluted with MeOH (1 mL) and was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 10 minutes. The product fractions were concentrated to ~½ volume. EtOAc (30 mL) and solid Na$_2$CO$_3$ (1 g) was added. The mixture was shaken in a separatory funnel. The aqueous layer was extracted with EtOAc (5 mL). The combined organic layers were washed with saturated NaHCO$_3$, dried over Na$_2$SO$_4$, filtered, and concentrated. The residue was taken in MeCN (3 mL) and water (2 mL) and lyophilized overnight to give 6-((Z)-2-(3-((1S,5S,6S)-3-amino-1-(3,3-difluoropyrrolidine-1-carbonyl)-5-methyl-2-thia-4-azabicyclo[4.1.0]hept-3-en-5-yl)-4-fluorophenyl)-1-fluorovinyl)nicotinonitrile (Example 122) (60 mg, 68% yield) as a light yellow sponge. MS m/z=515 [M+H]$^+$. $^1$H NMR (400 MHz, CDCl$_3$) δ 8.82 (s, 1H), 8.01 (d, J=8.41 Hz, 1H), 7.74 (d, J=7.82 Hz, 1H), 7.68 (d, J=8.02 Hz, 2H), 7.63-7.70 (m, 2H), 7.22 (d, J=36.2 Hz, 1H), 7.09 (dd, J=8.51, 11.44 Hz, 1H), 3.64-4.07 (m, 4H), 2.40 (br. s., 2H), 2.27 (t, J=8.41 Hz, 1H), 1.88 (s, 3H), 1.49 (dd, J=5.77, 9.49 Hz, 1H), 0.84 (t, J=6.26 Hz, 1H). $^{19}$F NMR (377 MHz, CDCl$_3$) δ -101.57 (d, J=78.03 Hz, 2F), -108.10 (br. s., 1F), -125.61 (br. s., 1F).

Preparation of 6-((Z)-2-(3-((1S,5S,6S)-3-amino-1-(azetidine-1-carbonyl)-5-methyl-2-thia-4-azabicyclo[4.1.0]hept-3-en-5-yl)-4-fluorophenyl)-1-fluorovinyl)nicotinonitrile (Example 123)

Example 123

This compound was prepared in a similar manner to the procedure described for the synthesis of Example 122 using acid 19 (0.15 g, 0.20 mmol) and azetidine (0.051 g, 0.89 mmol) to afford 6-((Z)-2-(3-((1S,5S,6S)-3-amino-1-(azetidine-1-carbonyl)-5-methyl-2-thia-4-azabicyclo[4.1.0]hept-3-en-5-yl)-4-fluorophenyl)-1-fluorovinyl)nicotinonitrile (Example 123) (0.072 g, 79% yield) as a light yellow sponge. MS m/z=466 [M+H]$^+$. $^1$H NMR (400 MHz, CDCl$_3$) δ 8.82 (s, 1H), 8.01 (d, J=8.41 Hz, 1H), 7.78 (d, J=7.04 Hz, 1H), 7.68 (d, J=7.82 Hz, 2H), 7.24 (d, J=32.47 Hz, 1H), 7.10 (dd, J=8.51, 11.64 Hz, 1H), 4.44 (br. s., 2H), 4.09 (br. s., 2H), 2.22-2.39 (m, 3H), 1.84 (s, 3H), 1.51-1.74 (m, 1H), 0.81 (t, J=6.16 Hz, 1H). $^{19}$F NMR (377 MHz, CDCl$_3$) δ -108.27 (br. s., 1F), -125.67 (br. s., 1F).

Preparation of 6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)nicotinonitrile (Example 124)

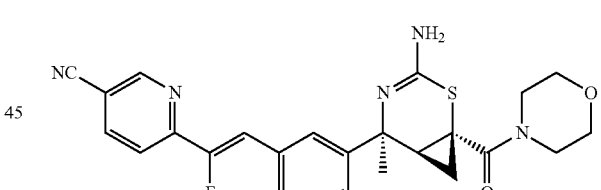

Example 124

This compound was prepared in a similar manner to the procedure described for the synthesis of Example 122 using acid 19 (0.15 g, 0.19 mmol) and morpholine (0.044 g, 0.51 mmol) to afford 6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)nicotinonitrile (Example 124) (54 mg, 57% yield) as a white sponge. MS m/z=496 [M+H]$^+$. $^1$H NMR (400 MHz, CDCl$_3$) δ 8.82 (s, 1H), 8.01 (dd, J=2.05, 8.31 Hz, 1H), 7.80 (d, J=7.82 Hz, 1H), 7.69 (d, J=7.43 Hz, 2H), 7.25 (d, J=38.9 Hz, 1H), 7.10 (dd, J=8.61, 11.54 Hz, 1H), 3.69 (d, J=3.52 Hz, 4H), 3.66 (br. s., 4H), 2.33 (s, 1H), 1.86 (s, 3H), 1.37 (dd, J=5.67, 9.98 Hz, 1H), 0.90 (t, J=6.55 Hz, 1H). $^{19}$F NMR (377 MHz, CDCl$_3$) δ -108.32 (br. s., 1F), -125.66 (br. s., 1F).

Preparation of 6-((Z)-2-(3-((1S,5S,6S)-3-amino-1-((S)-3-hydroxypyrrolidine-1-carbonyl)-5-methyl-2-thia-4-azabicyclo[4.1.0]hept-3-en-5-yl)-4-fluorophenyl)-1-fluorovinyl)nicotinonitrile (Example 125)

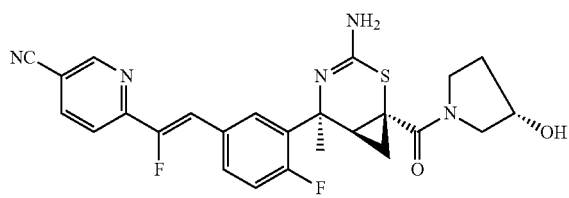 [SMILES: C[C@]1(c2cc(/C=C(\F)c3ccc(C#N)cn3)ccc2F)N=C(N)S[C@@]2(C(=O)N3CC[C@H](O)C3)C[C@H]21]

Example 125

This compound was prepared in a similar manner to the procedure described for the synthesis of Example 122 using acid 19, with the exception that (S)-(−)-3-hydroxypyrrolidine (0.10 mL, 1.2 mmol) was added after the acid 19 (0.15 g, 0.191 mmol) and the T3P reagent was aged for 5 min, to afford 6-((Z)-2-(3-((1S,5S,6S)-3-amino-1-((S)-3-hydroxypyrrolidine-1-carbonyl)-5-methyl-2-thia-4-azabicyclo[4.1.0]hept-3-en-5-yl)-4-fluorophenyl)-1-fluorovinyl)nicotinonitrile (Example 125) (39 mg, 41% yield) as a white sponge MS m/z=496 [M+H]+. 1H NMR (400 MHz, CDCl3) δ 8.82 (s, 1H), 8.01 (d, J=8.61 Hz, 1H), 7.66-7.76 (m, 3H), 7.24 (d, J=30.71 Hz, 1), 7.10 (t, J=9.76 Hz, 1H), 4.55 (br. s., 1H), 3.74 (br. s., 2H), 3.63 (br. s., 2H), 2.36 (br. s., 1H), 2.04 (m, 2H), 1.90 (s, 3H), 1.47 (br. s., 1H), 0.87 (br. s., 1H). 19F NMR (377 MHz, CDCl3) δ −107.97 (br. s., 1F), −125.55 (br. s., 1F).

Preparation of 6-((Z)-2-(3-((1S,5S,6S)-3-amino-1-((R)-3-fluoropyrrolidine-1-carbonyl)-5-methyl-2-thia-4-azabicyclo[4.1.0]hept-3-en-5-yl)-4-fluorophenyl)-1-fluorovinyl)nicotinonitrile (Example 126)

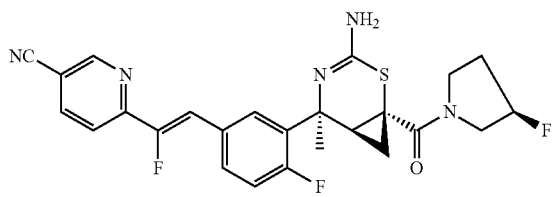 [SMILES: C[C@]1(c2cc(/C=C(\F)c3ccc(C#N)cn3)ccc2F)N=C(N)S[C@@]2(C(=O)N3CC[C@@H](F)C3)C[C@H]21]

Example 126

This compound was prepared in a similar manner to the procedure described for the synthesis of Example 122 using acid 19 (0.135 g, 0.172 mmol) and (R)-(−)-3-fluoropyrrolidine hydrochloride (40 mg, 0.319 mmol) to afford 6-((Z)-2-(3-((1S,5S,6S)-3-amino-1-((R)-3-fluoropyrrolidine-1-carbonyl)-5-methyl-2-thia-4-azabicyclo[4.1.0]hept-3-en-5-yl)-4-fluorophenyl)-1-fluorovinyl)nicotinonitrile (Example 126) (59 mg, 69% yield) as a white sponge. MS m/z=498 [M+H]+. 1H NMR (400 MHz, CDCl3) δ ppm 8.80-8.84 (m, 1H), 8.01 (dd, J=8.4, 2.2 Hz, 1H), 7.74 (d, J=7.6 Hz, 1H), 7.65-7.71 (m, 2H), 7.24 (d, J=34.2 Hz, 1H), 7.09 (dd, J=11.5, 8.4 Hz, 1H), 5.16-5.42 (m, 1H), 3.50-4.10 (m, 4H), 2.33 (br. s., 1H), 2.11-2.20 (m, 2H), 1.88 (s, 3H), 1.58 (dd, J=9.8, 5.7 Hz, 1H), 0.79 (br. s., 1H). 19F NMR (377 MHz, CDCl3) δ ppm −108.03 (d, J=36.4 Hz, 1F), −125.68 (s, 1F), −177.68 (s, 1F).

Preparation of 6-((Z)-2-(3-((1S,5S,6S)-3-amino-1-((S)-3-fluoropyrrolidine-1-carbonyl)-5-methyl-2-thia-4-azabicyclo[4.1.0]hept-3-en-5-yl)-4-fluorophenyl)-1-fluorovinyl)nicotinonitrile (Example 127)

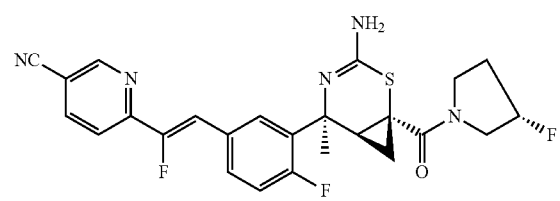 [SMILES: C[C@]1(c2cc(/C=C(\F)c3ccc(C#N)cn3)ccc2F)N=C(N)S[C@@]2(C(=O)N3CC[C@H](F)C3)C[C@H]21]

Example 127

This compound was prepared in a similar manner to the procedure described for the synthesis of Example 122 using acid 19 (0.135 g, 0.172 mmol) and (S)-(+)-3-fluoropyrrolidine hydrochloride (40 mg, 0.319 mmol) to afford 6-((Z)-2-(3-((1S,5S,6S)-3-amino-1-((S)-3-fluoropyrrolidine-1-carbonyl)-5-methyl-2-thia-4-azabicyclo[4.1.0]hept-3-en-5-yl)-4-fluorophenyl)-1-fluorovinyl)nicotinonitrile (Example 127) (27 mg, 32% yield) as a white sponge. MS m/z=498 [M+H]+. 1H NMR (400 MHz, CDCl3) δ ppm 8.82 (s, 1H), 8.01 (dd, J=8.3, 1.9 Hz, 1H), 7.76 (d, J=7.6 Hz, 1H), 7.69 (d, J=8.4 Hz, 2H), 7.24 (d, J=41.7 Hz, 1H), 7.10 (dd, J=11.5, 8.6 Hz, 1H), 5.28 (d, J=56.9 Hz, 1H), 3.52-4.17 (m, 4H), 2.23-2.42 (m, 2H), 1.94-2.11 (m, 1H), 1.88 (s, 3H), 1.41 (dd, J=9.8, 5.9 Hz, 1H), 0.88 (br. s., 1H). 19F NMR (377 MHz, CDCl3) δ ppm −108.06 (br. s., 1F), −125.65 (br. s., 1F), −177.72 (d, J=107.9 Hz, 1F).

Preparation of (1S,5S,6S)-3-amino-5-(5-((Z)-2-(5-cyanopyridin-2-yl)-2-fluorovinyl)-2-fluorophenyl)-5-methyl-N-(tetrahydro-2H-pyran-4-yl)-2-thia-4-azabicyclo[4.1.0]hept-3-ene-1-carboxamide (Example 128)

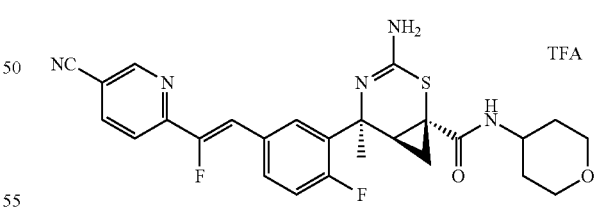

Example 128

This compound was prepared in a similar manner to the procedure described for the synthesis of Example 122 using acid 19 (0.020 g, 0.045 mmol) and 4-aminotetrahydropyran (0.050 g, 0.494 mmol) to afford, without basic workup after preparative HPLC, (1S,5S,6S)-3-amino-5-(5-((Z)-2-(5-cyanopyridin-2-yl)-2-fluorovinyl)-2-fluorophenyl)-5-methyl-N-(tetrahydro-2H-pyran-4-yl)-2-thia-4-azabicyclo[4.1.0]hept-3-ene-1-carboxamide (1:1 TFA salt based on FNMR)

(Example 128) (3 mg, 13% yield) as a white sponge. MS m/z=510 [M+H]+. 1H NMR (400 MHz, CDCl3) δ ppm 12.24 (br. s., 1H), 8.77 (s, 1H), 7.96 (dd, J=8.4, 2.0 Hz, 1H), 7.77 (br. s., 1H), 7.67 (d, J=8.0 Hz, 2H), 7.35 (d, J=7.0 Hz, 1H), 7.15-7.23 (m, 1H), 7.08 (d, J=35.6 Hz, 1H), 6.57 (d, J=7.6 Hz, 1H), 3.90-4.03 (m, 3H), 3.43-3.52 (m, 2H), 2.61 (dd, J=9.2, 7.6 Hz, 1H), 2.31 (dd, J=9.5, 5.6 Hz, 1H), 2.12 (s, 3H), 1.83-2.09 (m, 2H), 1.45-1.67 (m, 2H), 1.00 (t, J=5.7 Hz, 1H). 19F NMR (376 MHz, CDCl3) δ ppm −75.74 (s, 3F), −105.67 (s, 1F), −124.17 (s, 1F).

Preparation of 6-((Z)-2-(3-((1S,5S,6S)-3-amino-1-(isoindoline-2-carbonyl)-5-methyl-2-thia-4-azabicyclo[4.1.0]hept-3-en-5-yl)-4-fluorophenyl)-1-fluorovinyl)nicotinonitrile bis(2,2,2-trifluoroacetate) (Example 129)

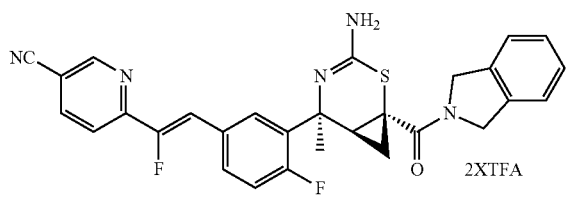

Example 129

This compound was prepared in a similar manner to the procedure described for the synthesis of Example 122 using acid 19 (0.025 g, 0.059 mmol) and isoindoline (0.012 g, 0.101 mmol) to afford, without basic workup after preparative HPLC, 6-((Z)-2-(3-((1S,5S,6S)-3-amino-1-(isoindoline-2-carbonyl)-5-methyl-2-thia-4-azabicyclo[4.1.0]hept-3-en-5-yl)-4-fluorophenyl)-1-fluorovinyl)nicotinonitrile bis (2,2,2-trifluoroacetate) (Example 129) (25 mg, 56% yield) as a white sponge. MS m/z=528 [M+H]+. 1H NMR (400 MHz, CD3OD) δ ppm 8.90 (s, 1H), 8.25 (dd, J=8.4, 2.0 Hz, 1H), 7.80 (d, J=8.0 Hz, 2H), 7.49 (d, J=7.0 Hz, 1H), 7.21-7.40 (m, 6H), 4.99 (q, J=14.1 Hz, 4H), 2.68 (dd, J=9.3, 7.3 Hz, 1H), 2.06-2.17 (m, 4H), 1.24 (t, J=6.1 Hz, 1H). 19F NMR (376 MHz, CD3OD) δ ppm −77.14 (s, 6F, TFA), −107.83 (br. s., 1F), −125.69 (br. s., 1F).

Preparation of (R)-methyl 1-((1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0] hept-3-ene-1-carbonyl)pyrrolidine-2-carboxylate bis(2,2,2-trifluoroacetate) (Example 130)

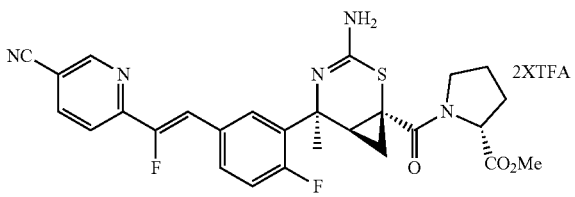 [SMILES: COC(=O)[C@H]1CCCN1C(=O)[C@]12C[C@H]1[C@@](C)(c1cc(/C=C(\F)c3ccc(C#N)cn3)ccc1F)N=C(N)S2]

Example 130

This compound was prepared in a similar manner to the procedure described for the synthesis of Example 122 using acid 19 (0.025 g, 0.059 mmol) and d-proline methyl ester hydrochloride (0.025 g, 0.151 mmol) to afford, without basic workup after preparative HPLC, (R)-methyl 1-((1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carbonyl)pyrrolidine-2-carboxylate bis(2,2,2-trifluoroacetate) (Example 130) (31 mg, 69% yield) as a white sponge. MS m/z=538 [M+H]+. 1H NMR (400 MHz, CD3OD) δ ppm 8.93 (s, 1H), 8.28 (dd, J=8.3, 2.1 Hz, 1H), 7.82 (d, J=7.6 Hz, 2H), 7.50 (d, J=7.2 Hz, 1H), 7.34 (dd, J=11.4, 8.7 Hz, 1H), 7.32 (d, J=38.5 Hz, 1H), 4.39-4.74 (m, 1H), 3.75 (s, m, 5H), 2.63 (dd, J=9.4, 7.4 Hz, 1H), 2.24-2.41 (m, 1H), 2.12 (s, 3H), 1.93-2.08 (m, 4H), 1.15-1.28 (m, 1H). 19F NMR (376 MHz, CD3OD) δ ppm −77.30 (m, 1F, TFA), −108.15 (s, 1F), −125.88 (br. s., 1F).

Preparation of 6-((Z)-2-(3-((1S,5S,6S)-3-amino-5-methyl-1-(4-phenylpiperazine-1-carbonyl)-2-thia-4-azabicyclo[4.1.0]hept-3-en-5-yl)-4-fluorophenyl)-1-fluorovinyl)nicotinonitrile (Example 131)

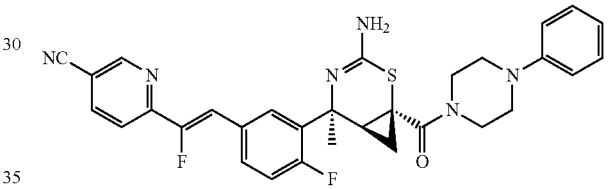

Example 131

The title compound was prepared in a similar manner to the procedure described for the synthesis of Example 122 using acid 19 (0.020 g, 0.047 mmol and 1-phenylpiperazine (0.185 mmol). After HPLC purification, the product fractions were loaded on a Phenomenex Strata-X-C 33 u cation exchange resin (1 g/12 mL). The resin was washed with MeOH (4×1 mL). The resin was then eluded with NH3 (2N) in MeOH (total 4×1 mL) to release the free base product. The product fractions were concentrated and suspended in MeCN-water (2 mL each). The suspension was frozen at −78° C. and was lyophilized overnight to give 6-((Z)-2-(3-((1S,5S,6S)-3-amino-5-methyl-1-(4-phenylpiperazine-1-carbonyl)-2-thia-4-azabicyclo[4.1.0]hept-3-en-5-yl)-4-fluorophenyl)-1-fluorovinyl)nicotinonitrile (Example 131) (11 mg, 35% yield) as a white sponge. MS m/z=571 [M+H]+. 1H NMR (400 MHz, CDCl3) δ ppm 8.82 (d, J=1.2 Hz, 1H), 8.02 (dd, J=8.4, 2.2 Hz, 1H), 7.70 (d, J=8.4 Hz, 3H), 7.18-7.35 (m, 3H), 7.11 (dd, J=11.6, 8.5 Hz, 1H), 6.89-6.97 (m, 3H), 3.80 (br. s., 4H), 3.21 (d, J=4.7 Hz, 4H), 2.33-2.45 (m, 1H), 1.91 (s, 3H), 1.45 (dd, J=9.6, 5.7 Hz, 1H), 0.94 (s, 1H). 19F NMR (377 MHz, CDCl3) δ ppm −108.09 (br. s., 1F), −125.50 (br. s., 1F).

Preparation of 6-((Z)-2-(3-((1S,5S,6S)-3-amino-1-(2-oxa-5-azabicyclo[2.2.1]heptane-5-carbonyl)-5-methyl-2-thia-4-azabicyclo[4.1.0]hept-3-en-5-yl)-4-fluorophenyl)-1-fluorovinyl)nicotinonitrile (Example 132)

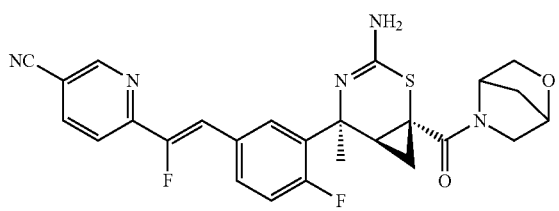 [SMILES: C[C@]1(c2cc(/C=C(\F)c3ccc(C#N)cn3)ccc2F)N=C(N)S[C@@]2(C(=O)N3CC4CC3CO4)C[C@H]21]

Example 132

This compound was prepared in a similar manner to the procedure described for the synthesis of Example 131 using acid 19 (0.020 g, 0.047 mmol) and 2-oxa-5-azabicyclo[2.2.1]heptane (0.185 mmol) to afford 6-((Z)-2-(3-((1S,5S,6S)-3-amino-1-(2-oxa-5-azabicyclo[2.2.1]heptane-5-carbonyl)-5-methyl-2-thia-4-azabicyclo[4.1.0]hept-3-en-5-yl)-4-fluorophenyl)-1-fluorovinyl)nicotinonitrile (Example 132) (18.2 mg, 45% yield) as a white sponge. MS m/z=508 [M+H]$^+$. $^1$H NMR (400 MHz, CDCl$_3$) δ ppm 8.82 (s, 1H), 8.01 (dd, J=8.3, 2.1 Hz, 1H), 7.74-7.90 (m, 1H), 7.69 (d, J=8.0 Hz, 2H), 7.25 (d, J=39.5 Hz, 1H), 7.10 (dd, J=11.6, 8.5 Hz, 1H), 4.80-5.05 (m, 1H), 4.66 (s, 1H), 3.76-4.08 (m, 2H), 3.37-3.73 (m, 2H), 2.37 (t, J=8.3 Hz, 1H), 1.75-1.98 (m, 5H), 1.37 (dd, J=9.8, 5.7 Hz, 1H), 0.90 (br. s., 1H). $^{19}$F NMR (376 MHz, CDCl$_3$) δ ppm −108.30 (d, J=225.6 Hz, 1F), −125.72 (br. s., 1F).

Preparation of 6-((Z)-2-(3-((1S,5S,6S)-3-amino-1-((2R,5R)-2,5-dimethylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 133)

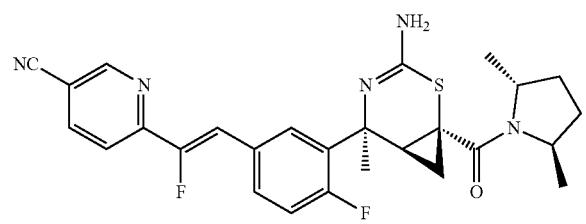 [SMILES: C[C@@H]1CC[C@@H](C)N1C(=O)[C@]12C[C@H]1[C@@](C)(c1cc(/C=C(\F)c3ccc(C#N)cn3)ccc1F)N=C(N)S2]

Example 133

This compound was prepared in a similar manner to the procedure described for the synthesis of Example 131 using acid 19 (0.020 g, 0.047 mmol) and (2R,5R)-2,5-dimethylpyrrolidine (0.185 mmol) to afford 6-((Z)-2-(3-((1S,5S,6S)-3-amino-1-((2R,5R)-2,5-dimethylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 133) (11 mg, 30% yield) as a white sponge. MS m/z=508 [M+H]$^+$. $^1$H NMR (400 MHz, CDCl$_3$) δ ppm 8.82 (s, 1H), 8.01 (dd, J=8.3, 2.1 Hz, 1H), 7.72-7.80 (m, 1H), 7.65-7.72 (m, 2H), 7.24 (d, J=30.3 Hz, 1H), 7.09 (dd, J=11.6, 8.5 Hz, 1H), 4.12-4.77 (br. m, 2H), 2.09-2.40 (m, 3H), 1.85-1.93 (2s, 3H), 1.69 (dd, J=9.7, 5.8 Hz, 2H), 1.57 (br. s., 2H), 1.31 (dd, J=11.2, 6.4 Hz, 3H), 1.08-1.26 (m, 4H), 0.76-0.95 (m, 1H). $^{19}$F NMR (377 MHz, CDCl$_3$) δ ppm −108.33 (br. s., 1F), −125.60 (d, J=44.1 Hz, 1F).

Preparation of 6-((Z)-2-(3-((1S,5S,6S)-3-amino-1-((R)-3-(dimethylamino)pyrrolidine-1-carbonyl)-5-methyl-2-thia-4-azabicyclo[4.1.0]hept-3-en-5-yl)-4-fluorophenyl)-1-fluorovinyl)nicotinonitrile (Example 134)

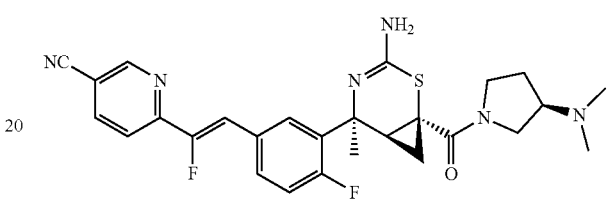

Example 134

This compound was prepared in a similar manner to the procedure described for the synthesis of Example 131 using acid 19 (0.020 g, 0.047 mmol) and (R)—N,N-dimethylpyrrolidin-3-amine (0.185 mmol) to afford 6-((Z)-2-(3-((1S,5S,6S)-3-amino-1-((R)-3-(dimethylamino)pyrrolidine-1-carbonyl)-5-methyl-2-thia-4-azabicyclo[4.1.0]hept-3-en-5-yl)-4-fluorophenyl)-1-fluorovinyl)nicotinonitrile (15 mg, 52% yield) as a white sponge MS m/z=523 [M+H]$^+$. $^1$H NMR (400 MHz, CDCl$_3$) δ ppm 8.82 (s, 1H), 8.01 (dd, J=8.4, 2.2 Hz, 1H), 7.77 (d, J=7.6 Hz, 1H), 7.65-7.71 (m, 2H), 7.24 (d, J=32.1 Hz, 1H), 7.09 (dd, J=11.6, 8.5 Hz, 1H), 3.53-4.09 (m, 3H), 3.16-3.51 (m, 2H), 2.73 (br. m, 1H), 2.29 (br. s, 6H), 2.12 (br. m, 1H), 1.71-1.95 (s, m, 4H), 1.39 (br. s, 1H), 0.76-0.87 (m, 1H). $^{19}$F NMR (376 MHz, CDCl$_3$) δ ppm −108.16 (br. s., 1F), −125.74 (br. s., 1F).

Preparation of 6-((Z)-2-(3-((1S,5S,6S)-3-amino-1-((4aS,8aR)-decahydroisoquinoline-2-carbonyl)-5-methyl-2-thia-4-azabicyclo[4.1.0]hept-3-en-5-yl)-4-fluorophenyl)-1-fluorovinyl)nicotinonitrile (Example 135)

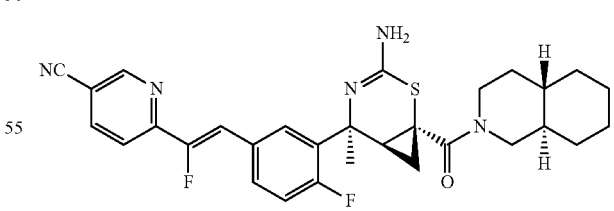

Example 135

This compound was prepared in a similar manner to the procedure described for the synthesis of Example 131 using acid 19 (0.020 g, 0.047 mmol) and (4aS,8aR)-decahydroisoquinoline (0.185 mmol) to afford 6-((Z)-2-(3-((1S,5S,6S)-3-amino-1-((4aS,8aR)-decahydroisoquinoline-2-carbonyl)-

5-methyl-2-thia-4-azabicyclo[4.1.0]hept-3-en-5-yl)-4-fluorophenyl)-1-fluorovinyl)nicotinonitrile (Example 135) (5.4 mg, 17% yield) as a white sponge. MS m/z=548 [M+H]⁺. ¹H NMR (400 MHz, CDCl₃) δ ppm 8.82 (s, 1H), 8.01 (dd, J=8.3, 2.1 Hz, 1H), 7.80 (d, J=7.6 Hz, 1H), 7.69 (d, J=7.3 Hz, 1H), 7.65-7.68 (m, 1H), 7.24 (d, J=30.1 Hz, 1H), 7.09 (dd, J=11.6, 8.5 Hz, 1H), 4.09-4.58 (m, 2H), 2.24-2.33 (m, 1H), 1.87 (s, 3H), 1.76 (br. s., 2H), 1.54-1.72 (m, 4H), 1.27 (m, 4H), 1.12 (m, 3H), 0.91-1.04 (m, 2H), 0.81-0.90 (m, 1H). ¹⁹F NMR (376 MHz, CDCl₃) δ ppm -108.24 (br. s., 1F), -125.75 (br. s., 1F).

Preparation of 6-((Z)-2-(3-((1S,5S,6S)-3-amino-5-methyl-1-(1,3,3-trimethyl-6-azabicyclo[3.2.1]octane-6-carbonyl)-2-thia-4-azabicyclo[4.1.0]hept-3-en-5-yl)-4-fluorophenyl)-1-fluorovinyl)nicotinonitrile (Example 136)

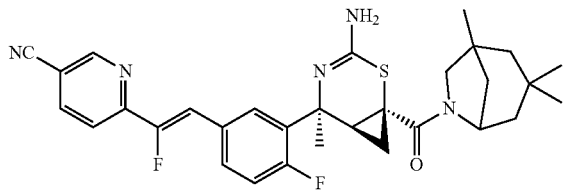 [SMILES: CC1(C)CC2CC(C)(CN2C(=O)[C@]23C[C@H]2[C@@](C)(c2cc(/C=C(\F)c4ccc(C#N)cn4)ccc2F)N=C(N)S3)C1]

Example 136

This compound was prepared in a similar manner to the procedure described for the synthesis of Example 131 using acid 19 (0.020 g, 0.047 mmol) and 1,3,3-trimethyl-6-azabicyclo[3.2.1]octane (0.185 mmol) to afford 6-((Z)-2-(3-((1S,5S,6S)-3-amino-5-methyl-1-(1,3,3-trimethyl-6-azabicyclo[3.2.1]octane-6-carbonyl)-2-thia-4-azabicyclo[4.1.0]hept-3-en-5-yl)-4-fluorophenyl)-1-fluorovinyl)nicotinonitrile (Example 136) (5.5 mg, 22% yield) as a white sponge. MS m/z=562 [M+H]⁺. ¹H NMR (400 MHz, CDCl₃) δ ppm 8.82 (s, 1H), 8.01 (dd, J=8.4, 2.2 Hz, 1H), 7.71-7.86 (m, 1H), 7.64-7.71 (m, 2H), 7.24 (d, J=31.7 Hz, 1H), 7.09 (dd, J=11.6, 8.5 Hz, 1H), 4.43-4.60 (m, 1H), 3.09-3.63 (m, 1H), 3.39 (m, 1H), 2.11-2.46 (m, 2H), 1.92-2.05 (m, 1H), 1.87 (br. s., 3H), 1.23-1.78 (m, 5H), 1.02-1.15 (m, 5H), 0.89-1.01 (m, 5H). ¹⁹F NMR (376 MHz, CDCl₃) δ ppm -108.76--107.39 (m, 1F), -125.71 (br. s., 1F).

Preparation of 6-((Z)-2-(3-((1S,5S,6S)-3-amino-1-(3,5-dimethylpiperidine-1-carbonyl)-5-methyl-2-thia-4-azabicyclo[4.1.0]hept-3-en-5-yl)-4-fluorophenyl)-1-fluorovinyl)nicotinonitrile (Example 137)

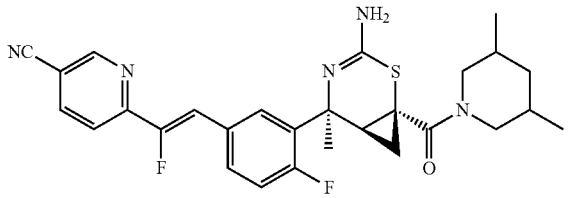 [SMILES: CC1CC(C)CN(C(=O)[C@]23C[C@H]2[C@@](C)(c2cc(/C=C(\F)c4ccc(C#N)cn4)ccc2F)N=C(N)S3)C1]

Example 137

This compound was prepared in a similar manner to the procedure described for the synthesis of Example 131 using acid 19 (0.020 g, 0.047 mmol) and 3,5-dimethylpiperidine (0.185 mmol) to afford 6-((Z)-2-(3-((1S,5S,6S)-3-amino-1-(3,5-dimethylpiperidine-1-carbonyl)-5-methyl-2-thia-4-azabicyclo[4.1.0]hept-3-en-5-yl)-4-fluorophenyl)-1-fluorovinyl)nicotinonitrile (Example 137) (14 mg, 56% yield) as a white sponge. MS m/z=522 [M+H]⁺. ¹H NMR (400 MHz, CDCl₃) δ ppm 8.81-8.84 (m, 1H), 8.01 (dd, J=8.3, 2.1 Hz, 1H), 7.80 (d, J=7.2 Hz, 1H), 7.66-7.71 (m, 2H), 7.24 (d, J=37.8 Hz, 1H), 7.09 (dd, J=11.5, 8.4 Hz, 1H), 4.29 (br. m., 2H), 2.19-2.45 (m, 2H), 1.79-2.00 (m, 5H), 1.60 (br. m., J=2.2 Hz, 2H), 1.30-1.51 (m, 2H), 0.83-1.00 (m, 7H). ¹⁹F NMR (376 MHz, CDCl₃) δ ppm -108.18 (d, J=72.8 Hz, 1F), -125.72 (br. s., 1F).

Preparation of 6-((Z)-2-(3-((1S,5S,6S)-3-amino-5-methyl-1-(2-methylpyrrolidine-1-carbonyl)-2-thia-4-azabicyclo[4.1.0]hept-3-en-5-yl)-4-fluorophenyl)-1-fluorovinyl)nicotinonitrile (Example 138)

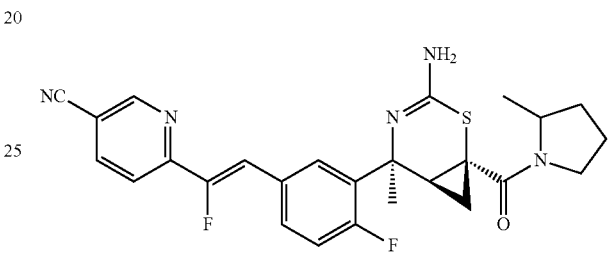

Example 138

This compound was prepared in a similar manner to the procedure described for the synthesis of Example 131 using acid 19 (0.020 g, 0.047 mmol) and 2-methylpyrrolidine (0.185 mmol) to afford 6-((Z)-2-(3-((1S,5S,6S)-3-amino-5-methyl-1-(2-methylpyrrolidine-1-carbonyl)-2-thia-4-azabicyclo[4.1.0]hept-3-en-5-yl)-4-fluorophenyl)-1-fluorovinyl) nicotinonitrile (13 mg, 49% yield). MS m/z=494 [M+H]⁺. ¹H NMR (400 MHz, CDCl₃) δ ppm 8.82 (s, 1H), 8.01 (dd, J=8.4, 2.2 Hz, 1H), 7.63-7.84 (m, 3H), 7.25 (d, J=31.1 Hz, 1H), 7.00-7.15 (m, 1H), 4.13-3.68 (m, 2H), 1.95-2.60 (m, 3H), 1.80-1.94 (m, s, 4H), 1.30-1.55 (m, 2H), 1.16-1.27 (m, 4H), 0.70-1.16 (m, 1H). ¹⁹F NMR (377 MHz, CDCl₃) δ ppm -108.00 (d, J=39.9 Hz, 1F), -125.70 (br. s., 1F).

Preparation of 6-((Z)-2-(3-((1S,5S,6S)-3-amino-5-methyl-1-(4-(trifluoromethyl)piperidine-1-carbonyl)-2-thia-4-azabicyclo[4.1.0]hept-3-en-5-yl)-4-fluorophenyl)-1-fluorovinyl)nicotinonitrile (Example 139)

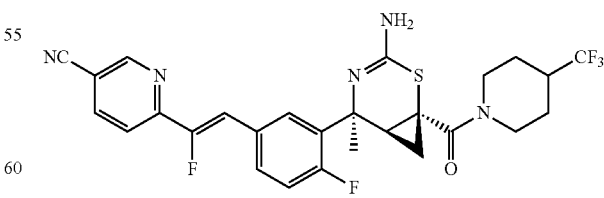

Example 139

This compound was prepared in a similar manner to the procedure described for the synthesis of Example 131 using acid 19 (0.020 g, 0.047 mmol) and 4-(trifluoromethyl)piperidine (0.185 mmol) to afford 6-((Z)-2-(3-((1S,5S,6S)-3-amino-5-methyl-1-(4-(trifluoromethyl)piperidine-1-carbonyl)-2-thia-4-azabicyclo[4.1.0]hept-3-en-5-yl)-4-fluorophenyl)-1-fluorovinyl)nicotinonitrile (Example 139) (11 mg, 41% yield). MS m/z=562 [M+H]$^+$. $^1$H NMR (400 MHz, CDCl$_3$) δ ppm 8.82 (s, 1H), 8.01 (dd, J=8.4, 2.2 Hz, 1H), 7.79 (d, J=7.6 Hz, 1H), 7.67-7.72 (m, 2H), 7.25 (d, J=39.1, 1H), 7.10 (dd, J=11.6, 8.5 Hz, 1H), 4.50 (d, J=10.0 Hz, 2H), 2.84 (br. s., 1H), 2.20-2.44 (m, 2H), 1.96 (d, J=13.7 Hz, 2H), 1.87 (s, 3H), 1.44-1.65 (m, 3H), 1.38 (d, J=3.7 Hz, 1H), 0.90 (t, J=6.4 Hz, 1H). $^{19}$F NMR (376 MHz, CDCl$_3$) δ ppm −73.79 (s, 3F), −108.29 (br. s., 1F), −125.65 (br. s., 1F).

Preparation of 6-((Z)-2-(3-((1S,5S,6S)-3-amino-5-methyl-1-(3-phenylpiperidine-1-carbonyl)-2-thia-4-azabicyclo[4.1.0]hept-3-en-5-yl)-4-fluorophenyl)-1-fluorovinyl)nicotinonitrile (Example 140)

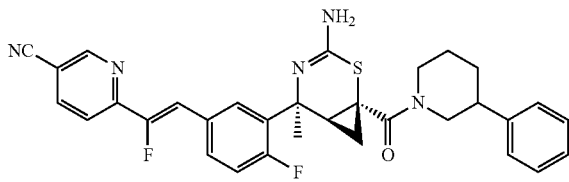 [SMILES: C[C@]1(c2cc(/C=C(\F)c3ccc(C#N)cn3)ccc2F)N=C(N)S[C@@]2(C(=O)N3CCCC(c4ccccc4)C3)C[C@H]21]

Example 140

This compound was prepared in a similar manner to the procedure described for the synthesis of Example 131 using acid 19 (0.020 g, 0.047 mmol) and 3-phenylpiperidine (0.185 mmol) to afford 6-((Z)-2-(3-((1S,5S,6S)-3-amino-5-methyl-1-(3-phenylpiperidine-1-carbonyl)-2-thia-4-azabicyclo[4.1.0]hept-3-en-5-yl)-4-fluorophenyl)-1-fluorovinyl)nicotinonitrile (Example 140) (12 mg, 44% yield) as a white sponge. MS m/z=570 [M+H]$^+$. $^1$H NMR (400 MHz, CDCl$_3$) δ ppm 8.82 (s, 1H), 8.00 (d, J=2.2 Hz, 1H), 7.72-7.81 (m, 1H), 7.69 (d, J=8.2 Hz, 2H), 7.32 (d, J=4.7 Hz, 2H), 7.16-7.29 (m, 4H), 7.06-7.14 (m, 1H), 4.46 (br. s., 2H), 2.67 (br. s., 2H), 2.40 (q, J=8.6 Hz, 1H), 2.09 (d, J=10.2 Hz, 1H), 1.89 (br. s., 4H), 1.22-1.83 (m, 4H), 0.93 (q, J=6.5 Hz, 1H). $^{19}$F NMR (376 MHz, CDCl$_3$) δ ppm −107.96 (s, 1F), −125.51 (s, 1F).

Preparation of 6-((Z)-2-(3-((1S,5S,6S)-3-amino-1-(4-(cyclopropylmethyl)piperazine-1-carbonyl)-5-methyl-2-thia-4-azabicyclo[4.1.0]hept-3-en-5-yl)-4-fluorophenyl)-1-fluorovinyl)nicotinonitrile (Example 141)

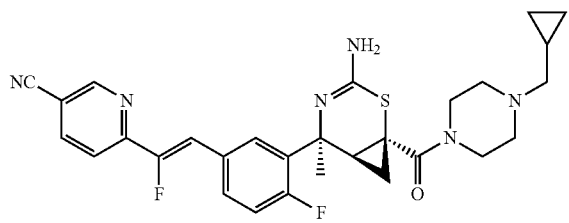 [SMILES: C[C@]1(c2cc(/C=C(\F)c3ccc(C#N)cn3)ccc2F)N=C(N)S[C@@]2(C(=O)N3CCN(CC4CC4)CC3)C[C@H]21]

Example 141

This compound was prepared in a similar manner to the procedure described for the synthesis of Example 131 using acid 19 (0.020 g, 0.047 mmol) and 1-(cyclopropylmethyl)piperazine (0.185 mmol) to afford 6-((Z)-2-(3-((1S,5S,6S)-3-amino-1-(4-(cyclopropylmethyl)piperazine-1-carbonyl)-5-methyl-2-thia-4-azabicyclo[4.1.0]hept-3-en-5-yl)-4-fluorophenyl)-1-fluorovinyl)nicotinonitrile (Example 141) (19 mg, 74% yield) as a white sponge. MS m/z=549 [M+H]$^+$. $^1$H NMR (400 MHz, CDCl$_3$) δ ppm 8.82 (s, 1H), 8.01 (dd, J=8.3, 2.1 Hz, 1H), 7.82 (dd, J=7.7, 2.2 Hz, 1H), 7.65-7.71 (m, 2H), 7.25 (d, J=39.1 Hz, 1H), 7.09 (dd, J=11.6, 8.5 Hz, 1H), 3.69 (br. s., 4H), 2.54 (br. s., 4H), 2.23-2.35 (m, 3H), 1.85 (s, 3H), 1.35 (dd, J=9.6, 5.7 Hz, 1H), 0.82-0.90 (m, 2H), 0.51-0.57 (m, 2H), 0.12 (q, J=4.8 Hz, 2H). $^{19}$F NMR (376 MHz, CDCl$_3$) δ ppm −108.36 (s, 1F), −125.80 (s, 1F).

Preparation of 6-((Z)-2-(3-((1S,5S,6S)-3-amino-5-methyl-1-(5-oxo-1,4-diazepane-1-carbonyl)-2-thia-4-azabicyclo[4.1.0]hept-3-en-5-yl)-4-fluorophenyl)-1-fluorovinyl)nicotinonitrile (Example 142)

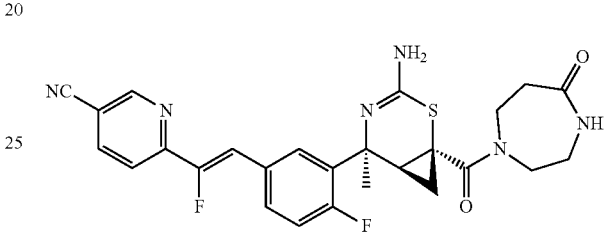

Example 142

This compound was prepared in a similar manner to the procedure described for the synthesis of Example 131 using acid 19 (0.020 g, 0.047 mmol) and 1,4-diazepan-5-one (0.185 mmol) to afford 6-((Z)-2-(3-((1S,5S,6S)-3-amino-5-methyl-1-(5-oxo-1,4-diazepane-1-carbonyl)-2-thia-4-azabicyclo[4.1.0]hept-3-en-5-yl)-4-fluorophenyl)-1-fluorovinyl)nicotinonitrile (Example 142) (17.5 mg, 71% yield) as a white sponge. MS m/z=523 [M+H]$^+$. $^1$H NMR (400 MHz, CDCl$_3$) δ ppm 8.82 (s, 1H), 8.01 (dd, J=8.4, 2.2 Hz, 1H), 7.78 (dd, J=7.7, 2.1 Hz, 1H), 7.65-7.71 (m, 2H), 7.24 (d, J=38.5 Hz, 1H), 7.10 (dd, J=11.6, 8.5 Hz, 1H), 6.11 (br. s., 1H), 3.81 (br. s., 4H), 3.35 (d, J=4.1 Hz, 2H), 2.69 (br. s., 2H), 2.21-2.36 (m, 1H), 1.86 (s, 3H), 1.40 (dd, J=9.9, 5.8 Hz, 1H), 0.91 (t, J=6.5 Hz, 1H). $^{19}$F NMR (376 MHz, CDCl$_3$) δ ppm −108.33 (br. s., 1F), −125.64 (br. s., 1F).

Preparation of 6-((Z)-2-(3-((1S,5S,6S)-3-amino-1-(3-cyanopiperidine-1-carbonyl)-5-methyl-2-thia-4-azabicyclo[4.1.0]hept-3-en-5-yl)-4-fluorophenyl)-1-fluorovinyl)nicotinonitrile (Example 143)

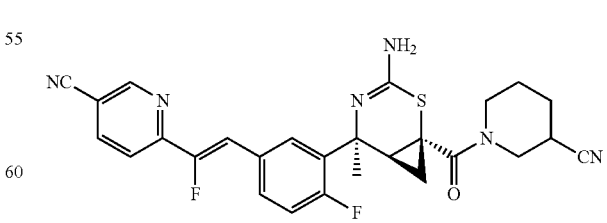

Example 143

This compound was prepared in a similar manner to the procedure described for the synthesis of Example 131 using acid 19 (0.020 g, 0.047 mmol) and piperidine-3-carbonitrile (0.185 mmol) to afford 6-((Z)-2-(3-((1S,5S,6S)-3-amino-1-(3-cyanopiperidine-1-carbonyl)-5-methyl-2-thia-4-azabicyclo[4.1.0]hept-3-en-5-yl)-4-fluorophenyl)-1-fluorovinyl)nicotinonitrile (Example 143) (22 mg, 90% yield) as a white sponge. MS m/z=519 [M+H]+. 1H NMR (400 MHz, CDCl3) δ ppm 8.83 (s, 1H), 8.01 (dd, J=8.3, 2.1 Hz, 1H), 7.77 (d, J=4.9 Hz, 1H), 7.66-7.72 (m, 2H), 7.24 (d, J=38.9 Hz, 1H), 7.10 (dd, J=11.5, 8.4 Hz, 1H), 3.86-4.09 (m, 1H), 3.42-3.84 (m, 3H), 2.70-2.87 (m, 1H), 2.26-2.43 (m, 1H), 2.01-2.14 (m, 1H), 1.44-1.98 (m, 1H), 1.88 (br. s, 3H), 1.63 (m, 2H), 1.44 (dd, J=9.9, 5.6 Hz, 1H), 0.82-1.02 (m, 1H). 19F NMR (376 MHz, CDCl3) δ ppm −108.15 (d, J=14.3 Hz, 1F), −125.62 (br. s., 1F).

Preparation of 6-((Z)-2-(3-((1S,5S,6S)-3-amino-5-methyl-1-(3-oxopiperazine-1-carbonyl)-2-thia-4-azabicyclo[4.1.0]hept-3-en-5-yl)-4-fluorophenyl)-1-fluorovinyl)nicotinonitrile (Example 144)

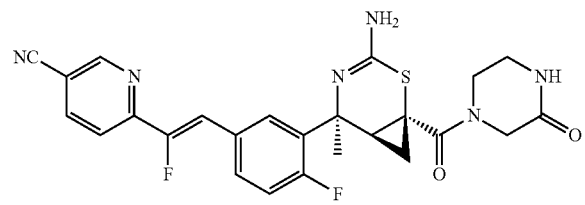 [SMILES: C[C@]1(c2cc(/C=C(\F)c3ccc(C#N)cn3)ccc2F)N=C(N)S[C@@]2(C(=O)N3CCNC(=O)C3)C[C@H]21]

Example 144

This compound was prepared in a similar manner to the procedure described for the synthesis of Example 131 using acid 19 (0.020 g, 0.047 mmol) and piperazin-2-one (0.185 mmol) to afford 6-((Z)-2-(3-((1S,5S,6S)-3-amino-5-methyl-1-(3-oxopiperazine-1-carbonyl)-2-thia-4-azabicyclo[4.1.0]hept-3-en-5-yl)-4-fluorophenyl)-1-fluorovinyl)nicotinonitrile (Example 144) (14 mg, 59% yield) as a white sponge. MS m/z=509 [M+H]+. 1H NMR (400 MHz, CDCl3) δ ppm 8.83 (s, 1H), 8.02 (dd, J=8.4, 2.2 Hz, 1H), 7.75-7.82 (m, 1H), 7.70 (d, J=7.2 Hz, 2H), 7.25 (d, J=39.9 Hz, 1H), 7.11 (dd, J=11.6, 8.5 Hz, 1H), 6.09 (br. s., 1H), 4.22-4.37 (m, 2H), 3.77-3.99 (m, 2H), 3.46 (br. s., 2H), 2.32-2.42 (m, 1H), 1.89 (s, 3H), 1.42 (dd, J=9.8, 6.3 Hz, 1H), 0.95 (t, J=6.5 Hz, 1H). 19F NMR (376 MHz, CDCl3) δ ppm −108.34 (br. s., 1F), −125.53 (br. s., 1F).

Preparation of 6-((Z)-2-(3-((1S,5S,6S)-3-amino-5-methyl-1-(3-methylpiperidine-1-carbonyl)-2-thia-4-azabicyclo[4.1.0]hept-3-en-5-yl)-4-fluorophenyl)-1-fluorovinyl)nicotinonitrile (Example 145)

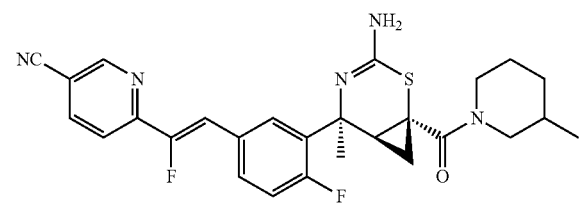 [SMILES: CC1CCCN(C(=O)[C@]23C[C@H]2[C@@](C)(c2cc(/C=C(\F)c4ccc(C#N)cn4)ccc2F)N=C(N)S3)C1]

Example 145

This compound was prepared in a similar manner to the procedure described for the synthesis of Example 131 using acid 19 (0.020 g, 0.047 mmol) and 3-methylpiperidine (0.185 mmol) to afford 6-((Z)-2-(3-((1S,5S,6S)-3-amino-5-methyl-1-(3-methylpiperidine-1-carbonyl)-2-thia-4-azabicyclo[4.1.0]hept-3-en-5-yl)-4-fluorophenyl)-1-fluorovinyl)nicotinonitrile (Example 145) (10 mg, 42% yield) as a white sponge. MS m/z=508 [M+H]+. 1H NMR (400 MHz, CDCl3) δ ppm 8.82 (s, 1H), 8.01 (dd, J=8.4, 2.2 Hz, 1H), 7.78 (d, J=7.6 Hz, 1H), 7.69 (d, J=8.2 Hz, 2H), 7.25 (d, J=38.7 Hz, 1H), 7.10 (dd, J=11.5, 8.4 Hz, 1H), 4.20 (br. s., 2H), 2.24-2.40 (m, 1H), 1.31-1.97 (m, 10H), 1.04-1.23 (m, 1H), 0.80-0.99 (m, 4H). 19F NMR (376 MHz, CDCl3) δ ppm −108.16 (br. s., 1F), −125.65 (br. s., m, 1F).

Preparation of 6-((Z)-2-(3-((1S,5S,6S)-3-amino-5-methyl-1-(piperidine-1-carbonyl)-2-thia-4-azabicyclo[4.1.0]hept-3-en-5-yl)-4-fluorophenyl)-1-fluorovinyl)nicotinonitrile (Example 146)

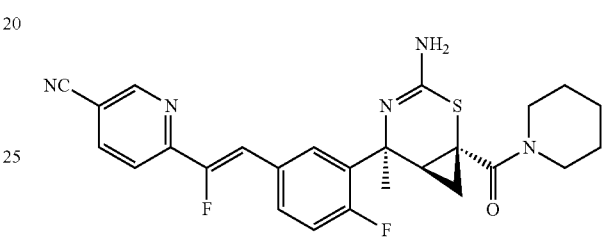

Example 146

This compound was prepared in a similar manner to the procedure described for the synthesis of Example 131 using acid 19 (0.020 g, 0.047 mmol) and piperidine (0.185 mmol) to afford 6-((Z)-2-(3-((1S,5S,6S)-3-amino-5-methyl-1-(piperidine-1-carbonyl)-2-thia-4-azabicyclo[4.1.0]hept-3-en-5-yl)-4-fluorophenyl)-1-fluorovinyl)nicotinonitrile (Example 146) (11 mg, 47% yield) as a white sponge. MS m/z=594 [M+H]+. 1H NMR (400 MHz, CDCl3) δ ppm 8.82 (s, 1H), 8.01 (dd, J=8.2, 2.2 Hz, 1H), 7.74 (d, J=7.4 Hz, 1H), 7.66-7.71 (m, 2H), 7.24 (d, J=38.7 Hz, 1H), 7.10 (dd, J=11.5, 8.4 Hz, 1H), 3.56 (br. s, 4H), 2.27-2.41 (m, 1H), 1.92 (s, 3H), 1.66 (d, J=5.3 Hz, 2H), 1.59 (br. m., 4H), 1.43 (dd, J=9.5, 5.8 Hz, 1H), 0.91 (t, J=6.3 Hz, 1H). 19F NMR (377 MHz, CDCl3) δ ppm −107.93 (br. s., 1F), −125.49 (br. s., 1F).

Preparation of 6-((Z)-2-(3-((1S,5S,6S)-3-amino-5-methyl-1-(4-methylpiperidine-1-carbonyl)-2-thia-4-azabicyclo[4.1.0]hept-3-en-5-yl)-4-fluorophenyl)-1-fluorovinyl)nicotinonitrile (Example 147)

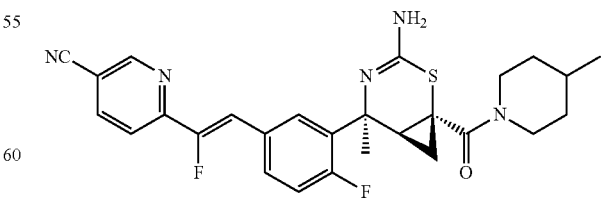

Example 147

This compound was prepared in a similar manner to the procedure described for the synthesis of Example 131 using acid 19 (0.020 g, 0.047 mmol) and 4-methylpiperidine (0.185 mmol) to afford 6-((Z)-2-(3-((1S,5S,6S)-3-amino-5-methyl-1-(4-methylpiperidine-1-carbonyl)-2-thia-4-azabicyclo[4.1.0]hept-3-en-5-yl)-4-fluorophenyl)-1-fluorovinyl)nicotinonitrile (4.6 mg, 19% yield) as a white sponge. MS m/z=508 [M+H]+. 1H NMR (400 MHz, CDCl3) δ ppm 8.82 (s, 1H), 8.01 (dd, J=8.3, 2.1 Hz, 1H), 7.65-7.72 (m, 3H), 7.08-7.18 (m, 2H), 4.27 (br. s., 2H), 2.62-2.99 (m, 1H), 2.31-2.40 (m, 1H), 1.95 (s, 3H), 1.54-1.77 (m, 4H), 1.48 (br. m, 1H), 1.13 (br. m, 2H), 0.88-0.99 (m, 4H). 19F NMR (377 MHz, CDCl3) δ ppm −107.68 (br. s., 1F), −125.30 (br. s., 1F).

Preparation of (1S,5S,6S)-5-(5-((Z)-2-(5-bromopyrazin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (Intermediate 20)

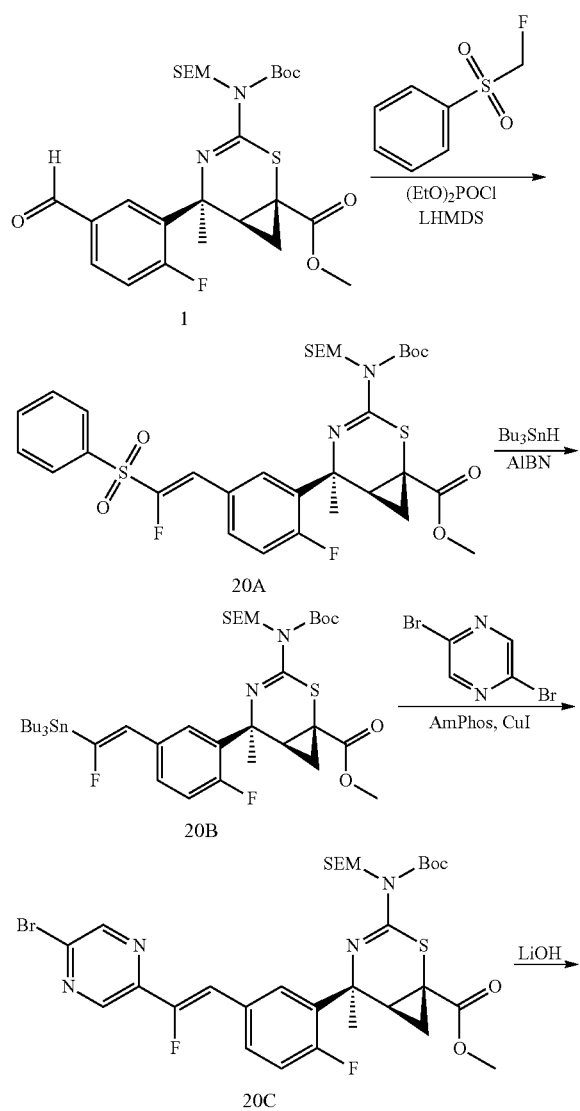

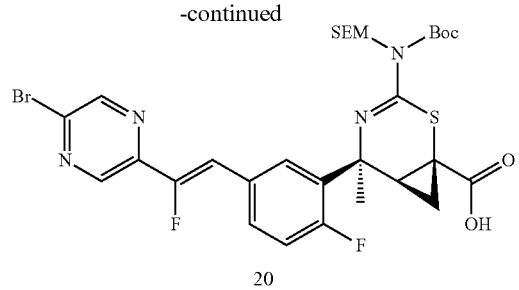

Preparation of (1S,5S,6S)-methyl 3-((tert-butoxycarbonyl)((2-(trimethylsilyl)ethoxy)methyl)amino)-5-(2-fluoro-5-((E)-2-fluoro-2-(phenylsulfonyl)vinyl)phenyl)-5-methyl-2-thia-4-azabicyclo[4.1.0]hept-3-ene-1-carboxylate (20A)

Fluoromethyl phenyl sulfone (3.15 g, 18.1 mmol) was azeotroped with toluene in a 500 mL RBF. To this was added diethyl chlorophosphate (2.62 mL, 18.1 mmol) and dry THF (60 mL) under N2. This was cooled to −70° C. in dry ice/acetone bath. A lithium bis(trimethylsilyl)amide, 1.0M solution in THF (38.9 mL, 38.9 mmol) was added dropwise and then the reaction was stirred at −70° C. for 1 hour. A solution of (1S,5S,6S)-methyl 3-((tert-butoxycarbonyl)((2-(trimethylsilyl)ethoxy)methyl)amino)-5-(2-fluoro-5-formylphenyl)-5-methyl-2-thia-4-azabicyclo[4.1.0]hept-3-ene-1-carboxylate (5.00 g, 9.05 mmol) (azeotroped with toluene) in 20 mL of dry THF was added dropwise. LCMS and TLC showed formation of desired product. The dry-ice bath was removed and the reaction was stirred at room temperature for 5 minutes, quenched with sat. NH4Cl, extracted with EtOAc, dried and concentrated. Flash chromatography (DCM to DCM/EtOAc=100:2) gave (1S,5S,6S)-methyl 3-((tert-butoxycarbonyl)((2-(trimethylsilyl)ethoxy)methyl)amino)-5-(2-fluoro-5-((E)-2-fluoro-2-(phenylsulfonyl)vinyl)phenyl)-5-methyl-2-thia-4-azabicyclo[4.1.0]hept-3-ene-1-carboxylate (20A) (5.0 g, 78% yield, E/Z>10:1) as a light yellow gum. MS m/z=709 [M+H]+. 1H NMR (400 MHz, CDCl3) δ 8.00 (d, J=7.43 Hz, 2H), 7.89 (dd, J=2.25, 7.73 Hz, 1H), 7.66-7.72 (m, 1H), 7.56-7.62 (m, 2H), 7.50-7.56 (m, 1H), 7.05 d, (J=36.0 Hz, 1H), 6.97-7.09 (m, 1H), 5.27 (d, J=10.76 Hz, 1H), 5.05 (d, J=10.76 Hz, 1H), 3.79 (s, 3H), 3.64 (t, J=8.22 Hz, 2H), 2.63 (t, J=8.61 Hz, 1H), 1.74 (s, 3H), 1.53 (s, 9H), 1.45 (dd, J=5.18, 9.88 Hz, 1H), 1.16-1.20 (m, 1H), 0.93 (dt, J=3.42, 8.26 Hz, 2H), 0.00 (s, 9H). 19F NMR (376 MHz, CDCl3) δ −107.72 (s, 1F), −125.63 (s, 1F), −125.64 (s, 1F).

Preparation of (1S,5S,6S)-methyl 3-((tert-butoxycarbonyl)((2-(trimethylsilyl)ethoxy)methyl)amino)-5-(2-fluoro-5-((E)-2-fluoro-2-(tributylstannyl)vinyl)phenyl)-5-methyl-2-thia-4-azabicyclo[4.1.0]hept-3-ene-1-carboxylate (20B)

A mixture of (1S,5S,6S)-methyl 3-((tert-butoxycarbonyl)((2-(trimethylsilyl)ethoxy)methyl)amino)-5-(2-fluoro-5-((E)-2-fluoro-2-(phenylsulfonyl)vinyl)phenyl)-5-methyl-2-thia-4-azabicyclo[4.1.0]hept-3-ene-1-carboxylate (20A) (600 mg, 0.846 mmol), tributylstannane (493 mg, 1.70 mmol), and 2,2′-azobis(2-methylpropionitrile) (14 mg, 0.085 mmol) in 1 mL of heptane was sealed and heated to 80° C. for 1 hour. TLC showed complete conversion to a less polar product. After cooling to room temperature, the reaction mixture was directly loaded onto a flash column (DCM/heptane=1:3, then pure DCM) to give (1S,5S,6S)-methyl 3-((tert-butoxycarbonyl)((2-(trimethylsilyl)ethoxy)methyl)amino)-5-(2-fluoro-5-((E)-2-fluoro-2-(tributylstannyl)vinyl)phenyl)-5-methyl-2-thia-4-azabicyclo[4.1.0]hept-3-ene-1-carboxylate (20B) (620 mg, 85% yield) as a colorless oil.

Preparation of (1S,5S,6S)-methyl 5-(5-((Z)-2-(5-bromopyrazin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (20C)

A mixture of 2,5-dibromopyrazine (1070 mg, 4.49 mmol), bis(di-tert-butyl(4-dimethylaminophenyl)phosphine)dichloropalladium(ii) (64 mg, 0.090 mmol) and copper(i) iodide (170 mg, 0.90 mmol) were suspended in 0.5 mL of DMF. To this was added dropwise a solution of (1S,5S,6S)-methyl 3-((tert-butoxycarbonyl)((2-(trimethylsilyl)ethoxy)methyl)amino)-5-(2-fluoro-5-((E)-2-fluoro-2-(tributylstannyl)vinyl)phenyl)-5-methyl-2-thia-4-azabicyclo[4.1.0]hept-3-ene-1-carboxylate (20B) (770 mg, 0.898 mmol) in 1 mL of DMF. After stirring at room temperature for 1 hour, the DMF was evaporated and the residue was loaded onto a flash column (DCM/heptane=1:1 to DCM to DCM/EA=50:1 to 20:1 to 10:1) to give (1S,5S,6S)-methyl 5-(5-((Z)-2-(5-bromopyrazin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (20C) (450 mg, 0.620 mmol, 69% yield) as a colorless oil. MS m/z=725/727 (M+H). $^1$H NMR (300 MHz, CDCl$_3$) δ 8.64 (s, 1H), 8.62 (s, 1H), 7.91-8.04 (m, 1H), 7.61-7.74 (m, 1H), 6.96-7.20 (m, 2H), 5.33 (d, J=10.67 Hz, 1H), 5.10 (d, J=10.52 Hz, 1H), 3.82 (s, 3H), 3.64-3.74 (m, 2H), 2.69 (t, J=8.77 Hz, 1H), 1.79 (s, 3H), 1.49-1.61 (m, 1H), 1.55 (s, 9H), 1.26-1.31 (m, 1H), 0.92-1.02 (m, 2H), −0.03-0.02 (m, 9H).

Preparation of (1S,5S,6S)-5-(5-((Z)-2-(5-bromopyrazin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (20)

(1S,5S,6S)-Methyl 5-(5-((Z)-2-(5-bromopyrazin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (20C) (1.0 g, 1.378 mmol) was used without further purification and was dissolved in 6 mL THF/2 mL water and was treated with lithium hydroxide hydrate (0.173 g, 4.13 mmol). After stirring at r.t. for 3 h, the organic solvent was removed in vacuo and the residue was diluted with water and the pH was adjusted to pH=4 with 1N HCl. The resulting mixture was extracted with DCM three times, dried and evaporated to give (1S,5S,6S)-5-(5-((Z)-2-(5-bromopyrazin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (20) (950 mg, 1.335 mmol, 97% yield) as a light greenish solid. MS m/z=711/713 (M+H).

Preparation of tert-butyl ((1S,5S,6S)-5-(5-((Z)-2-(5-bromopyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (Intermediate 21A) and tert-butyl ((1S,5S,6S)-5-(5-((Z)-2-(5-((3H-[1,2,3]triazolo[4,5-b]pyridin-3-yl)oxy)pyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (Intermediate 21B)

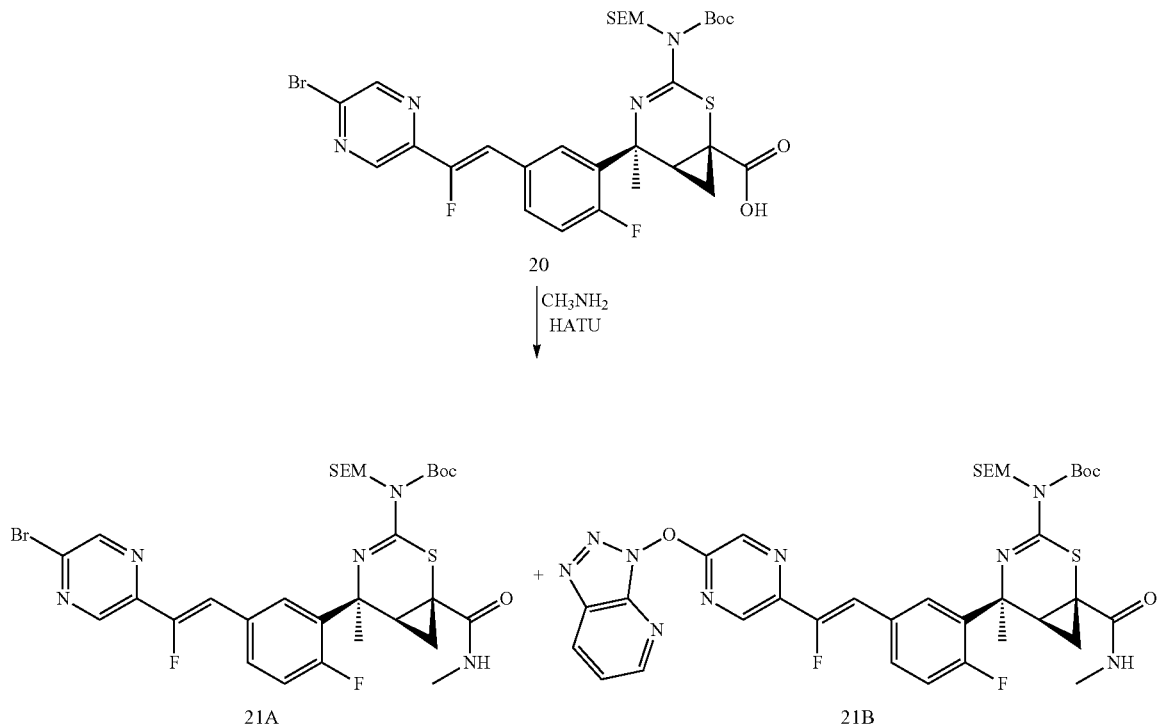

Preparation of tert-butyl ((1S,5S,6S)-5-(5-((Z)-2-(5-bromopyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (21A) and tert-butyl ((1S,5S,6S)-5-(5-((Z)-2-(5-((3H-[1,2,3]triazolo[4,5-b]pyridin-3-yl)oxy)pyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (21B)

To a solution of (1S,5S,6S)-5-(5-((Z)-2-(5-bromopyrazin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (20, 1.00 g, 1.40 mmol) which was used without further purification, and methylamine (2.0m solution in THF, 2.11 mL, 4.22 mmol) in 1 mL of DMF was added HATU (0.801 g, 2.11 mmol) followed by diisopropylethylamine (0.489 mL, 2.81 mmol). After stirring overnight, the solvent was removed under reduced pressure and the residue was loaded onto a flash column (DCM to DCM/EA=100:4 to 100:8 to 100:10) to give tert-butyl ((1S,5S,6S)-5-(5-((Z)-2-(5-bromopyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (21A) (380 mg, 37% yield) as a light yellow solid. MS m/z=724/726 (M+H). A byproduct, tert-butyl ((1S,5S,6S)-5-(5-((Z)-2-(5-((3H-[1,2,3]triazolo[4,5-b]pyridin-3-yl)oxy)pyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (21B) (180 mg, 16% yield) as a light yellow solid was also isolated. MS m/z=780 (M+H).

Preparation of tert-butyl ((1S,5S,6S)-5-(5-((Z)-2-(5-bromopyrazin-2-yl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (Intermediate 22)

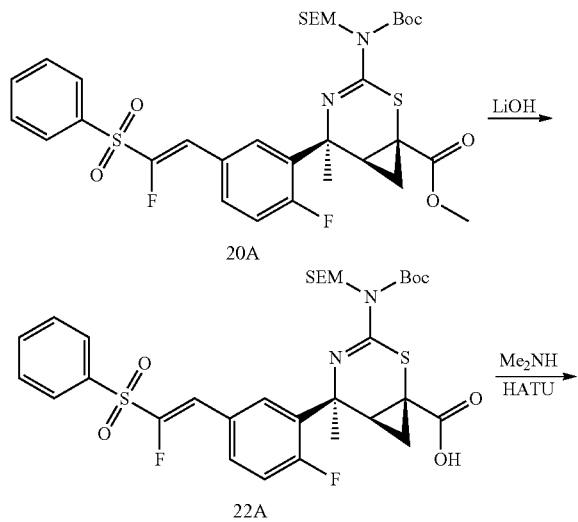

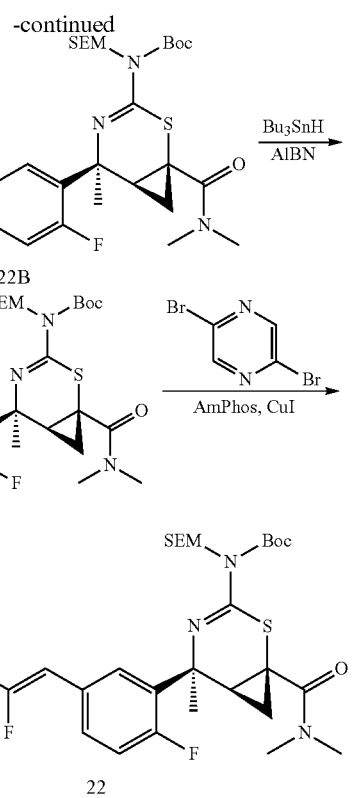

Preparation of (1S,5S,6S)-3-((tert-butoxycarbonyl)((2-(trimethylsilyl)ethoxy)methyl)amino)-5-(2-fluoro-5-((E)-2-fluoro-2-(phenylsulfonyl)vinyl)phenyl)-5-methyl-2-thia-4-azabicyclo[4.1.0]hept-3-ene-1-carboxylic acid (22A)

(1S,5S,6S)-Methyl 3-((tert-butoxycarbonyl)((2-(trimethylsilyl)ethoxy)methyl)amino)-5-(2-fluoro-5-((E)-2-fluoro-2-(phenylsulfonyl)vinyl)phenyl)-5-methyl-2-thia-4-azabicyclo[4.1.0]hept-3-ene-1-carboxylate (20A) (1.6 g, 2.3 mmol) was dissolved in 9 mL THF/3 mL water and was treated with lithium hydroxide hydrate (0.284 g, 6.77 mmol). After the reaction was stirred at room temperature for 3 hours, the organic solvent was removed in vacuo and the residue was diluted with water and the pH was adjusted to pH=4 with 1N HCl. It was extracted with DCM three times, dried and concentrated to give (1S,5S,6S)-3-((tert-butoxycarbonyl)((2-(trimethylsilyl)ethoxy)methyl)amino)-5-(2-fluoro-5-((E)-2-fluoro-2-(phenylsulfonyl)vinyl)phenyl)-5-methyl-2-thia-4-azabicyclo[4.1.0]hept-3-ene-1-carboxylic acid (22A) (1.2 g, 77% yield) as a light greenish solid. MS m/z=695 (M+H).

Preparation of tert-butyl ((1S,5S,6S)-1-(dimethylcarbamoyl)-5-(2-fluoro-5-((E)-2-fluoro-2-(phenylsulfonyl)vinyl)phenyl)-5-methyl-2-thia-4-azabicyclo[4.1.0]hept-3-en-3-yl)((2-(trimethylsilyl)ethoxy)methyl)carbamate (22B)

To a solution of (1S,5S,6S)-3-((tert-butoxycarbonyl)((2-(trimethylsilyl)ethoxy)methyl)amino)-5-(2-fluoro-5-((E)-2-fluoro-2-(phenylsulfonyl)vinyl) phenyl)-5-methyl-2-thia-4-azabicyclo[4.1.0]hept-3-ene-1-carboxylic acid (22A) (1.2 g, 1.7 mmol) (used without further purification) and dimethylamine (1.73 mL, 3.45 mmol) in 0.5 mL of DMF was added HATU (1.31 g, 3.45 mmol) followed by diisopropylethylamine (0.601 mL, 3.45 mmol). After stirring for 1 hour, most of the solvent was removed under reduced pressure and the residue was loaded onto a flash column (DCM to DCM/EtOAc=100:4 to 100:8 to 100:10) to give tert-butyl ((1S,5S,6S)-1-(dimethylcarbamoyl)-5-(2-fluoro-5-((E)-2-fluoro-2-(phenylsulfonyl)vinyl)phenyl)-5-methyl-2-thia-4-azabicyclo[4.1.0]hept-3-en-3-yl)((2-(trimethylsilyl)ethoxy)methyl)carbamate (22B) (750 mg, 60% yield). MS m/z=722 (M+H).

Preparation of tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C)

A mixture of tert-butyl ((1S,5S,6S)-1-(dimethylcarbamoyl)-5-(2-fluoro-5-((E)-2-fluoro-2-(phenylsulfonyl)vinyl)phenyl)-5-methyl-2-thia-4-azabicyclo[4.1.0]hept-3-en-3-yl)((2-(trimethylsilyl)ethoxy)methyl)carbamate (22B) (700 mg, 0.970 mmol), tributylstannane (564 mg, 1.94 mmol), and 2,2'-azobis(2-methylpropionitrile) (16 mg, 0.097 mmol) in 6 mL of heptane was sealed and heated to 80° C. for 1.5 hours. After cooling to room temperature, the reaction mixture was directly loaded onto a flash column (DCM/heptane=1:3, then pure DCM to DCM/EtOAc=100:5 to 100:8 to 100:10) to give tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (620 mg, 73% yield) as a colorless oil. $^1$H NMR (300 MHz, CDCl$_3$) δ 7.68 (d, J=8.18 Hz, 1H), 7.50 (br. s., 1H), 7.02 (dd, J=8.33, 11.69 Hz, 1H), 5.49-5.77 (m, 1H), 5.30 (d, J=10.52 Hz, 1H), 5.10 (d, J=10.52 Hz, 1H), 3.67 (t, J=8.11 Hz, 2H), 3.12 (br. s., 6H), 2.46 (t, J=8.48 Hz, 1H), 1.86 (s, 3H), 1.51-1.63 (m, 15H), 1.31-1.39 (m, 7H), 1.00-1.15 (m, 6H), 0.90-0.97 (m, 12H), 0.00 (s, 9H). $^{19}$F NMR (282 MHz, CDCl$_3$) δ −93.89 (s, 1F), −113.23 (s, 1F).

Preparation of tert-butyl ((1S,5S,6S)-5-(5-((Z)-2-(5-bromopyrazin-2-yl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (22)

A mixture of 2,5-dibromopyrazine (1.97 g, 8.27 mmol), bis(di-tert-butyl(4-dimethylaminophenyl)phosphine)dichloropalladium(ii) (0.078 g, 0.110 mmol) and copper(i) iodide (0.062 mL, 1.8 mmol) were suspended in 1.5 mL of DMF. To this was added dropwise tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (1.6 g, 1.8 mmol) in 3 mL of DMF. After stirring for 1 hour, the DMF was evaporated and the residue was loaded onto a flash column (DCM/heptane=1:1 to DCM to DCM/EtOAc=50:1) to give tert-butyl ((1S,5S,6S)-5-(5-((Z)-2-(5-bromopyrazin-2-yl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (22) (700 mg, 52% yield) as an off-white solid. MS m/z=738/740 (M+H). $^1$H NMR (300 MHz, CDCl$_3$) δ 8.63 (d, J=5.26 Hz, 2H), 7.93 (d, J=6.28 Hz, 1H), 7.67 (br. s., 1H), 6.99-7.21 (m, 2H), 5.36 (d, J=10.67 Hz, 1H), 5.14 (d, J=10.52 Hz, 1H), 3.71 (t, J=8.18 Hz, 2H), 3.13 (br. s., 6H), 2.51 (t, J=8.18 Hz, 1H), 1.89 (s, 3H), 1.55 (s, 9H), 1.22-1.35 (m, 1H), 1.09 (t, J=6.36 Hz, 1H), 0.91-1.03 (m, 2H), 0.00 (s, 9H).

Preparation of (1S,5S,6S)-methyl 3-amino-5-(5-((Z)-2-(5-bromopyrazin-2-yl)-2-fluorovinyl)-2-fluorophenyl)-5-methyl-2-thia-4-azabicyclo[4.1.0]hept-3-ene-1-carboxylate (Example 148)

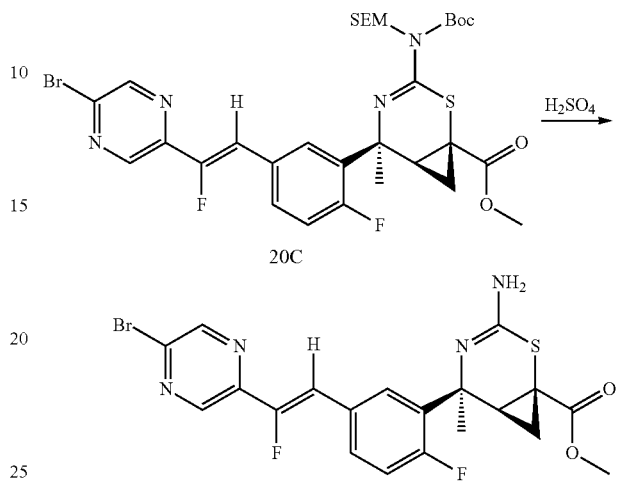

To neat (1S,5S,6S)-methyl 5-(5-((Z)-2-(5-bromopyrazin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (20C) (40 mg, 0.055 mmol) was added 0.2 mL of 96% sulfuric acid. After stirring for 10 minutes (mix thoroughly), the reaction was quenched with sat. NaHCO$_3$ to pH=8 and was extracted with DCM three times. The combined organic phases were dried over sodium sulfate, and concentrated. Flash chromatography (SiO$_2$, DCM/EtOAc=10:1 to 4:1 to 2:1) gave (1S,5S,6S)-methyl 3-amino-5-(5-((Z)-2-(5-bromopyrazin-2-yl)-2-fluorovinyl)-2-fluorophenyl)-5-methyl-2-thia-4-azabicyclo[4.1.0]hept-3-ene-1-carboxylate (Example 148) (18 mg, 65.9% yield) as a white solid. MS m/z=495/497 (M+H). $^1$H NMR (300 MHz, CDCl$_3$) δ 8.62 (br. s., 1H), 8.61 (br. s., 1H), 7.97 (d, J=7.60 Hz, 1H), 7.62-7.74 (m, 1H), 6.98-7.19 (m, 2H), 3.79 (s, 3H), 2.56 (t, J=8.70 Hz, 1H), 1.75 (s, 3H), 1.55 (dd, J=5.19, 9.72 Hz, 1H), 1.08-1.18 (m, 1H). $^{19}$F NMR (282 MHz, CDCl$_3$) δ −109.61 (s, 1F), −127.04 (s, 1F).

Preparation of (1S,5S,6S)-methyl 3-amino-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate (Example 149)

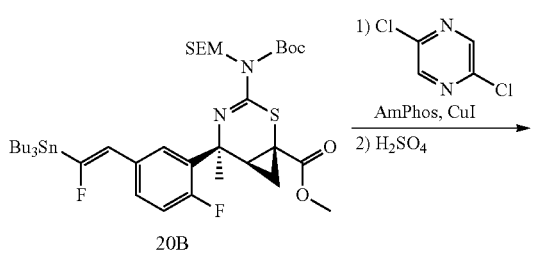

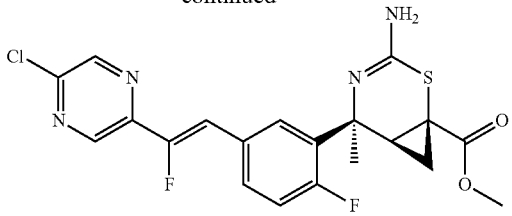

Example 149

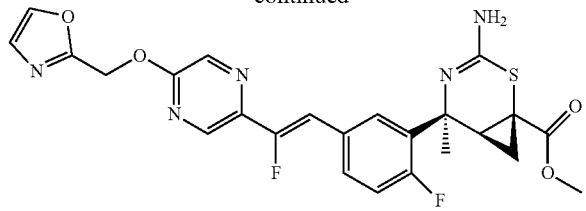

Example 150

A solution of (1S,5S,6S)-methyl 3-((tert-butoxycarbonyl)((2-(trimethylsilyl)ethoxy)methyl)amino)-5-(2-fluoro-5-((E)-2-fluoro-2-(tributylstannyl)vinyl)phenyl)-5- methyl-2-thia-4-azabicyclo[4.1.0]hept-3-ene-1-carboxylate (20B) (80 mg, 0.093 mmol) in 0.5 mL of DMF was added dropwise to a mixture of 2,5-dichloropyrazine (62.5 mg, 0.420 mmol), bis(di-tert-butyl(4-dimethylaminophenyl)phosphine)dichloropalladium(ii) (6.60 mg, 9.33 μmol) and copper(i) iodide (18 mg, 0.093 mmol) in 0.5 mL of DMF. After 1 hour, the mixture was directly loaded onto a flash column (DCM to DCM/EA=20:1) to give (1S,5S,6S)-methyl 3-((tert-butoxycarbonyl)((2-(trimethylsilyl)ethoxy)methyl)amino)-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate (22 mg, 35% yield) as a gum.

To neat (1S,5S,6S)-methyl 3-((tert-butoxycarbonyl)((2-(trimethylsilyl)ethoxy)methyl)amino)-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate (22 mg, 0.032 mmol) was added 0.2 mL of 96% sulfuric acid. After stirring for 10 minutes (mix thoroughly), the reaction was quenched with sat. NaHCO$_3$ to pH=8 and was extracted with DCM three times. The combined organic phases was dried over sodium sulfate, and concentrated. Flash chromatography (SiO$_2$, DCM/EtOAc=10:1 to 4:1 to 2:1) gave (1S,5S,6S)-methyl 3-amino-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate (Example 149) (13 mg, 0.029 mmol, 89% yield) as a white solid. MS m/z=451 (M+H). $^1$H NMR (300 MHz, CDCl$_3$) δ 8.65 (s, 1H), 8.56 (s, 1H), 7.99 (d, J=7.45 Hz, 1H), 7.64-7.81 (m, 1H), 7.00-7.20 (m, 2H), 3.81 (s, 3H), 2.58 (t, J=8.62 Hz, 1H), 1.77 (s, 3H), 1.57 (dd, J=4.82, 9.50 Hz, 1H), 1.10-1.21 (m, 1H).

Preparation of (1S,5S,6S)-methyl 3-amino-5-(2-fluoro-5-((Z)-2-fluoro-2-(5-(oxazol-2-ylmethoxy)pyrazin-2-yl)vinyl)phenyl)-5-methyl-2-thia-4-azabicyclo[4.1.0]hept-3-ene-1-carboxylate (Example 150)

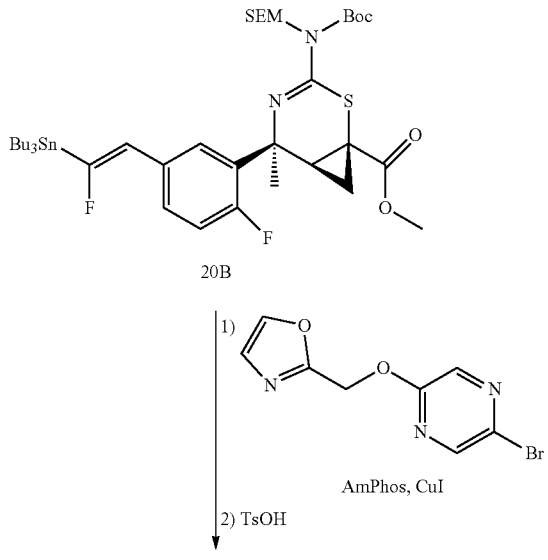

A mixture of 2-(((5-bromopyrazin-2-yl)oxy)methyl)oxazole (112 mg, 0.437 mmol), bis(di-tert-butyl(4-dimethylaminophenyl)phosphine)dichloropalladium(ii) (20 mg, 0.029 mmol) and copper(i) iodide (56 mg, 0.29 mmol) were suspended in 0.2 mL of DMF. To this was added dropwise (1S,5S,6S)-methyl 3-((tert-butoxycarbonyl)((2-(trimethylsilyl)ethoxy)methyl)amino)-5-(2-fluoro-5-((E)-2-fluoro-2-(tributylstannyl)vinyl)phenyl)-5-methyl-2-thia-4-azabicyclo[4.1.0]hept-3-ene-1-carboxylate (20B) (250 mg, 0.291 mmol) in 0.5 mL of DMF. After stirring at room temperature for 1 h, the DMF was evaporated and the residue was loaded on a flash column (DCM to DCM/EtOAc=20:1 to 10:1) to give (1S,5S,6S)-methyl 3-((tert-butoxycarbonyl)((2-(trimethylsilyl)ethoxy)methyl)amino)-5-(2-fluoro-5-((Z)-2-fluoro-2-(5-(oxazol-2-ylmethoxy)pyrazin-2-yl)vinyl)phenyl)-5-methyl-2-thia-4-azabicyclo[4.1.0]hept-3-ene-1-carboxylate (50 mg, 0.067 mmol, 23.06% yield) as a colorless oil. LCMS (ESI$^+$) m/z=744 (M+H). $^1$H NMR (300 MHz, CDCl$_3$) δ 8.39 (s, 1H), 8.32 (s, 1H), 7.94 (dd, J=2.19, 7.89 Hz, 1H), 7.73 (s, 1H), 7.66 (ddd, J=2.19, 4.68, 8.48 Hz, 1H), 7.20 (br. s., 1H), 7.12 (dd, J=8.48, 11.98 Hz, 1H), 6.75-7.02 (m, 1H), 5.55 (s, 2H), 5.32 (d, J=10.52 Hz, 1H), 5.11 (d, J=10.67 Hz, 1H), 3.82 (s, 3H), 3.64-3.75 (m, 2H), 2.69 (dd, J=8.26, 9.13 Hz, 1H), 1.80 (s, 3H), 1.56 (s, 9H), 1.48-1.53 (m, 1H), 0.91-1.02 (m, 2H), 0.00 (s, 9H). $^{19}$F NMR (282 MHz, CDCl$_3$) δ -111.92 (s, 1F), -125.83 (s, 1F).

(1S,5S,6S)-Methyl 3-((tert-butoxycarbonyl)((2-(trimethylsilyl)ethoxy)methyl)amino)-5-(2-fluoro-5-((Z)-2-fluoro-2-(5-(oxazol-2-ylmethoxy)pyrazin-2-yl)vinyl)phenyl)-5-methyl-2-thia-4-azabicyclo[4.1.0]hept-3-ene-1-carboxylate (50 mg, 0.067 mmol) was treated with 0.3 mL of 96% sulfuric acid. After stirring at room temperature for 10 minutes, the reaction was quenched with sat. NaHCO$_3$ to pH=8, extracted with DCM, dried and concentrated. Flash chromatography (DCM/EA=2:1 to 1:1 to 1:3) gave (1S,5S,6S)-methyl 3-amino-5-(2-fluoro-5-((Z)-2-fluoro-2-(5-(oxazol-2-ylmethoxy)pyrazin-2-yl)vinyl)phenyl)-5-methyl-2-thia-4-azabicyclo[4.1.0]hept-3-ene-1-carboxylate (Example 150) (32 mg, 0.062 mmol, 21% yield) as a white solid. MS m/z=514 (M+H). $^1$H NMR (300 MHz, CDCl$_3$) δ 8.38 (s, 1H), 8.30 (s, 1H), 7.92 (dd, J=2.19, 7.89 Hz, 1H), 7.70 (d, J=0.73 Hz, 1H), 7.65 (ddd, J=2.34, 4.57, 8.44 Hz, 1H), 7.17 (s, 1H), 7.08 (dd, J=8.48, 11.98 Hz, 1H), 6.78-6.98 (m, 1H), 5.53 (s, 2H), 3.79 (s, 3H), 2.49-2.63 (m, 1H), 1.75 (d, J=1.17 Hz, 3H), 1.55 (dd, J=5.12, 9.79 Hz, 1H), 1.14 (dd, J=5.41, 7.31 Hz, 1H). $^{19}$F NMR (282 MHz, CDCl$_3$) δ -111.11 (s, 1F), -125.95 (s, 1F).

Preparation of (1S,5S,6S)-3-amino-5-(2-fluoro-5-
((Z)-2-fluoro-2-(5-(prop-2-yn-1-yloxy)pyrazin-2-yl)
vinyl)phenyl)-N,5-dimethyl-2-thia-4-azabicyclo
[4.1.0]hept-3-ene-1-carboxamide (Example 151)
and (1S,5S,6S)-3-amino-5-(2-fluoro-5-((Z)-2-fluoro-
2-(5-(2-oxopropoxy)pyrazin-2-yl)vinyl)phenyl)-N,5-
dimethyl-2-thia-4-azabicyclo[4.1.0]hept-3-ene-1-
carboxamide (Example 152)

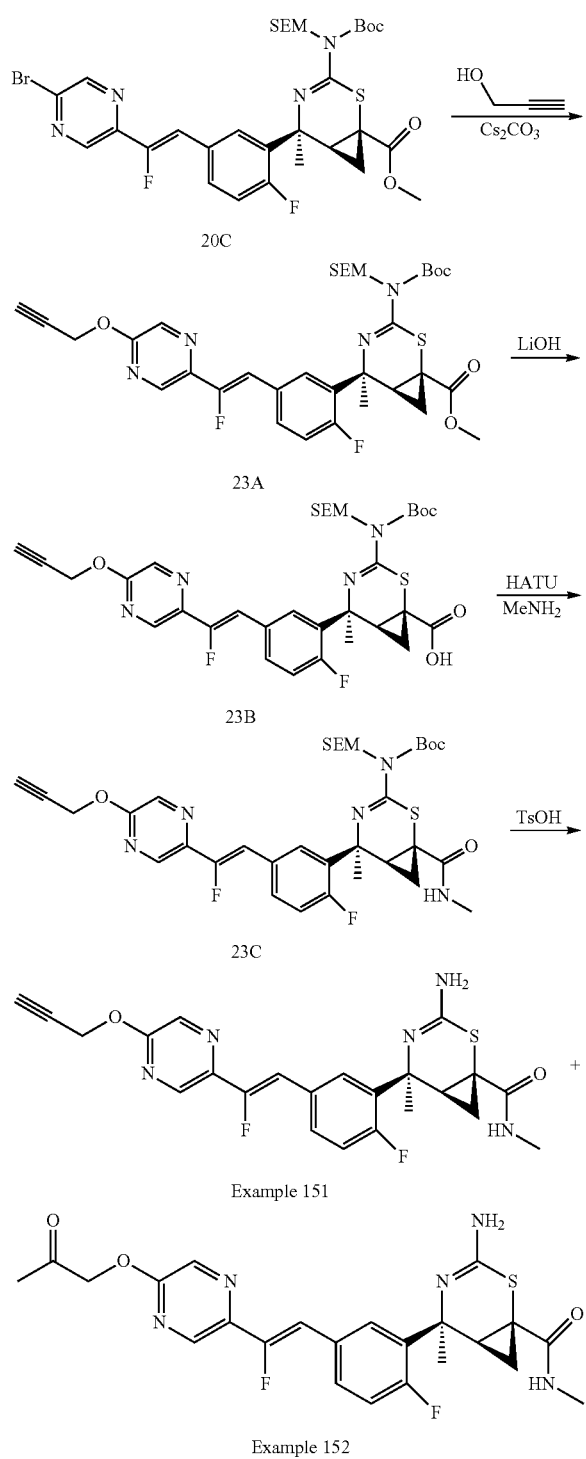

Preparation of (1S,5S,6S)-methyl 3-((tert-butoxy-
carbonyl)((2-(trimethylsilyl)ethoxy)methyl)amino)-
5-(2-fluoro-5-((Z)-2-fluoro-2-(5-(prop-2-yn-1-yloxy)
pyrazin-2-yl)vinyl)phenyl)-5-methyl-2-thia-4-
azabicyclo[4.1.0]hept-3-ene-1-carboxylate (23A)

To a mixture of (1S,5S,6S)-methyl 5-(5-((Z)-2-(5-bro-
mopyrazin-2-yl)-2-fluorovinyl)-2-fluorophenyl)-3-((tert-
butoxycarbonyl)((2-(trimethylsilyl)ethoxy)methyl)amino)-
5-methyl-2-thia-4-azabicyclo[4.1.0]hept-3-ene-1-
carboxylate (20C) (145 mg, 0.200 mmol) and propargyl
alcohol (44.8 mg, 0.799 mmol) in 0.3 mL of DMF was added
cesium carbonate (98 mg, 0.30 mmol) and the reaction was
stirred at 50° C. for 45 minutes. The solvent was evaporated
and the residue was loaded on a flash column (DCM to
DCM/EA=5:1) to provide (1S,5S,6S)-methyl 3-((tert-bu-
toxycarbonyl)((2-(trimethylsilyl)ethoxy)methyl)amino)-5-
(2-fluoro-5-((Z)-2-fluoro-2-(5-(prop-2-yn-1-yloxy)pyrazin-
2-yl)vinyl)phenyl)-5-methyl-2-thia-4-azabicyclo[4.1.0]
hept-3-ene-1-carboxylate (90 mg, 64% yield). It was
contaminated with (1S,5S,6S)-prop-2-yn-1-yl 3-((tert-bu-
toxycarbonyl)((2-(trimethylsilyl)ethoxy)methyl)amino)-5-
(2-fluoro-5-((Z)-2-fluoro-2-(5-(prop-2-yn-1-yloxy)pyrazin-
2-yl)vinyl)phenyl)-5-methyl-2-thia-4-azabicyclo[4.1.0]
hept-3-ene-1-carboxylate) as a white solid. MS m/z=701
(M+H).

Preparation of 1S,5S,6S)-3-((tert-butoxycarbonyl)
((2-(trimethylsilyl)ethoxy)methyl)amino)-5-(2-
fluoro-5-((Z)-2-fluoro-2-(5-(prop-2-yn-1-yloxy)
pyrazin-2-yl)vinyl)phenyl)-5-methyl-2-thia-4-
azabicyclo[4.1.0]hept-3-ene-1-carboxylic acid (23B)

To a solution of (1S,5S,6S)-methyl 3-((tert-butoxycarbo-
nyl)((2-(trimethylsilyl)ethoxy)methyl)amino)-5-(2-fluoro-
5-((Z)-2-fluoro-2-(5-(prop-2-yn-1-yloxy)pyrazin-2-yl)vi-
nyl)phenyl)-5-methyl-2-thia-4-azabicyclo[4.1.0]hept-3-ene-
1-carboxylate (23A) (80 mg, 0.11 mmol) in 1.5 mL of
THF/water (2:1) was added lithium hydroxide hydrate (14.4
mg, 0.342 mmol). After stirring for 3 hours at room tem-
perature, the THF was evaporated and the residue was
dissolved in water, acidified with 1N HCl to pH=4. This was
extracted with DCM three times, dried over Na₂SO₄, and
concentrated to give (1S,5S,6S)-3-((tert-butoxycarbonyl)
((2-(trimethylsilyl)ethoxy)methyl)amino)-5-(2-fluoro-5-
((Z)-2-fluoro-2-(5-(prop-2-yn-1-yloxy)pyrazin-2-yl)vinyl)
phenyl)-5-methyl-2-thia-4-azabicyclo[4.1.0]hept-3-ene-1-
carboxylic acid (23B) which was used directly in the next
step without further purification. MS m/z=687 (M+H).

Preparation of tert-butyl ((1S,5S,6S)-5-(2-fluoro-5-
((Z)-2-fluoro-2-(5-(prop-2-yn-1-yloxy)pyrazin-2-yl)
vinyl)phenyl)-5-methyl-1-(methylcarbamoyl)-2-thia-
4-azabicyclo[4.1.0]hept-3-en-3-yl)((2-
(trimethylsilyl)ethoxy)methyl) carbamate (23C)

To a solution of (1S,5S,6S)-3-((tert-butoxycarbonyl)((2-
(trimethylsilyl)ethoxy)methyl)amino)-5-(2-fluoro-5-((Z)-2-
fluoro-2-(5-(prop-2-yn-1-yloxy)pyrazin-2-yl)vinyl)phenyl)-
5-methyl-2-thia-4-azabicyclo[4.1.0]hept-3-ene-1-
carboxylic acid (120 mg, 0.175 mmol) which was used
without further purification and methylamine, 2.0m solution
in THF (349 µL, 0.699 mmol) in 0.5 mL of DMF was added
HATU (133 mg, 0.349 mmol) followed by diisopropyleth-
ylamine (60.8 µL, 0.349 mmol). After stirring for 1 hour, the
solvents was removed under reduced pressure and the resi-
due was loaded onto a flash column (DCM to DCM/

EtOAc=100:4 to 100:8 to 100:10) to give tert-butyl ((1S,5S,6S)-5-(2-fluoro-5-((Z)-2-fluoro-2-(5-(prop-2-yn-1-yloxy)pyrazin-2-yl)vinyl)phenyl)-5-methyl-1-(methylcarbamoyl)-2-thia-4-azabicyclo[4.1.0]hept-3-en-3-yl)((2-(trimethylsilyl)ethoxy)methyl)carbamate (23C) (70 mg, 57% yield) and (DCM/MeOH=10:1) to give recovered acid. MS m/z=700 (M+H). $^1$H NMR (400 MHz, CDCl$_3$) δ 8.39 (s, 1H), 8.26 (s, 1H), 7.64-7.74 (m, 2H), 7.12 (dd, J=9.10, 11.64 Hz, 1H), 6.80-6.96 (m, 2H), 5.45 (d, J=10.56 Hz, 1H), 5.20 (d, J=10.56 Hz, 1H), 5.06 (d, J=2.35 Hz, 2H), 3.65-3.80 (m, 2H), 2.90 (d, J=4.69 Hz, 3H), 2.55 (t, J=2.35 Hz, 1H), 2.27 (dd, J=7.73, 9.10 Hz, 1H), 1.94 (dd, J=5.09, 9.59 Hz, 1H), 1.86 (s, 3H), 1.58 (s, 9H), 0.95-1.09 (m, 2H), 0.88-0.94 (m, 1H), 0.00 (s, 9H).

Preparation of (1S,5S,6S)-3-amino-5-(2-fluoro-5-((Z)-2-fluoro-2-(5-(prop-2-yn-1-yloxy)pyrazin-2-yl)vinyl)phenyl)-N,5-dimethyl-2-thia-4-azabicyclo[4.1.0]hept-3-ene-1-carboxamide (Example 151) and (1S,5S,6S)-3-amino-5-(2-fluoro-5-((Z)-2-fluoro-2-(5-(2-oxopropoxy)pyrazin-2-yl)vinyl)phenyl)-N,5-dimethyl-2-thia-4-azabicyclo[4.1.0]hept-3-ene-1-carboxamide (Example 152)

A mixture of tert-butyl ((1S,5S,6S)-5-(2-fluoro-5-((Z)-2-fluoro-2-(5-(prop-2-yn-1-yloxy)pyrazin-2-yl)vinyl)phenyl)-5-methyl-1-(methylcarbamoyl)-2-thia-4-azabicyclo[4.1.0]hept-3-en-3-yl)((2-(trimethylsilyl)ethoxy)methyl)carbamate (62 mg, 0.089 mmol) and 4-methylbenzenesulfonic acid hydrate (42.1 mg, 0.221 mmol) in 0.5 mL of dioxane was sealed and heated at 70° C. for 2 hours. The solvent was removed and the residue was submitted to a flash column (DCM to EtOAc) to give (1S,5S,6S)-3-amino-5-(2-fluoro-5-((Z)-2-fluoro-2-(5-(prop-2-yn-1-yloxy)pyrazin-2-yl)vinyl)phenyl)-N,5-dimethyl-2-thia-4-azabicyclo[4.1.0]hept-3-ene-1-carboxamide (Example 151) (28 mg, 67% yield) as a white solid. MS m/z=470 (M+H). $^1$H NMR (300 MHz, CDCl$_3$) δ 8.35 (s, 1H), 8.24 (s, 1H), 7.58 (br. s., 1H), 7.47 (d, J=7.31 Hz, 1H), 7.37-7.52 (m, 1H), 6.99-7.13 (m, 1H), 6.55-6.87 (m, 2H), 5.02 (s, 2H), 2.86 (d, J=4.53 Hz, 3H), 2.53 (s, 1H), 2.20-2.32 (m, 1H), 2.01 (br. s., 1H), 1.87 (s, 3H), 0.80 (t, J=5.77 Hz, 1H). $^{19}$F NMR (282 MHz, CDCl$_3$) δ −108.38 (s, 1F), −125.68 (s, 1F). A byproduct, (1S,5S,6S)-3-amino-5-(2-fluoro-5-((Z)-2-fluoro-2-(5-(2-oxopropoxy)pyrazin-2-yl)vinyl)phenyl)-N,5-dimethyl-2-thia-4-azabicyclo[4.1.0]hept-3-ene-1-carboxamide (Example 152) (9 mg, 21% yield), was also isolated as a white solid. MS m/z=488 (M+H). $^1$H NMR (300 MHz, CDCl$_3$) δ 8.33 (s, 1H), 8.27 (s, 1H), 7.61 (br. s., 1H), 7.48 (d, J=7.31 Hz, 1H), 7.07 (dd, J=8.48, 11.25 Hz, 1H), 6.63-6.90 (m, 2H), 4.98 (s, 2H), 2.87 (d, J=4.68 Hz, 3H), 2.27 (br. s., 1H), 2.25 (s, 3H), 2.04-2.10 (m, 1H), 1.88 (s, 3H), 0.82 (t, J=5.99 Hz, 1H). $^{19}$F NMR (282 MHz, CDCl$_3$) δ −108.38 (s, 1F), −125.70 (s, 1F).

Preparation of (1S,5S,6S)-3-amino-5-(2-fluoro-5-((Z)-2-fluoro-2-(5-(prop-2-yn-1-yloxy)pyrazin-2-yl)vinyl)phenyl)-N,N,5-trimethyl-2-thia-4-azabicyclo[4.1.0]hept-3-ene-1-carboxamide (Example 153)

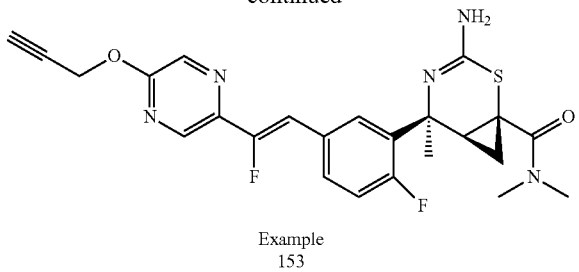

Example 153

Step 1.

To a solution of (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylic acid (120 mg, 0.175 mmol) (used without further purification) and dimethylamine (349 μL, 0.699 mmol) in 0.5 mL of DMF was added HATU (133 mg, 0.349 mmol) followed by diisopropylethylamine (60.8 μL, 0.349 mmol). After stirring for 1 hour, most of the solvent was removed under reduced pressure and the residue was loaded onto a flash column (DCM to DCM/EtOAc=100:4 to 100:8 to 100:10) to give tert-butyl ((1S,5S,6S)-1-(dimethylcarbamoyl)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-3-yl)((2-(trimethylsilyl)ethoxy)methyl)carbamate (80 mg, 64% yield). MS m/z=714 (M+H).

A mixture of tert-butyl ((1S,5S,6S)-1-(dimethylcarbamoyl)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-3-yl)((2-(trimethylsilyl)ethoxy)methyl)carbamate (80 mg, 0.11 mmol) and 4-methylbenzenesulfonic acid hydrate (63.9 mg, 0.336 mmol) in 0.5 mL of dioxane was sealed and heated at 70° C. for 2 hours. The solvent was evaporated and the residue was submitted to a flash column (DCM to EtOAc) to give (1S,5S,6S)-3-amino-5-(2-fluoro-5-((Z)-2-fluoro-2-(5-(prop-2-yn-1-yloxy)pyrazin-2-yl)vinyl)phenyl)-N,N,5-trimethyl-2-thia-4-azabicyclo[4.1.0]hept-3-ene-1-carboxamide (Example 153) (43 mg, 79% yield) as a white solid. MS m/z=484 (M+H). $^1$H NMR (300 MHz, CDCl$_3$) δ 8.37 (s, 1H), 8.25 (s, 1H), 7.71 (d, J=7.60 Hz, 1H), 7.61 (br. s., 1H), 7.00-7.14 (m, 1H), 6.73-6.94 (m, 1H), 5.03 (d, J=1.90 Hz, 2H), 3.06 (br. s., 6H), 2.53 (s, 1H), 2.23-2.35 (m, 1H), 1.87 (s, 3H), 1.38 (dd, J=5.77, 9.28 Hz, 1H), 0.87 (t, J=6.36 Hz, 1H). $^{19}$F NMR (282 MHz, CDCl$_3$) δ −109.97 (s, 1F), −125.95 (s, 1F).

Preparation of (1S,5S,6S)-3-amino-5-(2-fluoro-5-((Z)-2-fluoro-2-(5-(oxazol-2-ylmethoxy)pyrazin-2-yl)vinyl)phenyl)-N,N,5-trimethyl-2-thia-4-azabicyclo[4.1.0]hept-3-ene-1-carboxamide (Example 154)

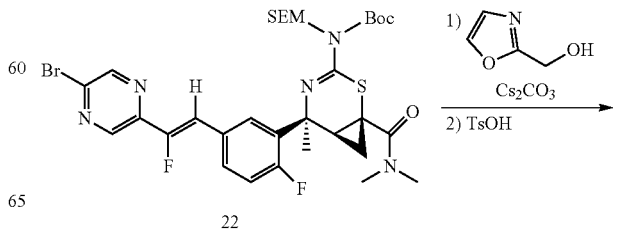

147

-continued

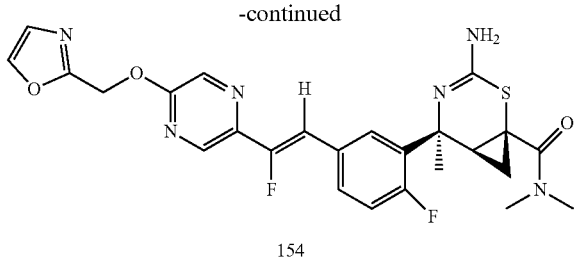

154

To a mixture of tert-butyl ((1S,5S,6S)-5-(5-((Z)-2-(5-bromopyrazin-2-yl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (22) (80 mg, 0.108 mmol) and oxazol-2-ylmethanol (21.5 mg, 0.217 mmol) in 0.3 mL of DMF was added cesium carbonate (52.9 mg, 0.162 mmol) and the reaction was stirred at 60° C. for 3 hours. The solvent was removed and the residue was directly submitted to a flash column (DCM to DCM/EtOAc=100:6 to 100:8 to 100:10) to give tert-butyl ((1S,5S,6S)-1-(dimethylcarbamoyl)-5-(2-fluoro-5-((Z)-2-fluoro-2-(5-(oxazol-2-ylmethoxy)pyrazin-2-yl)vinyl)phenyl)-5-methyl-2-thia-4-azabicyclo[4.1.0]hept-3-en-3-yl)((2-(trimethylsilyl)ethoxy)methyl)carbamate (65 mg, 79% yield) as a gum.

A mixture of tert-butyl ((1S,5S,6S)-1-(dimethylcarbamoyl)-5-(2-fluoro-5-((Z)-2-fluoro-2-(5-(oxazol-2-ylmethoxy)pyrazin-2-yl)vinyl)phenyl)-5-methyl-2-thia-4-azabicyclo[4.1.0]hept-3-en-3-yl)((2-(trimethylsilyl)ethoxy)methyl)carbamate (60 mg, 0.079 mmol) and 4-methylbenzenesulfonic acid hydrate (45.2 mg, 0.238 mmol) in 0.5 mL of dioxane was sealed and heated at 70° C. for 2 hours. The solvent was evaporated and the residue was submitted to a flash column (DCM to DCM/MeOH=100:6 to 100:8 to 100:10) to give (1S,5S,6S)-3-amino-5-(2-fluoro-5-((Z)-2-fluoro-2-(5-(oxazol-2-ylmethoxy)pyrazin-2-yl)vinyl)phenyl)-N,N,5-trimethyl-2-thia-4-azabicyclo[4.1.0]hept-3-ene-1-carboxamide (Example 154) (35 mg, 84% yield) as a white solid. MS m/z=527 (M+H). $^1$H NMR (300 MHz, CDCl$_3$) δ 8.37 (s, 1H), 8.30 (s, 1H), 7.66-7.76 (m, 2H), 7.61 (d, J=4.97 Hz, 1H), 7.17 (s, 1H), 7.07 (dd, J=8.55, 11.62 Hz, 1H), 6.72-6.93 (m, 1H), 5.53 (s, 2H), 3.06 (br. s., 6H), 2.25-2.41 (m, 1H), 1.89 (s, 3H), 1.41 (dd, J=5.77, 9.57 Hz, 1H), 0.89 (t, J=6.50 Hz, 1H). $^{19}$F NMR (282 MHz, CDCl$_3$) δ −109.85 (s, 1F), −125.88 (s, 1F).

Preparation of (1S,5S,6S)-3-amino-5-(2-fluoro-5-((Z)-2-fluoro-2-(5-(2,2,2-trifluoroethoxy)pyrazin-2-yl)vinyl)phenyl)-N,N,5-trimethyl-2-thia-4-azabicyclo[4.1.0]hept-3-ene-1-carboxamide (Example 155)

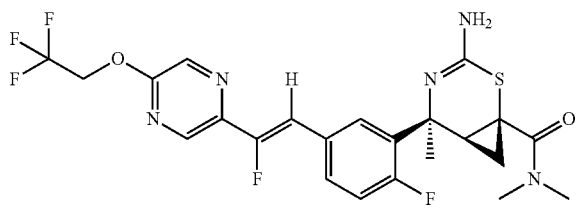 [SMILES: CN(C)C(=O)[C@]12C[C@H]1[C@@](C)(c1cc(/C=C(\F)c3cnc(OCC(F)(F)F)cn3)ccc1F)N=C(N)S2]

Example 155

Using a similar procedure to that described for Example 154, tert-butyl ((1S,5S,6S)-5-(5-((Z)-2-(5-bromopyrazin-2-yl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (22) (60 mg, 0.081 mmol), 2,2,2-trifluoroethanol (29.6 μL, 0.406 mmol) and cesium carbonate (52.9 mg, 0.162 mmol) were combined to provide the S$_N$Ar product, which, after deprotection with 4-methylbenzenesulfonic acid hydrate, gave (1S,5S,6S)-3-amino-5-(2-fluoro-5-((Z)-2-fluoro-2-(5-(2,2,2-trifluoroethoxy)pyrazin-2-yl)vinyl)phenyl)-N,N,5-trimethyl-2-thia-4-azabicyclo[4.1.0]hept-3-ene-1-carboxamide (Example 155) (32 mg, 75% yield over two steps) as a light yellow solid. MS m/z=528 (M+H). $^1$H NMR (300 MHz, CDCl$_3$) δ 8.35 (s, 1H), 8.32 (s, 1H), 7.71 (d, J=7.89 Hz, 1H), 7.58-7.66 (m, 1H), 7.07 (dd, J=8.48, 11.69 Hz, 1H), 6.75-6.97 (m, 1H), 4.81 (q, J=8.28 Hz, 2H), 3.06 (br. s., 6H), 2.24-2.35 (m, 1H), 1.88 (s, 3H), 1.40 (dd, J=5.70, 9.65 Hz, 1H), 0.88 (t, J=6.36 Hz, 1H). $^{19}$F NMR (282 MHz, CDCl$_3$) δ −73.68 (s, 3F), −109.65 (s, 1F), −126.14 (s, 1F).

Preparation of (1S,5S,6S)-3-amino-5-(2-fluoro-5-((Z)-2-fluoro-2-(5-(-1-(oxazol-2-yl)ethoxy)pyrazin-2-yl)vinyl)phenyl)-N,N,5-trimethyl-2-thia-4-azabicyclo[4.1.0]hept-3-ene-1-carboxamide (Example 156)

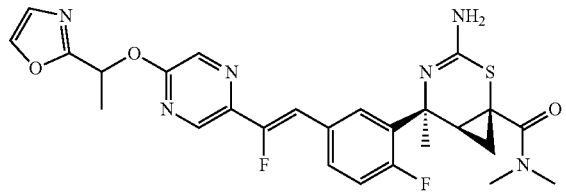 [SMILES: CC(Oc1cnc(/C(F)=C/c2ccc(F)c([C@@]3(C)N=C(N)S[C@@]4(C(=O)N(C)C)C[C@H]43)c2)cn1)c1ncco1]

Example 156

Using a similar procedure to that described for Example 154, tert-butyl ((1S,5S,6S)-5-(5-((Z)-2-(5-bromopyrazin-2-yl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (22) (130 mg, 0.176 mmol), 1-(oxazol-2-yl)ethanol (80 mg, 0.704 mmol) and cesium carbonate (115 mg, 0.352 mmol) were combined to provide the S$_N$Ar product, which, after deprotection with 4-methylbenzenesulfonic acid hydrate, gave (1S,5S,6S)-3-amino-5-(2-fluoro-5-((Z)-2-fluoro-2-(5-(-1-(oxazol-2-yl)ethoxy)pyrazin-2-yl)vinyl)phenyl)-N,N,5-trimethyl-2-thia-4-azabicyclo[4.1.0]hept-3-ene-1-carboxamide (Example 156) (90 mg, 95% yield over two steps) as a light yellow solid. MS m/z=541 (M+H). $^1$H NMR (300 MHz, CDCl$_3$) δ 8.33 (s, 1H), 8.25 (s, 1H), 7.68 (d, J=8.04 Hz, 1H), 7.64 (s, 1H), 7.60 (d, J=4.38 Hz, 1H), 7.11 (s, 1H), 7.06 (dd, J=8.40, 11.62 Hz, 1H), 6.72-6.93 (m, 1H), 6.35 (q, J=6.72 Hz, 1H), 3.06 (br. s., 6H), 2.25-2.33 (m, 1H), 1.88 (s, 3H), 1.81 (d, J=6.72 Hz, 3H), 1.40 (dd, J=5.77, 9.57 Hz, 1H), 0.88 (t, J=6.43 Hz, 1H). $^{19}$F NMR (282 MHz, CDCl$_3$) δ −109.95 (s, 1F), −125.85 (s, 1F).

Preparation of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (Example 157)

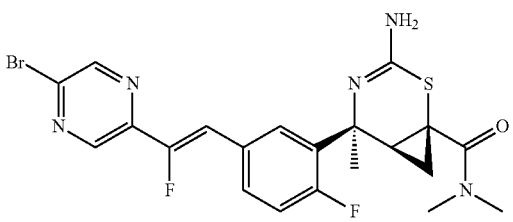 [SMILES: CN(C)C(=O)[C@]12C[C@H]1[C@@](C)(c1cc(/C=C(\F)c3cnc(Br)cn3)ccc1F)N=C(N)S2]

Example 157

A mixture of tert-butyl ((1S,5S,6S)-5-(5-((Z)-2-(5-bromopyrazin-2-yl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (22) (100 mg, 0.135 mmol) and 4-methylbenzenesulfonic acid hydrate (77 mg, 0.41 mmol) in 0.5 mL of dioxane was sealed and heated at 70° C. for 2 hours. The solvent was evaporated and the residue was submitted to a flash column (DCM to EA to DCM/MeOH=100:6 to 100:8 to 100:10) to give (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (Example 157) (65 mg, 94% yield) as a white solid. MS m/z=508/510 (M+H). $^1$H NMR (300 MHz, CDCl$_3$) δ 8.62 (s, 1H), 8.60 (br. s., 1H), 7.74 (d, J=7.45 Hz, 1H), 7.65 (br. s., 1H), 6.97-7.15 (m, 2H), 3.08 (br. s., 6H), 2.33 (t, J=8.26 Hz, 1H), 1.90 (s, 3H), 1.42 (dd, J=5.55, 9.50 Hz, 1H), 0.90 (t, J=6.58 Hz, 1H). $^{19}$F NMR (282 MHz, CDCl$_3$) δ −108.32 (s, 1F), −126.95 (s, 1F).

Preparation of (1S,5S,6S)-3-amino-5-(5-((Z)-2-(5-(cyanomethoxy)pyrazin-2-yl)-2-fluorovinyl)-2-fluorophenyl)-N,N,5-trimethyl-2-thia-4-azabicyclo[4.1.0]hept-3-ene-1-carboxamide (Example 158)

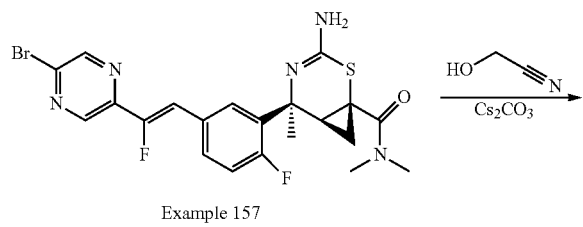

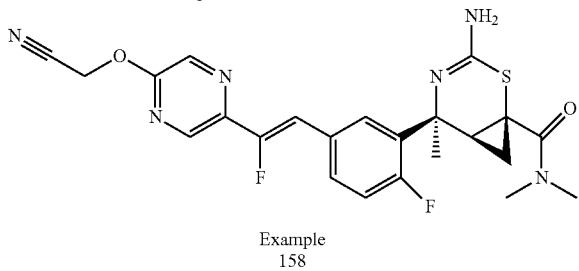

A mixture of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (Example 157) (30 mg, 0.059 mmol), formaldehyde cyanohydrin (30.6 mg, 0.295 mmol) and cesium carbonate (38.5 mg, 0.118 mmol) in 0.3 mL of DMF was sealed and heated at 50° C. for 3 hours. After cooling to room temperature, the mixture was concentrated and was purified by Preparatory TLC (DCM/MeOH=100:6) to give (1S,5S,6S)-3-amino-5-(5-((Z)-2-(5-(cyanomethoxy)pyrazin-2-yl)-2-fluorovinyl)-2-fluorophenyl)-N,N,5-trimethyl-2-thia-4-azabicyclo[4.1.0]hept-3-ene-1-carboxamide (Example 158) (9 mg, 32% yield) as a tan film. MS m/z=485 (M+H). $^1$H NMR (300 MHz, CDCl$_3$) δ 8.41 (s, 1H), 8.32 (s, 1H), 7.66 (d, J=6.43 Hz, 2H), 7.04-7.17 (m, 1H), 6.78-6.99 (m, 1H), 5.08 (s, 2H), 3.07 (br. s., 6H), 2.27-2.38 (m, 1H), 1.93 (s, 3H), 1.46 (dd, J=6.07, 9.87 Hz, 1H), 0.89-0.93 (m, 1H). $^{19}$F NMR (282 MHz, CDCl$_3$) δ −109.18 (s, 1F), −126.00 (s, 1F).

Preparation of (1S,5S,6S)-3-amino-5-(5-((Z)-2-(5-(cyclopropylethynyl)pyrazin-2-yl)-2-fluorovinyl)-2-fluorophenyl)-N,N,5-trimethyl-2-thia-4-azabicyclo[4.1.0]hept-3-ene-1-carboxamide (Example 159)

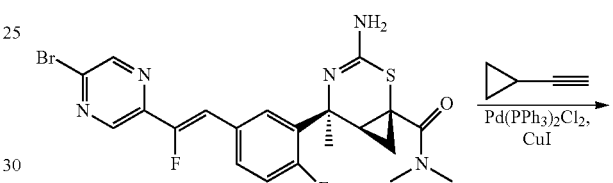

Example 157

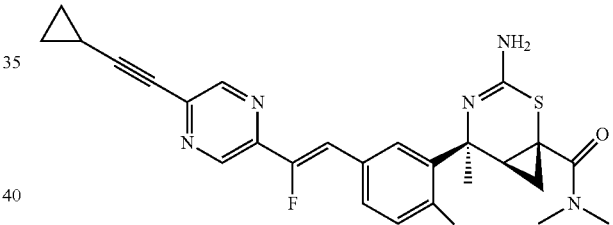

Example 159

(1S,5S,6S)-3-Amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (Example 157) (30 mg, 0.059 mmol), copper(i) iodide (1.1 mg, 5.9 μmol), trans-dichlorobis(triphenyl-phosphine)palladium (ii) (4.14 mg, 5.90 μmol) and N-ethyl-N-isopropylpropan-2-amine (76 mg, 0.59 mmol) in 0.5 mL DMF was degassed by bubbling nitrogen gas for 3 minutes. To this was added cyclopropylacetylene (25.0 μL, 0.295 mmol) and the reaction mixture was sealed and heated at 60° C. for 2 hours. The solvent was evaporated the residue was submitted to a flash column (DCM to EA to EA/MeOH=100:3 to 100:6 to 10:1) to give (1S,5S,6S)-3-amino-5-(5-((Z)-2-(5-(cyclopropylethynyl)pyrazin-2-yl)-2-fluorovinyl)-2-fluorophenyl)-N,N,5-trimethyl-2-thia-4-azabicyclo[4.1.0]hept-3-ene-1-carboxamide (Example 159) (20 mg, 69% yield) as a yellow solid. MS m/z=494 (M+H). $^1$H NMR (300 MHz, CDCl$_3$) δ 8.76 (br. s., 1H), 8.51 (s, 1H), 7.56-7.77 (m, 2H), 6.85-7.17 (m, 2H), 3.04 (br. s., 6H), 2.29 (br. s., 1H), 1.90 (br. s., 3H), 1.55 (t, J=6.28 Hz, 1H), 0.83-1.08 (m, 6H). $^{19}$F NMR (282 MHz, CDCl$_3$) δ −108.62 (s, 1F), −126.95 (s, 1F).

Preparation of 6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)-5-methylnicotinonitrile (Example 160)

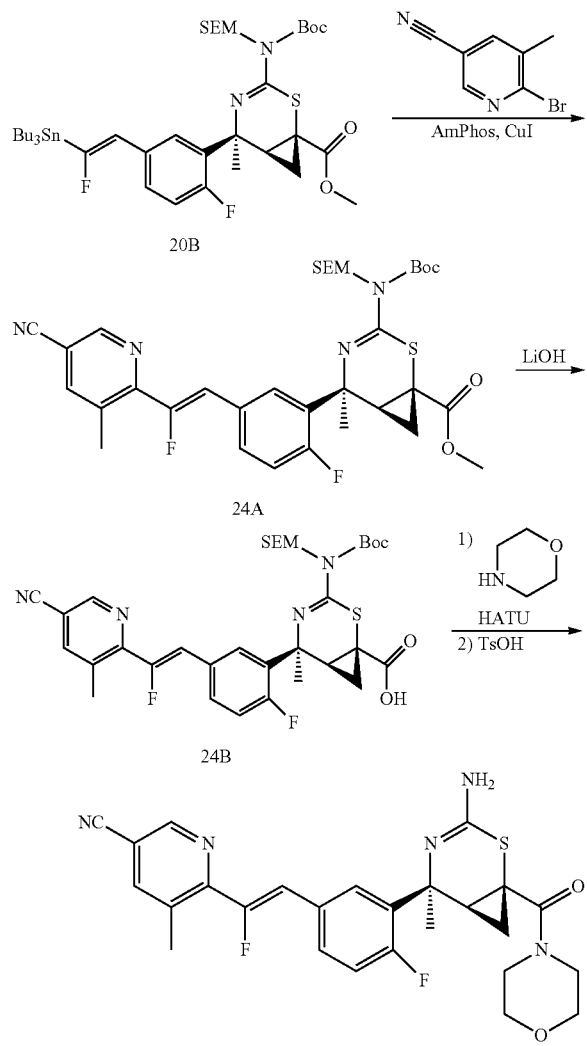

Example 160

Preparation of (1S,5S,6S)-methyl 3-((tert-butoxycarbonyl)((2-(trimethylsilyl)ethoxy)methyl)amino)-5-(5-((Z)-2-(5-cyano-3-methylpyridin-2-yl)-2-fluorovinyl)-2-fluorophenyl)-5-methyl-2-thia-4-azabicyclo[4.1.0]hept-3-ene-1-carboxylate (24A)

A mixture of 2-bromo-5-cyano-3-picoline (138 mg, 0.699 mmol), bis(di-tert-butyl(4-dimethylaminophenyl)phosphine)dichloropalladium(ii) (12 mg, 0.017 mmol) and copper(i) iodide (53 mg, 0.28 mmol) was suspended in 0.4 mL of DMF. To this was added dropwise (1S,5S,6S)-methyl 3-((tert-butoxycarbonyl)((2-(trimethylsilyl)ethoxy)methyl)amino)-5-(2-fluoro-5-((E)-2-fluoro-2-(tributylstannyl)vinyl)phenyl)-5-methyl-2-thia-4-azabicyclo[4.1.0]hept-3-ene-1-carboxylate (20B) (240 mg, 0.280 mmol) in 0.5 mL of DMF. After stirring for 1 hour, the DMF was evaporated and the residue was loaded onto a flash column (DCM/heptane=1:1 to DCM to DCM/EtOAc=50:1) to give impure product contaminated with destannated vinyl-fluoride. Further purification by preparatory TLC (DCM/EtOAc=50:1) gave (1S,5S,6S)-methyl 3-((tert-butoxycarbonyl)((2-(trimethylsilyl)ethoxy)methyl)amino)-5-(5-((Z)-2-(5-cyano-3-methylpyridin-2-yl)-2-fluorovinyl)-2-fluorophenyl)-5-methyl-2-thia-4-azabicyclo[4.1.0]hept-3-ene-1-carboxylate (24A) (55 mg, 29% yield) as a light yellow solid. MS m/z=685.3 (M+H). $^1$H NMR (300 MHz, CDCl$_3$) δ 8.70 (s, 1H), 7.96 (d, J=7.45 Hz, 1H), 7.55-7.89 (m, 2H), 7.15 (dd, J=8.40, 11.77 Hz, 1H), 6.94-7.10 (m, 1H), 5.04-5.47 (m, 2H), 3.83 (s, 3H), 3.70 (t, J=8.18 Hz, 2H), 2.70 (t, J=8.55 Hz, 1H), 2.60 (d, J=6.87 Hz, 3H), 1.81 (s, 3H), 1.56 (s, 9H), 1.48-1.54 (m, 1H), 1.23-1.33 (m, 1H), 0.90-1.06 (m, 2H), 0.00 (s, 9H).

Preparation of (1S,5S,6S)-3-((tert-butoxycarbonyl)((2-(trimethylsilyl)ethoxy)methyl)amino)-5-(5-((Z)-2-(5-cyano-3-methylpyridin-2-yl)-2-fluorovinyl)-2-fluorophenyl)-5-methyl-2-thia-4-azabicyclo[4.1.0]hept-3-ene-1-carboxylic acid (24B)

(1S,5S,6S)-Methyl 3-((tert-butoxycarbonyl)((2-(trimethylsilyl)ethoxy)methyl)amino)-5-(5-((Z)-2-(5-cyano-3-methylpyridin-2-yl)-2-fluorovinyl)-2-fluorophenyl)-5-methyl-2-thia-4-azabicyclo[4.1.0]hept-3-ene-1-carboxylate (50 mg, 0.073 mmol) was dissolved in 1.5 mL THF/0.5 mL water. To this was added lithium hydroxide hydrate (4.60 mg, 0.110 mmol) and the reaction was stirred at room temperature for 3 hours. The organic solvent was removed in vacuo and the residue was diluted with water and the pH was adjusted to pH=4 with 1N HCl. The mixture was extracted with DCM three times, dried and evaporated to give (1S,5S,6S)-3-((tert-butoxycarbonyl)((2-(trimethylsilyl)ethoxy)methyl)amino)-5-(5-((Z)-2-(5-cyano-3-methylpyridin-2-yl)-2-fluorovinyl)-2-fluorophenyl)-5-methyl-2-thia-4-azabicyclo[4.1.0]hept-3-ene-1-carboxylic acid (50 mg, 102% yield) as a light greenish solid which was used without further purification. MS m/z=671 (M+H).

Preparation of 6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)-5-methylnicotinonitrile (Example 160)

Using a similar procedure to that described for Example 153, (1S,5S,6S)-3-((tert-butoxycarbonyl)((2-(trimethylsilyl)ethoxy)methyl)amino)-5-(5-((Z)-2-(5-cyano-3-methylpyridin-2-yl)-2-fluorovinyl)-2-fluorophenyl)-5-methyl-2-thia-4-azabicyclo[4.1.0]hept-3-ene-1-carboxylic acid (50 mg, 0.075 mmol) (used without further purification), morpholine (19.5 μL, 0.224 mmol), HATU (42.5 mg, 0.112 mmol) and diisopropylethylamine (25.9 μL, 0.149 mmol) were combined to provide the amide coupling product, which, after deprotection with 4-methylbenzenesulfonic acid hydrate, gave 6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)-5-methylnicotinonitrile (Example 160) (17 mg, 45% yield over two steps). MS m/z=510.2 (M+H). $^1$H NMR (300 MHz, CDCl$_3$) δ 8.67 (s, 1H), 7.71-7.82 (m, 2H), 7.67 (br. s., 1H), 7.09 (dd, J=8.70, 11.62 Hz, 1H), 6.88-7.04 (m, 1H), 3.69 (t, J=5.04 Hz, 8H), 2.57 (d, J=6.72 Hz, 3H), 2.32 (t, J=8.48 Hz, 1H), 1.85 (s, 3H), 1.36 (dd, J=5.77, 9.72 Hz, 1H), 0.85-0.93 (m, 1H). $^{19}$F NMR (282 MHz, CDCl$_3$) δ −108.99 (s, 1F), −115.16 (s, 1F).

Preparation of (1S,5S,6S)-3-amino-5-(2-fluoro-5-((Z)-2-fluoro-2-(5-(2,2,3,3-tetrafluoropropoxy)pyrazin-2-yl)vinyl)phenyl)-N,5-dimethyl-2-thia-4-azabicyclo[4.1.0]hept-3-ene-1-carboxamide (Example 161)

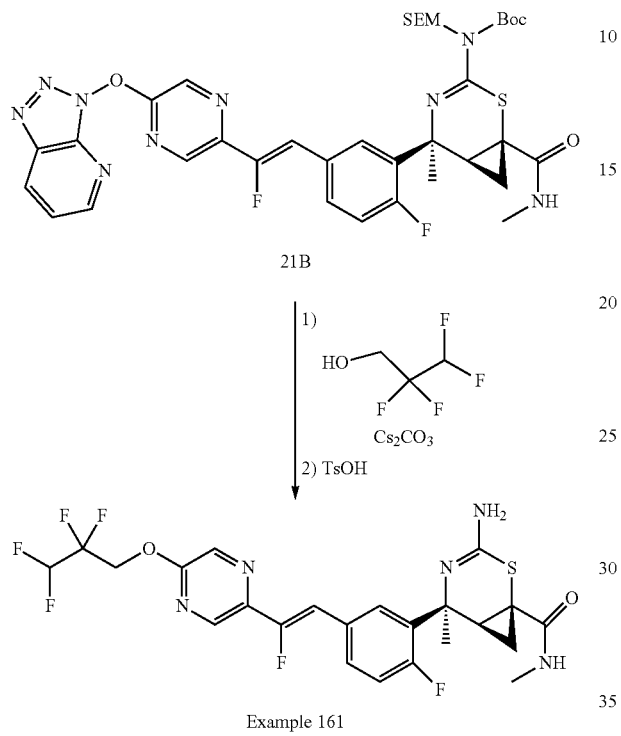

Example 161

To a mixture of tert-butyl ((1S,5S,6S)-5-(5-((Z)-2-(5-((3H-[1,2,3]triazolo[4,5-b]pyridin-3-yl)oxy)pyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (21B) (70 mg, 0.090 mmol) and 2,2,3,3-tetrafluoro-1-propanol (35.6 µL, 0.269 mmol) in 0.3 mL of DMF was added cesium carbonate (43.9 mg, 0.135 mmol) and the reaction was stirred at 60° C. for 3 hours. The solvent was removed and the residue was directly submitted to a flash column (DCM to DCM/EtOAc=100:6 to 100:8 to 100:10) to give tert-butyl ((1S,5S,6S)-5-(2-fluoro-5-((Z)-2-fluoro-2-(5-(2,2,3,3-tetrafluoropropoxy)pyrazin-2-yl)vinyl)phenyl)-5-methyl-1-(methylcarbamoyl)-2-thia-4-azabicyclo[4.1.0]hept-3-en-3-yl)((2-(trimethylsilyl)ethoxy)methyl)carbamate (48 mg, 69% yield) as a gum.

This intermediate was treated with 4-methylbenzenesulfonic acid hydrate (34.1 mg, 0.180 mmol) in 1 mL of dioxane at 70° C. for 2 hours. After cooling, it was directly loaded onto a flash column (DCM/MeOH=100:4 to 100:6 to 100:8 to 100:10) to give (1S,5S,6S)-3-amino-5-(2-fluoro-5-((Z)-2-fluoro-2-(5-(2,2,3,3-tetrafluoropropoxy)pyrazin-2-yl)vinyl)phenyl)-N,5-dimethyl-2-thia-4-azabicyclo[4.1.0]hept-3-ene-1-carboxamide (Example 161) (30 mg, 61.3% yield) as a white solid. MS m/z=546.0 (M+H). $^1$H NMR (300 MHz, CDCl$_3$) δ 8.35 (s, 1H), 8.29 (s, 1H), 7.60 (br. s., 1H), 7.53 (d, J=8.33 Hz, 1H), 7.02-7.14 (m, 1H), 6.73-6.93 (m, 1H), 6.63 (d, J=3.07 Hz, 1H), 5.78-6.25 (m, 1H), 4.80 (t, J=12.57 Hz, 2H), 2.87 (d, J=4.53 Hz, 3H), 2.19-2.33 (m, 1H), 2.01 (dd, J=4.90, 9.72 Hz, 1H), 1.86 (s, 3H), 0.80 (t, J=5.99 Hz, 1H). $^{19}$F NMR (282 MHz, CDCl$_3$) δ −108.23 (s, 1F), −123.87 (s, 1F), −125.95 (s, 1F), −137.84 (s, 1F), −137.86 (s, 1F).

Preparation of (1S,5S,6S)-3-amino-5-(2-fluoro-5-((Z)-2-fluoro-2-(5-(oxazol-2-ylmethoxy)pyrazin-2-yl)vinyl)phenyl)-N,5-dimethyl-2-thia-4-azabicyclo[4.1.0]hept-3-ene-1-carboxamide (Example 162)

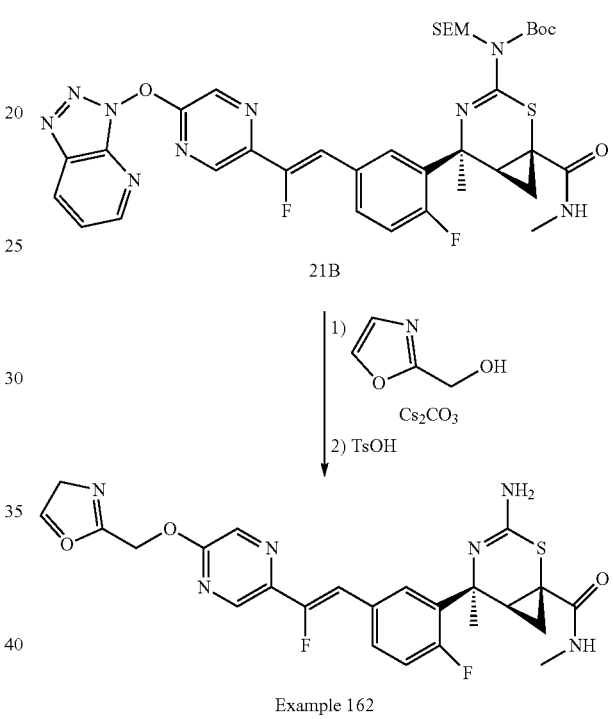

Example 162

Using a similar procedure to that described for Example 161, tert-butyl ((1S,5S,6S)-5-(5-((Z)-2-(5-((3H-[1,2,3]triazolo[4,5-b]pyridin-3-yl)oxy)pyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (21B) (70 mg, 0.090 mmol), oxazol-2-ylmethanol (22.2 mg, 0.224 mmol) and cesium carbonate (43.9 mg, 0.135 mmol) were combined to provide the S$_N$Ar product, which, after deprotection with 4-methylbenzenesulfonic acid hydrate, gave (1S,5S,6S)-3-amino-5-(2-fluoro-5-((Z)-2-fluoro-2-(5-(oxazol-2-ylmethoxy)pyrazin-2-yl)vinyl)phenyl)-N,5-dimethyl-2-thia-4-azabicyclo[4.1.0]hept-3-ene-1-carboxamide (Example 162) (12 mg, 26%) as a light yellow solid. MS m/z=513.0 (M+H). $^1$H NMR (300 MHz, CDCl$_3$) δ 8.36 (s, 1H), 8.29 (s, 1H), 7.70 (s, 1H), 7.60 (br. s., 1H), 7.50 (d, J=8.18 Hz, 1H), 7.17 (s, 1H), 7.00-7.12 (m, 1H), 6.72-6.90 (m, 1H), 6.65 (br. s., 1H), 5.52 (s, 2H), 2.87 (d, J=4.68 Hz, 3H), 2.19-2.30 (m, 1H), 1.98-2.06 (m, 1H), 1.86 (s, 3H), 0.75-0.86 (m, 1H). $^{19}$F NMR (282 MHz, CDCl$_3$) δ −108.42 (s, 1F), −125.76 (s, 1F).

Preparation of (1S,5S,6S)-3-amino-5-(5-((Z)-2-(5-bromopyrazin-2-yl)-2-fluorovinyl)-2-fluorophenyl)-N,5-dimethyl-2-thia-4-azabicyclo[4.1.0]hept-3-ene-1-carboxamide (Example 163)

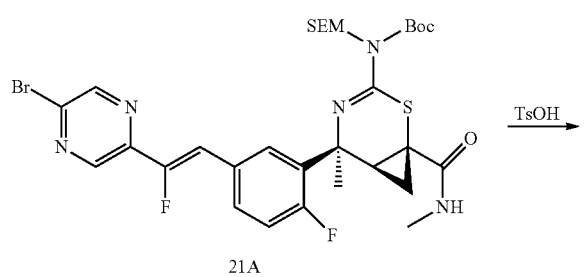

21A

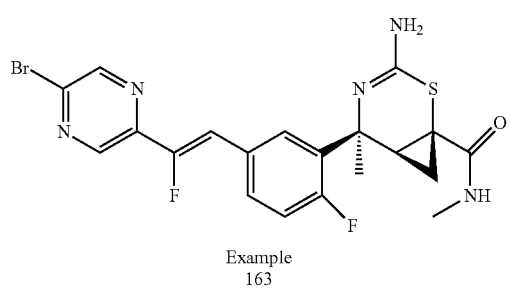

Example 163

A mixture of tert-butyl ((1S,5S,6S)-5-(5-((Z)-2-(5-bromopyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (21A) (330 mg, 0.455 mmol) and 4-methylbenzenesulfonic acid hydrate (217 mg, 1.14 mmol) in 1 mL of dioxane was sealed and heated at 70° C. for 2 hours. The solvent was evaporated and the residue was submitted to a flash column (DCM to DCM/MeOH=100:6 to 100:8 to 100:10) to give (1S,5S,6S)-3-amino-5-(5-((Z)-2-(5-bromopyrazin-2-yl)-2-fluorovinyl)-2-fluorophenyl)-N,5-dimethyl-2-thia-4-azabicyclo[4.1.0]hept-3-ene-1-carboxamide (Example 163) (170 mg, 76% yield) as a white solid. MS m/z=494.0 (M+H). ¹H NMR (300 MHz, CDCl₃) δ 8.62 (s, 1H), 8.59 (s, 1H), 7.59 (dd, J=7.09, 13.08 Hz, 2H), 6.92-7.16 (m, 2H), 6.63 (br. s., 1H), 2.87 (d, J=4.97 Hz, 3H), 2.21-2.31 (m, 1H), 2.01 (dd, J=5.12, 9.65 Hz, 1H), 1.86 (s, 3H), 0.75-0.84 (m, 1H). ¹⁹F NMR (282 MHz, CDCl₃) δ −106.99 (s, 1F), −126.89 (s, 1F).

Preparation of (1S,5S,6S)-3-amino-5-(2-fluoro-5-((Z)-2-fluoro-2-(5-(prop-1-yn-1-yl)pyrazin-2-yl)vinyl)phenyl)-N,5-dimethyl-2-thia-4-azabicyclo[4.1.0]hept-3-ene-1-carboxamide (Example 164)

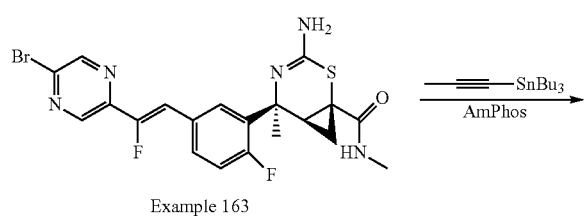

Example 163

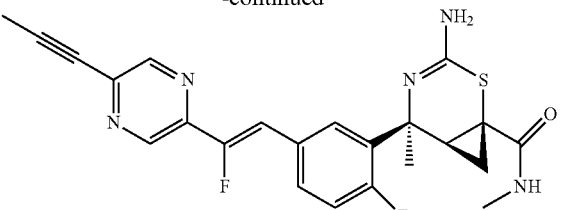

Example 164

(1S,5S,6S)-3-Amino-5-(5-((Z)-2-(5-bromopyrazin-2-yl)-2-fluorovinyl)-2-fluorophenyl)-N,5-dimethyl-2-thia-4-azabicyclo[4.1.0]hept-3-ene-1-carboxamide (Example 163) (30 mg, 0.061 mmol), 1,1-bis[di-t-butyl-p-methylaminophenyl]palladium(ii) chloride (4.30 mg, 6.07 μmol) and tributyl(prop-1-yn-1-yl)stannane (40 mg, 0.12 mmol) in 1 mL dioxane was heated under N₂ at 60° C. for 2 hours. The solvent was evaporated the residue was submitted to a flash column (DCM to EtOAc to EtOAc/MeOH=100:3 to 100:6 to 10:1) to give the desired product contaminated with tin reagent. Preparatory TLC (EtOAc) gave pure (1S,5S,6S)-3-amino-5-(2-fluoro-5-((Z)-2-fluoro-2-(5-(prop-1-yn-1-yl)pyrazin-2-yl)vinyl)phenyl)-N,5-dimethyl-2-thia-4-azabicyclo[4.1.0]hept-3-ene-1-carboxamide (Example 164) (13 mg, 47% yield) as an off-white solid. MS m/z=454.1 (M+H). ¹H NMR (300 MHz, CDCl₃) δ 8.71 (s, 1H), 8.51 (s, 1H), 7.50-7.68 (m, 2H), 7.06 (dd, J=8.62, 11.25 Hz, 1H), 6.85-7.01 (m, 1H), 6.68-6.79 (m, 1H), 4.82 (br. s., 2H), 2.86 (d, J=4.68 Hz, 3H), 2.21-2.31 (m, 1H), 2.16 (s, 3H), 2.04 (dd, J=4.46, 9.13 Hz, 1H), 1.88 (s, 3H), 0.79 (t, J=6.07 Hz, 1H). ¹⁹F NMR (282 MHz, CDCl₃) δ −107.05 (s, 1F), −126.81 (s, 1F).

Preparation of (1S,5S,6S)-3-amino-5-(5-((Z)-2-(5-(cyclopropylethynyl)pyrazin-2-yl)-2-fluorovinyl)-2-fluorophenyl)-N,5-dimethyl-2-thia-4-azabicyclo[4.1.0]hept-3-ene-1-carboxamide (Example 165)

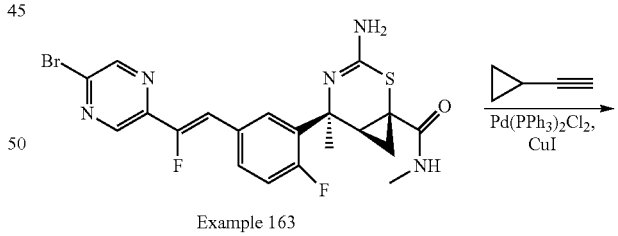

Example 163

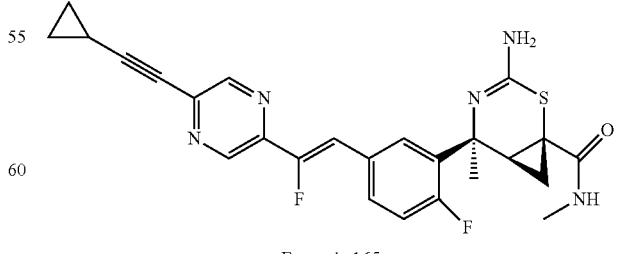

Example 165

Using a similar procedure to that described for Example 159, (1S,5S,6S)-3-amino-5-(5-((Z)-2-(5-bromopyrazin-2- yl)-2-fluorovinyl)-2-fluorophenyl)-N,5-dimethyl-2-thia-4-azabicyclo[4.1.0]hept-3-ene-1-carboxamide (Example 163) (40 mg, 0.081 mmol), copper(i) iodide (1.54 mg, 8.09 µmol), trans-dichlorobis(triphenyl-phosphine)palladium (ii) (5.68 mg, 8.09 µmol), N-ethyl-N-isopropylpropan-2-amine (105 mg, 0.809 mmol) and cyclopropylacetylene (34.3 µL, 0.405 mmol) were combined to give (1S,5S,6S)-3-amino-5-(5-((Z)-2-(5-(cyclopropylethynyl)pyrazin-2-yl)-2-fluorovinyl)-2-fluorophenyl)-N,5-dimethyl-2-thia-4-azabicyclo[4.1.0]hept-3-ene-1-carboxamide (Example 165) (22 mg, 57% yield) as a yellow solid. MS m/z=480 (M+H). $^1$H NMR (300 MHz, CDCl$_3$) δ 8.72 (br. s., 1H), 8.50 (s, 1H), 7.52-7.66 (m, 2H), 6.88-7.13 (m, 2H), 6.62 (br. s., 1H), 2.86 (d, J=3.07 Hz, 3H), 2.22 (d, J=7.31 Hz, 1H), 1.86 (br. s., 3H), 1.49-1.58 (m, 1H), 0.90-1.02 (m, 5H), 0.78 (m, 1H). $^{19}$F NMR (282 MHz, CDCl$_3$) δ −107.00 (s, 1F), −126.85 (s, 1F).

Preparation of (1S,5S,6S)-3-amino-5-(2-fluoro-5-((Z)-2-fluoro-2-(5-((trimethylsilyl)ethynyl)pyrazin-2-yl)vinyl)phenyl)-N,5-dimethyl-2-thia-4-azabicyclo[4.1.0]hept-3-ene-1-carboxamide (Example 166)

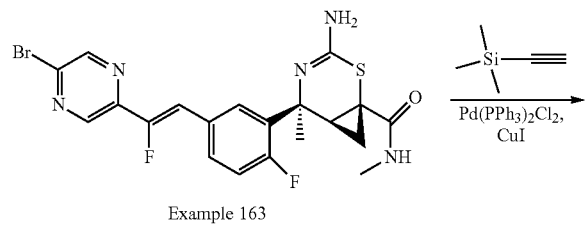

Example 163

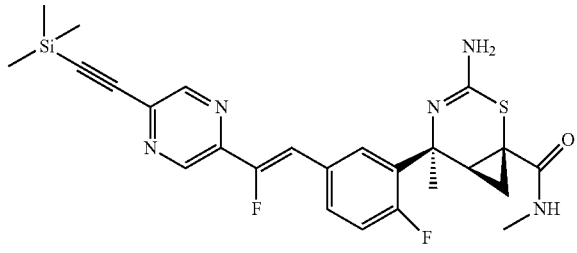

Example 166

Using a similar procedure to that described for Example 159, (1S,5S,6S)-3-amino-5-(5-((Z)-2-(5-bromopyrazin-2-yl)-2-fluorovinyl)-2-fluorophenyl)-N,5-dimethyl-2-thia-4-azabicyclo[4.1.0]hept-3-ene-1-carboxamide (Example 163) (50 mg, 0.101 mmol), copper(i) iodide (1.93 mg, 10.1 µmol), trans-dichlorobis(triphenyl-phosphine)palladium (ii) (7.10 mg, 10.1 µmol), N-ethyl-N-isopropylpropan-2-amine (131 mg, 1.01 mmol) and (trimethylsilyl)-acetylene (71.5 µL, 0.506 mmol) were combined to give (1S,5S,6S)-3-amino-5-(2-fluoro-5-((Z)-2-fluoro-2-(5-((trimethylsilyl)ethynyl)pyrazin-2-yl)vinyl)phenyl)-N,5-dimethyl-2-thia-4-azabicyclo[4.1.0]hept-3-ene-1-carboxamide (Example 166) (32 mg, 0.063 mmol, 61.8% yield) as a yellow solid. LCMS (ESI$^+$) m/z=512.2 (M+H). $^1$H NMR (400 MHz, CDCl$_3$) δ 8.76 (s, 1H), 8.59 (s, 1H), 7.51-7.73 (m, 2H), 6.93-7.13 (m, 2H), 6.62 (br. s., 1H), 2.87 (d, J=4.69 Hz, 3H), 2.23 (t, J=8.41 Hz, 1H), 2.00 (br. s., 1H), 1.85 (s, 3H), 0.77 (t, J=6.06 Hz, 1H), 0.31 (s, 9H).

Preparation of (1S,5S,6S)-3-amino-5-(5-((Z)-2-(5-ethynylpyrazin-2-yl)-2-fluorovinyl)-2-fluorophenyl)-N,5-dimethyl-2-thia-4-azabicyclo[4.1.0]hept-3-ene-1-carboxamide (Example 167)

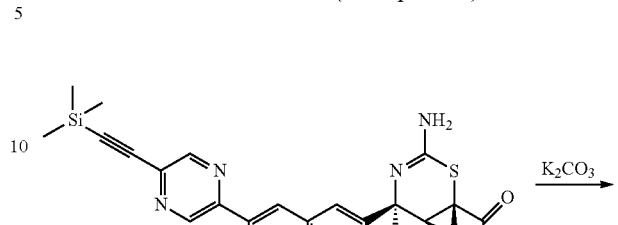

Example 166

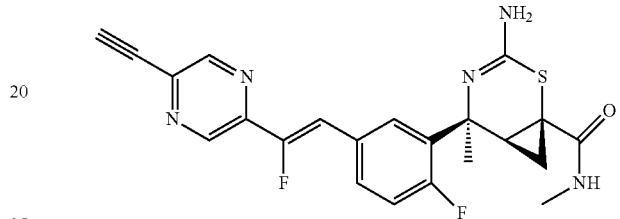

Example 167

To a solution of (1S,5S,6S)-3-amino-5-(2-fluoro-5-((Z)-2-fluoro-2-(5-((trimethylsilyl)ethynyl)pyrazin-2-yl)vinyl)phenyl)-N,5-dimethyl-2-thia-4-azabicyclo[4.1.0]hept-3-ene-1-carboxamide (Example 166) (30 mg, 0.059 mmol) in 3 mL of MeOH was added anhydrous potassium carbonate (8.1 mg, 0.059 mmol). After stirring at room temperature for 5 min, LCMS showed near complete conversion. The reaction was quenched with 1 mL of sat NH$_4$Cl and the MeOH was evaporated. It was diluted with water, extracted with DCM (×3), dried and concentrated. Flash chromatography (EtOAc to EtOAc/MeOH=100:5) gave (1S,5S,6S)-3-amino-5-(5-((Z)-2-(5-ethynylpyrazin-2-yl)-2-fluorovinyl)-2-fluorophenyl)-N,5-dimethyl-2-thia-4-azabicyclo[4.1.0]hept-3-ene-1-carboxamide (Example 167) (20 mg, 0.046 mmol, 78% yield) as a light yellow solid. MS m/z=440.1 (M+H). $^1$H NMR (300 MHz, CDCl$_3$) δ 8.77 (s, 1H), 8.62 (s, 1H), 7.59 (dd, J=3.07, 7.45 Hz, 2H), 6.90-7.15 (m, 2H), 6.62 (d, J=4.38 Hz, 1H), 3.42 (s, 1H), 2.87 (d, J=4.68 Hz, 3H), 2.17-2.28 (m, 1H), 2.03 (d, J=8.04 Hz, 1H), 1.86 (s, 3H), 0.72-0.82 (m, 1H). $^{19}$F NMR (282 MHz, CDCl$_3$) δ −106.79 (s, 1F), −127.21 (s, 1F).

Preparation of (1S,5S,6S)-3-amino-5-(5-((Z)-2-(4-cyanophenyl)-2-fluorovinyl)-2-fluorophenyl)-N,N,5-trimethyl-2-thia-4-azabicyclo[4.1.0]hept-3-ene-1-carboxamide (Example 168)

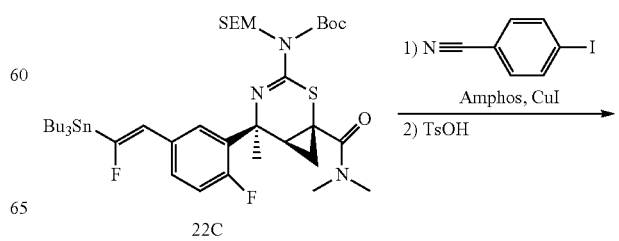

22C

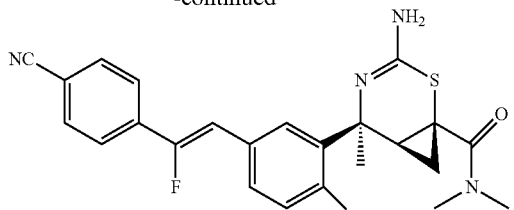

Example 168

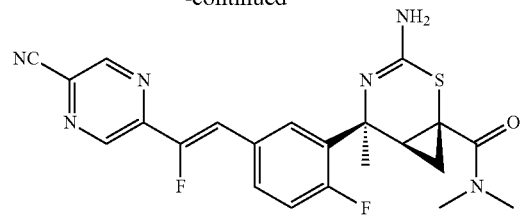

Example 169

A mixture of 4-iodobenzonitrile (47.3 mg, 0.207 mmol), bis(di-tert-butyl(4-dimethylaminophenyl)phosphine)dichloropalladium(ii) (4.88 mg, 6.89 µmol) and copper(i) iodide (13 mg, 0.069 mmol) was suspended in 0.2 mL of DMF. To this was added dropwise tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (60 mg, 0.069 mmol) in 0.2 mL of DMF (followed by rinsing with 1 mL of THF). After stirring for 10 minutes, the reaction was complete. The solvents were evaporated and the residue was loaded onto a flash column (DCM to DCM/EtOAc=50:1 to 10:1) to give tert-butyl ((1S,5S,6S)-5-(5-((Z)-2-(4-cyanophenyl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (24 mg, 51.0% yield) as a light yellow solid. MS m/z=685.3 (M+H).

This intermediate was mixed with 4-methylbenzenesulfonic acid hydrate (26.2 mg, 0.138 mmol) in 1 mL of dioxane and was stirred at 80° C. for 2 h. After cooling, it was directly loaded onto a flash column (DCM/MeOH=100:4 to 100:6 to 100:8 to 100:10) to give (1S,5S,6S)-3-amino-5-(5-((Z)-2-(4-cyanophenyl)-2-fluorovinyl)-2-fluorophenyl)-N,N,5-trimethyl-2-thia-4-azabicyclo[4.1.0]hept-3-ene-1-carboxamide (3158427, 12 mg, 0.027 mmol, 38.5% yield over two steps) as a light yellow solid. MS m/z=453.0 (M+H). ¹H NMR (300 MHz, CDCl₃) δ 7.58-7.76 (m, 6H), 7.08 (dd, J=8.40, 11.47 Hz, 1H), 6.30-6.54 (m, 1H), 3.06 (br. s., 6H), 2.28-2.39 (m, 1H), 1.89 (s, 3H), 1.42 (dd, J=5.77, 9.57 Hz, 1H), 0.89 (t, J=6.36 Hz, 1H). ¹⁹F NMR (282 MHz, CDCl₃) δ -109.09 (s, 1F), -117.35 (s, 1F).

Preparation of (1S,5S,6S)-3-amino-5-(5-((Z)-2-(5-cyanopyrazin-2-yl)-2-fluorovinyl)-2-fluorophenyl)-N,N,5-trimethyl-2-thia-4-azabicyclo[4.1.0]hept-3-ene-1-carboxamide (Example 169)

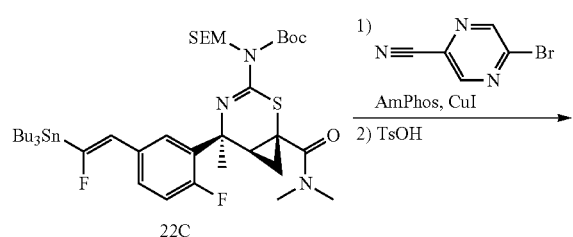

22C

Using a similar procedure to that described for Example 168, 2-bromo-5-cyanopyrazine (21.13 mg, 0.115 mmol), bis(di-tert-butyl(4-dimethylaminophenyl)phosphine)dichloropalladium(ii) (4.07 mg, 5.74 µmol), copper(i) iodide (11 mg, 0.057 mmol) and tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (50 mg, 0.057 mmol) were combined to provide the coupling product, which, after deprotection with 4-methylbenzenesulfonic acid hydrate (21.8 mg, 0.115 mmol), gave (1S,5S,6S)-3-amino-5-(5-((Z)-2-(5-cyanopyrazin-2-yl)-2-fluorovinyl)-2-fluorophenyl)-N,N,5-trimethyl-2-thia-4-azabicyclo[4.1.0]hept-3-ene-1-carboxamide (Example 169) (14 mg, 54% yield in two steps) as a light yellow solid. MS m/z=455.1 (M+H). ¹H NMR (300 MHz, CDCl₃) δ 8.94 (s, 1H), 8.82 (s, 1H), 7.82 (d, J=7.75 Hz, 1H), 7.64-7.73 (m, 1H), 7.17-7.32 (m, 1H), 7.12 (dd, J=8.62, 11.55 Hz, 1H), 3.07 (br. s., 6H), 2.27-2.37 (m, 1H), 1.88 (s, 3H), 1.39 (dd, J=5.70, 9.65 Hz, 1H), 0.88 (t, J=6.50 Hz, 1H). ¹⁹F NMR (282 MHz, CDCl₃) δ -106.83 (s, 1F), -128.23 (s, 1F).

Preparation of (1S,5S,6S)-3-amino-5-(5-((Z)-2-(5-cyanopyrimidin-2-yl)-2-fluorovinyl)-2-fluorophenyl)-N,N,5-trimethyl-2-thia-4-azabicyclo[4.1.0]hept-3-ene-1-carboxamide (Example 170)

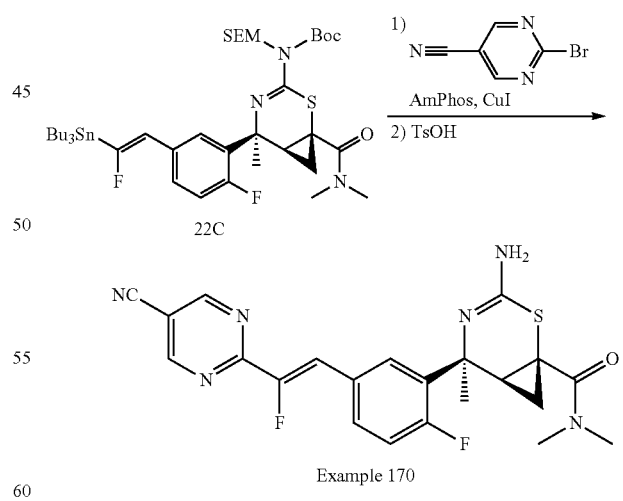

Example 170

Using a similar procedure to that described for Example 168, 2-chloro-pyrimidine-5-carbonitrile (28.8 mg, 0.207 mmol), bis(di-tert-butyl(4-dimethylaminophenyl)phosphine)dichloropalladium(ii) (4.88 mg, 6.89 µmol), copper(i) iodide (13.12 mg, 0.069 mmol) and tert-butyl ((1S,5S,6S)-1-(dimethylcarbamoyl)-5-(2-fluoro-5-((E)-2-fluoro-2-

(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (60 mg, 0.069 mmol) were combined to provide the coupling product, which, after deprotection with 4-methylbenzenesulfonic acid hydrate (21.8 mg, 0.115 mmol), gave (1S,5S,6S)-3-amino-5-(5-((Z)-2-(5-cyanopyrimidin-2-yl)-2-fluorovinyl)-2-fluorophenyl)-N,N,5-trimethyl-2-thia-4-azabicyclo[4.1.0]hept-3-ene-1-carboxamide (Example 170) (11 mg, 0.024 mmol, 35% yield over two steps) as a light yellow solid. MS m/z=455.1 (M+H). $^1$H NMR (300 MHz, CDCl$_3$) δ 8.99 (s, 2H), 7.86 (d, J=7.02 Hz, 1H), 7.72 (br. s., 1H), 7.41-7.58 (m, 1H), 7.12 (dd, J=8.62, 11.40 Hz, 1H), 3.06 (br. s., 6H), 2.25-2.37 (m, 1H), 1.88 (s, 3H), 1.40 (dd, J=5.70, 9.50 Hz, 1H), 0.87 (t, J=6.28 Hz, 1H). $^{19}$F NMR (282 MHz, CDCl$_3$) δ –106.41 (s, 1F), –126.78 (s, 1F).

Preparation of (1S,5S,6S)-3-amino-5-(5-((Z)-2-(6-cyanopyridin-3-yl)-2-fluorovinyl)-2-fluorophenyl)-N,N,5-trimethyl-2-thia-4-azabicyclo[4.1.0]hept-3-ene-1-carboxamide (Example 171)

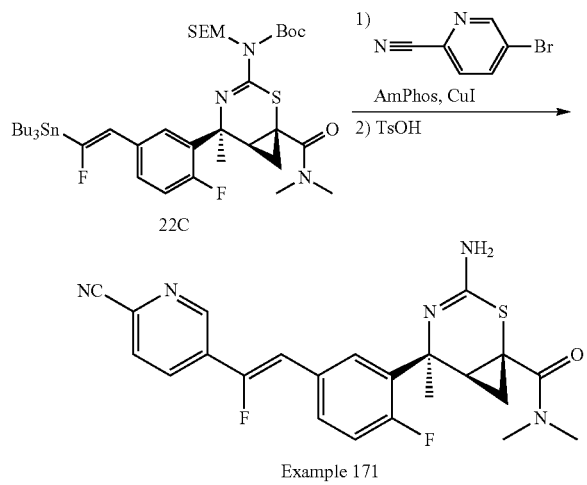

Example 171

Using a similar procedure to that described for Example 168, 5-bromo-2-cyanopyridine (37.8 mg, 0.207 mmol), bis(di-tert-butyl(4-dimethylaminophenyl)phosphine)dichloropalladium(ii) (4.88 mg, 6.89 µmol), copper(i) iodide (13 mg, 0.069 mmol) and tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (60 mg, 0.069 mmol) were combined to provide the coupling product, which, after deprotection with 4-methylbenzenesulfonic acid hydrate (26.2 mg, 0.138 mmol), gave (1S,5S,6S)-3-amino-5-(5-((Z)-2-(6-cyanopyridin-3-yl)-2-fluorovinyl)-2-fluorophenyl)-N,N,5-trimethyl-2-thia-4-azabicyclo[4.1.0]hept-3-ene-1-carboxamide (Example 171) (8.0 mg, 26% yield over two steps) as a light yellow solid. MS m/z=454.1 (M+H). $^1$H NMR (300 MHz, CDCl$_3$) δ 8.96 (s, 1H), 8.00 (d, J=7.75 Hz, 1H), 7.64-7.75 (m, 3H), 7.10 (dd, J=8.62, 11.25 Hz, 1H), 6.40-6.62 (m, 1H), 3.07 (br. s., 6H), 2.34 (t, J=8.48 Hz, 1H), 1.90 (s, 3H), 1.43 (dd, J=5.85, 9.79 Hz, 1H), 0.91 (t, J=6.58 Hz, 1H). $^{19}$F NMR (282 MHz, CDCl$_3$) δ –108.06 (s, 1F), –119.12 (s, 1F).

Preparation of (1S,5S,6S)-3-amino-5-(5-((Z)-2-(4-cyano-2-fluorophenyl)-2-fluorovinyl)-2-fluorophenyl)-N,N,5-trimethyl-2-thia-4-azabicyclo[4.1.0]hept-3-ene-1-carboxamide (Example 172)

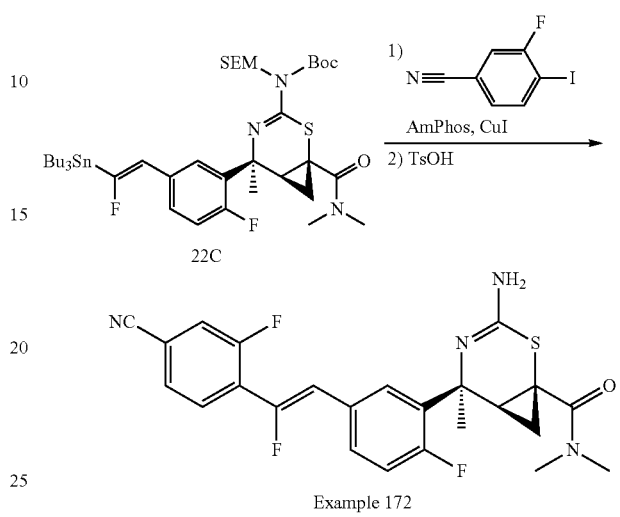

Example 172

Using a similar procedure to that described for Example 168, 3-fluoro-4-iodobenzonitrile (51 mg, 0.207 mmol), bis(di-tert-butyl(4-dimethylaminophenyl)phosphine)dichloropalladium(ii) (4.88 mg, 6.89 µmol), copper(i) iodide (13.1 mg, 0.069 mmol) and tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (60 mg, 0.069 mmol) were combined to provide the coupling product, which, after deprotection with 4-methylbenzenesulfonic acid hydrate (39.3 mg, 0.207 mmol), gave (1S,5S,6S)-3-amino-5-(5-((Z)-2-(4-cyano-2-fluorophenyl)-2-fluorovinyl)-2-fluorophenyl)-N,N,5-trimethyl-2-thia-4-azabicyclo[4.1.0]hept-3-ene-1-carboxamide (Example 172) (9.0 mg, 28% yield over two steps) as a light yellow solid. MS m/z=471.0 (M+H). $^1$H NMR (300 MHz, CDCl$_3$) δ 7.58-7.81 (m, 3H), 7.52 (d, J=8.33 Hz, 1H), 7.43 (d, J=11.25 Hz, 1H), 7.09 (dd, J=8.48, 11.55 Hz, 1H), 6.57-6.78 (m, 1H), 3.08 (br. s., 6H), 2.33 (t, J=8.33 Hz, 1H), 1.89 (s, 3H), 1.41 (dd, J=5.92, 9.43 Hz, 1H), 0.90 (t, J=6.50 Hz, 1H). $^{19}$F NMR (282 MHz, CDCl$_3$) δ –108.76 (s, 1F), –108.78 (d, J=8.46 Hz, 1F), –113.79 (d, J=8.46 Hz, 1F).

Preparation of (1S,5S,6S)-3-amino-5-(5-((Z)-2-(2-cyanopyrimidin-5-yl)-2-fluorovinyl)-2-fluorophenyl)-N,N,5-trimethyl-2-thia-4-azabicyclo[4.1.0]hept-3-ene-1-carboxamide (Example 173)

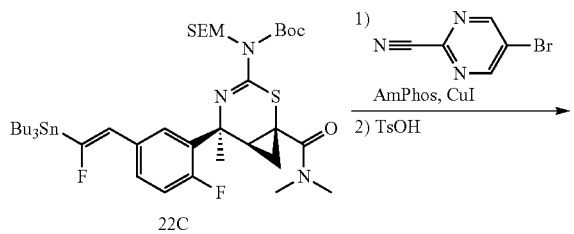

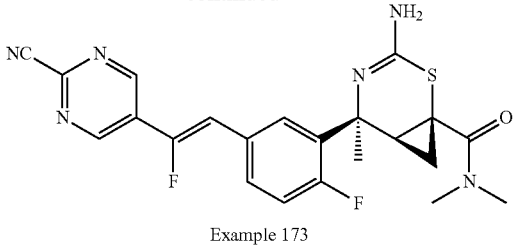

Example 173

Using a similar procedure to that described for Example 168, 5-bromo-2-cyanopyrimidine (38 mg, 0.21 mmol), bis(di-tert-butyl(4-dimethylaminophenyl)phosphine)dichloropalladium(ii) (4.88 mg, 6.89 µmol), copper(i) iodide (13.12 mg, 0.069 mmol) and tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (60 mg, 0.069 mmol) were combined to provide the coupling product, which, after deprotection with 4-methylbenzenesulfonic acid hydrate (39.3 mg, 0.207 mmol), gave (1S,5S,6S)-3-amino-5-(5-((Z)-2-(2-cyanopyrimidin-5-yl)-2-fluorovinyl)-2-fluorophenyl)-N,N,5-trimethyl-2-thia-4-azabicyclo[4.1.0]hept-3-ene-1-carboxamide (Example 173) (29 mg, 93% yield over two steps) as a light yellow solid. MS m/z=455.1 (M+H). $^1$H NMR (300 MHz, CDCl$_3$) δ 9.03 (s, 2H), 7.76 (d, J=7.31 Hz, 1H), 7.63 (d, J=5.12 Hz, 1H), 7.11 (dd, J=8.62, 11.40 Hz, 1H), 6.43-6.68 (m, 1H), 3.08 (br. s., 6H), 2.32 (t, J=8.48 Hz, 1H), 1.86 (s, 3H), 1.37 (dd, J=5.77, 9.72 Hz, 1H), 0.87 (t, J=6.36 Hz, 1H).

Preparation of (1S,5S,6S)-3-amino-5-(5-((Z)-2-(6-cyanopyridazin-3-yl)-2-fluorovinyl)-2-fluorophenyl)-N,N,5-trimethyl-2-thia-4-azabicyclo[4.1.0]hept-3-ene-1-carboxamide (Example 174)

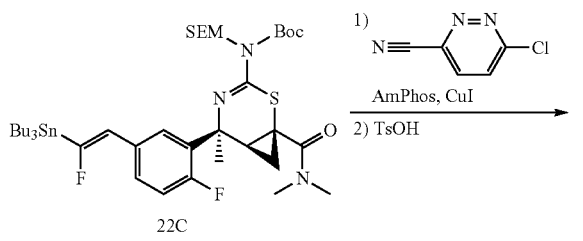

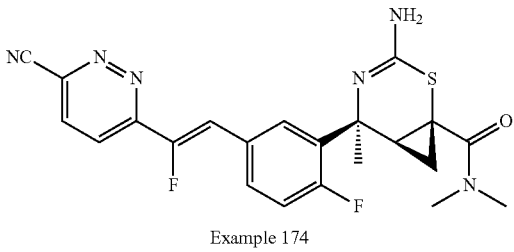

Example 174

Using a similar procedure to that described for Example 168, 6-chloropyridazine-3-carbonitrile (28.8 mg, 0.207 mmol), bis(di-tert-butyl(4-dimethylaminophenyl)phosphine)dichloropalladium(ii) (4.88 mg, 6.89 µmol), copper(i) iodide (13 mg, 0.069 mmol) and tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C (60 mg, 0.069 mmol) were combined to provide the coupling product, which, after deprotection with 4-methylbenzenesulfonic acid hydrate (39.3 mg, 0.207 mmol), gave (1S,5S,6S)-3-amino-5-(5-((Z)-2-(6-cyanopyridazin-3-yl)-2-fluorovinyl)-2-fluorophenyl)-N,N,5-trimethyl-2-thia-4-azabicyclo[4.1.0]hept-3-ene-1-carboxamide (Example 174) (7.0 mg, 22% yield over two steps) as a light yellow solid. MS m/z=455.1 (M+H). $^1$H NMR (300 MHz, CDCl$_3$) δ 7.80-7.94 (m, 3H), 7.73 (br. s., 1H), 7.54-7.70 (m, 1H), 7.12 (dd, J=8.62, 11.40 Hz, 1H), 3.07 (br. s., 6H), 2.26-2.36 (m, 1H), 1.88 (s, 3H), 1.37-1.43 (m, 1H), 0.90-0.97 (m, 1H).

Preparation of (1S,5S,6S)-3-amino-5-(5-((Z)-2-(5-chloropyridin-2-yl)-2-fluorovinyl)-2-fluorophenyl)-N,5-dimethyl-2-thia-4-azabicyclo[4.1.0]hept-3-ene-1-carboxamide (Example 175)

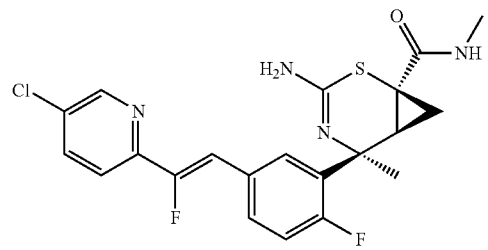 [SMILES: CNC(=O)[C@]12C[C@H]1[C@@](C)(c1cc(/C=C(\F)c3ccc(Cl)cn3)ccc1F)N=C(N)S2]

Example 175

This compound was prepared according to the procedure described for the synthesis of Example 116 using 15 (0.082 g, 0.19 mmol) and methylamine, 2.0M in THF (2.4 mL, 4.8 mmol), to afford (1S,5S,6S)-3-amino-5-(5-((Z)-2-(5-chloropyridin-2-yl)-2-fluorovinyl)-2-fluorophenyl)-N,5-dimethyl-2-thia-4-azabicyclo[4.1.0]hept-3-ene-1-carboxamide (Example 175) as an oil. MS m/z=449 [M+H]$^+$. 1H NMR (400 MHz, CDCl$_3$) δ ppm 8.47-8.51 (m, 1H) 7.68 (dd, J=8.61, 2.35 Hz, 1H) 7.50-7.56 (m, 2H) 7.43 (d, J=8.22 Hz, 1H) 6.97-7.06 (m, 1H) 6.90 (d, J=39.32 Hz, 1H) 6.62-6.71 (m, 1H) 4.02-4.95 (br s, 2H) 2.86 (d, J=4.89 Hz, 3H) 2.12-2.27 (m, 1H) 2.01 (dd, J=9.59, 4.89 Hz, 1H) 1.86 (s, 3H) 0.68-0.93 (m, 1H).

Synthesis of Intermediate 25

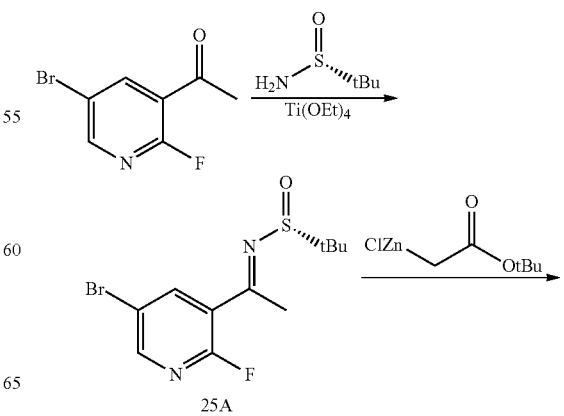

25A

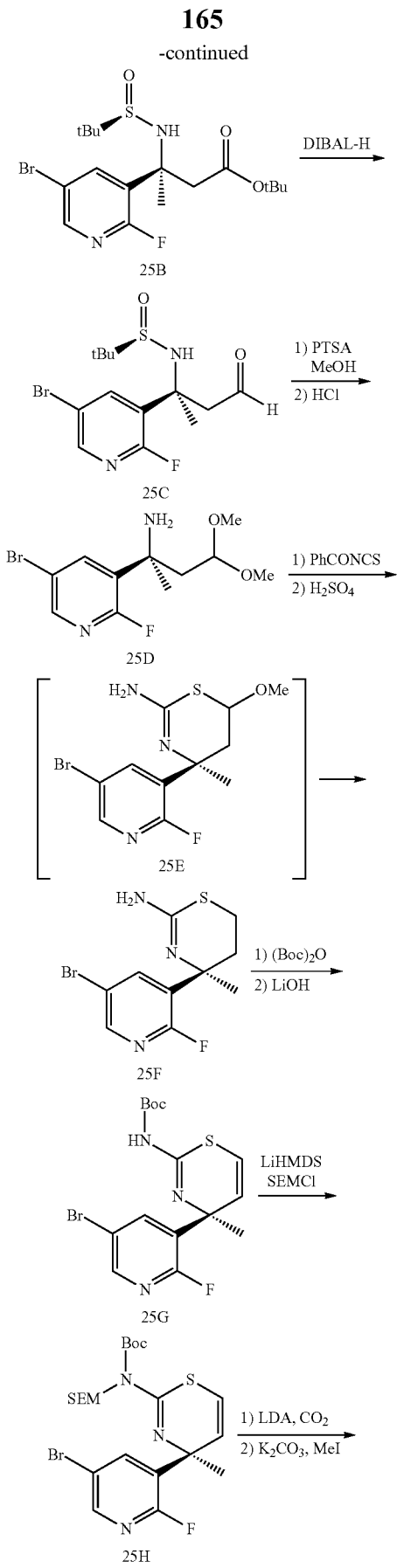
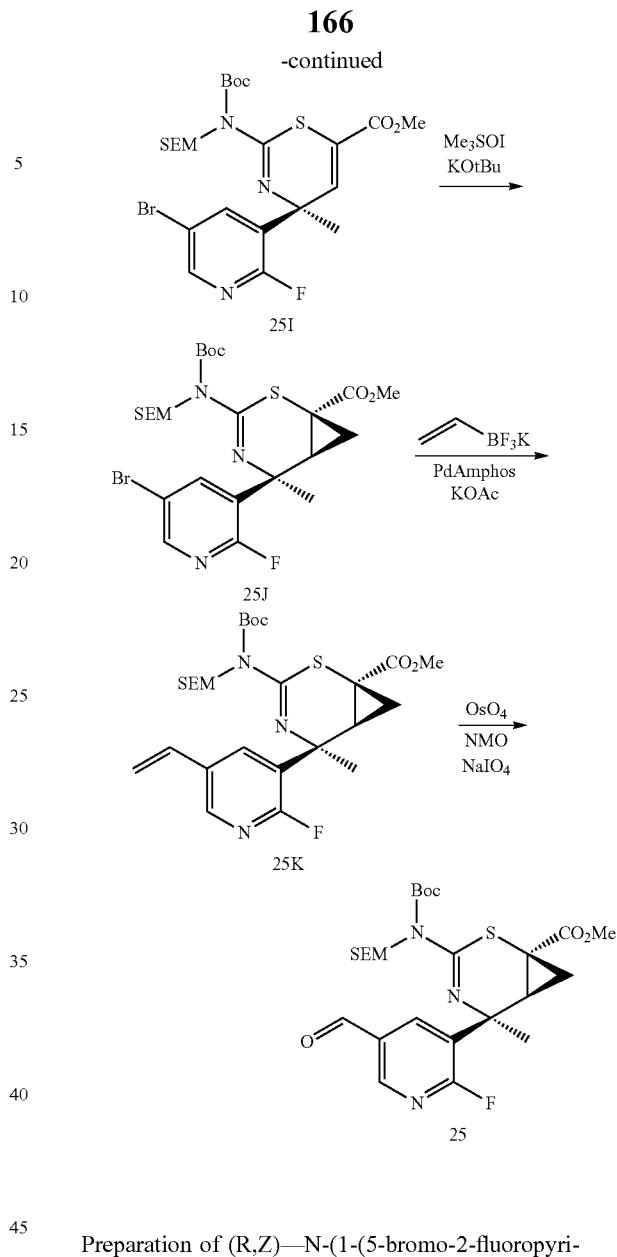

Preparation of (R,Z)—N-(1-(5-bromo-2-fluoropyridin-3-yl)ethylidene)-2-methylpropane-2-sulfinamide (25A)

A mixture of 1-(5-bromo-2-fluoropyridin-3-yl)ethanone (prepared according to procedures described in WO2009016460; 11.0 g, 50.5 mmol), (R)-2-methylpropane-2-sulfinamide (AK Scientific, 12.2 g, 101 mmol) and titanium(IV) ethoxide (Aldrich, 26.1 mL, 126.0 mmol) in THF (100 mL) was heated at reflux for 2 hours. The mixture was cooled to room temperature, and brine (200 mL) was added. The suspension was vigorously stirred for 10 minutes. The suspension was then filtered through a pad of silica gel and the organic phase was separated. The aqueous phase was extracted with EtOAc. The combined organic layers were washed with brine, dried over $Na_2SO_4$ and concentrated under reduced pressure. The residue was purified by silica gel chromatography (gradient 0-20% EtOAc/hexanes) to afford (R,Z)—N-(1-(5-bromo-2-fluoropyridin-3-yl)ethylidene)-2-methylpropane-2-sulfinamide (25A) as a bright yellow oil (16 g, 99% yield). MS m/z=320.8 (M+H).

Preparation of (S)-tert-butyl 3-(5-bromo-2-fluoropyridin-3-yl)-3-((R)-1,1-dimethylethylsulfinamido)butanoate (25B)

To a solution of (R,Z)—N-(1-(5-bromo-2-fluoropyridin-3-yl)ethylidene)-2-methylpropane-2-sulfinamide (25A) (41.0 g, 127 mmol) in THF (400 mL) in a 2 L flask at 0° C. was cannulated slowly (2-(tert-butoxy)-2-oxoethyl)zinc(II) chloride (0.5M in diethyl ether, 611 mL, 305 mmol) within 1 hour. The reaction mixture was stirred at room temperature overnight and then quenched with 200 mL of saturated NH$_4$Cl solution. The layers were separated. The aqueous layer was extracted again with 200 mL of EtOAc. The combined organic layers were then dried (Na$_2$SO$_4$) and concentrated to give an orange oil that was purified by flash column (DCM to DCM/ethyl acetate=10:1 to 5:1 to 3:1) to give (S)-tert-butyl 3-(5-bromo-2-fluoropyridin-3-yl)-3-((R)-1,1-dimethylethylsulfinamido)butanoate (25B) (43 g, 77% yield). LC/MS m/z=458.9 (M+Na). $^1$H NMR (300 MHz, CDCl$_3$) δ: 8.17 (dd, J=1.61, 2.34 Hz, 1H), 8.03 (dd, J=2.48, 8.77 Hz, 1H), 5.44 (s, 1H), 3.18-3.29 (m, 1H), 2.98-3.11 (m, 1H), 1.82 (s, 3H), 1.33 (s, 9H), 1.30 (s, 9H).

Preparation of (R)—N—((S)-2-(5-bromo-2-fluoropyridin-3-yl)-4-oxobutan-2-yl)-2-methylpropane-2-sulfinamide (25C)

A solution of (S)-tert-butyl 3-(5-bromo-2-fluoropyridin-3-yl)-3-((R)-1,1-dimethylethylsulfinamido)butanoate (25B) (42 g, 96 mmol) in 200 mL of anhydrous DCM in a 2 L round-bottom flask at −78° C. was treated with diisobutylaluminum hydride (1.0M in hexanes) (211 mL, 211 mmol) via a syringe dropwise along the inner wall of the flask within 1.5 hour. The stirring was continued for 1 hour. The reaction was quenched at −78° C. by slow addition of 25 mL of MeOH along the inner wall of the flask. The reaction mixture was then taken out of the dry ice-acetone bath, and treated with 300 mL of 1M aq. tartaric acid solution. The mixture was stirred at room temperature for 1 hour. A clear two phase separation was achieved, and the organic phase was isolated. The aqueous layer was extracted with DCM (3×). The combined organic layers were evaporated to dryness. The residue was purified via silica gel chromatography (20-50% EtOAc in DCM) to give (R)—N—((S)-2-(5-bromo-2-fluoropyridin-3-yl)-4-oxobutan-2-yl)-2-methylpropane-2-sulfinamide (25C) (31 g, 88% yield) as a yellow gum. LC/MS (ESI$^+$) m/z=365.0 (M+H). $^1$H NMR (300 MHz, CDCl$_3$) δ: 9.70 (s, 1H), 8.16 (dd, J=1.68, 2.41 Hz, 1H), 8.04 (dd, J=2.41, 8.84 Hz, 1H), 4.89 (s, 1H), 3.59-3.73 (m, 1H), 3.35-3.48 (m, 1H), 1.77 (s, 3H), 1.29 (s, 9H).

Preparation of (S)-2-(5-bromo-2-fluoropyridin-3-yl)-4,4-dimethoxybutan-2-amine (25D)

To a 1000 mL RBF equipped with a reflux condenser was added (R)—N—((S)-2-(5-bromo-2-fluoropyridin-3-yl)-4-oxobutan-2-yl)-2-methylpropane-2-sulfinamide (25C) (28.5 g, 78.0 mmol), methanol (200 mL) and p-toluenesulfonic acid monohydrate (0.70 g, 3.9 mmol). The solution was stirred at 65° C. overnight. It was cooled to room temperature and treated with hydrogen chloride (4.0M solution in 1,4-dioxane, 21.5 mL, 86.0 mmol) dropwise. After stirring at room temperature for 3 hour, the mixture was concentrated in vacuo. The residue was diluted with 300 mL of chloroform and treated with 50 mL of sat. aq. NaHCO$_3$. The layers were separated and the aqueous layer was extracted with EtOAc (50 mL). The chloroform extracts were washed with 10 mL of brine. The EtOAc extracts were washed with 10 mL of brine. The combined organic extracts were dried over magnesium sulfate, filtered and concentrated in vacuo to give a light yellow oil. The oil was purified by silica gel chromatography (50-100% EtOAc in DCM) to give (S)-2-(5-bromo-2-fluoropyridin-3-yl)-4,4-dimethoxybutan-2-amine (25D) (21 g, 86% yield) as a gum. LC/MS (ESI$^+$) m/z=307.0 (M+H). $^1$H NMR (300 MHz, CDCl$_3$) δ 8.26 (dd, J=2.48, 8.77 Hz, 1H), 8.12-8.19 (m, 1H), 4.10-4.19 (m, 1H), 3.23 (d, J=2.05 Hz, 6H), 2.24-2.45 (m, 1H), 1.79-2.14 (m, 1H), 1.75 (br. s., 2H), 1.54 (s, 3H).

Preparation of (S)-4-(5-bromo-2-fluoropyridin-3-yl)-4-methyl-4H-1,3-thiazin-2-amine (25F)

To a solution of (S)-2-(5-bromo-2-fluoropyridin-3-yl)-4,4-dimethoxybutan-2-amine (25D) (20.5 g, 66.7 mmol) in DCM (100 mL) at 0° C. under nitrogen was added a solution of benzoyl isothiocyanate (9.4 mL, 70 mmol) in DCM (30 mL) dropwise. The reaction was kept below 5° C. during the course of addition. After stirring at 0° C. for 20 minutes, the reaction mixture was treated with MeOH (1 mL). The solvents were removed under reduced pressure to afford a tan syrup. To the tan syrup at 0° C. was added neat sulfuric acid (53.4 mL, 1000 mmol). The mixture was stirred at room temperature for 20 minutes then heated at 60° C. for 5 hours, then 80° C. for 2 hours, then 65° C. overnight. LCMS indicated the ratio of 25E and 25F to be about 1:1. The mixture was heated at 85° C. for 3 hours. The reaction was cooled to 20° C. and then poured onto 200 g of ice. DCM (200 mL) was added to the slurry mixture. The resulting biphasic solution was chilled to 0° C. with an external wet ice bath, then basified to pH=8 with very slow addition of 10N NaOH solution. The organic layer was separated and the aqueous portion was extracted with DCM (3×) and EtOAc (1×). The combined organic layers were dried over Na$_2$SO$_4$, filtered, and then concentrated under reduced pressure. The residue was purified by flash column (10-100% EtOAc in DCM) to give two compounds. The first eluent was (S)-4-(5-bromo-2-fluoropyridin-3-yl)-4-methyl-4H-1,3-thiazin-2-amine (25F, 12.0 g, 59% yield) as a yellow solid. LC/MS (ESI$^+$) m/z=302.0 (M+H). $^1$H NMR (CDCl$_3$) δ: 8.12 (dd, J=2.5, 1.6 Hz, 1H), 8.02 (dd, J=8.6, 2.5 Hz, 1H), 6.30-6.39 (m, 1H), 6.17-6.27 (m, 1H), 1.66 (d, J=1.0 Hz, 3H). The second eluent was (4S)-4-(5-bromo-2-fluoropyridin-3-yl)-6-methoxy-4-methyl-5,6-dihydro-4H-1,3-thiazin-2-amine (25E) (6.0 g).

A mixture of (4S)-4-(5-bromo-2-fluoropyridin-3-yl)-6-methoxy-4-methyl-5,6-dihydro-4H-1,3-thiazin-2-amine (25E) (6.0 g, 18 mmol) in 18 mL of H$_2$SO$_4$ was heated at 80° C. overnight. The reaction mixture was cooled to 20° C. and then poured onto 200 g of ice. To the slurry was added DCM (200 mL), the resulting biphasic solution was chilled to 0° C. with external wet ice bath, then basified to pH=8 with very slow addition of 10N NaOH solution. The organic layer was separated and the aqueous portion was extracted with DCM (3×) and ethyl acetate (1×). The combined organic extracts were dried over Na$_2$SO4, filtered, and concentrated under reduced pressure. The residue was purified by flash column (10-30% EtOAc in DCM) to give (S)-4-(5-bromo-2-fluoropyridin-3-yl)-4-methyl-4H-1,3-thiazin-2-amine (25F) (4 g) as a yellow solid.

Preparation of (S)-tert-butyl (4-(5-bromo-2-fluoropyridin-3-yl)-4-methyl-4H-1,3-thiazin-2-yl)carbamate (25G)

Using a procedure similar to that described for Intermediate 1G, (S)-4-(5-bromo-2-fluoropyridin-3-yl)-4-methyl- 4H-1,3-thiazin-2-amine (25F) (1.74 g, 5.76 mmol), 4-(dimethylamino)pyridine (0.04 g, 0.29 mmol), Boc anhydride (3.30 mL, 14.40 mmol) and lithium hydroxide monohydrate (1.21 g, 28.80 mmol) were combined to afford the title compound (25G) (2.17 g, 94% yield). LC/MS (ESI+) m/z=403.0 (M+H). $^1$H NMR (300 MHz, CDCl$_3$) δ: 8.14-8.20 (m, 1H), 8.00 (br. s., 1H), 6.30 (d, J=9.79 Hz, 1H), 6.14 (d, J=6.87 Hz, 1H), 1.69 (s, 3H), 1.54 (s, 9H).

Preparation of (S)-tert-butyl (4-(5-bromo-2-fluoropyridin-3-yl)-4-methyl-4H-1,3-thiazin-2-yl)((2-(trimethylsilyl)ethoxy)methyl)carbamate (25H)

Using a procedure similar to that described for 1H, (S)-tert-butyl (4-(5-bromo-2-fluoropyridin-3-yl)-4-methyl-4H-1,3-thiazin-2-yl)carbamate (25G) (1.18 g, 2.93 mmol), lithium bis(trimethylsilyl)amide (3.8 mL of 1.0M solution in THF, 3.8 mmol) and 2-(chloromethoxy)ethyltrimethylsilane (0.7 mL, 3.8 mmol) were combined to afford the title compound (25H) (1.5 g, 95% yield). LC/MS (ESI+) m/z=532.0/534.0 (M+H). $^1$H NMR (300 MHz, CDCl$_3$) δ: 8.14-8.22 (m, 2H), 6.36 (d, J=9.50 Hz, 1H), 6.05-6.11 (m, 1H), 5.37 (d, J=10.38 Hz, 1H), 5.21 (d, J=10.38 Hz, 1H), 3.69 (dd, J=7.67, 8.84 Hz, 2H), 1.69 (d, J=1.17 Hz, 3H), 1.56 (s, 9H), 0.91-1.06 (m, 2H), 0.00 (s, 9H).

Preparation of (S)-methyl 4-(5-bromo-2-fluoropyridin-3-yl)-2-((tert-butoxycarbonyl)((2-(trimethylsilyl)ethoxy)methyl)amino)-4-methyl-4H-1,3-thiazine-6-carboxylate (25I)

LDA (2.0M heptane/tetrahydrofuran/ethylbenzene) (0.92 mL, 1.83 mmol) was added dropwise to a solution of (S)-tert-butyl (4-(5-bromo-2-fluoropyridin-3-yl)-4-methyl-4H-1,3-thiazin-2-yl)((2-(trimethylsilyl)ethoxy)methyl)carbamate (25H) (0.75 g, 1.4 mmol) in THF (10 mL) at −78° C. The mixture was stirred for 25 minutes before CO$_2$ gas was bubbled through the reaction mixture at −78° C. After 3 minutes, the cold bath was removed, the addition of CO$_2$ was stopped, and the reaction mixture was quenched with saturated NH$_4$Cl solution. The resulting solution was warmed to room temperature and extracted with EtOAc (2×). The aqueous layer was acidified to pH 4 with 1N HCl solution and extracted again with EtOAc. The combined organic layers were dried over MgSO$_4$, filtered, and concentrated in vacuo to give a yellow oil. The oil was taken up in DMF (2.0 mL) and potassium carbonate (0.19 g, 1.4 mmol) and methyl iodide (0.090 mL, 1.4 mmol) were added. The mixture was stirred at room temperature for 2 hours, diluted with water and extracted with EtOAc (2×). The combined organic extracts were dried over MgSO$_4$, filtered, and concentrated in vacuo. The residue was purified on an ISCO column using 0-15% EtOAc in hexanes to afford (S)-methyl 4-(5-bromo-2-fluoropyridin-3-yl)-2-((tert-butoxycarbonyl)((2-(trimethylsilyl)ethoxy)methyl) amino)-4-methyl-4H-1,3-thiazine-6-carboxylate (25I) (0.40 g, 48% yield). LC/MS (ESI+) m/z=590.0/592.0 (M+H). $^1$H NMR (300 MHz, CDCl$_3$) δ: 8.16-8.23 (m, 2H), 7.11 (d, J=3.07 Hz, 1H), 5.38 (d, J=10.38 Hz, 1H), 5.20 (d, J=10.38 Hz, 1H), 3.84 (s, 3H), 3.62-3.73 (m, 2H), 1.72 (d, J=1.02 Hz, 3H), 1.50-1.58 (m, 9H), 0.98 (dd, J=7.45, 8.92 Hz, 2H), −0.02 (s, 9H).

Preparation of (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (25J)

Using a procedure similar to that described for 1I, trimethylsulfoxonium iodide (0.30 g, 1.4 mmol), potassium tert-butoxide (0.15 g, 1.4 mmol), and (S)-methyl 4-(5-bromo-2-fluoropyridin-3-yl)-2-((tert-butoxycarbonyl)((2-(trimethylsilyl)ethoxy)methyl)amino)-4-methyl-4H-1,3-thiazine-6-carboxylate (25I) (0.40 g, 0.68 mmol) were combined to afford (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (25J) (0.27 g, 66% yield). LCMS m/z=604.0/606.0 (M+H) $^1$H NMR (300 MHz, CDCl$_3$) δ: 8.17-8.27 (m, 2H), 5.30 (d, J=10.52 Hz, 1H), 5.03 (d, J=10.52 Hz, 1H), 3.82 (s, 3H), 3.62-3.74 (m, 2H), 2.68 (ddd, J=1.53, 7.71, 9.61 Hz, 1H), 1.75 (d, J=1.17 Hz, 3H), 1.51-1.57 (m, 9H), 1.24-1.36 (m, 1H), 1.16 (dd, J=5.26, 7.60 Hz, 1H), 0.85-1.07 (m, 2H), −0.06 (s, 9H). $^{19}$F NMR (282 MHz, CDCl$_3$) δ: −67.27 (s, 1F).

Preparation of (1S,5S,6S)-methyl 3-((tert-butoxycarbonyl)((2-(trimethylsilyl)ethoxy)methyl)amino)-5-(2-fluoro-5-vinylpyridin-3-yl)-5-methyl-2-thia-4-azabicyclo[4.1.0]hept-3-ene-1-carboxylate (25K)

(1S,5S,6S)-Methyl 3-((tert-butoxycarbonyl)((2-(trimethylsilyl)ethoxy)methyl)amino)-5-(2-fluoro-5-vinylpyridin-3-yl)-5-methyl-2-thia-4-azabicyclo[4.1.0]hept-3-ene-1-carboxylate (25K) (1.08 g, 76% yield) was prepared using (1S,5S,6S)-methyl 5-(5-bromo-2-fluoropyridin-3-yl)-3-((tert-butoxycarbonyl)((2-(trimethylsilyl)ethoxy)methyl) amino)-5-methyl-2-thia-4-azabicyclo[4.1.0]hept-3-ene-1-carboxylate (25J) (1.56 g, 2.58 mmol), potassium vinyltrifluoroborate (0.449 g, 3.35 mmol), and potassium acetate (0.484 ml, 7.74 mmol) in a similar manner as 1J. LCMS (ESI+) m/z=552.2 (M+H). $^1$H NMR (300 MHz, CDCl$_3$) δ: 8.22 (dd, J=2.41, 9.57 Hz, 1H), 8.10 (s, J=2.79 Hz, 1H), 6.72 (dd, J=11.03, 17.61 Hz, 1H), 5.73-5.93 (m, 1H), 5.38 (dd, J=3.73, 10.89 Hz, 2H), 5.08 (d, J=10.52 Hz, 1H), 3.82 (s, 3H), 3.68 (t, J=8.33 Hz, 2H), 2.69 (ddd, J=1.32, 7.82, 9.57 Hz, 1H), 1.77 (d, J=1.02 Hz, 3H), 1.53-1.60 (m, 9H), 1.49 (dd, J=5.19, 9.87 Hz, 1H), 1.15 (dd, J=5.26, 7.45 Hz, 1H), 0.87-1.01 (m, 2H), 0.04 (s, 9H). $^{19}$F NMR (282 MHz, CDCl$_3$) δ: −66.47 (s, 1F).

Preparation of (1S,5S,6S)-methyl 3-((tert-butoxycarbonyl)((2-(trimethylsilyl)ethoxy)methyl)amino)-5-(2-fluoro-5-formylpyridin-3-yl)-5-methyl-2-thia-4-azabicyclo[4.1.0]hept-3-ene-1-carboxylate (25)

(1S,5S,6S)-Methyl 3-((tert-butoxycarbonyl)((2-(trimethylsilyl)ethoxy)methyl)amino)-5-(2-fluoro-5-formylpyridin-3-yl)-5-methyl-2-thia-4-azabicyclo[4.1.0]hept-3-ene-1-carboxylate, (25) (0.75 g, 1.354 mmol, 69.8% yield) was prepared using (1S,5S,6S)-methyl 3-((tert-butoxycarbonyl)((2-(trimethylsilyl)ethoxy)methyl)amino)-5-(2-fluoro-5-vinylpyridin-3-yl)-5-methyl-2-thia-4-azabicyclo[4.1.0]hept-3-ene-1-carboxylate (25K) (1.07 g, 1.93 mmol), 2.5 wt. % osmium tetroxide solution in tert-butanol (0.57 mL, 0.058 mmol) and sodium periodate (1.24 g, 5.82 mmol) in a similar manner as 1. LCMS (ESI+) m/z=554.1 (M+H). $^1$H NMR (300 MHz, CDCl$_3$) δ: 10.11 (s, 1H), 8.68 (d, J=2.88 Hz, 1H), 8.63 (d, J=9.30 Hz, 1H), 5.35 (d, J=10.52 Hz, 1H), 5.08 (d, J=10.52 Hz, 1H), 3.83 (s, 3H), 3.69 (dd, J=7.60, 9.06 Hz, 2H), 2.69 (ddd, J=1.39, 7.75, 9.57 Hz, 1H), 1.79 (d, J=1.17 Hz, 3H), 1.55-1.64 (m, 9H), 1.51 (dd, J=5.26, 9.79 Hz, 1H), 1.19 (dd, J=5.41, 7.45 Hz, 1H), 0.94-1.01 (m, 2H), 0.04 (s, 9H). $^{19}$F NMR (282 MHz, CDCl$_3$) δ: −55.75 (s, 1F).

Synthesis of Intermediates 26 and 27

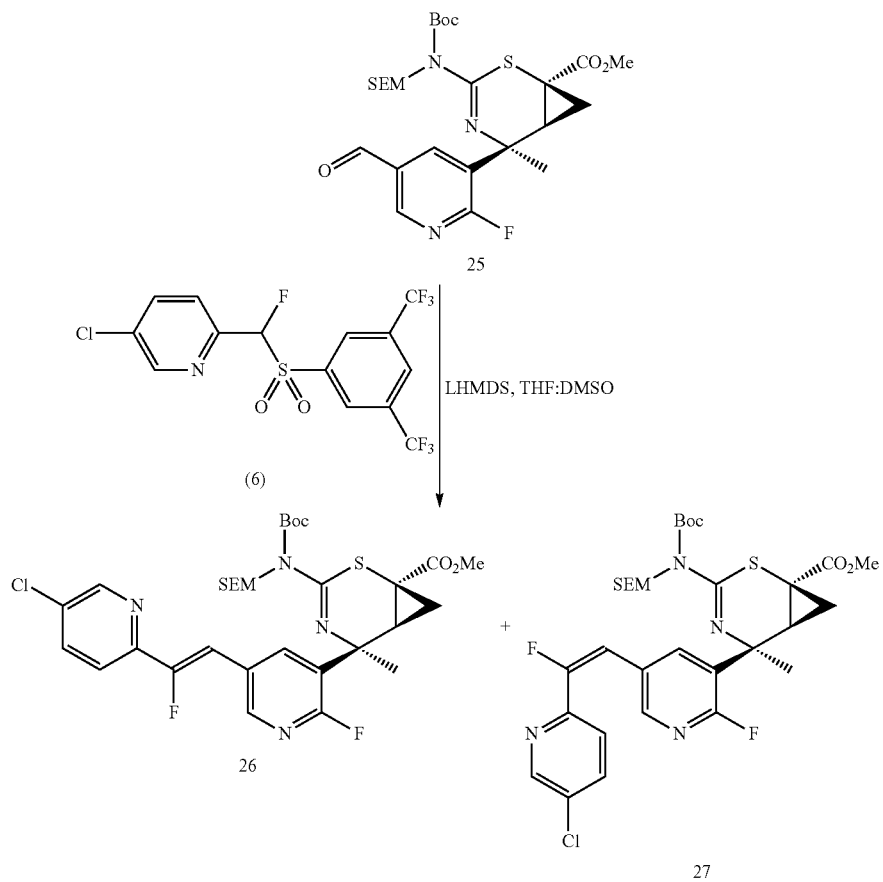

To a mixture of (1S,5S,6S)-methyl 3-((tert-butoxycarbonyl)((2-(trimethylsilyl)ethoxy)methyl)amino)-5-(2-fluoro-5-formylpyridin-3-yl)-5-methyl-2-thia-4-azabicyclo[4.1.0]hept-3-ene-1-carboxylate (25) (0.700 g, 1.26 mmol) and 2-(((3,5-bis(trifluoromethyl)phenyl)sulfonyl)fluoromethyl)-5-chloropyridine, 6, (0.640 g, 1.52 mmol) in THF (15 mL) and DMSO (4 mL) at 0° C. was added 1.0M lithium bis(trimethylsilyl)amide solution in THF (1.26 mL, 1.26 mmol) under nitrogen. The mixture was allowed to warm to room temperature and stirred for 4 hours. The mixture was quenched with saturated NH$_4$Cl and extracted with EtOAc. The organic extract was concentrated in vacuo and the residue purified with ISCO using 0-20% EtOAc in heptane to afford the title compounds (1S,5S,6S)-methyl 3-((tert-butoxycarbonyl)((2-(trimethylsilyl)ethoxy)methyl)amino)-5-(5-((Z)-2-(5-chloropyridin-2-yl)-2-fluorovinyl)-2-fluoropyridin-3-yl)-5-methyl-2-thia-4-azabicyclo[4.1.0]hept-3-ene-1-carboxylate, 26, (0.154 g, 18% yield) as peak 1 and (1S,5S,6S)-methyl 3-((tert-butoxycarbonyl)((2-(trimethylsilyl)ethoxy)methyl)amino)-5-(5-((E)-2-(5-chloropyridin-2-yl)-2-fluorovinyl)-2-fluoropyridin-3-yl)-5-methyl-2-thia-4-azabicyclo[4.1.0]hept-3-ene-1-carboxylate, 27, (0.280 g, 32% yield) as peak 2.

"Z" Isomer (26):
LCMS (ESI$^+$) m/z=681.1 (M+H). $^1$H NMR (300 MHz, CDCl$_3$) δ: 8.58 (s, 1H), 8.40-8.48 (m, 2H), 7.77 (dd, J=2.48, 8.48 Hz, 1H), 7.59 (d, J=8.55 Hz, 1H), 7.11 (d, J=39.17 Hz, 1H), 5.30-5.38 (m, 1H), 5.12 (d, J=10.52 Hz, 1H), 3.83 (s, 3H), 3.64-3.74 (m, 2H), 2.66-2.76 (m, 1H), 1.74-1.83 (m, 3H), 1.51-1.61 (m, 10H), 1.20-1.27 (m, 1H), 0.93-1.00 (m, 2H), -0.05-0.06 (m, 9H). $^{19}$F NMR (282 MHz, CDCl$_3$) δ: -65.08 (s, 1F), -120.74 (s, 1F).

"E" Isomer (27):
LCMS (ESI$^+$) m/z=681.2 (M+H). $^1$H NMR (300 MHz, CDCl$_3$) δ: 8.46 (d, J=2.48 Hz, 1H), 8.12-8.19 (m, 2H), 7.73 (dd, J=2.41, 8.55 Hz, 1H), 7.50 (d, J=8.65 Hz, 1H), 6.60 (d, J=23.24 Hz, 1H), 5.17 (d, J=10.52 Hz, 1H), 4.94 (d, J=10.52 Hz, 1H), 3.82 (s, 3H), 3.57-3.67 (m, 2H), 2.63-2.73 (m, 1H), 1.71-1.80 (m, 3H), 1.46-1.61 (m, 10H), 1.15-1.26 (m, 1H), 0.86-0.98 (m, 2H), -0.02-0.06 (m, 9H). $^{19}$F NMR (282 MHz, CDCl$_3$) δ: -66.27 (s, 1F), -104.44 (s, 1F).

Preparation of (1S,5S,6S)-methyl 3-amino-5-(5-((Z)-2-(5-chloropyridin-2-yl)-2-fluorovinyl)-2-fluoropyridin-3-yl)-5-methyl-2-thia-4-azabicyclo[4.1.0]hept-3-ene-1-carboxylate (Example 176)

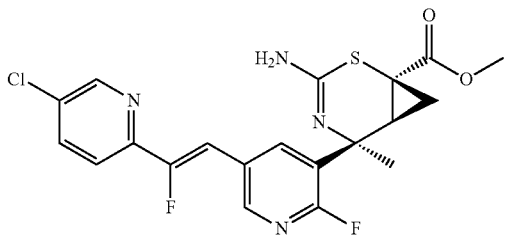 [SMILES: COC(=O)[C@]12C[C@H]1[C@@](C)(c1cc(/C=C(\F)c3ccc(Cl)cn3)cnc1F)N=C(N)S2]

Example 176

(1S,5S,6S)-Methyl 3-amino-5-(5-((Z)-2-(5-chloropyridin-2-yl)-2-fluorovinyl)-2-fluoropyridin-3-yl)-5-methyl-2-thia-4-azabicyclo[4.1.0]hept-3-ene-1-carboxylate (Example 176) (0.018 g, 0.040 mmol, 70% yield) was prepared from (1S,5S,6S)-methyl 3-((tert-butoxycarbonyl)((2-(trimethylsilyl)ethoxy)methyl)amino)-5-(5-((Z)-2-(5-chloropyridin-2-yl)-2-fluorovinyl)-2-fluoropyridin-3-yl)-5-methyl-2-thia-4-azabicyclo[4.1.0]hept-3-ene-1-carboxylate (26) (0.039 g, 0.057 mmol) and 4-methylbenzene sulfonic acid, monohydrate (0.044 g, 0.229 mmol) in dioxane (1.0 mL) in a similar manner to Example 151. LCMS (ESI+) m/z=451.2 (M+H). $^1$H NMR (300 MHz, CDCl$_3$) δ: 8.57 (d, J=3.06 Hz, 1H), 8.41-8.49 (m, 2H), 7.77 (dd, J=2.34, 8.48 Hz, 1H), 7.59 (dd, J=1.46, 8.48 Hz, 1H), 7.09 (d, J=39.17 Hz, 1H), 4.22-4.69 (br. s., 2H), 3.81 (s, 3H), 2.54-2.65 (m, 1H), 1.71-1.79 (m, 3H), 1.56 (dd, J=5.26, 9.79 Hz, 1H), 1.12 (dd, J=5.26, 7.45 Hz, 1H). $^{19}$F NMR (282 MHz, CDCl$_3$) δ: −64.60 (s, 1F), −120.63 (s, 1F).

Preparation of (1S,5S,6S)-methyl 3-amino-5-(5-((E)-2-(5-chloropyridin-2-yl)-2-fluorovinyl)-2-fluoropyridin-3-yl)-5-methyl-2-thia-4-azabicyclo[4.1.0]hept-3-ene-1-carboxylate (Example 177)

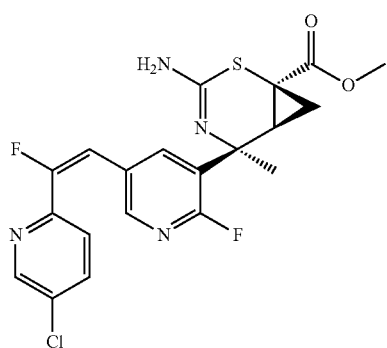 [SMILES: COC(=O)[C@]12C[C@H]1[C@@](C)(c1cc(/C=C(/F)c3ccc(Cl)cn3)cnc1F)N=C(N)S2]

Example 177

(1S,5S,6S)-Methyl 3-amino-5-(5-((E)-2-(5-chloropyridin-2-yl)-2-fluorovinyl)-2-fluoropyridin-3-yl)-5-methyl-2-thia-4-azabicyclo[4.1.0]hept-3-ene-1-carboxylate (0.015 g, 0.033 mmol, 68.7% yield), (Example 177) was prepared from (1S,5S,6S)-methyl 3-((tert-butoxycarbonyl)((2-(trimethylsilyl)ethoxy)methyl)amino)-5-(5-((E)-2-(5-chloropyridin-2-yl)-2-fluorovinyl)-2-fluoropyridin-3-yl)-5-methyl-2-thia-4-azabicyclo[4.1.0]hept-3-ene-1-carboxylate) (27) (0.033 g, 0.048 mmol) and 4-methylbenzene sulfonic acid, monohydrate (0.037 g, 0.194 mmol) in dioxane (1.0 mL) in a similar manner to Example 151. LCMS (ESI+) m/z=451.2 (M+H). $^1$H NMR (300 MHz, CDCl$_3$) δ: 8.50 (d, J=2.48 Hz, 1H), 8.17 (dd, J=2.41, 9.57 Hz, 1H), 8.10 (s, 1H), 7.71-7.77 (m, 1H), 7.49 (d, J=8.48 Hz, 1H), 6.61 (d, J=22.95 Hz, 1H), 4.38 (br. s., 2H), 3.81 (s, 3H), 2.50-2.63 (m, 1H), 1.64-1.77 (m, 3H), 1.55 (dd, J=5.12, 9.79 Hz, 1H), 1.05 (dd, J=5.19, 7.53 Hz, 1H). $^{19}$F NMR (282 MHz, CDCl$_3$) δ: −65.62 (s, 1F), −103.61 (s, 1F).

Preparation of (1S,5S,6S)-3-amino-5-(5-((Z)-2-(5-chloropyridin-2-yl)-2-fluorovinyl)-2-fluoropyridin-3-yl)-N,N,5-trimethyl-2-thia-4-azabicyclo[4.1.0]hept-3-ene-1-carboxamide (Example 178)

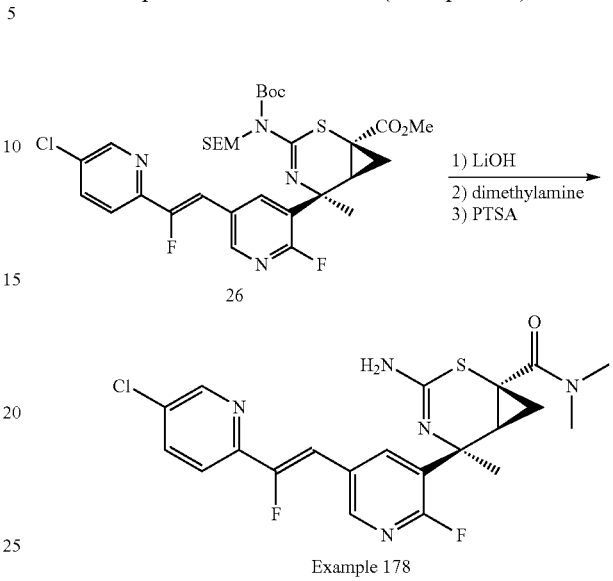

Example 178

A mixture of (1S,5S,6S)-methyl 3-((tert-butoxycarbonyl)((2-(trimethylsilyl)ethoxy)methyl)amino)-5-(5-((Z)-2-(5-chloropyridin-2-yl)-2-fluorovinyl)-2-fluoropyridin-3-yl)-5-methyl-2-thia-4-azabicyclo[4.1.0]hept-3-ene-1-carboxylate (26) (0.120 g, 0.176 mmol) and lithium hydroxide monohydrate (9.79 µl, 0.352 mmol) in THF (3 mL) and water (1 mL) was stirred at room temperature. After 1 hour, the mixture was concentrated under reduced pressure and the residue was dissolved in water (2 mL). The pH was adjusted to 4 by addition of 1N HCl solution. The resulting solution was extracted with EtOAc (2×). The organic layer was dried over Na$_2$SO$_4$, filtered, and concentrated to give a white foam as (1S,5S,6S)-3-((tert-butoxycarbonyl)((2-(trimethylsilyl)ethoxy)methyl)amino)-5-(5-((Z)-2-(5-chloropyridin-2-yl)-2-fluorovinyl)-2-fluoropyridin-3-yl)-5-methyl-2-thia-4-azabicyclo[4.1.0]hept-3-ene-1-carboxylic acid (0.104 g, 88% yield). The product thus obtained was used without further purification.

To the acid (1S,5S,6S)-3-((tert-butoxycarbonyl)((2-(trimethylsilyl)ethoxy)methyl)amino)-5-(5-((Z)-2-(5-chloropyridin-2-yl)-2-fluorovinyl)-2-fluoropyridin-3-yl)-5-methyl-2-thia-4-azabicyclo[4.1.0]hept-3-ene-1-carboxylic acid in DMF (1 mL), prepared as described above, was added dimethylamine hydrochloride (0.024 g, 0.30 mmol), DIEA (0.052 ml, 0.30 mmol) and (1-cyano-2-ethoxy-2-oxoethylidenaminooxy)dimethylaminomorpholinocarbenium hexafluorophosphate (COMU) (0.128 g, 0.300 mmol). The reaction mixture was stirred at room temperature for 2 hours, diluted with water, extracted with EtOAc and the organic layer was concentrated to dryness. The residue thus obtained, tert-butyl ((1S,5S,6S)-5-(5-((Z)-2-(5-chloropyridin-2-yl)-2-fluorovinyl)-2-fluoropyridin-3-yl)-1-(dimethylcarbamoyl)-5-methyl-2-thia-4-azabicyclo[4.1.0]hept-3-en-3-yl)((2-(trimethylsilyl)ethoxy)methyl)carbamate, was added to 4-methylbenzene sulfonic acid, monohydrate (0.086 g, 0.45 mmol) in a pressure relief valve vial with dioxane (2 mL). The vial was capped and heated at 85° C. for 2 hours. The reaction was diluted with water and extracted with EtOAc (2×). The combined organic layers were concentrated and the residue was purified by flash column chromatography on silica gel with ISCO eluting with 0-6% MeOH in DCM to afford the title compound (Example 178) (1S,5S,6S)-3-amino-5-(5-((Z)-2-(5-chloropyridin-2-yl)-2-fluorovinyl)-2-fluoropyridin-3-yl)-N,N,5-trimethyl-2-thia-4-azabicyclo[4.1.0]hept-3-ene-1-carboxamide (0.026 g, 37% yield). LCMS (ESI+) m/z=464.2 (M+H). $^1$H NMR (300 MHz, CDCl$_3$) δ: 8.53-8.58 (m, 1H), 8.34-8.42 (m, 1H), 8.27 (dd, J=2.41, 9.57 Hz, 1H), 7.76 (dd, J=2.41, 8.55 Hz, 1H), 7.56 (dd, J=1.46, 8.48 Hz, 1H), 7.11 (d, J=39.32 Hz, 1H), 3.84-4.79 (br. s., 2H), 3.08 (br. s., 6H), 2.33 (ddd, J=1.24, 7.31, 9.57 Hz, 1H), 1.82-1.89 (m, 3H), 1.65 (s, 1H), 0.76-0.99 (m, 1H). $^{19}$F NMR (282 MHz, CDCl$_3$) δ: -63.78 (s, 1F), -120.78 (s, 1F).

Preparation of (1S,5S,6S)-3-amino-5-(5-((E)-2-(5-chloropyridin-2-yl)-2-fluorovinyl)-2-fluoropyridin-3-yl)-N,N,5-trimethyl-2-thia-4-azabicyclo[4.1.0]hept-3-ene-1-carboxamide (Example 179)

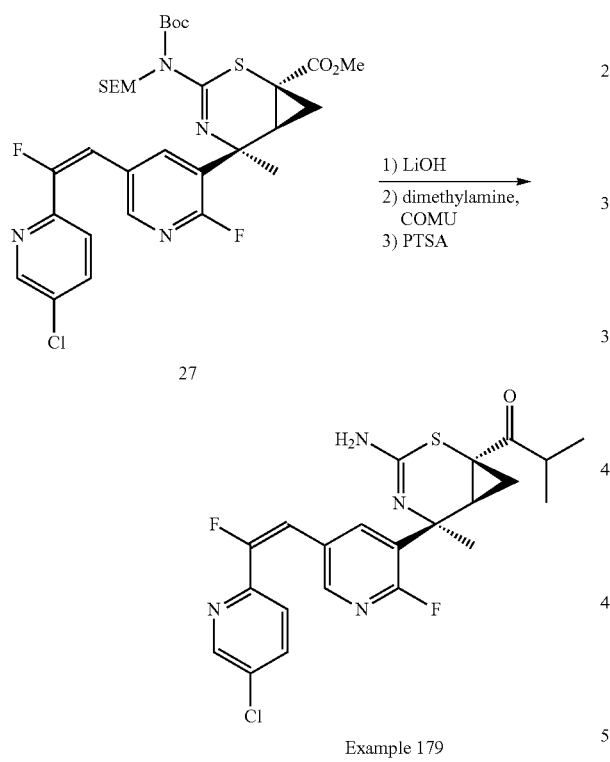

Example 179

(1S,5S,6S)-3-Amino-5-(5-((E)-2-(5-chloropyridin-2-yl)-2-fluorovinyl)-2-fluoropyridin-3-yl)-N,N,5-trimethyl-2-thia-4-azabicyclo[4.1.0]hept-3-ene-1-carboxamide (0.046 g, 61% yield) (Example 179), was prepared stepwise following the procedure described for Example 178, using (1S,5S,6S)-methyl 3-((tert-butoxycarbonyl)((2-(trimethylsilyl)ethoxy)methyl)amino)-5-(5-((E)-2-(5-chloropyridin-2-yl)-2-fluorovinyl)-2-fluoropyridin-3-yl)-5-methyl-2-thia-4-azabicyclo[4.1.0]hept-3-ene-1-carboxylate (27) (0.111 g, 0.163 mmol) and lithium hydroxide monohydrate (0.0089 g, 0.21 mmol). The acid, (1S,5S,6S)-3-((tert-butoxycarbonyl)((2-(trimethylsilyl)ethoxy)methyl)amino)-5-(5-((E)-2-(5-chloropyridin-2-yl)-2-fluorovinyl)-2-fluoropyridin-3-yl)-5-methyl-2-thia-4-azabicyclo[4.1.0]hept-3-ene-1-carboxylic acid, obtained was combined with dimethylamine hydrochloride (0.027 g, 0.326 mmol), DIEA (0.113 mL, 0.652 mmol), and COMU (0.140 g, 0.326 mmol), followed by 4-methylbenzene sulfonic acid, monohydrate (0.093 g, 0.49 mmol). LCMS (ESI+) m/z=464.2 (M+H). $^1$H NMR (300 MHz, CDCl$_3$) δ: 8.49 (d, J=2.48 Hz, 1H), 8.06 (d, J=2.96 Hz, 1H), 7.88-7.98 (m, 1H), 7.66-7.76 (m, 1H), 7.45 (d, J=8.48 Hz, 1H), 6.57 (d, J=22.80 Hz, 1H), 3.96-4.77 (m, 2H), 3.07 (br. s., 6H), 2.26 (ddd, J=1.39, 7.27, 9.61 Hz, 1H), 1.79 (d, J=1.17 Hz, 3H), 1.36 (dd, J=5.70, 9.79 Hz, 1H), 0.80 (dd, J=5.85, 6.87 Hz, 1H). $^{19}$F NMR (282 MHz, CDCl$_3$) δ: -64.87 (s, 1F), -103.52 (s, 1F).

Synthesis of Intermediates 28 and 29

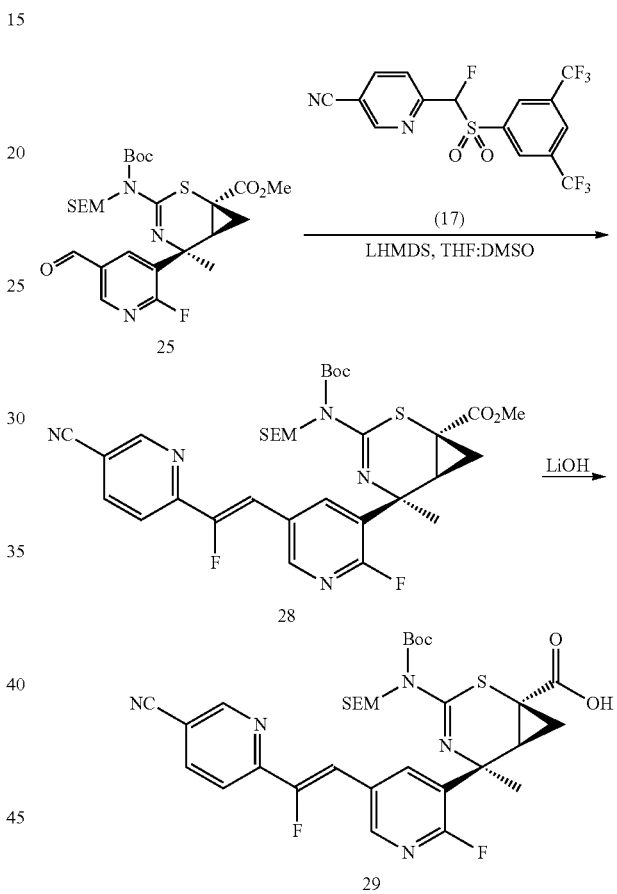

Preparation of (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate (28)

(1S,5S,6S)-Methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate (28) (1.00 g, 40.2% yield) was prepared using (1S,5S,6S)-methyl 3-((tert-butoxycarbonyl)((2-(trimethylsilyl)ethoxy)methyl)amino)-5-(2-fluoro-5-formylpyridin-3-yl)-5-methyl-2-thia-4-azabicyclo[4.1.0]hept-3-ene-1-carboxylate (25) (2.05 g, 3.70 mmol) and 6-(((3,5-bis(trifluoromethyl)phenyl)sulfonyl)fluoromethyl)nicotinonitrile (17) (1.83 g, 4.44 mmol) in a manner similar to 16 Method B. LCMS (ESI+) m/z=672.2

(M+H). ¹H NMR (300 MHz, CDCl₃) δ: 8.85-8.89 (m, 1H), 8.45-8.51 (m, 2H), 8.07 (dd, J=2.12, 8.26 Hz, 1H), 7.74 (d, J=7.45 Hz, 1H), 7.31 (d, J=38.73 Hz, 1H), 5.36 (d, J=10.52 Hz, 1H), 5.12 (d, J=10.67 Hz, 1H), 3.83 (s, 3H), 3.70 (t, J=8.18 Hz, 2H), 2.67-2.76 (m, 1H), 1.74-1.85 (m, 3H), 1.56 (s, 9H), 1.52 (dd, J=5.19, 9.87 Hz, 1H), 1.20-1.25 (m, 1H), 0.93-1.01 (m, 2H), 0.00 (s, 9H). ¹⁹F

A solution of (1S,5S,6S)-methyl 3-((tert-butoxycarbonyl) ((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate, 28, (0.900 g, 1.34 mmol) and lithium hydroxide monohydrate (0.080 g, 1.9 mmol) in THF:water (10 mL: 5 mL) was stirred at room temperature for 2 hours. The reaction mixture was concentrated, and the residue was dissolved in water (5 mL). The resulting solution was adjusted to pH 4 with 1N HCl solution and extracted with EtOAc (2×). The combined organic layers were concentrated to dryness to afford the title compound (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylic acid (29) (0.89 g, 100% yield). LCMS (ESI⁺) m/z=658.1 (M+H).

Preparation of (1S,5S,6S)-3-amino-5-(5-((Z)-2-(5-cyanopyridin-2-yl)-2-fluorovinyl)-2-fluoropyridin-3-yl)-N,N,5-trimethyl-2-thia-4-azabicyclo[4.1.0]hept-3-ene-1-carboxamide (Example 180)

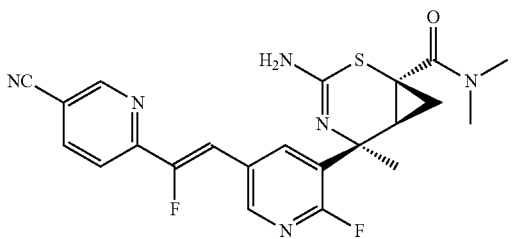 [SMILES: CN(C)C(=O)[C@]12C[C@H]1[C@@](C)(c1cc(/C=C(\F)c3ccc(C#N)cn3)cnc1F)N=C(N)S2]

Example 180

(1S,5S,6S)-3-Amino-5-(5-((Z)-2-(5-cyanopyridin-2-yl)-2-fluorovinyl)-2-fluoropyridin-3-yl)-N,N,5-trimethyl-2-thia-4-azabicyclo[4.1.0]hept-3-ene-1-carboxamide (Example 180) (0.019, 28% yield) was prepared from (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylic acid (29) (0.100 g, 0.152 mmol), dimethylamine hydrochloride (0.019 g, 0.23 mmol), DIEA (0.132 mL, 0.760 mmol), and COMU (0.130 g, 0.304 mmol), followed by 4-methylbenzene sulfonic acid, monohydrate (0.064 g, 0.34 mmol) in a similar manner to Example 178. LCMS (ESI⁺) m/z=455.2 (M+H). ¹H NMR (300 MHz, CDCl₃) δ: 8.84-8.88 (m, 1H), 8.44 (s, J=3.62 Hz, 1H), 8.33 (dd, J=2.34, 9.50 Hz, 1H), 8.07 (dd, J=2.12, 8.26 Hz, 1H), 7.73 (d, J=8.42 Hz, 1H), 7.27 (d, J=38.73 Hz, 1H), 4.32-4.83 (m, 2H), 3.10 (br. s., 6H), 2.31-2.40 (m, 1H), 1.83-1.90 (m, 3H), 1.38 (dd, J=5.70, 9.65 Hz, 1H), 0.82-0.94 (m, 1H). ¹⁹F NMR (282 MHz, CDCl₃) δ: -62.48 (s, 1F), -122.22 (s, 1F).

Preparation of 6-((Z)-2-(5-((1S,5S,6S)-3-amino-1-((R)-3-fluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile (Example 181)

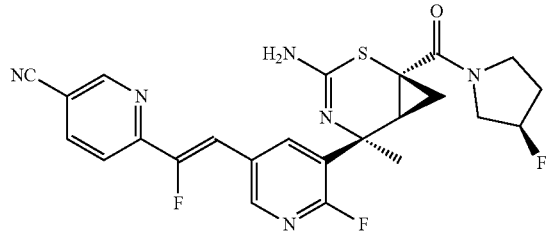 [SMILES: C[C@]1(c2cc(/C=C(\F)c3ccc(C#N)cn3)cnc2F)N=C(N)S[C@@]2(C(=O)N3CC[C@@H](F)C3)C[C@H]21]

Example 181

6-((Z)-2-(5-((1S,5S,6S)-3-Amino-1-((R)-3-fluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile (Example 181) (0.030 g, 40% yield) was prepared from (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylic acid (29) (0.100 g, 0.152 mmol), (R)-(−)-3-fluoropyrrolidine hydrochloride (0.023 g, 0.18 mmol), DIEA, (0.132 mL, 0.760 mmol), and COMU (0.130 g, 0.304 mmol), followed by 4-methylbenzene sulfonic acid, monohydrate (0.064 g, 0.33 mmol) in a similar manner to Example 178. LCMS (ESI⁺) m/z=499.2 (M+H). ¹H NMR (300 MHz, CDCl₃) δ: 8.84-8.88 (m, 1H), 8.44 (s, J=3.17 Hz, 1H), 8.25-8.34 (m, 1H), 8.03-8.11 (m, 1H), 7.74 (d, J=8.50 Hz, 1H), 7.28 (d, J=38.88 Hz, 1H), 5.29 (d, J=52.47 Hz, 1H), 4.27-4.84 (m, 2H), 3.44-4.04 (m, 4H), 2.36 (br. s., 1H), 2.24 (ddd, J=1.17, 7.16, 9.65 Hz, 2H), 1.84-1.93 (m, 3H), 1.55 (dd, J=5.85, 9.79 Hz, 1H), 0.82 (br. s., 1H). ¹⁹F NMR (282 MHz, CDCl₃) δ: -62.65 (s, 1F), -122.16 (s, 1F), -177.66 (s, 1F).

Preparation of 6-((Z)-2-(5-((1S,5S,6S)-3-amino-1-((S)-3-fluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile (Example 182)

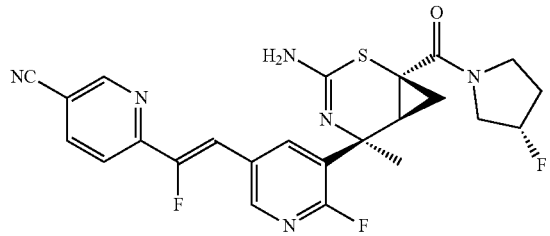 [SMILES: C[C@]1(c2cc(/C=C(\F)c3ccc(C#N)cn3)cnc2F)N=C(N)S[C@@]2(C(=O)N3CC[C@H](F)C3)C[C@H]21]

Example 182

Preparation of 6-((Z)-2-(5-((1S,5S,6S)-3-amino-1-((S)-3-fluoropyrrolidine-1-carbonyl)-5-methyl-2-thia-4-azabicyclo

[4.1.0]hept-3-en-5-yl)-6-fluoropyridin-3-yl)-1-fluorovinyl)nicotinonitrile (Example 182) (0.005 g, 6% yield) was prepared from (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylic acid (29) (0.100 g, 0.152 mmol), (S)-(+)-3-fluoropyrrolidine hydrochloride (0.019 g, 0.15 mmol), DIEA (0.132 mL, 0.760 mmol), and COMU (0.130 g, 0.304 mmol), followed by 4-methylbenzene sulfonic acid, monohydrate (0.064 g, 0.334 mmol) in a similar manner to Example 178. LCMS (ESI⁺) m/z=499.1 (M+H). $^1$H NMR (400 MHz, CDCl$_3$) δ: 8.85 (s, 1H), 8.44 (s, 1H), 8.27 (d, J=8.41 Hz, 1H), 8.05 (dd, J=2.05, 8.31 Hz, 1H), 7.73 (d, J=7.82 Hz, 1H), 7.26 (d, J=38.73 Hz, 1H), 5.08-5.46 (m, 1H), 3.93-4.22 (m, 2H), 3.58-3.86 (m, 3H), 2.38-2.49 (m, 1H), 2.32 (br. s., 1H), 1.93-2.19 (m, 2H), 1.89 (s, 3H), 1.43 (dd, J=5.77, 9.68 Hz, 1H), 0.82-0.95 (m, 1H). $^{19}$F NMR (282 MHz, CDCl$_3$) δ: −62.53 (s, 1F), −122.13 (s, 1F), −177.58 (s, 1F).

Preparation of 6-((Z)-2-(5-((1S,5S,6S)-3-amino-5-methyl-1-(morpholine-4-carbonyl)-2-thia-4-azabicyclo[4.1.0]hept-3-en-5-yl)-6-fluoropyridin-3-yl)-1-fluorovinyl)nicotinonitrile (Example 183)

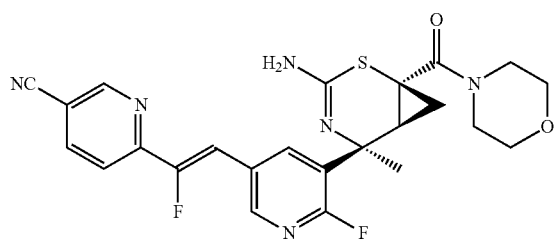 [SMILES: C[C@]1(c2cc(/C=C(\F)c3ccc(C#N)cn3)cnc2F)N=C(N)S[C@@]2(C(=O)N3CCOCC3)C[C@H]21]

Example 183

6-((Z)-2-(5-((1S,5S,6S)-3-Amino-5-methyl-1-(morpholine-4-carbonyl)-2-thia-4-azabicyclo[4.1.0]hept-3-en-5-yl)-6-fluoropyridin-3-yl)-1-fluorovinyl)nicotinonitrile (Example 183) (0.040 g, 53% yield) was prepared from (1S, 5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylic acid (29) (0.100 g, 0.152 mmol), morpholine (0.017 g, 0.20 mmol), DIEA (0.132 mL, 0.760 mmol), and COMU (0.130 g, 0.304 mmol), followed by 4-methylbenzene sulfonic acid, monohydrate (0.064 g, 0.33 mmol) in a similar manner to Example 178. LCMS (ESI⁺)m/z=497.2 (M+H). $^1$H NMR (400 MHz, CDCl$_3$) δ: 8.85 (s, 1H), 8.43 (s, J=3.48 Hz, 1H), 8.28-8.38 (m, 1H), 8.03-8.08 (m, 1H), 7.72 (d, J=8.02 Hz, 1H), 7.26 (d, J=40.88 Hz, 1H), 4.20-5.06 (br. s., 2H), 3.62-3.74 (m, 8H), 2.37 (dd, J=7.82, 9.19 Hz, 1H), 1.83 (s, 3H), 1.34 (dd, J=5.77, 9.68 Hz, 1H), 0.85-0.93 (m, 1H).

Synthesis of Intermediate 30

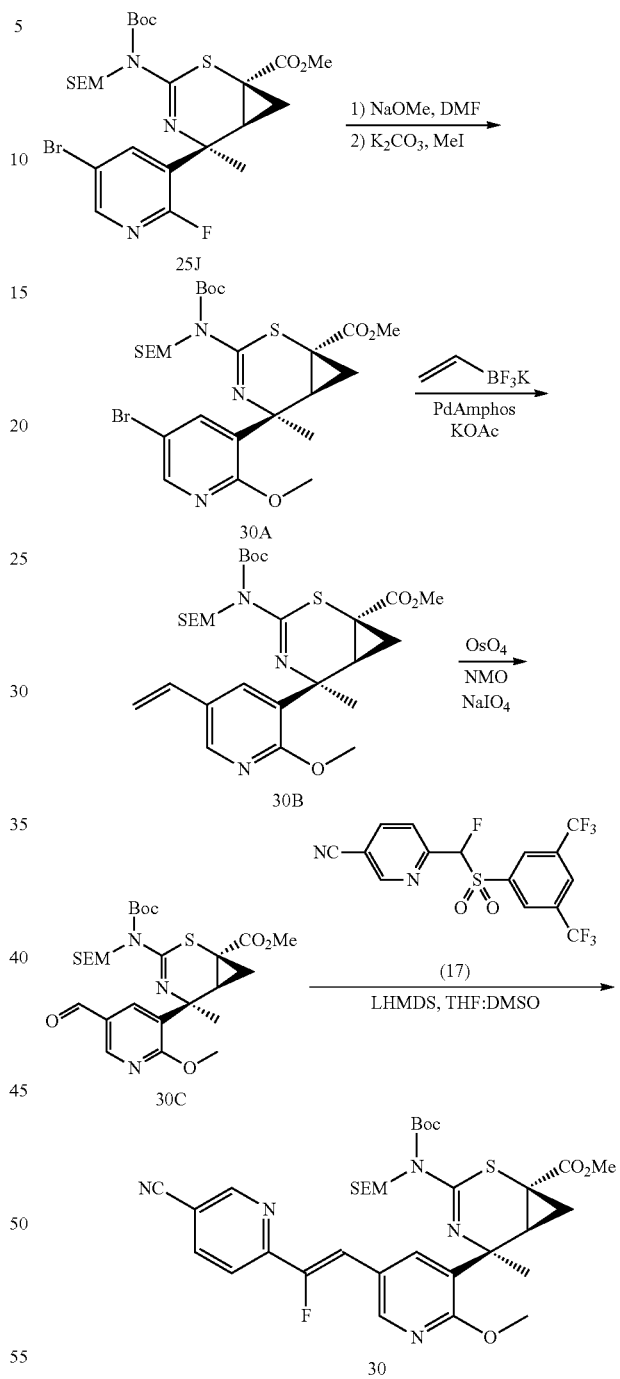

Preparation of (1S,5S,6S)-methyl 5-(5-bromo-2-methoxypyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (30A)

To a solution of (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]

hept-3-ene-1-carboxylate (25) (0.82 g, 1.4 mmol) in DMF (10 mL) was added anhydrous sodium methoxide powder (0.229 g, 4.07 mmol) portion wise. After 1 hour of stirring the suspension, iodomethane (0.152 mL, 2.44 mmol) was added. The reaction was stirred at room temperature for 2 hours and diluted with water and EtOAc. The organic layer was washed with brine and concentrated in vacuo. The residue thus obtained was purified by silica gel chromatography using 0-40% EtOAc in heptane to afford (1S,5S,6S)-methyl 5-(5-bromo-2-methoxypyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (30A) (0.61 g,]73% yield). LCMS (ESI$^+$) m/z=616.1/618.0 (M+H).

Preparation of (1S,5S,6S)-methyl 3-((tert-butoxycarbonyl)((2-(trimethylsilyl)ethoxy)methyl)amino)-5-(2-methoxy-5-vinylpyridin-3-yl)-5-methyl-2-thia-4-azabicyclo[4.1.0]hept-3-ene-1-carboxylate (30B)

(1S,5S,6S)-Methyl 3-((tert-butoxycarbonyl)((2-(trimethylsilyl)ethoxy)methyl)amino)-5-(2-methoxy-5-vinylpyridin-3-yl)-5-methyl-2-thia-4-azabicyclo[4.1.0]hept-3-ene-1-carboxylate (30B), (0.82 g, 72% yield) was prepared using (1S,5S,6S)-methyl 5-(5-bromo-2-methoxypyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate, 30A, (1.25 g, 2.03 mmol), potassium vinyltrifluoroborate (0.353 g, 2.64 mmol), 1,1-bis[di-t-butyl-p-methylaminophenyl]palladium(ii) chloride (0.072 g, 0.100 mmol), and potassium acetate (0.597 g, 6.08 mmol) in a similar manner as 1J. LCMS (ESI$^+$) m/z=564.2 (M+H).

Preparation of (1S,5S,6S)-methyl 3-((tert-butoxycarbonyl)((2-(trimethylsilyl)ethoxy)methyl)amino)-5-(5-formyl-2-methoxypyridin-3-yl)-5-methyl-2-thia-4-azabicyclo[4.1.0]hept-3-ene-1-carboxylate (30C)

(1S,5S,6S)-Methyl 3-((tert-butoxycarbonyl)((2-(trimethylsilyl)ethoxy)methyl)amino)-5-(5-formyl-2-methoxypyridin-3-yl)-5-methyl-2-thia-4-azabicyclo[4.1.0]hept-3-ene-1-carboxylate, 30C, (0.77 g, 96% yield) was prepared using (1S,5S,6S)-methyl 3-((tert-butoxycarbonyl)((2-(trimethylsilyl)ethoxy)methyl)amino)-5-(2-methoxy-5-vinylpyridin-3-yl)-5-methyl-2-thia-4-azabicyclo[4.1.0]hept-3-ene-1-carboxylate, 30B, (0.80 g, 1.4 mmol), 4-methylmorpholine-4-oxide (0.249 g, 2.13 mmol), osmium tetroxide, 2.5 wt. %, solution in tert-butanol (0.14 mL, 0.014 mmol), and sodium periodate (0.911 g, 4.26 mmol) in a similar manner as 25. LCMS (ESI$^+$) m/z=566.1 (M+H).

Preparation of (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-methoxypyridin-3-yl)-5-methyl-2-thia-4-azabicyclo[4.1.0]hept-3-ene-1-carboxylate (30)

(1S,5S,6S)-Methyl 3-((tert-butoxycarbonyl)((2-(trimethylsilyl)ethoxy)methyl)amino)-5-(5-((Z)-2-(5-cyanopyridin-2-yl)-2-fluorovinyl)-2-methoxypyridin-3-yl)-5-methyl-2-thia-4-azabicyclo[4.1.0]hept-3-ene-1-carboxylate, 30, (0.32 g, 34% yield) was prepared using (1S,5S,6S)-methyl 3-((tert-butoxycarbonyl)((2-(trimethylsilyl)ethoxy)methyl)amino)-5-(5-formyl-2-methoxypyridin-3-yl)-5-methyl-2-thia-4-azabicyclo[4.1.0]hept-3-ene-1-carboxylate, 30C, (0.77 g, 1.4 mmol), 6-(((3,5-bis(trifluoromethyl)phenyl)sulfonyl)fluoromethyl) nicotinonitrile, 17, (0.729 g, 1.77 mmol) and 1M lithium bis(trimethylsilyl)amide solution in THF (1.769 mL, 1.769 mmol) in a similar manner as 28. LCMS (ESI$^+$) m/z=684.2 (M+H). $^1$H NMR (400 MHz, CDCl$_3$) δ: 8.84 (s, 1H), 8.44 (d, J=2.15 Hz, 1H), 8.36 (d, J=2.15 Hz, 1H), 8.03 (d, J=8.51 Hz, 1H), 7.69 (d, J=8.02 Hz, 1H), 7.27 (d, J=39.52 Hz, 1H), 5.35 (d, J=10.56 Hz, 1H), 5.13 (d, J=10.56 Hz, 1H), 4.11 (s, 3H), 3.83 (s, 3H), 3.71 (t, J=8.22 Hz, 2H), 2.96 (dd, J=7.73, 9.88 Hz, 1H), 1.78 (s, 3H), 1.56 (s, 9H), 1.44 (dd, J=5.09, 9.98 Hz, 1H), 1.17 (dd, J=5.09, 7.63 Hz, 1H), 0.94-1.00 (m, 2H), 0.01 (s, 9H). $^{19}$F NMR (376 MHz, CDCl$_3$) δ: −124.84 (s, 1F).

Preparation of 6-((Z)-2-(5-((1S,5S,6S)-3-amino-1-((R)-3-fluoropyrrolidine-1-carbonyl)-5-methyl-2-thia-4-azabicyclo[4.1.0]hept-3-en-5-yl)-6-methoxypyridin-3-yl)-1-fluorovinyl)nicotinonitrile (Example 184)

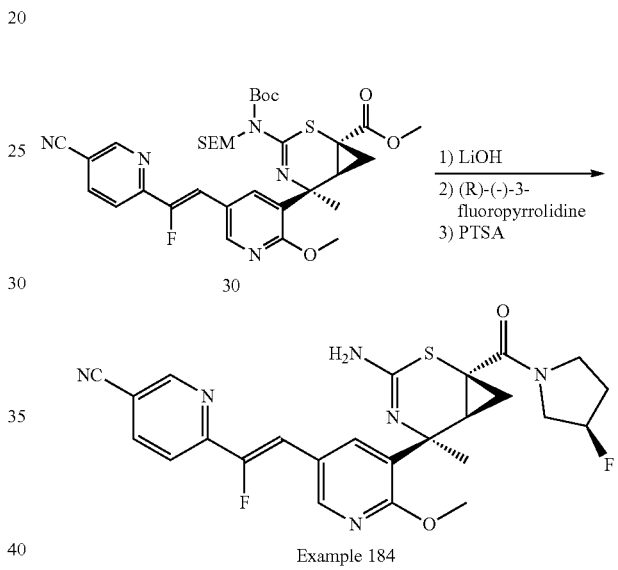

Example 184

A solution of (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-methoxypyridin-3-yl)-5-methyl-2-thia-4-azabicyclo[4.1.0]hept-3-ene-1-carboxylate (30) (0.060 g, 0.088 mmol) and lithium hydroxide monohydrate (0.0074 g, 0.18 mmol) in THF:water (2 mL: 1 mL) was stirred at room temperature for 2 hours. The reaction mixture was concentrated and to the lithium salt was added (R)-(−)-3-fluoropyrrolidine hydrochloride (0.015 g, 0.12 mmol), DIEA (0.076 ml, 0.439 mmol) and (1-cyano-2-ethoxy-2-oxoethylidenaminooxy)dimethylaminomorpholinocarbenium hexafluorophosphate (0.056 g, 0.13 mmol) in DMF (2 mL). The mixture was stirred at room temperature for 1 hour, diluted with water, and extracted with EtOAc (2×). The combined organic layers were concentrated to dryness to give tert-butyl ((1S,5S,6S)-5-(5-((Z)-2-(5-cyanopyridin-2-yl)-2-fluorovinyl)-2-methoxypyridin-3-yl)-1-((R)-3-fluoropyrrolidine-1-carbonyl)-5-methyl-2-thia-4-azabicyclo[4.1.0]hept-3-en-3-yl)((2-(trimethylsilyl)ethoxy)methyl)carbamate. To residue thus obtained was added 4-methylbenzene sulfonic acid, monohydrate (0.050 g, 0.26 mmol) in dioxane (2 mL) in a pressure relief valve vial. The vial was capped and heated to 85° C.

for 2 hours. The reaction was diluted with water and extracted with EtOAc (2×). The organic phase was concentrated, and the residue was purified by flash column chromatography on silica gel with ISCO eluting with 0-70% EtOAc in heptanes to afford the title compound, Example 184, 6-((Z)-2-(5-((1S,5S,6S)-3-amino-1-((R)-3-fluoropyrrolidine-1-carbonyl)-5-methyl-2-thia-4-azabicyclo[4.1.0]hept-3-en-5-yl)-6-methoxypyridin-3-yl)-1-fluorovinyl)nicotinonitrile (0.018 g, 40% yield). LCMS (ESI+) m/z=511.1 (M+H). $^1$H NMR (400 MHz, CDCl$_3$) δ: 8.81 (s, 1H), 8.39 (d, J=2.15 Hz, 1H), 8.09 (d, J=1.37 Hz, 1H), 8.00 (dd, J=2.05, 8.31 Hz, 1H), 7.65 (d, J=8.02 Hz, 1H), 7.19 (d, J=39.71 Hz, 1H), 5.28 (d, J=53.99 Hz, 1H), 4.04 (s, 3H), 3.51-3.99 (m, 6H), 2.18-2.49 (m, 3H), 1.87 (s, 3H), 1.53 (dd, J=5.67, 9.78 Hz, 1H), 0.63 (br. s., 1H). $^{19}$F NMR (376 MHz, CDCl$_3$) δ: −124.79 (s, 1F), −177.70 (s, 1F).

Synthesis of Intermediate 31

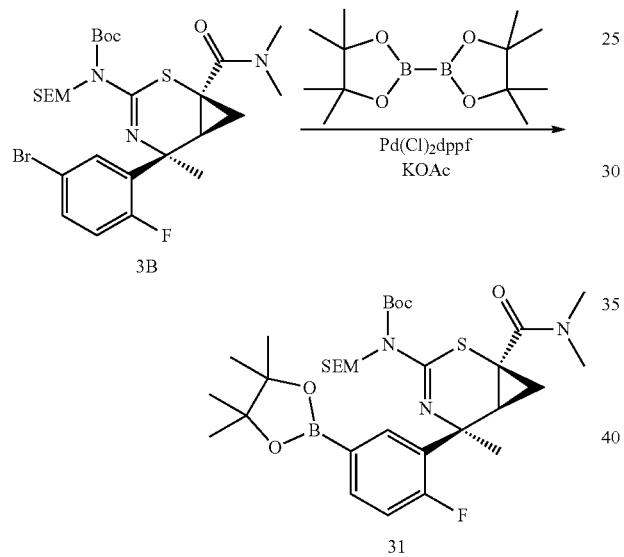

A mixture of tert-butyl ((1S,5S,6S)-5-(5-bromo-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (3B) (957 mg, 1.55 mmol), (1,1′-bis(diphenylphosphino)ferrocene)dichloropalladium(ii) (114 mg, 0.155 mmol), bis(pinacolato) diboron (591 mg, 2.33 mmol), and potassium acetate (0.291 mL, 4.66 mmol) in dioxane (10 mL) was placed under argon atmosphere and heated at 90° C. for 5 hours. The mixture was then cooled to room temperature. The mixture was concentrated and then suspended in 1:1 EtOAc/heptane. After stirring for 10 minutes, the suspension was filtered through a pad of Celite® brand filter aid. The Celite® brand filter aid was then washed with 1:1 EtOAc/heptane and then the filtrate was concentrated to give tert-butyl ((1S,5S,6S)-1-(dimethylcarbamoyl)-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (31) as a dark red oil (assume 100% mass recovery), which was used without further purification. LCMS (ESI+) m/z=664.2 (M+H).

Preparation (1S,5S,6S)-3-amino-5-(5-((Z)-2-(5-chloropyridin-2-yl)-1-fluorovinyl)-2-fluorophenyl)-N,N,5-trimethyl-2-thia-4-azabicyclo[4.1.0]hept-3-ene-1-carboxamide (Example 185)

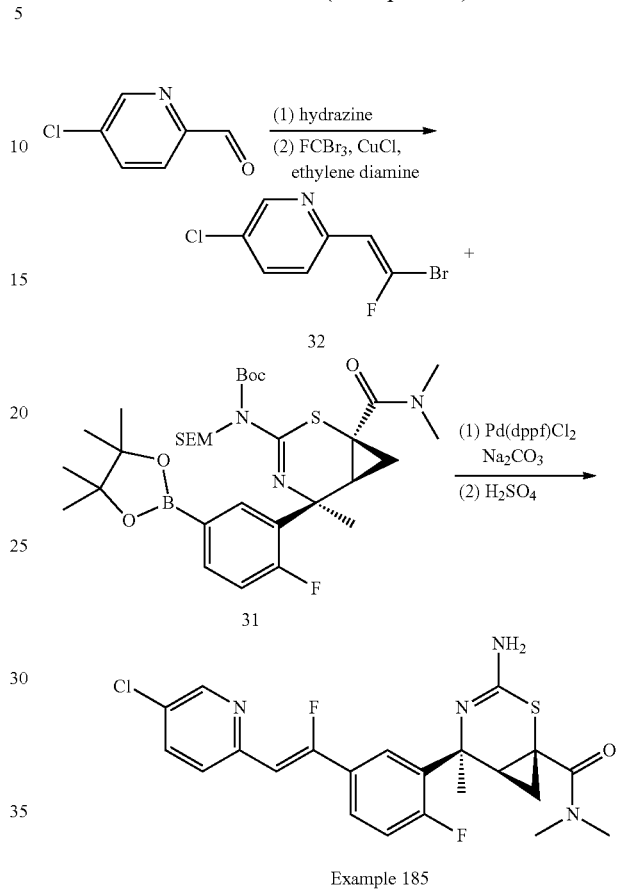

Example 185

Preparation of (E)-2-(2-bromo-2-fluorovinyl)-5-chloropyridine (32)

To a solution of hydrazine (0.050 mL, 2.2 mmol) in EtOH (5 mL) was added a solution of 5-chloro-2-pyridinecarbaldehyde (0.30 g, 2.2 mmol) in EtOH (5 mL) in drops. The mixture was stirred at room temperature overnight. The reaction mixture was then cooled in an ice bath. Ethylendiamine (0.22 mL, 3.3 mmol) and copper chloride (3.0 mg, 0.030 mmol) were added. To the resulting brown mixture was added tribromofluoromethane (0.35 mL, 3.57 mmol) in drops (5 minutes). After the addition, the cooling bath was removed and the mixture was stirred at room temperature for 1 h. EtOAc (50 mL) was added and the mixture was washed with aqueous ammonia (5%, 20 mL). The organic layer was further washed with saturated NaHCO$_3$ (5 mL), brine (5 mL), dried over Na$_2$SO$_4$, filtered, and concentrated. The residue was purified by chromatography on silica using EtOAc in heptane (0-10%) as eluent to give the product 32 as a clear oil (2.5:1 mixture of E-/Z-isomers based on $^1$H NMR integrations of the two isomers). Upon standing, the product formed white crystals (0.25 g, 50% yield). LCMS (ESI, pos.): calcd for C$_7$H$_4$BrClFN: 234.9/236.9; found: 235.9/237.9 (M+1). $^1$H NMR (400 MHz, CDCl$_3$): E-isomer: δ ppm 8.57 (d, J=2.2 Hz, 1H), 7.63-7.70 (m, 1H), 7.56-7.61 (d, J=9.4 Hz, 1H), 6.78 (d, J=14.9 Hz, 1H). $^{19}$F NMR (376 MHz, CDCl$_3$ δ ppm −59.90 (s, 1F). $^1$H NMR (400 MHz, CDCl₃) Z-isomer: δ ppm 8.52 (d, J=2.2 Hz, 1H), 7.63-7.70 (m, 1H), 7.53 (d, J=8.6 Hz, 1H), 6.26 (d, J=33.5 Hz, 1H). $^{19}$F NMR (376 MHz, CDCl₃) δ ppm −62.16 (s, 1F).

Preparation (1S,5S,6S)-3-amino-5-(5-((Z)-2-(5-chloropyridin-2-yl)-1-fluorovinyl)-2-fluorophenyl)-N,N,5-trimethyl-2-thia-4-azabicyclo[4.1.0]hept-3-ene-1-carboxamide (Example 185)

A mixture of 2-(2-bromo-2-fluorovinyl)-5-chloropyridine (Z/E ~2.5:1) (32) (40 mg, 0.169 mmol), tert-butyl ((1S,5S,6S)-1-(dimethylcarbamoyl)-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (31) (110 mg, 0.166 mmol), 1,1'-bis(diphenylphosphino)ferrocene palladium(II)dichloride dichloromethane adduct (12 mg, 0.015 mmol), and sodium carbonate (78 mg, 0.74 mmol) in dioxane/water=2:1 (3 mL) was degassed with a stream of Ar for 2 minutes before it was heated at 85° C. for 2 hours. The mixture was dried over Na₂SO₄ and filtered. The residue was concentrated and was purified by silica gel chromatography (10 to 35% EtOAc/heptane gradient) providing the intermediate (65 mg, 55% yield) as a light yellow foam (~4:1 mixture of olefin isomers).

The intermediate was dissolved in IPA (2 mL) and was treated with a solution prepared from addition of sulfuric acid (65.2 μL, 1.224 mmol) in water (2 mL). The mixture was heated at 65° C. for 2 hours and was purified by reverse-phase preparative HPLC (Gilson GX281) using a Phenomenex Gemini column, 5 micron, C18, 110 Å, 150×30 mm, 0.1% TFA in CH₃CN/H₂O, gradient 10% to 95% over 9 min. The product fractions were passed through a Phenomenex Strata-X-C 33 t cation exchange resin (1 g/12 mL). The resin was washed with MeOH (4×1 mL) and then eluted with NH₃ (2N) in MeOH (total 4×1 mL) to release the product fraction which, after concentration and lyophilizing (MeCN-water), afforded (1S,5S,6S)-3-amino-5-(5-((Z)-2-(5-chloropyridin-2-yl)-1-fluorovinyl)-2-fluorophenyl)-N,N,5-trimethyl-2-thia-4-azabicyclo[4.1.0]hept-3-ene-1-carboxamide as a white powder (Example 185) (25 mg, 32%). LCMS (ESI, pos.): calcd for C₂₂H₂₁ClF₂N₄OS: 462.1; found: 463.1 (M+1). $^1$H NMR (400 MHz, CDCl₃) δ ppm 8.53 (d, J=2.3 Hz, 1H), 7.90 (dd, J=7.4, 2.3 Hz, 1H), 7.86 (d, J=8.6 Hz, 1H), 7.67 (dd, J=8.6, 2.5 Hz, 1H), 7.55 (ddd, J=8.4, 4.5, 2.5 Hz, 1H), 7.11 (dd, J=11.3, 8.6 Hz, 1H), 6.53 (d, J=37.4 Hz, 1H), 3.07 (br. s., 6H), 2.31-2.40 (m, 1H), 1.85 (d, J=1.0 Hz, 3H), 1.33 (dd, J=9.6, 5.7 Hz, 1H), 0.89 (t, J=6.4 Hz, 1H). $^{19}$F NMR (376 MHz, CDCl₃) δ ppm −107.55 (s, 1F), −108.43 (s, 1F).

Synthesis of Intermediate 33

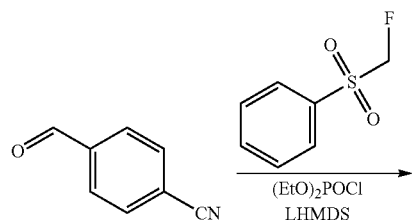

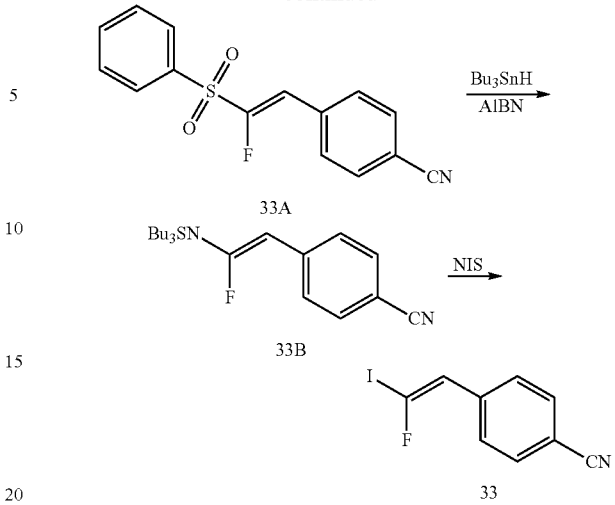

Preparation of (E)-4-(2-fluoro-2-(phenylsulfonyl)vinyl)benzonitrile (33A)

To a RBF (250 mL) was added fluoromethyl phenyl sulfone (1300 mg, 7.4 mmol) (azotroped with toluene) and diethyl chlorophosphate (1080 μl, 7.44 mmol) and dry THF (30 mL) under N₂. This was cooled to −70° C. in dry ice/acetone bath. A lithium bis(trimethylsilyl)amide, 1.0M solution in THF (1.64 ml, 16.4 mmol) was added dropwise and then the reaction was stirred at −70° C. for 1 hour. A solution of 4-formylbenzonitrile (650 mg, 4.96 mmol) (azeotroped with toluene) in 10 mL of dry THF was added dropwise. LCMS and TLC showed formation of desired product, but some starting material remained. The dry-ice bath was removed and the reaction was stirred at room temperature for 5 minutes, quenched with sat NH₄Cl, extracted with EtOAc, dried and evaporated. Flash column purification (DCM) gave (E)-4-(2-fluoro-2-(phenylsulfonyl)vinyl)benzonitrile (33A) (1.05 g, 74% yield) as a white solid. $^1$H NMR (300 MHz, CDCl₃) δ 8.02 (d, J=7.31 Hz, 2H), 7.59-7.73 (m, 7H), 6.98-7.15 (m, 1H).

Preparation of (E)-4-(2-fluoro-2-(tributylstannyl)vinyl)benzonitrile (33B)

A mixture of (E)-4-(2-fluoro-2-(phenylsulfonyl)vinyl)benzonitrile (33A) (650 mg, 2.26 mmol), tributylstannane (1320 mg, 4.52 mmol), and 2,2'-azobis(2-methylpropionitrile) (37.1 mg, 0.226 mmol) in 6 mL of dioxane was sealed and heated at 80° C. for 1.5 hours. TLC showed complete conversion to a less polar product. After cooling to room temperature, the reaction mixture was directly loaded onto a flash column (heptane to DCM/heptane=1:3, then pure DCM) to give (E)-4-(2-fluoro-2-(tributylstannyl)vinyl)benzonitrile (33B) (720 mg, 73% yield) as a colorless oil. $^1$H NMR (300 MHz, CDCl₃) δ 7.59 (s, 4H), 5.53-5.85 (m, 1H), 1.52-1.65 (m, 6H), 1.30-1.42 (m, 6H), 1.00-1.17 (m, 6H), 0.92 (t, J=7.31 Hz, 9H).

Preparation of (E)-4-(2-fluoro-2-iodovinyl)benzonitrile (33)

To a solution of (E)-4-(2-fluoro-2-(tributylstannyl)vinyl)benzonitrile (33B) (380 mg, 0.871 mmol) in 10 mL of DCM at −20° C. was added n-iodosuccinimide (255 mg, 1.13 mmol). The reaction was stirred and gradually warmed to 0° C. 0.5 mL of sat. NaHCO$_3$ was added. The reaction mixture was then directly loaded to flash column (heptane to DCM/heptane=1:3 to 1:1) to give (E)-4-(2-fluoro-2-iodovinyl)benzonitrile (33) (210 mg, 88% yield) as a colorless oil. LCMS (ESI$^+$) m/z=274 (M+H). $^1$H NMR (400 MHz, CDCl$_3$) δ 7.62 (d, J=8.41 Hz, 2H), 7.49 (d, J=8.41 Hz, 2H), 6.18-6.35 (m, 1H). $^{19}$F NMR (376 MHz, CDCl$_3$) δ −57.03 (s, 1F).

Preparation of (1S,5S,6S)-3-amino-5-(5-((Z)-2-(4-cyanophenyl)-1-fluorovinyl)-2-fluorophenyl)-N,N,5-trimethyl-2-thia-4-azabicyclo[4.1.0]hept-3-ene-1-carboxamide (Example 186)

The product obtained above was treated with 4-methylbenzenesulfonic acid hydrate (43.0 mg, 0.23 mmol) in 1 mL of dioxane at 80° C. for 2 hours. After cooling, the reaction mixture was directly loaded onto a flash column (DCM to DCM/MeOH=50:1 to 20:1) to give (1S,5S,6S)-3-amino-5-(5-((Z)-2-(4-cyanophenyl)-1-fluorovinyl)-2-fluorophenyl)-N,N,5-trimethyl-2-thia-4-azabicyclo[4.1.0]hept-3-ene-1-carboxamide (Example 186) (20 mg, 59% yield over two steps) as an off-white solid. LCMS (ESI$^+$) m/z=453 (M+H). $^1$H NMR (400 MHz, CDCl$_3$) δ 7.84 (dd, J=2.35, 7.43 Hz, 1H), 7.66-7.72 (m, 2H), 7.60-7.65 (m, 2H), 7.53 (ddd, J=2.45, 4.35, 8.46 Hz, 1H), 7.11 (dd, J=8.61, 11.35 Hz, 1H), 6.17-6.34 (m, 1H), 3.07 (br. s., 6H), 2.30-2.39 (m, 1H), 1.86 (s, 3H), 1.35 (dd, J=5.77, 9.68 Hz, 1H), 0.89 (t, J=6.46 Hz, 1H). $^{19}$F NMR (376 MHz, CDCl$_3$) δ −107.34 (s, 1F), −107.77 (s, 1F).

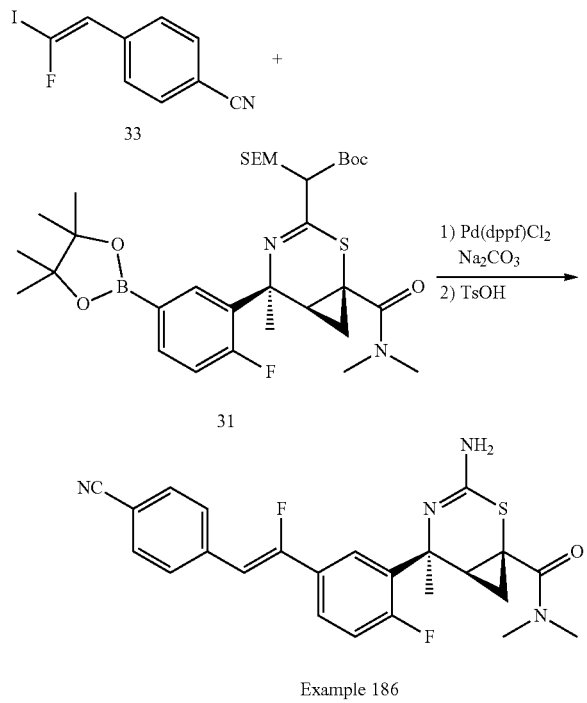

Example 186

Example 186

A mixture of (E)-4-(2-fluoro-2-iodovinyl)benzonitrile (33) (21 mg, 0.075 mmol), tert-butyl ((1S,5S,6S)-1-(dimethylcarbamoyl)-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl) carbamate (31) (50 mg, 0.075 mmol), 1,1'-bis(diphenylphosphino)ferrocene palladium(ii)dichloride dichloromethane adduct (6.15 mg, 7.53 μmol), and sodium carbonate (23.9 mg, 0.226 mmol) in dioxane/water=2:1 (1.5 mL) was heated at 85° C. for 1 hours and then cooled to room temperature. EtOAc was added and the mixture was washed with water, dried (MgSO$_4$), filtered, and concentrated in vacuo to give an oil that was purified by silica gel chromatography (0 to 5% EtOAc/DCM gradient) to give tert-butyl ((1S,5S,6S)-5-(5-((Z)-2-(4-cyanophenyl)-1-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (45 mg, 87% yield) as a light yellow oil.

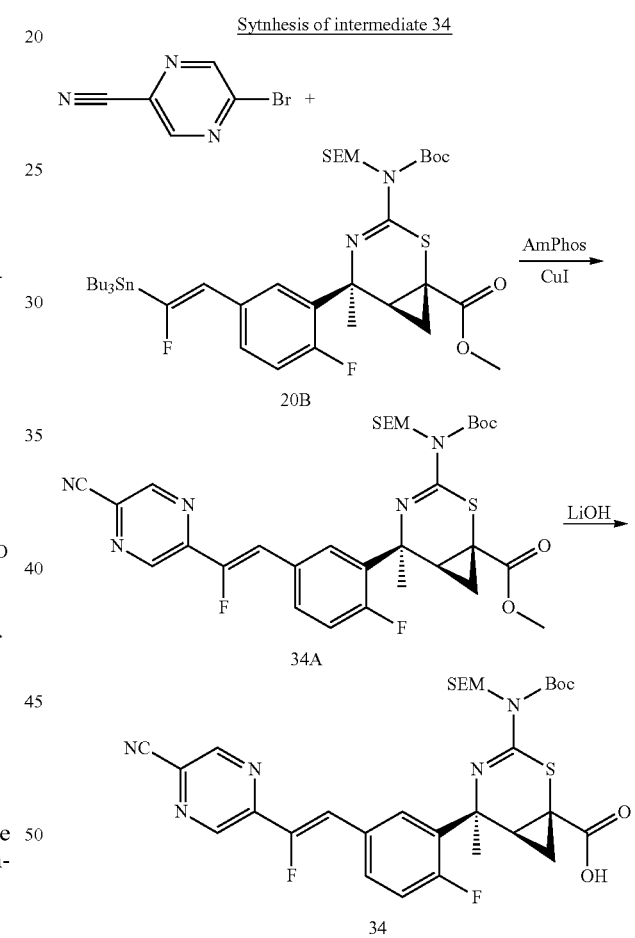

Sytnhesis of intermediate 34

Preparation of (1S,5S,6S)-methyl 3-((tert-butoxycarbonyl)((2-(trimethylsilyl)ethoxy)methyl)amino)-5-(5-((Z)-2-(5-cyanopyrazin-2-yl)-2-fluorovinyl)-2-fluorophenyl)-5-methyl-2-thia-4-azabicyclo[4.1.0]hept-3-ene-1-carboxylate (34A)

A mixture of 2-bromo-5-cyanopyrazine (0.708 g, 3.85 mmol), bis(di-tert-butyl(4-dimethylaminophenyl)phosphine)dichloropalladium(II) (0.064 g, 0.090 mmol) and copper(I) iodide (0.244 g, 1.28 mmol) were suspended in 0.2 mL of DMF. To this was added dropwise (1S,5S,6S)-methyl 3-((tert-butoxycarbonyl)((2-(trimethylsilyl)ethoxy)methyl)amino)-5-(2-fluoro-5-((E)-2-fluoro-2-(tributylstannyl)vinyl)phenyl)-5-methyl-2-thia-4-azabicyclo[4.1.0]hept-3-ene-1-carboxylate (20B) (1.1 g, 1.3 mmol) in 0.2 mL of DMF (followed by rinsing with 1 mL of THF). After stirring for 5 minutes, the reaction was complete. The DMF was evaporated and the residue was loaded to flash column (DCM/heptane=1:1 to DCM to DCM/EtOAc=50:1 to 10:1) to give (1S,5S,6S)-methyl 3-((tert-butoxycarbonyl)((2-(trimethylsilyl)ethoxy)methyl)amino)-5-(5-((Z)-2-(5-cyanopyrazin-2-yl)-2-fluorovinyl)-2-fluorophenyl)-5-methyl-2-thia-4-azabicyclo[4.1.0]hept-3-ene-1-carboxylate (34A) (760 mg, 88% yield) as a light yellow solid. LCMS (ESI+) m/z=672 (M+H).

Preparation of (1S,5S,6S)-3-((tert-butoxycarbonyl)((2-(trimethylsilyl)ethoxy)methyl)amino)-5-(5-((Z)-2-(5-cyanopyrazin-2-yl)-2-fluorovinyl)-2-fluorophenyl)-5-methyl-2-thia-4-azabicyclo[4.1.0]hept-3-ene-1-carboxylic acid (34)

(1S,5S,6S)-Methyl 3-((tert-butoxycarbonyl)((2-(trimethylsilyl)ethoxy)methyl)amino)-5-(5-((Z)-2-(5-cyanopyrazin-2-yl)-2-fluorovinyl)-2-fluorophenyl)-5-methyl-2-thia-4-azabicyclo[4.1.0]hept-3-ene-1-carboxylate (34A) (750 mg, 1.12 mmol) was dissolved in 6 mL THF/2 mL water and was treated with lithium hydroxide hydrate (94 mg, 2.2 mmol). The reaction was stirred at room temperature for 2 hours. Some over-hydrolyzed product was observed (M+1=676) by LCMS. The organic solvent was removed in vacuo and the residue was diluted with water and pH adjusted to pH=4 with 1N HCl. The residue was extracted with DCM 3 times, dried and evaporated to give (1S,5S,6S)-3-((tert-butoxycarbonyl)((2-(trimethylsilyl)ethoxy)methyl)amino)-5-(5-((Z)-2-(5-cyanopyrazin-2-yl)-2-fluorovinyl)-2-fluorophenyl)-5-methyl-2-thia-4-azabicyclo[4.1.0]hept-3-ene-1-carboxylic acid (34) (750 mg, 100% yield) as a light greenish solid. LCMS (ESI+) m/z=658 (M+H).

Preparation of 5-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)pyrazine-2-carbonitrile (Example 200)

To a solution of crude (1S,5S,6S)-3-((tert-butoxycarbonyl)((2-(trimethylsilyl)ethoxy)methyl)amino)-5-(5-((Z)-2-(5-cyanopyrazin-2-yl)-2-fluorovinyl)-2-fluorophenyl)-5-methyl-2-thia-4-azabicyclo[4.1.0]hept-3-ene-1-carboxylic acid (34) (50 mg, 0.076 mmol) and morpholine (19.9 µl, 0.228 mmol) in 0.5 mL of DMF was added HATU (43.4 mg, 0.114 mmol) followed by diisopropylethylamine (39.7 µl, 0.228 mmol). After stirring for 1 hour, most of the solvent was removed under reduced pressure and the residue was loaded to flash column (DCM to DCM/EA=100:6 to 100:10 to 100:20) to give tert-butyl ((1S,5S,6S)-5-(5-((Z)-2-(5-cyanopyrazin-2-yl)-2-fluorovinyl)-2-fluorophenyl)-5-methyl-1-(morpholine-4-carbonyl)-2-thia-4-azabicyclo[4.1.0]hept-3-en-3-yl)((2-(trimethylsilyl)ethoxy)methyl)carbamate as a gum. LCMS (ESI+) m/z=727.3 (M+H). This intermediate was dissolved in 0.5 mL of dioxane and was treated with 4-methylbenzenesulfonic acid hydrate (28.9 mg, 0.152 mmol). After stirred at 80° C. for 2 hours, the reaction mixture was directly loaded to flash column (DCM/MeOH=100:3 to 100:5 to 100:8) to give 5-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)pyrazine-2-carbonitrile (Example 200) (17 mg, 0.034 mmol, 45% yield) as a light-yellow solid. LCMS (ESI+) m/z=497 (M+H). $^1$H NMR (300 MHz, CHLOROFORM-d) δ 8.94 (s, 1H), 8.82 (s, 1H), 7.85 (dd, J=2.27, 7.67 Hz, 1H), 7.69 (ddd, J=2.27, 4.64, 8.44 Hz, 1H), 7.16-7.33 (m, 1H), 7.12 (dd, J=8.48, 11.55 Hz, 1H), 3.69 (br. s., 8H), 2.28-2.39 (m, 1H), 1.85 (d, J=1.02 Hz, 3H), 1.36 (dd, J=5.70, 9.65 Hz, 1H), 0.86-0.92 (m, 1H). $^{19}$F NMR (282 MHz, CHLOROFORM-d) δ −107.07 (s, 1F), −128.22 (s, 1F).

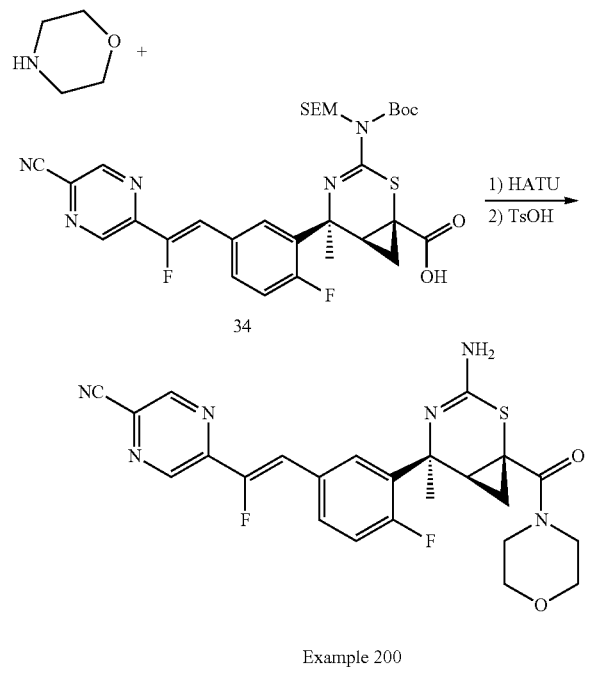

Example 200

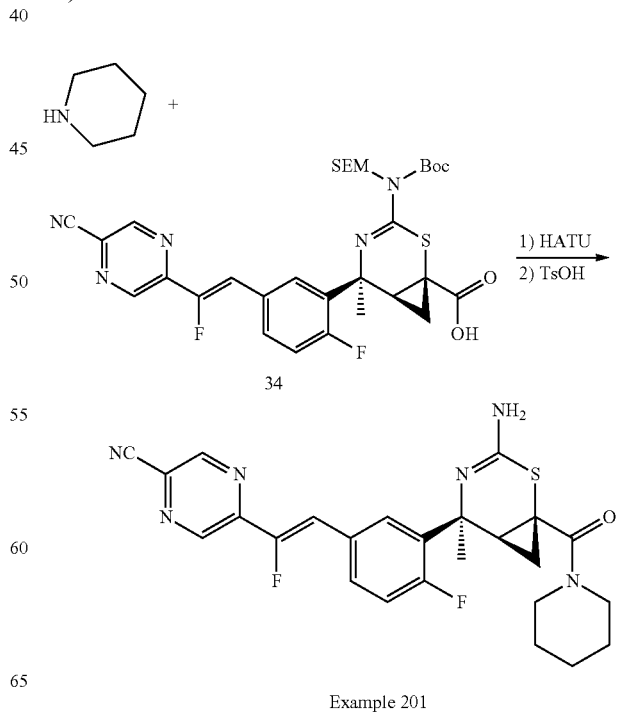

Example 201

Preparation of 5-((Z)-2-(3-((1S,5S,6S)-3-amino-5-methyl-1-(piperidine-1-carbonyl)-2-thia-4-azabicyclo[4.1.0]hept-3-en-5-yl)-4-fluorophenyl)-1-fluorovinyl)pyrazine-2-carbonitrile (Example 201)

Using a procedure similar to that described for Example 200, (1S,5S,6S)-3-((tert-butoxycarbonyl)((2-(trimethylsilyl)ethoxy)methyl)amino)-5-(5-((Z)-2-(5-cyanopyrazin-2-yl)-2-fluorovinyl)-2-fluorophenyl)-5-methyl-2-thia-4-azabicyclo[4.1.0]hept-3-ene-1-carboxylic acid (34) (50 mg, 0.076 mmol), piperidine (22.5 µl, 0.228 mmol), HATU (43.4 mg, 0.114 mmol) and diisopropylethylamine (39.7 µl, 0.228 mmol) were combined to provide the coupling product, which after deprotection with 4-methylbenzenesulfonic acid hydrate (28.9 mg, 0.152 mmol) gave 5-((Z)-2-(3-((1S,5S,6S)-3-amino-5-methyl-1-(piperidine-1-carbonyl)-2-thia-4-azabicyclo[4.1.0]hept-3-en-5-yl)-4-fluorophenyl)-1-fluorovinyl)pyrazine-2-carbonitrile (Example 201) (17 mg, 45% yield) as a light-yellow solid. LCMS (ESI+) m/z=495.2 (M+H). $^1$H NMR (300 MHz, CHLOROFORM-d) δ 8.94 (t, J=1.24 Hz, 1H), 8.80-8.84 (m, 1H), 7.84 (dd, J=2.27, 7.82 Hz, 1H), 7.69 (ddd, J=2.27, 4.60, 8.48 Hz, 1H), 7.17-7.36 (m, 1H), 7.11 (dd, J=8.48, 11.55 Hz, 1H), 3.58 (br. s., 4H), 2.31 (ddd, J=1.32, 7.34, 9.61 Hz, 1H), 1.86 (d, J=1.17 Hz, 3H), 1.56-1.64 (m, 6H), 1.35 (dd, J=5.70, 9.65 Hz, 1H), 0.84-0.90 (m, 1H). $^{19}$F NMR (282 MHz, CHLOROFORM-d) δ –106.95 (s, 1F), –128.28 (s, 1F).

2-fluorovinyl)-2-fluorophenyl)-5-methyl-2-thia-4-azabicyclo[4.1.0]hept-3-ene-1-carboxylic acid (34) (50 mg, 0.076 mmol), (R)-(–)-3-fluoropyrrolidine hydrochloride (28.6 mg, 0.228 mmol), HATU (43.4 mg, 0.114 mmol) and diisopropylethylamine (39.7 µl, 0.228 mmol) were combined to provide the coupling product, which after deprotection with 4-methylbenzenesulfonic acid hydrate (28.9 mg, 0.152 mmol) gave 5-((Z)-2-(3-((1S,5S,6S)-3-amino-1-((S)-3-fluoropyrrolidine-1-carbonyl)-5-methyl-2-thia-4-azabicyclo[4.1.0]hept-3-en-5-yl)-4-fluorophenyl)-1-fluorovinyl)pyrazine-2-carbonitrile (Example 202), (19 mg, 50% yield) as a light-yellow solid. LCMS (ESI+) m/z=499 (M+H). $^1$H NMR (300 MHz, CHLOROFORM-d) δ 8.93 (t, J=1.24 Hz, 1H), 8.82 (d, J=1.17 Hz, 1H), 7.74-7.82 (m, 1H), 7.68 (ddd, J=2.34, 4.60, 8.40 Hz, 1H), 7.16-7.33 (m, 1H), 7.11 (dd, J=8.48, 11.55 Hz, 1H), 5.15-5.45 (m, 1H), 3.73-3.97 (m, 4H), 2.21-2.51 (m, 2H), 2.13-2.21 (m, 1H), 1.88 (d, J=0.88 Hz, 3H), 1.58 (dd, J=5.70, 9.65 Hz, 1H), 0.78 (br. s., 1H). $^{19}$F NMR (282 MHz, CHLOROFORM-d) δ –106.76 (s, 1F), –128.17 (s, 1F), –177.70 (s, 1F).

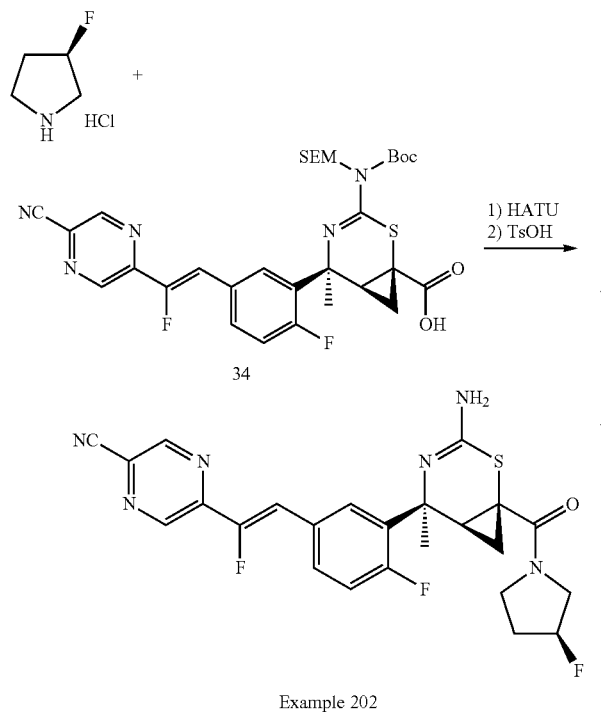

Example 202

Preparation of 5-((Z)-2-(3-((1S,5S,6S)-3-amino-1-((S)-3-fluoropyrrolidine-1-carbonyl)-5-methyl-2-thia-4-azabicyclo[4.1.0]hept-3-en-5-yl)-4-fluorophenyl)-1-fluorovinyl)pyrazine-2-carbonitrile (Example 202)

Using a procedure similar to that described for Example 200, (1S,5S,6S)-3-((tert-butoxycarbonyl)((2-(trimethylsilyl)ethoxy)methyl)amino)-5-(5-((Z)-2-(5-cyanopyrazin-2-yl)-

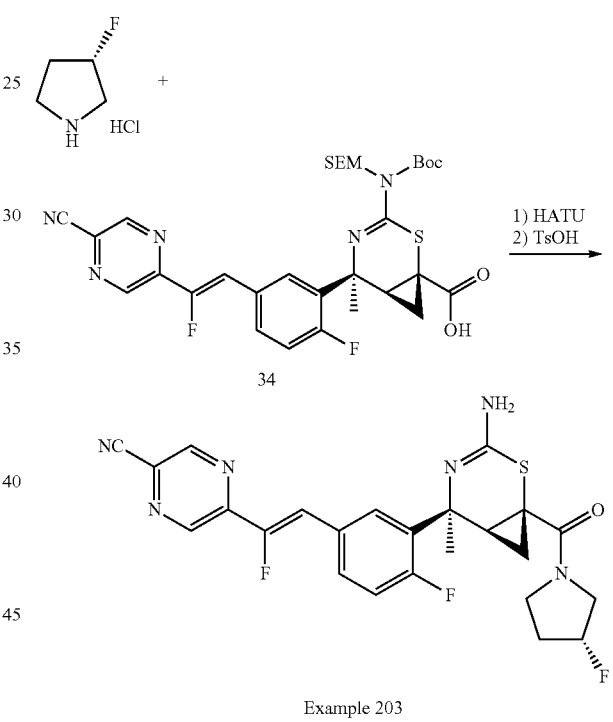

Example 203

Preparation of 5-((Z)-2-(3-((1S,5S,6S)-3-amino-1-((R)-3-fluoropyrrolidine-1-carbonyl)-5-methyl-2-thia-4-azabicyclo[4.1.0]hept-3-en-5-yl)-4-fluorophenyl)-1-fluorovinyl)pyrazine-2-carbonitrile (Example 203)

Using a procedure similar to that described for Example 200, (1S,5S,6S)-3-((tert-butoxycarbonyl)((2-(trimethylsilyl)ethoxy)methyl)amino)-5-(5-((Z)-2-(5-cyanopyrazin-2-yl)-2-fluorovinyl)-2-fluorophenyl)-5-methyl-2-thia-4-azabicyclo[4.1.0]hept-3-ene-1-carboxylic acid (34) (50 mg, 0.076 mmol), (S)-(–)-3-fluoropyrrolidine hydrochloride (28.6 mg, 0.228 mmol), HATU (43.4 mg, 0.114 mmol) and diisopropylethylamine (39.7 µl, 0.228 mmol) were combined to provide the coupling product, which after deprotection with 4-methylbenzenesulfonic acid hydrate (28.9 mg, 0.152 mmol) gave 5-((Z)-2-(3-((1S,5S,6S)-3-amino-1-((R)-3-fluoropyrrolidine-1-carbonyl)-5-methyl-2-thia-4-azabicyclo[4.1.0]hept-3-en-5-yl)-4-fluorophenyl)-1-fluorovinyl)pyrazine-2-carbonitrile (Example 203) (18 mg, 48% yield) as a light-yellow solid. LCMS (ESI⁺) m/z=499 (M+H). ¹H NMR (300 MHz, CHLOROFORM-d) δ 8.93 (s, 1H), 8.82 (s, 1H), 7.80 (dd, J=1.97, 7.67 Hz, 1H), 7.68 (ddd, J=2.34, 4.64, 8.51 Hz, 1H), 7.16-7.32 (m, 1H), 7.11 (dd, J=8.48, 11.55 Hz, 1H), 5.14-5.42 (m, 1H), 3.74-4.09 (m, 4H), 2.19-2.48 (m, 3H), 1.87 (d, J=0.88 Hz, 3H), 1.40 (dd, J=5.63, 9.72 Hz, 1H), 0.87 (t, J=6.14 Hz, 1H).

fluorovinyl)pyrazine-2-carbonitrile (Example 204) (17 mg, 39% yield) as a light-yellow solid. LCMS (ESI⁺) m/z=481 (M+H). ¹H NMR (300 MHz, CHLOROFORM-d) δ 8.93 (s, 1H), 8.82 (s, 1H), 7.80 (dd, J=2.19, 7.75 Hz, 1H), 7.68 (ddd, J=2.27, 4.60, 8.48 Hz, 1H), 7.16-7.33 (m, 1H), 7.11 (dd, J=8.48, 11.55 Hz, 1H), 3.63-3.67 (m, 2H), 3.42-3.53 (m, 2H), 2.22-2.35 (m, 1H), 1.90 (br. s., 4H), 1.87 (d, J=1.17 Hz, 3H), 1.45 (dd, J=5.70, 9.65 Hz, 1H), 0.81 (t, J=6.21 Hz, 1H). ¹⁹F NMR (282 MHz, CHLOROFORM-d) δ −106.81 (s, 1F), −128.23 (s, 1F).

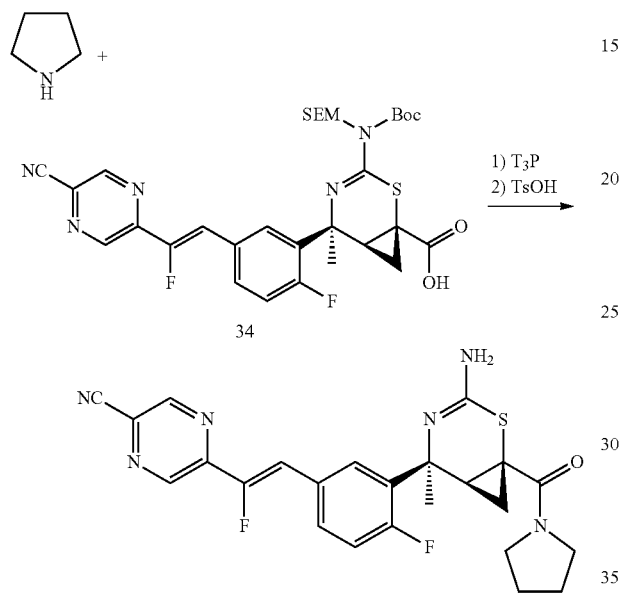

Example 204

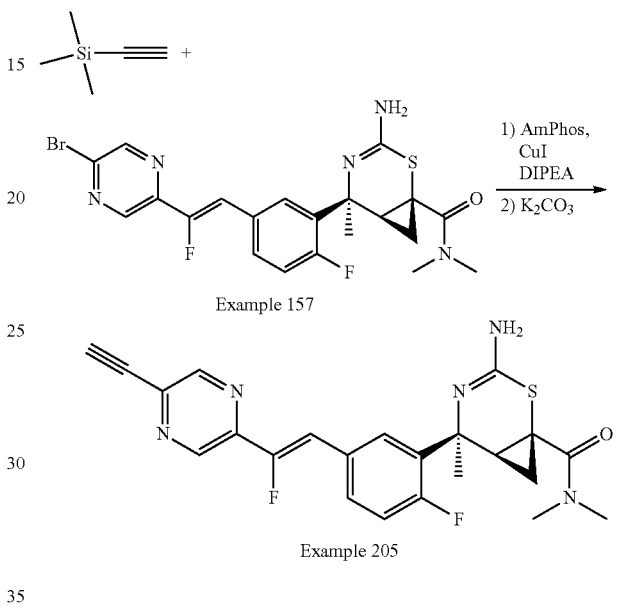

Example 157

Example 205

Preparation of 5-((Z)-2-(3-((1S,5S,6S)-3-amino-5-methyl-1-(pyrrolidine-1-carbonyl)-2-thia-4-azabicyclo[4.1.0]hept-3-en-5-yl)-4-fluorophenyl)-1-fluorovinyl)pyrazine-2-carbonitrile (Example 204)

To a solution of crude (1S,5S,6S)-3-((tert-butoxycarbonyl)((2-(trimethylsilyl)ethoxy)methyl)amino)-5-(5-((Z)-2-(5-cyanopyrazin-2-yl)-2-fluorovinyl)-2-fluorophenyl)-5-methyl-2-thia-4-azabicyclo[4.1.0]hept-3-ene-1-carboxylic acid (34) 60 mg, 0.091 mmol) and pyrrolidine (22.9 µl, 0.274 mmol) in 0.5 mL of DCM was added 1-propanephosphonic acid cyclic anhydride (174 µl, 0.274 mmol). After stirring for 5 hours, LCMS indicated the formation of the desired product. Most of the solvent was removed under reduced pressure and the residue was loaded to flash column (DCM to DCM/EtOAc=100:4 to 100:8 to 100:10 to 100:20) to give tert-butyl ((1S,5S,6S)-5-(5-((Z)-2-(5-cyanopyrazin-2-yl)-2-fluorovinyl)-2-fluorophenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate. LCMS (ESI⁺) m/z=711.2 (M+H).

This intermediate was dissolved in 0.5 mL of dioxane was treated 4-methylbenzenesulfonic acid hydrate (34.7 mg, 0.182 mmol). After stirring at 80° C. for 2 hours, the reaction mixture was directly loaded to flash column (DCM/MeOH=100:3 to 100:5 to 100:8) to give 5-((Z)-2-(3-((1S,5S,6S)-3-amino-5-methyl-1-(pyrrolidine-1-carbonyl)-2-thia-4-azabicyclo[4.1.0]hept-3-en-5-yl)-4-fluorophenyl)-1-

Preparation of (1S,5S,6S)-3-amino-5-(5-((Z)-2-(5-ethynylpyrazin-2-yl)-2-fluorovinyl)-2-fluorophenyl)-N,N,5-trimethyl-2-thia-4-azabicyclo[4.1.0]hept-3-ene-1-carboxamide (Example 205)

(1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (Example 157) (45 mg, 0.089 mmol), copper(I) iodide (1.69 mg, 8.85 µmol), 1,1-bis[di-t-butyl-p-methylaminophenyl]palladium (II) chloride (6.27 mg, 8.85 µmol) and N-ethyl-N-isopropylpropan-2-amine (114 mg, 0.885 mmol) in 0.5 ml dioxane was degassed by bubbling argon for 3 minutes. To this was added (trimethylsilyl)-acetylene (62.5 µl, 0.443 mmol) and the reaction mixture was sealed and heated at 50° C. for 2 hours. The solvent was evaporated and the residue was purified by flash column (DCM to EtOAc to EtOAc/MeOH=100:4 to 100:6 to 100:8 to 10:1) to give (1S,5S,6S)-3-amino-5-(2-fluoro-5-((Z)-2-fluoro-2-(5-((trimethylsilyl)ethynyl)pyrazin-2-yl)vinyl)phenyl)-N,N,5-trimethyl-2-thia-4-azabicyclo[4.1.0]hept-3-ene-1-carboxamide (30 mg, 0.057 mmol, 65% yield) as a yellow solid. LCMS (ESI⁺) m/z=512.2 (M+H).

To a solution of (1S,5S,6S)-3-amino-5-(2-fluoro-5-((Z)-2-fluoro-2-(5-((trimethylsilyl)ethynyl)pyrazin-2-yl)vinyl)phenyl)-N,N,5-trimethyl-2-thia-4-azabicyclo[4.1.0]hept-3-ene-1-carboxamide (30 mg, 0.057 mmol) in 3 mL of MeOH was added anhydrous potassium carbonate (7.9 mg, 0.057 mmol). After stirring at room temperature for 5 minutes, LCMS showed near complete conversion. The reaction was quenched with 1 mL of sat NH₄Cl and the solvent was evaporated. It was diluted with water, extracted with DCM (×3), dried and concentrated. Flash column (DCM/EtOAc=1:3 to EtOAc to EtOAc/MeOH=100:5) gave (1S,5S,6S)-3-amino-5-(5-((Z)-2-(5-ethynylpyrazin-2-yl)-2-fluorovinyl)-2-fluorophenyl)-N,N,5-trimethyl-2-thia-4-azabicyclo[4.1.0]hept-3-ene-1-carboxamide (Example 205) (7.5 mg, 29% yield). LCMS (ESI+) m/z=454 (M+H). ¹H NMR (300 MHz, CHLOROFORM-d) δ 8.82 (s, 1H), 8.64 (s, 1H), 7.77 (dd, J=2.12, 7.82 Hz, 1H), 7.59-7.69 (m, 1H), 7.00-7.18 (m, 2H), 3.42 (s, 1H), 3.06 (br. s., 6H), 2.30 (dd, J=7.75, 9.06 Hz, 1H), 1.88 (s, 3H), 1.39 (dd, J=5.70, 9.79 Hz, 1H), 0.85-0.92 (m, 1H). ¹⁹F NMR (282 MHz, CHLOROFORM-d) δ −108.31 (s, 1F), −127.28 (s, 1F).

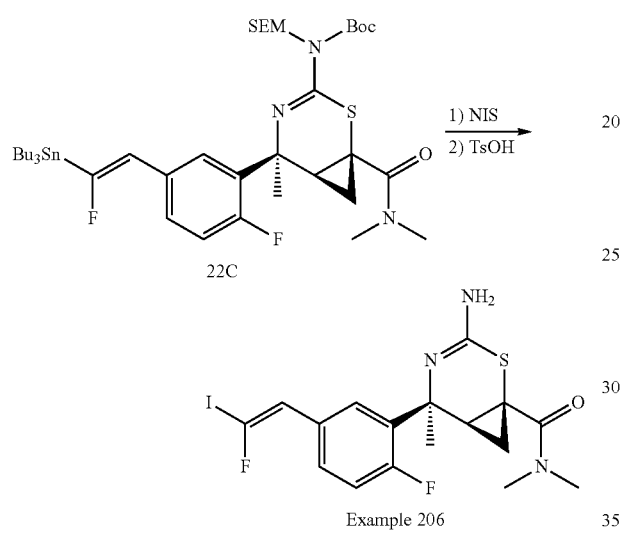

Example 206

Preparation of (1S,5S,6S)-3-amino-5-(2-fluoro-5-((E)-2-fluoro-2-iodovinyl)phenyl)-N,N,5-trimethyl-2-thia-4-azabicyclo[4.1.0]hept-3-ene-1-carboxamide (Example 206)

To a solution of tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (175 mg, 0.201 mmol) in 10 mL of DCM at −20° C. was added n-iodosuccinimide (58.8 mg, 0.261 mmol). The reaction was stirred and gradually warmed to 0° C. 0.5 mL of saturated aq. NaHCO₃ was added. The reaction mixture was directly loaded to flash column (DCM to DCM/EtOAc=20:1 to 10:1 to 5:1) to give tert-butyl ((1S,5S,6S)-1-(dimethylcarbamoyl)-5-(2-fluoro-5-((E)-2-fluoro-2-iodovinyl)phenyl)-5-methyl-2-thia-4-azabicyclo[4.1.0]hept-3-en-3-yl)((2-(trimethylsilyl)ethoxy)methyl)carbamate (120 mg, 84% yield) as a colorless oil.

This intermediate was treated with 4-methylbenzenesulfonic acid hydrate (76 mg, 0.40 mmol) in 1 mL of dioxane at 80° C. for 2 hours. After cooling to room temperature, direct purification by flash column (DCM to DCM/MeOH=20:1) gave (1S,5S,6S)-3-amino-5-(2-fluoro-5-((E)-2-fluoro-2-iodovinyl)phenyl)-N,N,5-trimethyl-2-thia-4-azabicyclo[4.1.0]hept-3-ene-1-carboxamide (Example 206) (80 mg, 83% yield) as a light-yellow gum. LCMS (ESI+) m/z=478 (M+H). ¹H NMR (300 MHz, CHLOROFORM-d) δ 7.29-7.47 (m, 2H), 7.01 (dd, J=8.48, 11.55 Hz, 1H), 6.01-6.31 (m, 1H), 3.05 (br. s., 6H), 2.28 (ddd, J=1.24, 7.27, 9.61 Hz, 1H), 1.85 (d, J=1.32 Hz, 3H), 1.39 (dd, J=5.77, 9.57 Hz, 1H), 0.80-0.90 (m, 1H).

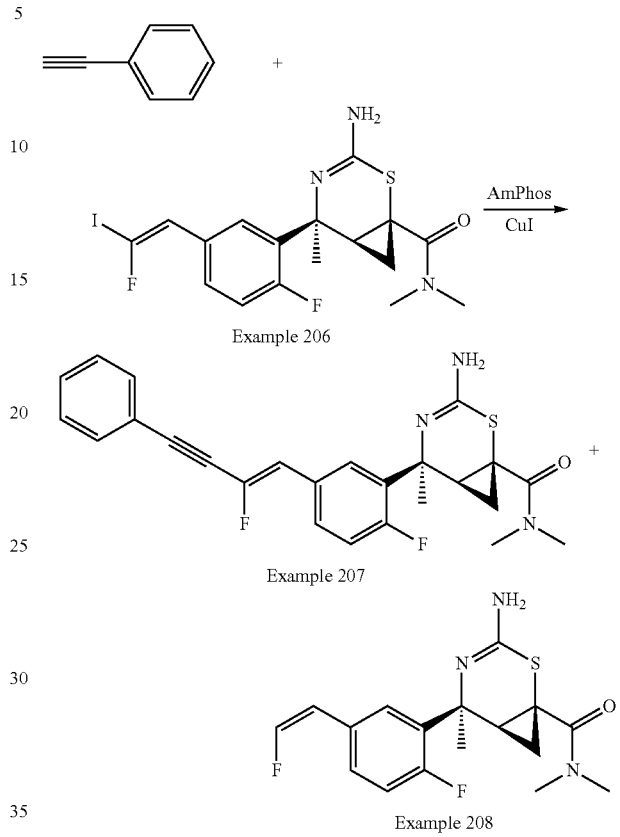

Preparation of (1S,5S,6S)-3-amino-5-(2-fluoro-5-((Z)-2-fluoro-4-phenylbut-1-en-3-yn-1-yl)phenyl)-N,N,5-trimethyl-2-thia-4-azabicyclo[4.1.0]hept-3-ene-1-carboxamide (Example 207) and (1S,5S,6S)-3-amino-5-(2-fluoro-5-((Z)-2-fluorovinyl)phenyl)-N,N,5-trimethyl-2-thia-4-azabicyclo[4.1.0]hept-3-ene-1-carboxamide (Example 208)

(1S,5S,6S)-3-amino-5-(2-fluoro-5-((E)-2-fluoro-2-iodovinyl)phenyl)-N,N,5-trimethyl-2-thia-4-azabicyclo[4.1.0]hept-3-ene-1-carboxamide (Example 206) (24 mg, 0.050 mmol), copper(I) iodide (0.958 mg, 5.03 μmol), 1,1-bis[di-tert-butyl-p-methylaminophenyl]palladium(II) chloride (3.56 mg, 5.03 μmol) and N-ethyl-N-isopropylpropan-2-amine (65 mg, 0.50 mmol) in 0.5 ml dioxane was degassed by sparging with argon for 3 min. Phenylacetylene (11.1 μl, 0.101 mmol) was added. After stirring at room temperature for 2 hours, the solvent was evaporated the residue was submitted to Prep TLC (EA) to give (1S,5S,6S)-3-amino-5-(2-fluoro-5-((Z)-2-fluoro-4-phenylbut-1-en-3-yn-1-yl)phenyl)-N,N,5-trimethyl-2-thia-4-azabicyclo[4.1.0]hept-3-ene-1-carboxamide (Example 207) (14 mg, 62% yield) as a light yellow solid and (1S,5S,6S)-3-amino-5-(2-fluoro-5-((Z)-2-fluorovinyl)phenyl)-N,N,5-trimethyl-2-thia-4-azabicyclo[4.1.0]hept-3-ene-1-carboxamide (Example 208) (2.4 mg, 14% yield) as an off white solid.

Example 207

LCMS (ESI+) m/z=452 (M+H). ¹H NMR (300 MHz, CHLOROFORM-d) δ 7.46-7.57 (m, 4H), 7.29-7.41 (m, 3H), 7.04 (dd, J=8.33, 11.69 Hz, 1H), 6.00-6.22 (m, 1H), 3.05 (br. s., 6H), 2.29 (dd, J=7.53, 8.55 Hz, 1H), 1.88 (d, J=1.02 Hz, 3H), 1.42 (dd, J=5.85, 9.65 Hz, 1H), 0.87 (t, J=6.36 Hz, 1H). $^{19}$F NMR (282 MHz, CHLOROFORM-d) δ −105.55 (s, 1F), −109.27 (s, 1F).

Example 208

LCMS (ESI$^+$) m/z=352 (M+H). $^1$H NMR (300 MHz, CHLOROFORM-d) δ 7.40-7.58 (m, 2H), 7.02 (dd, J=9.06, 11.84 Hz, 1H), 6.41-6.79 (m, 1H), 5.46-5.71 (m, 1H), 3.07 (d, J=11.40 Hz, 6H), 2.32 (dd, J=7.82, 9.13 Hz, 1H), 1.90 (d, J=1.17 Hz, 3H), 1.45 (dd, J=5.85, 9.65 Hz, 1H), 0.90 (t, J=6.07 Hz, 1H). $^{19}$F NMR (282 MHz, CHLOROFORM-d) δ −110.60 (s, 1F), −123.56 (s, 1F).

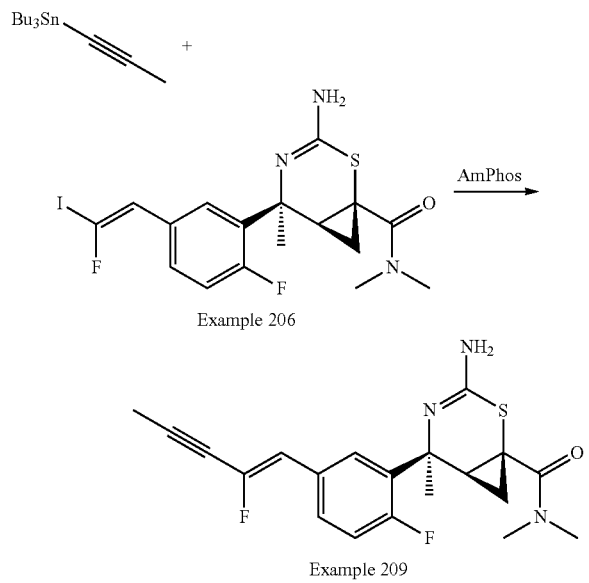

Preparation of (1S,5S,6S)-3-amino-5-(2-fluoro-5-((Z)-2-fluoropent-1-en-3-yn-1-yl)phenyl)-N,N,5-trimethyl-2-thia-4-azabicyclo[4.1.0]hept-3-ene-1-carboxamide (Example 209)

(1S,5S,6S)-3-amino-5-(2-fluoro-5-((E)-2-fluoro-2-iodovinyl)phenyl)-N,N,5-trimethyl-2-thia-4-azabicyclo[4.1.0]hept-3-ene-1-carboxamide (22 mg, 0.046 mmol), 1,1-bis[di-t-butyl-p-methylaminophenyl]palladium(II) chloride (3.26 mg, 4.61 μmol) and tributyl(prop-1-yn-1-yl)stannane (30 mg, 0.092 mmol) in 1 mL of dioxane was stirred under N$_2$ at 60° C. for 0.5 hours. The solvent was evaporated and the residue was purified by flash column (DCM to EtOAc to EA/MeOH=100:3 to 100:6 to 10:1) to give the desired product contaminated with tin reagent. Prep TLC (EtOAc) gave pure (1S,5S,6S)-3-amino-5-(2-fluoro-5-((Z)-2-fluoropent-1-en-3-yn-1-yl)phenyl)-N,N,5-trimethyl-2-thia-4-azabicyclo[4.1.0]hept-3-ene-1-carboxamide (Example 209) (7 mg, 39% yield) as a light-yellow tar. LCMS (ESI$^+$) m/z=390 (M+H). $^1$H NMR (300 MHz, CHLOROFORM-d) δ 7.35-7.49 (m, 2H), 7.01 (dd, J=8.92, 11.69 Hz, 1H), 5.80-5.99 (m, 1H), 3.08 (d, J=13.88 Hz, 6H), 2.29 (dd, J=8.33, 9.65 Hz, 1H), 2.04 (d, J=4.82 Hz, 3H), 1.88 (d, J=1.17 Hz, 3H), 1.42 (dd, J=5.85, 9.65 Hz, 1H), 0.87 (t, J=6.07 Hz, 1H). $^{19}$F NMR (282 MHz, CHLOROFORM-d) δ −103.67 (s, 1F), −109.98 (s, 1F).

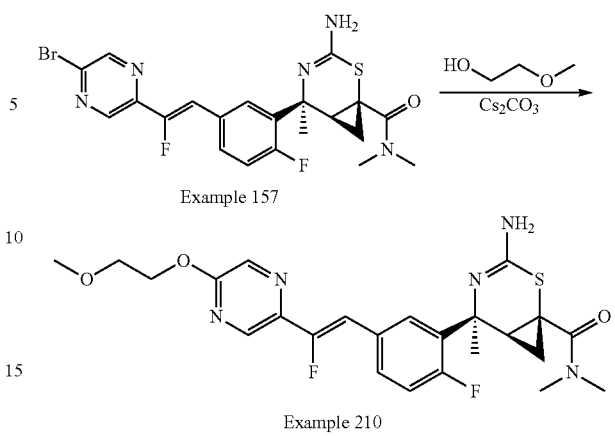

Preparation of (1S,5S,6S)-3-amino-5-(2-fluoro-5-((Z)-2-fluoro-2-(5-(2-methoxyethoxy)pyrazin-2-yl)vinyl)phenyl)-N,N,5-trimethyl-2-thia-4-azabicyclo[4.1.0]hept-3-ene-1-carboxamide (Example 210)

To a mixture of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (Example 157) (30 mg, 0.059 mmol), 2-methoxyethanol (0.070 mL, 0.88 mmol) in THF (0.5 mL) was added cesium carbonate (57.7 mg, 0.177 mmol). The reaction mixture was heated to 60° C. and stirred for 2 hours. LCMS showed clean conversion to the desired product. The solvent was evaporated and the residue was purified by prep TLC (EtOAc/DCM=3:1) to give (1S,5S,6S)-3-amino-5-(2-fluoro-5-((Z)-2-fluoro-2-(5-(2-methoxyethoxy)pyrazin-2-yl)vinyl)phenyl)-N,N,5-trimethyl-2-thia-4-azabicyclo[4.1.0]hept-3-ene-1-carboxamide (Example 210) (5.6 mg, 19% yield) as an off-white solid. LCMS (ESI$^+$) m/z=504 (M+H). $^1$H NMR (400 MHz, CHLOROFORM-d) δ 8.33 (s, 1H), 8.25 (s, 1H), 7.56-7.72 (m, 2H), 7.06 (dd, J=8.41, 11.74 Hz, 1H), 6.72-6.89 (m, 1H), 4.48-4.60 (m, 2H), 3.78 (dd, J=3.81, 5.38 Hz, 2H), 3.46 (s, 3H), 3.06 (br. s., 6H), 2.30 (dd, J=7.92, 9.10 Hz, 1H), 1.90 (s, 3H), 1.43 (dd, J=5.77, 9.68 Hz, 1H), 0.89 (t, J=6.26 Hz, 1H). $^{19}$F NMR (376 MHz, CHLOROFORM-d) δ −109.94 (s, 1F), −125.67 (s, 1F)

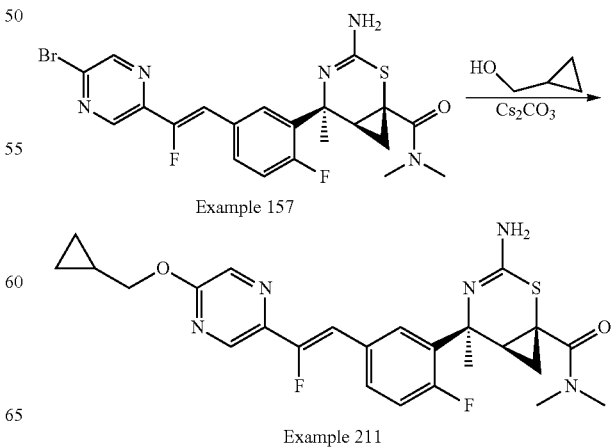

Preparation of (1S,5S,6S)-3-amino-5-(5-((Z)-2-(5-(cyclopropylmethoxy)pyrazin-2-yl)-2-fluorovinyl)-2-fluorophenyl)-N,N,5-trimethyl-2-thia-4-azabicyclo[4.1.0]hept-3-ene-1-carboxamide (Example 211)

Using a procedure similar to that described for Example 210, the combination of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (30 mg, 0.059 mmol), cyclopropylmethanol (64 mg, 0.88 mmol) in THF (0.5 mL) and cesium carbonate (57.7 mg, 0.177 mmol) gave (1S,5S,6S)-3-amino-5-(5-((Z)-2-(5-(cyclopropylmethoxy)pyrazin-2-yl)-2-fluorovinyl)-2-fluorophenyl)-N,N,5-trimethyl-2-thia-4-azabicyclo[4.1.0]hept-3-ene-1-carboxamide (Example 211) (5.5 mg, 19% yield) as a film. LCMS (ESI+) m/z=500 (M+H). $^1$H NMR (400 MHz, CHLOROFORM-d) δ 8.32 (s, 1H), 8.21 (s, 1H), 7.57-7.69 (m, 2H), 7.06 (dd, J=8.41, 11.54 Hz, 1H), 6.71-6.87 (m, 1H), 4.20 (d, J=7.24 Hz, 2H), 3.05 (br. s., 6H), 2.30 (dd, J=8.02, 9.19 Hz, 1H), 1.90 (s, 3H), 1.43 (dd, J=5.77, 9.68 Hz, 1H), 1.29-1.35 (m, 1H), 0.87-0.91 (m, 1H), 0.62-0.70 (m, 2H), 0.35-0.42 (m, 2H). $^{19}$F NMR (376 MHz, CHLOROFORM-d) δ −110.03 (s, 1F), −125.56 (s, 1F).

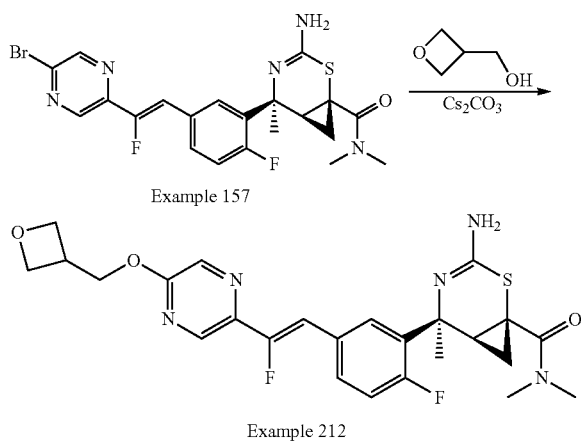

Example 157

Example 212

Preparation of (1S,5S,6S)-3-amino-5-(2-fluoro-5-((Z)-2-fluoro-2-(5-(oxetan-3-ylmethoxy)pyrazin-2-yl)vinyl)phenyl)-N,N,5-trimethyl-2-thia-4-azabicyclo[4.1.0]hept-3-ene-1-carboxamide (Example 212)

Using a procedure similar to that described for Example 210, the combination of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (30 mg, 0.059 mmol), 3-oxetanemethanol (0.071 mL, 0.88 mmol) and cesium carbonate (57.7 mg, 0.177 mmol) gave (1S,5S,6S)-3-amino-5-(2-fluoro-5-((Z)-2-fluoro-2-(5-(oxetan-3-ylmethoxy)pyrazin-2-yl)vinyl)phenyl)-N,N,5-trimethyl-2-thia-4-azabicyclo[4.1.0]hept-3-ene-1-carboxamide (Example 212) (13 mg, 43%) as a film. LCMS (ESI+) m/z=516 (M+H). $^1$H NMR (400 MHz, CHLOROFORM-d) δ 8.34 (s, 1H), 8.20 (s, 1H), 7.72 (dd, J=1.96, 7.82 Hz, 1H), 7.57-7.64 (m, 1H), 7.06 (dd, J=8.51, 11.64 Hz, 1H), 6.72-6.89 (m, 1H), 4.89 (dd, J=6.36, 7.73 Hz, 2H), 4.56-4.65 (m, 4H), 3.48 (td, J=6.97, 13.64 Hz, 1H), 3.05 (br. s., 6H), 2.24-2.32 (m, 1H), 1.87 (s, 3H), 1.38 (dd, J=5.58, 9.68 Hz, 1H), 0.87 (t, J=6.36 Hz, 1H). $^{19}$F NMR (376 MHz, CHLOROFORM-d) δ −109.74 (s, 1F), −125.68 (s, 1F).

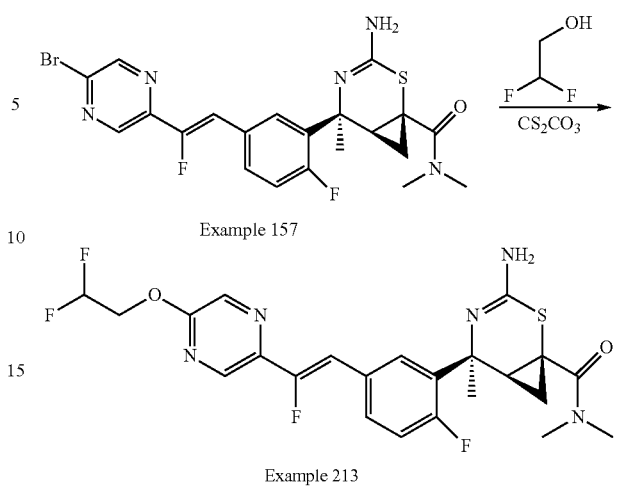

Example 157

Example 213

Preparation of (1S,5S,6S)-3-amino-5-(5-((Z)-2-(5-(2,2-difluoroethoxy)pyrazin-2-yl)-2-fluorovinyl)-2-fluorophenyl)-N,N,5-trimethyl-2-thia-4-azabicyclo[4.1.0]hept-3-ene-1-carboxamide (Example 213)

Using a procedure similar to that described for Example 210, the combination of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (30 mg, 0.059 mmol), 2,2-difluoroethanol (73 mg, 0.88 mmol) and cesium carbonate (57.7 mg, 0.177 mmol) gave (1S,5S,6S)-3-amino-5-(5-((Z)-2-(5-(2,2-difluoroethoxy)pyrazin-2-yl)-2-fluorovinyl)-2-fluorophenyl)-N,N,5-trimethyl-2-thia-4-azabicyclo[4.1.0]hept-3-ene-1-carboxamide (Example 213) (18 mg, 60%) as a film. LCMS (ESI+) m/z=510 (M+H). $^1$H NMR (400 MHz, CHLOROFORM-d) δ 8.34 (s, 1H), 8.28 (s, 1H), 7.69 (dd, J=2.05, 7.73 Hz, 1H), 7.62 (ddd, J=2.35, 4.65, 8.46 Hz, 1H), 7.07 (dd, J=8.51, 11.64 Hz, 1H), 6.77-6.92 (m, 1H), 5.96-6.33 (m, 1H), 4.59 (dt, J=4.11, 13.30 Hz, 2H), 3.06 (br. s., 6H), 2.30 (dd, J=7.82, 9.00 Hz, 1H), 1.89 (s, 3H), 1.42 (dd, J=5.77, 9.68 Hz, 1H), 0.85-0.91 (m, 1H). $^{19}$F NMR (376 MHz, CHLOROFORM-d) δ −109.65 (s, 1F), −125.65 (s, 1F), −125.66 (s, 1F), −125.96 (s, 1F).

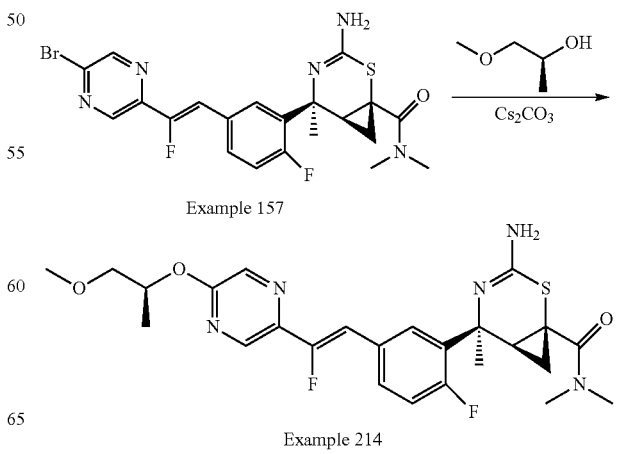

Example 157

Example 214

Preparation of (1S,5S,6S)-3-amino-5-(2-fluoro-5-((Z)-2-fluoro-2-(5-(((S)-1-methoxypropan-2-yl)oxy)pyrazin-2-yl)vinyl)phenyl)-N,N,5-trimethyl-2-thia-4-azabicyclo[4.1.0]hept-3-ene-1-carboxamide (Example 214)

Using a procedure similar to that described for Example 210, the combination of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (30 mg, 0.059 mmol), (S)-(+)-1-methoxy-2-propanol (0.080 mL, 0.88 mmol) and cesium carbonate (57.7 mg, 0.177 mmol) gave (1S,5S,6S)-3-amino-5-(2-fluoro-5-((Z)-2-fluoro-2-(5-(((S)-1-methoxypropan-2-yl)oxy)pyrazin-2-yl)vinyl)phenyl)-N,N,5-trimethyl-2-thia-4-azabicyclo[4.1.0]hept-3-ene-1-carboxamide (Example 214) (5.2 mg, 17% yield) as a film. LCMS (ESI$^+$) m/z=518 (M+H). $^1$H NMR (400 MHz, CHLOROFORM-d) δ 8.33 (s, 1H), 8.19 (s, 1H), 7.57-7.71 (m, 2H), 7.06 (dd, J=8.41, 11.54 Hz, 1H), 6.70-6.86 (m, 1H), 5.43 (dt, J=3.91, 6.26 Hz, 1H), 3.54-3.66 (m, 2H), 3.41 (s, 3H), 3.01 (br. s., 6H), 2.31 (dd, J=7.82, 9.19 Hz, 1H), 1.91 (s, 3H), 1.45 (dd, J=5.87, 9.59 Hz, 1H), 1.37 (d, J=6.46 Hz, 3H), 0.90 (t, J=6.55 Hz, 1H). $^{19}$F NMR (376 MHz, CHLOROFORM-d) δ −109.93 (s, 1F), −125.51 (s, 1F).

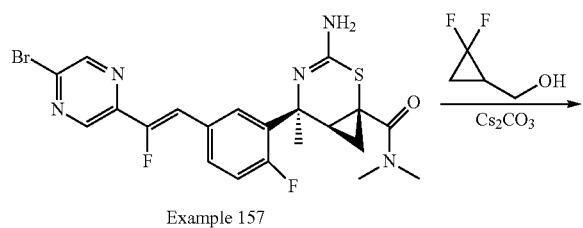

Example 157

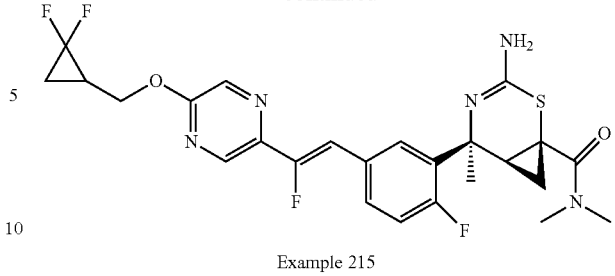

Example 215

Preparation of (1S,5S,6S)-3-amino-5-(5-((Z)-2-(5-((2,2-difluorocyclopropyl)methoxy)pyrazin-2-yl)-2-fluorovinyl)-2-fluorophenyl)-N,N,5-trimethyl-2-thia-4-azabicyclo[4.1.0]hept-3-ene-1-carboxamide (Example 215)

Using a procedure similar to that described for Example 210, the combination of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (30 mg, 0.059 mmol), (2,2-difluorocyclopropyl)methanol (64 mg, 0.590 mmol) and cesium carbonate (57.7 mg, 0.177 mmol) gave (1S,5S,6S)-3-amino-5-(5-((Z)-2-(5-((2,2-difluorocyclopropyl)methoxy)pyrazin-2-yl)-2-fluorovinyl)-2-fluorophenyl)-N,N,5-trimethyl-2-thia-4-azabicyclo[4.1.0]hept-3-ene-1-carboxamide (Example 215) (8 mg, 25% yield) as a film. LCMS (ESI$^+$) m/z=536 (M+H). $^1$H NMR (400 MHz, CHLOROFORM-d) δ 8.33 (s, 1H), 8.22 (s, 1H), 7.68 (dd, J=1.96, 7.82 Hz, 1H), 7.56-7.65 (m, 1H), 7.07 (dd, J=8.41, 11.74 Hz, 1H), 6.73-6.89 (m, 1H), 4.34-4.55 (m, 2H), 3.05 (br. s., 6H), 2.30 (dd, J=7.92, 9.29 Hz, 1H), 2.10-2.22 (m, 1H), 1.89 (s, 3H), 1.54-1.66 (m, 1H), 1.42 (dd, J=5.77, 9.68 Hz, 1H), 1.28-1.36 (m, 1H), 0.89 (t, J=6.36 Hz, 1H). $^{19}$F NMR (376 MHz, CHLOROFORM-d) δ −109.90 (s, 1F), −125.75 (s, 1F), −129.1 (d, J$_{F-F}$=157.92 Hz, 1F), 143.23 (d, J$_{F-F}$=161.68 Hz, 1F).

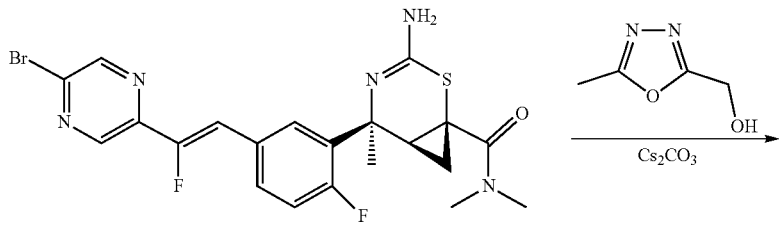

Example 157

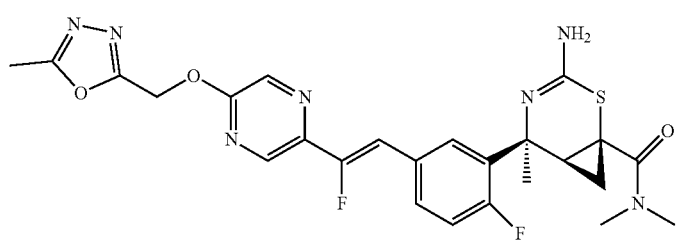

Example 216

Preparation of (1S,5S,6S)-3-amino-5-(2-fluoro-5-((Z)-2-fluoro-2-(5-((5-methyl-1,3,4-oxadiazol-2-yl)methoxy)pyrazin-2-yl)vinyl)phenyl)-N,N,5-trimethyl-2-thia-4-azabicyclo[4.1.0]hept-3-ene-1-carboxamide (Example 216)

Using a procedure similar to that described for Example 210, the combination of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (30 mg, 0.059 mmol), (5-methyl-1,3,4-oxadiazol-2-yl)methanol (67 mg, 0.59 mmol) and cesium carbonate (57.7 mg, 0.177 mmol) gave (1S,5S,6S)-3-amino-5-(2-fluoro-5-((Z)-2-fluoro-2-(5-((5-methyl-1,3,4-oxadiazol-2-yl)methoxy)pyrazin-2-yl)vinyl)phenyl)-N,N,5-trimethyl-2-thia-4-azabicyclo[4.1.0]hept-3-ene-1-carboxamide (Example 216) (17 mg, 53% yield) as a film. LCMS (ESI$^+$) m/z=542 (M+H). $^1$H NMR (400 MHz, CHLOROFORM-d) δ 8.37 (s, 1H), 8.30 (s, 1H), 7.70 (dd, J=2.15, 7.82 Hz, 1H), 7.56-7.65 (m, 1H), 7.07 (dd, J=8.51, 11.64 Hz, 1H), 6.74-6.95 (m, 1H), 5.60 (s, 2H), 2.91-3.22 (m, 6H), 2.58 (s, 3H), 2.26-2.35 (m, 1H), 1.89 (s, 3H), 1.40 (dd, J=5.77, 9.68 Hz, 1H), 0.89 (t, J=6.36 Hz, 1H). $^{19}$F NMR (376 MHz, CHLOROFORM-d) δ −109.68 (s, 1F), −126.00 (s, 1F).

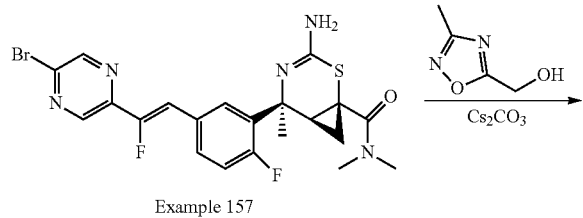

Example 157

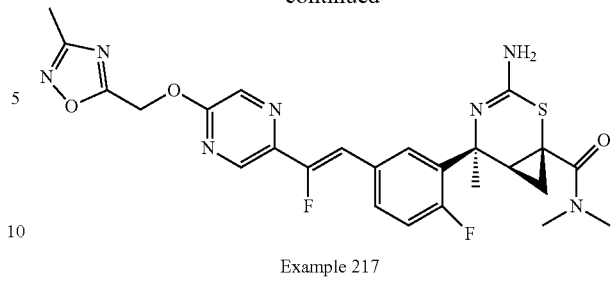

Example 217

Preparation of (1S,5S,6S)-3-amino-5-(2-fluoro-5-((Z)-2-fluoro-2-(5-((3-methyl-1,2,4-oxadiazol-5-yl)methoxy)pyrazin-2-yl)vinyl)phenyl)-N,N,5-trimethyl-2-thia-4-azabicyclo[4.1.0]hept-3-ene-1-carboxamide (Example 217)

Using a procedure similar to that described for Example 210, the combination of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (30 mg, 0.059 mmol), (3-methyl-1,2,4-oxadiazol-5-yl)methanol (67.3 mg, 0.590 mmol) and cesium carbonate (57.7 mg, 0.177 mmol) gave (1S,5S,6S)-3-amino-5-(2-fluoro-5-((Z)-2-fluoro-2-(5-((3-methyl-1,2,4-oxadiazol-5-yl)methoxy)pyrazin-2-yl)vinyl)phenyl)-N,N,5-trimethyl-2-thia-4-azabicyclo[4.1.0]hept-3-ene-1-carboxamide (Example 217) (9 mg, 28%) as a film. LCMS (ESI$^+$) m/z=542 (M+H). $^1$H NMR (400 MHz, CHLOROFORM-d) δ 8.37 (s, 1H), 8.32 (s, 1H), 7.59-7.69 (m, 2H), 7.08 (dd, J=8.70, 11.44 Hz, 1H), 6.75-6.92 (m, 1H), 5.54 (s, 2H), 3.05 (br. s., 6H), 2.63 (s, 3H), 2.29-2.38 (m, 1H), 1.92 (s, 3H), 1.46 (dd, J=5.87, 9.78 Hz, 1H), 0.91 (t, J=6.36 Hz, 1H).

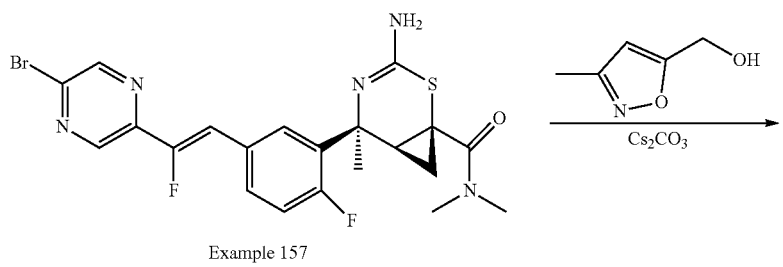

Example 157

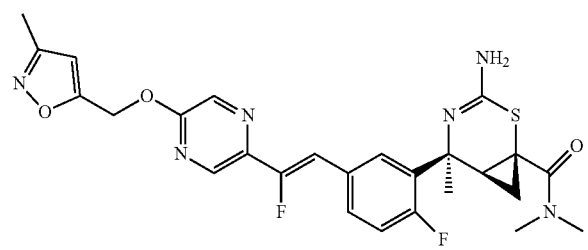

Example 218

Preparation of (1S,5S,6S)-3-amino-5-(2-fluoro-5-((Z)-2-fluoro-2-(5-((3-methylisoxazol-5-yl)methoxy)pyrazin-2-yl)vinyl)phenyl)-N,N,5-trimethyl-2-thia-4-azabicyclo[4.1.0]hept-3-ene-1-carboxamide (Example 218)

Using a procedure similar to that described for Example 210, the combination of (1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide (30 mg, 0.059 mmol), (3-methyl-1,2-oxazol-5-yl)methanol (0.056 mL, 0.59 mmol) and cesium carbonate (57.7 mg, 0.177 mmol) gave (1S,5S,6S)-3-amino-5-(2-fluoro-5-((Z)-2-fluoro-2-(5-((3-methylisoxazol-5-yl)methoxy)pyrazin-2-yl)vinyl)phenyl)-N,N,5-trimethyl-2-thia-4-azabicyclo[4.1.0]hept-3-ene-1-carboxamide (Example 218) (17 mg, 53% yield) as a film. LCMS (ESI+) m/z=541 (M+H). $^{1}$H NMR (400 MHz, CHLOROFORM-d) δ 8.37 (s, 1H), 8.26 (s, 1H), 7.69 (dd, J=2.05, 7.73 Hz, 1H), 7.58-7.65 (m, 1H), 7.07 (dd, J=8.51, 11.64 Hz, 1H), 6.77-6.92 (m, 1H), 6.21 (s, 1H), 5.49 (s, 2H), 3.06 (br. s., 6H), 2.32 (s, 3H), 2.27-2.31 (m, 1H), 1.88 (s, 3H), 1.40 (dd, J=5.77, 9.68 Hz, 1H), 0.89 (t, J=6.65 Hz, 1H). $^{19}$F NMR (376 MHz, CHLOROFORM-d) δ −109.80 (s, 1F), −125.95 (s, 1F).

carbamate (22C) (40 mg, 0.046 mmol) in 0.2 mL of DMF (followed by rinsing with 1 mL of THF). After stirring for 5 minutes, the reaction was complete. The DMF was evaporated and the residue was loaded to flash column (DCM/heptane=1:1 to DCM to DCM/EA=50:1 to 10:1) to give tert-butyl ((1S,5S,6S)-5-(5-((Z)-2-(5-cyanothiazol-2-yl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (8 mg, 25% yield) as a light yellow solid. LCMS (ESI+) m/z=685 (M+H). This intermediate was treated with 4-methylbenzenesulfonic acid hydrate (8.7 mg, 0.046 mmol) in 1 mL of dioxane at 80° C. for 2 hours. After cooling, it was directly loaded to flash column (DCM/MeOH=100:4 to 100:6 to 100:8 to 100:10) to give (1S,5S,6S)-3-amino-5-(5-((Z)-2-(5-cyanothiazol-2-yl)-2-fluorovinyl)-2-fluorophenyl)-N,N,5-trimethyl-2-thia-4-azabicyclo[4.1.0]hept-3-ene-1-carboxamide (Example 219) (2.4 mg, 11% yield) as a light yellow solid. LCMS (ESI+) m/z=460 (M+H). $^{1}$H NMR (400 MHz, CHLOROFORM-d) δ 8.26 (d, J=3.52 Hz, 1H), 7.74 (d, J=7.82 Hz, 1H), 7.57-7.68 (m, 1H), 6.97-7.18 (m, 2H), 2.82-3.29 (m, 6H), 2.30-2.35 (m, 1H), 1.89 (s, 3H), 1.42 (dd, J=5.97, 9.68 Hz, 1H), 0.86-0.90 (m, 1H). $^{19}$F NMR (376 MHz, CHLOROFORM-d) δ −106.56 (s, 1F), −116.45 (s, 1F).

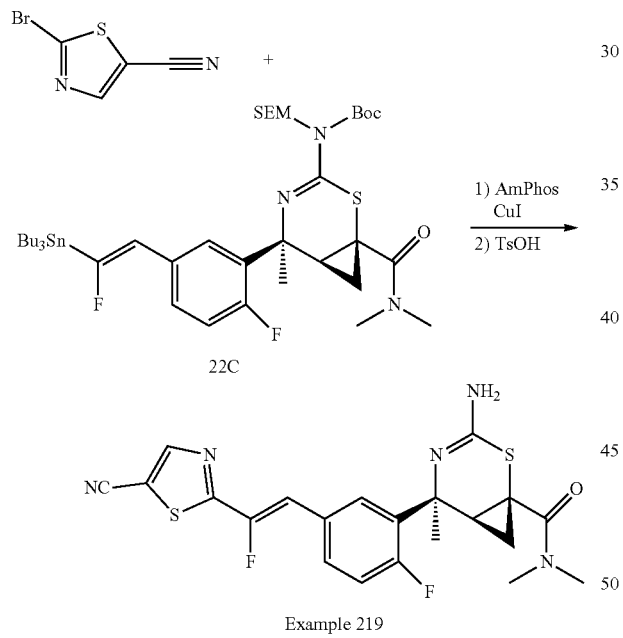

Example 219

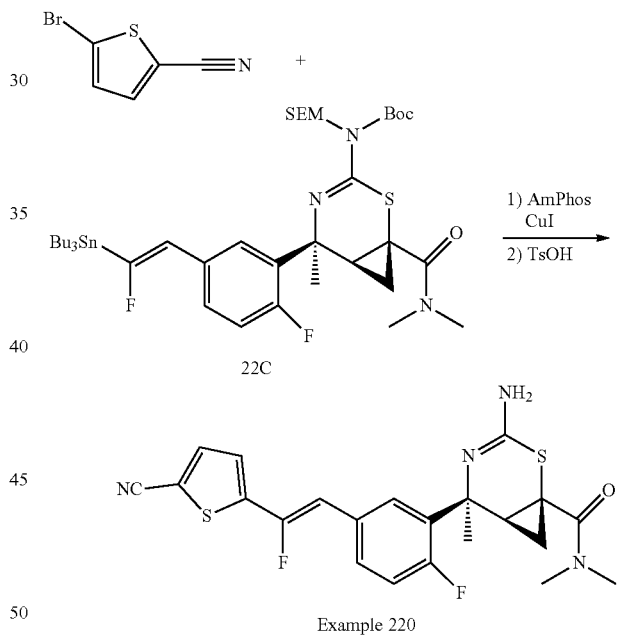

Example 220

Preparation of (1S,5S,6S)-3-amino-5-(5-((Z)-2-(5-cyanothiazol-2-yl)-2-fluorovinyl)-2-fluorophenyl)-N,N,5-trimethyl-2-thia-4-azabicyclo[4.1.0]hept-3-ene-1-carboxamide (Example 219)

A mixture of 2-bromo-5-cyanothiazole (26.0 mg, 0.138 mmol), bis(di-tert-butyl(4-dimethylaminophenyl)phosphine)dichloropalladium(II) (3.25 mg, 4.59 µmol) and copper(I) iodide (8.75 mg, 0.046 mmol) were suspended in 0.2 mL of DMF. To this was added dropwise tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)

Preparation of (1S,5S,6S)-3-amino-5-(5-((Z)-2-(5-cyanothiophen-2-yl)-2-fluorovinyl)-2-fluorophenyl)-N,N,5-trimethyl-2-thia-4-azabicyclo[4.1.0]hept-3-ene-1-carboxamide (Example 220)

Using a procedure similar to that described for Example 219, 5-bromothiophene-2-carbonitrile (25.9 µl, 0.138 mmol), bis(di-tert-butyl(4-dimethylaminophenyl)phosphine) dichloropalladium(II) (3.25 mg, 4.59 µmol), copper (I) iodide (8.75 mg, 0.046 mmol) and tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl) carbamate (40 mg, 0.046 mmol) were combined to give the coupling product, which after deprotection with 4-methyl-benzenesulfonic acid hydrate (8.7 mg, 0.046 mmol) gave (1S,5S,6S)-3-amino-5-(5-((Z)-2-(5-cyanothiophen-2-yl)-2-fluorovinyl)-2-fluorophenyl)-N,N,5-trimethyl-2-thia-4-azabicyclo[4.1.0]hept-3-ene-1-carboxamide (Example 220) (5.7 mg, 27% yield) as a light yellow solid. LCMS (ESI+) m/z=459 (M+H). $^1$H NMR (400 MHz, CHLOROFORM-d) δ 7.63 (d, J=7.63 Hz, 1H), 7.51-7.59 (m, 2H), 7.24 (d, J=4.11 Hz, 1H), 7.07 (dd, J=8.61, 11.54 Hz, 1H), 6.17-6.34 (m, 1H), 2.97-3.20 (m, 6H), 2.28-2.34 (m, 1H), 1.87 (s, 3H), 1.40 (dd, J=5.87, 9.59 Hz, 1H), 0.88 (t, J=6.55 Hz, 1H). $^{19}$F NMR (376 MHz, CHLOROFORM-d) δ −108.66 (s, 1F), −110.16 (s, 1F).

Synthesis of Intermediate 35

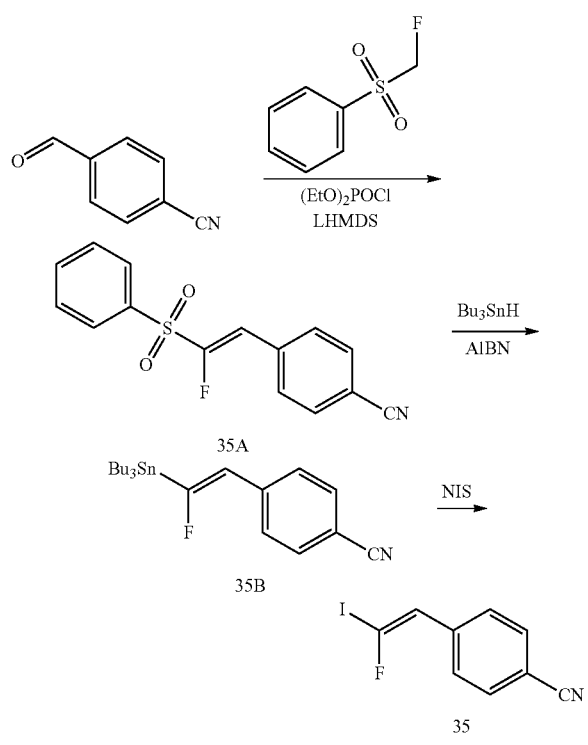

Preparation of (E)-4-(2-fluoro-2-(phenylsulfonyl)vinyl)benzonitrile (35A)

To a RBF (250 mL) was added fluoromethyl phenyl sulfone (1295 mg, 7.440 mmol) (azotroped with toluene) and diethyl chlorophosphate (1077 μl, 7.440 mmol) and dry THF (30 mL) under N$_2$. This was cooled to −70° C. in dry ice/acetone bath. A lithium bis(trimethylsilyl)amide, 1.0M solution in THF (1.64 ml, 16.4 mmol) was added dropwise and then the reaction was stirred at −70° C. for 1 hour. A solution of 4-formylbenzonitrile (650 mg, 4.96 mmol) (azeotroped with toluene) in 10 mL of dry THF was added dropwise. LCMS and TLC showed formation of desired product, while starting material remained. The dry-ice bath was removed and the reaction was stirred at room temperature for 5 minutes, quenched with sat NH$_4$Cl, extracted with ethyl acetate, dried and evaporated. Flash column purification (DCM) gave (E)-4-(2-fluoro-2-(phenylsulfonyl)vinyl)benzonitrile (35A) (1.05 g, 74% yield) as a white solid. $^1$H NMR (300 MHz, CHLOROFORM-d) δ 8.02 (d, J=7.31 Hz, 2H), 7.59-7.73 (m, 7H), 6.98-7.15 (m, 1H).

Preparation of (E)-4-(2-fluoro-2-(tributylstannyl)vinyl)benzonitrile (35B)

A mixture of (E)-4-(2-fluoro-2-(phenylsulfonyl)vinyl)benzonitrile (35A) (650 mg, 2.26 mmol), tributylstannane (1320 mg, 4.52 mmol), and 2,2'-azobis(2-methylpropionitrile) (37.1 mg, 0.226 mmol) in 6 mL of dioxane was sealed and heated to 80° C. for 1.5 hours. TLC showed complete conversion to a less polar product. After cooling to room temperature, the reaction mixture was directly loaded to flash column (heptane to DCM/heptane=1:3, then pure DCM) to give (E)-4-(2-fluoro-2-(tributylstannyl)vinyl)benzonitrile (35B) (720 mg, 73% yield) as a colorless oil. $^1$H NMR (300 MHz, CHLOROFORM-d) δ 7.59 (s, 4H), 5.53-5.85 (m, 1H), 1.52-1.65 (m, 6H), 1.30-1.42 (m, 6H), 1.00-1.17 (m, 6H), 0.92 (t, J=7.31 Hz, 9H).

Preparation of (E)-4-(2-fluoro-2-iodovinyl)benzonitrile (35)

To a solution of (E)-4-(2-fluoro-2-(tributylstannyl)vinyl)benzonitrile (35B) (380 mg, 0.871 mmol) in 10 mL of DCM at −20° C. was added n-iodosuccinimide (255 mg, 1.133 mmol). The reaction was stirred and gradually warmed up to 0° C. 0.5 mL of sat. NaHCO$_3$ was added. The reaction mixture was directly loaded to flash column (heptane to DCM/heptane=1:3 to 1:1) to give (E)-4-(2-fluoro-2-iodovinyl)benzonitrile (35) (210 mg, 88% yield) as a colorless oil. LCMS (ESI+) m/z=274 (M+H). $^1$H NMR (400 MHz, CHLOROFORM-d) δ 7.62 (d, J=8.41 Hz, 2H), 7.49 (d, J=8.41 Hz, 2H), 6.18-6.35 (m, 1H). $^{19}$F NMR (376 MHz, CHLOROFORM-d) δ −57.03 (s, 1F).

Synthesis of Intermediate 36

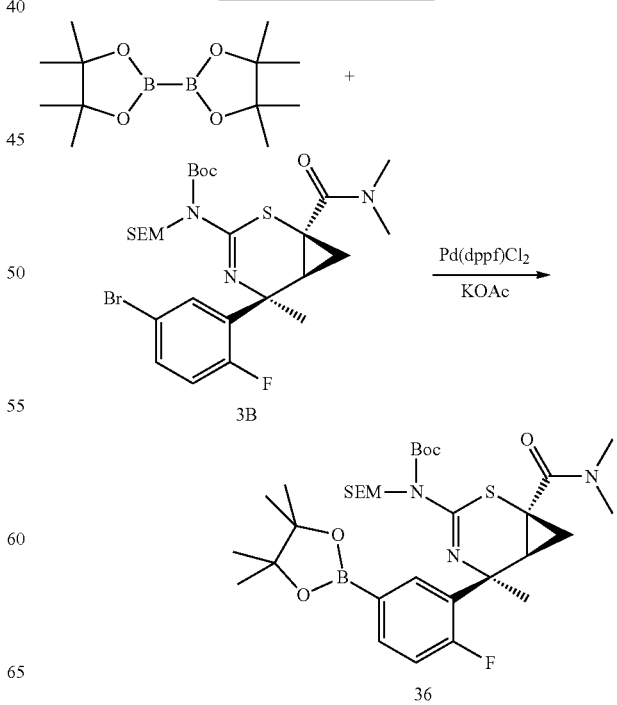

Preparation of tert-butyl ((1S,5S,6S)-1-(dimethyl-carbamoyl)-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (36)

A mixture of tert-butyl ((1S,5S,6S)-5-(5-bromo-2-fluorophenyl)-1-(dimethylcarbamoyl)-5-methyl-2-thia-4-azabicyclo[4.1.0]hept-3-en-3-yl)((2-(trimethylsilyl)ethoxy)methyl) carbamate (3B) (957 mg, 1.55 mmol), (1,1'-bis(diphenylphosphino)ferrocene)dichloropalladium(II) (114 mg, 0.155 mmol), bis(pinacolato) diboron (591 mg, 2.33 mmol), and potassium acetate (457 mg, 4.66 mmol) in dioxane (10 mL) was placed under argon atmosphere and heated to 90° C. for 5 hours, then cooled to room temperature. The mixture was concentrated and then suspended in 1:1 EtOAc/heptane. After stirring for 10 minutes, the suspension was filtered through a pad of celite. The celite was then washed with 1:1 EtOAc/heptane and then the filtrate was concentrated to give of tert-butyl ((1S,5S,6S)-1-(dimethylcarbamoyl)-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (36) as a dark red oil (assume 100% mass recovery), which was taken forward without further purification. LCMS (ESI$^+$) m/z=664 (M+H).

phino)ferrocene palladium(II)dichloride dichloromethane adduct (6.15 mg, 7.53 µmol), and sodium carbonate (24.0 mg, 0.226 mmol) in dioxane/water=2:1 (1.5 mL) was heated to 85° C. for 1 hour, then cooled to room temperature. EtOAc was added and the mixture was washed with water, dried (MgSO$_4$), filtered, and concentrated in vacuo to give an oil that was purified by silica gel chromatography (0 to 5% EtOAc/DCM gradient) to give tert-butyl ((1S,5S,6S)-5-(5-((Z)-2-(4-cyanophenyl)-1-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (45 mg, 87% yield) as a light yellow oil. This was treated with 4-methylbenzenesulfonic acid hydrate (43.0 mg, 0.226 mmol) in 1 mL of dioxane at 80° C. for 2 hours. After cooling, the reaction mixture was directly loaded to flash column (DCM to DCM/MeOH=50:1 to 20:1) to give (1S,5S,6S)-3-amino-5-(5-((Z)-2-(4-cyanophenyl)-1-fluorovinyl)-2-fluorophenyl)-N,N,5-trimethyl-2-thia-4-azabicyclo[4.1.0]hept-3-ene-1-carboxamide (Example 221) (20 mg, 59% yield over two steps) as a off-white solid. LCMS (ESI$^+$) m/z=453 (M+H). $^1$H NMR (400 MHz, CHLOROFORM-d) δ 7.84 (dd, J=2.35, 7.43 Hz, 1H), 7.66-7.72 (m, 2H), 7.60-7.65 (m, 2H), 7.53 (ddd, J=2.45, 4.35, 8.46 Hz, 1H), 7.11 (dd, J=8.61, 11.35 Hz, 1H), 6.17-6.34 (m, 1H), 3.07 (br. s., 6H), 2.30-2.39 (m, 1H), 1.86 (s, 3H), 1.35 (dd, J=5.77, 9.68 Hz, 1H), 0.89 (t, J=6.46 Hz, 1H). $^{19}$F NMR (376 MHz, CHLOROFORM-d) δ −107.34 (s, 1F), −107.77 (s, 1F).

Synthesis of Intermediate 37

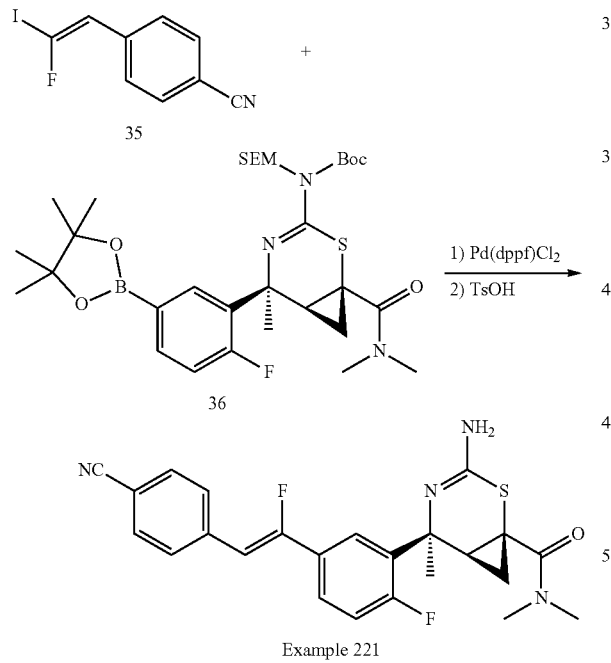

Preparation of (1S,5S,6S)-3-amino-5-(5-((Z)-2-(4-cyanophenyl)-1-fluorovinyl)-2-fluorophenyl)-N,N,5-trimethyl-2-thia-4-azabicyclo[4.1.0]hept-3-ene-1-carboxamide (Example 221)

A mixture of (E)-4-(2-fluoro-2-iodovinyl)benzonitrile (35) (20.57 mg, 0.075 mmol), tert-butyl ((1S,5S,6S)-1-(dimethylcarbamoyl)-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (36) (50 mg, 0.075 mmol), 1,1'-bis(diphenylphos-

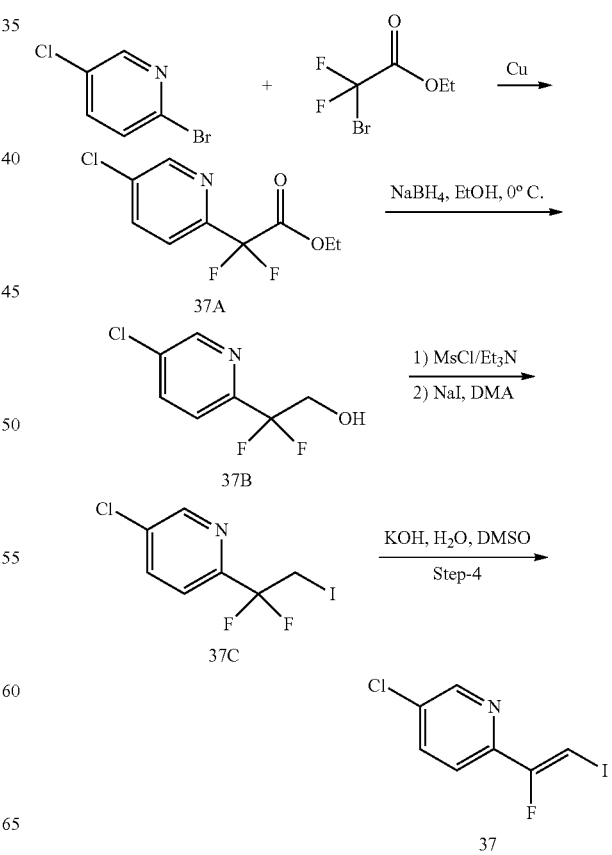

Preparation of ethyl 2-(5-chloropyridin-2-yl)-2,2-difluoroacetate (37A)

Ethyl 2-bromo-2,2-difluoroacetate (105 g, 520 mmol) was added slowly to a suspension of copper powder (66.0 g, 1039 mmol) in dimethyl sulfoxide (1250 mL) under nitrogen atmosphere at ambient temperature. The reaction mixture was stirred at ambient temperature for 1 hour and 2-bromo-5-chloropyridine (50.0 g, 260 mmol) was added in one portion. The reaction mixture was stirred at ambient temperature for 12 hours. The reaction mixture was filtered and the filtrate was partitioned between ethyl acetate (1000 mL) and saturated ammonium chloride (1000 mL) solution. The organic layer was separated and the aqueous layer was extracted with ethyl acetate (2×1000 mL). The combined organic layer was washed with water (2×1000 mL), dried over sodium sulfate and concentrated under reduced pressure to get crude residue which was purified by column chromatography (silica 230-400 mesh, elution 0 to 0-10% ethyl acetate in hexane) to afford ethyl 2-(5-chloropyridin-2-yl)-2,2-difluoroacetate (37A) (60 g, 64% yield) as clear liquid. LCMS (ESI$^+$) m/z=236 (M+H). $^1$H NMR (400 MHz, CHLOROFORM-d) δ 8.63-8.59 (m, 1H), 7.85 (dt, J=8.4, 1.6 Hz, 1H), 7.70 (dt, J=8.4, 0.9 Hz, 1H), 4.11 (q, J=7.1, 1.0 Hz, 2H), 1.26 (t, J=7.1, 1.0 Hz, 3H).

Preparation of 2-(5-chloropyridin-2-yl)-2,2-difluoroethan-1-ol (37B)

To a solution of ethyl 2-(5-chloropyridin-2-yl)-2,2-difluoroacetate (37A) (47.0 g, 199 mmol) in ethanol (600 mL) at 0° C. was added sodium borohydride (7.55 g, 199 mmol) portion-wise. The reaction mixture was stirred at ambient temperature for 1 hour. After completion of the reaction (monitored by TLC), the reaction mixture was quenched with water (500 mL) and concentrated under reduced pressure to give a crude residue. The crude material was diluted with water (500 mL) and extracted with ethyl acetate (2×500 mL). The combined organic extract was dried over sodium sulfate and concentrated under reduced pressure to get the crude material which was purified by column chromatography (silica 60-120 mesh size, mobile phase 0-10% ethyl acetate in hexane), affording 2-(5-chloropyridin-2-yl)-2,2-difluoroethan-1-ol (37B) (35 g, 91% yield) as light yellow solid. LCMS (ESI$^+$) m/z=194 (M+H). $^1$H NMR (400 MHz, CHLOROFORM-d) δ 8.64-8.58 (m, 1H), 7.86 (dd, J=8.4, 2.4 Hz, 1H), 7.70 (dt, J=8.5, 1.5 Hz, 1H), 4.24 (t, J=12.4 Hz, 2H).

Preparation of 5-chloro-2-(1,1-difluoro-2-iodoethyl)pyridine (37C)

To a solution of 2-(5-chloropyridin-2-yl)-2,2-difluoroethan-1-ol (37B) (31 g, 160 mmol) in dichloromethane (500 mL) at 0° C. was added triethylamine (49.1 mL, 352 mmol) followed by dropwise addition of methanesulfonyl chloride (23.71 mL, 304 mmol). The reaction mixture was stirred at ambient temperature for 1 hour. The reaction mixture was diluted with water (500 mL) and extracted with dichloromethane (2×500 mL). The combined organic extracts were washed with brine (250 mL), dried over sodium sulfate and concentrated under reduced pressure to get crude residue. To the solution of crude residue in N,N-dimethyl acetamide (600 mL) was added sodium iodide (96 g, 641 mmol) portion-wise. The reaction mixture was heated at 110° C. for 36 hours. After the completion of reaction (monitored by TLC), the reaction mixture was diluted with water (500 mL) and extracted with ethyl acetate (2×500 mL). The combined organic layer was washed with brine (500 mL), dried over sodium sulfate and concentrated under reduced pressure to get crude residue which was purified by column chromatography (silica 60-120 mesh size, mobile phase 0-10% ethyl acetate in hexane) to afford 5-chloro-2-(1,1-difluoro-2-iodoethyl)pyridine (37C) (30 g, 60% yield) as brown solid. LCMS (ESI$^+$) m/z=304 (M+H). $^1$H NMR (400 MHz, CHLOROFORM-d) δ 8.59 (s, 1H), 7.87-7.84 (m, 1H), 7.27 (d, J=2.0 Hz, 1H), 4.27 (t, J=12.4 Hz, 2H).

Preparation of (Z)-5-chloro-2-(1-fluoro-2-iodovinyl)pyridine (37)

To a solution of 5-chloro-2-(1,1-difluoro-2-iodoethyl)pyridine (37C) (30 g, 99 mmol) in dimethyl sulfoxide (50 mL) was added a solution of KOH (19.41 g, 346 mmol) in water (50 mL) dropwise at 0° C. The reaction mixture was stirred at ambient temperature for 10 hours. After the completion of reaction (monitored by TLC and LCMS), the reaction mixture was diluted with water (150 mL) and stirred for 15 minutes. The precipitate thus formed was collected by filtration, washed with water (2×100 mL), and dried to afford (Z)-5-chloro-2-(1-fluoro-2-iodovinyl)pyridine (37) (24.7 g, 87% yield) as white crystalline solid. LCMS (ESI$^+$) m/z=284 (M+H). $^1$H NMR (400 MHz, CHLOROFORM-d) δ 8.54-8.51 (m, 1H), 7.74 (dd, J=8.5, 2.4 Hz, 1H), 7.50 (ddd, J=8.5, 1.8, 0.8 Hz, 1H), 6.94 (d, J=34.3 Hz, 1H).

Synthesis of Intermediate 38

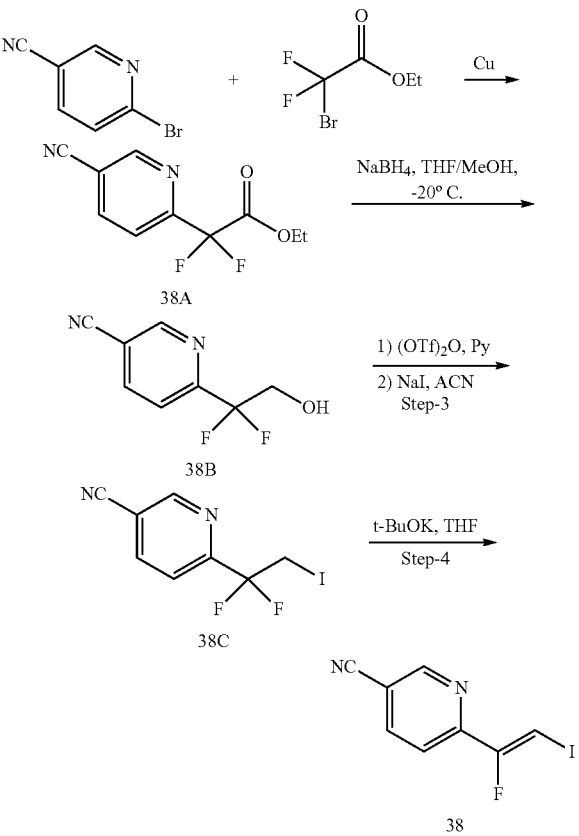

Preparation of ethyl 2-(5-cyanopyridin-2-yl)-2,2-difluoroacetate (38A)

To a suspension of copper powder (344 g, 5464 mmol) in dimethyl sulfoxide (5000 mL) was added ethyl 2-bromo-2,2-difluoroacetate (550 g, 2736 mmol) dropwise under nitrogen atmosphere at ambient temperature. The reaction mixture was stirred at ambient temperature for 1 h and 2-bromo-5-cyanopyridine (250 g, 1366 mmol) was added portion-wise. The reaction mixture was stirred at ambient temperature for 12 hours. The reaction mixture was filtered and the filtrate was partitioned between ethyl acetate (2500 mL) and saturated ammonium chloride (2500 mL) solution. The organic layer was separated and the aqueous layer was extracted with ethyl acetate (2×1000 mL). The combined organic layer was washed with water (2×1000 mL), dried over sodium sulfate and concentrated under reduced pressure to get crude residue which was purified by column chromatography (silica 230-400 mesh, elution 0-10% ethyl acetate in hexane) affording ethyl 2-(5-cyanopyridin-2-yl)-2,2-difluoroacetate (38A) (275 g, 89% yield) as a colorless oil. LCMS (ESI$^+$) m/z=227 (M+H). $^1$H NMR (400 MHz, CHLOROFORM-d) δ 8.93 (d, J=2.0 Hz, 1H), 8.18 (dd, J=8.2, 2.1 Hz, 1H), 7.90 (dd, J=8.1, 1.0 Hz, 1H), 4.39 (q, J=7.1 Hz, 2H), 1.34 (t, J=7.1 Hz, 3H).

Preparation of 6-(1,1-difluoro-2-hydroxyethyl)nicotinonitrile (38B)

To a solution of ethyl 2-(5-cyanopyridin-2-yl)-2,2-difluoroacetate (38A) (92 g, 407 mmol) in tetrahydrofuran (1380 mL, 15 mL/g) was added sodium borohydride (9.23 g, 244 mmol) portion wise at −20° C. The reaction mixture was stirred at −20° C. for 30 minutes and methanol (460 mL, 5 mL/g) was added drop wise at −20° C. The reaction mixture was stirred at −20° C. for 1 hour. After the completion of reaction (monitored by LCMS), the reaction mixture was quenched with water (500 mL) and concentrated under reduced pressure to get crude residue which was diluted with water (500 mL) and extracted with ethyl acetate (2×500 mL). The combined organic extracts were dried over sodium sulfate. Filtration and concentration under reduced pressure, followed by flash chromatography (silica 60-120 mesh size, mobile phase 0-25% ethyl acetate in hexane) afforded 6-(1,1-difluoro-2-hydroxyethyl)nicotinonitrile (38B) (33.0 g, 44%) as light-yellow solid. LCMS (ESI$^+$) m/z=185 (M+H). $^1$H NMR (400 MHz, CHLOROFORM-d) δ 8.97-8.90 (m, 1H), 8.18 (dd, J=8.2, 2.1 Hz, 1H), 7.89 (dd, J=8.3, 0.9 Hz, 1H), 4.29 (t, J=12.4 Hz, 2H).

Preparation of 6-(1,1-difluoro-2-iodoethyl)nicotinonitrile (38C)

To a solution of 6-(1,1-difluoro-2-hydroxyethyl)nicotinonitrile (38B) (99 g, 538 mmol) in acetonitrile (1980 mL) was added pyridine (87 mL, 1075 mmol) followed by dropwise addition of triflouoromethanesulfonic anhydride (100 mL, 591 mmol) at −10° C. under a nitrogen atmosphere. The reaction mixture was stirred at ambient temperature for 5 hours. The reaction mixture was cooled to 0° C. and sodium iodide (242 g, 1613 mmol) was added portion-wise. The reaction mixture was heated at 60° C. for 2 hours. After the completion of reaction (monitored by TLC), the reaction mixture was diluted with water (2000 mL) and extracted with ethyl acetate (3×3000 mL). The combined organic extracts were dried over sodium sulfate and concentrated under reduced pressure to get the crude material, which was purified by column chromatography (silica 60-120 mesh size, mobile phase 0-10% ethyl acetate in hexane) affording 6-(1,1-difluoro-2-iodoethyl)nicotinonitrile (38C) (100 g, 63% yield) as light-yellow solid. LCMS (ESI$^+$) m/z=295 (M+H). $^1$H NMR (400 MHz, CHLOROFORM-d) δ 8.95 (s, 1H), 8.17-8.14 (m, 1H), 7.87-7.85 (d, J=8.0 Hz, 1H), 3.97 (t, J=14.4 Hz, 2H).

Preparation of (Z)-6-(1-fluoro-2-iodovinyl)nicotinonitrile (38)

To a solution of 6-(1,1-difluoro-2-iodoethyl)nicotinonitrile (38C) (100 g, 340 mmol) in tetrahydrofuran (1000 mL) was added potassium tert-butoxide (45.8 g, 408 mmol) portion-wise at 0° C. The reaction mixture was stirred at 0° C. for 2 hours. Upon completion of the reaction, the reaction mixture was diluted with water (500 mL) and extracted with ethyl acetate (3×500 mL). The combined organic extracts were dried over sodium sulfate and concentrated under reduced pressure to get the crude material, which was purified by column chromatography (silica 60-120 mesh size, mobile phase 0-5% ethyl acetate in hexane) affording (Z)-6-(1-fluoro-2-iodovinyl)nicotinonitrile (38) (40 g, 43% yield) as light yellow solid. LCMS (ESI$^+$) m/z=275 (M+H). $^1$H NMR (400 MHz, DMSO-d$_6$) δ 9.04 (dd, J=2.1, 1.0 Hz, 1H), 8.45 (dd, J=8.3, 2.1 Hz, 1H), 7.81 (dt, J=8.3, 1.1 Hz, 1H), 7.42 (d, J=36.4 Hz, 1H).

Synthesis of Intermediate 39

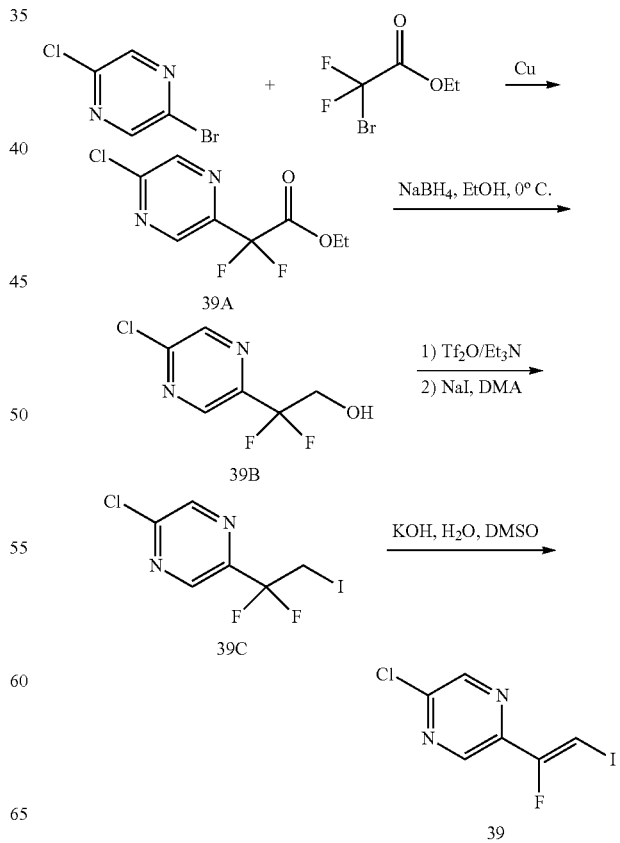

Preparation of ethyl 2-(5-chloropyrazin-2-yl)-2,2-difluoroacetate (39A)

To a suspension of copper powder (244 g, 3877 mmol) in DMSO (5000 mL) was added ethyl 2-bromo-2,2-difluoroacetate (394 g, 1939 mmol) at ambient temperature. The reaction mixture was stirred at ambient temperature for 1 hour. 2-Bromo-5-chloropyrazine (250 g, 1292 mmol) was added to the reaction mixture portion-wise. The reaction mixture was stirred at ambient temperature for 3 hours. After the completion of reaction (monitored by TLC), the reaction mixture was quenched with aq. NH$_4$Cl (2.0 L), filtrate through celite pad and filtrate was extracted with ethyl acetate (2×2 L). The combined organic extracts were dried over sodium sulfate and concentration under reduced pressure to get crude residue, which was purified by column chromatography (60-120 silica mesh, mobile phase 0-2% ethyl acetate in hexane) affording ethyl 2-(5-chloropyrazin-2-yl)-2,2-difluoroacetate (39A) (215 g, 70% yield) as viscous clear liquid. $^1$H NMR (400 MHz, DMSO-d$_6$) δ 9.05 (d, J=1.4 Hz, 1H), 8.98 (dd, J=1.4, 0.7 Hz, 1H), 4.39-4.34 (m, 2H), 1.24 (t, J=7.1 Hz, 3H).

Preparation of 2-(5-chloropyrazin-2-yl)-2,2-difluoroethanol (39B)

To a solution of ethyl 2-(5-chloropyrazin-2-yl)-2,2-difluoroacetate (39A) (215 g, 909 mmol) in ethanol (400 mL, 1.80 mL/g) was added sodium borohydride (34.4 g, 909 mmol) portion-wise at 0° C. The reaction mixture was stirred for 30 minutes at 0° C. After completion of reaction (monitored by TLC), the reaction mixture was quenched with water (200 mL) and concentrated under reduced pressure to give the crude residue. The crude material was diluted with water (750 mL) and extracted with ethyl acetate (2×1.0 L). The combined organic layer was dried over sodium sulfate, concentration under reduced pressure to get crude residue which was purified by column chromatography (60-120 silica mesh, mobile phase 0-10% ethyl acetate in hexane) to afford 2-(5-chloropyrazin-2-yl)-2,2-difluoroethanol (39B) (130 g, 73% yield) as colorless liquid. LCMS (ESI$^+$) m/z=195 (M+H). $^1$H NMR (300 MHz, DMSO-d$_6$) δ 8.97 (dt, J=1.4, 0.7 Hz, 1H), 8.82 (d, J=1.4 Hz, 1H), 5.70 (t, J=6.4 Hz, 1H), 4.01 (td, J=13.8, 6.4 Hz, 2H).

Preparation of 2-chloro-5-(1,1-difluoro-2-iodoethyl)pyrazine (39C)

To a solution of 2-(5-chloropyrazin-2-yl)-2,2-difluoroethanol (39B) (130 g, 668 mmol) in acetonitrile (1300 mL) was added pyridine (54.0 mL, 668 mmol) followed by dropwise addition of triflic anhydride (147 mL, 869 mmol) at below 0° C. The reaction mixture was stirred at 0° C. for 30 minutes. After the consumption of starting material (monitored by TLC), sodium iodide (300 g, 2004 mmol) was added portion-wise to the reaction mixture at ambient temperature. The reaction mixture was stirred at 70° C. for 2 hours. The reaction mixture was cooled to room temperature and quenched with sat. sodium thiosulfate solution (2.0 L) and extracted with ethyl acetate (2×2.0 L). The combined organic layer was washed with brine (2.0 L), dried over sodium sulfate and concentration under reduced pressure to get crude residue which was purified by column chromatography (60-120 silica mesh, mobile phase 0-2% ethyl acetate in hexane) to afford 2-chloro-5-(1,1-difluoro-2-iodoethyl)pyrazine (39C) (150.0 g, 71% yield) as yellow solid. $^1$H NMR (300 MHz, DMSO-d$_6$) δ 8.96 (s, 1H), 8.89 (s, 1H), 4.07 (t, J=16.4 Hz, 2H).

Preparation of (Z)-2-chloro-5-(1-fluoro-2-iodovinyl)pyrazine (39)

To a solution of 2-chloro-5-(1,1-difluoro-2-iodoethyl)pyrazine (39C) (150 g 493 mmol) in dimethyl sulfoxide (900 mL) was added 5.0M aqueous NaOH solution (148 mL, 740 mmol) at 0° C. The reaction mixture was stirred at 0° C. for 2 hours. After the completion of reaction (monitored by TLC), the mixture was quenched with water (100 mL) and extracted with EtOAc (2×200 mL). The combined organic layer was washed with brine (300 mL), dried over sodium sulfate and concentration under reduced pressure to get crude residue. The crude material was purified by column chromatography (60-120 silica mesh, mobile phase 0-3% ethyl acetate in hexane) to afford (Z)-2-chloro-5-(1-fluoro-2-iodovinyl)pyrazine (39) (78 g, 54% yield) as white solid. $^1$H NMR (400 MHz, CHLOROFORM-d) δ 8.59 (q, J=1.4 Hz, 1H), 8.54 (q, J=1.4 Hz, 1H), 7.05 (dd, J=34.1, 1.3 Hz, 1H).

Synthesis of Intermediate 40

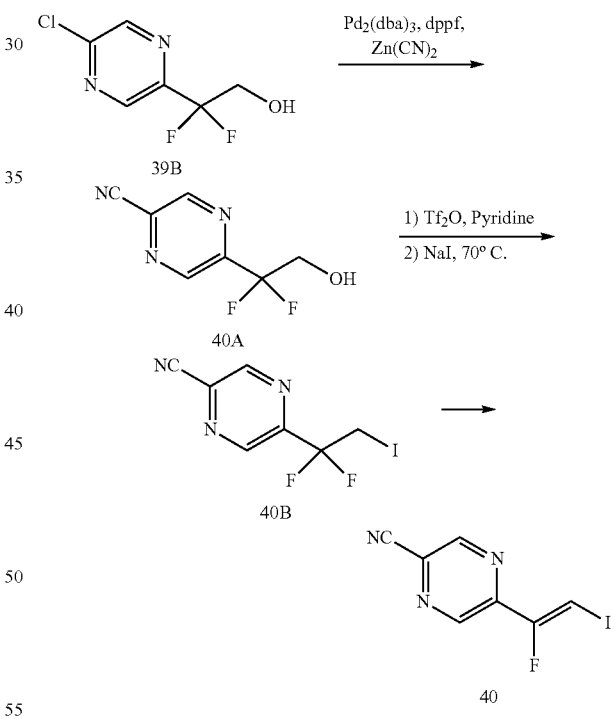

Preparation of 5-(1,1-difluoro-2-hydroxyethyl)pyrazine-2-carbonitrile (40A)

To a solution of 2-(5-chloropyrazin-2-yl)-2,2-difluoroethanol (39B) (30 g, 154 mmol) in N,N-dimethylformamide (300 mL) was degassed with nitrogen for 10 minutes and dppf (4.27 g, 7.71 mmol), Pd$_2$(dba)$_3$ (7.06 g, 7.71 mmol) followed by Zn(CN)$_2$ (36.2 g, 308 mmol) was added. The reaction mixture was heated at 80° C. for 5 hours. The reaction mixture was cooled to room temperature and quenched with water (200 mL) and EtOAc (200 mL). The reaction mixture was filtered through celite and filtrate was then extracted with ethyl acetate (2×500 mL). The combined organic layer was washed with brine (300 mL), dried over sodium sulfate and concentrated under reduced pressure to get crude residue which was purified by column chromatography (silica 60-120 mesh, mobile phase 0-20% ethyl acetate in hexane) affording 5-(1,1-difluoro-2-hydroxyethyl) pyrazine-2-carbonitrile (40A) (18 g, 62% yield) as clear oil. $^1$H NMR (400 MHz, DMSO-$d_6$) δ 9.39 (d, J=1.5 Hz, 1H), 9.16 (d, J=1.5 Hz, 1H), 5.77 (t, J=6.4 Hz, 1H), 4.04 (td, J=13.8, 6.4 Hz, 2H).

Preparation of 5-(1,1-difluoro-2-iodoethyl)pyrazine-2-carbonitrile (40B)

To a solution of 5-(1,1-difluoro-2-hydroxyethyl)pyrazine-2-carbonitrile (40A) (18 g, 97 mmol) in acetonitrile (180 mL) at 0° C. was added pyridine (15.73 mL, 194 mmol) followed by dropwise addition of triflic anhydride (65.7 mL, 389 mmol). The reaction mixture was stirred at 0° C. for 30 minutes. To the reaction mixture was added sodium iodide (72.9 g, 486 mmol) portion-wise at ambient temperature. The reaction mixture was stirred at 70° C. for 3 hours. The reaction mixture was cooled to room temperature and quenched with saturated aqueous sodium thiosulfate solution (100 mL) and extracted with ethyl acetate (2×200 mL). The combined organic layer was washed with brine (200 mL), dried over sodium sulfate and concentrated under reduced pressure to get crude residue which was purified by column chromatography (60-120 silica mesh, mobile phase 0-2% ethyl acetate in hexane) to afford 5-(1,1-difluoro-2-iodoethyl)pyrazine-2-carbonitrile (40B) (10.0 g, 35% yield) as yellow solid. $^1$H NMR (400 MHz, CHLOROFORM) δ 9.10 (t, J=1.2 Hz, 1H), 8.98 (dd, J=1.6, 0.8 Hz, 1H), 3.91 (td, J=14.3, 1.0 Hz, 2H).

Preparation of (Z)-5-(1-fluoro-2-iodovinyl)pyrazine-2-carbonitrile (40)

To a solution of 5-(1,1-difluoro-2-iodoethyl)pyrazine-2-carbonitrile (40B) (1.0 g, 3.39 mmol) in tetrahydrofuran (10.00 mL) was added potassium tert-butoxide (0.761 g, 6.78 mmol) at −75° C. The reaction mixture was stirred at −75° C. for 30 minutes. The reaction mixture was quenched with water (10 mL) and extracted with ethyl acetate (2×25 mL). The combined organic layer was dried over sodium sulfate, concentration under reduced pressure to get crude residue, which was purified by chromatography (60-120 silica mesh, mobile phase 0-3% ethyl acetate in hexane) affording (Z)-5-(1-fluoro-2-iodovinyl)pyrazine-2-carbonitrile (40) (0.34 g, 36.1% yield) as white solid. $^1$H NMR (400 MHz, CHLOROFORM-d) δ 8.92 (t, J=1.4 Hz, 1H), 8.84 (t, J=1.2 Hz, 1H), 7.38 (d, J=33.5 Hz, 1H).

Synthesis of Intermediate 41

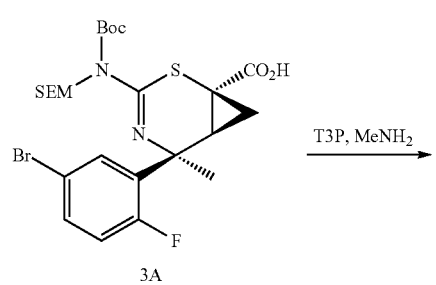

3A

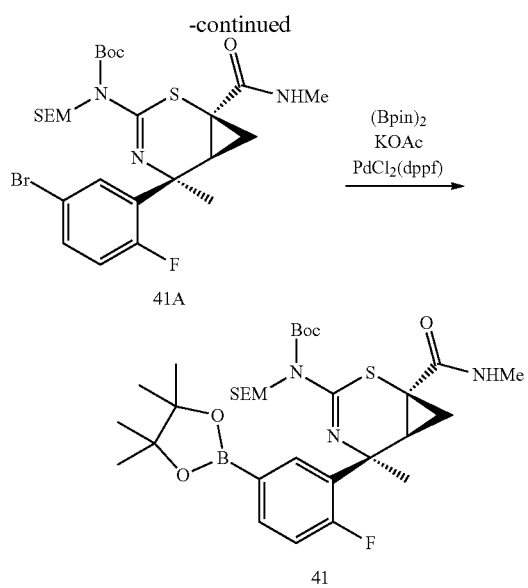

Preparation of tert-butyl ((1S,5S,6S)-5-(5-bromo-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (41A)

(1S,5S,6S)-5-(5-Bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (3A) (3.0 g, 5.09 mmol) was taken up in 25 mL of DCM. Methylamine, 2.0M in THF (5.09 ml, 10.2 mmol) and 1-propanephosphonic acid cyclic anhydride, 50% in EtOAc (8.09 ml, 12.7 mmol) were added. The mixture as stirred for 15 hours. The reaction was quenched with 75 mL of aq. NaHCO$_3$. The mixture was extracted with 100 mL of EtOAc and the organic extracts were washed with 50 mL of brine and dried over MgSO$_4$.

Filtration and concentration under reduced pressure afforded tert-butyl ((1S,5S,6S)-5-(5-bromo-2-fluorophenyl)-5-methyl-1-(methylcarbamoyl)-2-thia-4-azabicyclo [4.1.0]hept-3-en-3-yl)((2-(trimethylsilyl)ethoxy)methyl) carbamate (41A) (2.87 g, 94% yield) as a sticky yellow solid. LCMS (ESI$^+$) m/z=602 (M+H).

Preparation of tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (41)

Tert-butyl ((1S,5S,6S)-5-(5-bromo-2-fluorophenyl)-5-methyl-1-(methylcarbamoyl)-2-thia-4-azabicyclo[4.1.0] hept-3-en-3-yl)((2-(trimethylsilyl)ethoxy)methyl)carbamate (41A) (2.87 g, 4.76 mmol) was taken up in 40 mL of dioxane. Bis(pinacolato)diboron (2.42 g, 9.52 mmol), potassium acetate (1.63 g, 16.7 mmol), and 1,1'-bis(diphenylphosphino)ferrocene palladium(II)dichloride dichloromethane adduct (0.39 g, 0.48 mmol) were added. The mixture was purged with nitrogen, then heated to 90° C. After 2.5 hours, the mixture was cooled to room temperature. The mixture was diluted with 75 mL of EtOAc and washed with 50 mL of aq. NaHCO$_3$ and 50 mL of brine, then dried over MgSO$_4$. Filtration and concentration under reduced pressure, followed by flash chromatography on silica gel (40 g Isco RediSep Rf gold column, elute with 1% to 40% 3:1 EtOAc:EtOH/heptane gradient) afforded tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (41) (2.85 g, 92% yield) as a sticky solid. LCMS (ESI+) m/z=650 (M+H).

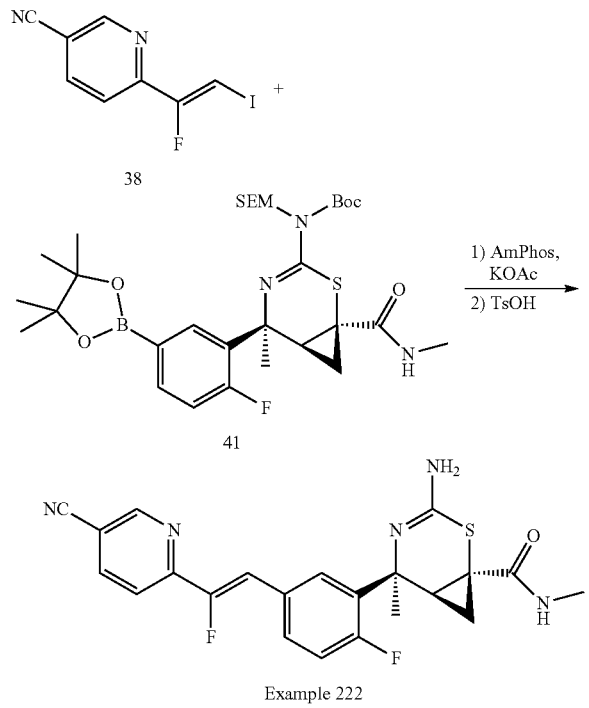

Preparation of (1S,5S,6S)-3-amino-5-(5-((Z)-2-(5-cyanopyridin-2-yl)-2-fluorovinyl)-2-fluorophenyl)-N,5-dimethyl-2-thia-4-azabicyclo[4.1.0]hept-3-ene-1-carboxamide (Example 222)

Tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (41) (0.545 g, 0.839 mmol), (Z)-6-(1-fluoro-2-iodovinyl)nicotinonitrile (38) (0.20 g, 0.73 mmol), potassium acetate (0.251 g, 2.55 mmol), and 1,1-bis[di-tert-butyl-p-methylaminophenyl]palladium(II) chloride (0.052 g, 0.073 mmol) were taken up in 6 mL of 3:1 MeCN:water. The mixture was heated to 65° C. After 18 hours, the reaction was cooled to room temperature and quenched with 20 mL of aq. NH4Cl. The mixture was diluted with 5 mL of water. The mixture was extracted with 30 mL of EtOAc and the organic extracts were washed with 15 mL of brine and dried over MgSO4. Filtration and concentration under reduced pressure, followed by flash chromatography on silica gel (40 Isco RediSep Rf gold column, elute with 5% to 50% 3:1 EtOAc:EtOH/heptane gradient) afforded tert-butyl ((1S,5S,6S)-5-(5-((Z)-2-(5-cyanopyridin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (0.27 g, 55% yield) as a brick color solid.

Tert-butyl ((1S,5S,6S)-5-(5-((Z)-2-(5-cyanopyridin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (0.27 g, 0.40 mmol) was taken up in 2 mL of dioxane. p-Toluenesulfonic acid monohydrate (0.307 g, 1.61 mmol) was added, and the mixture was heated to 80° C. After 15 hours, the mixture was cooled to room temperature and diluted with 25 mL of EtOAc and washed with 15 mL of aq. NaHCO3 and 15 mL of brine, then dried over MgSO4. Filtration and concentration under reduced pressure, followed by flash chromatography on silica gel (12 g Isco RediSep Rf Gold column, elute with 5% to 70% 3:1 EtOAc:EtOH/heptane gradient) afforded (1S,5S,6S)-3-amino-5-(5-((Z)-2-(5-cyanopyridin-2-yl)-2-fluorovinyl)-2-fluorophenyl)-N,5-dimethyl-2-thia-4-azabicyclo[4.1.0]hept-3-ene-1-carboxamide (0.095 g, 54% yield) as a crystalline yellow solid. 1H NMR (400 MHz, DMSO-d6) δ 8.96-9.15 (m, 1H), 8.44 (dd, J=2.05, 8.31 Hz, 1H), 8.04 (dd, J=1.96, 7.82 Hz, 1H), 7.85 (d, J=8.22 Hz, 1H), 7.63-7.75 (m, 2H), 7.21-7.37 (m, 2H), 6.20 (s, 2H), 2.62 (d, J=4.50 Hz, 3H), 2.11-2.21 (m, 1H), 1.59-1.66 (m, 3H), 1.37-1.45 (m, 1H), 0.76 (br d, J=1.76 Hz, 1H).

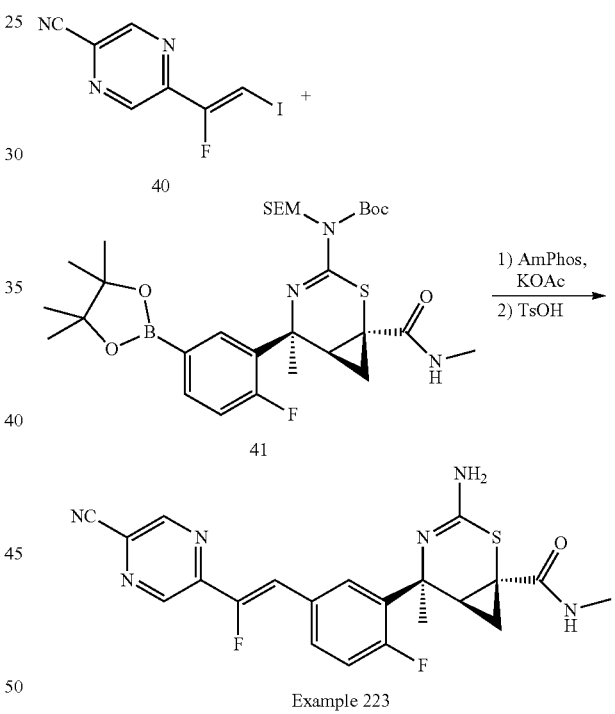

Preparation of (1S,5S,6S)-3-amino-5-(5-((Z)-2-(5-cyanopyrazin-2-yl)-2-fluorovinyl)-2-fluorophenyl)-N,5-dimethyl-2-thia-4-azabicyclo[4.1.0]hept-3-ene-1-carboxamide Using a procedure similar to that described for Example 222, tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (41) (0.20 g, 0.31 mmol), (Z)-5-(1-fluoro-2-iodovinyl)pyrazine-2-carbonitrile (0.071 g, 0.26 mmol), 1,1-bis[di-tert-butyl-p-methylaminophenyl]palladium(II) chloride (0.018 g, 0.026 mmol), and potassium acetate (0.10 g, 1.0 mmol) were combined to provide the coupling product, which after deprotection with 4-methylbenzenesulfonic acid hydrate (0.095 g, 0.0.50 mmol) gave (1S,5S,6S)-3-amino-5-(5-((Z)-2-(5-cyanopyrazin-2-yl)-2-fluorovinyl)-2-fluorophenyl)-N,5-dimethyl-2-thia-4-azabicyclo[4.1.0]hept-3-ene-1-carboxamide (Example 223), (30 mg, 54% yield) as a light-yellow solid. $^1$H NMR (400 MHz, CHLOROFORM-d) δ 8.95 (s, 1H), 8.83 (s, 1H), 7.60-7.73 (m, 2H), 7.05-7.25 (m, 2H), 6.55 (br s, 1H), 2.89 (d, J=4.69 Hz, 3H), 2.18-2.30 (m, 1H), 1.98 (dd, J=4.99, 9.68 Hz, 1H), 1.84 (s, 3H), 0.77 (br d, J=5.28 Hz, 1H).

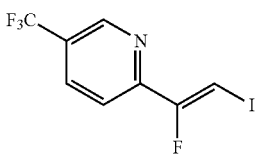

Preparation of (Z)-2-(1-fluoro-2-iodovinyl)-5-(trifluoromethyl)pyridine (42)

Using a procedure similar to that described for 37, (Z)-2-(1-fluoro-2-iodovinyl)-5-(trifluoromethyl)pyridine (42) was prepared starting from 2-bromo-5-trifluoromethylpyridine.

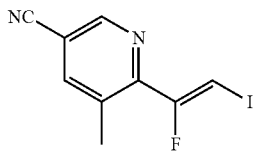

Preparation of (Z)-6-(1-fluoro-2-iodovinyl)-5-methylnicotinonitrile (43)

Using a procedure similar to that described for 38, (Z)-6-(1-fluoro-2-iodovinyl)-5-methylnicotinonitrile (43) was prepared starting from 6-bromo-5-methylnicotinonitrile.

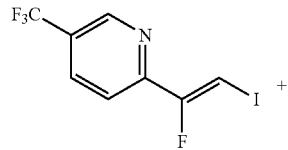

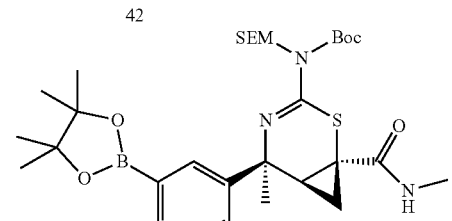

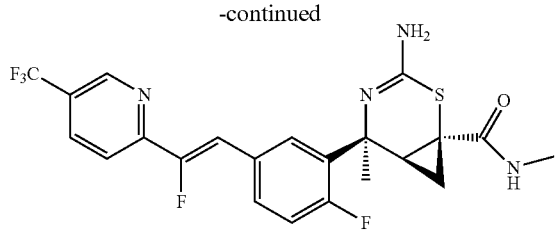

Example 224

Preparation of (1S,5S,6S)-3-amino-5-(2-fluoro-5-((Z)-2-fluoro-2-(5-(trifluoromethyl)pyridin-2-yl)vinyl)phenyl)-N,5-dimethyl-2-thia-4-azabicyclo[4.1.0]hept-3-ene-1-carboxamide (Example 224)

Using a procedure similar to that described for Example 222, tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (41) (0.15 g, 0.23 mmol), (Z)-2-(1-fluoro-2-iodovinyl)-5-(trifluoromethyl)pyridine (42) (0.073 g, 0.231 mmol), potassium acetate (0.091 g, 0.92 mmol), and bis-(di-tert-butyl(4-dimethylaminophenyl)phosphine)dichloropalladium(II) (0.016 g, 0.023 mmol) were combined to provide the coupling product, which after deprotection with 4-methylbenzenesulfonic acid hydrate (0.067 g, 0.35 mmol) gave (1S,5S,6S)-3-amino-5-(2-fluoro-5-((Z)-2-fluoro-2-(5-(trifluoromethyl)pyridin-2-yl)vinyl)phenyl)-N,5-dimethyl-2-thia-4-azabicyclo[4.1.0]hept-3-ene-1-carboxamide (Example 224) (0.031 g, 54% yield) as an off white solid. LCMS (ESI$^+$) m/z=483 (M+H). $^1$H NMR (400 MHz, CHLOROFORM-d) δ 8.85-9.01 (m, 1H), 8.01-8.19 (m, 1H), 7.70-7.80 (m, 2H), 7.66 (dd, J=1.76, 7.63 Hz, 1H), 7.10-7.29 (m, 2H), 6.65-6.80 (m, 1H), 2.96 (d, J=4.70 Hz, 3H), 2.27-2.38 (m, 1H), 2.10 (dd, J=5.09, 9.59 Hz, 1H), 1.95 (s, 3H), 0.88 (s, 1H).

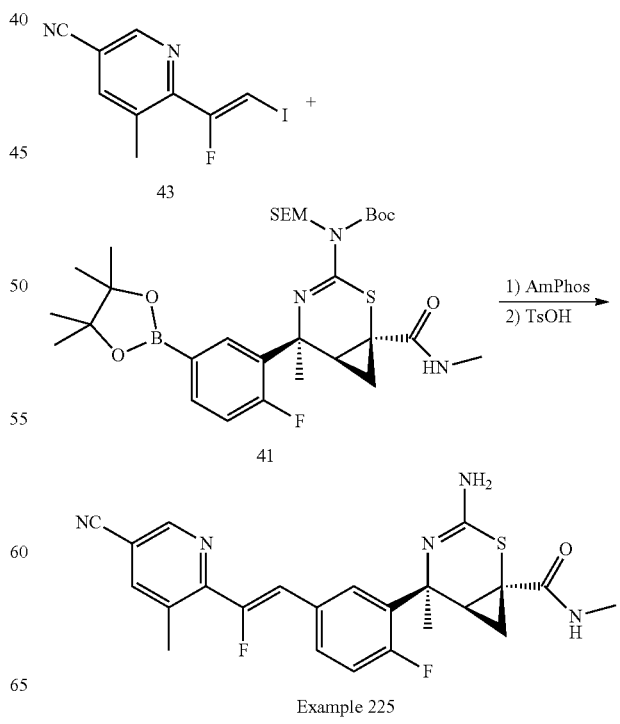

Example 225

Preparation of (1S,5S,6S)-3-amino-5-(5-((Z)-2-(5-cyano-3-methylpyridin-2-yl)-2-fluorovinyl)-2-fluorophenyl)-N,5-dimethyl-2-thia-4-azabicyclo[4.1.0]hept-3-ene-1-carboxamide (Example 225)

Using a procedure similar to that described for Example 222, tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (0.20 g, 0.31 mmol), (Z)-6-(1-fluoro-2-iodovinyl)-5-methylnicotinonitrile (0.074 g, 0.28 mmol), potassium acetate (0.101 g, 1.03 mmol), and bis-(di-tert-butyl(4-dimethylaminophenyl)phosphine)dichloropalladium(II) (0.018 g, 0.026 mmol) were combined to provide the coupling product, which after deprotection with 4-methylbenzenesulfonic acid hydrate (0.078 g, 0.41 mmol) gave (1S,5S,6S)-3-amino-5-(5-((Z)-2-(5-cyano-3-methylpyridin-2-yl)-2-fluorovinyl)-2-fluorophenyl)-N,5-dimethyl-2-thia-4-azabicyclo[4.1.0]hept-3-ene-1-carboxamide (Example 225) (0.041 g, 66% yield) as an off white solid. LCMS (ESI⁺) m/z=454 (M+H). ¹H NMR (400 MHz, CHLOROFORM-d) δ 8.60-8.65 (m, 1H), 7.72-7.75 (m, 1H), 7.58-7.66 (m, 1H), 7.49 (dd, J=1.96, 7.63 Hz, 1H), 6.99-7.10 (m, 1H), 6.88 (d, J=38.73 Hz, 1H), 6.53-6.65 (m, 1H), 2.84 (d, J=4.69 Hz, 3H), 2.53 (d, J=6.85 Hz, 3H), 2.21 (t, J=8.51 Hz, 1H), 1.97 (dd, J=5.18, 9.68 Hz, 1H), 1.82 (s, 3H), 0.68-0.79 (m, 1H).

Synthesis of Intermediate 44

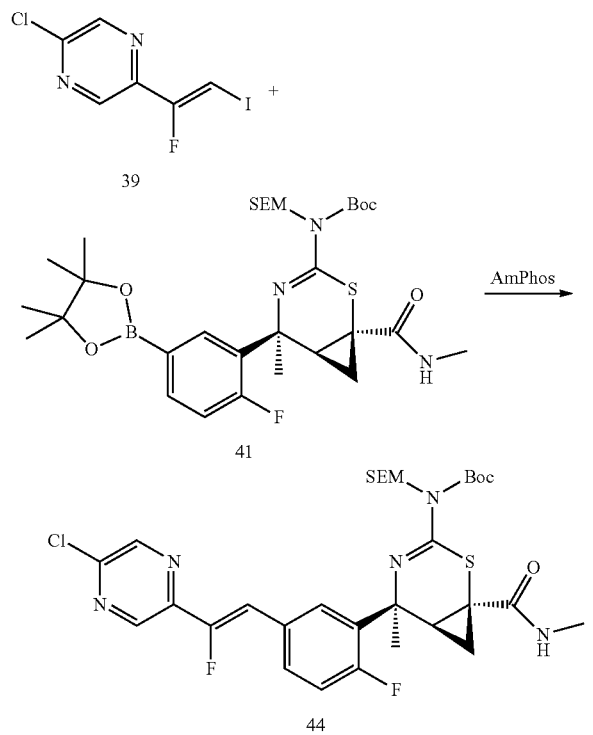

Preparation of tert-butyl ((1S,5S,6S)-5-(5-((Z)-2-(5-chloropyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (44)

Tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (41) (1.31 g, 2.02 mmol), (Z)-2-chloro-5-(1-fluoro-2-iodovinyl)pyrazine (39) (0.50 g, 1.8 mmol), potassium acetate (0.604 g, 6.15 mmol), and 1,1-bis[di-t-butyl-p-methylaminophenyl]palladium(II) chloride (0.124 g, 0.176 mmol) were taken up in 10 mL of 3:1 MeCN:water. The mixture was heated to 65° C. for 15 hours. The reaction was cooled to room temperature and diluted with 40 mL of EtOAc. The mixture was washed with 20 mL of water and 20 mL of brine, then dried over MgSO₄. Filtration and concentration under reduced pressure, followed by flash chromatography on silica gel (24 g Isco RediSep Rf Gold column, elute with 5% to 30% EtOAc/heptane) afforded tert-butyl ((1S,5S,6S)-5-(5-((Z)-2-(5-chloropyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (44) (0.62 g, 52% yield) as a tan solid. ¹H NMR (400 MHz, CHLOROFORM-d) δ 8.59-8.68 (m, 1H), 8.48-8.55 (m, 1H), 7.64-7.74 (m, 2H), 7.11-7.17 (m, 1H), 7.04 (d, J=38.54 Hz, 1H), 6.80-6.88 (m, 1H), 5.42-5.49 (m, 1H), 5.15-5.22 (m, 1H), 3.66-3.75 (m, 2H), 2.87-2.90 (m, 3H), 2.22-2.30 (m, 1H), 1.91-1.96 (m, 1H), 1.83-1.87 (m, 3H), 1.57 (s, 9H), 0.91-1.05 (m, 3H), −0.03−−0.01 (m, 9H).

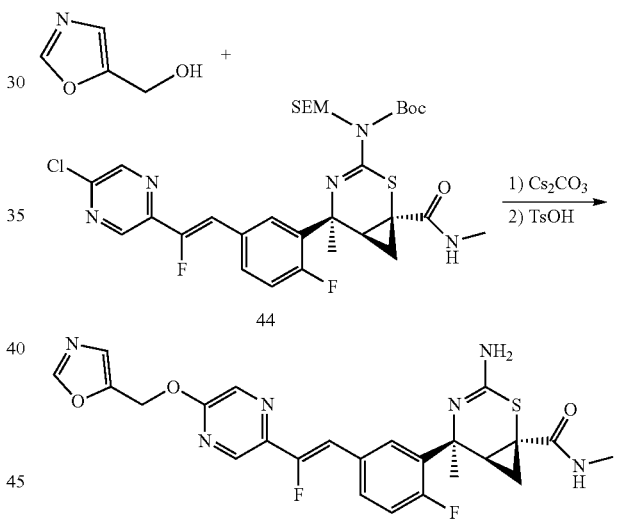

Example 226

Preparation of (1S,5S,6S)-3-amino-5-(2-fluoro-5-((Z)-2-fluoro-2-(5-(oxazol-5-ylmethoxy)pyrazin-2-yl)vinyl)phenyl)-N,5-dimethyl-2-thia-4-azabicyclo[4.1.0]hept-3-ene-1-carboxamide (Example 226)

Tert-butyl ((1S,5S,6S)-5-(5-((Z)-2-(5-chloropyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (44) (0.075 g, 0.11 mmol), 1,3-oxazol-5-methanol (0.022 ml, 0.22 mmol), and cesium carbonate (0.144 g, 0.441 mmol) were taken up in 1 mL of THF and heated to 50° C. After 15 hours, the mixture was cooled to room temperature The mixture was diluted with 20 mL of EtOAc and washed with 10 mL of water and 10 mL of brine, then dried over MgSO₄. Filtration and concentration under reduced pressure, followed by flash chromatography on silica gel (4 g Isco RediSep Rf Gold column, elute with 5% to 60% EtOAc/heptane) afforded a sticky white solid. The solid was taken up in 1 mL of dioxane in a sealable tube with a pressure release septum. 4-methylbenzene sulfonic acid, monohydrate (0.023 g, 0.12 mmol) was added. The mixture was heated to 80° C. behind a blast shield. After 15 hours, the mixture was cooled to rt. The reaction was diluted with 15 mL of EtOAc, washed with 5 mL of aq. NaHCO$_3$, 5 mL of brine, and dried over MgSO$_4$. Filtration and concentration under reduced pressure, followed by flash chromatography on silica gel (4 g Isco RediSep Rf gold column, elute with 5% to 50% 3:1 EtOAc:EtOH/heptane mixture) afforded (1S,5S,6S)-3-amino-5-(2-fluoro-5-((Z)-2-fluoro-2-(5-(oxazol-5-ylmethoxy)pyrazin-2-yl)vinyl)phenyl)-N,5-dimethyl-2-thia-4-azabicyclo[4.1.0]hept-3-ene-1-carboxamide (Example 226) (0.0065 g, 21% yield) as a white solid. $^1$H NMR (400 MHz, METHANOL-d$_4$) δ 8.45-8.52 (m, 1H), 8.32-8.34 (m, 1H), 8.27-8.31 (m, 1H), 7.61-7.71 (m, 2H), 7.37 (s, 1H), 7.13-7.23 (m, 1H), 6.93 (d, J=40.10 Hz, 1H), 5.58-5.63 (m, 2H), 2.84 (s, 3H), 2.16-2.24 (m, 1H), 1.91 (br d, J=4.89 Hz, 1H), 1.89 (s, 3H), 0.90 (br t, J=5.48 Hz, 1H).

Synthesis of Intermediate 45

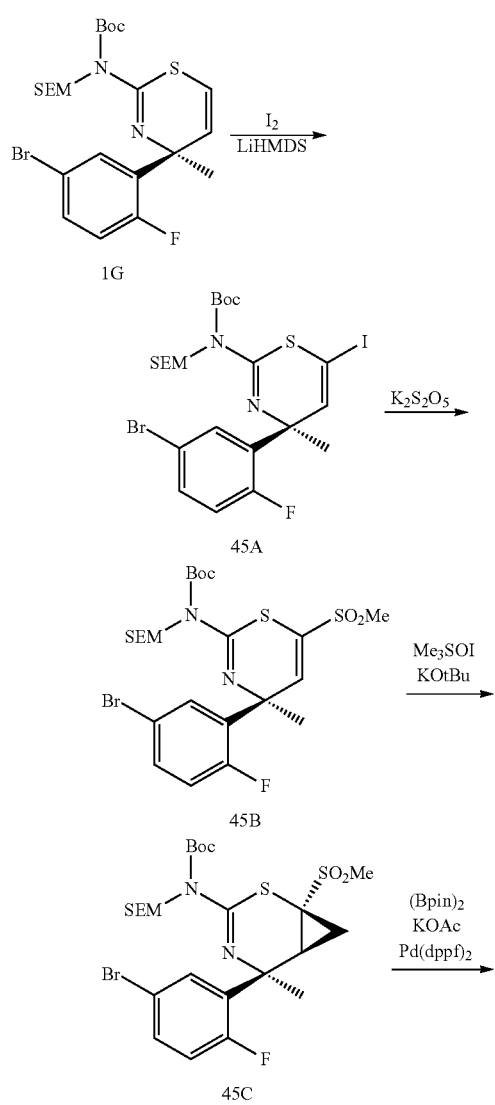

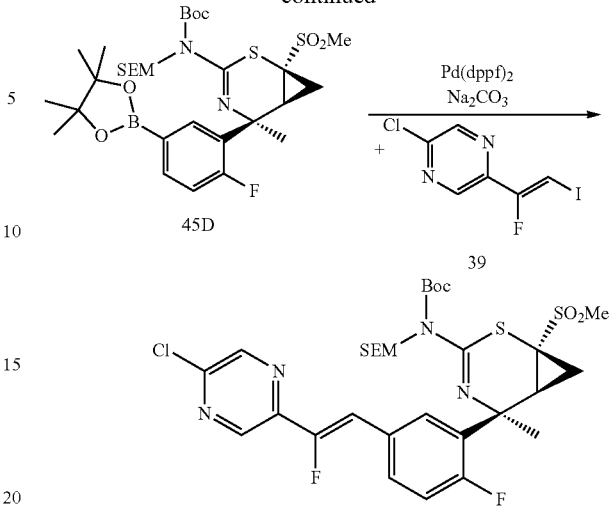

Preparation of (S)-tert-butyl (4-(5-bromo-2-fluorophenyl)-6-iodo-4-methyl-4H-1,3-thiazin-2-yl)((2-(trimethylsilyl)ethoxy)methyl)carbamate (45A)

To a stirring solution of (S)-tert-butyl (4-(5-bromo-2-fluorophenyl)-4-methyl-4H-1,3-thiazin-2-yl)((2-(trimethylsilyl)ethoxy)methyl)carbamate (1G) (7.2 g, 14 mmol) in tetrahydrofuran (70 ml) at −78° C. under nitrogen was added lithium diisopropylamide, 2.0M in heptane/THF/ethylbenzene (7.45 ml, 14.9 mmol) dropwise. After 25 minutes at −78° C., a solution of iodine (4.13 g, 16.2 mmol) in THF (30 mL) was added dropwise to the mixture within a 3 minute period. After 20 minutes, the reaction was quenched with 40 mL of aq. Na$_2$S$_2$O$_3$ and diluted with 40 mL of water. The mixture was warmed to 20° C. and extracted with 250 mL of EtOAc. The organic extracts were washed with sat. NaCl (2×40 mL), dried over Na$_2$SO$_4$, filtered and concentrated under reduced pressure. The residue was then purified by silica gel chromatography (220 g) eluting products with a gradient of 2.5>10% (4:1 blend EtOAc/EtOH)/heptane to afford (S)-tert-butyl (4-(5-bromo-2-fluorophenyl)-6-iodo-4-methyl-4H-1,3-thiazin-2-yl)((2-(trimethylsilyl)ethoxy)methyl)carbamate (45A) as colorless oil. MS m/z=657.0 (M+H).

Preparation of ((S)-tert-butyl (4-(5-bromo-2-fluorophenyl)-4-methyl-6-(methylsulfonyl)-4H-1,3-thiazin-2-yl)((2-(trimethylsilyl)ethoxy)methyl)carbamate (45B)

A suspension of (S)-tert-butyl (4-(5-bromo-2-fluorophenyl)-6-iodo-4-methyl-4H-1,3-thiazin-2-yl)((2-(trimethylsilyl)ethoxy)methyl)carbamate (45A) (7.3 g, 11 mmol), dipotassium disulfite (2.98 g, 22.2 mmol), tetrabutylammonium bromide (3.58 g, 11.1 mmol), palladium(II) acetate (0.125 g, 0.555 mmol), triphenylphosphine (0.437 g, 1.67 mmol), 1,10-phenanthroline (0.300 g, 1.67 mmol) in dimethyl sulfoxide (60 ml) was degassed by sparging argon through with stirring for 10 minutes. The flask was then heated 70° C. and stirred for 1 hour. The reaction was cooled to room temperature, then iodomethane, 2.0M in tert-butyl methyl ether (8.33 ml, 16.7 mmol) added. The solution was stirred at 20° C. for 30 minutes and water (250 mL) was added. The mixture was extracted twice with EtOAc (2×75 mL). The combined organic extracts were washed with brine (40 mL), dried over MgSO₄, filtered, and concentrated under reduced pressure. The residue was then purified silica gel chromatography (120 g) eluting products with a gradient of 2.5>10% (4:1 blend EtOAc/EtOH)/heptane to afford ((S)-tert-butyl (4-(5-bromo-2-fluorophenyl)-4-methyl-6-(methylsulfonyl)-4H-1,3-thiazin-2-yl)((2-(trimethylsilyl)ethoxy)methyl)carbamate (45B) (2.3 g, 34% yield) as colorless oil. MS m/z=631.0 (M+Na).

Preparation of tert-butyl ((1R,5S,6S)-5-(5-bromo-2-fluorophenyl)-5-methyl-1-(methylsulfonyl)-2-thia-4-azabicyclo[4.1.0]hept-3-en-3-yl)((2-(trimethylsilyl)ethoxy)methyl) (45C)

To a stirring solution of trimethylsulfoxonium iodide (0.913 g, 4.15 mmol) in DMSO (10 mL) under nitrogen at 20° C. was added potassium tert-butoxide (0.466 g, 4.15 mmol). The yellow suspension became a clear, colorless solution. The mixture was stirred at 20° C. for 1 hour A separate solution of (S)-tert-butyl (4-(5-bromo-2-fluorophenyl)-4-methyl-6-(methylsulfonyl)-4H-1,3-thiazin-2-yl)((2-(trimethylsilyl)ethoxy)methyl)carbamate (45B) (2.3 g, 3.8 mmol) in THF (10 mL) was prepared under nitrogen atmosphere. The DMSO solution was transferred to a syringe, and added to the yellow THF mixture over 5 minutes. The solution became cloudy at the start of the addition but became homogeneous again before the end of the addition. The yellow solution was then stirred at 20° C. for 1 hour. The reaction was quenched with saturated aqueous NH₄Cl (40 mL) and diluted with water (150 mL). The mixture was extracted 1:1 heptane/EtOAc (75 mL) and the organic extract was then washed with water (100 mL) followed by brine (30 mL). The organic was then dried over MgSO₄, concentrated under reduced pressure then purified by silica gel chromatography (80 g) eluting products with a gradient of 2.5>10% (4:1 blend EtOAc/EtOH)/heptane to afford tert-butyl ((1R,5S,6S)-5-(5-bromo-2-fluorophenyl)-5-methyl-1-(methylsulfonyl)-2-thia-4-azabicyclo[4.1.0]hept-3-en-3-yl)((2-(trimethylsilyl)ethoxy)methyl)carbamate (45C) as colorless oil. MS m/z=645.0 (M+Na). ¹H NMR (400 MHz, CHLOROFORM-d) δ ppm 7.68 (dd, J=7.04, 2.54 Hz, 1H) 7.38 (ddd, J=8.61, 4.21, 2.64 Hz, 1H) 6.97 (dd, J=11.54, 8.61 Hz, 1H) 5.34 (d, J=10.37 Hz, 1H) 5.09 (d, J=10.37 Hz, 1H) 3.66 (dd, J=8.71, 7.73 Hz, 2H) 3.09 (s, 3H) 2.55 (dd, J=10.07, 8.12 Hz, 1H) 1.88 (dd, J=10.47, 6.16 Hz, 1H) 1.77 (s, 3H) 1.53 (s, 9H) 1.10 (t, J=6.94 Hz, 1H) 0.96 (dd, J=9.29, 7.34 Hz, 2H) −0.03-0.03 (m, 9H).

Preparation of tert-butyl ((1R,5S,6S)-5-(2-fluoro-5-(4,4,5,5-tetramethyl-1,3,2-dioxaborolan-2-yl)phenyl)-5-methyl-1-(methylsulfonyl)-2-thia-4-azabicyclo[4.1.0]hept-3-en-3-yl)((2-(trimethylsilyl)ethoxy)methyl)carbamate (45D)

A suspension of tert-butyl ((1R,5S,6S)-5-(5-bromo-2-fluorophenyl)-5-methyl-1-(methylsulfonyl)-2-thia-4-azabicyclo[4.1.0]hept-3-en-3-yl)((2-(trimethylsilyl)ethoxy)methyl)carbamate (45C) (1.6 g, 2.6 mmol), bis(pinacolato) diboron (1.30 g, 5.13 mmol), potassium acetate (0.755 g, 7.70 mmol) in 1,4-dioxane (15 mL) was sparged with argon for 5 minutes the heated to 100° C. for 1 hour. The reaction was then partitioned between EtOAc (50 mL) and 5% NaHCO₃ (100 mL). The organic was then washed with brine (2×50 mL), dried over MgSO₄, concentrated under reduced pressure (the residue azeotroped with heptane (50 mL)), then purified via silica gel chromatography (80 g) eluting products with a 0>20% gradient of (3:1 EtOAc/EtOH blend)/heptane to afford tert-butyl ((1R,5S,6S)-5-(2-fluoro-5-(4,4,5,5-tetramethyl-1,3,2-dioxaborolan-2-yl)phenyl)-5-methyl-1-(methylsulfonyl)-2-thia-4-azabicyclo[4.1.0]hept-3-en-3-yl)((2-(trimethylsilyl)ethoxy)methyl)carbamate (45D) (1.6 g, 93% yield) as colorless oil.

Preparation of tert-butyl ((1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-yl)((2-(trimethylsilyl)ethoxy)methyl)carbamate (45)

A suspension of tert-butyl ((1R,5S,6S)-5-(2-fluoro-5-(4,4,5,5-tetramethyl-1,3,2-dioxaborolan-2-yl)phenyl)-5-methyl-1-(methylsulfonyl)-2-thia-4-azabicyclo[4.1.0]hept-3-en-3-yl)((2-(trimethylsilyl)ethoxy)methyl)carbamate (45D) (1.6 g, 2.4 mmol), (Z)-2-chloro-5-(1-fluoro-2-iodovinyl)pyrazine (39) (1.02 g, 3.58 mmol), 1,1'-bis(diphenylphosphino)ferrocene palladium(II)dichloride dichloromethane adduct (0.097 g, 0.12 mmol), sodium carbonate (7.16 ml, 7.16 mmol) in 1,4-dioxane (15 mL) was sparged with argon for 5 minutes then heated to 80° C. for 30 minutes. The reaction was then partitioned between EtOAc (50 mL) and 5% aq. NaHCO₃ (30 mL). The separated organic was dried over MgSO₄, concentrated under reduced pressure, then purified by silica gel chromatography (80 g) eluting products with a gradient of 0>35% (3:1 EtOAc/EtOH)/heptane to afford tert-butyl ((1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-yl)((2-(trimethylsilyl)ethoxy)methyl)carbamate (45) (1.1 g, 66% yield) as tan foam. MS m/z=701.2 (M+1).

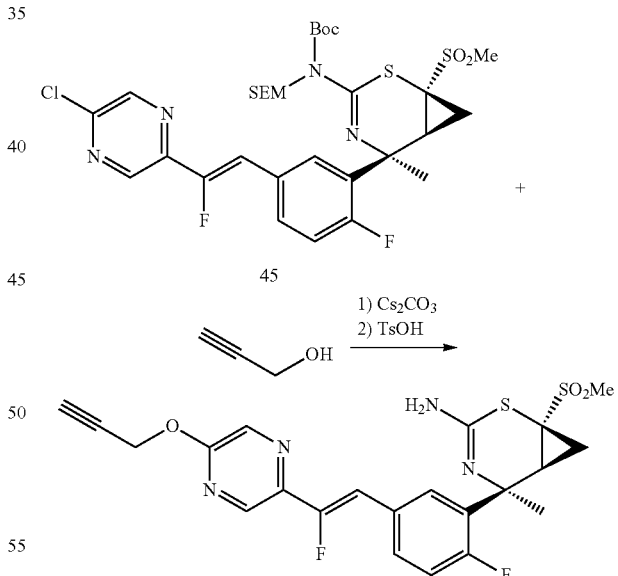

Preparation of (1R,5S,6S)-5-(2-fluoro-5-((Z)-2-fluoro-2-(5-(prop-2-yn-1-yloxy)pyrazin-2-yl)vinyl)phenyl)-5-methyl-1-(methylsulfonyl)-2-thia-4-azabicyclo[4.1.0]hept-3-en-3-amine (Example 227)

A suspension of tert-butyl ((1R,5S,6S)-5-(5-((Z)-2-(5-chloropyrazin-2-yl)-2-fluorovinyl)-2-fluorophenyl)-5- methyl-1-(methylsulfonyl)-2-thia-4-azabicyclo[4.1.0]hept-3-en-3-yl)((2-(trimethylsilyl)ethoxy)methyl)carbamate (45) (250 mg, 0.356 mmol), 2-propyn-1-ol (211 μl, 3.56 mmol), cesium carbonate (348 mg, 1.07 mmol) in THF (1.5 mL) was heated to 90° C. for 90 minutes. The reaction was then partitioned between EtOAc (15 mL) and 5% NaHCO$_3$ (5 mL). The organic was dried over MgSO$_4$, and concentrated under reduced pressure. The resulting residue was then first dissolved in 1,4-dioxane (1 mL) and 4-methylbenzene sulfonic acid, monohydrate (271 mg, 1.43 mmol) added. The mixture was heated to 80° C. for 30 minutes. The reaction was then partitioned between 9:1 CHCl$_3$/IPA (10 mL) and 5% NaHCO$_3$ (10 mL). The aqueous was further extracted with 9:1 CHCl$_3$/IPA (2×2 mL). The organic was then dried over MgSO$_4$, concentrated under reduced pressure, then purified by silica gel chromatography (12 g) eluting products with a gradient of 0>30% ((3:1 EtOAc/EtOH blend)/heptane) to afford (1R,5S,6S)-5-(2-fluoro-5-((Z)-2-fluoro-2-(5-(prop-2-yn-1-yloxy)pyrazin-2-yl)vinyl)phenyl)-5-methyl-1-(methylsulfonyl)-2-thia-4-azabicyclo[4.1.0]hept-3-en-3-amine (Example 227) (90 mg, 52% yield) as white solid. MS m/z=491.0 (M+1). $^1$H NMR (400 MHz, DMSO-d$_6$) δ ppm 8.49 (s, 1H) 8.45 (s, 1H) 7.71 (dd, J=7.83, 1.96 Hz, 1H) 7.59-7.67 (m, 1H) 7.22-7.30 (m, 1H) 6.87 (d, J=40.69 Hz, 1H) 6.69 (s, 2H) 5.08 (d, J=2.35 Hz, 2H) 3.61 (t, J=2.35 Hz, 1H) 3.11 (s, 3H) 2.15-2.24 (m, 1H) 1.89 (dd, J=10.07, 5.97 Hz, 1H) 1.73 (s, 3H) 0.79-0.90 (m, 1H).

fonyl)-2-thia-4-azabicyclo[4.1.0]hept-3-en-3-yl)((2-(trimethylsilyl)ethoxy)methyl)carbamate (45) (340 mg, 0.485 mmol), (5-methyl-1,3,4-oxadiazol-2-yl)methanol (215 μl, 2.42 mmol), cesium carbonate (632 mg, 1.94 mmol) were combined to create the SnAr product, which after deprotection with pyridine hydrochloride (840 mg, 7.27 mmol) gave (1R,5S,6S)-5-(2-fluoro-5-((Z)-2-fluoro-2-(5-((5-methyl-1,3,4-oxadiazol-2-yl)methoxy)pyrazin-2-yl)vinyl)phenyl)-5-methyl-1-(methylsulfonyl)-2-thia-4-azabicyclo[4.1.0]hept-3-en-3-amine (Example 228) (40 mg, 15% yield) as colorless film. The film was dissolved in MeCN/water (1:1; 1 mL), frozen, and lyophilized to afford product as white fluffy solid. MS m/z=549.0 (M+1). $^1$H NMR (400 MHz, DMSO-d$_6$) δ ppm 8.52 (s, 1H) 8.49 (s, 1H) 7.67-7.74 (m, 1H) 7.59-7.67 (m, 1H) 7.26 (dd, J=11.84, 8.51 Hz, 1H) 6.88 (d, J=40.10 Hz, 1H) 6.70 (br s, 2H) 5.67 (s, 2H) 3.11 (s, 3H) 2.52 (s, 3H) 2.21 (dd, J=9.88, 8.12 Hz, 1H) 1.89 (dd, J=10.27, 6.16 Hz, 1H) 1.73 (s, 3H) 0.84 (br t, J=6.65 Hz, 1H).

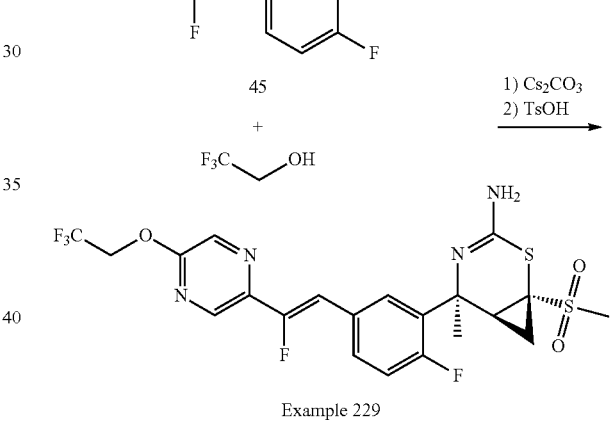

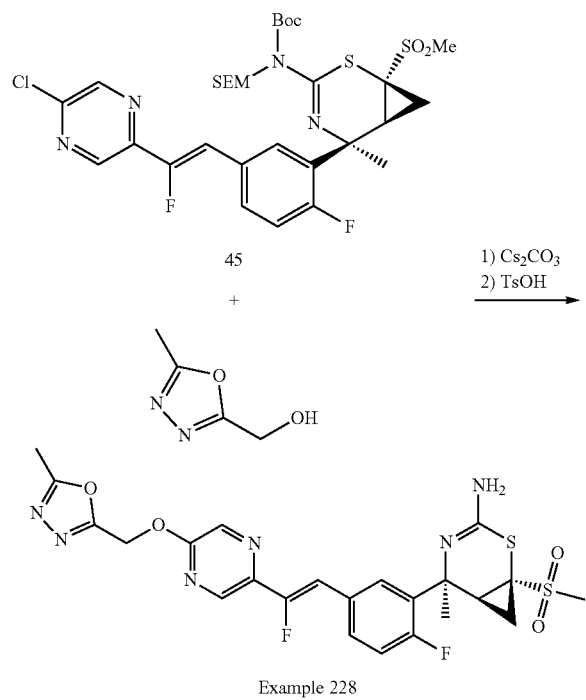

Example 228

Preparation of (1R,5S,6S)-5-(2-fluoro-5-((Z)-2-fluoro-2-(5-((5-methyl-1,3,4-oxadiazol-2-yl)methoxy)pyrazin-2-yl)vinyl)phenyl)-5-methyl-1-(methylsulfonyl)-2-thia-4-azabicyclo[4.1.0]hept-3-en-3-amine (Example 228)

Using a procedure similar to that described for Example 227, tert-butyl ((1R,5S,6S)-5-(5-((Z)-2-(5-chloropyrazin-2-yl)-2-fluorovinyl)-2-fluorophenyl)-5-methyl-1-(methylsul- Example 229

Preparation of (1R,5S,6S)-5-(2-fluoro-5-((Z)-2-fluoro-2-(5-(2,2,2-trifluoroethoxy)pyrazin-2-yl)vinyl)phenyl)-5-methyl-1-(methylsulfonyl)-2-thia-4-azabicyclo[4.1.0]hept-3-en-3-amine (Example 229)

Using a procedure similar to that described for Example 227 tert-butyl ((1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-yl)((2-(trimethylsilyl)ethoxy)methyl)carbamate (45) (160 mg, 0.228 mmol), 2,2,2-trifluoroethanol (166 μl, 2.28 mmol), cesium carbonate (297 mg, 0.913 mmol) were combined to create the SnAr product, which after deprotection with 4-methylbenzenesulfonic acid hydrate (325 mg, 1.71 mmol) gave (1R,5S,6S)-5-(2-fluoro-5-((Z)-2-fluoro-2-(5-(2,2,2-trifluoroethoxy)pyrazin-2-yl)vinyl)phenyl)-5-methyl-1-(methylsulfonyl)-2-thia-4-azabicyclo[4.1.0]hept-3-en-3-amine (Example 229) (51 mg, 41.8% yield). LCMS (ESI$^+$) m/z=491.0 (M+H). $^1$H NMR (400 MHz, DMSO-d$_6$) δ ppm 8.59 (s, 1H) 8.52 (s, 1H) 7.73 (br d, J=7.63 Hz, 1H) 7.65 (br s, 1H) 7.28 (dd, J=11.74, 8.61 Hz, 1H) 6.92 (d, J=40.49 Hz, 1H) 6.70 (s, 2H) 5.11 (q, J=8.93 Hz, 2H) 3.12 (s, 3H) 2.21 (t, J=8.90 Hz, 1H) 1.90 (dd, J=10.17, 6.06 Hz, 1H) 1.74 (s, 3H) 0.85 (br t, J=6.65 Hz, 1H).

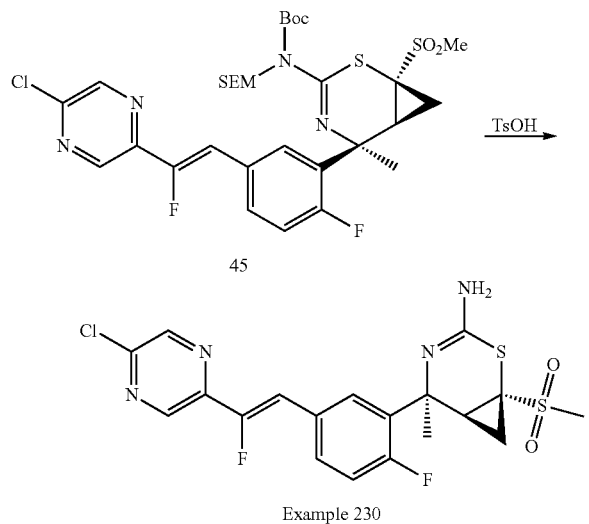

Example 230

Preparation of (1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-amine ((Example 230)

Using a procedure similar to that described for Example 227 tert-butyl ((1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-yl)((2-(trimethylsilyl)ethoxy)methyl)carbamate (45) (40 mg, 0.057 mmol) was deprotected with methylbenzene sulfonic acid, monohydrate (54.2 mg, 0.285 mmol) to give (1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-amine (Example 230) (15 mg, 56% yield). LCMS (ESI+) m/z=471.0 (M+H). 1H NMR (400 MHz, DMSO-d6) δ ppm 8.85 (s, 1H) 8.78 (s, 1H) 7.77 (dd, J=7.83, 2.15 Hz, 1H) 7.64-7.72 (m, 1H) 7.30 (dd, J=11.93, 8.41 Hz, 1H) 7.10 (d, J=40.10 Hz, 1H) 6.70 (s, 2H) 3.11 (s, 3H) 2.21 (dd, J=10.07, 7.73 Hz, 1H) 1.90 (dd, J=10.07, 5.97 Hz, 1H) 1.74 (s, 3H) 0.84 (t, J=6.65 Hz, 1H).

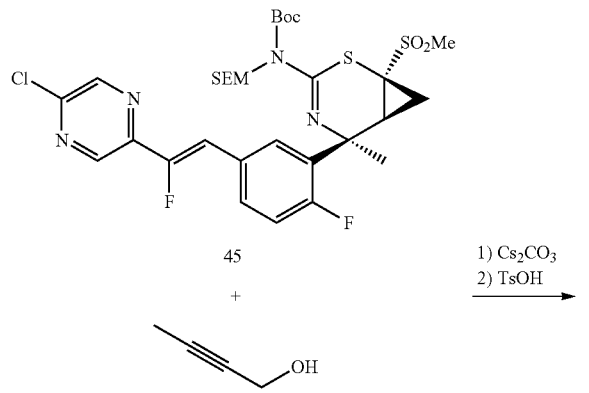

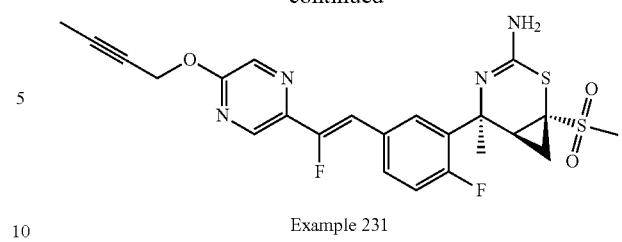

Example 231

Preparation of (1R,5S,6S)-5-(5-((Z)-2-(5-(but-2-yn-1-yloxy)pyrazin-2-yl)-2-fluorovinyl)-2-fluorophenyl)-5-methyl-1-(methylsulfonyl)-2-thia-4-azabicyclo[4.1.0]hept-3-en-3-amine ((Example 331)

Using a procedure similar to that described for Example 227, tert-butyl ((1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-yl)((2-(trimethylsilyl)ethoxy)methyl)carbamate (45) (160 mg, 0.228 mmol), 2-butyn-1-ol (160 µl, 2.28 mmol), cesium carbonate (372 mg, 1.14 mmol) were combined to create the SnAr product, which after deprotection with 4-methylbenzene sulfonic acid, monohydrate (325 mg, 1.71 mmol) created (1R,5S,6S)-5-(5-((Z)-2-(5-(but-2-yn-1-yloxy)pyrazin-2-yl)-2-fluorovinyl)-2-fluorophenyl)-5-methyl-1-(methylsulfonyl)-2-thia-4-azabicyclo[4.1.0]hept-3-en-3-amine (Example 231) (11.6 mg, 10% yield) as white solid. LCMS (ESI+) m/z=505.2 (M+H). 1H NMR (400 MHz, DMSO-d6) δ ppm 8.49 (s, 1H) 8.43 (s, 1H) 7.71 (br d, J=7.82 Hz, 1H) 7.64 (br s, 1H) 7.27 (dd, J=11.74, 8.61 Hz, 1H) 6.87 (d, J=40.69 Hz, 1H) 6.70 (s, 2H) 5.05 (br s, 2H) 3.12 (s, 3H) 2.21 (t, J=9.00 Hz, 1H) 1.90 (dd, J=10.07, 6.16 Hz, 1H) 1.85 (s, 3H) 1.74 (s, 3H) 0.85 (br t, J=6.85 Hz, 1H).

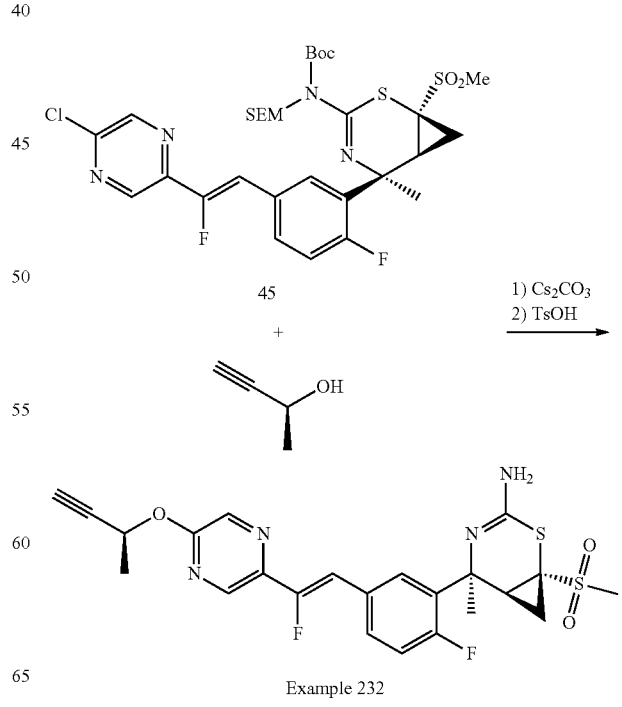

Example 232

Preparation of (1R,5S,6S)-5-(5-((Z)-2-(5-((S)-but-3-yn-2-yloxy)pyrazin-2-yl)-2-fluorovinyl)-2-fluorophenyl)-5-methyl-1-(methylsulfonyl)-2-thia-4-azabicyclo[4.1.0]hept-3-en-3-amine (Example 232)

Using a procedure similar to that described for Example 227, tert-butyl ((1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-yl)((2-(trimethylsilyl)ethoxy)methyl)carbamate (45) (120 mg, 0.171 mmol), (S)-(−)-3-butyn-2-ol (136 μl, 1.71 mmol), cesium carbonate (279 mg, 0.856 mmol) were combined to create the SnAr product, which after deprotection with 4-methylbenzene sulfonic acid, monohydrate (244 mg, 1.28 mmol) gave (1R,5S,6S)-5-(5-((Z)-2-(5-((S)-but-3-yn-2-yloxy)pyrazin-2-yl)-2-fluorovinyl)-2-fluorophenyl)-5-methyl-1-(methylsulfonyl)-2-thia-4-azabicyclo[4.1.0]hept-3-en-3-amine (Example 232) (32 mg, 37% yield). LCMS (ESI$^+$) m/z=505.2 (M+H). $^1$H NMR (400 MHz, DMSO-d$_6$) δ ppm 8.51 (s, 1H) 8.42 (s, 1H) 7.71 (dd, J=8.02, 2.15 Hz, 1H) 7.60-7.68 (m, 1H) 7.27 (dd, J=11.93, 8.41 Hz, 1H) 6.87 (d, J=40.69 Hz, 1H) 6.70 (s, 2H) 5.74 (qd, J=6.65, 1.96 Hz, 1H) 3.57 (d, J=1.96 Hz, 1H) 3.12 (s, 3H) 2.21 (dd, J=9.78, 8.02 Hz, 1H) 1.90 (dd, J=10.17, 6.06 Hz, 1H) 1.74 (s, 3H) 1.61 (d, J=6.65 Hz, 3H) 0.82-0.90 (m, 1H).

(123 mg, 0.447 mmol), 1,1'-bis(diphenylphosphino)ferrocene palladium(II)dichloride dichloromethane adduct (12 mg, 0.015 mmol), sodium carbonate, 1M (298 μl, 0.298 mmol) were combined to provide the coupling product, which after deprotection with 4-methylbenzene sulfonic acid, monohydrate (248 mg, 1.30 mmol) gave 6-((Z)-2-(3-((1R,5S,6S)-3-amino-5-methyl-1-(methylsulfonyl)-2-thia-4-azabicyclo[4.1.0]hept-3-en-5-yl)-4-fluorophenyl)-1-fluorovinyl)nicotinonitrile (Example 233) (58 mg, 72% yield). LCMS (ESI$^+$) m/z=461.0 (M+H). $^1$H NMR (400 MHz, DMSO-d$_6$) δ ppm 9.08 (s, 1H) 8.45 (br d, J=8.22 Hz, 1H) 7.85 (d, J=8.22 Hz, 1H) 7.79 (br d, J=6.85 Hz, 1H) 7.72 (br s, 1H) 7.18-7.36 (m, 2H) 6.72 (s, 2H) 3.12 (s, 3H) 2.17-2.27 (m, 1H) 1.90 (dd, J=10.17, 6.06 Hz, 1H) 1.74 (s, 3H) 0.79-0.93 (m, 1H).

Synthesis of Intermediate 46

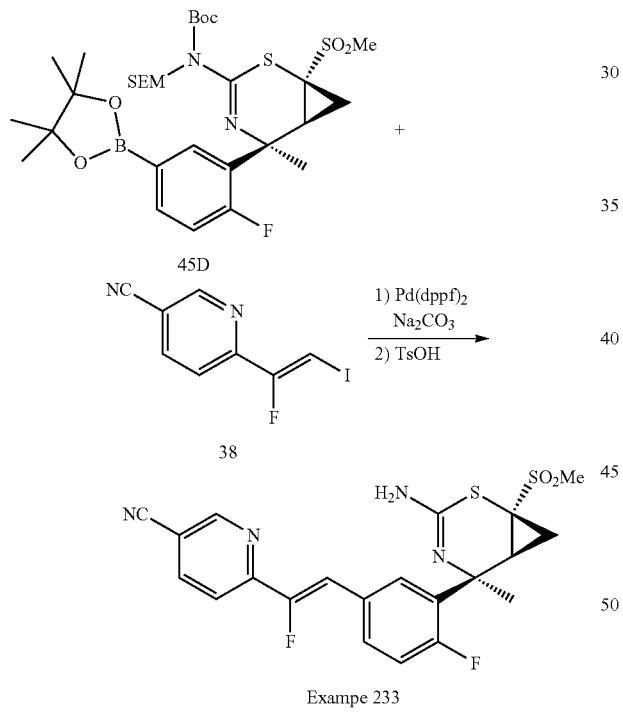

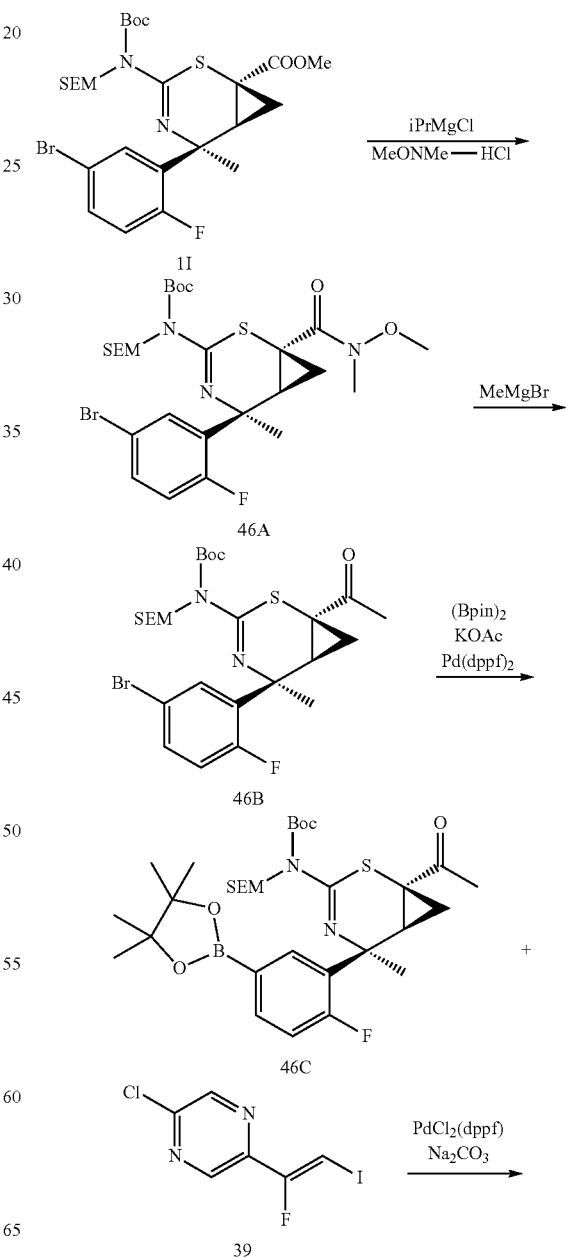

Preparation of 6-((Z)-2-(3-((1R,5S,6S)-3-amino-5-methyl-1-(methylsulfonyl)-2-thia-4-azabicyclo[4.1.0]hept-3-en-5-yl)-4-fluorophenyl)-1-fluorovinyl)nicotinonitrile (Example 233)

Using similar procedures described for 45 and Example 230, tert-butyl ((1R,5S,6S)-5-(2-fluoro-5-(4,4,5,5-tetramethyl-1,3,2-dioxaborolan-2-yl)phenyl)-5-methyl-1-(methylsulfonyl)-2-thia-4-azabicyclo[4.1.0]hept-3-en-3-yl)((2-(trimethylsilyl)ethoxy)methyl)carbamate (200 mg, 0.298 mmol), (Z)-6-(1-fluoro-2-iodovinyl)nicotinonitrile (38)

-continued

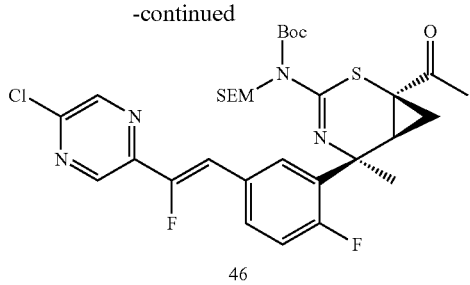

46

Preparation of tert-butyl ((1S,5S,6S)-5-(5-bromo-2-fluorophenyl)-1-(methoxy(methyl)carbamoyl)-5-methyl-2-thia-4-azabicyclo[4.1.0]hept-3-en-3-yl)((2-(trimethylsilyl)ethoxy)methyl)carbamate (46A)

To a stirring suspension of (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (11) (2.5 g, 4.1 mmol) and n,o-dimethylhydroxylamine hydrochloride (0.808 g, 8.28 mmol) in THF (25 mL) at −20° C. under nitrogen was added isopropyl magnesium chloride, isopropyl magnesium chloride, 2.0M in THF (12.43 ml, 24.85 mmol) at a rate that did not exceed −15° C. internal temp. After 5 minutes, the cooling bath was removed and the reaction stirred at 20° C. for 20 minutes. The reaction was then chilled to 0° C. and quenched with sat $NH_4Cl$. The reaction was then partitioned between 1:1 EtOAc (100 mL) and 1M HCl (100 mL). The organic was washed with brine (2×20 mL), dried over $MgSO_4$, concentrated under reduced pressure, then purified by silica gel chromatography (120 g) eluting products with a gradient of 0>20% (3:1 EtOAc/EtOH blend)/heptane to afford tert-butyl ((1S,5S,6S)-5-(5-bromo-2-fluorophenyl)-1-(methoxy(methyl)carbamoyl)-5-methyl-2-thia-4-azabicyclo[4.1.0]hept-3-en-3-yl)((2-(trimethylsilyl)ethoxy)methyl)carbamate (46A) (2.6 g, 99% yield) as colorless tar. LCMS (ESI$^+$) m/z=632.0/634.0 (M+H). $^1$H NMR (400 MHz, CHLOROFORM-d) δ ppm 7.68-7.73 (m, 1H) 7.30-7.38 (m, 1H) 6.89-6.99 (m, 1H) 5.18-5.26 (m, 1H) 4.92-5.01 (m, 1H) 3.76-3.81 (m, 3H) 3.60-3.74 (m, 2H) 3.20-3.26 (m, 3H) 2.51-2.62 (m, 1H) 1.76-1.80 (m, 3H) 1.49-1.52 (m, 9H) 1.32-1.36 (m, 1H) 0.99-1.06 (m, 1H) 0.82-0.92 (m, 2H) 0.00 (s, 9H).

Preparation of tert-butyl ((1S,5S,6S)-1-acetyl-5-(5-bromo-2-fluorophenyl)-5-methyl-2-thia-4-azabicyclo[4.1.0]hept-3-en-3-yl)((2-(trimethylsilyl)ethoxy)methyl)carbamate (46B)

To a stirring solution of tert-butyl ((1S,5S,6S)-5-(5-bromo-2-fluorophenyl)-1-(methoxy(methyl)carbamoyl)-5-methyl-2-thia-4-azabicyclo[4.1.0]hept-3-en-3-yl)((2-(trimethylsilyl)ethoxy)methyl)carbamate (46A) (2.6 g, 4.1 mmol) in THF (30 mL) at 0° C. under nitrogen was added methyl magnesium bromide 3.0m in diethyl ether (4.11 ml, 12.3 mmol) dropwise onto the side of the flask with internal temperature rising to 5° C. After stirring for 15 minutes at 0° C. the reaction was slowly quenched with dropwise addition of sat. $NH_4Cl$ (5 mL). The reaction was then partitioned between EtOAc (120 mL) and 1M HCl (75 mL). The separated organic was washed with sat NaCl (2×25 mL), dried over $MgSO_4$, filtered, then concentrated under reduced pressure, then purified by silica gel chromatography (120 g) eluting products with a gradient of 0>10% (3:1 EtOAc/EtOH blend)/heptane to afford tert-butyl ((1S,5S,6S)-1-acetyl-5-(5-bromo-2-fluorophenyl)-5-methyl-2-thia-4-azabicyclo[4.1.0]hept-3-en-3-yl)((2-(trimethylsilyl)ethoxy)methyl)carbamate (46B) (1.95 g, 81% yield) as colorless tar. LCMS (ESI$^+$) m/z=586.0/588.0 (M+H).

Preparation of tert-butyl ((1S,5S,6S)-1-acetyl-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (46C)

A suspension of tert-butyl ((1S,5S,6S)-1-acetyl-5-(5-bromo-2-fluorophenyl)-5-methyl-2-thia-4-azabicyclo[4.1.0]hept-3-en-3-yl)((2-(trimethylsilyl)ethoxy)methyl)carbamate (46B) (1.88 g, 3.20 mmol), bis(pinacolato)diboron (1.62 g, 6.40 mmol), 1,1'-bis(diphenylphosphino)ferrocene palladium(II)dichloride dichloromethane adduct (0.131 g, 0.160 mmol), potassium acetate (0.942 g, 9.60 mmol) in 1,4-dioxane (12 mL) was sparged with argon for 5 minutes then heated to 100° C. for 1 hour. The reaction was then partitioned between EtOAc (100 mL) and 5% $NaHCO_3$ (75 mL). The organic was then washed with sat. NaCl (2×50 mL), dried over $MgSO_4$, concentrated under reduced pressure (the residue azeotroped with 2×75 mL heptane), then purified via silica gel chromatography (120 g) eluting products with a 0>15% gradient of (3:1 EtOAc/EtOH blend)/heptane to afford tert-butyl ((1S,5S,6S)-1-acetyl-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (46C) (1.93 g, 95% yield) as colorless oil. LCMS (ESI$^+$) m/z=635.2 (M+H).

Preparation of tert-butyl ((1S,5S,6S)-1-acetyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (46)

A suspension of tert-butyl ((1S,5S,6S)-1-acetyl-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (46C) (1.6 g, 2.5 mmol), (Z)-2-chloro-5-(1-fluoro-2-iodovinyl)pyrazine (1.08 g, 3.78 mmol), 1,1'-bis(diphenylphosphino)ferrocene palladium(II)dichloride dichloromethane adduct (0.103 g, 0.126 mmol), sodium carbonate, 1M (7.56 ml, 7.56 mmol) in 1,4-dioxane (20 mL) was sparged with argon for 5 min then heated to 80° C. for 30 minutes. The reaction was then partitioned between EtOAc (75 mL) and 5% $NaHCO_3$ (50 mL). The separated organic was dried over $MgSO_4$, concentrated under reduced pressure, then purified by silica gel chromatography (80 g) eluting products with a gradient of 0>40% (3:1 EtOAc/EtOH)/heptane to afford tert-butyl ((1S,5S,6S)-1-acetyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (46) (1.0 g, 60% yield) as tan foam. LCMS (ESI$^+$) m/z=655.2 (M+H).

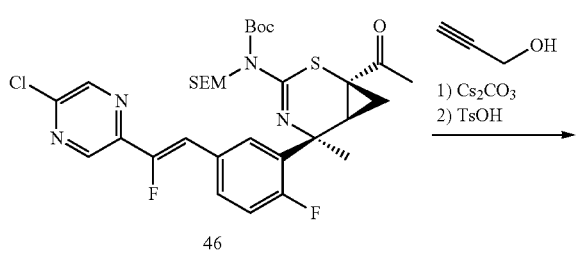

46

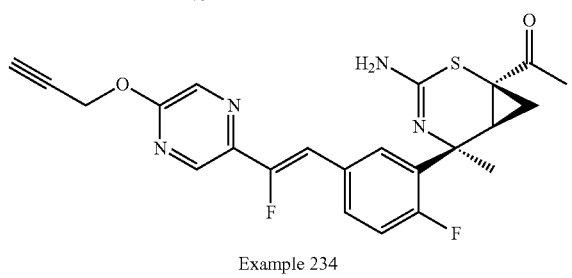

Example 234

Preparation of 1-((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)ethanone (Example 234)

A suspension of tert-butyl ((1S,5S,6S)-1-acetyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (46) (160 mg, 0.241 mmol), 2-propyn-1-ol (71.1 μl, 1.20 mmol), cesium carbonate (235 mg, 0.722 mmol) in 1,4-dioxane (1.5 mL) was to 95° C. for 3 hours. The reaction was then partitioned between EtOAc (15 mL) and 5% NaHCO$_3$ (5 mL). The organic was dried over MgSO$_4$, concentrated under reduced pressure. The residue was first dissolved in 1,4-dioxane (1 mL) and 4-methylbenzene sulfonic acid, monohydrate (45.7 mg, 0.241 mmol) added. The mixture was heated to 80° C. for 30 minutes. The reaction was then partitioned between EtOAc (20 mL) and 5% NaHCO$_3$ (10 mL). The organic was washed with brine. The organic was then dried over MgSO$_4$, concentrated under reduced pressure, then purified by silica gel chromatography (4 g) eluting products with a gradient of 0>25% ((3:1 EtOAc/EtOH blend)/heptane) to afford 1-((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)ethanone (Example 234) (52 mg, 48% yield) as white solid. LCMS (ESI$^+$) m/z=455.0 (M+H). $^1$H NMR (400 MHz, DMSO-d$_6$) δ ppm 8.52 (s, 1H) 8.46 (s, 1H) 8.07 (br d, J=6.85 Hz, 1H) 7.58-7.70 (m, 1H) 7.26 (dd, J=12.03, 8.51 Hz, 1H) 6.93 (d, J=40.49 Hz, 1H) 6.21 (s, 2H) 5.09 (d, J=1.96 Hz, 2H) 3.62 (s, 1H) 2.43 (t, J=8.51 Hz, 1H) 2.12 (s, 3H) 1.69 (dd, J=9.68, 5.38 Hz, 1H) 1.60 (s, 3H) 1.06 (t, J=6.36 Hz, 1H).

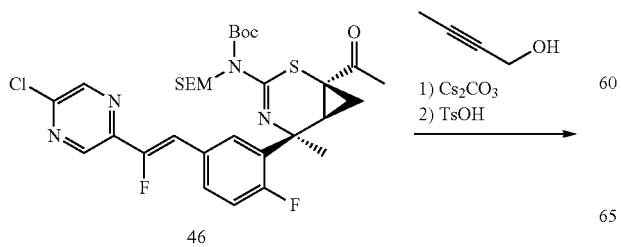

46

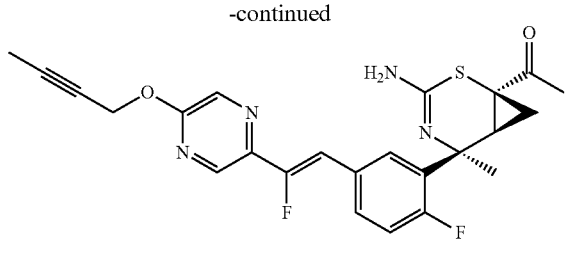

Example 235

Preparation of 1-((1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-en-1-yl)ethanone (Example 235)

Using a procedure similar to that described for (Example 234), tert-butyl ((1S,5S,6S)-1-acetyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (46) (160 mg, 0.241 mmol), 2-butyn-1-ol (180 μl, 2.40 mmol), cesium carbonate (392 mg, 1.20 mmol) were combined to afford SnAr product, which after deprotection with 4-methylbenzene sulfonic acid, monohydrate (343 mg, 1.80 mmol) gave 1-((1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-en-1-yl)ethanone (Example 235) (44 mg, 39% yield) as white solid. LCMS (ESI$^+$) m/z=469.2 (M+H). $^1$H NMR (400 MHz, DMSO-d$_6$) δ ppm 8.51 (s, 1H) 8.43 (s, 1H) 8.07 (br d, J=7.04 Hz, 1H) 7.65 (br d, J=3.52 Hz, 1H) 7.25 (dd, J=11.93, 8.61 Hz, 1H) 6.92 (d, J=40.49 Hz, 1H) 6.21 (s, 2H) 5.05 (br d, J=1.76 Hz, 2H) 2.43 (t, J=8.71 Hz, 1H) 2.12 (s, 3H) 1.86 (s, 3H) 1.69 (dd, J=9.68, 5.38 Hz, 1H) 1.60 (s, 3H) 1.05 (t, J=6.46 Hz, 1H)

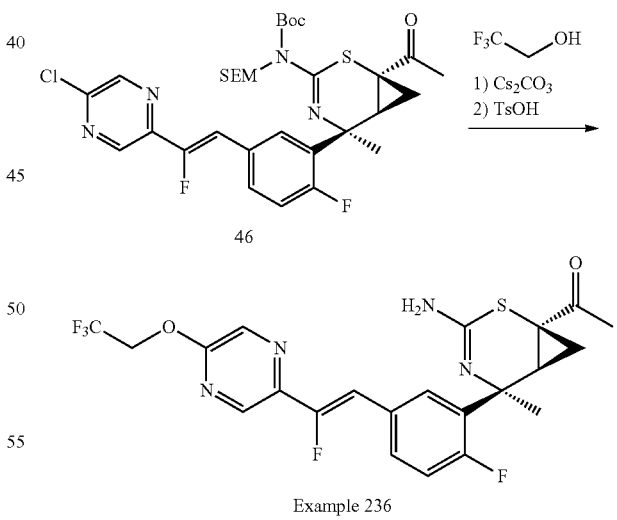

Example 236

Preparation of 1-((1S,5S,6S)-3-amino-5-(2-fluoro-5-((Z)-2-fluoro-2-(5-(2,2,2-trifluoroethoxy)pyrazin-2-yl)vinyl)phenyl)-5-methyl-2-thia-4-azabicyclo[4.1.0]hept-3-en-1-yl)ethanone (Example 236)

Using a procedure similar to that described for (Example 234), tert-butyl ((1S,5S,6S)-1-acetyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (46) (160 mg, 0.241 mmol), 2,2,2-trifluoroethanol (175 µl, 2.40 mmol), cesium carbonate (313 mg, 0.962 mmol) were combined to afford SnAr product, which after deprotection with 4-methylbenzene sulfonic acid, monohydrate (325 mg, 1.71 mmol gave 1-((1S,5S,6S)-3-amino-5-(2-fluoro-5-((Z)-2-fluoro-2-(5-(2,2,2-trifluoroethoxy)pyrazin-2-yl)vinyl)phenyl)-5-methyl-2-thia-4-azabicyclo[4.1.0]hept-3-en-1-yl)ethanone (Example 236) (85 mg, 71% yield) as white solid. LCMS (ESI⁺) m/z=499.0 (M+H). ¹H NMR (400 MHz, DMSO-d₆) δ ppm 8.59 (s, 1H) 8.55 (s, 1H) 8.08 (br d, J=7.43 Hz, 1H) 7.67 (br s, 1H) 7.26 (dd, J=12.03, 8.71 Hz, 1H) 6.98 (d, J=40.30 Hz, 1H) 6.21 (s, 2H) 5.12 (q, J=8.93 Hz, 2H) 2.43 (br t, J=8.80 Hz, 1H) 2.12 (s, 3H) 1.69 (br dd, J=9.59, 5.28 Hz, 1H) 1.61 (s, 3H) 1.05 (br t, J=6.26 Hz, 1H).

J=2.15 Hz, 1H) 2.38-2.47 (m, 1H) 2.12 (s, 3H) 1.69 (dd, J=9.68, 5.38 Hz, 1H) 1.57-1.65 (m, 6H) 1.06 (dd, J=7.14, 5.58 Hz, 1H).

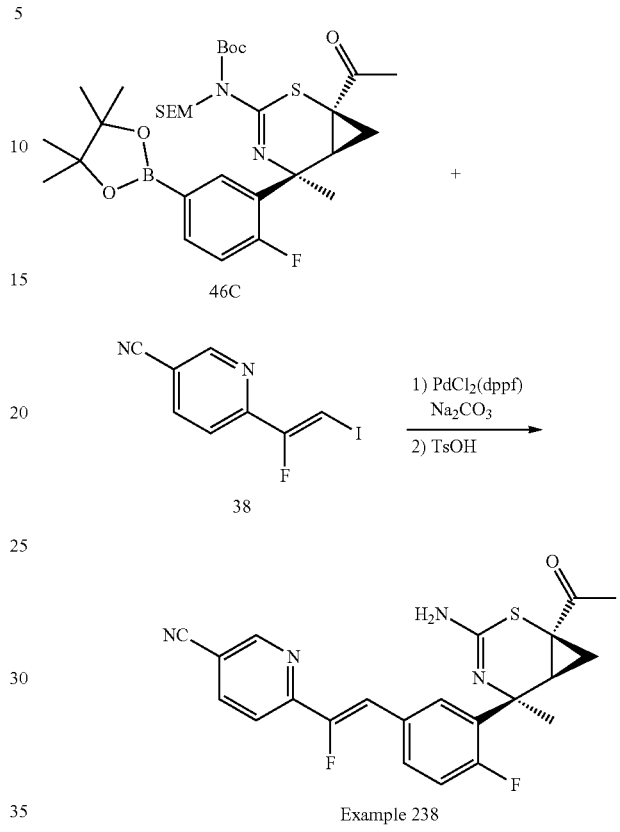

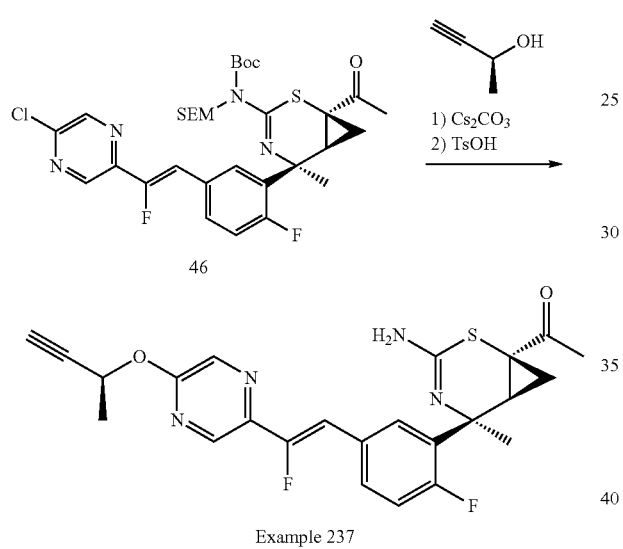

Preparation of 1-((1S,5S,6S)-3-amino-5-(5-((Z)-2-(5-((S)-but-3-yn-2-yloxy)pyrazin-2-yl)-2-fluorovinyl)-2-fluorophenyl)-5-methyl-2-thia-4-azabicyclo[4.1.0]hept-3-en-1-yl)ethanone (Example 237)

Using a procedure similar to that described for (Example 234), tert-butyl ((1S,5S,6S)-1-acetyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (46) (150 mg, 0.225 mmol), (S)-(−)-3-butyn-2-ol (179 µl, 2.26 mmol), cesium carbonate (367 mg, 1.13 mmol) were combined to afford SnAr product, which after deprotection with 4-methylbenzene sulfonic acid, monohydrate (343 mg, 1.80 mmol) gave 1-((1S,5S,6S)-3-amino-5-(5-((Z)-2-(5-((S)-but-3-yn-2-yloxy)pyrazin-2-yl)-2-fluorovinyl)-2-fluorophenyl)-5-methyl-2-thia-4-azabicyclo[4.1.0]hept-3-en-1-yl)ethanone (Example 237) (46 mg, 44% yield) as white solid. LCMS (ESI⁺) m/z=469.2 (M+H). ¹H NMR (400 MHz, DMSO-d₆) δ ppm 8.53 (s, 1H) 8.43 (s, 1H) 8.07 (dd, J=7.92, 2.05 Hz, 1H) 7.61-7.70 (m, 1H) 7.26 (dd, J=12.13, 8.41 Hz, 1H) 6.93 (d, J=40.88 Hz, 1H) 6.21 (s, 2H) 5.75 (qd, J=6.62, 1.86 Hz, 1H) 3.57 (d, Preparation of 6-((Z)-2-(3-((1S,5S,6S)-1-acetyl-3-amino-5-methyl-2-thia-4-azabicyclo[4.1.0]hept-3-en-5-yl)-4-fluorophenyl)-1-fluorovinyl)nicotinonitrile (Example 238)

Using a procedure similar to that described for Example 233, tert-butyl ((1S,5S,6S)-1-acetyl-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (350 mg, 0.551 mmol), (Z)-6-(1-fluoro-2-iodovinyl)nicotinonitrile 38 (227 mg, 0.827 mmol), 1,1'-bis(diphenylphosphino)ferrocene palladium(II)dichloride dichloromethane adduct (23 mg, 0.028 mmol), and sodium carbonate were combined to afford the coupling product, which after deprotection with 4-methylbenzene sulfonic acid, monohydrate (160 mg, 0.840 mmol) gave 6-((Z)-2-(3-((1S,5S,6S)-1-acetyl-3-amino-5-methyl-2-thia-4-azabicyclo[4.1.0]hept-3-en-5-yl)-4-fluorophenyl)-1-fluorovinyl)nicotinonitrile (Example 238) (78 mg, 55% yield) as white solid. LCMS (ESI⁺) m/z=425.0 (M+H). ¹H NMR (400 MHz, DMSO-d₆) δ ppm 9.08 (s, 1H) 8.45 (d, J=8.22 Hz, 1H) 8.14 (br d, J=7.24 Hz, 1H) 7.87 (d, J=8.41 Hz, 1H) 7.74 (br s, 1H) 7.24-7.40 (m, 2H) 6.23 (br s, 2H) 2.44 (brt, J=8.41 Hz, 1H) 2.12 (s, 3H) 1.70 (br dd, J=9.19, 5.48 Hz, 1H) 1.61 (s, 3H) 1.06 (br t, J=5.97 Hz, 1H).

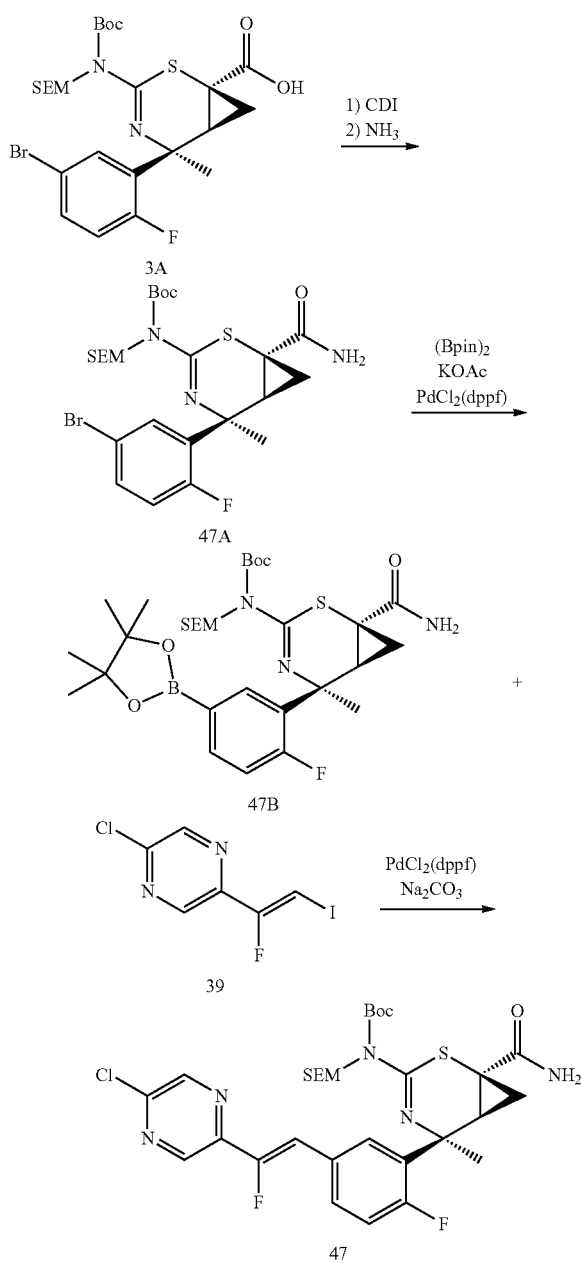

Preparation of tert-butyl ((1S,5S,6S)-5-(5-bromo-2-fluorophenyl)-1-carbamoyl-5-methyl-2-thia-4-azabicyclo[4.1.0]hept-3-en-3-yl)((2-(trimethylsilyl)ethoxy)methyl)carbamate (47A)

To a stirring solution (1S,5S,6S)-5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (3A) (24 g, 41 mmol) in THF (250 mL) at 20° C. was added 1,1'-carbonyldiimidazole (9.9 g, 61 mmol) in one portion. The solution was stirred for 0.75 hour at 20° C., then chilled to 0° C., and gaseous ammonia introduced into the flask headspace. After 5 min the reaction was then partitioned between EtOAc (400 mL) and 0.5M HCl (400 mL). The organic was washed with brine (2×50 mL), dried over MgSO$_4$, concentrated under reduced, then purified by silica gel chromatography (330 g) eluting products with a gradient of 0>25% EtOAc/heptane to afford tert-butyl ((1S,5S,6S)-5-(5-bromo-2-fluorophenyl)-1-carbamoyl-5-methyl-2-thia-4-azabicyclo[4.1.0]hept-3-en-3-yl)((2-(trimethylsilyl)ethoxy)methyl)carbamate (47A) (17.5 g, 73% yield) as colorless oil. LCMS (ESI$^+$) m/z=588.1/590.0 (M+H).

Preparation of tert-butyl ((1S,5S,6S)-1-carbamoyl-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (47B)

A suspension of tert-butyl ((1S,5S,6S)-5-(5-bromo-2-fluorophenyl)-1-carbamoyl-5-methyl-2-thia-4-azabicyclo[4.1.0]hept-3-en-3-yl)((2-(trimethylsilyl)ethoxy)methyl)carbamate (24 g, 40.8 mmol), bis(pinacolato)diboron (47A) (21 g, 82 mmol), 1,1'-bis(diphenylphosphino)ferrocene palladium(II)dichloride dichloromethane adduct (0.666 g, 0.815 mmol), potassium acetate (12.0 g, 122 mmol) in 1,4-dioxane (200 mL) was sparged with argon for 5 min then heated to 100° C. for 45 minutes. The reaction was then partitioned between EtOAc (1 L) and 5% aq. NaHCO$_3$ (300 mL). The organic was then washed with brine (2×50 mL), dried over MgSO$_4$, concentrated under reduced pressure (the residue azeotroped with heptane (50 mL)), then purified via silica gel chromatography (330 g) eluting products with a 0>20% gradient of (3:1 EtOAc/EtOH)/heptane to afford tert-butyl ((1S,5S,6S)-1-carbamoyl-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (47B) (7.5 g, 12 mmol, 29% yield) as colorless oil. LCMS (ESI$^+$) m/z=636.2 (M+H).

Preparation of tert-butyl ((1S,5S,6S)-1-carbamoyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (47)

A suspension of tert-butyl ((1S,5S,6S)-1-carbamoyl-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (47B) (7.5 g, 12 mmol), (Z)-2-chloro-5-(1-fluoro-2-iodovinyl)pyrazine (4.36 g, 15.3 mmol) (39), 1,1'-bis(diphenylphosphino)ferrocene palladium(II)dichloride dichloromethane adduct (0.241 g, 0.295 mmol), sodium carbonate (3.75 g, 35.4 mmol) in 1,4-dioxane (75 mL) was sparged with argon for 5 minutes then heated to 80° C. for 30 min. The reaction was then partitioned between EtOAc (300 mL) and 5% aq. NaHCO$_3$ (200 mL). The organic extract was dried over MgSO$_4$, concentrated under reduced pressure, then purified by silica gel chromatography (220 g) eluting products with a gradient of 0>30% (3:1 EtOAc/EtOH)/heptane to afford tert-butyl ((1S,5S,6S)-1-carbamoyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (47) (6.4, 81% yield) as amber viscous oil. LCMS (ESI$^+$) m/z=666.2 (M+H). $^1$H NMR (400 MHz, DMSO-d$_6$) δ ppm 8.85 (s, 1H) 8.78 (s, 1H) 7.99 (br d, J=6.26 Hz, 1H) 7.68-7.80 (m, 1H) 7.25-7.45 (m, 3H) 7.18 (d, J=40.10 Hz, 1H) 5.17 (d, J=10.76 Hz, 1H) 4.99 (d, J=10.76 Hz, 1H) 3.55-3.64 (m, 2H) 2.45 (br d, J=9.19 Hz, 1H) 1.68 (s, 3H) 1.46 (s, 9H) 1.39-1.44 (m, 1H) 1.03 (t, J=6.36 Hz, 1H) 0.80-0.90 (m, 2H) −0.09--0.06 (m, 9H).

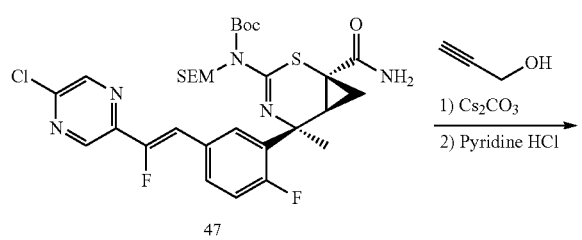

47

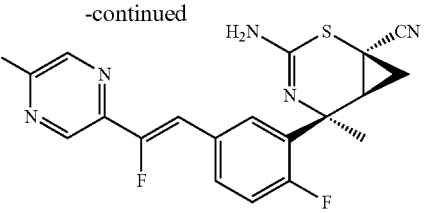

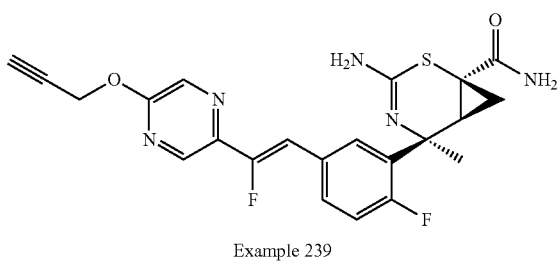

Example 239

Preparation of (1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxamide (Example 239)

Using a procedure similar to that described for (Example 234), tert-butyl ((1S,5S,6S)-1-carbamoyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (47) (2.0 g, 3.0 mmol), propargyl alcohol (1.346 g, 24.01 mmol), cesium carbonate (3.91 g, 12.0 mmol) were combined to afford SnAr product. The product was treated with pyridine hydrochloride (505 mg, 4.37 mmol) in MeCN (2 mL) was heated to 70° C. for 6 h. The reaction was partitioned between 9:1 CHCl3/IPA (20 mL) and sat NaHCO₃ (20 mL). The aqueous was further extracted with 9:1 CHCl₃/IPA (5 mL). The combined organics were dried over MgSO4, filtered, concentrated under reduced pressure, then purified by silica gel chromatography (40 g) eluting products with a gradient of 0>50% 4:1 EtOAc/EtOH blend/heptane to afford (1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxamide (Example 239) (57 mg, 43% yield) as white solid. LCMS (ESI⁺) m/z=456.0 (M+H). ¹H NMR (400 MHz, DMSO-d₆) δ ppm 8.52 (s, 1H) 8.46 (s, 1H) 8.01 (br d, J=6.06 Hz, 1H) 7.60-7.67 (m, 1H) 7.25 (br dd, J=12.13, 8.41 Hz, 3H) 6.91 (d, J=40.69 Hz, 1H) 6.15 (s, 2H) 5.09 (d, J=2.15 Hz, 2H) 3.62 (t, J=2.25 Hz, 1H) 2.20 (t, J=8.41 Hz, 1H) 1.62 (s, 3H) 1.40 (dd, J=9.59, 5.09 Hz, 1H) 0.77-0.84 (m, 1H).

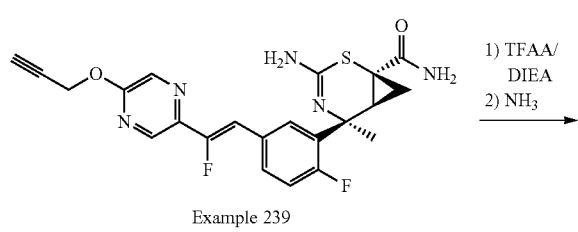

Example 239

1) TFAA/DIEA
2) NH₃

→

Example 240

Preparation of (1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carbonitrile (Example 240)

To a stirring solution of (1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxamide (Example 239) (300 mg, 0.659 mmol) and n,n-diisopropylethylamine (115 µl, 6.59 mmol) in THF (5 mL) at −70° C. under nitrogen was added 2,2,2-trifluoroacetic anhydride (549 µl, 3.95 mmol). The solution was stirred for 15 minutes then quenched with sat NH₄Cl (5 mL). After the reaction was warmed to 0° C., the mixture was partitioned between 9:1 CHCl₃/IPA (20 mL) and sat NaHCO₃ (20 mL). The aqueous was extracted with 9:1 CHCl₃/IPA (5 mL). The combined organic extracts were dried over MgSO₄, filtered, then concentrated under reduced pressure. The intermediate was dissolved in a freshly prepared saturated solution of ammonia in THF (3 mL) in a closed screw top vial. After 10 minutes, the solvent was removed under reduced pressure and the residue was then purified by silica gel chromatography (40 g) eluting products with a gradient of 0>25% EtOAc/heptane to afford (1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carbonitrile (Example 240) (96 mg, 33% yield) as white foam. LCMS (ESI⁺) m/z=438.2 (M+H). ¹H NMR (400 MHz, DMSO-d₆) δ ppm 8.49 (s, 1H) 8.45 (s, 1H) 7.78 (br d, J=6.06 Hz, 1H) 7.64 (br dd, J=7.24, 3.72 Hz, 1H) 7.26 (dd, J=11.93, 8.61 Hz, 1H) 6.88 (d, J=41.28 Hz, 1H) 6.61 (s, 2H) 5.08 (d, J=2.15 Hz, 2H) 3.61 (s, 1H) 2.39 (t, J=8.71 Hz, 1H) 1.87 (dd, J=9.68, 5.97 Hz, 1H) 1.74 (s, 3H) 0.98 (t, J=6.75 Hz, 1H).

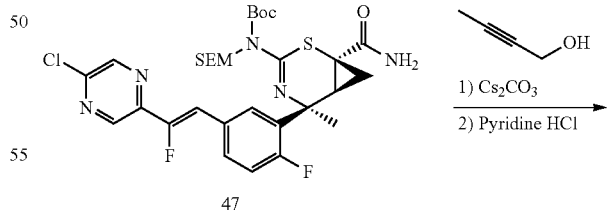

47

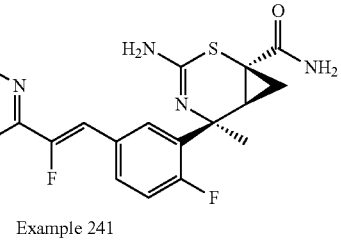

Example 241

Preparation of (1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-ene-1-carboxamide (Example 241)

Using a procedure similar to that described for Example 239, tert-butyl ((1S,5S,6S)-1-carbamoyl-5-(5-((Z)-2-(5-chloropyrazin-2-yl)-2-fluorovinyl)-2-fluorophenyl)-5-methyl-2-thia-4-azabicyclo[4.1.0]hept-3-en-3-yl)((2-(trimethylsilyl)ethoxy)methyl)carbamate (47) (1.0 g, 1.5 mmol), 2-butyn-1-ol (0.842 g, 12.0 mmol), cesium carbonate (1.96 g, 6.00 mmol) were combined to afford SnAr product, which was treated with pyridine hydrochloride (2.353 g, 20.36 mmol) were combined to afford (1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-ene-1-carboxamide (Example 241) (290 mg, 0.618 mmol, 46% yield) as white solid. LCMS (ESI$^+$) m/z=470.0 (M+H). $^1$H NMR (400 MHz, DMSO-d$_6$) δ ppm 8.50 (br s, 1H) 8.42 (br s, 1H) 8.00 (br s, 1H) 7.63 (br s, 1H) 7.23 (br s, 3H) 6.89 (d, J=41.08 Hz, 1H) 6.14 (br s, 2H) 5.04 (br s, 2H) 2.19 (br s, 1H) 1.85 (br s, 3H) 1.61 (br s, 3H) 1.39 (br s, 1H) 0.86 (br s, 1H).

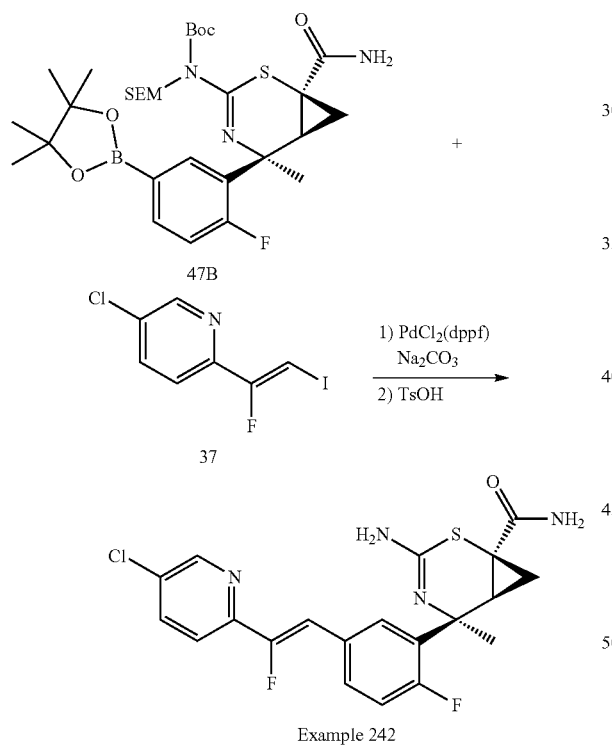

Example 242

Preparation of (1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxamide (Example 242)

Using procedures similar to those described for 47 and Example 239, tert-butyl ((1S,5S,6S)-1-carbamoyl-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (47B) (500 mg, 0.787 mmol), (Z)-5-chloro-2-(1-fluoro-2-iodovinyl)pyridine (37) (334 mg, 1.18 mmol), 1,1'-bis(diphenylphosphino)ferrocene palladium(II)dichloride dichloromethane adduct (32.1 mg, 0.039 mmol), sodium carbonate (250 mg, 2.360 mmol) were combined to afford cross-coupled product which was treated with pyridine hydrochloride (782 mg, 6.76 mmol) to afford (1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxamide (Example 242) (80 mg, 41% yield) as a white solid. LCMS (ESI$^+$) m/z=435.0 (M+H).

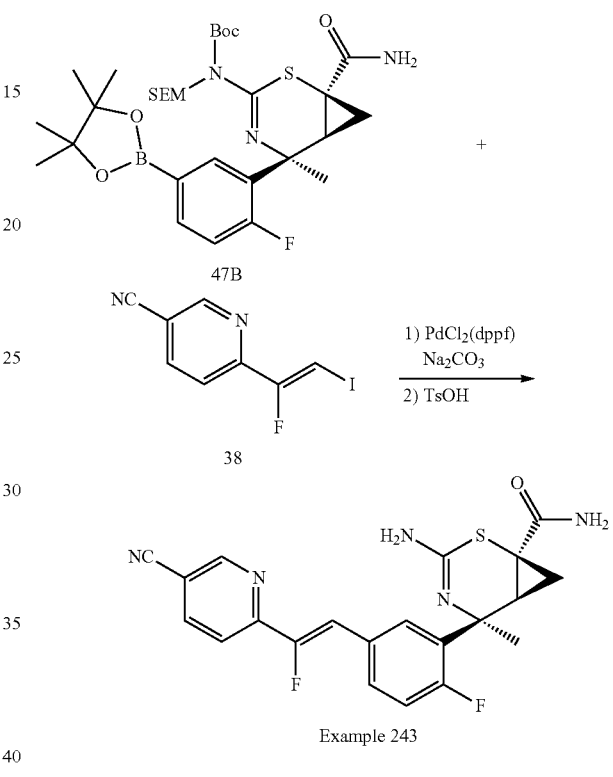

Example 243

Preparation of (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxamide (Example 243)

Using a procedure similar to that described for Example 242 tert-butyl ((1S,5S,6S)-1-carbamoyl-5-(2-fluoro-5-(4,4,5,5-tetramethyl-1,3,2-dioxaborolan-2-yl)phenyl)-5-methyl-2-thia-4-azabicyclo[4.1.0]hept-3-en-3-yl)((2-(trimethylsilyl)ethoxy)methyl)carbamate (500 mg, 0.787 mmol), (Z)-5-chloro-2-(1-fluoro-2-iodovinyl)pyridine (334 mg, 1.180 mmol), 1,1'-bis(diphenylphosphino)ferrocene palladium(II) dichloride dichloromethane adduct (32.1 mg, 0.039 mmol), sodium carbonate (250 mg, 2.360 mmol) were combined to afford cross-coupled product, which was treated with pyridine hydrochloride (925 mg, 8.01 mmol) to afford (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxamide (Example 243) (100 mg, 22% yield) as a white solid. LCMS (ESI$^+$) m/z=426.0 (M+H). $^1$H NMR (400 MHz, DMSO-d$_6$) δ ppm 9.07 (d, J=1.96 Hz, 1H) 8.44 (dd, J=8.41, 2.15 Hz, 1H) 8.07 (dd, J=8.02, 2.15 Hz, 1H) 7.85 (d, J=8.02 Hz, 1H) 7.67-7.75 (m, 1H) 7.15-7.36 (m, 4H) 6.16 (s, 2H) 2.20 (dd, J=9.00, 7.83 Hz, 1H) 1.61 (s, 3H) 1.40 (dd, J=9.78, 5.09 Hz, 1H) 0.80 (dd, J=6.94, 5.38 Hz, 1H).

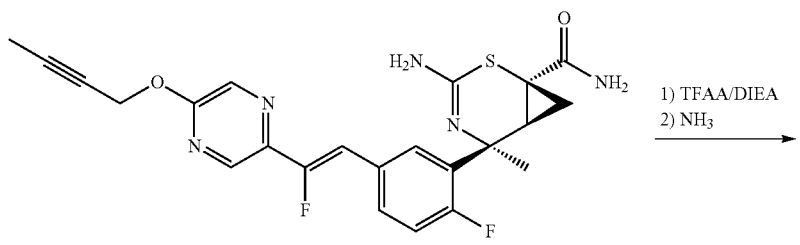

Example 241

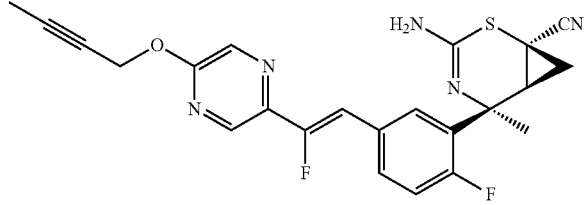

Example 244

Preparation of (1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-ene-1-carbonitrile (Example 244)

Using a procedure similar to that described for Example 240 (1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-ene-1-carboxamide (Example 241) (175 mg, 0.373 mmol), n,n-diisopropylethylamine (648 µl, 3.73 mmol), 2,2,2-trifluoroacetic anhydride (311 µl, 2.236 mmol) were combined to create trifluoroacetamide intermediate, which after deprotection gave (1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-ene-1-carbonitrile (Example 244) (58 mg, 34% yield) as a white solid. LCMS (ESI+) m/z=452.1 (M+H). $^1$H NMR (400 MHz, DMSO-d$_6$) δ ppm 8.48 (s, 1H) 8.42 (s, 1H) 7.74-7.81 (m, 1H) 7.59-7.67 (m, 1H) 7.25 (dd, J=11.93, 8.61 Hz, 1H) 6.86 (d, J=40.69 Hz, 1H) 6.61 (s, 2H) 5.03 (d, J=2.35 Hz, 2H) 2.35-2.43 (m, 1H) 1.82-1.90 (m, 4H) 1.74 (s, 3H) 0.97 (t, J=6.85 Hz, 1H).

Preparation of (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carbonitrile (Example 245)

Using a procedure similar to that described for (Example 240), (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxamide (Example 243) (400 mg, 0.940 mmol), n,n-diisopropylethylamine (1.60 mL, 9.40 mmol), and 2,2,2-trifluoroacetic anhydride (784 µl, 5.64 mmol) were combined to create trifluoroacetamide intermediate, which after deprotection gave (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carbonitrile (Example 245) (100 mg, 26% yield) as a white solid. LCMS (ESI+) m/z=408.0 (M+H). $^1$H NMR (400 MHz, DMSO-d$_6$) δ ppm 9.07 (d, J=1.96 Hz, 1H) 8.44 (dd, J=8.41, 2.15 Hz, 1H) 7.80-7.88 (m, 2H) 7.68-7.76 (m, 1H) 7.17-7.35 (m, 2H) 6.63 (s, 2H) 2.40 (dd, J=9.59, 8.02 Hz, 1H) 1.88 (dd, J=9.78, 5.87 Hz, 1H) 1.74 (s, 3H) 0.98 (t, J=6.65 Hz, 1H).

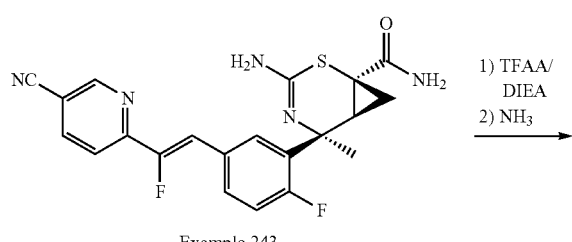

Example 243

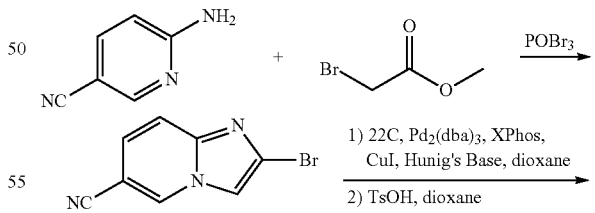

48

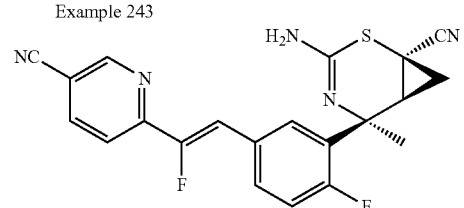

Example 245

246

249

Preparation of (1S,5S,6S)-3-amino-5-(5-((Z)-2-(6-cyanoimidazo[1,2-a]pyridin-2-yl)-2-fluorovinyl)-2-fluorophenyl)-N,N,5-trimethyl-2-thia-4-azabicyclo[4.1.0]hept-3-ene-1-carboxamide (Example 246)

2-Amino-5-cyanopyridine (1.0 g, 8.4 mmol) and methyl bromoacetate (4.66 ml, 50.4 mmol) were combined in a round bottom flask and heated to 80° C. for 2 hours. The mixture was concentrated in vacuo, combined with phosphorous (V) oxybromide (5.13 ml, 50.5 mmol) and heated to 130° C. for 2 hours at which point LCMS analysis indicated full consumption of the starting material. The mixture was diluted with acetonitrile, and carefully poured into pH 10 water at 10° C. 1N aqueous sodium hydroxide was added to the mixture until it reached pH 8.5, at which point it was extracted with EtOAc (50 mL×2). The organic layers were dried over MgSO₄, concentrated, fused onto silica and purified via column chromatography (0 to 60% 3:1 EtOAc/EtOH gradient in heptane) to give 2-bromoimidazo[1,2-a]pyridine-6-carbonitrile (48) (0.45 g, 25% yield) as an intractable mixture with 2,3-dibromoimidazo[1,2-a]pyridine-6-carbonitrile in a 2.5:1 ratio.

2-(Dicyclohexylphosphino)-2',4',6',-tri-isopropyl-1,1'-biphenyl (0.026 g, 0.054 mmol), tris(dibenzylideneacetone)dipalladium (0.021 g, 0.036 mmol), 2-bromoimidazo[1,2-a]pyridine-6-carbonitrile (48) (0.160 g, 0.721 mmol), copper iodide (0.069 g, 0.36 mmol), and Hunig's base (0.140 g, 1.08 mmol) were combined in heat-gun dried vial in a nitrogen filled dry-box. The vial was capped, removed from the drybox and 0.3 mL of dioxane were added. This mixture was stirred at 23° C. for 1 hour, at which point a solution of tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (0.314 g, 0.360 mmol) in 0.1 mL of dioxane was added. The mixture was then heated to 80° C. for 24 hours. Upon completion, the reaction mixture was diluted with DCM (2 mL), fused onto SiO₂ and then purified via column chromatography using a 0-50% 3:1 EtOAc/EtOH gradient in heptane. Deprotection was achieved by combining the reaction product, tert-butyl ((1S,5S,6S)-5-(5-((Z)-2-(6-cyanoimidazo[1,2-a]pyridin-2-yl)-2-fluorovinyl)-2-fluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (0.061 g, 0.084 mmol), with 4-methylbenzene sulfonic acid monohydrate (0.048 g, 0.25 mmol) in 1,4-dioxane (0.844 ml). The mixture was stirred at 80° C. for 10 hours, at which point LCMS analysis indicated full consumption of the starting material and conversion to the desired product. The mixture was then diluted with EtOAc (5 mL) and quenched with sat. aqueous NaHCO₃. The aqueous layer was extracted with EtOAc (5 mL×3), the combined organic washings were dried over MgSO₄ and concentrated. The crude residue was purified via reverse phase HPLC (0-95% gradient of MeCN in water). The combined HPLC fractions were liberated of salts by washing with sat. aqueous NaHCO₃ and concentrated to give (1S,5S,6S)-3-amino-5-(5-((Z)-2-(6-cyanoimidazo[1,2-a]pyridin-2-yl)-2-fluorovinyl)-2-fluorophenyl)-N,N,5-trimethyl-2-thia-4-azabicyclo[4.1.0]hept-3-ene-1-carboxamide (Example 246) (0.020 g, 48% yield) as an off-white solid. LCMS (ESI) m/z=493.4 (M+H). 1H NMR (400 MHz, DMSO-d6) δ 9.26-9.37 (m, 1H), 8.26 (s, 1H), 7.85 (d, J=7.04 Hz, 1H), 7.68-7.77 (m, 1H), 7.54-7.67 (m, 2H), 7.22 (dd, J=8.61, 11.93 Hz, 1H), 6.69-6.86 (m, 1H), 6.22-6.57 (m, 2H), 2.70-3.24 (m, 6H), 2.09 (t, J=8.22 Hz, 1H), 1.70 (s, 3H), 1.26-1.38 (m, 1H), 0.70 (t, J=6.06 Hz, 1H). NMR (376 MHz, DMSO-d₆) δ -110.65 (br. s., 1F), -121.15 (br. s., 1F).

250

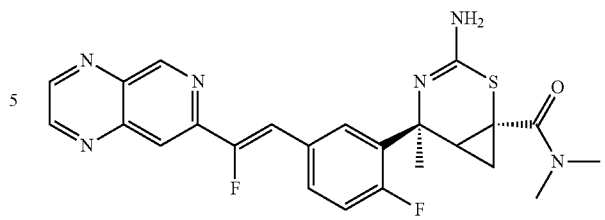

Example 247

Preparation of (1S,5S,6S)-3-amino-5-(2-fluoro-5-((Z)-2-fluoro-2-(pyrido[3,4-b]pyrazin-7-yl)vinyl)phenyl)-N,N,5-trimethyl-2-thia-4-azabicyclo[4.1.0]hept-3-ene-1-carboxamide (Example 247)

Using a procedure similar to that described for Example 219, 7-bromopyrido[3,4-b]pyrazine (121 mg, 0.574 mmol), bis(di-tert-butyl(4-dimethylaminophenyl)phosphine)dichloropalladium(II) (9.8 mg, 0.014 mmol) and copper(I) iodide (43 mg, 0.23 mmol), tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (200 mg, 0.230 mmol) were combined to give the coupling product, which after deprotection with 4-methylbenzenesulfonic acid hydrate (0.013 g, 0.066 mmol) gave (1S,5S,6S)-3-amino-5-(2-fluoro-5-((Z)-2-fluoro-2-(pyrido[3,4-b]pyrazin-7-yl)vinyl)phenyl)-N,N,5-trimethyl-2-thia-4-azabicyclo[4.1.0]hept-3-ene-1-carboxamide (Example 247) (0.014 mg, 44% yield) as a light yellow solid. 1H NMR (400 MHz, DMSO-d6) δ ppm 9.54 (s, 1H), 9.08-9.30 (m, 2H), 8.14 (s, 1H), 7.61-7.81 (m, 2H), 7.35-7.61 (m, 1H), 7.21-7.31 (m, 1H), 6.33 (br s, 2H), 2.70-3.20 (m, 6H), 1.86 (s, 1H), 1.70 (s, 3H), 1.30 (br dd, J=9.49, 5.58 Hz, 1H), 0.85 (br s, 1H).

Synthesis of Intermediate 49

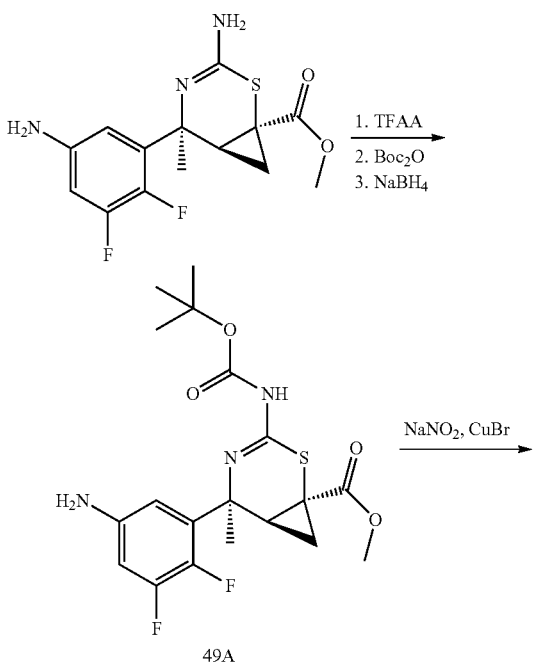

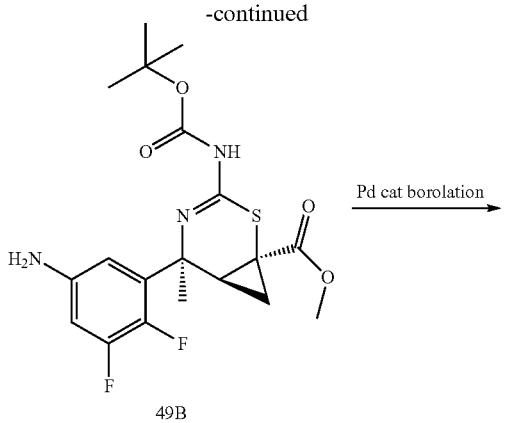

49B

Preparation of (1S,5S,6S)-methyl 5-(5-amino-2,3-difluorophenyl)-3-((tert-butoxycarbonyl)amino)-5-methyl-2-thia-4-azabicyclo[4.1.0]hept-3-ene-1-carboxylate (49A)

(1S,5S,6S)-Methyl 3-amino-5-(5-amino-2,3-difluorophenyl)-5-methyl-2-thia-4-azabicyclo[4.1.0]hept-3-ene-1-carboxylate (WO 2016/022724) (3.50 g, 10.7 mmol) was dissolved in dichloromethane (50 mL) and treated with 2,2,2-trifluoroacetic anhydride (4.0 ml, 29 mmol). The reaction was stirred for 5 minutes after which the dark solution was evaporated to dryness under reduced pressure and the crude oil re-dissolved in methanol (150 mL). Sodium hydroxide (10N, 1.0 ml, 10.00 mmol) was added and the solution stirred at room temperature for 5 minutes. 5N Hydrochloric acid (2 mL) was added followed by 50% brine (150 mL) and ethyl acetate (150 mL). The phases were mixed and separated and the organic dried with brine (75 mL) before evaporating to dryness under reduced pressure. The crude was dissolved in dry tetrahydrofuran (10 mL) and treated with di-tert-butyl dicarbonate (2.50 g, 11.4 mmol) and 4-dimethylaminopyridine (0.250 g, 2.05 mmol). The dark mixture was heated in a 50° C. bath for 16 hours. The reaction was cooled to room temperature and ethyl acetate (200 mL) and 0.5N hydrochloric acid (75 mL) were added. The phases mixed and separated. The organic was dried with brine (75 mL) and evaporated to dryness under reduced pressure. The crude (1S,5S,6S)-methyl 3-((tert-butoxycarbonyl)amino)-5-(2,3-difluoro-5-(2,2,2-trifluoroacetamido)phenyl)-5-methyl-2-thia-4-azabicyclo[4.1.0]hept-3-ene-1-carboxylate (5.6 g, 11 mmol) was dissolved in ethanol (25 mL) and cooled in an ice water bath. Sodium borohydride (0.405 g, 10.7 mmol) was added in one portion and the reaction stirred for 40 minutes. Ethyl acetate (150 mL) and 50% saturated aq. NH$_4$Cl (75 mL) were added and the phases mixed for 5 minutes. The organic was dried with brine (75 mL) and evaporated to dryness under reduced pressure. Purification using silica chromatography (heptane to ethyl acetate gradient) gave (1S,5S,6S)-methyl 5-(5-amino-2,3-difluorophenyl)-3-((tert-butoxycarbonyl)amino)-5-methyl-2-thia-4-azabicyclo[4.1.0]hept-3-ene-1-carboxylate (49A) (2.7 g, 59% yield). LC/MS (ESI$^+$) m/z=428.1 (M+H).

Preparation of (1S,5S,6S)-methyl 5-(5-bromo-2,3-difluorophenyl)-3-((tert-butoxycarbonyl)amino)-5-methyl-2-thia-4-azabicyclo[4.1.0]hept-3-ene-1-carboxylate (49B)

(1S,5S,6S)-Methyl 5-(5-amino-2,3-difluorophenyl)-3-((tert-butoxycarbonyl)amino)-5-methyl-2-thia-4-azabicyclo[4.1.0]hept-3-ene-1-carboxylate (2.7 g, 6.3 mmol) (49A), 4-methylbenzene sulfonic acid, monohydrate (1.40 g, 7.36 mmol), tetrabutylammonium bromide (5.0 g, 16 mmol), copper(I) bromide (1.02 g, 7.11 mmol), and sodium nitrite (0.55 g, 8.0 mmol) were placed in a RBF and subjected to house vac/nitrogen flush twice. Acetonitrile (25 mL) was added and the reaction stirred at room temperature under nitrogen for 2.5 hours. Additional acetonitrile (75 mL) and sodium nitrite (0.55 g) were added and the reaction stirred at room temperature for another 15 hours. Water (150 mL), brine (50 mL) and ethyl acetate (250 mL) were added and the phases mixed and separated. The organic portion was washed with a mixture of water (100 mL), saturated aq. NH$_4$Cl (50 mL) and aq. NH$_4$OH (30 mL), and subsequently washed with brine (100 mL). The organic portion was evaporated to dryness under reduced pressure. The crude was purified using silica chromatography (heptane to ethyl acetate gradient) to give (1S,5S,6S)-methyl 5-(5-bromo-2,3-difluorophenyl)-3-((tert-butoxycarbonyl)amino)-5-methyl-2-thia-4-azabicyclo[4.1.0]hept-3-ene-1-carboxylate (49B) (1.7 g, 55% yield) as a white solid. LC/MS (ESI$^+$) m/z=435.0 (M+H).

Preparation of (1S,5S,6S)-methyl 3-((tert-butoxycarbonyl)amino)-5-(2,3-difluoro-5-(4,4,5,5-tetramethyl-1,3,2-dioxaborolan-2-yl)phenyl)-5-methyl-2-thia-4-azabicyclo[4.1.0]hept-3-ene-1-carboxylate (49)

(1S,5S,6S)-Methyl 5-(5-bromo-2,3-difluorophenyl)-3-((tert-butoxycarbonyl)amino)-5-methyl-2-thia-4-azabicyclo[4.1.0]hept-3-ene-1-carboxylate (1.73 g, 3.52 mmol) (49B), cesium carbonate (3.44 g, 10.6 mmol), potassium acetate (0.346 g, 3.52 mmol), 1,1'-bis(diphenylphosphino)ferrocene palladium(II)dichloride, dichloromethane adduct (0.288 g, 0.352 mmol), and bis(pinacolato) diboron (1.79 g, 7.04 mmol) were combined in a round bottomed flask and placed under house vac/flushed with nitrogen twice. Dry dimethylsulfoxide (12 mL) was added and the mixture once again subjected to house vac/nitrogen flush before heating to 70° C. The reaction was stirred for 12 hours then cooled and diluted with ethyl acetate (100 mL). The suspension was filtered through a sintered glass frit and the filtrate transferred to a separatory funnel. Water (100 mL), methyl tert-butyl ether (250 mL), and brine (50 mL) were added and the phases mixed and separated. The organic was washed with water (75 mL) then dried with brine (75 mL) and evaporated to dryness under reduced pressure. Purification using silica chromatography (heptane to ethyl acetate gradient, wash with 1:1 heptane:(3:1 ethyl acetate:ethanol)) gave the desired (1S,5S,6S)-methyl 3-((tert-butoxycarbonyl)amino)-5-(2,3-difluoro-5-(4,4,5,5-tetramethyl-1,3,2-dioxaborolan-2-yl)phenyl)-5-methyl-2-thia-4-azabicyclo

[4.1.0]hept-3-ene-1-carboxylate (49) (0.77 g, 40% yield) as a colorless tar. LC/MS (ESI+) m/z=539.2 (M+H).

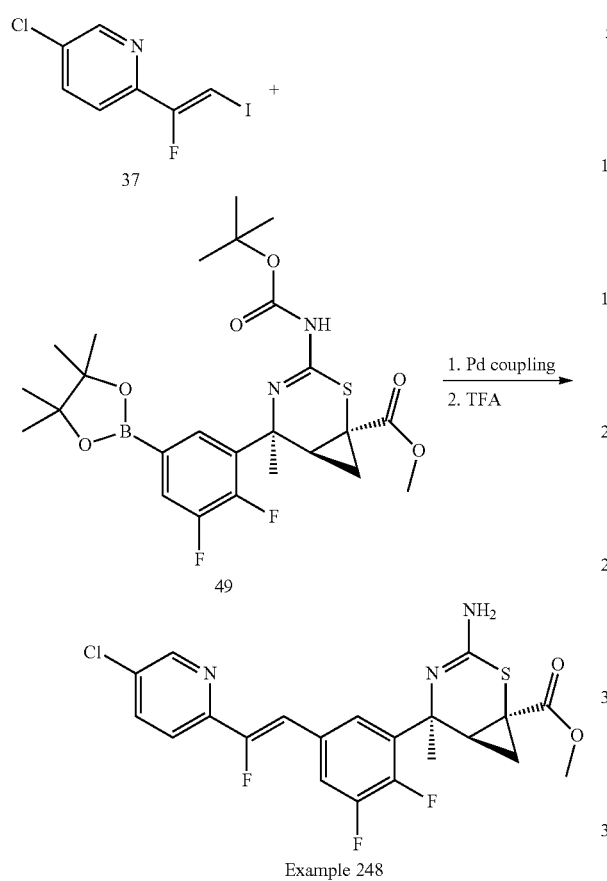

49

Example 248

Preparation of (1S,5S,6S)-methyl 3-amino-5-(5-((Z)-2-(5-chloropyridin-2-yl)-2-fluorovinyl)-2,3-difluorophenyl)-5-methyl-2-thia-4-azabicyclo[4.1.0]hept-3-ene-1-carboxylate (Example 248)

Using a similar procedure to that described for Example 222, (1S,5S,6S)-methyl 3-((tert-butoxycarbonyl)amino)-5-(2,3-difluoro-5-(4,4,5,5-tetramethyl-1,32-dioxaborolan-2-yl)phenyl)-5-methyl-2-thia-4-azabicyclo[4.1.0]hept-3-ene-1-carboxylate (49) (0.600 g, 1.11 mmol), (Z)-5-chloro-2-(1-fluoro-2-iodovinyl)pyridine (37) (0.400 g, 1.41 mmol), 1,1'-bis(diphenylphosphino)ferrocene palladium(II)dichloride dichloromethane adduct (0.094 g, 0.12 mmol), and cesium carbonate (0.550 g, 1.69 mmol) were combined to provide the coupling product, which after deprotection with trifluoroacetic acid gave (1S,5S,6S)-methyl 3-amino-5-(5-((Z)-2-(5-chloropyridin-2-yl)-2-fluorovinyl)-2,3-difluorophenyl)-5-methyl-2-thia-4-azabicyclo[4.1.0]hept-3-ene-1-carboxylate (Example 248) (0.093 g, 18% yield) as an off white solid. LC/MS (ESI+) m/z=467.8 (M+H). $^1$H NMR (400 MHz, CHLOROFORM-d) δ ppm 8.54 (d, J=2.35 Hz, 1H) 7.74 (dd, J=8.51, 2.45 Hz, 1H) 7.64-7.70 (m, 1H) 7.53-7.62 (m, 2H) 7.03 (d, J=38.50 Hz, 1H) 4.40 (br. s., 2H) 3.79 (s, 3H) 2.53 (ddd, J=9.68, 7.73, 1.00 Hz, 1H) 1.74 (d, J=1.17 Hz, 3H) 1.55 (dd, J=9.78, 5.28 Hz, 1H) 1.13 (dd, J=7.43, 5.28 Hz, 1H); $^{19}$F NMR (376 MHz, CHLOROFORM-d) δ ppm −123.07 (s, 1F) −137.12 (d, J=20.15 Hz, 1F) −137.94 (d, J=20.16 Hz, 1F).

Synthesis of Intermediate 50

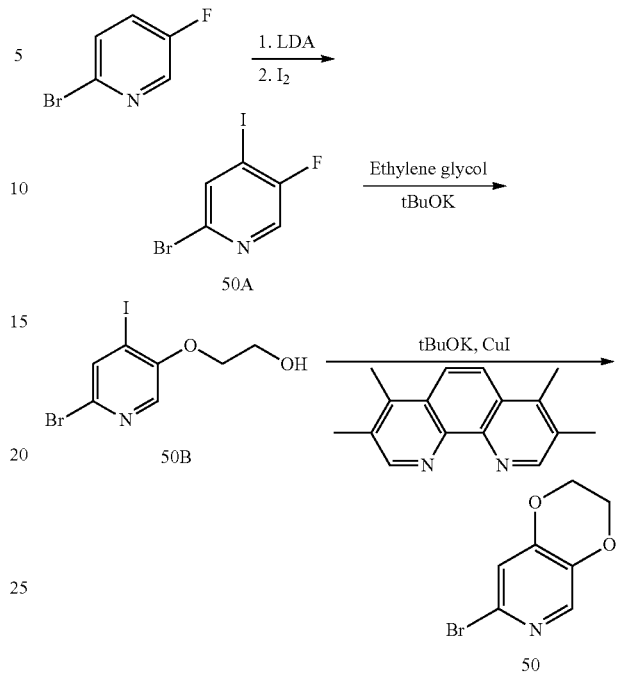

Preparation of 2-bromo-5-fluoro-4-iodopyridine (50A)

Diisopropylamine (3.5 ml, 25 mmol) was dissolved in dry tetrahydrofuran (50 mL) under nitrogen and cooled in a dry ice bath. n-Butyllithium (1.6M in hexanes, 15 ml) was added and the solution stirred for 10 minutes. A solution of 2-bromo-5-fluoropyridine (4.00 g, 22.7 mmol) in dry tetrahydrofuran (20 mL) was cooled in a −40° C. bath and slowly added to the LDA solution via cannula over 5 minutes, keeping the internal temperature <−65° C. The clear solution stirred for another 75 minutes. A solution of iodine (6.0 g, 24 mmol) in dry tetrahydrofuran (15 mL) was added slowly over 2 minutes keeping the internal temperature <−50° C. and the mixture stirred for another 5 minutes. Saturated ammonium chloride (40 mL), water (100 mL) and ethyl acetate (200 mL) were added and the phases mixed and separated. The organic was washed with aq. sodium sulfite (100 mL) then dried with brine (75 mL) and evaporated to dryness under reduced pressure. The crude 2-bromo-5-fluoro-4-iodopyridine (50A) (6.6 g, 96% yield) was used without further purification.

Preparation of 2-((6-bromo-4-iodopyridin-3-yl)oxy)ethanol (50B)

Potassium t-butoxide (2.8 g, 25 mmol) was suspended in a mixture of ethylene glycol (6.0 ml, 110 mmol) and N-methylpyrrolidinone (6 mL). The mixture was added to a solution of 2-bromo-5-fluoro-4-iodopyridine (6.8 g, 23 mmol) (50A) in N-methylpyrrolidinone (10 mL). It was heated in a 60° C. bath for 1 hour then the bath temperature was raised to 80° C. and the reaction stirred for another 30 minutes. The mixture was cooled, diluted with water (300 mL) and extracted with ethyl acetate (2×200 mL). The combined organic layers were washed with water (150 mL), dried with brine (100 mL) and evaporated to dryness under reduced pressure. Purification using silica chromatography (10-60% ethyl acetate in dichloromethane gradient) gave 2-((6-bromo-4-iodopyridin-3-yl)oxy)ethanol (50B) (3.4 g, 44% yield). LC/MS (ESI⁺) m/z=343.8 (M+H). ¹H NMR (400 MHz, CHLOROFORM-d) δ ppm 8.12 (d, J=2.74 Hz, 1H), 7.90 (d, J=2.74 Hz, 1H), 4.17-4.28 (m, 2H) 3.92-4.09 (m, 2H), 2.15 (br t, J=6.2 Hz, 1H).

Preparation of 7-bromo-2,3-dihydro-[1,4]dioxino[2,3-c]pyridine (50)

2-((6-Bromo-4-iodopyridin-3-yl)oxy)ethanol (50B) (5.7 g, 13 mmol), potassium t-butoxide (2.0 g, 18 mmol), 3,4,7,8-tetramethyl-1,10-phenanthroline (0.250 g, 1.06 mmol) and copper(I) iodide (0.150 g, 0.788 mmol) were dissolved in isopropanol (100 mL) under nitrogen. The orange solution was heated in an 80° C. bath for 50 minutes then concentrated to dryness under reduced pressure. Ethyl acetate (200 mL), water (100 mL), saturated ammonium chloride (50 mL) and ammonium hydroxide (20 mL) were added and the phases mixed. The phases were separated and the organic dried with brine (75 mL) before evaporating to dryness under reduced pressure. Purification using silica chromatography (0-50% ethyl acetate in dichloromethane gradient) gave 7-bromo-2,3-dihydro-[1,4]dioxino[2,3-c]pyridine (50) (2.4 g, 11 mmol, 87% yield). LC/MS (ESI⁺) m/z=216.0 (M+H). ¹H NMR (400 MHz, CHLOROFORM-d) δ ppm 7.92-7.96 (m, 1H) 6.97-7.01 (m, 1H) 4.27-4.37 (m, 4H).

Synthesis of Intermediate 51

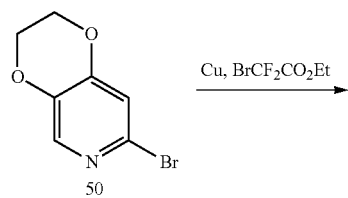

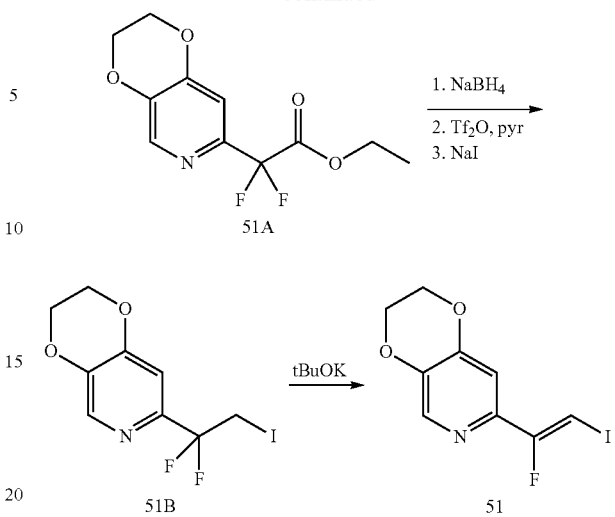

Using a procedure similar to that described for the synthesis of 37, 7-bromo-2,3-dihydro-[1,4]dioxino[2,3-c]pyridine (50) (2.4 g, 11.11 mmol), copper (4.0 g, 63 mmol), and ethyl bromodifluoroacetate (1.6 ml, 12 mmol) were combined to provide coupling product 51A (2.2 g, 76% yield). The ester was reduced with sodium borohydride (0.350 g, 9.26 mmol), converted to the triflate using pyridine (1.25 ml, 15.3 mmol) and trifluoromethanesulfonic anhydride (1.6 ml, 9.5 mmol) and treated with sodium iodide (5.4 g, 36 mmol) to give 51B (1.9 g, 63% yield). Treatment with potassium t-butoxide (0.65 g, 5.8 mmol) gave desired vinyliodide (51) (1.5 g, 94% yield). LC/MS (ESI⁺) m/z=307.9 (M+H).

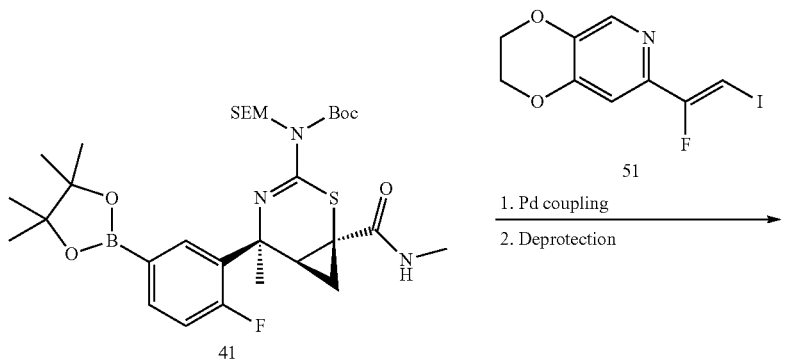

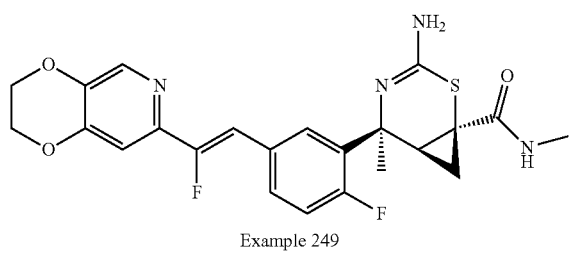

Example 249

Preparation of (1S,5S,6S)-3-amino-5-(5-((Z)-2-(2,3-dihydro-[1,4]dioxino[2,3-c]pyridin-7-yl)-2-fluorovinyl)-2-fluorophenyl)-N,5-dimethyl-2-thia-4-azabicyclo[4.1.0]hept-3-ene-1-carboxamide (Example 249)

Using a procedure similar to that described for Example 222, tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (41) (0.350 g, 0.539 mmol), (Z)-7-(1-fluoro-2-iodovinyl)-2,3-dihydro-[1,4]dioxino[2,3-c]pyridine (51) (0.20 g, 0.651 mmol), potassium phosphate (0.35 g, 1.6 mmol), and 1,1-bis[di-tert-butyl-p-methylaminophenyl]palladium(II) chloride (0.019 g, 0.027 mmol) were combined to provide the coupling product, which after deprotection gave (1S,5S,6S)-3-amino-5-(5-((Z)-2-(2,3-dihydro-[1,4]dioxino[2,3-c]pyridin-7-yl)-2-fluorovinyl)-2-fluorophenyl)-N,5-dimethyl-2-thia-4-azabicyclo[4.1.0]hept-3-ene-1-carboxamide (Example 249) (0.084 g, 33% yield) as an off white solid. LC/MS (ESI$^+$) m/z=467.8 (M+H). $^1$H NMR (400 MHz, CHLOROFORM-d) δ ppm 8.14 (s, 1H) 7.46-7.56 (m, 2H) 7.04 (d, J=1.37 Hz, 1H) 7.00 (dd, J=11.44, 8.51 Hz, 1H) 6.64-6.84 (m, 2H) 5.00 (br. s, 2H) 4.27-4.39 (m, 4H) 2.84 (d, J=4.89 Hz, 3H) 2.18 (dd, J=9.19, 7.83 Hz, 1H) 2.00 (dd, J=9.59, 4.89 Hz, 1H) 1.85 (s, 3H) 0.74-0.80 (m, 1H).

Synthesis of Intermediate 52

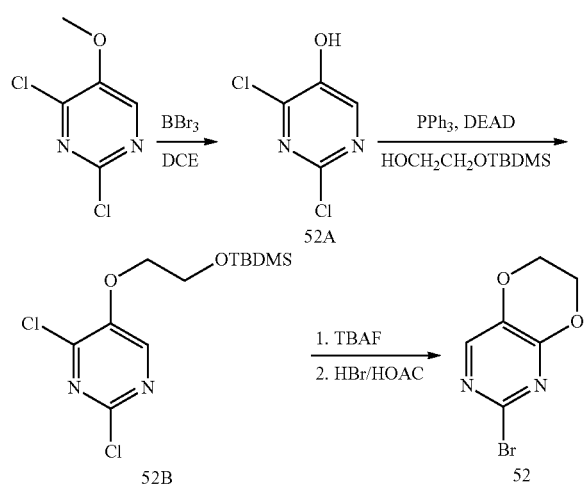

Preparation of 2,4-dichloropyrimidin-5-ol (52A)

2,4-Dichloro-5-methoxypyrimidine (2.2 g, 12 mmol) was suspended in 1,2-dichloroethane (10 mL) under nitrogen and cooled in an ice bath. Boron tribromide (7.0 ml, 73 mmol) was added slowly over 5 minutes and the resulting pale orange solution stirred for 10 minutes. It was removed from the cold bath and heated in an 80° C. bath for 2 hours after which it was cooled, diluted with dichloromethane (50 mL) and cooled in an ice bath. The crude was treated with 5N sodium hydroxide until the pH was >9. The mixture was stirred for 30 minutes then saturated aq. NH$_4$Cl (50 mL) and dichloromethane (50 mL) were added. Acetic acid (3 mL) was added and the phases mixed and separated. The aqueous was extracted with ethyl acetate (100 mL) and the organic layers combined, dried with brine (50 mL) and evaporated to dryness under reduced pressure. The crude product was triturated with 1:1 dichloromethane:heptane (40 mL) and filtered through a sintered glass frit, affording 2,4-dichloropyrimidin-5-ol (52A). The crude solids were used without further purification. LC/MS (ESI$^+$) m/z=165.0 (M+H).

Preparation of 5-(2-((tert-butyldimethylsilyl)oxy)ethoxy)-2,4-dichloropyrimidine (52B)

2,4-Dichloropyrimidin-5-ol (0.75 g, 4.6 mmol) (52A) and triphenylphosphine (1.3 g, 5.0 mmol) were suspended in dry tetrahydrofuran (40 mL) under nitrogen and cooled in an ice bath. 2-(t-Butyldimethylsiloxy)ethanol (1.0 ml, 5.0 mmol) was added, followed by dropwise addition of diethyl azodicarboxylate (40 wt % solution in toluene, 2.6 ml, 5.7 mmol). The mixture was allowed to warm to room temperature overnight. Water (100 mL) and ethyl acetate (150 mL) were added and the phases mixed and separated. The organic was dried with brine (50 mL) then evaporated to dryness under reduced pressure. Purification using silica chromatography (heptane to ethyl acetate gradient) gave 5-(2-((tert-butyldimethylsilyl)oxy)ethoxy)-2,4-dichloropyrimidine (52B) (1.2, 85% yield) as a colorless oil. LC/MS (ESI$^+$) m/z=322.9 (M+H).

Preparation of 2-bromo-6,7-dihydro-[1,4]dioxino[2,3-d]pyrimidine (52)

5-(2-((Tert-butyldimethylsilyl)oxy)ethoxy)-2,4-dichloropyrimidine (52B) (1.25 g, 3.87 mmol) was dissolved in dry tetrahydrofuran (75 mL) under nitrogen. Tetra-n-butylammonium fluoride (1M in THF, 4 ml) was added slowly and the reaction stirred at room temperature. After 15 minutes the starting material had been consumed. Dichloromethane (100 mL), brine (20 mL) and water (100 mL) were added and the phases mixed and separated. The organic was dried with brine (50 mL) and evaporated to dryness under reduced pressure. The crude was dissolved in acetic acid (10 mL) and treated with hydrogen bromide (33 wt. % in acetic acid, 10 ml, 61 mmol). The mixture was stirred at room temperature under nitrogen overnight then evaporated to dryness under reduced pressure. Toluene (30 mL) was added and the mixture evaporated to dryness once more. The crude was dissolved in ethyl acetate (75 mL) and washed with 50% saturated aq. NaHCO$_3$ (50 mL) before evaporating to dryness under reduced pressure. Purification using silica chromatography (dichloromethane to ethyl acetate gradient) gave 2-bromo-6,7-dihydro-[1,4]dioxino[2,3-d]pyrimidine (52) (0.32 g, 38% yield) as a white solid. LC/MS (ESI$^+$) m/z=217.0 (M+H).

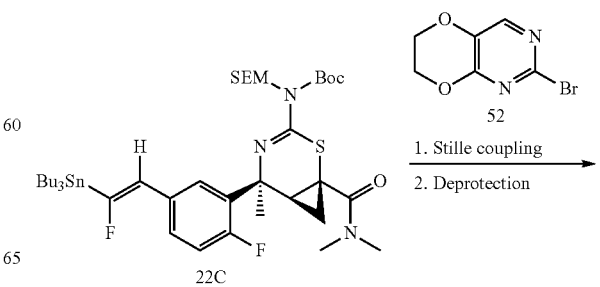

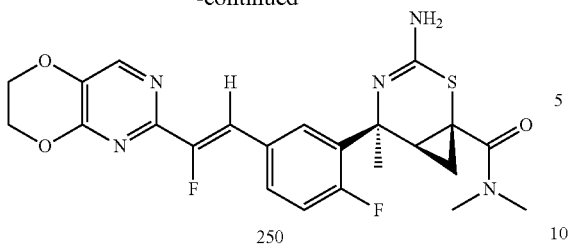

250

Preparation of (1S,5S,6S)-3-amino-5-(5-((Z)-2-(6,7-dihydro-[1,4]dioxino[2,3-d]pyrimidin-2-yl)-2-fluorovinyl)-2-fluorophenyl)-N,N,5-trimethyl-2-thia-4-azabicyclo[4.1.0]hept-3-ene-1-carboxamide (Example 250)

Using a procedure similar to that described for Example 22, tert-butyl ((1S,5S,6S)-1-(dimethylcarbamoyl)-5-(2-fluoro-5-((E)-2-fluoro-2-(tributylstannyl)vinyl)phenyl)-5-methyl-2-thia-4-azabicyclo[4.1.0]hept-3-en-3-yl)((2-(trimethylsilyl)ethoxy)methyl)carbamate (22C) (0.10 g, 0.115 mmol), 2-bromo-6,7-dihydro-[1,4]dioxino[2,3-d]pyrimidine (52) (0.058 g, 0.267 mmol), tris (dibenzylideneacetone) dipalladium (0) (0.024 g, 0.026 mmol), and 1,1'-bis(diphenylphosphino)ferrocene (0.025 g, 0.045 mmol were combined to provide the Stille coupling product, which after deprotection gave (1S,5S,6S)-3-amino-5-(5-((Z)-2-(6,7-dihydro-[1,4]dioxino[2,3-d]pyrimidin-2-yl)-2-fluorovinyl)-2-fluorophenyl)-N,N,5-trimethyl-2-thia-4-azabicyclo[4.1.0]hept-3-ene-1-carboxamide (Example 250) (18 mg, 33% yield) as an off white solid. LC/MS (ESI$^+$) m/z=488.0 (M+H). $^1$H NMR (400 MHz, CHLOROFORM-d) δ ppm 8.27 (s, 1H) 7.77 (dd, J=7.82, 1.96 Hz, 1H) 7.64 (ddd, J=8.41, 4.50, 2.15 Hz, 1H) 7.03-7.16 (m, 2H) 4.53-4.60 (m, 2H) 4.33-4.38 (m, 2H) 3.06 (br. s., 6H) 2.23-2.30 (m, 1H) 1.87 (s, 3H) 1.39 (dd, J=9.59, 5.67 Hz, 1H) 0.86 (t, J=6.36 Hz, 1H).

Synthesis of Example 251

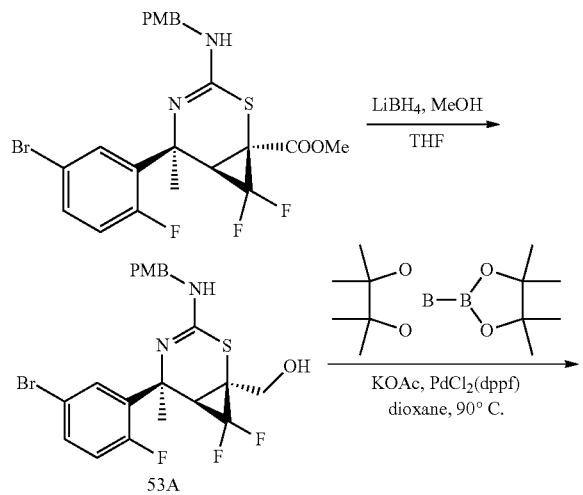

53A

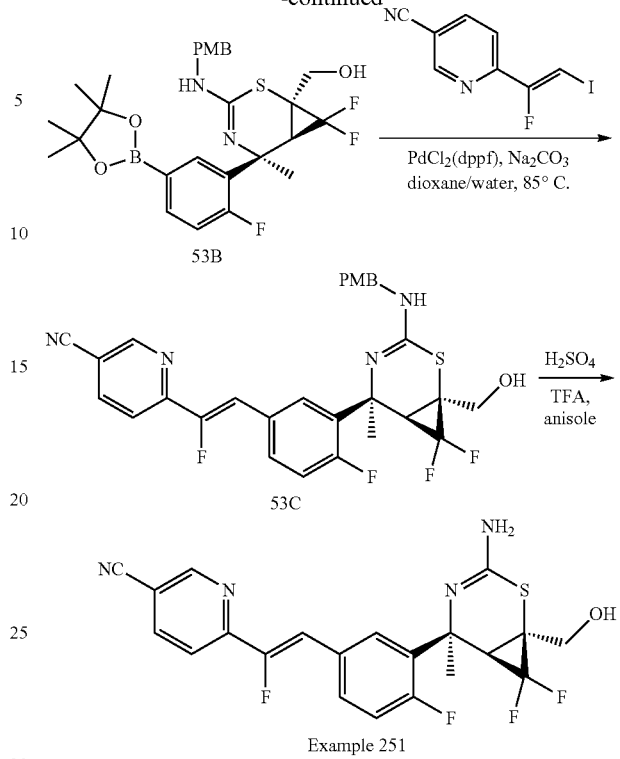

Example 251

Preparation of ((1S,5S,6R)-5-(5-bromo-2-fluorophenyl)-7,7-difluoro-3-((4-methoxybenzyl)amino)-5-methyl-2-thia-4-azabicyclo[4.1.0]hept-3-en-1-yl)methanol (53A)

To a solution of (1S,5S,6R)-methyl 5-(5-bromo-2-fluorophenyl)-7,7-difluoro-3-((4-methoxybenzyl)amino)-5-methyl-2-thia-4-azabicyclo[4.1.0]hept-3-ene-1-carboxylate (WO 2016/022724) (3.3 g, 6.3 mmol) in THF (45 mL) was added lithium tetrahydroborate (6.3 ml, 2.0M solution in THF) dropwise followed by methanol (2.0 ml, 51 mmol). The solution was stirred at room temperature for 3 hours. The reaction was quenched with water and diluted with water and EtOAc. The organic layer was separated, washed with brine, dried over sodium sulfate and concentrated under reduced pressure to afford ((1S,5S,6R)-5-(5-bromo-2-fluorophenyl)-7,7-difluoro-3-((4-methoxybenzyl)amino)-5-methyl-2-thia-4-azabicyclo[4.1.0]hept-3-en-1-yl)methanol (53A) (3.2 g, 100% yield) as a white sticky oil, which was used without further purification. MS (pos.) m/e: 501.0, 503.0 (M+H)$^+$.

Preparation of ((1S,5S,6R)-7,7-difluoro-5-(2-fluoro-5-(4,4,5,5-tetramethyl-1,3,2-dioxaborolan-2-yl)phenyl)-3-((4-methoxybenzyl)amino)-5-methyl-2-thia-4-azabicyclo[4.1.0]hept-3-en-1-yl)methanol (53B)

A mixture of ((1S,5S,6R)-5-(5-bromo-2-fluorophenyl)-7,7-difluoro-3-((4-methoxybenzyl)amino)-5-methyl-2-thia-4-azabicyclo[4.1.0]hept-3-en-1-yl)methanol (53A) (1.4 g, 2.8 mmol), bis(pinacolato) diboron (1.4 g, 5.6 mmol), potassium acetate (0.96 g, 9.8 mmol), and 1,1'-bis(diphenylphosphino) ferrocene palladium(II)dichloride dichloromethane adduct (0.46 g, 0.56 mmol) in dioxane (14 mL) was heated at 90° C. for 3 hours. After cooling to room temperature, 60 mL 30% EtOAc/Heptane was added to triturate. The solid was filtered off and the filtrate was concentrated. The residue was purified on Biotage 50 g ultra column, using 0-30% EtOAc/Heptane as eluent to give ((1S,5S,6R)-7,7-difluoro-5-(2-fluoro-5-(4,4,5,5-tetramethyl-1,3,2-dioxaborolan-2-yl)phenyl)-3-((4-methoxybenzyl)amino)-5-methyl-2-thia-4-azabicyclo[4.1.0]hept-3-en-1-yl)methanol (53B) (1.3 g, 86% yield) as off-white solid. MS (pos.) m/e: 549.2 (M+H)+.

Preparation of 6-((Z)-2-(3-((1S,5S,6R)-7,7-difluoro-1-(hydroxymethyl)-3-((4-methoxybenzyl)amino)-5-methyl-2-thia-4-azabicyclo[4.1.0]hept-3-en-5-yl)-4-fluorophenyl)-1-fluorovinyl)nicotinonitrile (53C)

A mixture of (Z)-6-(1-fluoro-2-iodovinyl)nicotinonitrile (38) (42.6 mg, 0.155 mmol), ((1S,5S,6R)-7,7-difluoro-5-(2-fluoro-5-(4,4,5,5-tetramethyl-1,3,2-dioxaborolan-2-yl)phenyl)-3-((4-methoxybenzyl)amino)-5-methyl-2-thia-4-azabicyclo[4.1.0]hept-3-en-1-yl)methanol (53B) (71 mg, 0.13 mmol), 1,1'-bis(diphenylphosphino)ferrocene-palladium dichloride (9.5 mg, 0.013 mmol), and sodium carbonate (41 mg, 0.39 mmol) in a mixture of 1,4-dioxane (570 μl) and water (290 μl) was heated to 85° C. for 2 hours. After cooling to room temperature, EtOAc was added and the mixture was dried (Na2SO4), filtered, and concentrated in vacuo. The residue was purified by silica gel chromatography (Biotage 10 g ultra column, 0 to 30% EtOAc/heptane gradient) to give 6-((Z)-2-(3-((1S,5S,6R)-7,7-difluoro-1-(hydroxymethyl)-3-((4-methoxybenzyl)amino)-5-methyl-2-thia-4-azabicyclo[4.1.0]hept-3-en-5-yl)-4-fluorophenyl)-1-fluorovinyl)nicotinonitrile (53C) (44 mg, 60% yield) as a light yellow solid. MS (pos.) m/e: 569.0 (M+H)+.

Preparation of 6-((Z)-2-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-1-fluorovinyl)nicotinonitrile (Example 251)

To a solution of 6-((Z)-2-(3-((1S,5S,6R)-7,7-difluoro-1-(hydroxymethyl)-3-((4-methoxybenzyl)amino)-5-methyl-2-thia-4-azabicyclo[4.1.0]hept-3-en-5-yl)-4-fluorophenyl)-1-fluorovinyl)nicotinonitrile (53C) (92 mg, 0.16 mmol) in TFA (1.1 ml) was added anisole (53 μl, 0.49 mmol) followed by dropwise addition of sulfuric acid (170 μl, 3.2 mmol). The reaction was stirred at room temperature for 2 hours. The reaction was poured into an Erlenmeyer flask containing wet ice. 5N NaOH was added to basify the reaction to pH=12. The basic aqueous layer was extracted with EtOAc (2×50 mL). The combined organic layers were washed with brine, dried over sodium sulfate and concentrated under reduced pressure. The crude residue was purified via Biotage (25 g Biotage ultra silica column, 0-25% 3:1 EtOAc in EtOH/heptane) to afford 6-((Z)-2-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-1-fluorovinyl)nicotinonitrile (27 mg, 37% yield) (Example 251) as a white solid. 1H NMR (CHLOROFORM-d) δ: 8.83 (s, 1H), 7.94-8.07 (m, 2H), 7.66-7.78 (m, 2H), 7.28 (d, J=40 Hz, 1H), 7.12 (dd, J=11.9, 8.6 Hz, 1H), 4.46 (br. s., 2H), 3.88-4.03 (m, 2H), 2.41-2.52 (m, 1H), 1.67 (s, 3H). MS (pos.) m/e: 449.0 (M+H)+.

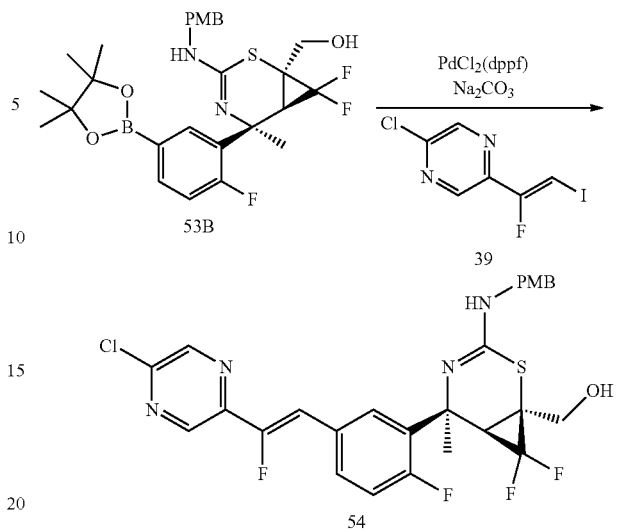

Preparation of ((1S,5S,6R)-5-(5-((Z)-2-(5-chloropyrazin-2-yl)-2-fluorovinyl)-2-fluorophenyl)-7,7-difluoro-3-((4-methoxybenzyl)amino)-5-methyl-2-thia-4-azabicyclo[4.1.0]hept-3-en-1-yl)methanol (54)

A mixture of (Z)-2-chloro-5-(1-fluoro-2-iodovinyl)pyrazine (39) (88 mg, 0.31 mmol), ((1S,5S,6R)-7,7-difluoro-5-(2-fluoro-5-(4,4,5,5-tetramethyl-1,3,2-dioxaborolan-2-yl)phenyl)-3-((4-methoxybenzyl)amino)-5-methyl-2-thia-4-azabicyclo[4.1.0]hept-3-en-1-yl)methanol (53B) (142 mg, 0.259 mmol), sodium carbonate (82 mg, 0.777 mmol) and 1,1'-bis(diphenylphosphino)ferrocene palladium(II)dichloride dichloromethane adduct (21 mg, 0.026 mmol) in a mixture of 1,4-dioxane (1.1 mL) and water (0.6 mL) was heated to 85° C. for 2 hours, then cooled to room temperature. The reaction mixture was diluted with EtOAc, dried (Na2SO4), filtered, and concentrated in vacuo to give an oil that was purified by silica gel chromatography (Biotage 25 g ultra column, 0 to 30% EtOAc/heptane gradient) to give ((1S,5S,6R)-5-(5-((Z)-2-(5-chloropyrazin-2-yl)-2-fluorovinyl)-2-fluorophenyl)-7,7-difluoro-3-((4-methoxybenzyl) amino)-5-methyl-2-thia-4-azabicyclo[4.1.0]hept-3-en-1-yl) methanol (54) (92 mg, 61% yield) as off-white solid. MS (pos.) m/e: 579.0 (M+H)+.

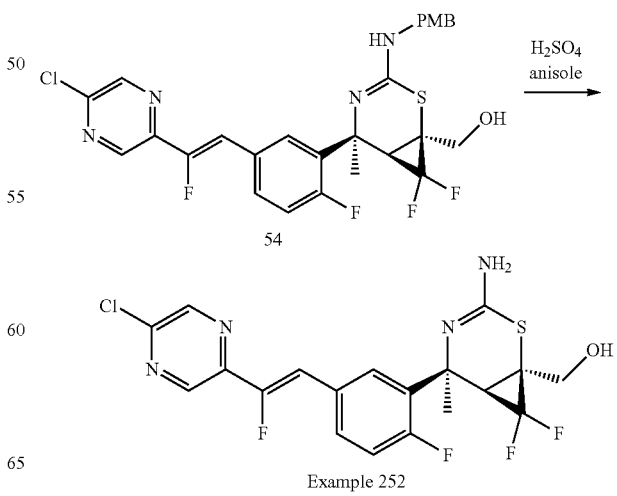

Example 252

Preparation of ((1S,5S,6R)-3-amino-5-(5-((Z)-2-(5-chloropyrazin-2-yl)-2-fluorovinyl)-2-fluorophenyl)-7,7-difluoro-5-methyl-2-thia-4-azabicyclo[4.1.0]hept-3-en-1-yl)methanol (252)

To a solution of ((1S,5S,6R)-5-(5-((Z)-2-(5-chloropyrazin-2-yl)-2-fluorovinyl)-2-fluorophenyl)-7,7-difluoro-3-((4-methoxybenzyl)amino)-5-methyl-2-thia-4-azabicyclo[4.1.0]hept-3-en-1-yl)methanol (54) (17 mg, 0.029 mmol) in TFA (196 µl) was added anisole (9.6 µl, 0.088 mmol) followed by dropwise addition of sulfuric acid (31.3 µl, 0.587 mmol). The reaction was stirred at room temperature for 2 hours. The reaction was poured into an Erlenmeyer flask containing wet ice. 5N NaOH was added to basify the reaction to pH=12. The basic aqueous layer was extracted with EtOAc (2×50 mL). The combined organic layers were washed with brine, dried over magnesium sulfate and concentrated under reduced pressure. The crude residue was purified via column chromatography (10 g Biotage ultra silica column, 0-30% 3:1 EtOAc to EtOH/heptane) to afford ((1S,5S,6R)-3-amino-5-(5-((Z)-2-(5-chloropyrazin-2-yl)-2-fluorovinyl)-2-fluorophenyl)-7,7-difluoro-5-methyl-2-thia-4-azabicyclo[4.1.0]hept-3-en-1-yl)methanol (Example 252) (8.0 mg, 59% yield) as a white solid. (8 mg, 59% yield) was obtained as a white solid. MS (pos.) m/e: 459.0 (M+H)$^+$. $^1$H NMR (CHLOROFORM-d) δ: 8.63 (s, 1H), 8.54 (s, 1H), 7.95 (br. s., 1H), 7.65-7.75 (m, 1H), 7.07 (d, J=40 Hz, 1H), 6.97-7.17 (m, 1H), 4.50 (br. s., 2H), 3.87-4.04 (m, 2H), 2.47 (d, J=16.2 Hz, 1H), 1.68 (br. s., 3H).

by chromatography through a Biotage 10 g ultra column, eluting with a gradient of 0% to 30% EtOAc in heptane, to provide ((1S,5S,6R)-7,7-difluoro-5-(2-fluoro-5-((Z)-2-fluoro-2-(5-(prop-2-yn-1-yloxy)pyrazin-2-yl)vinyl)phenyl)-3-((4-methoxybenzyl)amino)-5-methyl-2-thia-4-azabicyclo[4.1.0]hept-3-en-1-yl)methanol (50 mg, 69% yield) as white solid. MS (pos.) m/e: 599.0 (M+H)$^+$.

Using a procedure similar to that described for Example 252, a solution of ((1S,5S,6R)-7,7-difluoro-5-(2-fluoro-5-((Z)-2-fluoro-2-(5-(prop-2-yn-1-yloxy)pyrazin-2-yl)vinyl)phenyl)-3-((4-methoxybenzyl)amino)-5-methyl-2-thia-4-azabicyclo[4.1.0]hept-3-en-1-yl)methanol (50 mg, 0.084 mmol) in TFA (560 µl), anisole (27 µl, 0.25 mmol), and sulfuric acid (89 µl, 1.7 mmol) was combined to afford ((1S,5S,6R)-3-amino-7,7-difluoro-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)methanol (Example 253) (23 mg, 59% yield) as a white solid. MS (pos.) m/e: 459.0 (M+H)$^+$. $^1$H NMR (CHLOROFORM-d) δ: 8.01 (s, 1H), 7.88 (s, 1H), 7.53 (dd, J=7.8, 2.0 Hz, 1H), 7.24-7.33 (m, 1H), 6.70 (dd, J=12.0, 8.5 Hz, 1H), 6.59 (d, J=40 Hz, 1H), 4.65 (d, J=2.3 Hz, 2H), 3.47-3.65 (m, 2H), 2.15 (t, J=2.4 Hz, 1H), 2.08 (dd, J=15.5, 2.5 Hz, 1H), 1.28 (s, 3H).

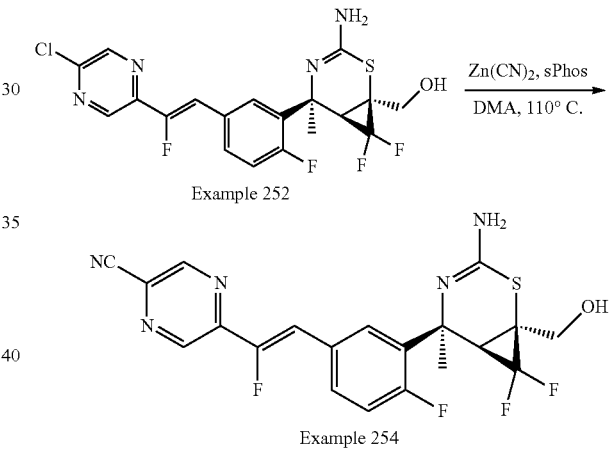

Example 252

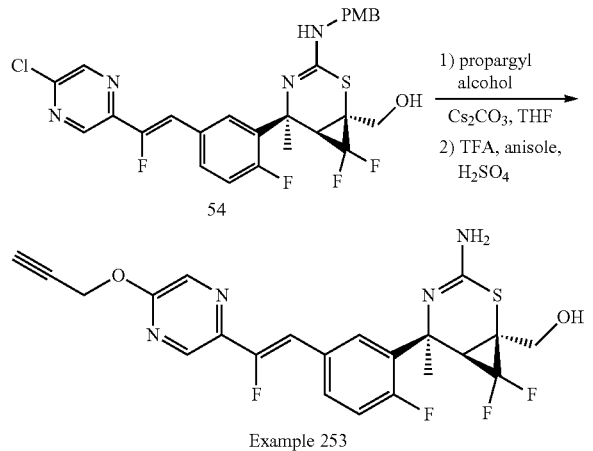

Example 253

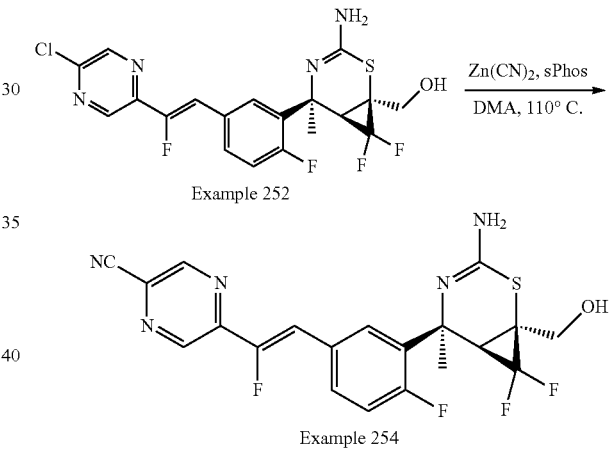

Example 254

Preparation of 5-((Z)-2-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-1-fluorovinyl)pyrazine-2-carbonitrile trifluoromethyl acetate (Example 254)

Preparation of ((1S,5S,6R)-3-amino-7,7-difluoro-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)methanol (Example 253)

To ((1S,5S,6R)-5-(5-((Z)-2-(5-chloropyrazin-2-yl)-2-fluorovinyl)-2-fluorophenyl)-7,7-difluoro-3-((4-methoxybenzyl)amino)-5-methyl-2-thia-4-azabicyclo[4.1.0]hept-3-en-1-yl)methanol (54) (70 mg, 0.12 mmol) dissolved in tetrahydrofuran (600 µl) was added cesium carbonate (118 mg, 0.363 mmol), and propargyl alcohol (36 µl, 0.60 mmol). The reaction mixture was stirred at room temperature for 16 hours. The reaction mixture was partitioned between EtOAc and 50% NaCl solution. The aqueous layer was extracted with EtOAc (2×) and the combined organics was dried (Na$_2$SO$_4$) and concentrated. The crude product was purified A 4-mL vial was charged with ((1S,5S,6R)-3-amino-5-(5-((Z)-2-(5-chloropyrazin-2-yl)-2-fluorovinyl)-2-fluorophenyl)-7,7-difluoro-5-methyl-2-thia-4-azabicyclo[4.1.0]hept-3-en-1-yl)methanol (Example 252) (59 mg, 0.13 mmol), zinc cyanide (45 mg, 0.39 mmol), dicyclohexyl(2',6'-dimethoxy-[1,1'-biphenyl]-2-yl)phosphine (16 mg, 0.039 mmol), Pd$_2$(dba)$_3$ (18 mg, 0.019 mmol) and N, N-dimethylacetamide (1.3 ml). The vial was purged with argon and sealed. The mixture was heated at 115° C. for 1.5 hours. The mixture was filtered through celite and the cake was washed with EtOAc. The filtrate was concentrated in vacuo. The crude was purified by silica gel chromatography (10 g Biotage ultra silica column, 0-30% 3:1 EtOAc to EtOH/heptane), followed by reverse-phase preparative HPLC using a Phenomenex Gemini column, 10 micron, C18, 110 Å, 150×30 mm, 0.1% TFA in CH₃CN/H₂O, gradient 10% to 70% over 15 min to provide the TFA salt of 5-((Z)-2-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-1-fluorovinyl)pyrazine-2-carbonitrile (Example 254) (16 mg, 28% yield) as a light-yellow solid. MS (pos.) m/e: 450.0 (M+H)⁺. ¹H NMR (CHLOROFORM-d) δ: 8.96 (s, 1H), 8.82 (s, 1H), 7.70 (d, J=5.7 Hz, 1H), 7.48 (d, J=7.8 Hz, 1H), 7.19 (d, J=40 Hz, 1H), 7.17-7.25 (m, 1H), 3.88-4.08 (m, 2H), 2.64 (d, J=13.5 Hz, 1H), 2.09 (s, 3H).

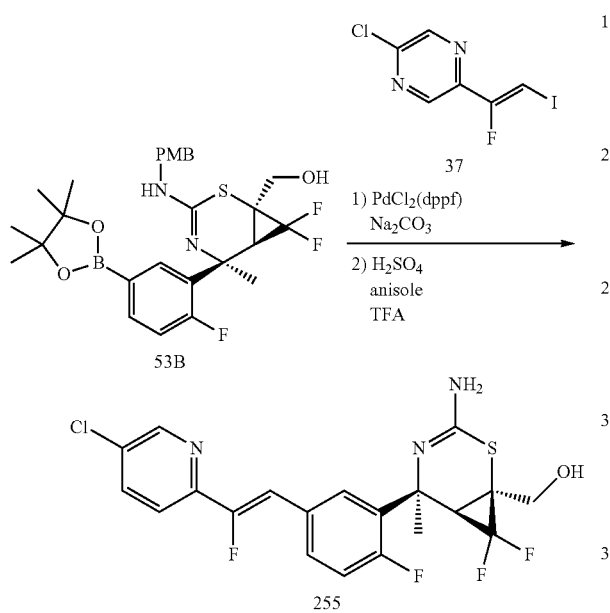

Preparation of ((1S,5S,6R)-3-amino-5-(5-((Z)-2-(5-chloropyridin-2-yl)-2-fluorovinyl)-2-fluorophenyl)-7,7-difluoro-5-methyl-2-thia-4-azabicyclo[4.1.0]hept-3-en-1-yl)methanol (Example 255)

Using procedures similar to those described for 54 and Example 252, a mixture of (Z)-5-chloro-2-(1-fluoro-2-iodovinyl)pyridine (37) (87 mg, 0.31 mmol), ((1S,5S,6R)-7,7-difluoro-5-(2-fluoro-5-(4,4,5,5-tetramethyl-1,3,2-dioxaborolan-2-yl)phenyl)-3-((4-methoxybenzyl)amino)-5-methyl-2-thia-4-azabicyclo[4.1.0]hept-3-en-1-yl)methanol (53) (140 mg, 0.26 mmol), 1,1'-bis(diphenylphosphino)ferrocene palladium(II)dichloride dichloromethane adduct (21 mg, 0.026 mmol) and sodium carbonate (81 mg, 0.77 mmol) in a mixture of 1,4-dioxane (1.1 ml) and water (0.57 ml) were combined and reacted. After deprotection with TFA (1.1 ml), anisole (52 μl, 0.47 mmol) and sulfuric acid (168 μl, 3.15 mmol), ((1S,5S,6R)-3-amino-5-(5-((Z)-2-(5-chloropyridin-2-yl)-2-fluorovinyl)-2-fluorophenyl)-7,7-difluoro-5-methyl-2-thia-4-azabicyclo[4.1.0]hept-3-en-1-yl)methanol (Example 255) (46 mg, 64% yield) was obtained as a white solid. MS (pos.) m/e: 457.8 (M+H)⁺. ¹H NMR (CHLOROFORM-d) δ: 8.55 (s, 1H), 7.95 (d, J=8.0 Hz, 1H), 7.66-7.78 (m, 2H), 7.57 (d, J=7.2 Hz, 1H), 7.07 (d, J=40 Hz, 1H), 7.05-7.15 (m, 1H), 4.46 (br. s., 2H), 3.85-4.05 (m, 2H), 2.47 (dd, J=15.6, 2.4 Hz, 1H), 1.68 (s, 3H).

Synthesis of Intermediate 55

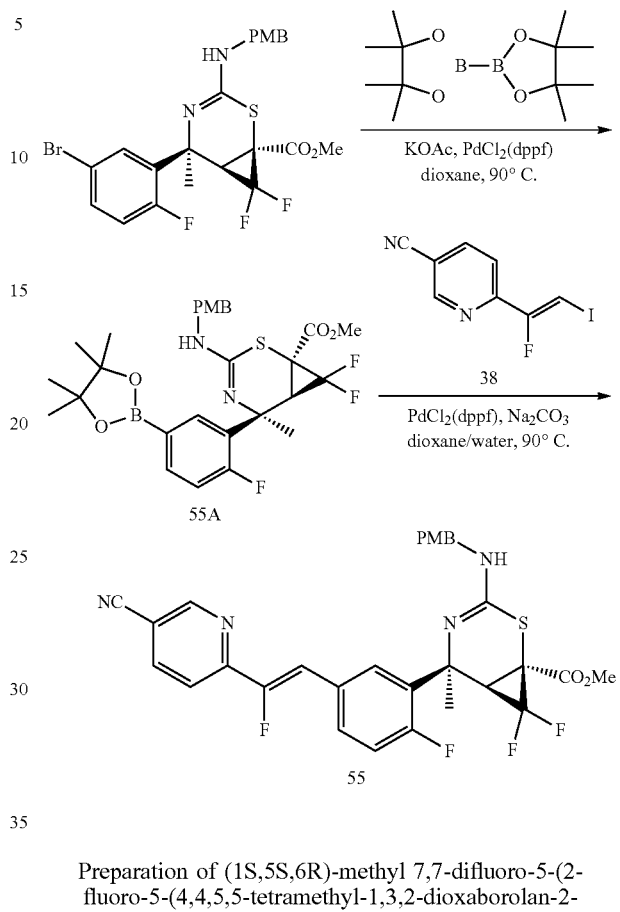

Preparation of (1S,5S,6R)-methyl 7,7-difluoro-5-(2-fluoro-5-(4,4,5,5-tetramethyl-1,3,2-dioxaborolan-2-yl)phenyl)-3-((4-methoxybenzyl)amino)-5-methyl-2-thia-4-azabicyclo[4.1.0]hept-3-ene-1-carboxylate (55A)

A mixture of (1S,5S,6R)-methyl 5-(5-bromo-2-fluorophenyl)-7,7-difluoro-3-((4-methoxybenzyl)amino)-5-methyl-2-thia-4-azabicyclo[4.1.0]hept-3-ene-1-carboxylate (WO 2016/022724) (0.57 g, 1.1 mmol), bis(pinacolato) diboron (0.54 g, 2.1 mmol), potassium acetate (0.37 g, 3.7 mmol), and 1,1'-bis(diphenylphosphino)ferrocene palladium(II)dichloride dichloromethane adduct (0.175 g, 0.214 mmol) in dioxane (5.4 mL) was heated at 90° C. for 3 hours. The reaction was allowed to cool to room temperature, 20 mL 30% EtAOc/Heptane was added to triturate. The solid formed was filtered off. The filtrate was concentrated, purified by Biotage 25 g ultra column (0-30% EtOAc/Heptane) to give (1S,5S,6R)-methyl 7,7-difluoro-5-(2-fluoro-5-(4,4,5,5-tetramethyl-1,3,2-dioxaborolan-2-yl)phenyl)-3-((4-methoxybenzyl)amino)-5-methyl-2-thia-4-azabicyclo[4.1.0]hept-3-ene-1-carboxylate (55A) (0.52 g, 85% yield) as colorless oil. MS (pos.) m/e: 577.2 (M+H)⁺.

Preparation of (1S,5S,6R)-methyl 5-(5-((Z)-2-(5-cyanopyridin-2-yl)-2-fluorovinyl)-2-fluorophenyl)-7,7-difluoro-3-((4-methoxybenzyl)amino)-5-methyl-2-thia-4-azabicyclo[4.1.0]hept-3-ene-1-carboxylate (55)

A mixture of (Z)-6-(1-fluoro-2-iodovinyl)nicotinonitrile (38) (297 mg, 1.08 mmol), (1S,5S,6R)-methyl 7,7-difluoro- 5-(2-fluoro-5-(4,4,5,5-tetramethyl-1,3,2-dioxaborolan-2-yl) phenyl)-3-((4-methoxybenzyl)amino)-5-methyl-2-thia-4-azabicyclo[4.1.0]hept-3-ene-1-carboxylate (55A) (520 mg, 0.90 mmol), 1,1'-bis(diphenylphosphino)ferrocene palladium(II)dichloride dichloromethane adduct (74 mg, 0.090 mmol) and sodium carbonate (287 mg, 2.71 mmol) in a mixture of 1,4-dioxane (4 ml) and water (2 ml) was heated to 85° C. for 3 hours, then cooled to room temperature. The reaction mixture was partitioned between EtOAc and diluted brine. The aqueous layer was back extracted with EtOAc and the combined organics was dried (Na₂SO₄) and concentrated. The residue was purified by silica gel chromatography (Biotage 25 g ultra column, 0 to 30% EtOAc/heptane gradient) to give (1S,5S,6R)-methyl 5-(5-((Z)-2-(5-cyanopyridin-2-yl)-2-fluorovinyl)-2-fluorophenyl)-7,7-difluoro-3-((4-methoxybenzyl)amino)-5-methyl-2-thia-4-azabicyclo [4.1.0]hept-3-ene-1-carboxylate (55) (300 mg, 56% yield) as white solid. MS (pos.) m/e: 597.0 (M+H)⁺.

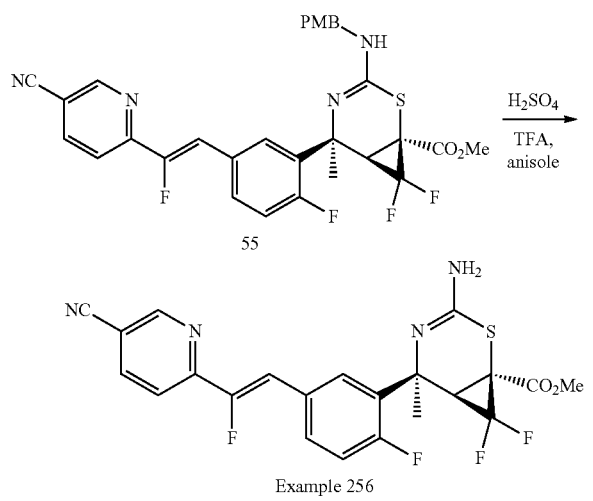

Preparation of (1S,5S,6R)-methyl 3-amino-5-(5-((Z)-2-(5-cyanopyridin-2-yl)-2-fluorovinyl)-2-fluorophenyl)-7,7-difluoro-5-methyl-2-thia-4-azabicyclo [4.1.0]hept-3-ene-1-carboxylate (Example 256)

To a solution of (1S,5S,6R)-methyl 5-(5-((Z)-2-(5-cyanopyridin-2-yl)-2-fluorovinyl)-2-fluorophenyl)-7,7-difluoro-3-((4-methoxybenzyl)amino)-5-methyl-2-thia-4-azabicyclo [4.1.0]hept-3-ene-1-carboxylate (55) (253 mg, 0.424 mmol) in TFA (2.8 ml) was added anisole (139 μl, 1.27 mmol) followed by dropwise addition of sulfuric acid (339 μl, 6.36 mmol). The reaction was stirred at room temperature for 3 hours. The reaction mixture was poured into an Erlenmeyer flask containing wet ice. 5N NaOH was added to basify the reaction to pH=8. The basic aqueous layer was extracted with EtOAc (2×50 mL). The combined organic layers were washed with brine, dried over magnesium sulfate and concentrated under reduced pressure. The crude residue was purified via chromatography (25 g Biotage ultra silica column, 0-30% 3:1 EtOAc to EtOH/heptane) to give (1S,5S, 6R)-methyl 3-amino-5-(5-((Z)-2-(5-cyanopyridin-2-yl)-2-fluorovinyl)-2-fluorophenyl)-7,7-difluoro-5-methyl-2-thia-4-azabicyclo[4.1.0]hept-3-ene-1-carboxylate (Example 256) (217 mg, 92% yield) as white solid. MS (pos.) m/e: 477.0 (M+H)⁺. ¹H NMR (CHLOROFORM-d) δ: 8.80 (s, 1H), 7.93 (d, J=8.2 Hz, 1H), 7.60-7.70 (m, 2H), 7.57 (d, J=7.4 Hz, 1H), 7.13-7.23 (m, 1H), 7.13 (d, J=40 Hz, 1H), 3.93 (s, 3H), 3.53 (d, J=13.3 Hz, 1H), 2.10 (s, 3H). ¹⁹F NMR (CHLOROFORM-d) δ: -111.14 (s, 1F), -123.98 (s, 1F), -129.72 (d, J=147.8 Hz, 1F), -136.15 (d, J=147.8 Hz, 1F).

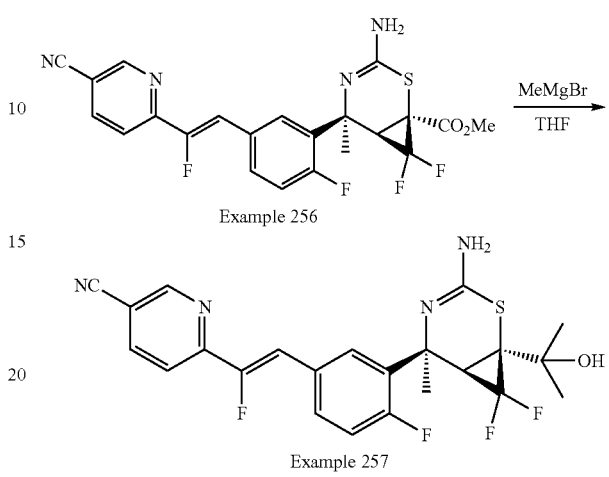

Preparation of 6-((Z)-2-(3-((1S,5S,6R)-3-amino-7,7-difluoro-1-(2-hydroxypropan-2-yl)-5-methyl-2-thia-4-azabicyclo[4.1.0]hept-3-en-5-yl)-4-fluorophenyl)-1-fluorovinyl)nicotinonitrile trifluoromethyl acetate (Example 257)

A flame-dried round bottom flask was charged with (1S, 5S,6R)-methyl 3-amino-5-(5-((Z)-2-(5-cyanopyridin-2-yl)-2-fluorovinyl)-2-fluorophenyl)-7,7-difluoro-5-methyl-2-thia-4-azabicyclo[4.1.0]hept-3-ene-1-carboxylate (Example 256) (45 mg, 0.094 mmol). THF (8.3 ml) was added and the solution was cooled to 0° C. Methyl magnesium bromide, 3.2M solution in 2-methyltetrahydrofuran (140 μl, 0.47 mmol) was added dropwise to the stirring solution and the reaction was stirred at 0° C. for 30 minutes. Added more methyl magnesium bromide, 3.2M solution in 2-methyltetrahydrofuran (140 μl, 0.47 mmol) and stirred at 0° C. for another 1.5 hours. The reaction was carefully quenched with saturated aq. NH₄Cl and diluted with water and EtOAc. The organic layer was separated, washed with brine, dried over sodium sulfate and concentrated under reduced pressure. The crude material was purified by reverse-phase preparative HPLC using a Phenomenex Gemini column, 10 micron, C18, 110 Å, 150×30 mm, 0.1% TFA in CH₃CN/H₂O, gradient 10% to 70% over 15 min to provide the TFA salt of 6-((Z)-2-(3-((1S,5S,6R)-3-amino-7,7-difluoro-1-(2-hydroxypropan-2-yl)-5-methyl-2-thia-4-azabicyclo[4.1.0] hept-3-en-5-yl)-4-fluorophenyl)-1-fluorovinyl)nicotinonitrile (Example 257) (1.5 mg, 3.3% yield) as an off-white solid. MS (pos.) m/e: 477.0 (M+H)⁺. ¹H NMR (CHLOROFORM-d) δ: 8.75 (s, 1H), 7.83 (d, J=8.2 Hz, 1H), 7.46-7.62 (m, 3H), 7.12-7.22 (m, 1H), 7.04 (d, J=40 Hz, 1H), 3.17 (d, J=13.9 Hz, 1H), 2.07 (s, 3H), 1.49 (d, J=12.5 Hz, 6H). ¹⁹F NMR (CHLOROFORM-d) δ: -75.93 (s, 3F), -111.16 (br. s., 1F), -124.19 (s, 1F), -130.45 (d, J=161.5 Hz, 1F), -133.90 (d, J=161.5 Hz, 1F).

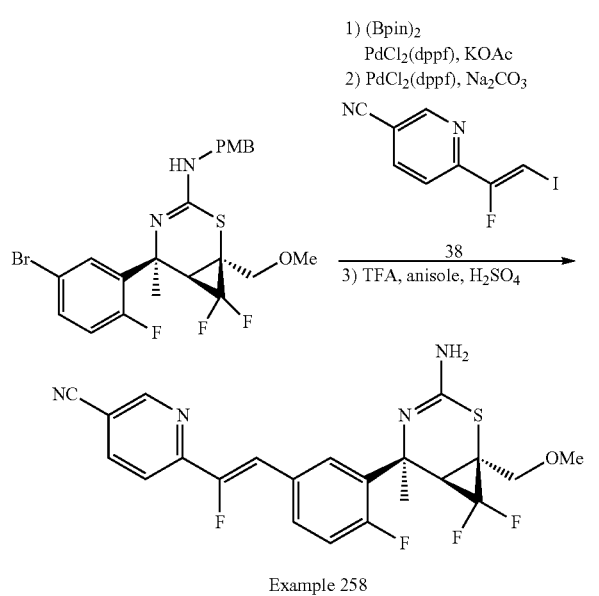

Example 258

Preparation of 6-((Z)-2-(3-((1S,5S,6R)-3-amino-7,7-difluoro-1-(methoxymethyl)-5-methyl-2-thia-4-azabicyclo[4.1.0]hept-3-en-5-yl)-4-fluorophenyl)-1-fluorovinyl)nicotinonitrile (Example 258)

Using a procedure similar to that described for Example 256, a mixture of (1S,5S,6R)-5-(5-bromo-2-fluorophenyl)-7,7-difluoro-N-(4-methoxybenzyl)-1-(methoxymethyl)-5-methyl-2-thia-4-azabicyclo[4.1.0]hept-3-en-3-amine (WO 2016/022724) (0.15 g, 0.29 mmol), bis(pinacolato) diboron (0.15 g, 0.58 mmol), potassium acetate (0.10 g, 1.0 mmol), and 1,1'-bis(diphenylphosphino)ferrocene palladium(II)dichloride dichloromethane adduct (0.048 g, 0.058 mmol) in p-dioxane (1.5 mL) were combined and reacted to give (1S,5S,6R)-7,7-difluoro-5-(2-fluoro-5-(4,4,5,5-tetramethyl-1,3,2-dioxaborolan-2-yl)phenyl)-N-(4-methoxybenzyl)-1-(methoxymethyl)-5-methyl-2-thia-4-azabicyclo[4.1.0]hept-3-en-3-amine (104 mg, 64% yield), which reacted with (Z)-6-(1-fluoro-2-iodovinyl)nicotinonitrile (38) (61 mg, 0.22 mmol), 1,1'-bis(diphenylphosphino)ferrocene palladium(II)dichloride dichloromethane adduct (15 mg, 0.018 mmol) and sodium carbonate (59 mg, 0.56 mmol) in a mixture of 1,4-dioxane (820 µl) and water (400 µl). After deprotection with TFA (778 µl), anisole (38 µl, 0.35 mmol), and sulfuric acid (124 µl, 2.33 mmol), 6-((Z)-2-(3-((1S,5S,6R)-3-amino-7,7-difluoro-1-(methoxymethyl)-5-methyl-2-thia-4-azabicyclo[4.1.0]hept-3-en-5-yl)-4-fluorophenyl)-1-fluorovinyl)nicotinonitrile (Example 258) (27 mg, 50% yield) was obtained as white solid. MS (pos.) m/e: 463.1 (M+H)$^+$. $^1$H NMR (CHLOROFORM-d) δ: 8.83 (s, 1H), 8.01 (d, J=8.2 Hz, 2H), 7.66-7.78 (m, 2H), 7.28 (d, J=40 Hz, 1H), 7.11 (dd, J=11.7, 8.6 Hz, 1H), 4.44 (br. s., 2H), 3.97 (dd, J=11.1, 3.4 Hz, 1H), 3.54 (d, J=11.2 Hz, 1H), 3.40 (s, 3H), 2.31-2.43 (m, 1H), 1.66 (s, 3H). $^{19}$F NMR (CHLOROFORM-d) δ: -111.19 (s, 1F), -125.64 (br. s., 1F), -128.47 (d, J=156.8 Hz, 1F), -143.21 (d, J=156.2 Hz, 1F).

Synthesis of Intermediate 56

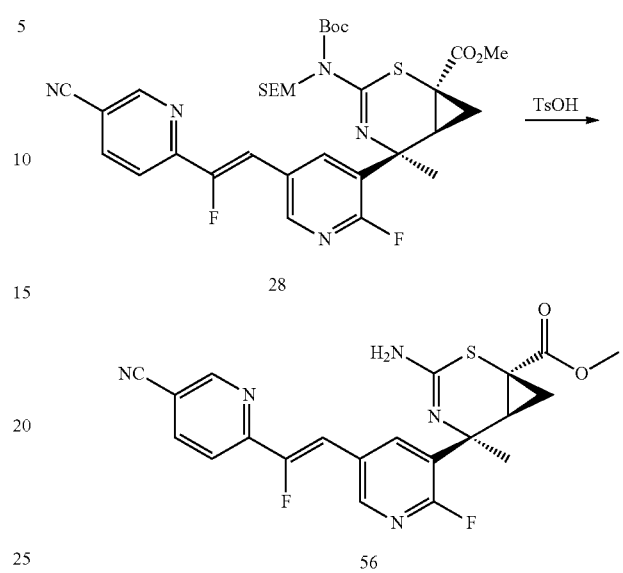

Preparation of (1S,5S,6S)-methyl 3-amino-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate Using a procedure similar to that described for Example 151, (1S,5S,6S)-methyl 3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate, 28, (1.9 g, 2.83 mmol) was reacted with 4-methylbenzene sulfonic acid, monohydrate (1.61 g, 8.48 mmol) to afford (1S,5S,6S)-methyl 3-amino-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate (0.91 g, 73% yield). LCMS (ESI+) m/z=442.1 (M+H). $^1$H NMR (400 MHz, CHLOROFORM-d) δ 8.85 (d, J=1.17 Hz, 1H), 8.36-8.57 (m, 2H), 8.06 (dd, J=2.05, 8.31 Hz, 1H), 7.74 (d, J=7.82 Hz, 1H), 7.28 (d, J=38.73 Hz, 1H), 4.27-4.81 (m, 2H), 3.81 (s, 3H), 2.60 (t, J=8.71 Hz, 1H), 1.74 (s, 3H), 1.55 (dd, J=5.18, 9.68 Hz, 1H), 1.11 (dd, J=5.28, 7.43 Hz, 1H).

Synthesis of Intermediate 57

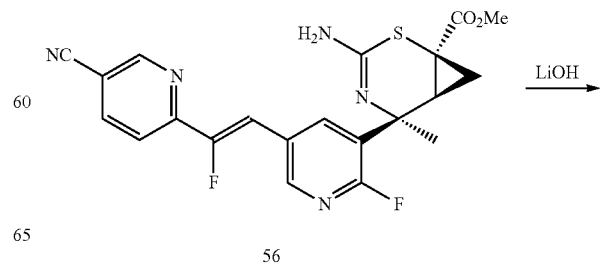

56

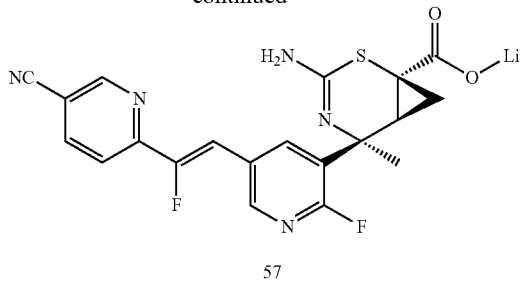

57

Preparation of lithium (1S,5S,6S)-3-amino-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate (57)

A mixture of (1S,5S,6S)-methyl-3-amino-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate (0.98 g, 2.2 mmol) and lithium hydroxide monohydrate (0.074 mL, 2.7 mmol) in THF (10 ml) and water (4 mL) was stirred at room temperature for 2 hours. The reaction mixture was then concentrated and dried to afford lithium (1S,5S,6S)-3-amino-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate (57) (0.98 g, 100% yield). LCMS (ESI+) m/z=428.0 (M+H) acid.

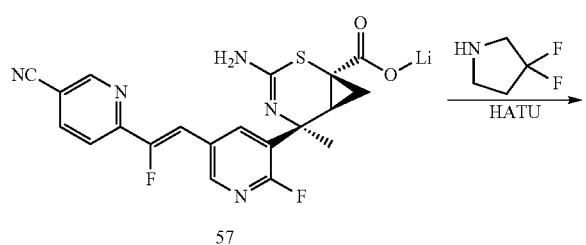

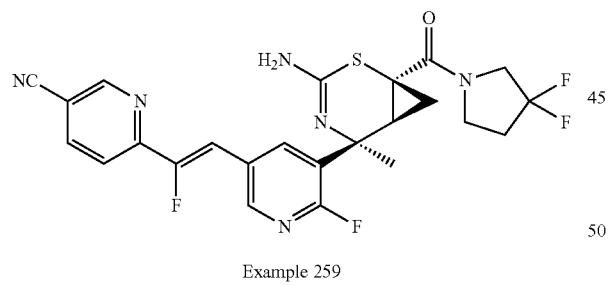

Example 259

Preparation of 6-((Z)-2-(5-((1S,5S,6S)-3-amino-1-(3,3-difluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile (Example 259)

To a mixture of lithium (1S,5S,6S)-3-amino-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate (57) (0.150 g, 0.346 mmol), 3,3-difluoropyrrolidine hydrochloride (0.099 g, 0.69 mmol), di-isopropylethylamine (0.241 mL, 1.39 mmol) in DMF (1 mL) was added HATU (0.263 g, 0.692 mmol). The reaction mixture was stirred at room temperature for 2 hours, diluted with water and extracted with EtOAc. The organic layer was concentrated to dryness and the residue purified by flash column chromatography on silica gel with ISCO eluting with 0-40% EtOAc/EtOH (3:1) in heptane to afford the final product with some minor impurities. The solid obtained was triturated in MeOH and the solid filtered and dried to give 6-((Z)-2-(5-((1S,5S,6S)-3-amino-1-(3,3-difluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile (Example 259) (0.045 g, 25% yield). LCMS (ESI+) m/z=517.1 (M+H). $^1$H NMR (400 MHz, CHLOROFORM-d) δ: 8.85 (s, 1H), 8.44 (s, 1H), 8.27 (d, J=9.19 Hz, 1H), 8.05 (d, J=7.63 Hz, 1H), 7.73 (d, J=8.02 Hz, 1H), 7.26 (d, J=38.54 Hz, 1H), 4.29-5.23 (m, 2H), 3.67-4.22 (m, 4H), 2.28-2.52 (m, 3H), 1.86 (s, 3H), 1.47 (dd, J=6.26, 9.39 Hz, 1H), 0.87 (t, J=6.26 Hz, 1H). $^{19}$F NMR (376 MHz, CHLOROFORM-d) δ: −62.53 (s, 1F), −101.71 (s, 1F), −122.04 (s, 2F).

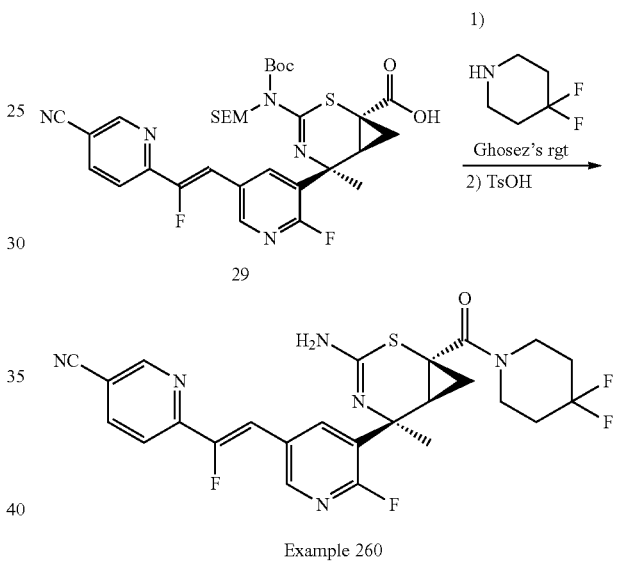

Preparation of 6-((Z)-2-(5-((1S,5S,6S)-3-amino-1-(4,4-difluoropiperidine-1-carbonyl)-5-methyl-2-thia-4-azabicyclo[4.1.0]hept-3-en-5-yl)-6-fluoropyridin-3-yl)-1-fluorovinyl)nicotinonitrile (Example 260)

To a solution of (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylic acid (29) (0.205 g, 0.312 mmol) in acetonitrile (2 mL) was added 1-chloro-N,N,2-trimethyl-1-propenylamine (0.416 mL, 3.12 mmol). The reaction mixture was stirred at room temperature 2 hours and concentrated. The residue obtained was added to a solution of 4,4-difluoropiperidine hydrochloride (0.098 g, 0.62 mmol) and triethylamine (0.032 g, 0.31 mmol) in MeCN (4 mL). The resulting solution was stirred for 3 hours, diluted with water and extracted with EtOAc (2×). The organic layer was concentrated to dryness to give crude residue. To this crude residue was added to p-toluenesulfonic acid monohydrate (0.059 g, 0.31 mmol), and dioxane (2 mL) in sealed vial with pressure relief cap. The vial was heated to 80° C. for 2 hours. The reaction was cooled to room temperature, diluted with water and extracted with EtOAc (2×). The organic phase was concentrated and the residue purified by flash column chromatography on silica gel with ISCO eluting with 0-60% EtOAc in heptanes to afford 6-((Z)-2-(5-((1S,5S,6S)-3-amino-1-(4,4-difluoropiperidine-1-carbonyl)-5-methyl-2-thia-4-azabicyclo[4.1.0]hept-3-en-5-yl)-6-fluoropyridin-3-yl)-1-fluorovinyl)nicotinonitrile (Example 260) (0.009 g, 5% yield). LCMS (ESI+) m/z=531.0 (M+H). ¹H NMR (400 MHz, CHLOROFORM-d) δ 8.85 (s, 1H), 8.43 (s, 1H), 8.28-8.37 (m, 1H), 8.02-8.09 (m, 1H), 7.73 (d, J=8.02 Hz, 1H), 7.26 (d, J=38.73 Hz, 1H), 4.02-4.96 (br. s., 2H), 3.77 (br. s., 4H), 2.37 (t, J=8.51 Hz, 1H), 1.92-2.09 (m, 4H), 1.84 (s, 3H), 1.35 (dd, J=5.67, 9.78 Hz, 1H), 0.91 (t, J=6.46 Hz, 1H). ¹⁹F NMR (376 MHz, CHLOROFORM-d) δ −62.68 (s, 1F), −98.22 (br. d., 2F), −122.14 (s, 1F).

Synthesis of Intermediate 58

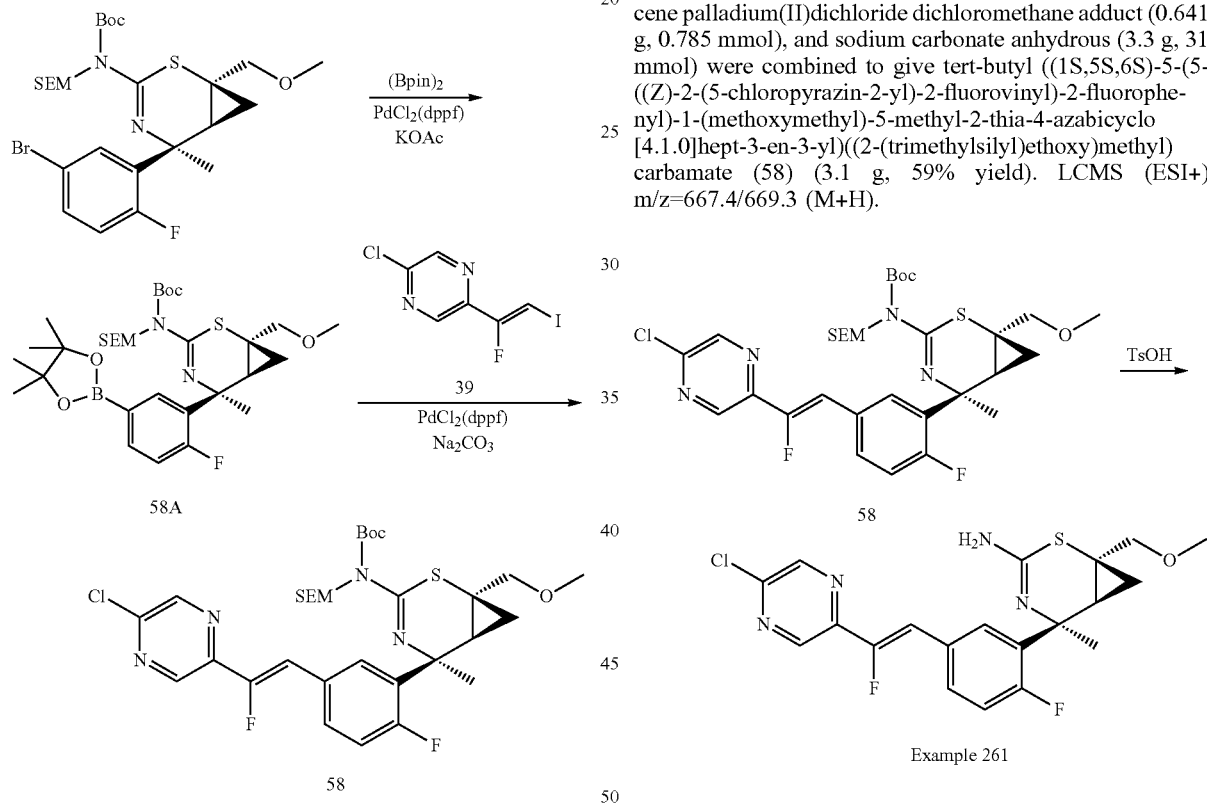

Preparation of tert-butyl ((1S,5S,6S)-5-(2-fluoro-5-(4,4,5,5-tetramethyl-1,3,2-dioxaborolan-2-yl)phenyl)-1-(methoxymethyl)-5-methyl-2-thia-4-azabicyclo[4.1.0]hept-3-en-3-yl)((2-(trimethylsilyl)ethoxy)methyl)carbamate (58A)

Using a procedure similar to that described for 31, tert-butyl ((1S,5S,6S)-5-(5-bromo-2-fluorophenyl)-1-(methoxymethyl)-5-methyl-2-thia-4-azabicyclo[4.1.0]hept-3-en-3-yl)((2-(trimethylsilyl)ethoxy)methyl)carbamate (WO 2016/022724) (5.13 g, 8.70 mmol), bis(pinacolato)diboron (4.42 g, 17.4 mmol), potassium acetate (2.99 g, 30.5 mmol), and 1,1'-bis(diphenylphosphino)ferrocene palladium(II)dichloride dichloromethane adduct (1.421 g, 1.740 mmol) were combined to give crude residue. The residue was purified by ISCO 0-30% EtOAc in heptane to afford tert-butyl ((1S,5S,6S)-5-(2-fluoro-5-(4,4,5,5-tetramethyl-1,3,2-dioxaborolan-2-yl)phenyl)-1-(methoxymethyl)-5-methyl-2-thia-4-azabicyclo[4.1.0]hept-3-en-3-yl)((2-(trimethylsilyl)ethoxy)methyl)carbamate (58A) (5.23 g, 94% yield). LCMS (ESI+) m/z=637.3 (M+H).

Preparation of tert-butyl ((1S,5S,6S)-5-(5-((Z)-2-(5-chloropyrazin-2-yl)-2-fluorovinyl)-2-florophenyl)-1-(methoxymethyl)-5-methyl-2-thia-4-azabicyclo[4.1.0]hept-3-en-3-yl)((2-(trimethylsilyl)ethoxy)methyl)carbamate (58)

Using a procedure similar to that described for Example 222, tert-butyl ((1S,5S,6S)-5-(2-fluoro-5-(4,4,5,5-tetramethyl-1,3,2-dioxaborolan-2-yl)phenyl)-1-(methoxymethyl)-5-methyl-2-thia-4-azabicyclo[4.1.0]hept-3-en-3-yl)((2-(trimethylsilyl)ethoxy)methyl)carbamate (5.0 g, 7.8 mmol), 39 (2.68 g, 9.42 mmol), 1,1'-bis(diphenylphosphino)ferrocene palladium(II)dichloride dichloromethane adduct (0.641 g, 0.785 mmol), and sodium carbonate anhydrous (3.3 g, 31 mmol) were combined to give tert-butyl ((1S,5S,6S)-5-(5-((Z)-2-(5-chloropyrazin-2-yl)-2-fluorovinyl)-2-fluorophenyl)-1-(methoxymethyl)-5-methyl-2-thia-4-azabicyclo[4.1.0]hept-3-en-3-yl)((2-(trimethylsilyl)ethoxy)methyl)carbamate (58) (3.1 g, 59% yield). LCMS (ESI+) m/z=667.4/669.3 (M+H).

Preparation of (1S,5S,6S)-5-(5-((Z)-2-(5-chloropyrazin-2-yl)-2-fluorovinyl)-2-fluorophenyl)-1-(methoxymethyl)-5-methyl-2-thia-4-azabicyclo[4.1.0]hept-3-en-3-amine (Example 261)

A solution of tert-butyl ((1S,5S,6S)-5-(5-((Z)-2-(5-chloropyrazin-2-yl)-2-fluorovinyl)-2-fluorophenyl)-1-(methoxymethyl)-5-methyl-2-thia-4-azabicyclo[4.1.0]hept-3-en-3-yl)((2-(trimethylsilyl)ethoxy)methyl)carbamate (58B) (0.600 g, 0.899 mmol), p-toluenesulfonic acid monohydrate (0.684 g, 3.60 mmol) and dioxane (2 mL) in a sealed vial with pressure relief cap was heated to 80° C. for 2 hours. The reaction was diluted with saturated aq. NaHCO₃ and extracted with EtOAc (2×). The organic phase was concentrated and the residue purified by flash column chromatography on silica gel with ISCO eluting with 0-30% EtOAc/

EtOH (3:1) in heptane to afford (1S,5S,6S)-5-(5-((Z)-2-(5-chloropyrazin-2-yl)-2-fluorovinyl)-2-fluorophenyl)-1-(methoxymethyl)-5-methyl-2-thia-4-azabicyclo[4.1.0]hept-3-en-3-amine (Example 261) (0.36 g, 92% yield). LCMS (ESI+) m/z=437.2 (M+H). $^1$H NMR (400 MHz, CHLOROFORM-d) δ 8.62 (s, 1H), 8.54 (s, 1H), 7.92 (d, J=7.82 Hz, 1H), 7.66 (br. s., 1H), 7.00-7.14 (m, 2H), 4.15-4.98 (m, 2H), 3.65 (d, J=10.56 Hz, 1H), 3.41 (s, 3H), 3.35 (d, J=10.56 Hz, 1H), 1.70-1.81 (m, 4H), 0.89-0.95 (m, 1H), 0.75-0.84 (m, 1H). $^{19}$F NMR (376 MHz, CHLOROFORM-d) δ −109.94 (s, 1F), −127.01 (s, 1F).

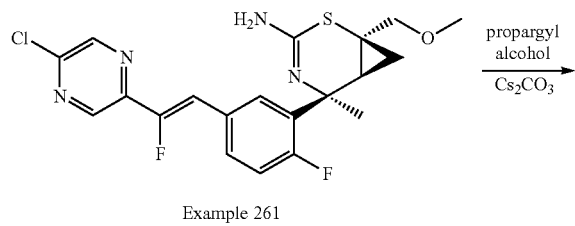

Example 261

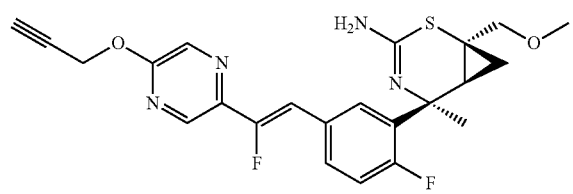

Example 262

Preparation of (1S,5S,6S)-5-(2-fluoro-5-((Z)-2-fluoro-2-(5-(prop-2-yn-1-yloxy)pyrazin-2-yl)vinyl)phenyl)-1-(methoxymethyl)-5-methyl-2-thia-4-azabicyclo[4.1.0]hept-3-en-3-amine. (Example 262)

To a mixture of (1S,5S,6S)-5-(5-((Z)-2-(5-chloropyrazin-2-yl)-2-fluorovinyl)-2-fluorophenyl)-1-(methoxymethyl)-5-methyl-2-thia-4-azabicyclo[4.1.0]hept-3-en-3-amine (0.060 g, 0.14 mmol) and propargyl alcohol (0.012 mL, 0.21 mmol) in THF (2 mL) was added cesium carbonate (0.134 g, 0.412 mmol). The reaction mixture was heated to 60° C. with stirring for 2 hours. The solvent was evaporated and the residue was purified by PREP LC/MS-2 System using column: XBridge Shield RP18 19×100 mm×10 um and mobile phase of 0.1% NH4OH in water/acetonitrile at a flow rate of 40 ml/min to afford (1S,5S,6S)-5-(2-fluoro-5-((Z)-2-fluoro-2-(5-(prop-2-yn-1-yloxy)pyrazin-2-yl)vinyl)phenyl)-1-(methoxymethyl)-5-methyl-2-thia-4-azabicyclo[4.1.0]hept-3-en-3-amine (Example 262) (0.042 g, 67% yield). LCMS (ESI+) m/z=457.2 (M+H). $^1$H NMR (400 MHz, CHLOROFORM-d) δ 8.38 (s, 1H), 8.26 (s, 1H), 7.87 (dd, J=1.96, 8.02 Hz, 1H), 7.61-7.67 (m, 1H), 7.06 (dd, J=8.51, 12.03 Hz, 1H), 6.87 (d, J=40.10 Hz, 1H), 5.03 (d, J=2.54 Hz, 2H), 4.01-4.90 (br. s., 2H), 3.65 (d, J=10.56 Hz, 1H), 3.41 (s, 3H), 3.35 (d, J=10.56 Hz, 1H), 2.53 (t, J=2.45 Hz, 1H), 1.66-1.83 (m, 4H), 0.92 (dd, J=5.67, 9.39 Hz, 1H), 0.77-0.84 (m, 1H). $^{19}$F NMR (376 MHz, CHLOROFORM-d) δ −111.37 (s, 1F), −126.01 (s, 1F).

Preparation of Examples 263-278

Using similar procedure described for Example 262, the following compounds were prepared in a parallel reaction format by reacting (1S,5S,6S)-5-(5-((Z)-2-(5-chloropyrazin-2-yl)-2-fluorovinyl)-2-fluorophenyl)-1-(methoxymethyl)-5-methyl-2-thia-4-azabicyclo[4.1.0]hept-3-en-3-amine (Example 261) (0.360 g, 0.824 mmol) and cesium carbonate (3 eq.) with the appropriate alcohols as shown in the table below.

| Ex. | Structure | Alcohols | Spectral Data |
|---|---|---|---|
| 263 | (1S,5S,6S)-5-(5-((Z)-2-(5-(but-2-yn-1-yloxy)pyrazin-2-yl)-2-fluorovinyl)-2-fluorophenyl)-1-(methoxymethyl)-5-methyl-2-thia-4-azabicyclo[4.1.0]hept-3-en-3-amine | but-2-yn-1-ol (1.5 eq.). | LCMS (ESI+) m/z = 471.0 (M + H). $^1$H NMR (500 MHz, DMSO-d6) δ 8.51 (s, 1H), 8.41 (s, 1H), 8.03 (d, J = 7.80 Hz, 1H), 7.58-7.65 (m, 1H), 7.20 (br dd, J = 8.50, 12.13 Hz, 1H), 6.90 (d, J = 40.87 Hz, 1H), 6.02 (br s, 2H), 5.71-5.77 (m, 1H), 3.49-3.62 (m, 2H), 3.35 (br d, J = 11.16 Hz, 1H), 3.29 (s, 3H), 1.64-1.74 (m, 1H), 1.57-1.63 (m, 6H), 0.85 (br dd, J = 5.13, 9.15 Hz, 1H), 0.56 (br t, J = 5.64 Hz, 1H) |

| Ex. | Structure | Alcohols | Spectral Data |
|---|---|---|---|
| 264 | 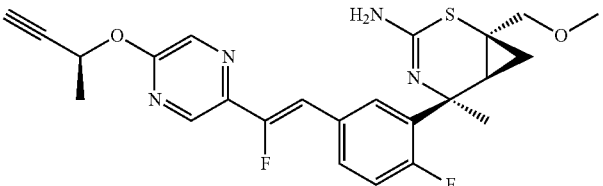<br>(1S,5S,6S)-5-(5-((Z)-2-(5-((S)-but-3-yn-2-yloxy)pyrazin-2-yl)-2-fluorovinyl)-2-fluorophenyl)-1-(methoxymethyl)-5-methyl-2-thia-4-azabicyclo[4.1.0]hept-3-en-3-amine | (S)-but-3-yn-2-ol | LCMS (ESI+) m/z = 471.0 (M + H). $^1$H NMR (500 MHz, DMSO-d6) δ 8.47-8.53 (m, 1H), 8.39-8.44 (m, 1H), 8.00-8.06 (m, 1H), 7.57-7.65 (m, 1H), 7.17-7.25 (m, 1H), 6.87 (d, J = 41.00 Hz, 1H), 6.01 (br s, 2H), 5.03 (br d, J = 2.21 Hz, 2H), 3.55 (br d, J = 10.90 Hz, 1H), 3.34 (br d, J = 10.90 Hz, 1H), 3.28-3.30 (m, 3H), 1.85 (d, J = 2.08 Hz, 3H), 1.65-1.76 (m, 1H), 1.54-1.64 (m, 3H), 0.80-0.89 (m, 1H), 0.51-0.61 (m, 1H) |
| 265 | 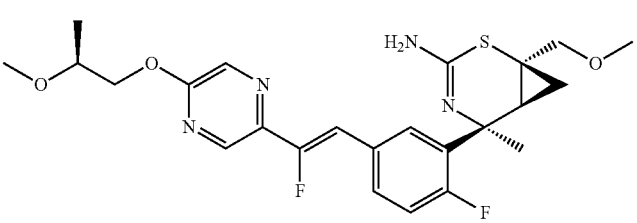<br>(1S,5S,6S)-5-(2-fluoro-5-((Z)-2-fluoro-2-(5-((S)-2-methoxypropoxy)pyrazin-2-yl)vinyl)phenyl)-1-(methoxymethyl)-5-methyl-2-thia-4-azabicyclo[4.1.0]hept-3-en-3-amine | (S)-2-methoxy propan-1-ol | LCMS (ESI+) m/z = 491.2 (M + H). $^1$H NMR (500 MHz, DMSO-d$_6$) δ 8.46 (s, 1H), 8.41 (s, 1H), 8.02 (d, J = 7.69 Hz, 1H), 7.57-7.66 (m, 1H), 7.20 (br dd, J = 8.43, 12.07 Hz, 1H), 6.87 (d, J = 41.00 Hz, 1H), 6.01 (br s, 2H), 4.26-4.39 (m, 2H), 3.72 (dt, J = 4.09, 6.13 Hz, 1H), 3.55 (br d, J = 10.90 Hz, 1H), 3.36 (br d, J = 10.90 Hz, 1H), 3.31 (br s, 3H), 3.29 (br s, 3H), 1.68 (br t, J = 7.59 Hz, 1H), 1.59 (s, 3H), 1.18 (d, J = 6.36 Hz, 3H), 0.84 (br dd, J = 5.19, 9.21 Hz, 1H), 0.56 (br t, J = 5.64 Hz, 1H) |
| 266 | 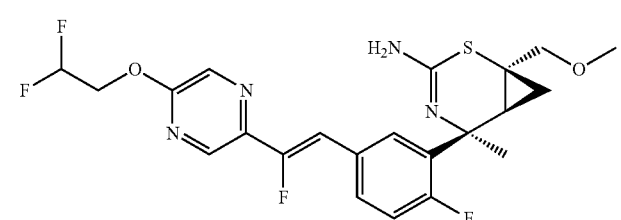<br>(1S,5S,6S)-5-(5-((Z)-2-(5-(2,2-difluoroethoxy)pyrazin-2-yl)-2-fluorovinyl)-2-fluorophenyl)-1-(methoxymethyl)-5-methyl-2-thia-4-azabicyclo[4.1.0]hept-3-en-3-amine | 2,2-difluoro-ethanol | LCMS (ESI+) m/z = 483.0 (M + H). $^1$H NMR (500 MHz, DMSO-d$_6$) δ 8.41-8.57 (m, 2H), 8.03 (br d, J = 6.36 Hz, 1H), 7.61 (br d, J = 7.97 Hz, 1H), 7.21 (dd, J = 8.56, 12.07 Hz, 1H), 6.91 (d, J = 40.61 Hz, 1H), 6.45 (dd, J = 2.98, 53.98 Hz, 1H), 6.01 (br s, 2H), 4.69 (dt, J = 3.18, 15.08 Hz, 2H), 3.55 (br d, J = 10.90 Hz, 1H), 3.36 (br d, J = 10.90 Hz, 1H), 3.29 (s, 3H), 1.68 (br t, J = 7.85 Hz, 1H), 1.59 (s, 3H), 0.76-0.93 (m, 1H), 0.46-0.66 (m, 1H). |

| Ex. | Structure | Alcohols | Spectral Data |
|---|---|---|---|
| 267 | (1S,5S,6S)-5-(2-fluoro-5-((Z)-2-fluoro-2-(5-(2,2,2-trifluoroethoxy)pyrazin-2-yl)vinyl)phenyl)-1-(methoxymethyl)-5-methyl-2-thia-4-azabicyclo[4.1.0]hept-3-en-3-amine | 2,2,2-trifluoroethanol | LCMS (ESI+) m/z = 501.0 (M + H). $^1$H NMR (500 MHz, DMSO-d$_6$) δ 8.57 (s, 1H), 8.53 (s, 1H), 8.04 (d, J = 7.60 Hz, 1H), 7.59-7.66 (m, 1H), 7.21 (br dd, J = 8.56, 12.07 Hz, 1H), 6.94 (d, J = 40.61 Hz, 1H), 6.01 (br s, 2H), 5.10 (q, J = 8.82 Hz, 2H), 3.55 (br d, J = 10.90 Hz, 1H), 3.36 (br d, J = 10.90 Hz, 1H), 3.30 (br s, 3H), 1.68 (br t, J = 7.72 Hz, 1H), 1.59 (s, 3H), 0.85 (br dd, J = 5.13, 9.15 Hz, 1H), 0.56 (br t, J = 5.64 Hz, 1H) |
| 268 | (1S,5S,6S)-5-(2-fluoro-5-((Z)-2-fluoro-2-(5-(3,3,3-trifluoropropoxy)pyrazin-2-yl)vinyl)phenyl)-1-(methoxymethyl)-5-methyl-2-thia-4-azabicyclo[4.1.0]hept-3-en-3-amine | 3,3,3-trifluoropropan-1-ol | LCMS (ESI$^+$) m/z = 515.0 (M + H). $^1$H NMR (500 MHz, DMSO-d$_6$) δ 8.49 (s, 1H), 8.41 (s, 1H), 8.03 (d, J = 7.54 Hz, 1H), 7.58-7.64 (m, 1H), 7.20 (dd, J = 8.56, 12.07 Hz, 1H), 6.89 (d, J = 41.00 Hz, 1H), 6.01 (s, 2H), 4.60 (t, J = 5.90 Hz, 2H), 3.55 (br d, J = 10.90 Hz, 1H), 3.36 (br d, J = 10.90 Hz, 1H), 3.30 (br s., 3H), 2.86 (m, 2H), 1.63-1.72 (m, 1H), 1.59 (s, 3H), 0.84 (br dd, J = 5.13, 9.15 Hz, 1H), 0.56 (br t, J = 5.58 Hz, 1H) |
| 269 | (1S,5S,6S)-5-(2-fluoro-5-((Z)-2-fluoro-2-(5-(2-fluoroethoxy)pyrazin-2-yl)vinyl)phenyl)-1-(methoxymethyl)-5-methyl-2-thia-4-azabicyclo[4.1.0]hept-3-en-3-amine | 2-fluoroethanol | LCMS (ESI+) m/z = 465.0 (M + H). $^1$H NMR (500 MHz, DMSO-d$_6$) δ 8.47 (s, 1H), 8.45 (s, 1H), 8.02 (br d, J = 6.75 Hz, 1H), 7.61 (br d, J = 8.01 Hz, 1H), 7.21 (br dd, J = 8.50, 12.00 Hz, 1H), 6.89 (d, J = 41.00 Hz, 1H), 6.02 (br s, 2H), 4.80 (ddd, J = 4.15, 48.01 Hz, 2H), 4.62 (dd, J = 3.63, 30.10 Hz, 2H), 3.55 (br d, J = 11.03 Hz, 1H), 3.35 (br d, J = 11.03 Hz, 1H), 3.30 (br s, 3H), 1.69 (br t, J = 7.46 Hz, 1H), 1.60 (s, 3H), 0.78-0.92 (m, 1H), 0.53-0.62 (m, 1H) |

| Ex. | Structure | Alcohols | Spectral Data |
|---|---|---|---|
| 270 | (1S,5S,6S)-5-(5-((Z)-2-(5-(cyclopropylmethoxy)pyrazin-2-yl)-2-fluorovinyl)-2-fluorophenyl)-1-(methoxymethyl)-5-methyl-2-thia-4-azabicyclo[4.1.0]hept-3-en-3-amine | cyclo-propyl-methanol | LCMS (ESI+) m/z = 473.2 (M + H). $^1$H NMR (500 MHz, DMSO-d$_6$) δ 8.44 (s, 1H), 8.35-8.41 (m, 1H), 8.02 (d, J = 7.78 Hz, 1H), 7.60 (br d, J = 1.91 Hz, 1H), 7.20 (br dd, J = 8.63, 12.13 Hz, 1H), 6.86 (d, J = 40.87 Hz, 1H), 6.02 (br s, 2H), 4.20 (d, J = 7.27 Hz, 2H), 3.55 (br d, J = 10.90 Hz, 1H), 3.34 (br d, J = 10.90 Hz, 1H), 3.29-3.30 (m, 3H), 1.68 (br t, J = 7.72 Hz, 1H), 1.59 (s, 3H), 1.22-1.32 (m, 1H), 0.85 (br dd, J = 5.06, 9.21 Hz, 1H), 0.54-0.62 (m, 3H), 0.32-0.43 (m, 2H) |
| 271 | (1S,5S,6S)-5-(5-((Z)-2-(5-(cyclobutylmethoxy)pyrazin-2-yl)-2-fluorovinyl)-2-fluorophenyl)-1-(methoxymethyl)-5-methyl-2-thia-4-azabicyclo[4.1.0]hept-3-en-3-amine | cyclo-butyl-methanol | LCMS (ESI+) m/z = 487.2 (M + H). $^1$H NMR (500 MHz, DMSO-d$_6$) δ 8.45 (s, 1H), 8.37 (s, 1H), 8.01 (br d, J = 6.88 Hz, 1H), 7.57-7.64 (m, 1H), 7.20 (br dd, J = 8.50, 12.00 Hz, 1H), 6.86 (d, J = 40.87 Hz, 1H), 5.93-6.14 (m, 2H), 4.34 (d, J = 6.75 Hz, 2H), 3.55 (br d, J = 10.90 Hz, 1H), 3.35 (br d, J = 11.03 Hz, 1H), 3.29 (s, 3H), 2.72-2.81 (m, 1H), 2.01-2.14 (m, 2H), 1.79-1.98 (m, 4H), 1.69 (br t, J = 7.66 Hz, 1H), 1.60 (s, 3H), 0.85 (br dd, J = 5.32, 7.91 Hz, 1H), 0.56 (br t, J = 5.38 Hz, 1H) |
| 272 | (1S,5S,6S)-5-(2-fluoro-5-((Z)-2-fluoro-2-(5-(oxetan-3-ylmethoxy)pyrazin-2-yl)vinyl)phenyl)-1-(methoxymethyl)-5-methyl-2-thia-4-azabicyclo[4.1.0]hept-3-en-3-amine | oxetan-3-yl-methanol | LCMS (ESI+) m/z = 489.0 (M + H). $^1$H NMR (500 MHz, DMSO-d6) Shift 8.47 (s, 1H), 8.40 (s, 1H), 8.02 (br d, J = 5.97 Hz, 1H), 7.57-7.64 (m, 1H), 7.20 (br dd, J = 8.63, 12.00 Hz, 1H), 6.88 (d, J = 40.87 Hz, 1H), 6.02 (br s, 2H), 4.72 (dd, J = 6.10, 7.79 Hz, 2H), 4.58 (d, J = 6.75 Hz, 2H), 4.46 (t, J = 6.10 Hz, 2H), 3.55 (br d, J = 10.90 Hz, 1H), 3.44 (td, J = 7.06, 13.79 Hz, 1H), 3.35 (br d, J = 10.90 Hz, 1H), 3.28-3.30 (m, 3H), 1.68 (br t, J = 7.66 Hz, 1H), 1.59 (s, 3H), 0.85 |

| Ex. | Structure | Alcohols | Spectral Data |
|---|---|---|---|
| | | | (br dd, J = 5.19, 9.08 Hz, 1H), 0.56 (br t, J = 5.71 Hz, 1H) |
| 273 | (1S,5S,6S)-5-(2-fluoro-5-((Z)-2-fluoro-2-(5-(oxetan-2-ylmethoxy)pyrazin-2-yl)vinyl)phenyl)-1-(methoxymethyl)-5-methyl-2-thia-4-azabicyclo[4.1.0]hept-3-en-3-amine | oxetan-2-yl-methanol | LCMS (ESI+) m/z = 489.0 (M + H). $^1$H NMR (500 MHz, DMSO-d6) Shift 8.47 (s, 1H), 8.45 (s, 1H), 8.03 (d, J = 7.52 Hz, 1H), 7.58-7.64 (m, 1H), 7.20 (dd, J = 8.50, 12.13 Hz, 1H), 6.88 (d, J = 40.87 Hz, 1H), 6.02 (br s, 2H), 5.03-5.09 (m, 1H), 4.46-4.59 (m, 4H), 3.55 (br d, J = 11.03 Hz, 1H), 3.35 (br d, J = 11.03 Hz, 1H), 3.29-3.30 (m, 3H), 2.63-2.77 (m, 1H), 2.52-2.60 (m, 1H), 1.68 (br t, J = 7.98 Hz, 1H), 1.59 (s, 3H), 0.85 (br dd, J = 5.19, 9.34 Hz, 1H), 0.56 (br t, J = 5.58 Hz, 1H) |
| 274 | (1S,5S,6S)-5-(2-fluoro-5-((Z)-2-fluoro-2-(5-isobutoxypyrazin-2-yl)vinyl)phenyl)-1-(methoxymethyl)-5-methyl-2-thia-4-azabicyclo[4.1.0]hept-3-en-3-amine | 2-methyl-propan-1-ol | LCMS (ESI+) m/z = 475.2 (M + H). $^1$H NMR (500 MHz, DMSO-d6) Shift 8.45 (s, 1H), 8.38 (s, 1H), 8.02 (br d, J = 6.23 Hz, 1H), 7.57-7.64 (m, 1H), 7.20 (br dd, J = 8.56, 12.07 Hz, 1H), 6.86 (d, J = 41.00 Hz, 1H), 6.01 (br s, 2H), 4.14 (d, J = 6.49 Hz, 2H), 3.55 (br d, J = 10.90 Hz, 1H), 3.34 (br d, J = 10.90 Hz, 1H), 3.29 (br s, 3H), 2.03-2.13 (m, 1H), 1.68 (br t, J = 7.59 Hz, 1H), 1.59 (s, 3H), 0.99 (d, J = 6.75 Hz, 6H), 0.84 (br dd, J = 5.06, 9.21 Hz, 1H), 0.56 (br t, J = 5.58 Hz, 1H) |
| 275 | (1S,5S,6S)-5-(2-fluoro-5-((Z)-2-fluoro-2-(5-((5-methylisoxazol-3-yl)methoxy)pyrazin-2-yl)vinyl)phenyl)-1-(methoxymethyl)-5-methyl-2-thia-4-azabicyclo[4.1.0]hept-3-en-3-amine | (5-methyl-isoxazol-3-yl)methanol | LCMS (ESI+) m/z = 514.0 (M + H). $^1$H NMR (500 MHz, DMSO-d$_6$) δ 8.50 (s, 1H), 8.46 (s, 1H), 8.02 (br d, J = 7.27 Hz, 1H), 7.58-7.67 (m, 1H), 7.21 (br dd, J = 8.69, 12.07 Hz, 1H), 6.90 (d, J = 41.00 Hz, 1H), 6.35 (s, 1H), 6.02 (br s, 2H), 5.48 (s, 2H), 3.55 (br d, J = 10.90 Hz, 1H), 3.35 (br d, J = 10.90 Hz, 1H), 3.30 (br s, 3H), 2.41 (s, 3H), 1.69 (br t, J = 7.46 Hz, 1H), 1.60 (s, |

| Ex. | Structure | Alcohols | Spectral Data |
|---|---|---|---|
| | | | 3H), 0.79-0.92 (m, 1H), 0.56 (br t, J = 5.51 Hz, 1H) |
| 276 | 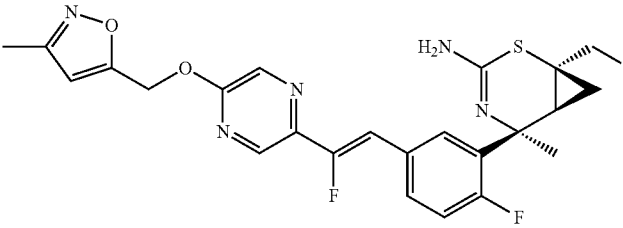<br>(1S,5S,6S)-5-(2-fluoro-5-((Z)-2-fluoro-2-(5-((3-methylisoxazol-5-yl)methoxy)pyrazin-2-yl)vinyl)phenyl)-1-(methoxymethyl)-5-methyl-2-thia-4-azabicyclo[4.1.0]hept-3-en-3-amine | (3-methyl-isoxazol-5-yl)methanol | LCMS (ESI+) m/z = 514.0 (M + H). $^1$H NMR (500 MHz, DMSO-d$_6$) δ 8.51 (s, 1H), 8.47 (s, 1H), 8.03 (br d, J = 6.10 Hz, 1H), 7.61 (d, J = 7.95 Hz, 1H), 7.21 (br dd, J = 8.56, 12.07 Hz, 1H), 6.90 (d, J = 40.74 Hz, 1H), 6.46-6.58 (m, 1H), 6.02 (br s, 2H), 5.56 (s, 2H), 3.55 (br d, J = 11.03 Hz, 1H), 3.35 (br d, J = 11.03 Hz, 1H), 3.29 (s, 3H), 2.24 (s, 3H), 1.69 (br t, J = 7.79 Hz, 1H), 1.60 (s, 3H), 0.85 (br dd, J = 5.19, 9.08 Hz, 1H), 0.56 (br t, J = 5.64 Hz, 1H) |
| 277 | 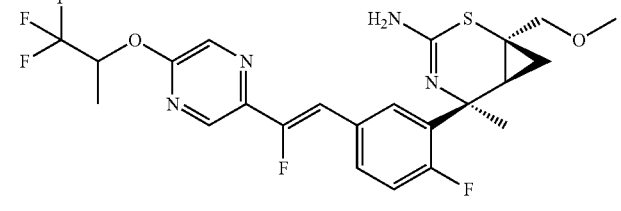<br>(1S,5S,6S)-5-(2-fluoro-5-((Z)-2-fluoro-2-(5-((1,1,1-trifluoropropan-2-yl)oxy)pyrazin-2-yl)vinyl)phenyl)-1-(methoxymethyl)-5-methyl-2-thia-4-azabicyclo[4.1.0]hept-3-en-3-amine | 1,1,1-trifluoro-propan-2-ol | LCMS (ESI+) m/z = 515.0 (M + H). $^1$H NMR (500 MHz, DMSO-d$_6$) δ 8.52 (s, 2H), 8.04 (br d, J = 6.62 Hz, 1H), 7.59-7.66 (m, 1H), 7.21 (br dd, J = 8.56, 12.07 Hz, 1H), 6.93 (d, J = 40.87 Hz, 1H), 6.02 (br s, 2H), 5.87-5.97 (m, 1H), 3.55 (br d, J = 10.90 Hz, 1H), 3.35 (br d, J = 10.90 Hz, 1H), 3.30 (s, 3H), 1.63-1.74 (m, 1H), 1.59 (s, 3H), 1.51 (br d, J = 6.49 Hz, 3H), 0.85 (br dd, J = 5.13, 9.15 Hz, 1H), 0.56 (br t, J = 5.64 Hz, 1H) |
| 278 | 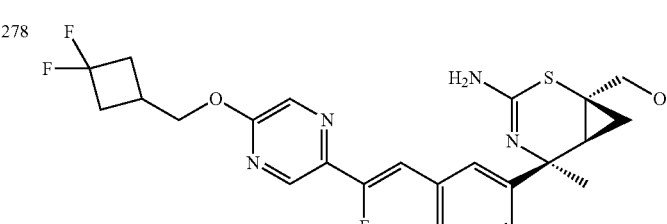<br>(1S,5S,6S)-5-(5-((Z)-2-(5-((3,3-difluorocyclobutyl)methoxy)pyrazin-2-yl)-2-fluorovinyl)-2-fluorophenyl)-1-(methoxymethyl)-5-methyl-2-thia-4-azabicyclo[4.1.0]hept-3-en-3-amine | (3,3-difluoro-cyclo-butyl)methanol | LCMS (ESI+) m/z = 523.0 (M + H). $^1$H NMR (500 MHz, DMSO-d$_6$) δ 8.46 (s, 1H), 8.39 (s, 1H), 8.02 (br d, J = 6.10 Hz, 1H), 7.57-7.64 (m, 1H), 7.20 (br dd, J = 8.50, 12.00 Hz, 1H), 6.88 (d, J = 40.87 Hz, 1H), 6.01 (br s, 2H), 4.43 (br d, J = 6.49 Hz, 2H), 3.55 (br d, J = 10.90 Hz, 1H), 3.34 (br d, J = 10.90 Hz, 1H), 3.29 (s, 3H), 2.67-2.79 (m, 2H), 2.60-2.67 (m, 1H), 2.52-2.59 (m, 1H), 2.44-2.49 (m, 1H), 1.68 (br t, J = 7.72 Hz, 1H), 1.59 (s, 3H), 0.84 |

| Ex. | Structure | Alcohols | Spectral Data |
|---|---|---|---|
| | | | (br dd, J = 5.13, 9.15 Hz, 1H), 0.56 (br t, J = 5.64 Hz, 1H) |

Synthesis of Intermediate 59

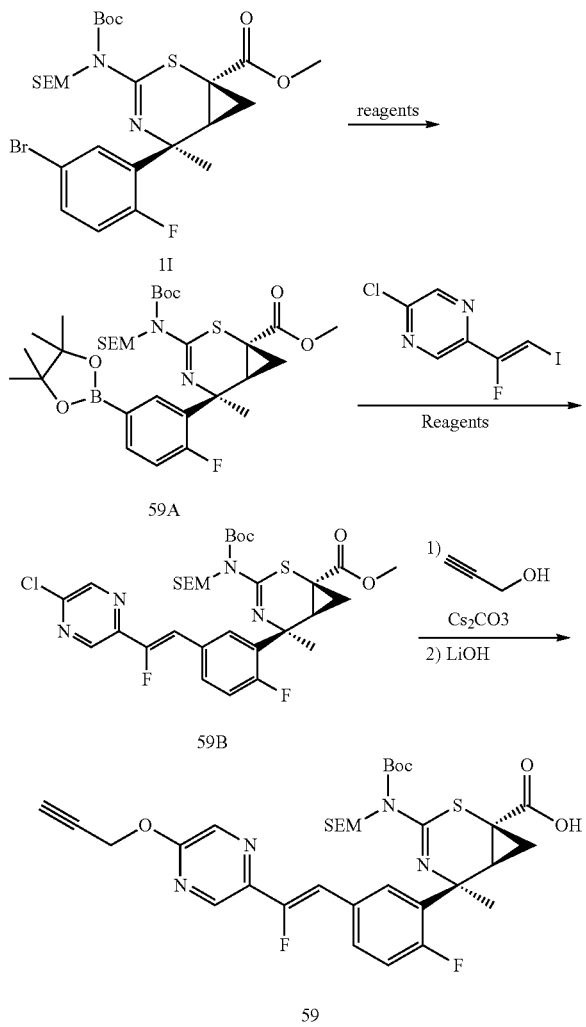

59

Preparation of (1S,5S,6S)-methyl 3-((tert-butoxycarbonyl)((2-(trimethylsilyl)ethoxy)methyl)amino)-5-(2-fluoro-5-(4,4,5,5-tetramethyl-1,3,2-dioxaborolan-2-yl)phenyl)-5-methyl-2-thia-4-azabicyclo[4.1.0]hept-3-ene-1-carboxylate (59A)

Using a procedure similar to that described for 31, (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (1I) (6.0 g, 9.9 mmol), bis(pinacolato) diboron (10.1 g, 39.8 mmol), potassium acetate (4.88 g, 49.7 mmol), and 1,1'-bis(diphenylphosphino)ferrocene palladium(II)dichloride dichloromethane adduct (2.43 g, 2.98 mmol) were reacted to afford (1S,5S,6S)-methyl 3-((tert-butoxycarbonyl)((2-(trimethylsilyl)ethoxy)methyl)amino)-5-(2-fluoro-5-(4,4,5,5-tetramethyl-1,3,2-dioxaborolan-2-yl)phenyl)-5-methyl-2-thia-4-azabicyclo[4.1.0]hept-3-ene-1-carboxylate (59A) (6.1 g, 94% yield). LCMS (ESI+) m/z=651.4 (M+H).

Preparation of (1S,5S,6S)-methyl 3-((tert-butoxycarbonyl)((2-(trimethylsilyl)ethoxy)methyl)amino)-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate (59B)

Using a procedure similar to that described for Example 222, (1S,5S,6S)-methyl 3-((tert-butoxycarbonyl)((2-(trimethylsilyl)ethoxy)methyl)amino)-5-(2-fluoro-5-(4,4,5,5-tetramethyl-1,3,2-dioxaborolan-2-yl)phenyl)-5-methyl-2-thia-4-azabicyclo[4.1.0]hept-3-ene-1-carboxylate (5.02 g, 7.71 mmol), (Z)-2-chloro-5-(1-fluoro-2-iodovinyl)pyrazine, (39) (2.63 g, 9.26 mmol), 1,1'-bis(diphenylphosphino)ferrocene palladium(II)dichloride dichloromethane adduct (0.630 g, 0.771 mmol), and sodium carbonate (2.453 g, 23.14 mmol) were reacted to afford (1S,5S,6S)-methyl 3-((tert-butoxycarbonyl)((2-(trimethylsilyl)ethoxy)methyl)amino)-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate (59B) (1.87 g, 36% yield). LCMS (ESI+) m/z=681.2 (M+H).

(1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylic acid (59)

Using a procedure similar to that described for Example 234, (1S,5S,6S)-methyl 3-((tert-butoxycarbonyl)((2-(trimethylsilyl)ethoxy)methyl)amino)-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate (1.87 g, 2.74 mmol) was reacted with propargyl alcohol (0.324 ml, 5.49 mmol) and cesium carbonate (2.68 g, 8.23 mmol), and after purification with column chromatography using ISCO eluting with 0-40% EtOAc in heptane afforded (1S,5S,6S)-methyl 3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylate (1.5 g, 78% yield). This intermediate was reacted with lithium hydroxide monohydrate (0.126 g, 3.00 mmol) using a procedure similar to that described in the synthesis of 29 to give (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylic acid (59) (1.3, 89% yield). LCMS (ESI+) m/z=687.5 (M+H). $^1$H NMR (400 MHz, CHLOROFORM-d) δ 8.40 (s, 1H), 8.28 (s, 1H), 7.90-7.96 (m, 1H), 7.63-7.71 (m, 1H), 7.08-7.17 (m, 1H), 6.89 (d, J=39.91 Hz, 1H), 5.33 (d, J=10.76 Hz, 1H), 5.12 (d, J=10.56 Hz, 1H), 5.05 (d, J=2.35 Hz, 2H), 3.66-3.75 (m, 2H), 2.74 (brt, J=8.71 Hz, 1H), 2.55 (t, J=2.35 Hz, 1H), 1.82 (s, 3H), 1.63 (br dd, J=5.28, 9.78 Hz, 1H), 1.56 (s, 9H), 1.33-1.46 (m, 1H), 0.98 (dd, J=7.43, 9.00 Hz, 2H), 0.00 (s, 9H). $^{19}$F NMR (376 MHz, CHLOROFORM-d) δ −111.90 (s, 1F), −125.74 (s, 1F).

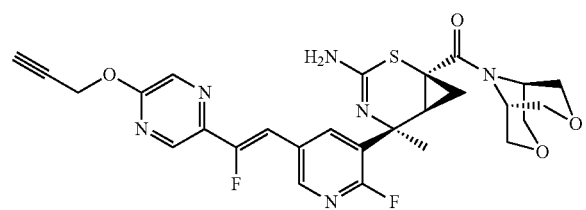 [SMILES: C#CCOc1cnc(/C(F)=C/c2cnc(F)c([C@@]3(C)N=C(N)S[C@@]4(C(=O)N5[C@H]6COC[C@@H]5COC6)C[C@H]43)c2)cn1]

Example 279

Preparation of ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((1R,5R)-3,7-dioxa-9-azabicyclo[3.3.1]nonan-9-yl)methanone (Example 279)

Using a procedure similar to that described for Example 260, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylic acid (59) (0.120 g, 0.175 mmol), 1-chloro-N,N,2-trimethyl-1-propenylamine (0.093 ml, 0.60 mmol), triethylamine (0.088 g, 0.87 mmol), and (1S,5S)-3,7-dioxa-9-azabicyclo[3.3.1]nonane (0.034 g, 0.26 mmol) were combined to provide the amide, which after deprotection with p-toluenesulfonic acid monohydrate (0.100 g, 0.524 mmol) afforded ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((1R,5R)-3,7-dioxa-9-azabicyclo[3.3.1]nonan-9-yl)methanone (Example 279) (0.035 g, 35.3% yield). LCMS (ESI+) m/z=568.2 (M+H). $^1$H NMR (400 MHz, CHLOROFORM-d) δ 8.34 (s, 1H), 8.23 (s, 1H), 7.72 (d, J=7.74 Hz, 1H), 7.56-7.64 (m, 1H), 7.00-7.10 (m, 1H), 6.80 (d, J=40.30 Hz, 1H), 5.02 (d, J=2.35 Hz, 2H), 4.38-4.90 (br. s., 2H), 4.25 (br s, 1H), 4.05-4.20 (m, 5H), 3.93-4.04 (m, 1H), 3.80-3.93 (m, 3H), 2.54 (t, J=2.25 Hz, 1H), 2.27-2.34 (m, 1H), 1.83 (s, 3H), 1.42 (dd, J=5.67, 9.78 Hz, 1H), 0.87 (t, J=6.36 Hz, 1H). $^{19}$F NMR (376 MHz, CHLOROFORM-d) δ −110.26 (s, 1F), −125.90 (s, 1F).

Synthesis of Intermediate 60

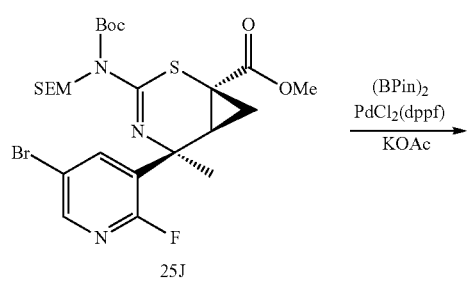

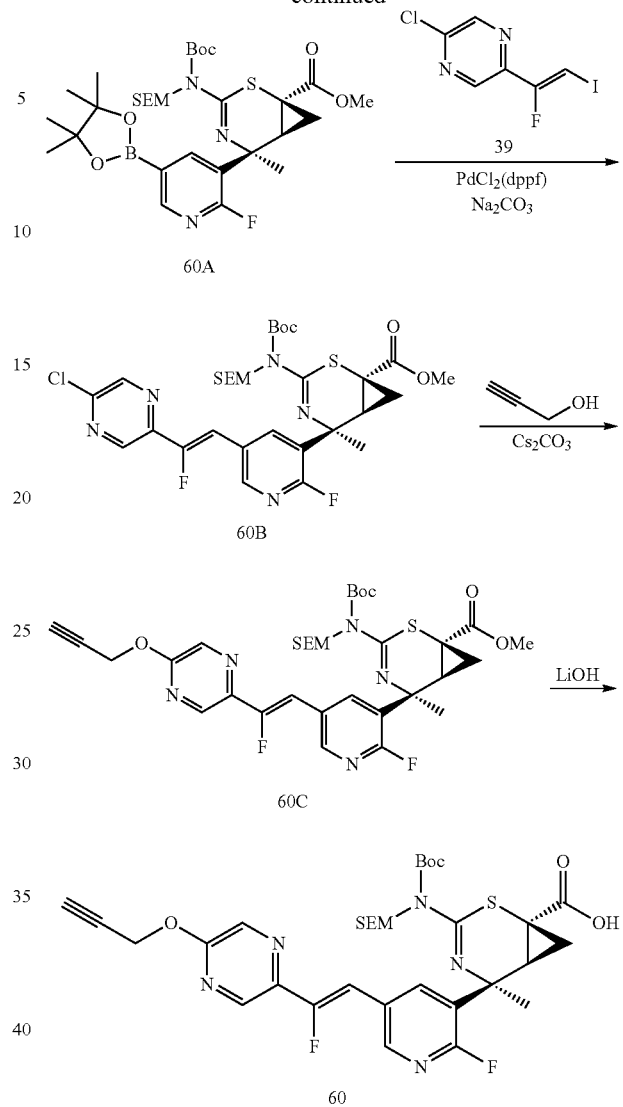

Preparation of (1S,5S,6S)-methyl 3-((tert-butoxycarbonyl)((2-(trimethylsilyl)ethoxy)methyl)amino)-5-(2-fluoro-5-(4,4,5,5-tetramethyl-1,3,2-dioxaborolan-2-yl)pyridin-3-yl)-5-methyl-2-thia-4-azabicyclo[4.1.0]hept-3-ene-1-carboxylate (60A)

Using a procedure similar to that described for 31, (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (25J) (5.31 g, 8.78 mmol), bis(pinacolato)diboron (6.69 g, 26.3 mmol), potassium acetate (4.31 g, 43.9 mmol), and 1,1'-bis(diphenylphosphino)ferrocene palladium (II)dichloride dichloromethane adduct (60A) (2.15 g, 2.63 mmol) were reacted to afford (1S,5S,6S)-methyl 3-((tert-butoxycarbonyl)((2-(trimethylsilyl)ethoxy)methyl)amino)-5-(2-fluoro-5-(4,4,5,5-tetramethyl-1,3,2-dioxaborolan-2-yl)pyridin-3-yl)-5-methyl-2-thia-4-azabicyclo[4.1.0]hept-3-ene-1-carboxylate (60A) (5.60 g, 98% yield). LCMS (ESI+) m/z=652.2 (M+H).

Preparation of (1S,5S,6S)-methyl 3-((tert-butoxycarbonyl)((2-(trimethylsilyl)ethoxy)methyl)amino)-5-(5-((Z)-2-(5-chloropyrazin-2-yl)-2-fluorovinyl)-2-fluoropyridin-3-yl)-5-methyl-2-thia-4-azabicyclo[4.1.0]hept-3-ene-1-carboxylate (60B)

Using a procedure similar to that described for Example 222, (1S,5S,6S)-methyl 3-((tert-butoxycarbonyl)((2-(trimethylsilyl)ethoxy)methyl)amino)-5-(2-fluoro-5-(4,4,5,5-tetramethyl-1,3,2-dioxaborolan-2-yl)pyridin-3-yl)-5-methyl-2-thia-4-azabicyclo[4.1.0]hept-3-ene-1-carboxylate (60A) (5.12 g, 7.86 mmol), 39 (2.91 g, 10.2 mmol), 1,1'-bis(diphenylphosphino)ferrocene palladium(II)dichloride dichloromethane adduct (0.642 g, 0.786 mmol), and sodium carbonate (2.498 g, 23.57 mmol) were combined to form the coupling product which was purified with ISCO using 0-20% EtOAc in heptane to afford (1S,5S,6S)-methyl 3-((tert-butoxycarbonyl)((2-(trimethylsilyl)ethoxy)methyl)amino)-5-(5-((Z)-2-(5-chloropyrazin-2-yl)-2-fluorovinyl)-2-fluoropyridin-3-yl)-5-methyl-2-thia-4-azabicyclo[4.1.0]hept-3-ene-1-carboxylate (60B) (4.2, 78% yield). LCMS (ESI+) m/z=682.0/684.2 (M+). $^1$H NMR (400 MHz, CHLOROFORM-d) δ 8.66 (s, 1H), 8.58 (s, 1H), 8.41-8.49 (m, 2H), 7.05 (d, J=39.52 Hz, 1H), 5.36 (d, J=10.76 Hz, 1H), 5.12 (d, J=10.56 Hz, 1H), 3.83 (s, 3H), 3.69 (t, J=8.22 Hz, 2H), 2.71 (t, J=8.61 Hz, 1H), 1.79 (s, 3H), 1.50-1.61 (m, 10H), 1.20-1.25 (m, 1H), 0.93-1.00 (m, 2H), 0.00 (s, 9H). $^{19}$F NMR (376 MHz, CHLOROFORM-d) δ −64.09 (s, 1F), −123.36 (s, 1F).

Preparation of (1S,5S,6S)-methyl 3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylate (60C)

Using a procedure similar to that described for Example 234, (1S,5S,6S)-methyl 3-((tert-butoxycarbonyl)((2-(trimethylsilyl)ethoxy)methyl)amino)-5-(5-((Z)-2-(5-chloropyrazin-2-yl)-2-fluorovinyl)-2-fluoropyridin-3-yl)-5-methyl-2-thia-4-azabicyclo[4.1.0]hept-3-ene-1-carboxylate (2.4 g, 3.52 mmol) (60B) was reacted with propargyl alcohol (0.270 mL, 4.57 mmol) and cesium carbonate (3.44 g, 10.55 mmol) to afford (1S,5S,6S)-methyl 3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylate (60C) (1.4 g, 57% yield). LCMS (ESI+) m/z=702.2 (M+H).

Preparation of (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (60)

Using a procedure similar to that described for 29, (1S,5S,6S)-methyl 3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylate (60C) (1.400 g, 1.995 mmol) was reacted with lithium hydroxide monohydrate (0.126 g, 2.99 mmol) to afford the titled compound (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (60) (1.2 g, 87% yield). LCMS (ESI+) m/z=688.4 (M+H).

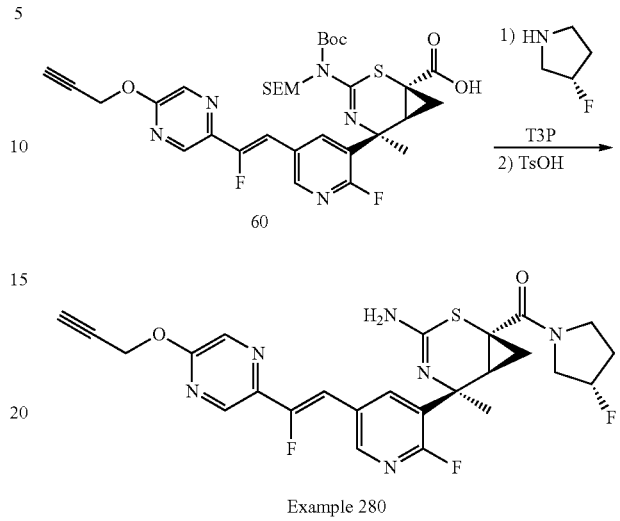

Example 280

Preparation of ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((S)-3-fluoropyrrolidin-1-yl)methanone (Example 280)

Following the procedure described for Example 122 (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (60) (0.110 g, 0.160 mmol), (S)-3-fluoropyrrolidine hydrochloride (0.030 g, 0.240 mmol), triethylamine (0.10 mL, 0.74 mmol), and 1-propanephosphonic acid cyclic anhydride (0.509 ml, 0.800 mmol) were reacted to give a crude product, which after deprotection with p-toluenesulfonic acid monohydrate (0.091 g, 0.48 mmol) afforded ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((S)-3-fluoropyrrolidin-1-yl)methanone (Example 280) (0.019 g, 22% yield). LCMS (ESI+) m/z=529.1 (M+H). $^1$H NMR (400 MHz, CHLOROFORM-d) δ 8.39 (s, 1H), 8.34 (s, 1H), 8.20-8.29 (m, 2H), 6.85 (d, J=39.71 Hz, 1H), 5.30 (d, J=52.04 Hz, 1H), 5.04 (d, J=2.35 Hz, 2H), 4.22-4.87 (m, 1H), 4.01 (d, J=11.93 Hz, 1H), 3.43-3.88 (m, 3H), 2.54 (t, J=2.35 Hz, 1H), 2.22-2.45 (m, 2H), 1.90-2.17 (m, 1H), 1.93 (br. s., 1H), 1.85 (s, 3H), 1.39 (dd, J=5.67, 9.59 Hz, 1H), 0.80-0.94 (m, 1H). $^{19}$F NMR (376 MHz, CHLOROFORM-d) δ −63.92 (s, 1F), −122.54 (s, 1F), −177.55 (s, 1F).

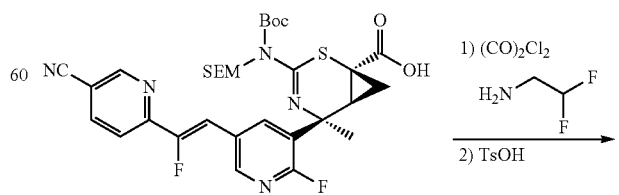

293
-continued

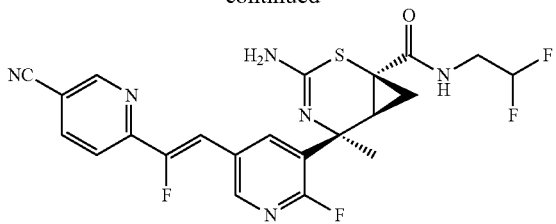

Example 281

Preparation of (1S,5S,6S)-3-amino-5-(5-((Z)-2-(5-cyanopyridin-2-yl)-2-fluorovinyl)-2-fluoropyridin-3-yl)-N-(2,2-difluoroethyl)-5-methyl-2-thia-4-azabicyclo[4.1.0]hept-3-ene-1-carboxamide (Example 281)

To a solution of (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylic acid (29), (0.205 g, 0.312 mmol) and oxalyl chloride, 2.0M solution in dichloromethane (0.234 mL, 0.467 mmol) in DCM (2 mL) was added a drop of diluted DMF. The resulting mixture was stirred at room temperature for 2 hours and concentrated. The residue obtained was added to a solution of 2,2-difluoroethylamine (0.025 mL, 0.312 mmol) and triethylamine (0.043 mL, 0.312 mmol). The resulting mixture was stirred for 2 hours, diluted with water and extracted with EtOAc (2×). The organic layer was concentrated to dryness and the residue purified by flash column chromatography on silica gel with ISCO eluting with 0-40% EtOAc in heptane to afford tert-butyl ((1S,5S,6S)-5-(5-((Z)-2-(5-cyanopyridin-2-yl)-2-fluorovinyl)-2-fluoropyridin-3-yl)-1-((2,2-difluoroethyl)carbamoyl)-5-methyl-2-thia-4-azabicyclo[4.1.0]hept-3-en-3-yl)((2-(trimethylsilyl)ethoxy)methyl)carbamate (0.142, 6% yield). LCMS (ESI+) m/z=721.3 (M+H).

Using a procedure similar to that described for Example 261, tert-butyl ((1S,5S,6S)-5-(5-((Z)-2-(5-cyanopyridin-2-yl)-2-fluorovinyl)-2-fluoropyridin-3-yl)-1-((2,2-difluoroethyl)carbamoyl)-5-methyl-2-thia-4-azabicyclo[4.1.0]hept-3-en-3-yl)((2-(trimethylsilyl)ethoxy)methyl)carbamate (0.140 g, 0.194 mmol) was reacted with p-toluenesulfonic acid monohydrate (0.092 g, 0.49 mmol) to afford (1S,5S,6S)-3-amino-5-(5-((Z)-2-(5-cyanopyridin-2-yl)-2-fluorovinyl)-2-fluoropyridin-3-yl)-N-(2,2-difluoroethyl)-5-methyl-2-thia-4-azabicyclo[4.1.0]hept-3-ene-1-carboxamide (Example 281) (0.064 g, 67% yield). LCMS (ESI+) m/z=491.0 (M+H). $^1$H NMR (400 MHz, DMSO-d6) δ 9.11 (s, 1H), 8.59 (dd, J=1.76, 9.78 Hz, 1H), 8.45-8.51 (m, 2H), 8.12 (t, J=5.67 Hz, 1H), 7.90 (d, J=8.22 Hz, 1H), 7.40 (d, J=39.71 Hz, 1H), 6.33 (s, 2H), 6.03 (tt, J=3.91, 56.30 Hz, 1H), 3.51 (tt, J=4.60, 15.36 Hz, 1H), 3.32 (s, 1H), 2.26 (t, J=8.51 Hz, 1H), 1.62 (s, 3H), 1.46 (dd, J=5.38, 9.68 Hz, 1H), 0.82-0.92 (m, 1H). $^{19}$F NMR (376 MHz, DMSO-d6) δ −63.63 (s, 1F), −121.46 (s, 1F), −121.93 (s, 2F).

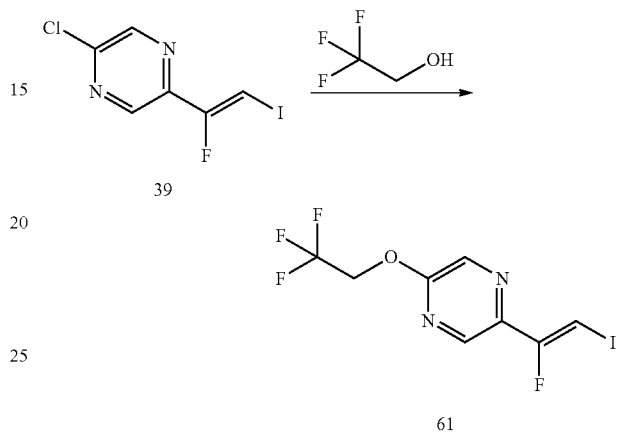

Preparation of (Z)-2-(1-fluoro-2-iodovinyl)-5-(2,2,2-trifluoroethoxy)pyrazine

To a mixture of (Z)-2-chloro-5-(1-fluoro-2-iodovinyl)pyrazine (39) (0.150 g, 0.527 mmol) and 2,2,2-trifluoroethanol (0.106 g, 1.055 mmol) in THF (5 mL) was added cesium carbonate (0.687 g, 2.109 mmol). The resulting mixture was heated to 60° C. and stirred for 2 hours. The reaction mixture was concentrated and the residue dissolved in water and extracted with EtOAc. The EtOAc extract was concentrated and the residue was purified with column chromatography using ISCO eluting with 0-15% EtOAc in heptane to afford (Z)-2-(1-fluoro-2-iodovinyl)-5-(2,2,2-trifluoroethoxy)pyrazine (61) (0.17 g, 93% yield). LCMS (ESI+) m/z=349.0 (M+H).

Synthesis of Intermediate 62

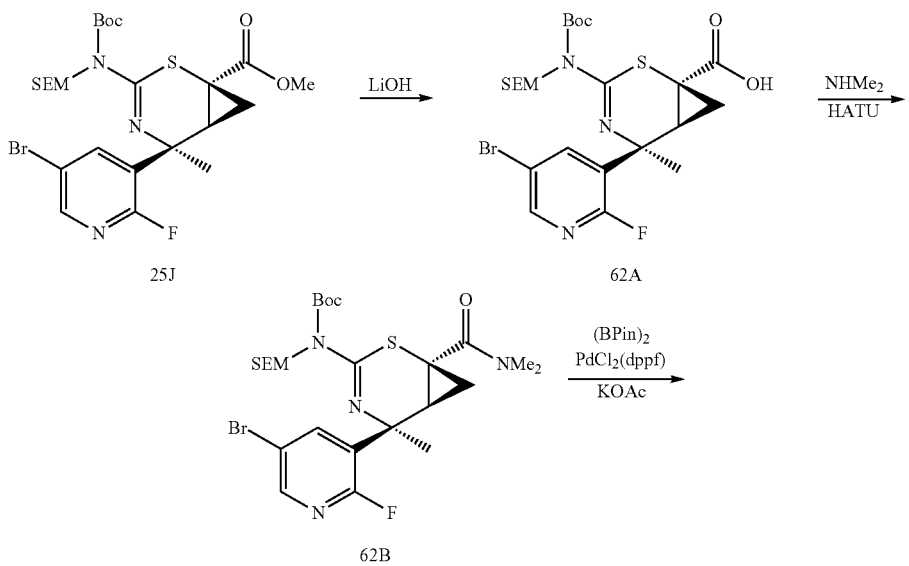

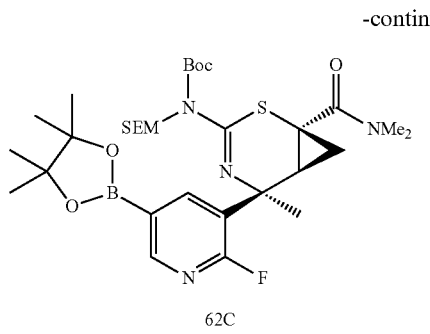
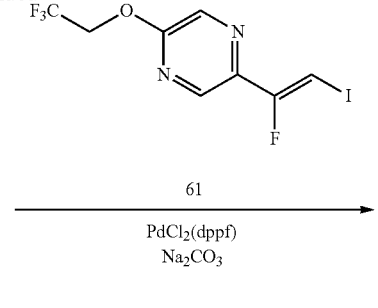

62C     61

PdCl₂(dppf)
Na₂CO₃

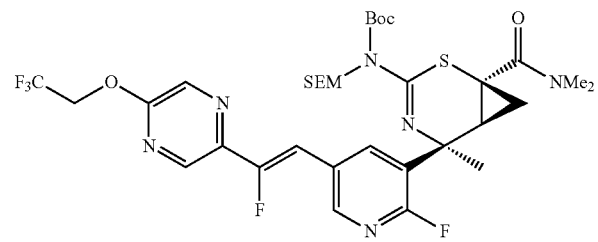

62

Preparation of (1S,5S,6S)-5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (62A)

Using a procedure similar to that described for 29, (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (25J) (7.77 g, 12.8 mmol) was reacted with lithium hydroxide monohydrate (0.755 g, 18.0 mmol) to afford (1S,5S,6S)-5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (62A) (7.5 g, 99% yield). LCMS (ESI+) m/z=590.2/592.1 (M+H).

Preparation of tert-butyl ((1S,5S,6S)-5-(5-bromo-2-fluoropyridin-3-yl)-1-(dimethylcarbamoyl)-5-methyl-2-thia-4-azabicyclo[4.1.0]hept-3-en-3-yl)((2-(trimethylsilyl)ethoxy)methyl)carbamate (62B)

Using a procedure similar to that described for Example 259, (1S,5S,6S)-5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (62A) (3.35 g, 5.67 mmol), dimethylamine hydrochloride (0.694 g, 8.51 mmol), diisopropylethylamine (4.93 ml, 28.4 mmol), HATU (4.86 g, 11.3 mmol) were reacted to afford tert-butyl ((1S,5S,6S)-5-(5-bromo-2-fluoropyridin-3-yl)-1-(dimethylcarbamoyl)-5-methyl-2-thia-4-azabicyclo[4.1.0]hept-3-en-3-yl)((2-(trimethylsilyl)ethoxy)methyl)carbamate (62B) (2.7 g, 77% yield). LCMS (ESI+) m/z=617.2/619.1 (M+H). ¹H NMR (400 MHz, CHLOROFORM-d) δ 8.13-8.19 (m, 2H), 5.30 (d, J=10.56 Hz, 1H), 5.01 (d, J=10.56 Hz, 1H), 3.61-3.69 (m, 2H), 3.15 (br. s., 3H), 3.01 (br. s., 3H), 2.46 (ddd, J=1.76, 7.43, 9.59 Hz, 1H), 1.80 (s, 3H), 1.50-1.54 (m, 9H), 1.19-1.23 (m, 1H), 0.98 (d, J=1.96 Hz, 1H), 0.92-0.97 (m, 2H), −0.01-0.02 (m, 9H). ¹⁹F NMR (376 MHz, CHLOROFORM-d) δ −66.96 (s, 1F).

Preparation of tert-butyl ((1S,5S,6S)-1-(dimethylcarbamoyl)-5-(2-fluoro-5-(4,4,5,5-tetramethyl-1,3,2-dioxaborolan-2-yl)pyridin-3-yl)-5-methyl-2-thia-4-azabicyclo[4.1.0]hept-3-en-3-yl)((2-(trimethylsilyl)ethoxy)methyl)carbamate (62C)

Using a procedure similar to that described for 31, tert-butyl ((1S,5S,6S)-5-(5-bromo-2-fluoropyridin-3-yl)-1-(dimethylcarbamoyl)-5-methyl-2-thia-4-azabicyclo[4.1.0]hept-3-en-3-yl)((2-(trimethylsilyl)ethoxy)methyl)carbamate (62B) (2.0 g, 3.2 mmol), bis(pinacolato) diboron (1.645 g, 6.48 mmol), potassium acetate (1.112 g, 11.33 mmol), and 1,1'-bis(diphenylphosphino)ferrocene palladium(II)dichloride dichloromethane adduct (0.529 g, 0.648 mmol) were reacted to afford tert-butyl ((1S,5S,6S)-1-(dimethylcarbamoyl)-5-(2-fluoro-5-(4,4,5,5-tetramethyl-1,3,2-dioxaborolan-2-yl)pyridin-3-yl)-5-methyl-2-thia-4-azabicyclo[4.1.0]hept-3-en-3-yl)((2-(trimethylsilyl)ethoxy)methyl)carbamate (62C) (2.1, 97% yield). LCMS (ESI+) m/z=665.3 (M+H). 1H NMR (400 MHz, CHLOROFORM-d) δ 8.49 (s, 1H), 8.32 (dd, J=1.86, 10.66 Hz, 1H), 5.27 (d, J=10.56 Hz, 1H), 5.06 (d, J=10.56 Hz, 1H), 3.64-3.72 (m, 2H), 3.22 (br. s., 3H), 3.01 (br. s., 3H), 2.43-2.50 (m, 1H), 1.85 (s, 3H), 1.54 (s, 9H), 1.35 (s, 12H), 1.26-1.31 (m, 1H), 1.02-1.15 (m, 1H), 0.95 (dd, J=7.24, 9.00 Hz, 2H), −0.01 (s, 9H). ¹⁹F NMR (376 MHz, CHLOROFORM-d) δ −61.03 (s, 1F).

Preparation of tert-butyl ((1S,5S,6S)-1-(dimethylcarbamoyl)-5-(2-fluoro-5-((Z)-2-fluoro-2-(5-(2,2,2-trifluoroethoxy)pyrazin-2-yl)vinyl)pyridin-3-yl)-5-methyl-2-thia-4-azabicyclo[4.1.0]hept-3-en-3-yl)((2-(trimethylsilyl)ethoxy)methyl)carbamate (62)

Using a procedure similar to that described for Example 222, tert-butyl ((1S,5S,6S)-1-(dimethylcarbamoyl)-5-(2- fluoro-5-(4,4,5,5-tetramethyl-1,3,2-dioxaborolan-2-yl)pyridin-3-yl)-5-methyl-2-thia-4-azabicyclo[4.1.0]hept-3-en-3-yl)((2-(trimethylsilyl)ethoxy)methyl)carbamate (62C) (0.150 g, 0.226 mmol), (Z)-2-(1-fluoro-2-iodovinyl)-5-(2,2,2-trifluoroethoxy)pyrazine (61) (0.170 g, 0.488 mmol), 1,1'-bis(diphenylphosphino)ferrocene palladium(II)dichloride dichloromethane adduct (0.018 g, 0.023 mmol), and sodium carbonate (0.072 g, 0.68 mmol) were combined to form tert-butyl ((1S,5S,6S)-1-(dimethylcarbamoyl)-5-(2-fluoro-5-((Z)-2-fluoro-2-(5-(2,2,2-trifluoroethoxy)pyrazin-2-yl)vinyl)pyridin-3-yl)-5-methyl-2-thia-4-azabicyclo[4.1.0]hept-3-en-3-yl)((2-(trimethylsilyl)ethoxy)methyl)carbamate (62) (0.089 g, 52% yield). LCMS (ESI+) m/z=759.3 (M+H).

Preparation of (1S,5S,6S)-3-amino-5-(2-fluoro-5-((Z)-2-fluoro-2-(5-(2,2,2-trifluoroethoxy)pyrazin-2-yl)vinyl)pyridin-3-yl)-N,N,5-trimethyl-2-thia-4-azabicyclo[4.1.0]hept-3-ene-1-carboxamide
(Example 282)

Using a procedure similar to that described for Example 261, tert-butyl ((1S,5S,6S)-1-(dimethylcarbamoyl)-5-(2-fluoro-5-((Z)-2-fluoro-2-(5-(2,2,2-trifluoroethoxy)pyrazin-2-yl)vinyl)pyridin-3-yl)-5-methyl-2-thia-4-azabicyclo[4.1.0]hept-3-en-3-yl)((2-(trimethylsilyl)ethoxy)methyl)carbamate (62) (0.080 g, 0.10 mmol) was reacted with p-toluenesulfonic acid monohydrate (0.050 g, 0.26 mmol) to afford (1S,5S,6S)-3-amino-5-(2-fluoro-5-((Z)-2-fluoro-2-(5-(2,2,2-trifluoroethoxy)pyrazin-2-yl)vinyl)pyridin-3-yl)-N,N,5-trimethyl-2-thia-4-azabicyclo[4.1.0]hept-3-ene-1-carboxamide (Example 282) (0.040 g, 72% yield). LCMS (ESI+) m/z=529.1 (M+H). $^1$H NMR (400 MHz, CHLOROFORM-d) δ 8.30-8.38 (m, 3H), 8.26 (d, J=9.59 Hz, 1H), 6.87 (d, J=38.93 Hz, 1H), 4.82 (q, J=8.28 Hz, 2H), 4.29-4.74 (br. s., 2H), 3.05 (br. s., 6H), 2.32 (t, J=8.41 Hz, 1H), 1.86 (s, 3H), 1.37 (dd, J=5.77, 9.68 Hz, 1H), 0.87 (t, J=6.26 Hz, 1H). $^{19}$F NMR (376 MHz, CHLOROFORM-d) δ −63.80 (s, 1F), −73.66 (s, 3F), −122.80 (s, 1F).

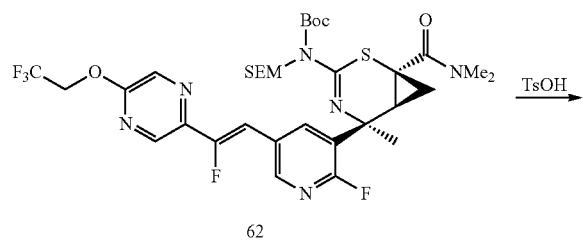

62

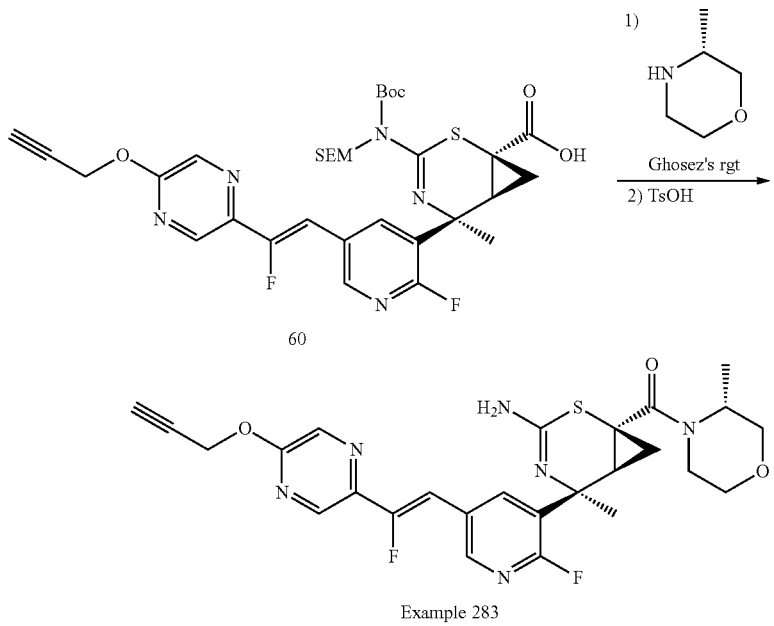

60

Example 283

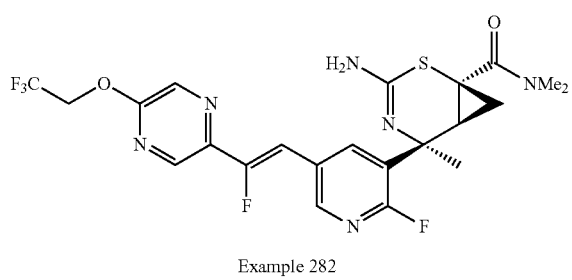

Example 282

Preparation of ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((R)-3-methylmorpholino)methanone (Example 283)

Using a procedure similar to that described for Example 260, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (60) (0.105 g, 0.153 mmol), 1-chloro-N,N,2-trimethyl- 1-propenylamine (0.061 ml, 0.458 mmol), (R)-3-methyl-morpholine (0.031 ml, 0.305 mmol) and triethylamine (0.088 ml, 0.611 mmol) were combined to form tert-butyl ((1S,5S,6S)-5-(2-fluoro-5-((Z)-2-fluoro-2-(5-(prop-2-yn-1-yloxy)pyrazin-2-yl)vinyl)pyridin-3-yl)-5-methyl-1-((R)-3-methylmorpholine-4-carbonyl)-2-thia-4-azabicyclo[4.1.0]hept-3-en-3-yl)((2-(trimethylsilyl)ethoxy)methyl)carbamate, which after deprotection with 4-methylbenzenesulfonic acid hydrate (0.087 g, 0.46 mmol) gave ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((R)-3-methylmorpholino)methanone (Example 283) (0.046 g, 56% yield). LCMS (ESI+) m/z=541.2 (M+H). $^1$H NMR (400 MHz, CHLOROFORM-d) δ 8.41 (s, 1H), 8.37 (s, 1H), 8.22-8.32 (m, 2H), 6.86 (d, J=39.71 Hz, 1H), 5.04 (d, J=2.54 Hz, 2H), 4.44 (br dd, J=2.15, 6.46 Hz, 1H), 3.98-4.21 (m, 1H), 3.93 (dd, J=2.93, 11.35 Hz, 1H), 3.70 (d, J=11.54 Hz, 1H), 3.58 (dd, J=2.84, 11.44 Hz, 1H), 3.40-3.53 (m, 1H), 3.21-3.39 (m, 1H), 2.54 (t, J=2.45 Hz, 1H), 2.32-2.45 (m, 1H), 1.85 (s, 3H), 1.29-1.43 (m, 4H), 0.88-0.93 (m, 1H), NH2 very broad at 4.25-5.00. $^{19}$F NMR (376 MHz, CHLOROFORM-d) δ −64.19 (s, 1F), −122.50 (s, 1F).

1-propenylamine (0.061 ml, 0.458 mmol), (1S,5S)-3,7-dioxa-9-azabicyclo[3.3.1]nonane (0.039 g, 0.30 mmol) and triethylamine (0.088 ml, 0.611 mmol) were combined to form tert-butyl ((1S,5S,6S)-1-((1R,5R)-3,7-dioxa-9-azabicyclo[3.3.1]nonane-9-carbonyl)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-3-yl)((2-(trimethylsilyl)ethoxy)methyl)carbamate, which after deprotection with 4-methylbenzenesulfonic acid hydrate (0.087 g, 0.46 mmol) gave ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((1R,5R)-3,7-dioxa-9-azabicyclo[3.3.1]nonan-9-yl)methanone (Example 284) (0.050 g, 58% yield). LCMS (ESI+) m/z=569.2 (M+H). $^1$H NMR (400 MHz, CHLOROFORM-d) δ 8.41 (s, 1H), 8.37 (s, 1H), 8.26-8.28 (m, 1H), 8.27 (s, 1H), 6.87 (d, J=39.91 Hz, 1H), 5.05 (d, J=2.35 Hz, 2H), 4.38-4.85 (m, 1H), 4.27 (br s, 1H), 4.06-4.22 (m, 5H), 4.02 (br d, J=4.89 Hz, 1H), 3.78-3.94 (m, 3H), 2.54 (t, J=2.35 Hz, 1H), 2.31-2.48 (m, 1H), 1.82 (s, 3H), 1.40 (dd, J=5.67, 9.78 Hz, 1H), 1.17-1.33 (m, 1H), 0.82-0.95

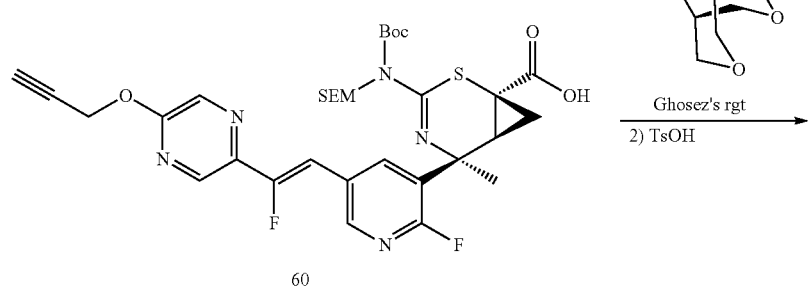

60

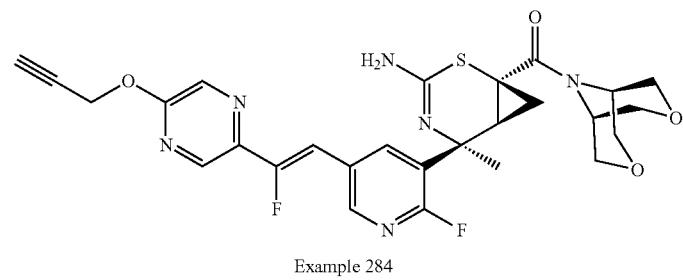

Example 284

Preparation of ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((1R,5R)-3,7-dioxa-9-azabicyclo[3.3.1]nonan-9-yl)methanone (Example 284)

Using a procedure similar to that described for Example 260, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (60) (0.105 g, 0.153 mmol) 1-chloro-N,N,2-trimethyl- (m, 1H). $^{19}$F NMR (376 MHz, CHLOROFORM-d) δ −64.33 (s, 1F), −122.50 (s, 1F).

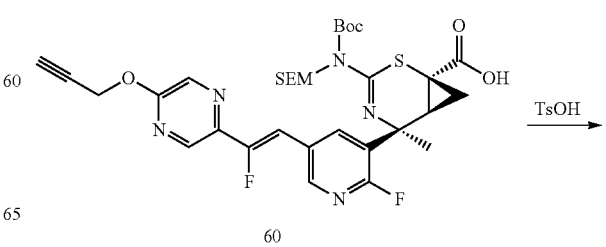

60

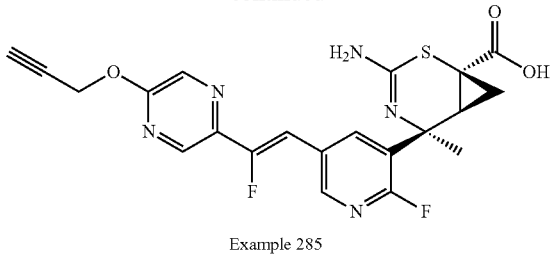

Example 285

Preparation of (1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (Example 285)

Using a procedure similar to that described for Example 261, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (0.133 g, 0.193 mmol) was reacted with p-toluenesulfonic acid monohydrate (0.092 g, 0.48 mmol) to afford (1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (Example 285) (0.020 g, 23% yield). LC/MS (ESI+) m/z=458.0 (M+H). $^1$H NMR (400 MHz, DMSO-d6) δ 8.60 (br d, J=9.39 Hz, 1H), 8.56 (s, 1H), 8.48 (s, 1H), 8.41 (br s, 1H), 7.04 (br s, 3H), 6.07-6.63 (br. s., 1H), 5.09 (s, 2H), 3.62 (s, 1H), 3.17 (br s, 3H), 2.27-2.38 (m, 1H), 1.31-1.37 (m, 1H), 0.93 (br s, 1H). $^{19}$F NMR (376 MHz, DMSO-d6) δ −73.46 (s, 1F), −121.73 (s, 1F).

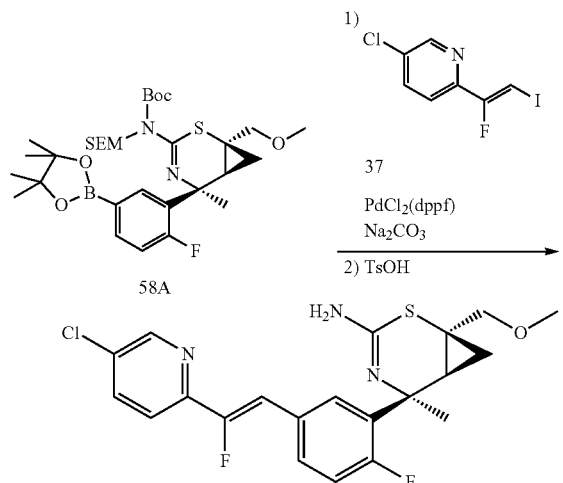

Example 286

Preparation of (1S,5S,6S)-5-(5-((Z)-2-(5-chloropyridin-2-yl)-2-fluorovinyl)-2-fluorophenyl)-1-(methoxymethyl)-5-methyl-2-thia-4-azabicyclo[4.1.0]hept-3-en-3-amine (Example 286)

Using a procedure similar to that described for Example 261, tert-butyl ((1S,5S,6S)-5-(2-fluoro-5-(4,4,5,5-tetramethyl-1,3,2-dioxaborolan-2-yl)phenyl)-1-(methoxymethyl)-5-methyl-2-thia-4-azabicyclo[4.1.0]hept-3-en-3-yl)((2-(trimethylsilyl)ethoxy)methyl)carbamate (58A) (0.220 g, 0.346 mmol), (Z)-5-chloro-2-(1-fluoro-2-iodovinyl)pyridine (37) (0.127 g, 0.449 mmol), potassium phosphate (0.118 g, 0.864 mmol), and 1,1-bis[di-tert-butyl-p-methylaminophenyl]palladium(II) chloride (0.024 g, 0.035 mmol) were combined to give the coupling product, which after deprotection with p-toluenesulfonic acid monohydrate (0.197 g, 1.04 mmol) afforded (1S,5S,6S)-5-(5-((Z)-2-(5-chloropyridin-2-yl)-2-fluorovinyl)-2-fluorophenyl)-1-(methoxymethyl)-5-methyl-2-thia-4-azabicyclo[4.1.0]hept-3-en-3-amine (0.024 g, 16% yield). LCMS (ESI+) m/z=436.1 (M+H). $^1$H NMR (400 MHz, CHLOROFORM-d) δ 8.52 (d, J=2.35 Hz, 1H), 7.92 (dd, J=2.25, 7.92 Hz, 1H), 7.70 (d, J=8.08 Hz, 1H), 7.65 (ddd, J=2.35, 4.60, 8.31 Hz, 1H), 7.53 (d, J=8.52 Hz, 1H), 6.99-7.12 (m, 2H), 3.94-4.74 (m, 2H), 3.65 (d, J=10.56 Hz, 1H), 3.40 (s, 3H), 3.34 (d, J=10.76 Hz, 1H), 1.69-1.79 (m, 4H), 0.89 (dd, J=5.87, 9.39 Hz, 1H), 0.76-0.84 (m, 1H). $^{19}$F NMR (376 MHz, CHLOROFORM-d) δ −111.04 (s, 1F), −124.36 (s, 1F).

Synthesis of Intermediate 63

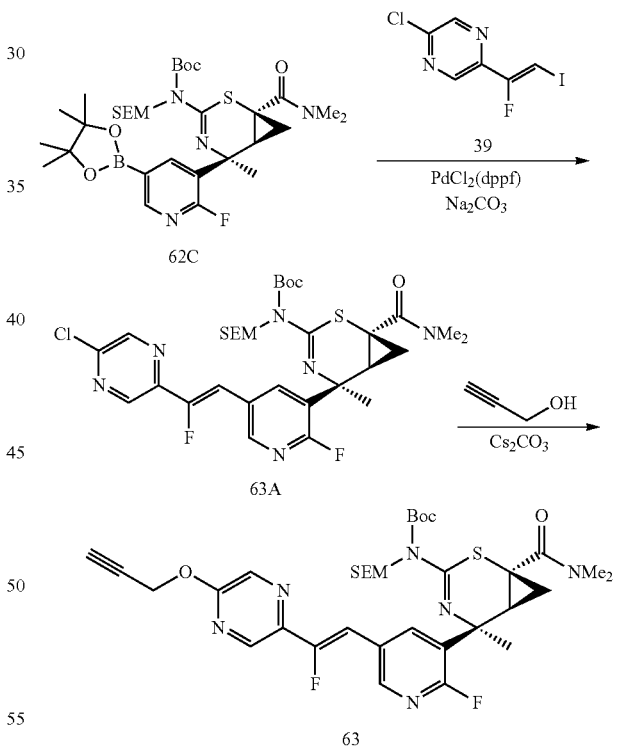

Preparation of give tert-butyl ((1S,5S,6S)-5-(5-((Z)-2-(5-chloropyrazin-2-yl)-2-fluorovinyl)-2-fluoropyridin-3-yl)-1-(dimethylcarbamoyl)-5-methyl-2-thia-4-azabicyclo[4.1.0]hept-3-en-3-yl)((2-(trimethylsilyl)ethoxy)methyl)carbamate (63A)

Using a procedure similar to that described for Example 222, tert-butyl ((1S,5S,6S)-1-(dimethylcarbamoyl)-5-(2- fluoro-5-(4,4,5,5-tetramethyl-1,3,2-dioxaborolan-2-yl)pyridin-3-yl)((2-(trimethylsilyl)ethoxy)methyl)carbamate (62C) (2.9 g, 4.36 mmol), (Z)-2-chloro-5-(1-fluoro-2-iodovinyl)pyrazine (39) (1.74 g, 6.11 mmol), 1,1'-bis(diphenylphosphino)ferrocene palladium(II)dichloride dichloromethane adduct (0.356 g, 0.436 mmol), and sodium carbonate anhydrous (0.462 g, 4.36 mmol) were combined to form tert-butyl ((1S,5S,6S)-5-(5-((Z)-2-(5-chloropyrazin-2-yl)-2-fluorovinyl)-2-fluoropyridin-3-yl)-1-(dimethylcarbamoyl)-5-methyl-2-thia-4-azabicyclo[4.1.0]hept-3-en-3-yl)((2-(trimethylsilyl)ethoxy)methyl)carbamate (63A) (1.2, 39% yield). LCMS (ESI+) m/z=695.2 (M+H).

Preparation of tert-butyl ((1S,5S,6S)-1-(dimethylcarbamoyl)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-3-yl)((2-(trimethylsilyl)ethoxy)methyl)carbamate (63)

Using a procedure similar to that described for Example 262, tert-butyl ((1S,5S,6S)-5-(5-((Z)-2-(5-chloropyrazin-2-yl)-2-fluorovinyl)-2-fluoropyridin-3-yl)-1-(dimethylcarbamoyl)-5-methyl-2-thia-4-azabicyclo[4.1.0]hept-3-en-3-yl)((2-(trimethylsilyl)ethoxy)methyl)carbamate (0.180 g, 0.259 mmol) (63A) was reacted with propargyl alcohol (0.023 ml, 0.39 mmol), and cesium carbonate (0.253 g, 0.777 mmol) at room temperature for 18 hours to afford tert-butyl ((1S,5S,6S)-1-(dimethylcarbamoyl)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-3-yl)((2-(trimethylsilyl)ethoxy)methyl)carbamate (63) (0.150 g, 81% yield). LCMS (ESI+) m/z=715.3 (M+H). $^1$H NMR (400 MHz, CHLOROFORM-d) δ 8.36-8.45 (m, 3H), 8.29 (s, 1H), 6.92 (d, J=39.71 Hz, 1H), 5.37 (d, J=10.56 Hz, 1H), 5.14 (d, J=10.56 Hz, 1H), 5.07 (d, J=2.35 Hz, 2H), 3.64-3.76 (m, 2H), 3.23 (br. s., 3H), 3.03 (br. s., 3H), 2.49-2.59 (m, 2H), 1.81-1.93 (m, 3H), 1.56 (s, 9H), 1.21-1.40 (m, 1H), 1.08 (t, J=6.46 Hz, 1H), 0.97 (ddd, J=1.76, 6.85, 9.59 Hz, 2H), −0.04-0.01 (m, 9H). $^{19}$F NMR (376 MHz, CHLOROFORM-d) δ −65.06 (s, 1F), −122.64 (s, 1F).

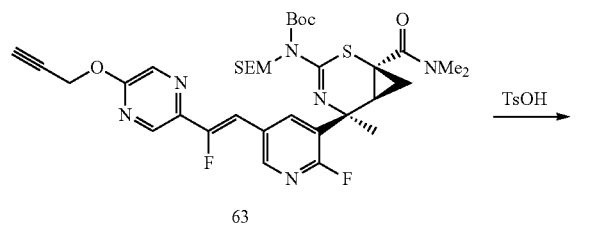

Example 287

Preparation of (1S,5S,6S)-3-amino-5-(2-fluoro-5-((Z)-2-fluoro-2-(5-(prop-2-yn-1-yloxy)pyrazin-2-yl)vinyl)pyridin-3-yl)-N,N,5-trimethyl-2-thia-4-azabicyclo[4.1.0]hept-3-ene-1-carboxamide (Example 287)

Using a procedure similar to that described for Example 261, tert-butyl ((1S,5S,6S)-1-(dimethylcarbamoyl)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-3-yl)((2-(trimethylsilyl)ethoxy)methyl)carbamate (62) (0.170 g, 0.238 mmol) was reacted with p-toluenesulfonic acid monohydrate (0.090 g, 0.48 mmol) to afford (1S,5S,6S)-3-amino-5-(2-fluoro-5-((Z)-2-fluoro-2-(5-(prop-2-yn-1-yloxy)pyrazin-2-yl)vinyl)pyridin-3-yl)-N,N,5-trimethyl-2-thia-4-azabicyclo[4.1.0]hept-3-ene-1-carboxamide (Example 287) (0.048 g, 42% yield). LCMS (ESI+) m/z=485.1 (M+H). $^1$H NMR (400 MHz, CHLOROFORM-d) δ 8.41 (s, 1H), 8.37 (s, 1H), 8.19-8.30 (m, 2H), 6.86 (d, J=39.71 Hz, 1H), 5.04 (d, J=2.35 Hz, 2H), 4.30-4.91 (br. s., 2H), 3.06 (br. s., 6H), 2.54 (t, J=2.35 Hz, 1H), 2.32-2.41 (m, 1H), 1.89 (s, 3H), 1.42 (dd, J=5.77, 9.68 Hz, 1H), 0.90 (t, J=6.46 Hz, 1H). $^{19}$F NMR (376 MHz, CHLOROFORM-d) δ −63.90 (s, 1F), −122.39 (s, 1F).

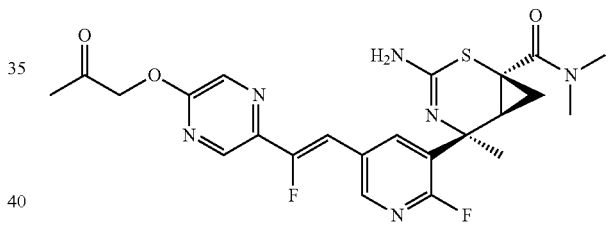

Example 288

Preparation of (1S,5S,6S)-3-amino-5-(2-fluoro-5-((Z)-2-fluoro-2-(5-(2-oxopropoxy)pyrazin-2-yl)vinyl)pyridin-3-yl)-N,N,5-trimethyl-2-thia-4-azabicyclo[4.1.0]hept-3-ene-1-carboxamide (Example 288)

The title compound (1S,5S,6S)-3-amino-5-(2-fluoro-5-((Z)-2-fluoro-2-(5-(2-oxopropoxy)pyrazin-2-yl)vinyl)pyridin-3-yl)-N,N,5-trimethyl-2-thia-4-azabicyclo[4.1.0]hept-3-ene-1-carboxamide (Example 288) (0.013 g, 11% yield) was obtained as a side product from Example 287. LCMS (ESI+) m/z=503.2 (M+H). $^1$H NMR (400 MHz, CHLOROFORM-d) δ 8.28-8.40 (m, 3H), 8.23 (dd, J=2.15, 9.59 Hz, 1H), 6.86 (d, J=39.91 Hz, 1H), 5.00 (s, 2H), 4.30-4.91 (br. s, 2H), 3.06 (br. s., 6H), 2.29-2.45 (m, 1H), 2.25 (s, 3H), 1.86 (s, 3H), 1.38 (dd, J=5.77, 9.68 Hz, 1H), 0.90 (d, J=1.96 Hz, 1H). $^{19}$F NMR (376 MHz, CHLOROFORM-d) δ −64.02 (s, 1F), −122.56 (s, 1F).

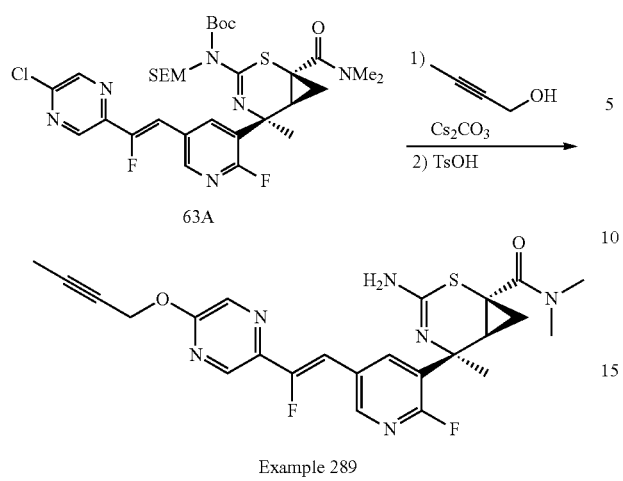

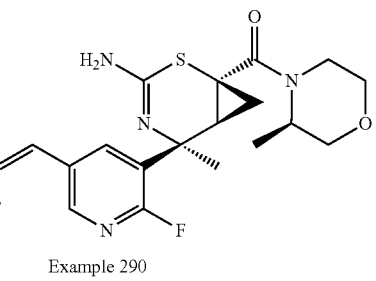

Preparation of (1S,5S,6S)-3-amino-5-(5-((Z)-2-(5-(but-2-yn-1-yloxy)pyrazin-2-yl)-2-fluorovinyl)-2-fluoropyridin-3-yl)-N,N,5-trimethyl-2-thia-4-azabicyclo[4.1.0]hept-3-ene-1-carboxamide (Example 289)

To a mixture of tert-butyl ((1S,5S,6S)-5-(5-((Z)-2-(5-chloropyrazin-2-yl)-2-fluorovinyl)-2-fluoropyridin-3-yl)-1-(dimethylcarbamoyl)-5-methyl-2-thia-4-azabicyclo[4.1.0]hept-3-en-3-yl)((2-(trimethylsilyl)ethoxy)methyl)carbamate (63A) (0.157 g, 0.226 mmol) and 2-butyn-1-ol (0.034 ml, 0.48 mmol) in THF (2 mL) was added cesium carbonate (0.221 g, 0.677 mmol). The reaction mixture was stirred at room temperature for 18 hours, diluted with water and extracted with EtOAc (2×). The organic layer was concentrated to give crude residue which was treated with p-toluenesulfonic acid monohydrate (0.129 g, 0.677 mmol) in dioxane (2 mL). The reaction mixture was heated to 85° C. for 2 hours, diluted with saturated aq. NaHCO₃ solution and extracted with EtOAc (2×). The organic phase was concentrated and the residue purified by flash column chromatography on silica gel with ISCO eluting with 0-30% EtOAc/EtOH (3:1) in heptane to afford (1S,5S,6S)-3-amino-5-(5-((Z)-2-(5-(but-2-yn-1-yloxy)pyrazin-2-yl)-2-fluorovinyl)-2-fluoropyridin-3-yl)-N,N,5-trimethyl-2-thia-4-azabicyclo[4.1.0]hept-3-ene-1-carboxamide (Example 289) (0.015 g, 13% yield). LCMS (ESI+) m/z=499.2 (M+H). ¹H NMR (400 MHz, CHLOROFORM-d) δ 8.38-8.41 (m, 1H), 8.34-8.36 (m, 1H), 8.23-8.28 (m, 2H), 6.84 (d, J=40.10 Hz, 1H), 4.92-5.10 (m, 2H), 4.22-4.84 (br. s, 2H), 2.97-3.33 (m, 6H), 2.28-2.41 (m, 1H), 1.89 (s, 3H), 1.85 (s, 3H), 1.32-1.42 (m, 1H), 0.81-0.96 (m, 1H). ¹⁹F NMR (376 MHz, CHLOROFORM-d) δ −64.17 (s, 1F), −122.51 (s, 1F).

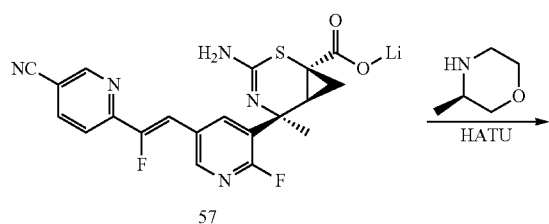

Preparation of 6-((Z)-2-(5-((1S,5S,6S)-3-amino-5-methyl-1-((R)-3-methylmorpholine-4-carbonyl)-2-thia-4-azabicyclo[4.1.0]hept-3-en-5-yl)-6-fluoropyridin-3-yl)-1-fluorovinyl)nicotinonitrile (Example 290)

Using a procedure similar to that described for Example 259, lithium (1S,5S,6S)-3-amino-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate (57) (0.150 g, 0.346 mmol), (R)-3-methylmorpholine hydrochloride (0.095 g, 0.69 mmol), diisopropylethylamine (0.241 mL, 1.38 mmol), and HATU (0.263 g, 0.692 mmol) were reacted to afford 6-((Z)-2-(5-((1S,5S,6S)-3-amino-5-methyl-1-((R)-3-methylmorpholine-4-carbonyl)-2-thia-4-azabicyclo[4.1.0]hept-3-en-5-yl)-6-fluoropyridin-3-yl)-1-fluorovinyl)nicotinonitrile (Example 290) (0.009 g, 5% yield). LCMS (ESI+) m/z=511.1 (M+H). ¹H NMR (400 MHz, CHLOROFORM-d) δ 8.85 (s, 1H), 8.44 (s, 1H), 8.33 (dd, J=2.35, 9.59 Hz, 1H), 8.05 (dd, J=2.15, 8.41 Hz, 1H), 7.73 (d, J=7.82 Hz, 1H), 7.27 (d, J=38.73 Hz, 1H), 4.51-5.04 (br. s., 2H), 4.38-4.49 (m, 1H), 4.03 (d, J=12.13 Hz, 1H), 3.93 (dd, J=3.03, 11.25 Hz, 1H), 3.70 (d, J=11.54 Hz, 1H), 3.58 (dd, J=2.93, 11.54 Hz, 1H), 3.38-3.52 (m, 1H), 3.31 (br. s., 1H), 2.36-2.42 (m, 1H), 1.85 (s, 3H), 1.23-1.45 (m, 4H), 0.86-0.92 (m, 1H). ¹⁹F NMR (376 MHz, CHLOROFORM-d) δ −62.64 (s, 1F), −122.10 (s, 1F).

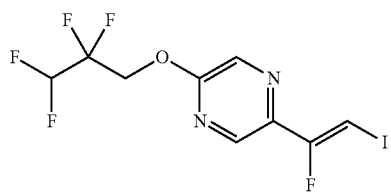

Preparation of (Z)-2-(1-fluoro-2-iodovinyl)-5-(2,2,3,3-tetrafluoropropoxy)pyrazine (64)

Using a procedure similar to that described for 61, (Z)-2-chloro-5-(1-fluoro-2-iodovinyl)pyrazine (0.150 g, 0.527 mmol), 2,2,3,3-tetrafluoropropan-1-ol (0.139 g, 1.06 mmol) and cesium carbonate (0.687 g, 2.11 mmol) were reacted to afford (Z)-2-(1-fluoro-2-iodovinyl)-5-(2,2,3,3-tetrafluoropropoxy)pyrazine (64) (0.198 g, 99% yield). LCMS (ESI+) m/z=380.9 (M+H).

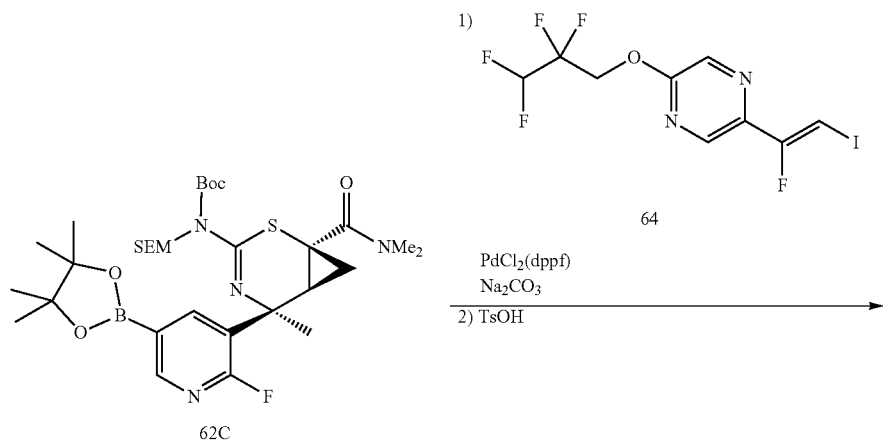

Preparation of (1S,5S,6S)-3-amino-5-(2-fluoro-5-((Z)-2-fluoro-2-(5-(2,2,3,3-tetrafluoropropoxy)pyrazin-2-yl)vinyl)pyridin-3-yl)-N,N,5-trimethyl-2-thia-4-azabicyclo[4.1.0]hept-3-ene-1-carboxamide (Example 291)

Using a procedure similar to that described for Example 222, tert-butyl ((1S,5S,6S)-1-(dimethylcarbamoyl)-5-(2-fluoro-5-(4,4,5,5-tetramethyl-1,3,2-dioxaborolan-2-yl)pyridin-3-yl)-5-methyl-2-thia-4-azabicyclo[4.1.0]hept-3-en-3-yl)((2-(trimethylsilyl)ethoxy)methyl)carbamate (62C) (0.150 g, 0.226 mmol), (Z)-2-(1-fluoro-2-iodovinyl)-5-(2,2,3,3-tetrafluoropropoxy)pyrazine (64) (0.170 g, 0.447 mmol), 1,1'-bis(diphenylphosphino)ferrocene palladium(II) dichloride dichloromethane adduct (0.018 g, 0.023 mmol), and sodium carbonate (0.072 g, 0.68 mmol) were combined to afford a crude product which was reacted with p-toluenesulfonic acid monohydrate (0.066 g, 0.35 mmol) to afford (1S,5S,6S)-3-amino-5-(2-fluoro-5-((Z)-2-fluoro-2-(5-(2,2,3,3-tetrafluoropropoxy)pyrazin-2-yl)vinyl)pyridin-3-yl)-N,N,5-trimethyl-2-thia-4-azabicyclo[4.1.0]hept-3-ene-1-carboxamide (Example 291) (0.051 g, 65% yield). LCMS (ESI+) m/z=561.1 (M+H). $^1$H NMR (400 MHz, CHLOROFORM-d) δ 8.23-8.42 (m, 4H), 6.88 (d, J=39.52 Hz, 1H), 6.02 (dd, J=4.30, 53.01 Hz, 1H), 4.82 (t, J=12.62 Hz, 2H), 4.29-4.74 (br. s., 2H), 3.06 (br. s., 6H), 2.33 (t, J=8.41 Hz, 1H), 1.86 (s, 3H), 1.37 (dd, J=5.77, 9.49 Hz, 1H), 0.88 (t, J=6.46 Hz, 1H). $^{19}$F NMR (376 MHz, CHLOROFORM-d) δ −63.80 (s, 1F), −122.72 (s, 1F), −123.81 (m, 2F), −137.77 (m, 2F).

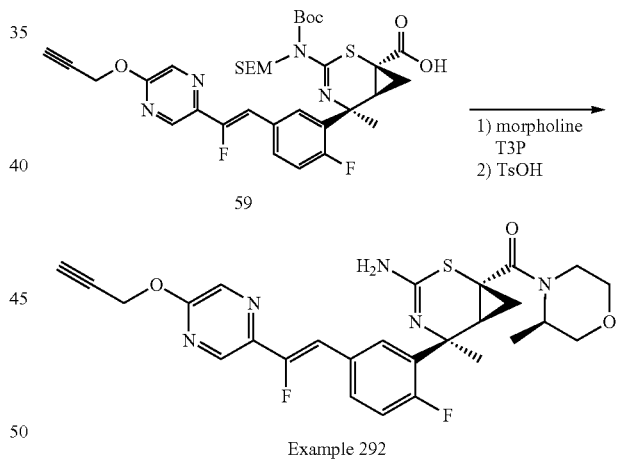

Preparation of ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)(morpholino)methanone (Example 292)

Using a procedure similar to that described for Example 122, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylic acid (59) (0.120 g, 0.175 mmol), morpholine (0.023 mL, 0.26 mmol), and 1-propanephosphonic acid cyclic anhydride, 50 wt. % solution in EtOAc (0.222 ml, 0.349 mmol) were combined to form a product, which after deprotection with p-toluenesulfonic acid monohydrate (0.100 g, 0.524 mmol) afforded ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)(morpholino)methanone (Example 292) (0.051 g, 56% yield). LCMS (ESI+) m/z=526.2 (M+H). $^1$H NMR (400 MHz, CHLOROFORM-d) δ 8.36 (s, 1H), 8.24 (s, 1H), 7.73 (dd, J=1.76, 7.82 Hz, 1H), 7.48-7.64 (m, 1H), 7.06 (dd, J=8.51, 11.64 Hz, 1H), 6.82 (d, J=39.91 Hz, 1H), 5.03 (d, J=2.35 Hz, 2H), 4.18-4.79 (br. s., 2H), 3.60-3.74 (m, 8H), 2.54 (t, J=2.25 Hz, 1H), 2.21-2.38 (m, 1H), 1.86 (s, 3H), 1.37 (dd, J=5.77, 9.68 Hz, 1H), 0.88 (t, J=6.36 Hz, 1H). $^{19}$F NMR (376 MHz, CHLOROFORM-d) δ −110.13 (s, 1F), −125.94 (s, 1F).

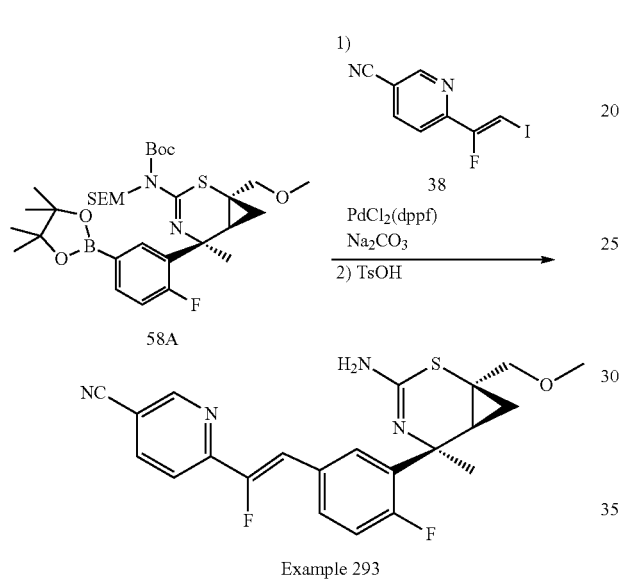

Example 293

Preparation of 6-((Z)-2-(3-((1S,5S,6S)-3-amino-1-(methoxymethyl)-5-methyl-2-thia-4-azabicyclo[4.1.0]hept-3-en-5-yl)-4-fluorophenyl)-1-fluorovinyl)nicotinonitrile (Example 293)

Using a procedure similar to that described for Example 261, tert-butyl ((1S,5S,6S)-5-(2-fluoro-5-(4,4,5,5-tetramethyl-1,3,2-dioxaborolan-2-yl)phenyl)-1-(methoxymethyl)-5-methyl-2-thia-4-azabicyclo[4.1.0]hept-3-en-3-yl)((2-(trimethylsilyl)ethoxy)methyl)carbamate (58A) (0.184 g, 0.289 mmol), 38 (0.103 g, 0.376 mmol), potassium phosphate (0.098 g, 0.72 mmol), and 1,1-bis[di-t-butyl-p-methylaminophenyl]palladium(II) chloride (0.020 g, 0.029 mmol) were combined to give the coupling product, which after deprotection with p-toluenesulfonic acid monohydrate (0.165 g, 0.867 mmol) afforded 6-((Z)-2-(3-((1S,5S,6S)-3-amino-1-(methoxymethyl)-5-methyl-2-thia-4-azabicyclo[4.1.0]hept-3-en-5-yl)-4-fluorophenyl)-1-fluorovinyl)nicotinonitrile (Example 293) (0.060 g, 49% yield). LCMS (ESI+) m/z=427.1 (M+H). $^1$H NMR (400 MHz, CHLOROFORM-d) δ 8.79-8.83 (m, 1H), 8.00 (d, J=7.84 Hz, 1H), 7.96 (d, J=7.37 Hz, 1H), 7.61-7.74 (m, 2H), 7.26 (d, J=38.15 Hz, 1H), 7.08 (dd, J=8.51, 11.84 Hz, 1H), 4.18-4.86 (br. s., 2H), 3.65 (d, J=10.56 Hz, 1H), 3.41 (s, 3H), 3.35 (d, J=10.56 Hz, 1H), 1.70-1.80 (m, 4H), 0.90 (dd, J=5.77, 9.49 Hz, 1H), 0.73-0.84 (m, 1H). $^{19}$F NMR (376 MHz, CHLOROFORM-d) δ −109.52 (s, 1F), −125.83 (s, 1F).

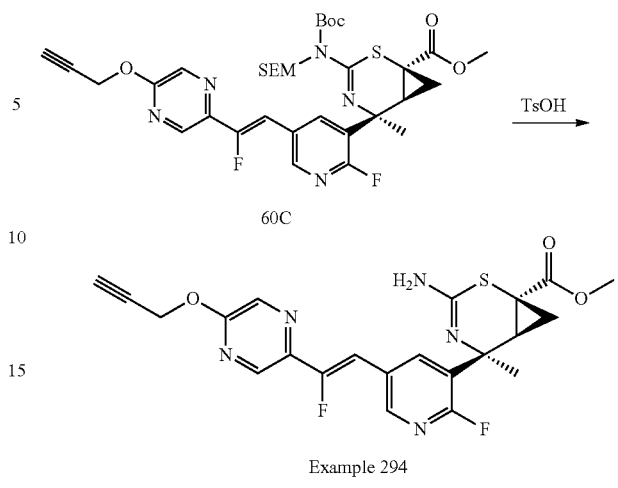

Example 294

Preparation of (1S,5S,6S)-methyl 3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylate methanone ((Example 294)

Using a procedure similar to that described for Example 261, (1S,5S,6S)-methyl 3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylate (60C) (0.200 g, 0.285 mmol) was reacted with p-toluenesulfonic acid monohydrate (0.163 g, 0.855 mmol) to afford (1S,5S,6S)-methyl 3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylate methanone (Example 294) (0.035 g, 26% yield). LCMS (ESI+) m/z=472.2 (M+H). $^1$H NMR (400 MHz, CHLOROFORM-d) δ 8.37-8.46 (m, 3H), 8.27 (s, 1H), 6.89 (d, J=40.491 Hz, 1H), 5.05 (d, J=2.54 Hz, 2H), 4.13-4.96 (m, 2H), 3.80 (s, 3H), 2.59 (t, J=8.71 Hz, 1H), 2.54 (t, J=2.45 Hz, 1H), 1.74 (s, 3H), 1.56 (dd, J=5.28, 9.78 Hz, 1H), 1.12 (dd, J=5.38, 7.53 Hz, 1H). $^{19}$F NMR (376 MHz, CHLOROFORM-d) δ −64.84 (s, 1F), −122.41 (s, 1F).

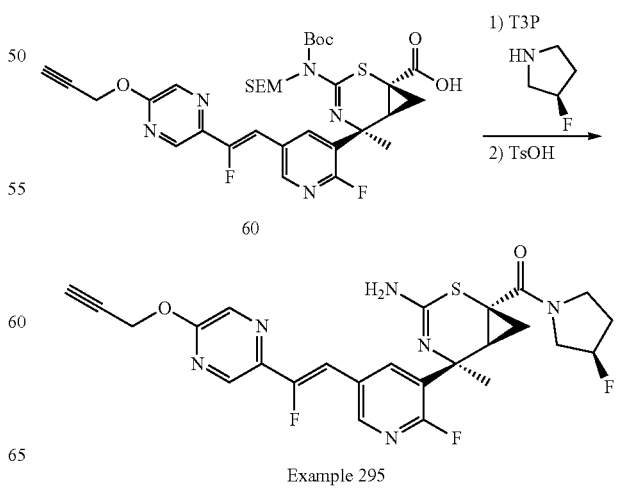

Example 295

Preparation of ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((R)-3-fluoropyrrolidin-1-yl)methanone (Example 295)

Using a procedure similar to that described for Example 122, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (60) (0.100 g, 0.145 mmol), (R)-(−)-3-fluoropyrrolidine hydrochloride (0.027 g, 0.22 mmol), triethylamine (0.061 mL, 0.44 mmol), and 1-propanephosphonic acid cyclic anhydride (0.463 mL, 0.727 mmol) were combined to a product, which after deprotection with p-toluenesulfonic acid monohydrate (0.083 g, 0.44 mmol) afforded ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((R)-3-fluoropyrrolidin-1-yl)methanone (Example 295) (0.040 g, 52% yield). LCMS (ESI+) m/z=529.1 (M+H). $^1$H NMR (400 MHz, CHLOROFORM-d) δ 8.38 (s, 1H), 8.33 (s, 1H), 8.26 (s, 1H), 8.21 (d, J=9.10 Hz, 1H), 6.84 (d, J=39.81 Hz, 1H), 5.13-5.46 (m, 1H), 5.04 (d, J=2.40 Hz, 2H), 4.26-4.97 (m, 2H), 3.41-4.13 (m, 4H), 2.54 (t, J=2.37 Hz, 1H), 2.27-2.42 (m, 1H), 2.20 (dd, J=7.78, 8.95 Hz, 1H), 1.87 (s, 3H), 1.55 (dd, J=5.84, 9.61 Hz, 1H), 1.26 (m, 1H), 0.80 (br. s., 1H). $^{19}$F NMR (376 MHz, CHLOROFORM-d) δ −64.06 (s, 1F), −122.47 (s, 1F), −177.68 (s, 1F).

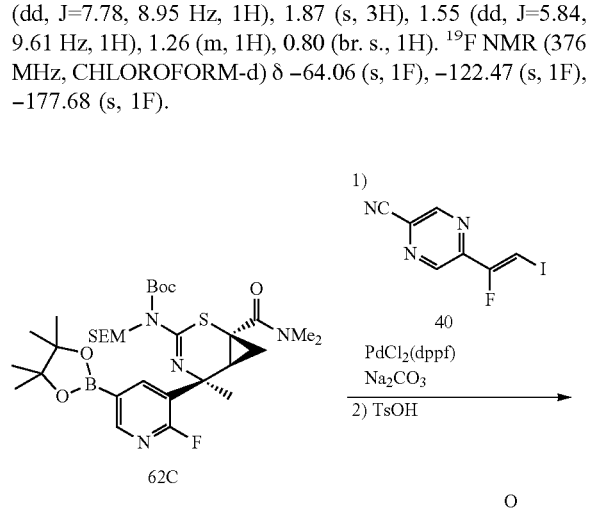

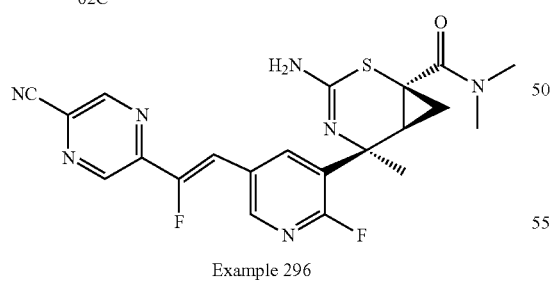

Example 296

Preparation of (1S,5S,6S)-3-amino-5-(5-((Z)-2-(5-cyanopyrazin-2-yl)-2-fluorovinyl)-2-fluoropyridin-3-yl)-N,N,5-trimethyl-2-thia-4-azabicyclo[4.1.0]hept-3-ene-1-carboxamide (Example 296)

Using a procedure similar to that described for Example 222, tert-butyl ((1S,5S,6S)-1-(dimethylcarbamoyl)-5-(2-fluoro-5-(4,4,5,5-tetramethyl-1,3,2-dioxaborolan-2-yl)pyridin-3-yl)-5-methyl-2-thia-4-azabicyclo[4.1.0]hept-3-en-3-yl)((2-(trimethylsilyl)ethoxy)methyl)carbamate (62C) (0.200, 0.301 mmol), intermediate 40 (0.099 g, 0.36 mmol), 1,1'-bis(diphenylphosphino)ferrocene palladium(II)dichloride dichloromethane adduct (0.025 g, 0.030 mmol), and sodium carbonate anhydrous (0.128 g, 1.20 mmol) were combined to give the coupling product, which after deprotection with p-toluenesulfonic acid monohydrate (0.114 g, 0.602 mmol) afforded (1S,5S,6S)-3-amino-5-(5-((Z)-2-(5-cyanopyrazin-2-yl)-2-fluorovinyl)-2-fluoropyridin-3-yl)-N,N,5-trimethyl-2-thia-4-azabicyclo[4.1.0]hept-3-ene-1-carboxamide (Example 296) (0.063 g, 46% yield). LCMS (ESI+) m/z=456.2 (M+H). $^1$H NMR (400 MHz, CHLOROFORM-d) δ 8.99 (s, 1H), 8.86 (s, 1H), 8.43 (s, 1H), 8.37 (dd, J=2.15, 9.39 Hz, 1H), 7.27 (d, J=38.73 Hz, 1H), 3.92-5.21 (br. s., 2H), 3.08 (br. s., 6H), 2.33-2.42 (m, 1H), 1.86 (s, 3H), 1.37 (dd, J=5.77, 9.68 Hz, 1H), 0.86-0.93 (m, 1H). $^{19}$F NMR (376 MHz, CHLOROFORM-d) δ −61.41 (s, 1F), −124.63 (s, 1F).

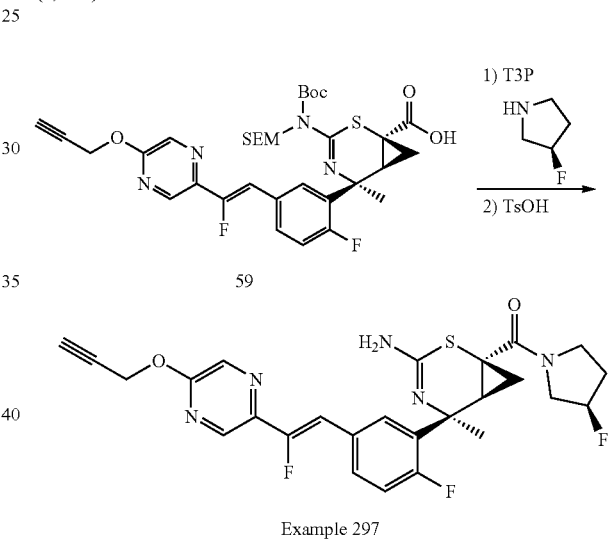

Example 297

Preparation of ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((R)-3-fluoropyrrolidin-1-yl)methanone (Example 297)

Using a procedure similar to that described for Example 122, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylic acid (59) (0.120 g, 0.175 mmol), (R)-(−)-3-fluoropyrrolidine hydrochloride (0.033 g, 0.26 mmol), triethylamine (0.053 g, 0.52 mmol), and 1-propanephosphonic acid cyclic anhydride, 50 wt. % solution in DMF (0.222 ml, 0.349 mmol) were combined to a product, which after deprotection with p-toluenesulfonic acid monohydrate (0.100 g, 0.524 mmol)

afforded ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((R)-3-fluoropyrrolidin-1-yl)methanone (Example 297) (0.035 g, 38% yield). LCMS (ESI+) m/z=528.1 (M+H). ¹H NMR (400 MHz, CHLOROFORM-d) δ 8.37 (s, 1H), 8.25 (s, 1H), 7.70 (d, J=7.13 Hz, 1H), 7.55-7.65 (m, 1H), 7.05 (dd, J=8.51, 11.64 Hz, 1H), 6.82 (d, J=40.30 Hz, 1H), 5.29 (d, J=51.45 Hz, 1H), 5.03 (d, J=2.35 Hz, 2H), 4.25-4.78 (br. s., 2H), 3.95-4.04 (m, 1H), 3.60-3.95 (m, 3H), 2.54 (t, J=2.35 Hz, 1H), 2.35 (br s, 2H), 1.93-2.15 (m, 1H), 1.87 (s, 3H), 1.40 (dd, J=5.67, 9.78 Hz, 1H), 0.87 (br s, 1H). ¹⁹F NMR (376 MHz, CHLOROFORM-d) δ −109.72 (s, 1F), −125.90 (s, 1F), −177.67 (s, 1F).

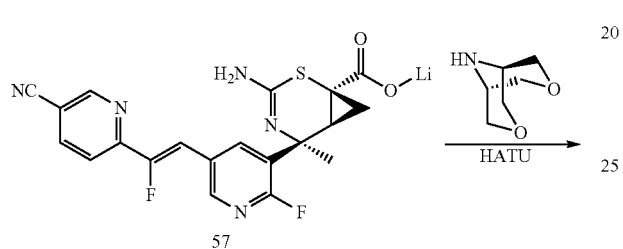

57

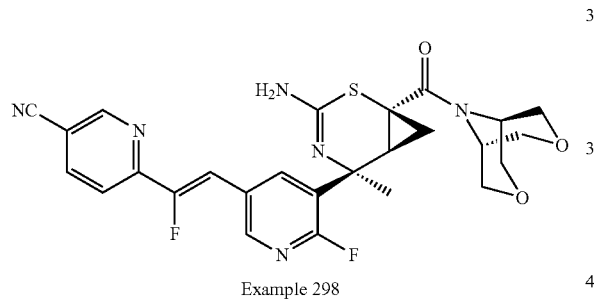

Example 298

Preparation of 6-((Z)-2-(5-(((1S,5S,6S)-3-amino-1-((1R,5R)-3,7-dioxa-9-azabicyclo[3.3.1]nonane-9-carbonyl)-5-methyl-2-thia-4-azabicyclo[4.1.0]hept-3-en-5-yl)-6-fluoropyridin-3-yl)-1-fluorovinyl)nicotinonitrile (Example 298)

Using a procedure similar to that described for Example 259, lithium (1S,5S,6S)-3-amino-5-(5-((Z)-2-(5-cyanopyridin-2-yl)-2-fluorovinyl)-2-fluoropyridin-3-yl)-5-methyl-2-thia-4-azabicyclo[4.1.0]hept-3-ene-1-carboxylate (57) (0.150 g, 0.346 mmol), (1S,5S)-3,7-dioxa-9-azabicyclo[3.3.1]nonane (0.089 g, 0.69 mmol), diisopropylethylamine (0.241 mL, 1.38 mmol) and HATU (0.263 g, 0.692 mmol) were reacted to afford 6-((Z)-2-(5-(((1S,5S,6S)-3-amino-1-((1R,5R)-3,7-dioxa-9-azabicyclo[3.3.1]nonane-9-carbonyl)-5-methyl-2-thia-4-azabicyclo[4.1.0]hept-3-en-5-yl)-6-fluoropyridin-3-yl)-1-fluorovinyl)nicotinonitrile (Example 298) (0.015 g, 8% yield). LCMS (ESI+) m/z=539.2 (M+H). ¹H NMR (400 MHz, CHLOROFORM-d) δ 8.85 (s, 1H), 8.45 (s, J=3.51 Hz, 1H), 8.31-8.35 (m, 1H), 8.03-8.08 (m, 1H), 7.73 (d, J=7.83 Hz, 1H), 7.26 (d, J=38.54 Hz, 1H), 4.65 (br. s., 2H), 4.03-4.32 (m, 7H), 3.86 (br. s., 3H), 2.42 (dd, J=7.82, 9.00 Hz, 1H), 1.83 (s, 3H), 1.41 (dd, J=5.77, 9.68 Hz, 1H), 0.87-0.96 (m, 1H). ¹⁹F NMR (376 MHz, CHLOROFORM-d) δ −62.74 (s, 1F), −122.06 (s, 1F)

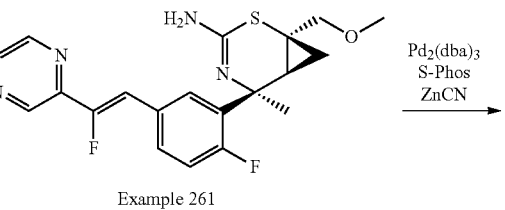

Example 261

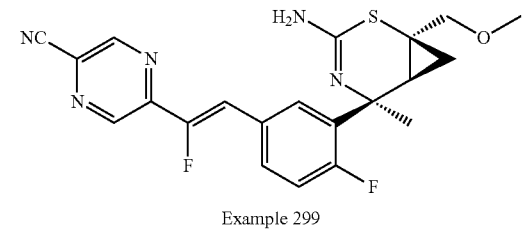

Example 299

Preparation of 5-((Z)-2-(3-((1S,5S,6S)-3-amino-1-(methoxymethyl)-5-methyl-2-thia-4-azabicyclo[4.1.0]hept-3-en-5-yl)-4-fluorophenyl)-1-fluorovinyl)pyrazine-2-carbonitrile (Example 299)

A 4-mL vial was charged with (1S,5S,6S)-5-(5-((Z)-2-(5-chloropyrazin-2-yl)-2-fluorovinyl)-2-fluorophenyl)-1-(methoxymethyl)-5-methyl-2-thia-4-azabicyclo[4.1.0]hept-3-en-3-amine (Example 261) (0.094 g, 0.22 mmol), 2-(dicyclohexylphosphino)-2',6'-dimethoxy-1,1'-biphenyl (0.026 g, 0.065 mmol), tris(dibenzylideneacetone)dipalladium (0) (0.030 g, 0.032 mmol), zinc cyanide (0.076 g, 0.64 mmol) and N,N-dimethylacetamide (1 mL). The vial was purged with argon, sealed and heated at 115° C. for 1.5 hours. The mixture was filtered through celite and the cake was washed with EtOAc. The filtrate was concentrated and the crude mixture was purified by silica gel chromatography with ISCO eluting with 0-6% MeOH in DCM to afford 5-((Z)-2-(3-((1S,5S,6S)-3-amino-1-(methoxymethyl)-5-methyl-2-thia-4-azabicyclo[4.1.0]hept-3-en-5-yl)-4-fluorophenyl)-1-fluorovinyl)pyrazine-2-carbonitrile (Example 299) (0.015 g, 16% yield). LCMS (ESI+) m/z=428.2 (M+H). ¹H NMR (400 MHz, CHLOROFORM-d) δ 8.95 (s, 1H), 8.83 (s, 1H), 7.99 (dd, J=2.13, 7.85 Hz, 1H), 7.69-7.74 (m, 1H), 7.28 (d, J=38.98 Hz, 1H), 7.12 (dd, J=8.51, 11.84 Hz, 1H), 3.92-5.13 (m, 2H), 3.66 (d, J=10.56 Hz, 1H), 3.42 (s, 3H), 3.36 (d, J=10.66 Hz, 1H), 1.79 (dd, J=7.43, 8.71 Hz, 1H), 1.75 (d, J=1.03 Hz, 3H), 0.90-0.96 (m, 1H), 0.78-0.85 (m, 1H). ¹⁹F NMR (376 MHz, CHLOROFORM-d) δ −108.27 (s, 1F), −128.31 (s, 1F).

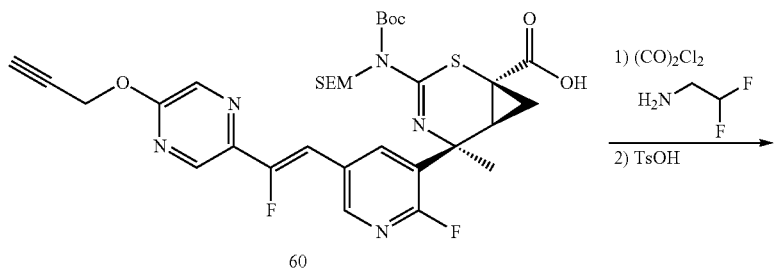

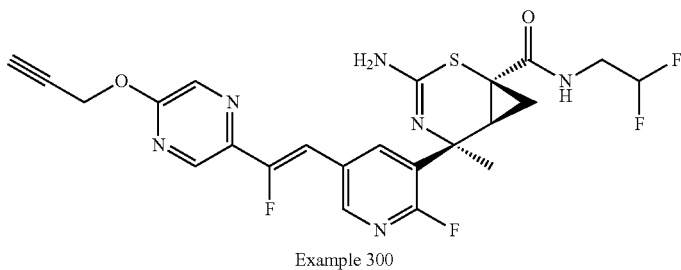

Example 300

Preparation of (1S,5S,6S)-3-amino-N-(2,2-difluoro-ethyl)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxamide (Example 300)

Using a procedure similar to that described for Example 281, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (60) (0.100 g, 0.145 mmol), oxalyl chloride, 2.0M solution in dichloromethane (0.145 ml, 0.291 mmol), 2,2-difluoroethylamine (0.012 ml, 0.14 mmol), and triethylamine (0.105 mL, 0.727 mmol) were combined to give a product, which was subsequently deprotected with p-toluenesulfonic acid monohydrate (0.083 g, 0.44 mmol) to afford (1S,5S,6S)-3-amino-N-(2,2-difluoroethyl)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxamide (Example 300) (0.021 g, 0.040 mmol, 28% yield). LCMS (ESI+) m/z=521.2 (M+H). $^1$H NMR (400 MHz, CHLOROFORM-d) δ 8.35 (s, 1H), 8.31 (s, 1H), 8.25 (s, 1H), 8.02 (dd, J=2.15, 9.59 Hz, 1H), 6.71-6.91 (m, 2H), 5.87 (dd, J=4.30, 56.34 Hz, 1H), 5.01-5.09 (m, 2H), 3.68-3.81 (m, 1H), 3.55-3.68 (m, 1H), 2.54 (t, J=2.35 Hz, 1H), 2.24 (dd, J=7.73, 9.49 Hz, 1H), 1.99-2.09 (m, 1H), 1.86 (s, 3H), 0.80 (dd, J=5.38, 6.94 Hz, 1H). NH$_2$ not visible. $^{19}$F NMR (376 MHz, CHLOROFORM-d) δ −62.96 (s, 1F), −122.51 (s, 1F), −122.97 (s, 1F), −122.98 (s, 1F).

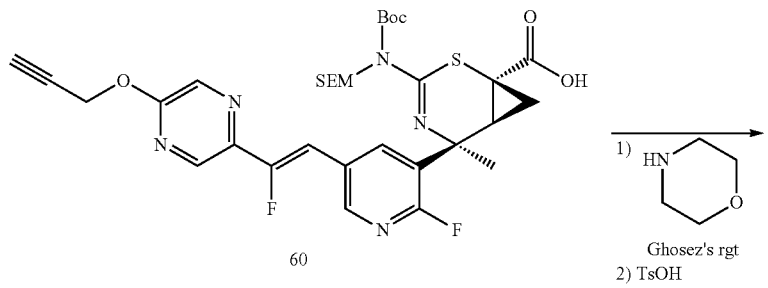

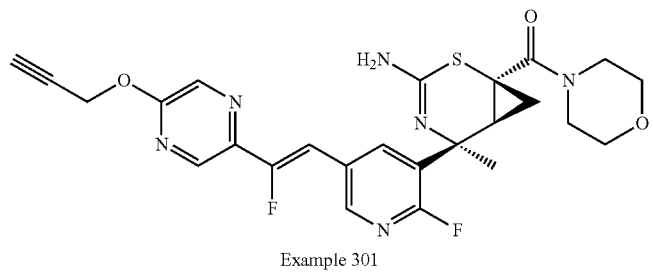

Example 301

Preparation of ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)(morpholino)methanone (Example 301)

Using a procedure similar to that described for Example 260, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid (60) (0.110 g, 0.160 mmol), 1-chloro-N,N,2-trimethyl-1-propenylamine (0.043 ml, 0.32 mmol), morpholine (0.021 ml, 0.24 mmol), and triethylamine (0.065 g, 0.64 mmol) were combined to form a product, which was deprotected with p-toluenesulfonic acid monohydrate (0.091 g, 0.48 mmol) to afford ((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)(morpholino)methanone (Example 301) (0.025 g, 30% yield). LCMS (ESI+) m/z=527.2 (M+H). $^1$H NMR (400 MHz, CHLOROFORM-d) δ 8.41 (s, 1H), 8.37 (s, 1H), 8.21-8.32 (m, 2H), 6.87 (d, J=39.91 Hz, 1H), 5.04 (d, J=2.15 Hz, 2H), 3.59-3.77 (m, 8H), 2.54 (t, J=2.15 Hz, 1H), 2.38 (t, J=8.22 Hz, 1H), 1.86 (s, 3H), 1.37 (dd, J=5.87, 9.59 Hz, 1H), 0.84-0.95 (m, 1H). NH$_2$ not showing. $^{19}$F NMR (376 MHz, CHLOROFORM-d) δ −64.20 (s, 1F), −122.57 (s, 1F).

Preparation of (1S,5S,6S)-3-amino-N-(2,2-difluoroethyl)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxamide (Example 302)

Using a similar procedure to that described for Example 122, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylic acid (59) (0.120 g, 0.175 mmol), 2,2-difluoroethylamine (0.020 ml, 0.24 mmol), and 1-propanephosphonic acid cyclic anhydride, 50 wt. % solution in DMF (0.222 ml, 0.349 mmol) were combined to give a product, which after deprotection with p-toluenesulfonic acid monohydrate (0.100 g, 0.524 mmol) afforded (1S,5S,6S)-3-amino-N-(2,2-difluoroethyl)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxamide (Example 302) (0.054 g, 60% yield). LCMS (ESI+) m/z=520.1 (M+H). $^1$H NMR (400 MHz, CHLOROFORM-d) δ 8.27 (s, 1H), 8.21 (s, 1H), 7.45-7.53 (m, 2H), 6.89-7.07 (m, 2H), 6.70 (d, J=41.08 Hz, 1H), 5.90 (d, J=4.1, 56.34 Hz, 1H), 5.03 (d, J=2.35 Hz, 2H), 5.11-4.91 (br. s., 2H), 3.53-3.80 (m, 2H), 2.54 (t, J=2.45 Hz, 1H), 2.16-2.24 (m, 1H), 2.05 (dd, J=4.99, 9.68 Hz, 1H), 1.88 (s, 3H), 0.78-0.83 (m, 1H). $^{19}$F NMR (376 MHz, CHLOROFORM-d) δ −108.29 (s, 1F), −122.88 (s, 1F), −122.90 (s, 1F), −125.82 (s, 1F).

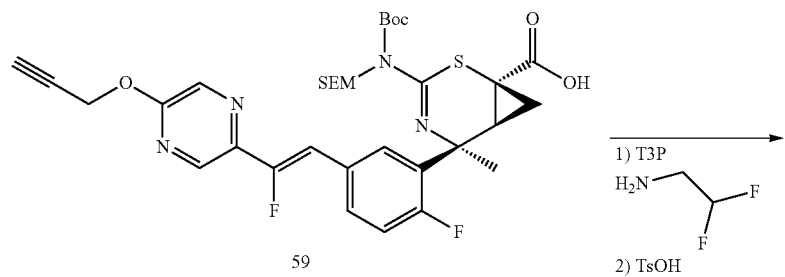

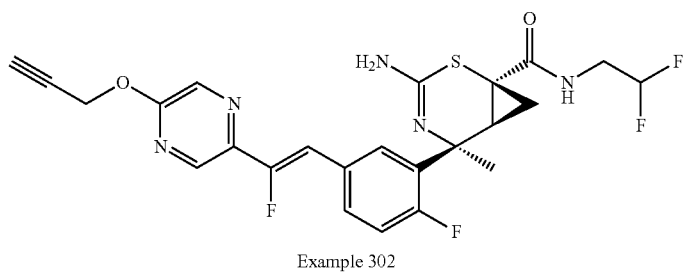

Example 302

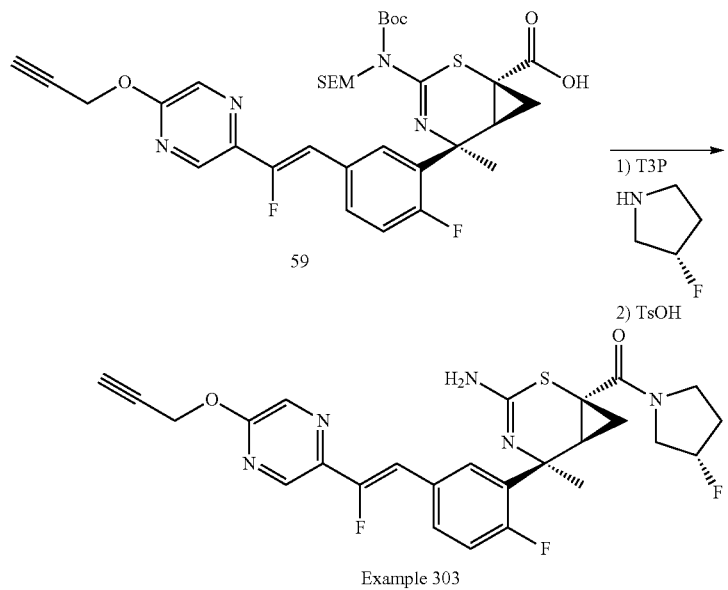

Example 303

Preparation of ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((S)-3-fluoropyrrolidin-1-yl)methanone (Example 303)

Using a similar procedure to that described for Example 122, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylic acid (59) (0.120 g, 0.175 mmol), (S)-(+)-3-fluoropyrrolidine hydrochloride (0.033 g, 0.262 mmol), triethylamine (0.076 ml, 0.524 mmol), and 1-propanephosphonic acid cyclic anhydride, 50 wt. % solution in EtOAc (0.222 ml, 0.349 mmol) were combined to form a product which was deprotected with p-toluenesulfonic acid monohydrate (0.100 g, 0.524 mmol) to afford ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((S)-3-fluoropyrrolidin-1-yl)methanone (Example 303) (0.029 g, 32% yield). LCMS (ESI+) m/z=528.1 (M+H). $^1$H NMR (400 MHz, CHLOROFORM-d) δ 8.37 (s, 1H), 8.25 (s, 1H), 7.70 (d, J=7.13 Hz, 1H), 7.55-7.65 (m, 1H), 7.05 (dd, J=8.51, 11.64 Hz, 1H), 6.82 (d, J=40.30 Hz, 1H), 5.29 (d, J=51.45 Hz, 1H), 5.03 (d, J=2.35 Hz, 2H), 4.25-4.78 (br. s., 2H), 3.95-4.04 (m, 1H), 3.60-3.95 (m, 3H), 2.54 (t, J=2.35 Hz, 1H), 2.35 (br s, 2H), 1.93-2.15 (m, 1H), 1.87 (s, 3H), 1.40 (dd, J=5.67, 9.78 Hz, 1H), 0.87 (br s, 1H). $^{19}$F NMR (376 MHz, CHLOROFORM-d) δ −109.87 (s, 1F), −125.94 (s, 1F), −177.51 (s, 1F).

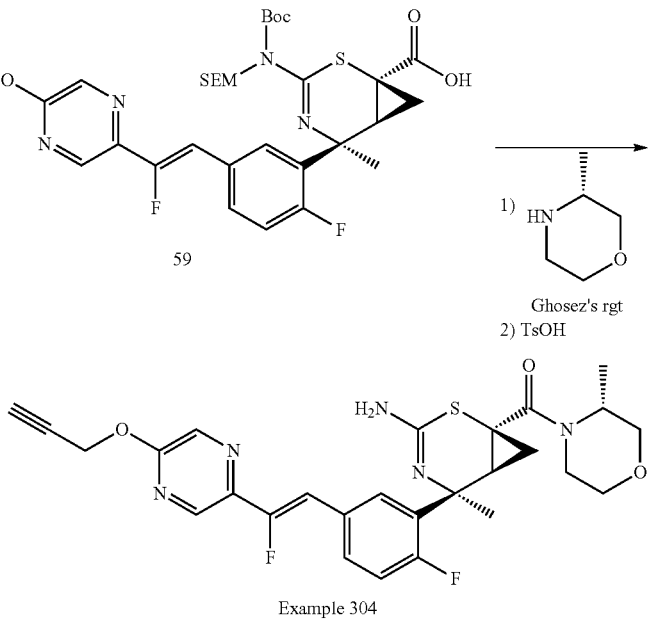

Example 304

Preparation of ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((R)-3-methylmorpholino)methanone (Example 304)

The title compound was prepared following the procedure described for Example 260, (1S,5S,6S)-3-((tert-butoxycarbonyl)((2-(trimethylsilyl)ethoxy)methyl)amino)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxylic acid (59) (0.120 g, 0.175 mmol), 1-chloro-N,N,2-trimethyl-1-propenylamine (0.070 ml, 0.52 mmol), (R)-3-methyl-morpholine (0.027 ml, 0.26 mmol) and triethylamine (0.026 ml, 0.18 mmol) were combined to form a product, which was deprotected with p-toluenesulfonic acid monohydrate (0.100 g, 0.524 mmol) to afford ((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((R)-3-methylmorpholino)methanone (Example 304) (0.029 g, 31% yield). LCMS (ESI+) m/z=540.2 (M+H). $^1$H NMR (400 MHz, CHLOROFORM-d) δ 8.35 (s, 1H), 8.24 (s, 1H), 7.74 (dd, J=1.96, 7.82 Hz, 1H), 7.56-7.63 (m, 1H), 7.01-7.08 (m, 1H), 6.81 (d, J=40.10 Hz, 1H), 5.03 (d, J=2.35 Hz, 2H), 4.44 (br dd, J=1.96, 6.65 Hz, 1H), 4.02 (br d, J=13.69 Hz, 1H), 3.91 (dd, J=2.74, 11.35 Hz, 1H), 3.69 (d, J=11.54 Hz, 1H), 3.58 (dd, J=2.74, 11.54 Hz, 1H), 3.37-3.52 (m, 1H), 3.30 (br s, 1H), 2.54 (t, J=2.35 Hz, 1H), 2.29 (dd, J=7.92, 8.90 Hz, 1H), 1.85 (s, 3H), 1.33 (br d, J=6.06 Hz, 3H), 1.26 (br t, J=7.14 Hz, 1H), 0.87 (t, J=6.46 Hz, 1H). NH$_2$ is broad at 5.00-4.25. $^{19}$F NMR (376 MHz, CHLOROFORM-d) δ −110.19 (s, 1F), −125.97 (s, 1F).

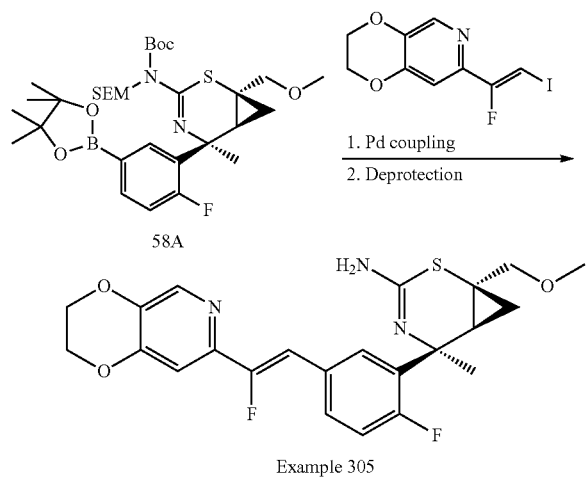

Example 305

Preparation of (1S,5S,6S)-5-(5-((Z)-2-(2,3-dihydro-[1,4]dioxino[2,3-c]pyridin-7-yl)-2-fluorovinyl)-2-fluorophenyl)-1-(methoxymethyl)-5-methyl-2-thia-4-azabicyclo[4.1.0]hept-3-en-3-amine (Example 305)

Using a similar procedure to that described for Example 249, tert-butyl ((1S,5S,6S)-5-(2-fluoro-5-(4,4,5,5-tetramethyl-1,3,2-dioxaborolan-2-yl)phenyl)-1-(methoxymethyl)-5-methyl-2-thia-4-azabicyclo[4.1.0]hept-3-en-3-yl)((2-(trimethylsilyl)ethoxy)methyl)carbamate (58A) (0.400 g, 0.628 mmol), (Z)-7-(1-fluoro-2-iodovinyl)-2,3-dihydro-[1,4]dioxino[2,3-c]pyridine (51) (0.193 g, 0.628 mmol), 1,1-bis[di-t-butyl-p-methylaminophenyl]palladium(II) chloride (0.089 g, 0.13 mmol) and potassium phosphate tribasic monohydrate (0.434 g, 1.88 mmol) were combined to provide the coupling product, which after deprotection with p-toluenesulfonic acid monohydrate (0.239 g, 1.26 mmol) afforded (1S,5S,6S)-5-(5-((Z)-2-(2,3-dihydro-[1,4]dioxino[2,3-c]pyridin-7-yl)-2-fluorovinyl)-2-fluorophenyl)-1-(methoxymethyl)-5-methyl-2-thia-4-azabicyclo[4.1.0]hept-3-en-3-amine (Example 305) (0.050 g, 17% yield). LCMS (ESI+) m/z=460.2 (M+H). $^1$H NMR (400 MHz, CHLOROFORM-d) δ 8.16 (s, 1H), 7.85-7.92 (m, 1H), 7.58-7.66 (m, 1H), 7.10-7.15 (m, 1H), 6.99-7.08 (m, 1H), 6.89 (d, J=40.10 Hz, 1H), 4.77-4.10 (br. s., 2H), 4.34 (br dd, J=4.99, 14.38 Hz, 4H), 3.66 (d, J=10.76 Hz, 1H), 3.41 (s, 3H), 3.34 (d, J=10.76 Hz, 1H), 1.73 (s, 4H), 0.89 (dd, J=5.77, 9.49 Hz, 1H), 0.76-0.84 (m, 1H). $^{19}$F NMR (376 MHz, CHLOROFORM-d) δ −112.19 (s, 1F), −122.84 (s, 1F)

Synthesis of Intermediate 65

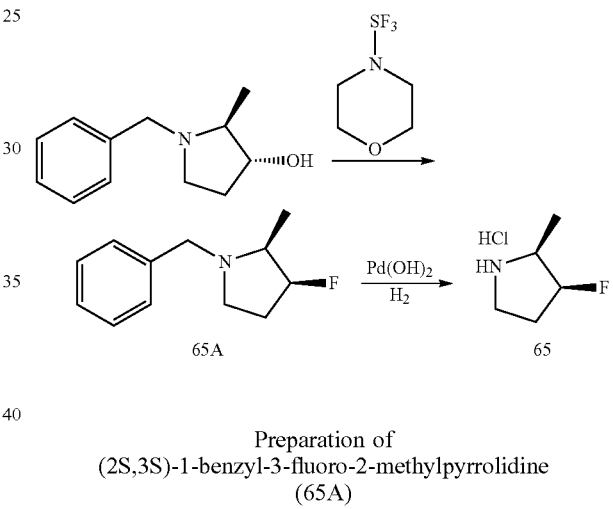

Preparation of (2S,3S)-1-benzyl-3-fluoro-2-methylpyrrolidine (65A)

To a solution of (2S,3R)-1-benzyl-2-methylpyrrolidin-3-ol (Tetrahedron 67 (2011) 7829-7837) (1.15 g, 6.01 mmol) in DCM (4 mL) cooled in ice water bath under nitrogen was added a solution of morpholinosulfur trifluoride (1.19 ml, 9.77 mmol) in DCM (0.4 mL). After stirring for 30 minutes at 0° C., the flask was lifted above the cooling bath and the mixture was stirred at room temperature for 20 minutes. The reaction mixture was diluted with EtOAc followed by slow addition of saturated NaHCO$_3$ solution. The resulting mixture was stirred for 20 minutes and the layers were separated. The aqueous layer was extracted with EtOAc (3×). The combined organic phases were dried over Na$_2$SO$_4$, filtered, and concentrated. The residue was purified by chromatography on silica using 0-15% EtOAc in heptane to afford (2S,3S)-1-benzyl-3-fluoro-2-methylpyrrolidine (65A) (0.210 g, 14% yield) as a brown oil. LCMS (ESI+) m/z=194.1 (M+H).

Preparation of (2S,3S)-3-fluoro-2-methylpyrrolidine hydrochloride (65)

A solution of (2S,3S)-1-benzyl-3-fluoro-2-methylpyrrolidine (65A) (0.200 g, 1.04 mmol) and palladium hydroxide, 20 wt % Pd (dry basis) on carbon, wet (0.291 g, 2.07 mmol) in EtOAc (10 mL) was hydrogenated at 40 psi for 2 hour. The reaction mixture was filtered and 2N HCl (3 mL) was added to the filtrate. The filtrate was concentrated and dried to give (2S,3S)-3-fluoro-2-methylpyrrolidine hydrochloride (0.130 g, 90% yield). It was used in the next step without further purification. LCMS (ESI+) m/z=104.3 (M+H).

Synthesis of Intermediate 66

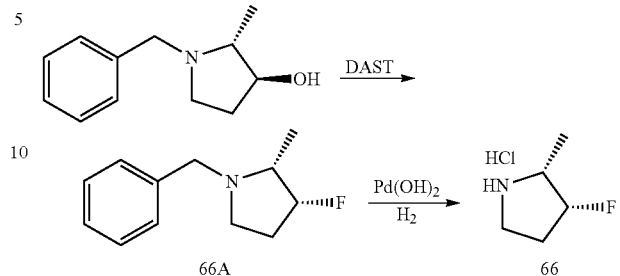

Preparation of (2R,3R)-1-benzyl-3-fluoro-2-methylpyrrolidine (66A)

Using a similar procedure to that described for (2S,3S)-1-benzyl-3-fluoro-2-methylpyrrolidine (65A), (2S,3R)-1-benzyl-2-methylpyrrolidin-3-ol (1.15 g, 6.01 mmol) was reacted with DAST to afford (2R,3R)-1-benzyl-3-fluoro-2-methylpyrrolidine (66A) (0.210 g, 14% yield). LCMS (ESI+) m/z=194.1 (M+H).

Preparation of (2R,3R)-3-fluoro-2-methylpyrrolidine hydrochloride (66)

Using a similar procedure to that described for (2S,3S)-3-fluoro-2-methylpyrrolidine hydrochloride (65), (2R,3R)-1-benzyl-3-fluoro-2-methylpyrrolidine (0.200 g, 1.04 mmol) was hydrogenated to afford (2R,3R)-3-fluoro-2-methylpyrrolidine hydrochloride (0.120 g, 83% yield). LCMS (ESI+) m/z=104.2 (M+H)

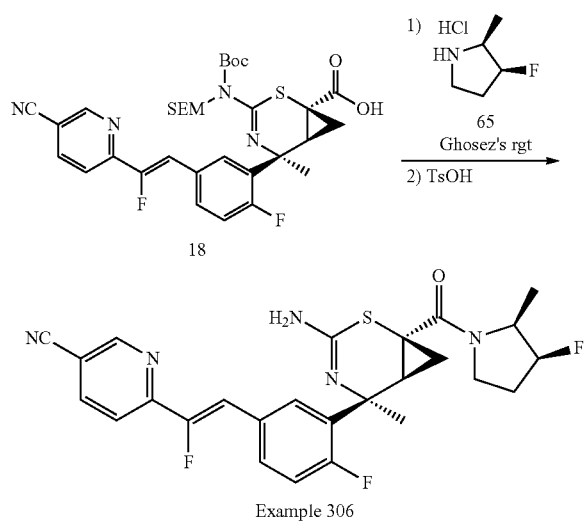

Example 306

Preparation of 6-((Z)-2-(3-((1S,5S,6S)-3-amino-1-((2S,3S)-3-fluoro-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 306)

Using a similar procedure to that described for Example 260, (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (18) (0.28 g, 0.43 mmol), 1-chloro-N,N,2-trimethyl-1-propenylamine (1.0 ml, 7.5 mmol), (2S,3S)-3-fluoro-2-methylpyrrolidine hydrochloride (65) (0.077 g, 0.55 mmol) and triethylamine (2.0 ml, 14 mmol) were combined to form a coupled product, which was deprotected with p-toluenesulfonic acid monohydrate (0.162 g, 0.853 mmol) to afford 6-((Z)-2-(3-((1S,5S,6S)-3-amino-1-((2S,3S)-3-fluoro-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 307) (0.037 g, 17% yield). LCMS (ESI+) m/z=512.2 (M+H). $^1$H NMR (400 MHz, CHLOROFORM-d) δ 8.81 (s, 1H), 7.95-8.05 (m, 1H), 7.75-7.84 (m, 1H), 7.60-7.70 (m, 2H), 7.20 (d, J=39.13 Hz, 1H), 7.02-7.12 (m, 1H), 5.07 (d, J=54.19 Hz, 1H), 4.59 (br s, 2H), 4.03-4.28 (m, 1H), 3.93 (brt, J=9.19 Hz, 1H), 3.58-3.84 (m, 1H), 2.52 (dd, J=8.02, 9.00 Hz, 1H), 2.16-2.37 (m, 1H), 2.05 (s, 1H), 1.87 (s, 3H), 1.35 (dd, J=3.23, 6.55 Hz, 3H), 1.21-1.29 (m, 1H), 0.82-0.97 (m, 1H). $^{19}$F NMR (376 MHz, CHLOROFORM-d) δ −107.96 (s, 1F), −125.78 (s, 1F), −193.86 (s, 1F).

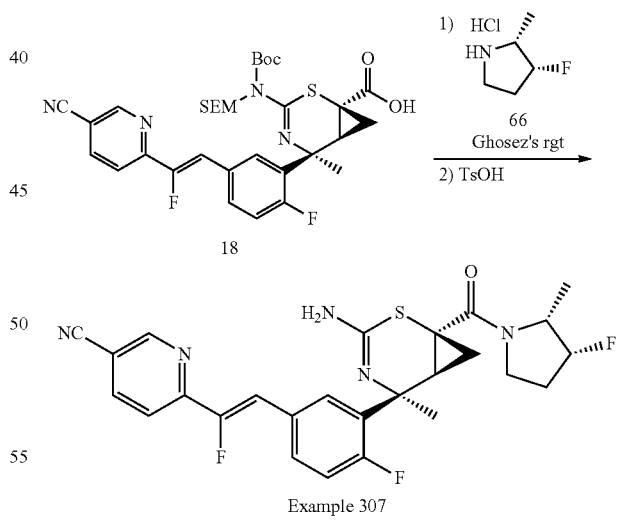

Example 307

Preparation of 6-((Z)-2-(3-((1S,5S,6S)-3-amino-1-((2R,3R)-3-fluoro-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 307)

Using a similar procedure to that described for Example 260, (1S,5S,6S)-3-((tert-butoxycarbonyl)((2-(trimethylsilyl)

ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (0.200 g, 0.304 mmol), 1-chloro-N,N,2-trimethyl-1-propenylamine (0.80 ml, 6.0 mmol), (2R,3R)-3-fluoro-2-methylpyrrolidine hydrochloride (66) (0.085 g, 0.61 mmol) and triethylamine (0.212 ml, 1.52 mmol) were combined to form a coupling product which was deprotected with 4-methylbenzene sulfonic acid, monohydrate (0.116 g, 0.609 mmol) to afford 6-((Z)-2-(3-((1S,5S,6S)-3-amino-1-((2R,3R)-3-fluoro-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 307) (0.100 g, 64% yield). LCMS (ESI+) m/z=512.2 (M+H). $^1$H NMR (400 MHz, DMSO-d6) δ ppm 9.06 (s, 1H), 8.41-8.46 (m, 1H), 7.80-7.89 (m, 2H), 7.65-7.73 (m, 1H), 7.18-7.31 (m, 2H), 6.39 (s, 2H), 5.00-5.28 (m, 1H), 3.95-4.12 (m, 1H), 3.81 (br t, J=7.73 Hz, 1H), 3.64 (br d, J=6.46 Hz, 1H), 1.91-2.16 (m, 3H), 1.72 (s, 3H), 1.51 (dd, J=5.28, 9.39 Hz, 1H), 1.18 (dd, J=2.64, 6.36 Hz, 3H), 0.50 (br t, J=5.77 Hz, 1H). $^{19}$F NMR (376 MHz, DMSO-d6) δ −108.48 (s, 1F), −124.58 (s, 1F), −193.11 (s, 1F).

mmol), trimethylamine (300 uL, 2.16 mmol), and 2,5-dioxa-8-azaspiro[3.5]nonane hemioxalate (0.070 g, 0.32 mmol, AZ Chemical) were allowed to react to afford 6-((Z)-2-(3-((1S,5S,6S)-3-amino-5-methyl-1-(2,5-dioxa-8-azaspiro[3.5]nonane-8-carbonyl)-2-thia-4-azabicyclo[4.1.0]hept-3-en-5-yl)-4-fluorophenyl)-1-fluorovinyl)nicotinonitrile (Example 208) (23 mg, 23% yield). LCMS (ESI, pos.): calcd for $C_{27}H_{25}F_2N_5O_3S$: 537.1; found: 538.1 (M+1). $^1$H NMR (400 MHz, CHLOROFORM-d) δ ppm 8.82 (s, 1H), 7.99-8.03 (m, 1H), 7.78-7.83 (m, 1H), 7.65-7.71 (m, 2H), 7.24 (d, J=32.5 Hz, 1H), 7.11 (d, J=8.4 Hz, 1H), 4.61 (d, J=6.8 Hz, 2H), 4.50 (d, J=6.5 Hz, 1H), 4.44 (d, J=6.8 Hz, 1H), 3.87 (br. s., 2H), 3.63-3.70 (m, 2H), 3.60 (br. s., 2H), 2.21-2.43 (m, 1H), 1.88 (s, 3H), 1.38 (dd, J=9.8, 5.7 Hz, 1H), 0.93 (t, J=6.3 Hz, 1H). $^{19}$F NMR (376 MHz, CHLOROFORM-d) δ ppm −108.36 (s, 1F), −125.66 (s, 1F).

Preparation of Intermediate 67 and Examples 309 and 310

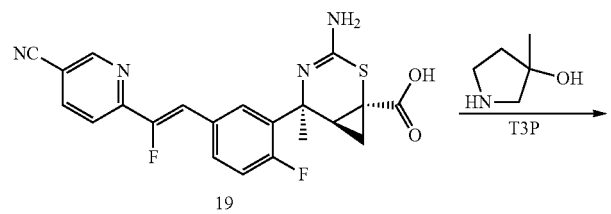

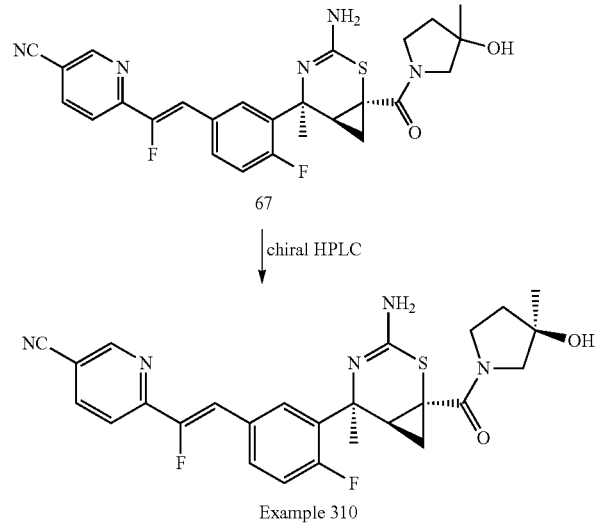

Example 309

Example 310

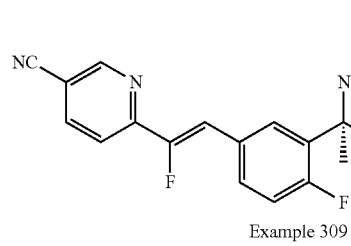

Example 308

Preparation of 6-((Z)-2-(3-((1S,5S,6S)-3-amino-5-methyl-1-(2,5-dioxa-8-azaspiro[3.5]nonane-8-carbonyl)-2-thia-4-azabicyclo[4.1.0]hept-3-en-5-yl)-4-fluorophenyl)-1-fluorovinyl)nicotinonitrile (Example 308)

Using a similar procedure to that described for Example 122, acid 19 (0.080 g, 0.19 mmol), 1-propanephosphonic acid cyclic anhydride (50% in EtOAc) (300 μL, 0.471

Preparation of: 6-((Z)-2-(3-((1S,5S,6S)-3-amino-1-((S)-3-hydroxy-3-methylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 309) and 6-((Z)-2-(3-((1S,5S,6S)-3-amino-1-((R)-3-hydroxy-3-methylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 310)

A mixture of 19 (100 mg, 0.235 mmol), 3-methyl-pyrrolidin-3-ol (90 mg, 0.89 mmol) and triethylamine (0.15 mL, 1.1 mmol) in DMF (1 mL) was solubilized via sonication. Then a solution of propylphosphonic anhydride solution 50% in DMF (0.59 mL, 0.79 mmol) was added. After 10 minutes, the mixture was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 15 min to give 6-((Z)-2-(3-((1S,5S,6S)-3-amino-1-(3-hydroxy-3-methylpyrrolidine-1-carbonyl)-5-methyl-2-thia-4-azabicyclo

[4.1.0]hept-3-en-5-yl)-4-fluorophenyl)-1-fluorovinyl)nicotinonitrile (67) as a white foam (56 mg, 47% yield). A total of 130 mg of 67 from two purifications were subject to preparative chiral SFC separation (Column: IC 21.2×150 mm, 5μ; Mobile Phase: 60:40 Liquid $CO_2$— methanol containing 20 mM $NH_3$); Flow Rate: 55 g/min; Column/Oven temp.: 40° C.). The chirality of the tertiary alcohol was arbitrarily assigned as S for Peak 1 (99.19% purity, 100% ee) and R for Peak 2 (99.56% purity, 100% ee).

Peak-1: 6-((Z)-2-(3-((1S,5S,6S)-3-amino-1-((S)-3-hydroxy-3-methylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 309). Yield: 42 mg (35%). LCMS (ESI, pos.): calcd for $C_{26}H_{25}F_2N_5O_2S$: 509.2; found: 510.2 (M+1). 1H NMR (400 MHz, CHLOROFORM-d) δ 8.82 (s, 1H), 8.01 (dd, J=2.15, 8.41 Hz, 1H), 7.76 (br d, J=7.04 Hz, 1H), 7.62-7.71 (m, 2H), 7.14-7.30 (d, J=36.0 Hz, 1H), 7.08 (dd, J=8.41, 11.54 Hz, 1H), 3.28-3.96 (m, 4H), 2.33 (br t, J=8.31 Hz, 1H), 1.89-2.09 (m, 2H), 1.87 (s, 3H), 1.46 (s, 3H), 1.40 (m, 1H), 0.84 (t, J=6.26 Hz, 1H). 19F NMR (376 MHz, CHLOROFORM-d) δ −108.04 (br d, J=55.27 Hz, 1F), −125.72 (br s, 1F).

Peak-2: 6-((Z)-2-(3-((1S,5S,6S)-3-amino-1-((R)-3-hydroxy-3-methylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 310). Yield: 44 mg (37%). LCMS (ESI, pos.): calcd for $C_{26}H_{25}F_2N_5O_2S$: 509.2; found: 510.2 (M+1). 1H NMR (400 MHz, CHLOROFORM-d) δ 8.81 (s, 1H), 8.00 (br d, J=7.43 Hz, 1H), 7.61-7.79 (m, 3H), 7.26 (d, J=39.52 Hz, 1H), 7.08 (dd, J=8.61, 11.35 Hz, 1H), 3.29-3.97 (m, 4H), 2.18 (m, 1H), 1.98 (m, 1H), 1.89 (br, 4H), 1.48-1.65 (m, 1H), 1.45 (br s, 3H), 0.79 (br t, J=6.06 Hz, 1H). 19F NMR (376 MHz, CHLOROFORM-d) δ −107.93 (br s, 1F), −125.65 (br s, 1F).

Preparation of Intermediate 68 and Examples 311 and 312

Preparation of 6-((Z)-2-(3-((1S,5S,6S)-3-amino-1-((1S,6R)-2-oxa-5-azabicyclo[4.1.0]heptane-5-carbonyl)-5-methyl-2-thia-4-azabicyclo[4.1.0]hept-3-en-5-yl)-4-fluorophenyl)-1-fluorovinyl)nicotinonitrile (Example 311) and 6-((Z)-2-(3-((1S,5S,6S)-3-amino-1-((1R,6S)-2-oxa-5-azabicyclo[4.1.0]heptane-5-carbonyl)-5-methyl-2-thia-4-azabicyclo[4.1.0]hept-3-en-5-yl)-4-fluorophenyl)-1-fluorovinyl)nicotinonitrile (Example 312)

Using a similar procedure to that described for Example 121, acid 19 (270 mg, 0.411 mmol) and 2-oxa-5-azabicyclo[4.1.0]heptane hydrochloride (55.7 mg, 0.411 mmol, Enamine) were combined to afford 6-((Z)-2-(3-((1S,5S,6S)-3-amino-1-(2-oxa-5-azabicyclo[4.1.0]heptane-5-carbonyl)-5-methyl-2-thia-4-azabicyclo[4.1.0]hept-3-en-5-yl)-4-fluorophenyl)-1-fluorovinyl)nicotinonitrile (68). The diastereoisomers were subject to chiral separation as described for Examples 309 and 310 to afford the two isomers. The chirality of the 2-oxa-5-azabicyclo[4.1.0]heptane ring was arbitrarily assigned as S, R for Peak 1 (99% ee) and R,S for Peak 2 (99% ee).

Peak-1:
6-((Z)-2-(3-((1S,5S,6S)-3-amino-1-((1S,6R)-2-oxa-5-azabicyclo[4.1.0]heptane-5-carbonyl)-5-methyl-2-thia-4-azabicyclo[4.1.0]hept-3-en-5-yl)-4-fluorophenyl)-1-fluorovinyl)nicotinonitrile (Example 311). Yield: 58 mg (28%). LCMS (ESI, pos.): calcd for $C_{26}H_{23}F_2N_5O_2S$: 507.2; found: 508.1 (M+1). $^1$H NMR (400 MHz, CHLOROFORM-d) δ 8.82 (s, 1H), 8.02 (dd, J=2.05, 8.31 Hz, 1H), 7.60-7.83 (m, 3H), 7.25 (d, J=37.76 Hz, 1H), 7.10 (dd, J=8.61, 11.54 Hz, 1H), 3.66-3.86 (m, 3H), 3.36 (br s, 2H), 3.07 (br s, 1H), 2.32 (br d, J=7.83 Hz, 1H), 1.89 (s, 3H), 1.54 (br s, 1H), 1.00 (q, J=7.24 Hz, 1H), 0.91 (br s, 1H), 0.74-0.83 (m, 1H). $^{19}$F NMR (376 MHz, CHLOROFORM-d) δ −107.99 (m, 1F), −125.74 (br s, 1F).

Peak-2:
6-((Z)-2-(3-((1S,5S,6S)-3-amino-1-((1R,6S)-2-oxa-5-azabicyclo[4.1.0]heptane-5-carbonyl)-5-methyl-2-thia-4-azabicyclo[4.1.0]hept-3-en-5-yl)-4-fluorophenyl)-1-fluorovinyl)nicotinonitrile (Example 312). Yield: 56 mg (26%).

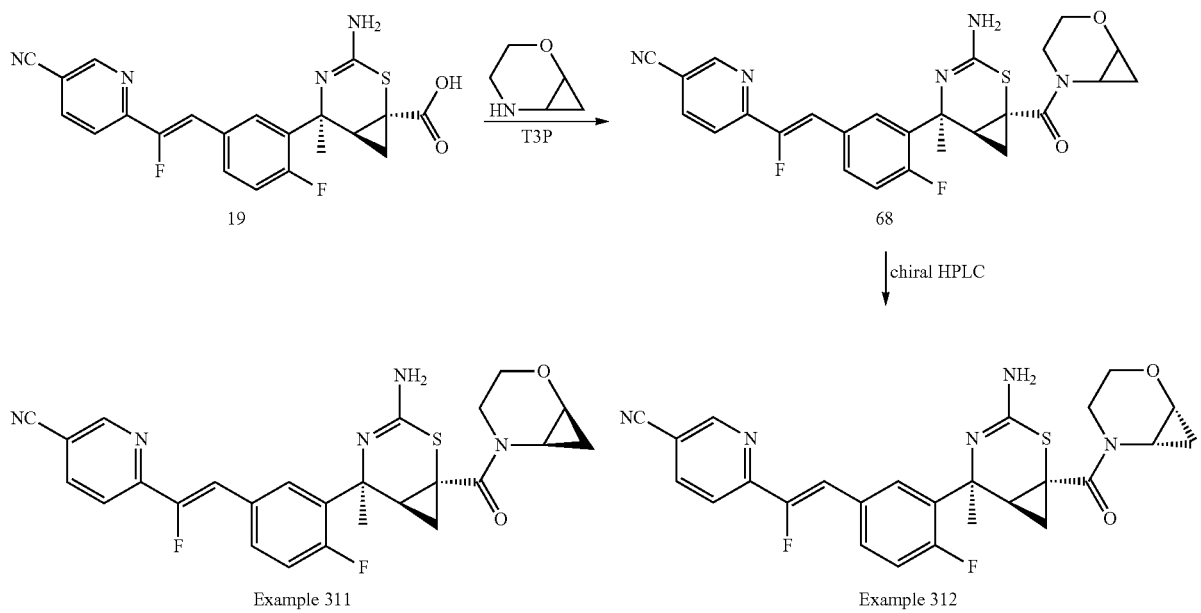

LCMS (ESI, pos.): calcd for $C_{26}H_{23}F_2N_5O_2S$: 507.2; found: 508.1 (M+1). $^1$H NMR (400 MHz, CHLOROFORM-d) δ 8.82 (s, 1H), 8.01 (dd, J=1.96, 8.22 Hz, 1H), 7.68 (br d, J=8.02 Hz, 3H), 7.21 (d, J=43.62 Hz, 1H), 7.09 (dd, J=8.51, 11.44 Hz, 1H), 3.63-3.85 (m, 3H), 3.37 (br s, 2H), 3.07 (br s, 1H), 2.39 (br s, 1H), 1.90 (s, 3H), 1.50 (br s, 1H), 0.93-1.17 (m, 2H), 0.88 (br t, J=6.06 Hz, 1H). $^{19}$F NMR (376 MHz, CHLOROFORM-d) δ −107.53 (br s, 1F), −125.70 (br s, 1F).

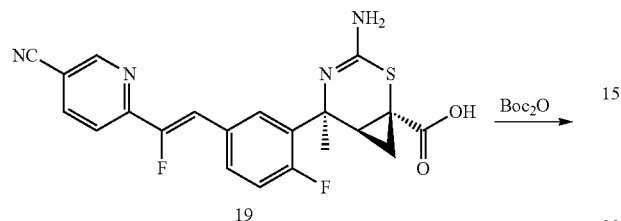

19

Boc$_2$O

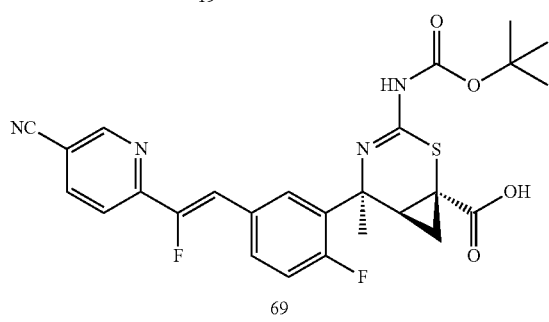

69

Preparation of (1S,5S,6S)-3-((tert-butoxycarbonyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (69)

A mixture of (1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (480 mg, 1.13 mmol), di-t-butyldicarbonate (252 µL, 1.10 mmol) and triethylamine (160 µL, 1.15 mmol) in DMF (3.0 mL) was heated at 50° C. After 4 hours, the mixture was diluted with water (5 mL) and HCl (1N, 1.0 mL) and was stirred at room temperature for 10 minutes. The slurry was filtered and the solid was washed with water (1 mL) to give (1S,5S,6S)-3-((tert-butoxycarbonyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (69) as a yellow solid (0.45 g, mmol, 76% yield). MS m/z=527.2 [M+H]$^+$.

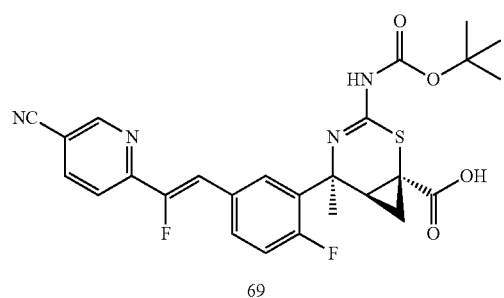

69

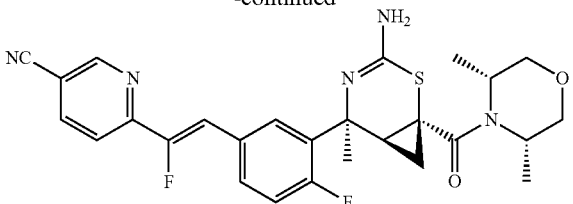

Example 313

Preparation of 6-((Z)-2-(3-((1S,5S,6S)-3-amino-1-((3S,5R)-3,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile (Example 313)

A solution of 1-chloro-N, N-2-trimethylpropenylamine (30 µL, 0.225 mmol) in MeCN (0.2 mL) was added to a slurry of (1S,5S,6S)-3-((tert-butoxycarbonyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (69) (35 mg, 0.066 mmol) in MeCN (1 mL) at rt. The resulting solution was stirred at room temperature for 10 minutes. To the above solution was added cis-2,6-dimethylpiperidine hydrochloride (35 mg, 0.234 mmol, J&W Pharmlab) followed by triethylamine (40 µL, 0.29 mmol). After 30 minutes, MeOH (0.5 mL) was added followed by the addition of aqueous hydrochloric acid (5N) (0.5 mL, 2.500 mmol). The mixture was heated at 60° C. for 30 minutes and was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 15 min. The product fractions were passed through a Phenomenex Strata-X-C 33 u cation exchange resin (1 g/12 mL). The resin was washed with MeOH (4×1 mL). The resin was then eluted with NH$_3$ in MeOH (2N, total 4×1 mL) to release the free-base product. The product fractions were concentrated and the residue was suspended in MeCN-water (2-1 mL). The suspension was frozen at −78° C. and was lyophilized overnight to give 6-((Z)-2-(3-((1S,5S,6S)-3-amino-1-((3S,5R)-3,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile as a white sponge (Example 313) (20 mg, 82% yield). LCMS (ESI, pos.): calcd for $C_{27}H_{27}F_2N_5O_2S$: 523.2; found: 524.2 (M+1). $^1$H NMR (400 MHz, CHLOROFORM-d) δ ppm 8.82 (s, 1H), 8.01 (dd, J=8.3, 2.1 Hz, 1H), 7.80 (dd, J=7.8, 2.2 Hz, 1H), 7.65-7.74 (m, 2H), 7.26 (d, J=40.5 Hz, 1H), 7.06-7.15 (m, 1H), 4.34 (br. s., 2H), 3.69-3.78 (m, 2H), 3.58 (br. s., 2H), 2.34 (t, J=8.0 Hz, 1H), 1.87 (s, 3H), 1.57 (dd, J=10.0, 5.3 Hz, 1H), 1.26-1.47 (m, 6H), 0.90 (br. s., 1H). $^{19}$F NMR (376 MHz, CHLOROFORM-d) δ ppm −108.09 (br. s., 0.5F), −108.67 (br. s., 0.5F), −125.69 (d, J=5.9 Hz, 1F).

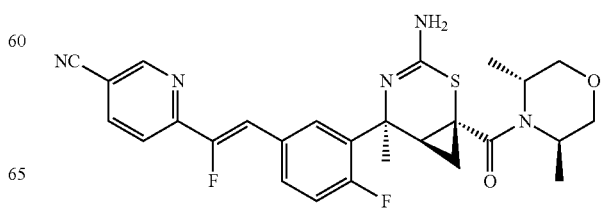

Example 314

Preparation of 6-((Z)-2-(3-((1S,5S,6S)-3-amino-1-((3R,5R)-3,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile (Example 314)

This compound was prepared in a similar manner to the procedure described for the synthesis of Example 313 using acid 69 (0.033 g, 0.063 mmol) and (2R,6R)-2,6-dimethylpiperidine hydrochloride (0.025 mg, 0.167 mmol, J&W Pharmlab) to afford 6-((Z)-2-(3-((1S,5S,6S)-3-amino-1-((3R,5R)-3,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile (Example 314) (0.009 g, 27% yield). LCMS (ESI, pos.): calcd for $C_{27}H_{27}F_2N_5O_2S$: 523.2; found: 524.2 (M+1). $^1$H NMR (400 MHz, CHLOROFORM-d) δ ppm 8.83 (s, 1H), 8.02 (dd, J=8.3, 2.1 Hz, 1H), 7.85 (dd, J=7.9, 1.9 Hz, 1H), 7.67-7.74 (m, 2H), 7.26 (d, J=37.0 Hz, 1H), 7.10 (dd, J=11.7, 8.4 Hz, 1H), 4.07-4.19 (m, 2H), 3.77 (dd, J=11.5, 3.3 Hz, 2H), 3.48 (dd, J=11.5, 5.9 Hz, 2H), 2.19-2.30 (m, 1H), 1.83 (s, 3H), 1.63 (dd, J=9.9, 5.6 Hz, 1H), 1.34 (d, J=6.5 Hz, 6H), 0.79-0.87 (m, 1H). $^{19}$F NMR (376 MHz, CHLOROFORM-d) δ ppm −109.19 (br. s., 1F), −125.59 (br. s., 1F).

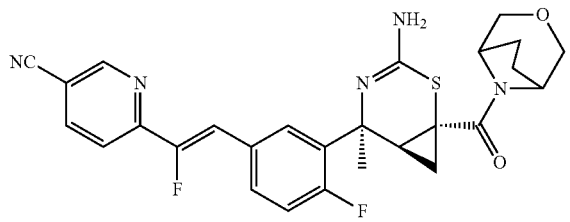 [SMILES: C[C@]1(c2cc(/C=C(\F)c3ccc(C#N)cn3)ccc2F)N=C(N)S[C@@]2(C(=O)N3C4CCC3COC4)C[C@H]21]

Example 315

Preparation of 6-((Z)-2-(3-((1S,5S,6S)-3-amino-1-(3-oxa-8-azabicyclo[3.2.1]octane-8-carbonyl)-5-methyl-2-thia-4-azabicyclo[4.1.0]hept-3-en-5-yl)-4-fluorophenyl)-1-fluorovinyl)nicotinonitrile (Example 315)

This compound was prepared in a similar manner to the procedure described for the synthesis of Example 313 using acid 69 (0.035 g, 0.066 mmol) and 3-oxa-8-azabicyclo[3.2.1]octane (0.030 mg, 0.201 mmol,) to afford 6-((Z)-2-(3-((1S,5S,6S)-3-amino-1-(3-oxa-8-azabicyclo[3.2.1]octane-8-carbonyl)-5-methyl-2-thia-4-azabicyclo[4.1.0]hept-3-en-5-yl)-4-fluorophenyl)-1-fluorovinyl)nicotinonitrile (Example 315) (0.010 g, 30% yield). LCMS (ESI, pos.): calcd for $C_{27}H_{25}F_2N_5O_2S$: 521.2; found: 522.2 (M+1). $^1$H NMR (400 MHz, CHLOROFORM-d) δ ppm 8.83 (s, 1H), 8.02 (dd, J=8.3, 2.1 Hz, 1H), 7.63-7.81 (m, 3H), 7.24 (d, J=37.6 Hz, 1H), 7.12 (dd, J=11.5, 8.6 Hz, 1H), 4.48 (br. s., 2H), 3.60-3.82 (m, 4H), 2.37 (br. s., 1H), 1.99-2.12 (m, 3H), 1.87-1.98 (m, 5H), 0.91 (t, J=6.3 Hz, 1H). $^{19}$F NMR (376 MHz, CHLOROFORM-d) δ ppm −107.96 (s, 1F), −125.34 (s, 1F).

The following compounds (Examples 316-326) were prepared using a procedure similar to that described for Example 122 with acid 19 (40 mg, 0.084 mmol), triethylamine (100 μL, 0.718 mmol), and amines (25 mg) to afford:

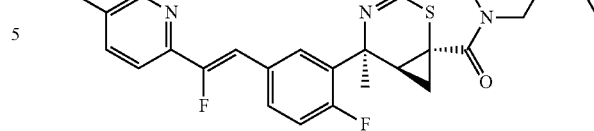

Example 316

6-((Z)-2-(3-((1S,5S,6S)-3-amino-1-((S)-2-isopropylmorpholine-4-carbonyl)-5-methyl-2-thia-4-azabicyclo[4.1.0]hept-3-en-5-yl)-4-fluorophenyl)-1-fluorovinyl)nicotinonitrile (Example 316)

Yield: 12.5 mg (28%). MS m/z=538 [M+H]$^+$. $^1$H NMR (500 MHz, DMSO-d$_6$) δ ppm 9.06 (s, 1H), 8.43 (dd, J=8.3, 1.7 Hz, 1H), 7.95 (br s, 1H), 7.84 (br d, J=8.2 Hz, 1H), 7.67-7.72 (m, 1H), 7.20-7.30 (m, 2H), 6.32 (br s, 2H), 4.14 (br d, J=12.9 Hz, 1H), 4.05 (br d, J=12.7 Hz, 1H), 3.91 (br s, 1H), 3.02 (br s, 2H), 2.10 (br t, J=8.6 Hz, 1H), 1.59-1.74 (m, 5H), 1.34 (br s, 1H), 0.89 (br dd, J=13.9, 6.7 Hz, 7H), 0.67 (br s, 1H).

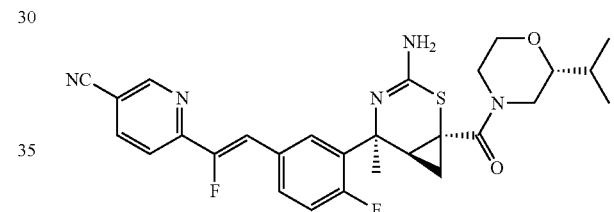

Example 317

6-((Z)-2-(3-((1S,5S,6S)-3-amino-1-((R)-2-isopropylmorpholine-4-carbonyl)-5-methyl-2-thia-4-azabicyclo[4.1.0]hept-3-en-5-yl)-4-fluorophenyl)-1-fluorovinyl)nicotinonitrile (Example 317)

Yield: 6.3 mg (14%). MS m/z=538 [M+H]$^+$. $^1$H NMR (500 MHz, DMSO-d$_6$) δ ppm 9.06 (s, 1H), 8.43 (dd, J=8.3, 1.8 Hz, 1H), 7.94 (br d, J=8.0 Hz, 1H), 7.84 (br d, J=8.2 Hz, 1H), 7.70 (br s, 1H), 7.20-7.34 (m, 2H), 6.33 (br s, 2H), 4.14 (br d, J=11.9 Hz, 1H), 4.03 (br d, J=12.2 Hz, 1H), 3.87 (br d, J=11.7 Hz, 1H), 3.02 (br s, 2H), 2.10 (br t, J=8.1 Hz, 1H), 1.59-1.80 (m, 5H), 1.34 (br dd, J=9.3, 5.2 Hz, 1H), 0.90 (dt, J=13.9, 7.1 Hz, 7H), 0.61-0.79 (m, 1H).

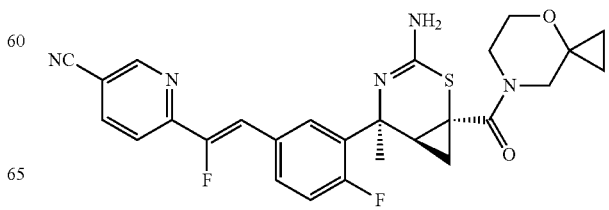

Example 318

6-((Z)-2-(3-((1S,5S,6S)-3-amino-5-methyl-1-(4-oxa-7-azaspiro[2.5]octane-7-carbonyl)-2-thia-4-azabicyclo[4.1.0]hept-3-en-5-yl)-4-fluorophenyl)-1-fluorovinyl)nicotinonitrile (Example 318)

Yield: 40.5 mg (92%). MS m/z=522 [M+H]$^+$. $^1$H NMR (500 MHz, DMSO-d$_6$) δ ppm 9.06 (s, 1H), 8.43 (dd, J=8.3, 1.7 Hz, 1H), 7.95 (br d, J=7.1 Hz, 1H), 7.83 (br d, J=8.2 Hz, 1H), 7.68 (br s, 1H), 7.19-7.30 (m, 2H), 6.32 (br s, 2H), 3.56-3.76 (m, 4H), 3.42-3.56 (m, 2H), 2.09 (br t, J=8.2 Hz, 1H), 1.67 (s, 3H), 1.27-1.33 (m, 1H), 0.65-0.76 (m, 4H), 0.61 (br s, 1H).

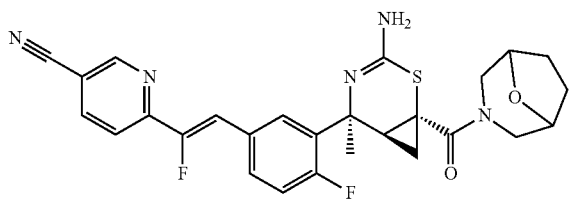 [SMILES: C[C@]1(c2cc(/C=C(\F)c3ccc(C#N)cn3)ccc2F)N=C(N)S[C@@]2(C(=O)N3CC4CCC(C3)O4)C[C@H]21]

Example 319

6-((Z)-2-(3-((1S,5S,6S)-3-amino-5-methyl-1-(4-oxa-7-azaspiro[2.5]octane-7-6-((Z)-2-(3-((1S,5S,6S)-3-amino-1-(8-oxa-3-azabicyclo[3.2.1]octane-3-carbonyl)-5-methyl-2-thia-4-azabicyclo[4.1.0]hept-3-en-5-yl)-4-fluorophenyl)-1-fluorovinyl)nicotinonitrile (Example 319)

Yield: 40.9 mg (93%). MS m/z=522 [M+H]$^+$. $^1$H NMR (500 MHz, DMSO-d$_6$) δ ppm 9.06 (s, 1H), 8.43 (dd, J=8.3, 1.8 Hz, 1H), 7.96 (br s, 1H), 7.84 (br d, J=8.2 Hz, 1H), 7.66-7.72 (m, 1H), 7.20-7.31 (m, 2H), 6.31 (br s, 2H), 4.34 (br s, 2H), 3.82 (br d, J=12.2 Hz, 2H), 2.10 (br d, J=8.1 Hz, 1H), 1.81 (br s, 3H), 1.68 (m, 6H), 1.30 (br dd, J=9.5, 5.4 Hz, 1H), 0.69 (br t, J=6.2 Hz, 1H).

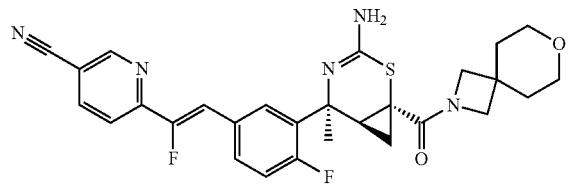 [SMILES: C[C@]1(c2cc(/C=C(\F)c3ccc(C#N)cn3)ccc2F)N=C(N)S[C@@]2(C(=O)N3CC4(CCOCC4)C3)C[C@H]21]

Example 320

6-((Z)-2-(3-((1S,5S,6S)-3-amino-5-methyl-1-(7-oxa-2-azaspiro[3.5]nonane-2-carbonyl)-2-thia-4-azabicyclo[4.1.0]hept-3-en-5-yl)-4-fluorophenyl)-1-fluorovinyl)nicotinonitrile (Example 320)

Yield: 7.4 mg (16%). MS m/z=536 [M+H]$^+$. $^1$H NMR (500 MHz, DMSO-d$_6$) δ ppm 9.06 (s, 1H), 8.43 (dd, J=8.2, 1.8 Hz, 1H), 7.96 (br d, J=6.4 Hz, 1H), 7.84 (br d, J=8.1 Hz, 1H), 7.70 (br s, 1H), 7.18-7.31 (m, 2H), 6.29 (br s, 2H), 4.08 (br d, J=14.4 Hz, 2H), 3.65 (br s, 2H), 3.46-3.55 (m, 4H), 2.13 (brt, J=8.1 Hz, 1H), 1.64-1.74 (m, 7H), 1.37 (br dd, J=9.4, 5.1 Hz, 1H), 0.64 (br t, J=5.9 Hz, 1H).

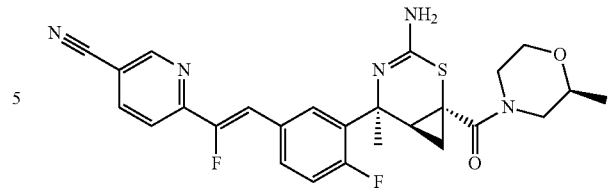

Example 321

6-((Z)-2-(3-((1S,5S,6S)-3-amino-5-methyl-1-((S)-2-methylmorpholine-4-carbonyl)-2-thia-4-azabicyclo[4.1.0]hept-3-en-5-yl)-4-fluorophenyl)-1-fluorovinyl)nicotinonitrile (Example 321)

Yield: 17 mg (39%). MS m/z=510 [M+H]. $^1$H NMR (500 MHz, DMSO-d$_6$) δ ppm 9.06 (s, 1H), 8.43 (dd, J=8.3, 1.8 Hz, 1H), 7.95 (br s, 1H), 7.84 (br d, J=7.9 Hz, 1H), 7.69 (br s, 1H), 7.20-7.30 (m, 2H), 6.33 (br s, 2H), 4.05 (br t, J=12.3 Hz, 2H), 3.84 (br s, 1H), 3.36-3.57 (m, 4H), 2.10 (br t, J=8.1 Hz, 1H), 1.68 (s, 3H), 1.30-1.37 (m, 1H), 1.09 (br d, J=6.2 Hz, 3H), 0.72 (br d, J=6.0 Hz, 1H).

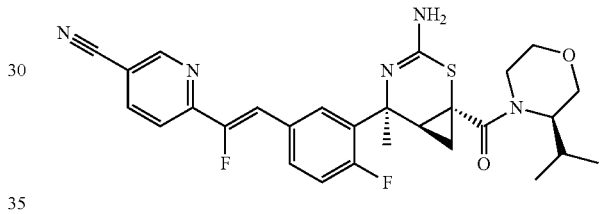

Example 322

6-((Z)-2-(3-((1S,5S,6S)-3-amino-1-((R)-3-isopropylmorpholine-4-carbonyl)-5-methyl-2-thia-4-azabicyclo[4.1.0]hept-3-en-5-yl)-4-fluorophenyl)-1-fluorovinyl)nicotinonitrile (Example 322)

Yield: 3.6 mg (8%). MS m/z=538 [M+H]$^+$.

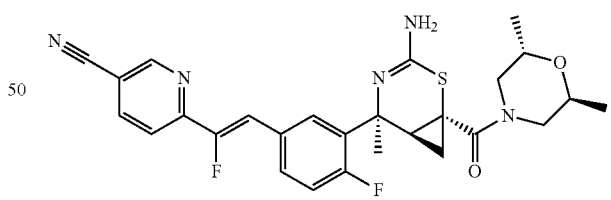

Example 323

6-((Z)-2-(3-((1S,5S,6S)-3-amino-1-((2S,6S)-2,6-dimethylmorpholine-4-carbonyl)-5-methyl-2-thia-4-azabicyclo[4.1.0]hept-3-en-5-yl)-4-fluorophenyl)-1-fluorovinyl)nicotinonitrile (Example 323)

Yield: 6.2 mg (14%). MS m/z=524 [M+H]$^+$. $^1$H NMR (500 MHz, DMSO-d$_6$) δ ppm 9.06 (s, 1H), 8.43 (dd, J=8.2, 1.6 Hz, 1H), 7.88-7.97 (m, 1H), 7.84 (br d, J=8.4 Hz, 1H), 7.69 (br s, 1H), 7.17-7.31 (m, 2H), 6.36 (s, 1H), 6.33 (br s, 1H), 3.86-4.02 (m, 2H), 3.45-3.72 (m, 2H), 3.25 (br s, 2H), 2.04-2.14 (m, 1H), 1.69 (br d, J=6.6 Hz, 3H), 1.35 (br dd, J=9.3, 5.3 Hz, 0.5H), 1.28 (br dd, J=9.8, 5.5 Hz, 0.5H), 1.10 (br d, J=6.3 Hz, 6H), 0.75 (br t, J=6.2 Hz, 0.5H), 0.67 (br t, J=6.1 Hz, 0.5H).

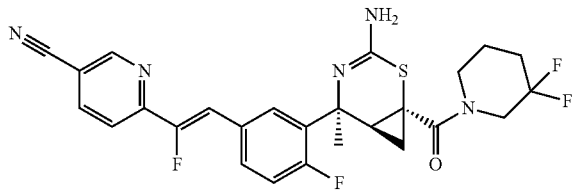 [SMILES: C[C@]1(c2cc(/C=C(\F)c3ccc(C#N)cn3)ccc2F)N=C(N)S[C@@]2(C(=O)N3CCCC(F)(F)C3)C[C@H]21]

Example 324

6-((Z)-2-(3-((1S,5S,6S)-3-amino-1-(3,3-difluoropiperidine-1-carbonyl)-5-methyl-2-thia-4-azabicyclo[4.1.0]hept-3-en-5-yl)-4-fluorophenyl)-1-fluorovinyl)nicotinonitrile (Example 324)

Yield: 6.6 mg (15%). MS m/z=530 [M+H]$^+$. $^1$H NMR (500 MHz, DMSO-d$_6$) δ ppm 9.07 (s, 1H), 8.43 (dd, J=8.3, 1.8 Hz, 1H), 7.97 (br d, J=6.1 Hz, 1H), 7.84 (br d, J=8.2 Hz, 1H), 7.70 (br s, 1H), 7.21-7.34 (m, 2H), 6.35 (s, 2H), 3.72-3.94 (m, 2H), 3.60 (br s, 2H), 2.01-2.16 (m, 3H), 1.68 (s, 5H), 1.30 (br dd, J=9.5, 5.5 Hz, 1H), 0.74 (br t, J=6.3 Hz, 1H).

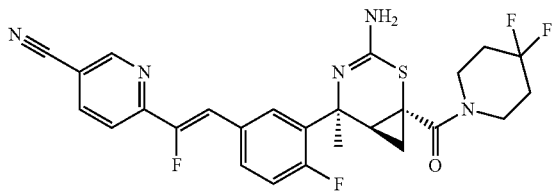 [SMILES: C[C@]1(c2cc(/C=C(\F)c3ccc(C#N)cn3)ccc2F)N=C(N)S[C@@]2(C(=O)N3CCC(F)(F)CC3)C[C@H]21]

Example 325

6-((Z)-2-(3-((1S,5S,6S)-3-amino-1-(4,4-difluoropiperidine-1-carbonyl)-5-methyl-2-thia-4-azabicyclo[4.1.0]hept-3-en-5-yl)-4-fluorophenyl)-1-fluorovinyl)nicotinonitrile (Example 325)

Yield: 7.9 mg (17%). MS m/z=530 [M+H]$^+$. $^1$H NMR (500 MHz, DMSO-d$_6$) δ ppm 9.07 (s, 1H), 8.43 (dd, J=8.2, 1.6 Hz, 1H), 7.96 (br d, J=6.2 Hz, 1H), 7.84 (br d, J=8.2 Hz, 1H), 7.70 (br s, 1H), 7.19-7.32 (m, 2H), 6.33 (s, 2H), 3.57-3.75 (m, 4H), 2.10-2.20 (m, 1H), 1.93-2.09 (m, 4H), 1.68 (s, 3H), 1.40 (br dd, J=9.3, 5.4 Hz, 1H), 0.70 (br t, J=6.2 Hz, 1H).

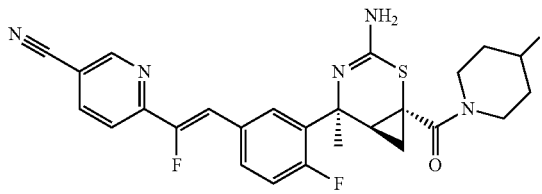

Example 326

6-((Z)-2-(3-((1S,5S,6S)-3-amino-1-(4-fluoropiperidine-1-carbonyl)-5-methyl-2-thia-4-azabicyclo[4.1.0]hept-3-en-5-yl)-4-fluorophenyl)-1-fluorovinyl)nicotinonitrile (Example 326)

Yield: 6.1 mg (14%). MS m/z=512 [M+H]$^+$. $^1$H NMR (500 MHz, DMSO-d$_6$) δ ppm 9.06 (s, 1H), 8.43 (dd, J=8.3, 1.7 Hz, 1H), 7.97 (br d, J=6.0 Hz, 1H), 7.84 (br d, J=8.2 Hz, 1H), 7.70 (br s, 1H), 7.20-7.33 (m, 2H), 6.31 (br s, 2H), 4.93 (br s, 0.5H), 4.84 (br s, 0.5H), 3.49-3.70 (m, 4H), 2.12 (br t, J=8.3 Hz, 1H), 1.82-2.02 (m, 2H), 1.68 (s, 5H), 1.33 (br dd, J=9.4, 5.4 Hz, 1H), 0.70 (br t, J=6.2 Hz, 1H).

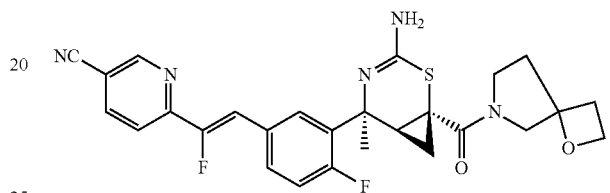

Example 327

Preparation of 6-((Z)-2-(3-((1S,5S,6S)-3-amino-5-methyl-1-(1-oxa-6-azaspiro[3.4]octane-6-carbonyl)-2-thia-4-azabicyclo[4.1.0]hept-3-en-5-yl)-4-fluorophenyl)-1-fluorovinyl)nicotinonitrile (Example 327)

Using a similar procedure to that described for 122, acid 19 (0.050 g, 0.117 mmol), 1-propanephosphonic acid cyclic anhydride (50% in EtOAc) (400 μL, 0.629 mmol), trimethylamine (100 uL, 0.719 mmol), and 1-oxa-6-azaspiro[3.4]octane hemioxalate (0.034 g, 0.167 mmol, Advanced Chemblocks Inc.) were allowed to react to afford 6-((Z)-2-(3-((1S,5S,6S)-3-amino-5-methyl-1-(1-oxa-6-azaspiro[3.4]octane-6-carbonyl)-2-thia-4-azabicyclo[4.1.0]hept-3-en-5-yl)-4-fluorophenyl)-1-fluorovinyl)nicotinonitrile (Example 327) (16 mg, 25% yield). LCMS (ESI, pos.): calcd for C$_{27}$H$_{25}$F$_2$N$_5$O$_2$S: 521.2; found: 522.2 (M+1). $^1$H NMR (400 MHz, CHLOROFORM-d) δ ppm 8.82 (s, 1H), 8.01 (dd, J=8.3, 2.1 Hz, 1H), 7.75 (br. s., 1H), 7.68 (d, J=8.0 Hz, 2H), 7.24 (d, J=35.4 Hz, 1H), 7.09 (dd, J=11.5, 8.6 Hz, 1H), 4.48-4.59 (m, 2H), 3.45-4.13 (m, 4H), 2.60-2.83 (m, 2H), 1.80-2.52 (m, 6H), 1.34-1.60 (m, 1H), 0.73-0.95 (m, 1H). $^{19}$F NMR (376 MHz, CHLOROFORM-d) δ ppm −107.98 (s, 0.5F), −107.92 (s, 1F), −125.75 (br. s., 1F).

The following compounds (Examples 328-336) were prepared using a procedure similar to that described for Example 122 with acid 19 (40 mg, 0.076 mmol), triethylamine (50 μL, 0.311 mmol), and amines (25 mg) to afford:

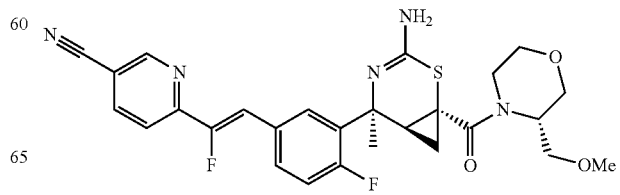

Example 328

6-((Z)-2-(3-((1S,5S,6S)-3-amino-1-((S)-3-(methoxymethyl)morpholine-4-carbonyl)-5-methyl-2-thia-4-azabicyclo[4.1.0]hept-3-en-5-yl)-4-fluorophenyl)-1-fluorovinyl)nicotinonitrile (Example 328)

Yield: 16 mg (39%). LCMS (ESI, pos.): calcd for $C_{27}H_{27}F_2N_5O_3S$: 539.2; found: 540.2 (M+1). $^1$H NMR (400 MHz, CHLOROFORM-d) δ ppm 8.82 (s, 1H), 8.01 (d, J=7.4 Hz, 1H), 7.25 (d, J=39.1 Hz, 1H), 7.60-7.74 (m, 2H), 7.25 (d, J=39.1 Hz, 1H), 7.10 (dd, J=11.3, 8.6 Hz, 1H), 3.85-4.66 (m, 5H), 3.43-3.73 (m, 4H), 3.35 (br. s., 3H), 2.28-2.48 (m, 1H), 1.87 (br. s., 3H), 1.48 (br. s., 1H), 0.94 (br. s., 1H).

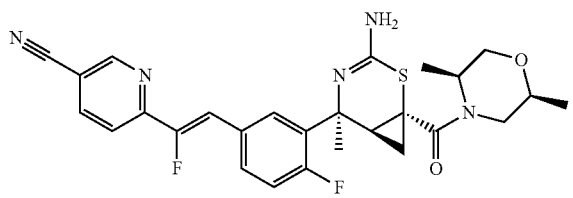 [SMILES: C[C@H]1CN(C(=O)[C@]23C[C@H]2[C@@](C)(c2cc(/C=C(\F)c4ccc(C#N)cn4)ccc2F)N=C(N)S3)[C@@H](C)CO1]

Example 329

6-((Z)-2-(3-((1S,5S,6S)-3-amino-1-((2S,5S)-2,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile (Example 329)

Yield: 16 mg (39%). LCMS (ESI, pos.): calcd for $C_{27}H_{27}F_2N_5O_2S$: 523.2; found: 524.2 (M+1). $^1$H NMR (400 MHz, CHLOROFORM-d) δ ppm 8.82 (s, 1H), 8.01 (br d, J=6.3 Hz, 1H), 7.68 (br dd, J=8.3, 4.0 Hz, 3H), 7.16-7.36 (m, 1H), 7.10 (br dd, J=11.2, 8.5 Hz, 1H), 3.82-4.55 (m, 2H), 2.82-3.76 (m, 4H), 2.19-2.74 (m, 2H), 1.78-2.04 (m, 3H), 0.76-1.53 (m, 7H). $^{19}$F NMR (376 MHz, CHLOROFORM-d) δ ppm -108.12 (br s, 1F), -125.57 (br s, 1F).

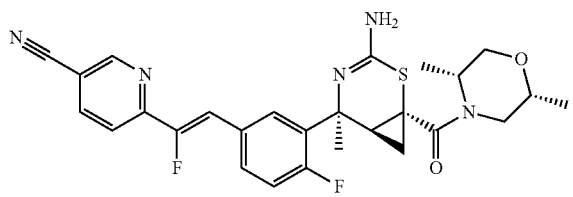 [SMILES: C[C@@H]1CN(C(=O)[C@]23C[C@H]2[C@@](C)(c2cc(/C=C(\F)c4ccc(C#N)cn4)ccc2F)N=C(N)S3)[C@H](C)CO1]

Example 330

6-((Z)-2-(3-((1S,5S,6S)-3-amino-1-((2R,5R)-2,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile (Example 330)

Yield: 19 mg (49%). LCMS (ESI, pos.): calcd for $C_{27}H_{27}F_2N_5O_2S$: 523.2; found: 524.2 (M+1). $^1$H NMR (400 MHz, CHLOROFORM-d) δ ppm 8.82 (s, 1H), 8.01 (dd, J=8.3, 2.1 Hz, 1H), 7.79 (br d, J=7.2 Hz, 1H), 7.65-7.74 (m, 2H), 7.26 (d, J=39.3 Hz, 1H), 7.10 (dd, J=11.7, 8.4 Hz, 1H), 4.41 (br s, 1H), 3.83-4.25 (m, 1H), 2.62-3.76 (m, 4H), 2.27-2.61 (m, 1H), 1.87 (s, 3H), 1.23 (br d, J=5.9 Hz, 7H), 0.90 (t, J=6.4 Hz, 1H). $^{19}$F NMR (376 MHz, CHLOROFORM-d) δ ppm -108.74--107.91 (m, 1F), -125.62 (br s, 1F).

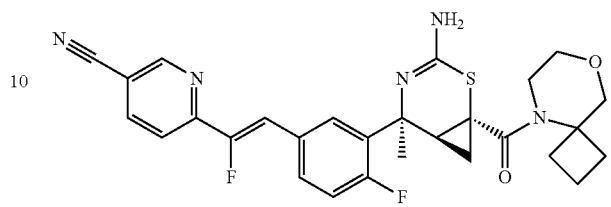

Example 331

6-((Z)-2-(3-((1S,5S,6S)-3-amino-5-methyl-1-(8-oxa-5-azaspiro[3.5]nonane-5-carbonyl)-2-thia-4-azabicyclo[4.1.0]hept-3-en-5-yl)-4-fluorophenyl)-1-fluorovinyl)nicotinonitrile (Example 331)

Yield: 13 mg (32%). LCMS (ESI, pos.): calcd for $C_{28}H_{27}F_2N_5O_2S$: 535.2; found: 536.2 (M+1). $^1$H NMR (400 MHz, CHLOROFORM-d) δ ppm 8.82 (s, 1H), 8.01 (dd, J=8.3, 2.1 Hz, 1H), 7.83 (br d, J=7.8 Hz, 1H), 7.69 (br d, J=7.0 Hz, 2H), 7.26 (d, J=38.9 Hz, 1H), 7.10 (dd, J=11.6, 8.5 Hz, 1H), 3.51-3.77 (m, 6H), 2.17-2.44 (m, 5H), 1.83 (s, 4H), 1.65-1.75 (m, 1H), 1.39 (br dd, J=9.7, 5.8 Hz, 1H), 0.88 (t, J=6.3 Hz, 1H). $^{19}$F NMR (376 MHz, CHLOROFORM-d) δ ppm -108.50 (br s, 1F), -125.66 (br s, 1F).

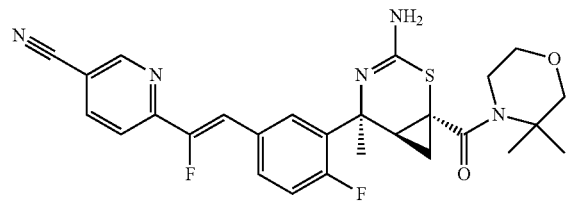 [SMILES: CC1(C)COCCN1C(=O)[C@]12C[C@H]1[C@@](C)(c1cc(/C=C(\F)c3ccc(C#N)cn3)ccc1F)N=C(N)S2]

Example 332

6-((Z)-2-(3-((1S,5S,6S)-3-amino-1-(3,3-dimethylmorpholine-4-carbonyl)-5-methyl-2-thia-4-azabicyclo[4.1.0]hept-3-en-5-yl)-4-fluorophenyl)-1-fluorovinyl)nicotinonitrile (Example 332)

Yield: 7.2 mg (18%). LCMS (ESI, pos.): calcd for $C_{27}H_{27}F_2N_5O_2S$: 523.2; found: 524.2 (M+1). $^1$H NMR (400 MHz, CHLOROFORM-d) δ ppm 8.82 (s, 1H), 8.01 (dd, J=8.3, 2.1 Hz, 1H), 7.85 (dd, J=7.7, 1.9 Hz, 1H), 7.69 (br d, J=7.4 Hz, 2H), 7.26 (d, J=39.1 Hz, 1H), 7.10 (dd, J=11.6, 8.5 Hz, 1H), 3.71-3.87 (m, 3H), 3.50-3.62 (m, 1H), 3.28-3.47 (m, 2H), 2.37 (t, J=8.6 Hz, 1H), 1.83 (s, 3H), 1.42 (s, 3H), 1.36 (s, 3H), 1.31 (dd, J=9.7, 5.6 Hz, 1H), 0.81-0.91 (m, 1H). $^{19}$F NMR (376 MHz, CHLOROFORM-d) δ ppm -108.48 (s, 1F), -125.76 (s, 1F).

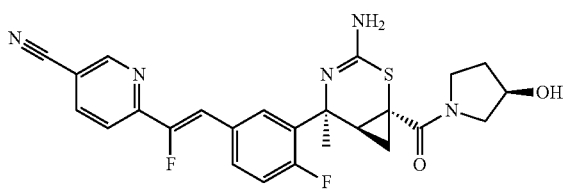 [SMILES: C[C@]1(c2cc(/C=C(\F)c3ccc(C#N)cn3)ccc2F)N=C(N)S[C@@]2(C(=O)N3CC[C@@H](O)C3)C[C@H]21]

Example 333

6-((Z)-2-(3-((1S,5S,6S)-3-amino-1-((R)-3-hydroxypyrrolidine-1-carbonyl)-5-methyl-2-thia-4-azabicyclo[4.1.0]hept-3-en-5-yl)-4-fluorophenyl)-1-fluorovinyl)nicotinonitrile (Example 333)

Yield: 6.1 mg (15%). LCMS (ESI, pos.): calcd for $C_{25}H_{23}F_2N_5O_2S$: 495.2; found: 496.2 (M+1). $^1$H NMR (400 MHz, CHLOROFORM-d) δ ppm 8.82 (br. s., 1H), 8.01 (d, J=7.4 Hz, 1H), 7.61-7.77 (m, 3H), 7.15-7.27 (m, 1H), 7.02-7.14 (m, 1H), 4.53 (br. s., 1H), 3.44-4.05 (m, 4H), 2.19 (br. s., 1H), 1.80-2.11 (m, 5H), 1.55 (br. s., 1H), 0.79 (br. s., 1H). $^{19}$F NMR (376 MHz, CHLOROFORM-d) δ ppm −107.89 (s, 1F), −125.67 (s, 1F).

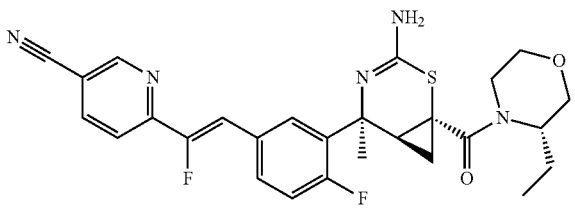 [SMILES: CC[C@H]1COCCN1C(=O)[C@]12C[C@H]1[C@@](C)(c1cc(/C=C(\F)c3ccc(C#N)cn3)ccc1F)N=C(N)S2]

Example 334

6-((Z)-2-(3-((1S,5S,6S)-3-amino-1-((S)-3-ethylmorpholine-4-carbonyl)-5-methyl-2-thia-4-azabicyclo[4.1.0]hept-3-en-5-yl)-4-fluorophenyl)-1-fluorovinyl)nicotinonitrile (Example 334)

Yield: 21.6 mg (54%). LCMS (ESI, pos.): calcd for $C_{27}H_{27}F_2N_5O_2S$: 523.2; found: 524.2 (M+1). 1H NMR (400 MHz, CHLOROFORM-d) δ ppm 8.82 (d, J=1.0 Hz, 1H), 8.01 (dd, J=8.3, 2.1 Hz, 1H), 7.80 (br d, J=7.0 Hz, 1H), 7.63-7.73 (m, 2H), 7.26 (d, J=41.5 Hz, 1H), 7.10 (dd, J=11.6, 8.5 Hz, 1H), 3.94-4.37 (m, 2H), 3.75-3.92 (m, 2H), 3.33-3.65 (m, 3H), 2.35 (br t, J=8.5 Hz, 1H), 1.66-1.96 (m, 2H), 1.86 (s, 3H), 1.36 (dd, J=9.7, 5.6 Hz, 1H), 0.93 (t, J=7.5 Hz, 4H). $^{19}$F NMR (376 MHz, CHLOROFORM-d) δ ppm −108.27 (br dd, J=21.1, 4.2 Hz, 1F), −125.73 (s, 1F).

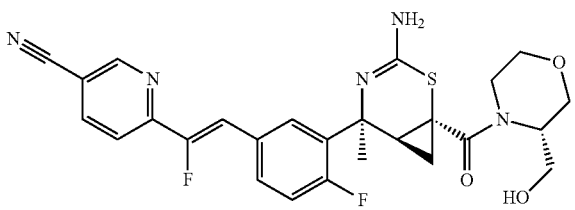 [SMILES: C[C@]1(c2cc(/C=C(\F)c3ccc(C#N)cn3)ccc2F)N=C(N)S[C@@]2(C(=O)N3CCOC[C@@H]3CO)C[C@H]21]

Example 335

6-((Z)-2-(3-((1S,5S,6S)-3-amino-1-((S)-3-ethylmorpholine-4-carbonyl)-5-methyl-2-thia-4-azabicyclo[4.1.0]hept-3-en-5-yl)-4-fluorophenyl)-1-fluorovinyl)nicotinonitrile (Example 335)

Yield: 2.3 mg (6.5%). LCMS (ESI, pos.): calcd for $C_{28}H_{29}F_2N_5O_3S$: 525.2; found: 526.2 (M+1). 1H NMR (400 MHz, CHLOROFORM-d) δ 8.82 (s, 1H), 8.02 (dd, J=1.66, 8.12 Hz, 1H), 7.62-7.80 (m, 3H), 7.18 (s, 1H), 7.05-7.14 (m, 1H), 3.76-4.52 (m, 6H), 3.39-3.69 (m, 3H), 2.26-2.32 (m, 1H), 1.88 (s, 3H), 1.41-1.61 (m, 1H), 0.86-0.93 (m, 1H).

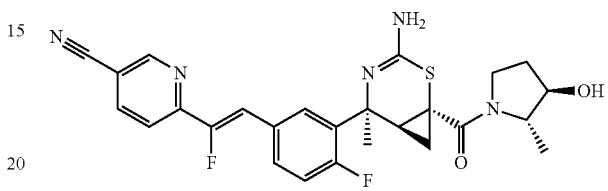

Example 336

6-((Z)-2-(3-((1S,5S,6S)-3-amino-1-((2S,3R)-3-hydroxy-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile (Example 336)

Yield: 3.3 mg (3.8%). LCMS (ESI, pos.): calcd for $C_{26}H_{25}F_2N_5O_2S$: 509.2; found: 510.2 (M+1). $^1$H NMR (400 MHz, CHLOROFORM-d) δ ppm 8.82 (s, 1H), 8.01 (d, J=6.7 Hz, 1H), 7.63-7.77 (m, 3H), 7.15-7.31 (d, J=41.5 Hz, 1H), 7.10 (dd, J=11.4, 8.5 Hz, 1H), 3.69-4.21 (m, 4H), 2.30 (br. s., 1H), 2.15-2.24 (m, 1H), 1.97 (br. s., 2H), 1.91 (br. s., 3H), 1.48 (br. s., 1H), 1.18 (d, J=6.5 Hz, 3H), 0.85 (br. s., 1H). $^{19}$F NMR (376 MHz, CHLOROFORM-d) δ ppm −107.78 (br. s., 1F), −125.60 (br. s., 1F).

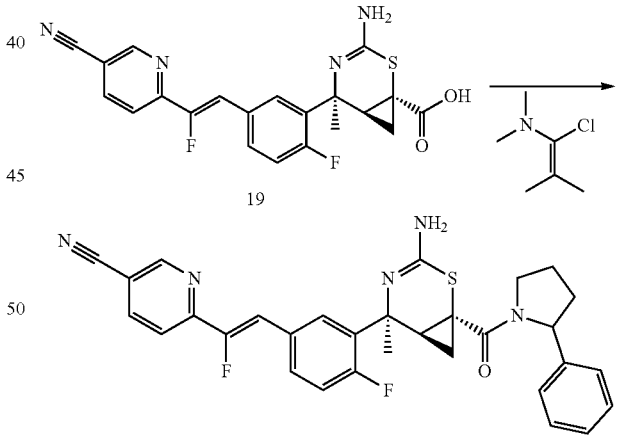

Example 337

Preparation of 6-((Z)-2-(3-((1S,5S,6S)-3-amino-5-methyl-1-(2-phenylpyrrolidine-1-carbonyl)-2-thia-4-azabicyclo[4.1.0]hept-3-en-5-yl)-4-fluorophenyl)-1-fluorovinyl)nicotinonitrile (Example 337)

A solution of 1-chloro-N,N,2-trimethylpropenylamine (50 μL, 0.374 mmol) in MeCN (0.5 mL) was added to a slurry of 19 (37 mg, 0.087 mmol) in MeCN (0.5 mL) at room temperature. The resulting mixture was stirred at room temperature for 30 minutes. Additional 1-chloro-N,N,2- trimethylpropenylamine (50 µL, 0.37 mmol) was added. After 1 hour, 2-phenylpyrrolidine (35 mg, 0.24 mmol) and triethylamine (35 mg, 0.72 mmol) was added. After 20 minutes of reaction, MeOH (0.5 mL) was added and the resulting solution was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 10% to 95% over 15 minutes. The product fractions were passed through a Phenomenex Strata-X-C 33 u cation exchange resin (1 g/12 mL). The resin was washed with MeOH (4×1 mL). The resin was then eluted with NH$_3$ in MeOH (2N, total 4×1 mL) to release the free base product. The product fractions were concentrated and the residue was suspended in MeCN-water (2-1 mL). The suspension was frozen at −78° C. and was lyophilized overnight to give 6-((Z)-2-(3-((1S,5S,6S)-3-amino-5-methyl-1-(2-phenylpyrrolidine-1-carbonyl)-2-thia-4-azabicyclo[4.1.0]hept-3-en-5-yl)-4-fluorophenyl)-1-fluorovinyl)nicotinonitrile (Example 337) (16.3 mg, 34% yield) as a white sponge. LCMS (ESI, pos.): calcd for C$_{31}$H$_{27}$F$_2$N$_5$OS: 555.2; found: 556.2 (M+1). $^1$H NMR (400 MHz, CHLOROFORM-d) δ ppm 8.82 (br. s., 1H), 7.99 (br. s., 1H), 7.53-7.89 (m, 3H), 6.87-7.38 (m, 7H), 4.36-5.65 (m, 1H), 3.61-4.10 (m, 2H), 2.33 (br. s., 1H), 1.76-2.19 (m, 7H), 1.08-1.38 (m, 1H), 0.62-1.00 (m, 1H). $^{19}$F NMR (376 MHz, CHLOROFORM-d) δ ppm −107.91, −108.05 (2s, 1F), −125.74, −125.84 (2s, 1F).

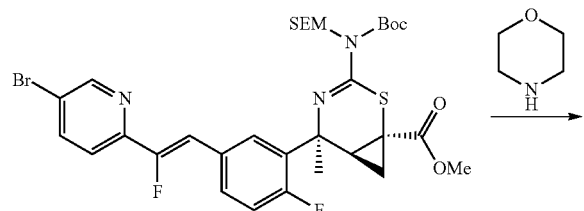

Example 105

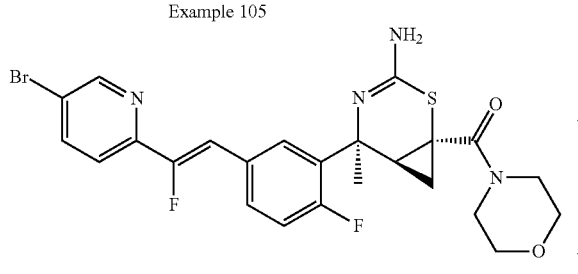

Example 338

Preparation of ((1S,5S,6S)-3-amino-5-(5-((Z)-2-(5-bromopyridin-2-yl)-2-fluorovinyl)-2-fluorophenyl)-5-methyl-2-thia-4-azabicyclo[4.1.0]hept-3-en-1-yl)(morpholino)methanone (Example 338)

A mixture of (1S,5S,6S)-methyl 5-(5-((Z)-2-(5-bromopyridin-2-yl)-2-fluorovinyl)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (Example 105) (1.9 g, 2.6 mmol) and lithium hydroxide monohydrate (0.220 g, 5.24 mmol) in THF (10 mL) and water (4 mL) was stirred at room temperature for 1.5 hours. The mixture was neutralized with HCl (1N, 5.2 mL) and was diluted with EtOAc (30 mL). NaCl was added to saturate the aqueous layer and the layers were separated. The organic layer was dried over Na$_2$SO$_4$, filtered, and concentrated to give (1S,5S,6S)-3-amino-5-(5-((Z)-2-(5-bromopyridin-2-yl)-2-fluorovinyl)-2-fluorophenyl)-5-methyl-2-thia-4-azabicyclo[4.1.0]hept-3-ene-1-carboxylic acid as a yellow foam. The crude acid was dissolved in EtOAc (10 mL) and to this was added 1-propanephosphonic acid cyclic anhydride, 50 wt. % solution in DMF (3.5 mL, 5.5 mmol) followed by morpholine (0.50 mL, 5.7 mmol). The solution was heated at 50° C. for 2 hours. MeOH (5 mL) was added. The mixture was concentrated to give the protected amide tert-butyl ((1S,5S,6S)-5-(5-((Z)-2-(5-bromopyridin-2-yl)-2-fluorovinyl)-2-fluorophenyl)-5-methyl-1-(morpholine-4-carbonyl)-2-thia-4-azabicyclo[4.1.0]hept-3-en-3-yl)((2-(trimethylsilyl)ethoxy)methyl)carbamate. The material thus obtained was dissolved in dioxane (15 mL) and to this solution was added p-toluenesulfonic acid monohydrate (1.0 g, 5.3 mmol). The mixture was heated at 80° C. for 2 hours. More TsOH (0.5 g) was added and the heating was continued for a total of 5 hours. Water (30 mL) and EtOAc (50 mL) were added and the pH of the aqueous layer was adjusted to ~12 with solid Na$_2$CO$_3$. The organic layer was washed with water (10 mL), brine (10 mL), dried over Na$_2$SO$_4$, filtered, and concentrated. The residue was purified by chromatography on silica using EtOAc-EtOH (3:1) in heptane (10-50%) as eluent to give ((1S,5S,6S)-3-amino-5-(5-((Z)-2-(5-bromopyridin-2-yl)-2-fluorovinyl)-2-fluorophenyl)-5-methyl-2-thia-4-azabicyclo[4.1.0]hept-3-en-1-yl)(morpholino)methanone (Example 338) (1.1 g, 2.002 mmol, 76% yield) as a white foam. LCMS (ESI, pos.): calcd for C$_{24}$H$_{23}$BrF$_2$N$_4$O$_2$S: 548.1/550.1; found: 549.0/551.0 (M+1). $^1$H NMR (400 MHz, CHLOROFORM-d) δ 8.64 (d, J=2.15 Hz, 1H), 7.88 (dd, J=2.35, 8.41 Hz, 1H), 7.77 (dd, J=2.15, 7.82 Hz, 1H), 7.66 (ddd, J=2.25, 4.60, 8.41 Hz, 1H), 7.50 (dd, J=1.08, 8.51 Hz, 1H), 6.98-7.13 (m, 2H), 3.60-3.73 (m, 8H), 2.32 (dd, J=7.73, 8.71 Hz, 1H), 1.87 (s, 3H), 1.37 (dd, J=5.67, 9.78 Hz, 1H), 0.90 (t, J=6.36 Hz, 1H). $^{19}$F NMR (376 MHz, CHLOROFORM-d) δ −109.79 (br s, 1F), −124.40 (s, 1F).

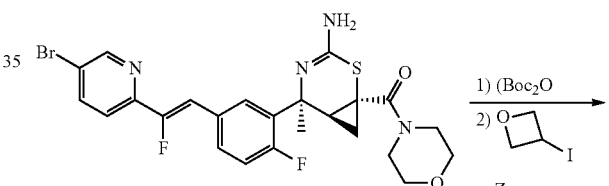

Example 338

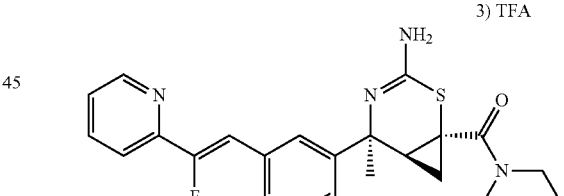

Example 339

+

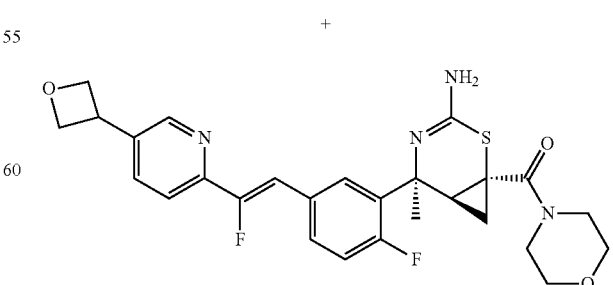

Example 340

Preparation of ((1S,5S,6S)-3-amino-5-(2-fluoro-5-((Z)-2-fluoro-2-(pyridin-2-yl)vinyl)phenyl)-5-methyl-2-thia-4-azabicyclo[4.1.0]hept-3-en-1-yl)(morpholino)methanone (Example 339) and ((1S,5S,6S)-3-amino-5-(2-fluoro-5-((Z)-2-fluoro-2-(5-(oxetan-3-yl)pyridin-2-yl)vinyl)phenyl)-5-methyl-2-thia-4-azabicyclo[4.1.0]hept-3-en-1-yl)(morpholino)methanone (Example 340)

A mixture of di-tert-butyl dicarbonate (0.337 ml, 1.466 mmol) and ((1S,5S,6S)-3-amino-5-(5-((Z)-2-(5-bromopyridin-2-yl)-2-fluorovinyl)-2-fluorophenyl)-5-methyl-2-thia-4-azabicyclo[4.1.0]hept-3-en-1-yl)(morpholino)methanone (Example 338) (0.34 g, 0.62 mmol) in the presence of 4-dimethylaminopyridine (0.002 g, 0.02 mmol) in DCM (5 mL) was stirred at 50° C. for 2 hours. The solvent was evaporated and the residue was used in the next step assuming quantitative yield. Water was degassed with a stream of $N_2$ for 1 hour prior to use. A mixture of zinc dust (250 mg, 3.82 mmol), sodium caprylate (60 mg, 0.36 mmol), sodium chloride (80 mg, 1.4 mmol), 1-octanol (160 µL, 1.02 mmol), and the Boc-protected intermediate (460 mg, 0.614 mmol) was briefly evacuated and backfilled with $N_2$ (3×). Degassed water (3 mL) was added followed by 3-bromooxetane (100 µL, 1.20 mmol), N,N,N',N'-tetra-methyl-ethylenediamine (250 µL, 1.67 mmol) and (2-dicyclohexylphosphino-2',4',6'-triisopropyl-1,1'-biphenyl)[2-(2'-amino-1,1'-biphenyl)]palladium(II) methanesulfonate (50 mg, 0.059 mmol, xPhos-G3, Strem Chemical, Inc.). The mixture was sealed and heated with stirring at 45° C. Occasional sonication was used to help mixing. After 80 hours, the mixture was shaken with EtOAc (10 mL) and filtered through a pad of Celite. The residue was washed with HCl (0.5N, 5 mL), EtOAc (3×10 mL). The organic layer was washed with brine (5 mL), dried over $Na_2SO_4$, filtered, and concentrated to give the crude product mixture as orange oil. The residue thus obtained was dissolved in DCM (5 mL) and was treated with trifluoroacetic acid (500 µL, 6.73 mmol). The solution was stirred at room temperature for 20 minutes. Additional trifluoroacetic acid (500 µL, 6.73 mmol) was added. After another 20 minutes, the mixture was quenched with saturated aq. $NaHCO_3$ (20 mL) and vigorously stirred for 10 minutes. The aqueous layer was extracted with DCM (3×5 mL). The combined organic phase was dried over $Na_2SO_4$, filtered, and concentrated. The residue was purified by chromatography on silica using $NH_3$-MeOH (2N) in DCM (5-40%) as eluent. The products were further purified by reverse-phase preparative HPLC (Agilent) using a Kinetex 5 µm Evo C18 100 column (21.2×150 mm) with 0.1% TFA in CH3CN/$H_2O$, gradient 5% to 95% over 16 minutes at 35 mL/min. The product fractions were basified with $Na_2CO_3$ and concentrated to a slurry. The slurry was filtered and the resulting solid was combined with the bulky material from trituration and lyophilized to give:

Example 339

((1S,5S,6S)-3-amino-5-(2-fluoro-5-((Z)-2-fluoro-2-(pyridin-2-yl)vinyl)phenyl)-5-methyl-2-thia-4-azabicyclo[4.1.0]hept-3-en-1-yl)(morpholino)methanone. LCMS (ESI, pos.): calcd for $C_{24}H_{24}F_2N_4O_2S$: 470.2; found: 471.2 (M+1). $^1H$ NMR (400 MHz, CHLOROFORM-d) δ 8.60 (d, J=4.50 Hz, 1H), 7.71-7.80 (m, 2H), 7.64-7.70 (m, 1H), 7.61 (d, J=8.02 Hz, 1H), 7.21-7.25 (m, 1H), 6.98-7.12 (m, 2H), 3.59-3.74 (m, 8H), 2.29 (dd, J=7.92, 8.90 Hz, 1H), 1.86 (s, 3H), 1.36 (dd, J=5.77, 9.68 Hz, 1H), 0.88 (t, J=6.36 Hz, 1H). $^{19}F$ NMR (376 MHz, CHLOROFORM-d) δ −110.29 (s, 1F), −124.27 (s, 1F).

Example 340

((1S,5S,6S)-3-amino-5-(2-fluoro-5-((Z)-2-fluoro-2-(5-(oxetan-3-yl)pyridin-2-yl)vinyl)phenyl)-5-methyl-2-thia-4-azabicyclo[4.1.0]hept-3-en-1-yl)(morpholino)methanone (76 mg, 24% yield) as a white sponge. LCMS (ESI, pos.): calcd for $C_{27}H_{28}F_2N_4O_3S$: 526.2; found: 527.2 (M+1). $^1H$ NMR (400 MHz, CHLOROFORM-d) δ 8.57 (s, 1H), 7.91 (dd, J=2.15, 8.22 Hz, 1H), 7.78 (dd, J=1.96, 7.83 Hz, 1H), 7.61-7.71 (m, 2H), 7.03-7.13 (m, 1H), 6.99 (d, J=36.39 Hz, 1H), 5.14 (dd, J=6.26, 8.22 Hz, 2H), 4.76 (t, J=6.36 Hz, 2H), 4.20-4.34 (m, 1H), 3.58-3.77 (m, 8H), 2.24-2.36 (m, 1H), 1.86 (s, 3H), 1.37 (dd, J=5.67, 9.78 Hz, 1H), 0.89 (t, J=6.46 Hz, 1H). $^{19}F$ NMR (376 MHz, CHLOROFORM-d) δ −110.22 (s, 1F), −124.07 (s, 1F).

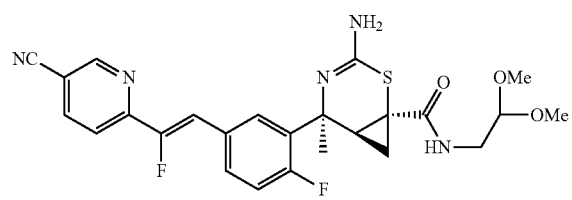 [SMILES: COC(CNC(=O)[C@]12C[C@H]1[C@@](C)(c1cc(/C=C(\F)c3ccc(C#N)cn3)ccc1F)N=C(N)S2)OC]

Example 341

(1S,5S,6S)-3-amino-5-(5-((Z)-2-(5-cyanopyridin-2-yl)-2-fluorovinyl)-2-fluorophenyl)-N-(2,2-dimethoxyethyl)-5-methyl-2-thia-4-azabicyclo[4.1.0]hept-3-ene-1-carboxamide (Example 341)

Using a similar procedure to that described for 122, acid 19 (110 mg, 0.230 mmol) and 2,2-dimethoxyethanamine (0.052 mL, 0.48 mmol) were coupled to afford (1S,5S,6S)-3-amino-5-(5-((Z)-2-(5-cyanopyridin-2-yl)-2-fluorovinyl)-2-fluorophenyl)-N-(2,2-dimethoxyethyl)-5-methyl-2-thia-4-azabicyclo[4.1.0]hept-3-ene-1-carboxamide (Example 341) (37 mg, 31% yield) as a white film. LCMS (ESI, pos.): calcd for $C_{25}H_{25}F_2N_5O_3S$: 513.2; found: 514.1 (M+1). $^1H$ NMR (400 MHz, CHLOROFORM-d) δ 8.82 (s, 1H), 8.01 (dd, J=2.05, 8.31 Hz, 1H), 7.57-7.70 (m, 3H), 7.19 (d, J=39.91 Hz, 1H), 7.09 (dd, J=8.51, 11.44 Hz, 1H), 6.76 (br t, J=5.58 Hz, 1H), 4.40 (t, J=5.28 Hz, 1H), 3.45-3.55 (m, 1H), 3.43 (s, 6H), 3.35-3.41 (m, 1H), 2.17-2.27 (m, 1H), 1.92-2.00 (m, 1H), 1.84 (s, 3H), 0.74-0.84 (m, 1H). $^{19}F$ NMR (376 MHz, CHLOROFORM-d) δ −106.88 (s, 1F), −125.64 (s, 1F).

Synthesis of Example 342

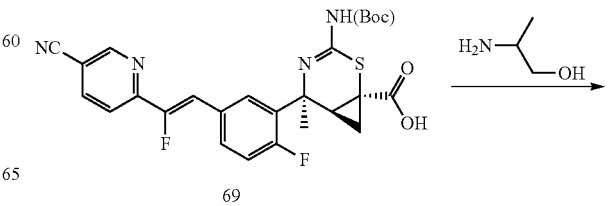

69

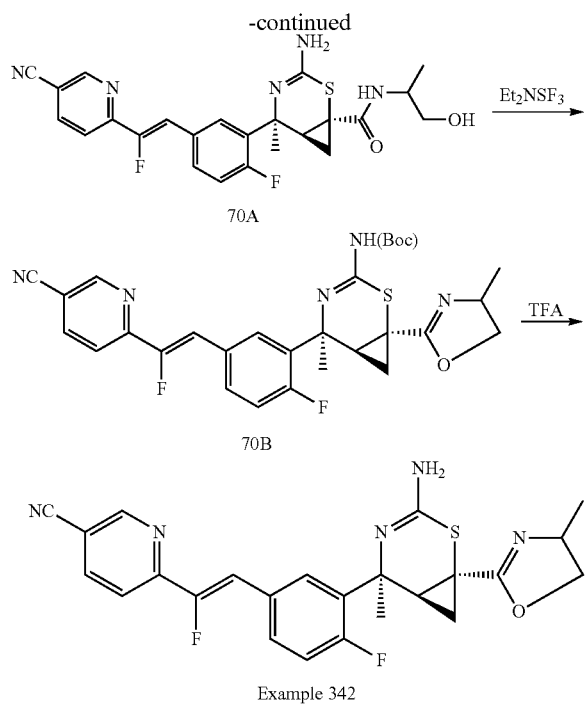

Example 342

Preparation of tert-butyl ((1S,5S,6S)-5-(5-((Z)-2-(5-cyanopyridin-2-yl)-2-fluorovinyl)-2-fluorophenyl)-1-((1-hydroxypropan-2-yl)carbamoyl)-5-methyl-2-thia-4-azabicyclo[4.1.0]hept-3-en-3-yl)carbamate (70A)

The amide coupling step was carried out in a similar manner to the procedure described for the synthesis of Example 313 using acid 69 (75 mg, 0.14 mmol) and D/L-alaninol (62.2 μL, 0.799 mmol).

Preparation of tert-butyl ((1S,5S,6S)-5-(5-(5-((Z)-2-(5-cyanopyridin-2-yl)-2-fluorovinyl)-2-fluorophenyl)-5-methyl-1-(4-methyl-4,5-dihydrooxazol-2-yl)-2-thia-4-azabicyclo[4.1.0]hept-3-en-3-yl)carbamate (70B)

The residue from the previous step was dissolved in DCM (2 mL) and was treated with diethylaminosulfur trifluoride (1M in DCM) (200 μL, 0.200 mmol). After 20 minutes, the contents were purified by chromatography on silica using EtOAc in DCM (0-50%) as eluent to give the product as a white foam. $^1$H NMR (400 MHz, CHLOROFORM-d) δ ppm 8.83 (d, J=1.8 Hz, 1H), 8.03 (dd, J=8.3, 2.1 Hz, 1H), 7.85 (br. s., 1H), 7.66-7.79 (m, 2H), 7.26 (d, J=39.3 Hz, 1H), 7.14 (dd, J=11.7, 8.6 Hz, 1H), 4.35-4.42 (m, 1H), 4.18-4.29 (m, 1H), 3.82 (dt, J=9.9, 7.9 Hz, 1H), 2.55 (q, J=7.8 Hz, 1H), 1.83 (br. s., 3H), 1.58 (d, J=9.0 Hz, 1H), 1.51 (s, 9H), 1.13-1.32 (m, 4H)

Preparation of 6-((Z)-2-(3-((1S,5S,6S)-3-amino-5-methyl-1-(4-methyl-4,5-dihydrooxazol-2-yl)-2-thia-4-azabicyclo[4.1.0]hept-3-en-5-yl)-4-fluorophenyl)-1-fluorovinyl)nicotinonitrile (Example 342)

To a solution of tert-butyl ((1S,5S,6S)-5-(5-(5-((Z)-2-(5-cyanopyridin-2-yl)-2-fluorovinyl)-2-fluorophenyl)-5-methyl-1-(4-methyl-4,5-dihydrooxazol-2-yl)-2-thia-4-azabicyclo[4.1.0]hept-3-en-3-yl)carbamate (70B) (28 mg, 0.050 mmol) in DCM (2.5 mL) was added trifluoroacetic acid (250 μL, 3.37 mmol). The yellow mixture was stirred at room temperature. After 30 min at room temperature, the mixture was diluted with DCM (5 mL) and was shaken with saturated NaHCO$_3$ (2×). The aqueous layer as extracted with DCM (2×3 mL). The combined organic phase was dried over Na$_2$SO$_4$ and concentrated. The residue was purified by chromatography on silica using NH$_3$-MeOH (1N) in DCM (1-5%) as eluent. The product fraction was concentrated and the residue was suspended in MeCN-water (1 mL each) and was lyophilized to give 6-((Z)-2-(3-((1S,5S,6S)-3-amino-5-methyl-1-(4-methyl-4,5-dihydrooxazol-2-yl)-2-thia-4-azabicyclo[4.1.0]hept-3-en-5-yl)-4-fluorophenyl)-1-fluorovinyl)nicotinonitrile (Example 342)(10 mg, 45% yield) as a white powder. Note: on LCMS the major peak was shown as the hydrolyzed amino alcohol (streaking). LCMS (ESI, pos.): calcd for C$_{24}$H$_{21}$F$_2$N$_5$OS: 465.1; found: 466.1 (M+1). $^1$H NMR (400 MHz, CHLOROFORM-d) δ ppm 8.83 (s, 1H), 7.92-8.07 (m, 2H), 7.64-7.78 (m, 2H), 7.27 (d, J=38.9 Hz, 1H), 7.10 (dd, J=11.9, 8.4 Hz, 1H), 4.33-4.49 (m, 1H), 4.17-4.31 (m, 1H), 3.75-3.89 (m, 1H), 2.41-2.54 (m, 1H), 1.77 (2xs, 3H), 1.48 (ddd, J=9.7, 5.4, 1.8 Hz, 1H), 1.23-1.35 (m, 3H), 1.03-1.12 (m, 1H).

$^{19}$F NMR (376 MHz, CHLOROFORM-d) δ ppm −109.28/−109.32 (2s, 1F), −125.77 (br. s., 1F).

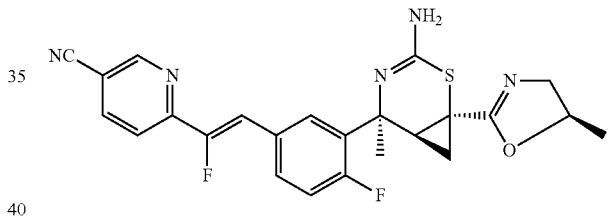

Example 343

Preparation of 6-((Z)-2-(3-((1S,5S,6S)-3-amino-5-methyl-1-((R)-5-methyl-4,5-dihydrooxazol-2-yl)-2-thia-4-azabicyclo[4.1.0]hept-3-en-5-yl)-4-fluorophenyl)-1-fluorovinyl)nicotinonitrile (Example 343)

Using a procedure similar to that described for the preparation of Example 341, acid 69 (50 mg, 0.095 mmol) and (s)-(+)-1-amino-2-propanol (30 mg, 0.40 mmol) were coupled, cyclized, and deprotected to give 6-((Z)-2-(3-((1S,5S,6S)-3-amino-5-methyl-1-((R)-5-methyl-4,5-dihydrooxazol-2-yl)-2-thia-4-azabicyclo[4.1.0]hept-3-en-5-yl)-4-fluorophenyl)-1-fluorovinyl)nicotinonitrile (Example 343) (5.3 mg, 72% yield). LCMS (ESI, pos.): calcd for C$_{24}$H$_{21}$F$_2$N$_5$OS: 465.1; found: 466.1 (M+1). $^1$H NMR (400 MHz, CHLOROFORM-d) δ 8.83 (d, J=0.98 Hz, 1H), 8.02 (dd, J=2.05, 8.31 Hz, 1H), 7.95 (br d, J=6.85 Hz, 1H), 7.66-7.75 (m, 2H), 7.26 (d, J=39.12 Hz, 1H), 7.11 (dd, J=8.51, 11.83 Hz, 1H), 4.70-4.83 (m, 1H), 4.01 (dd, J=9.29, 13.99 Hz, 1H), 3.45 (dd, J=7.34, 13.99 Hz, 1H), 2.44-2.52 (m, 1H), 1.80 (s, 3H), 1.54 (br t, J=3.52 Hz, 1H), 1.31 (d, J=6.26 Hz, 3H), 1.06-1.13 (m, 1H).

Synthesis of Example 344
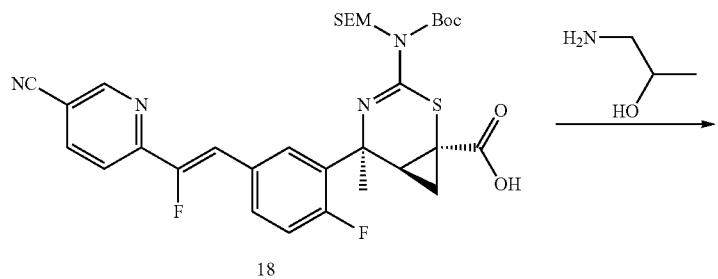
18
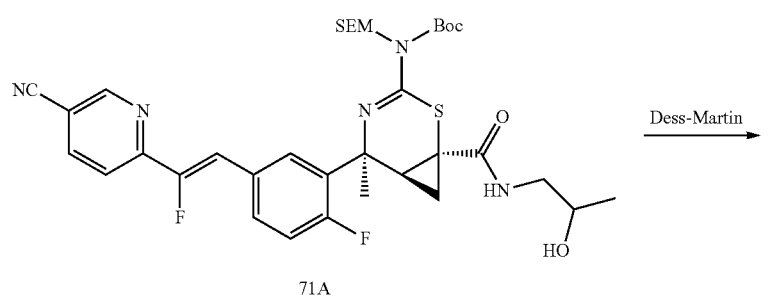
71A
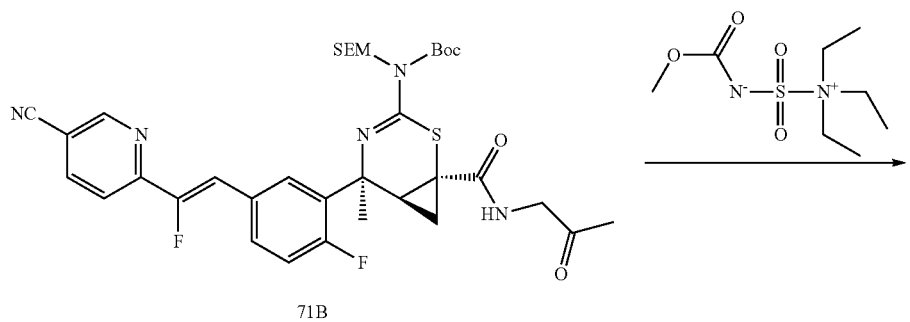
71B
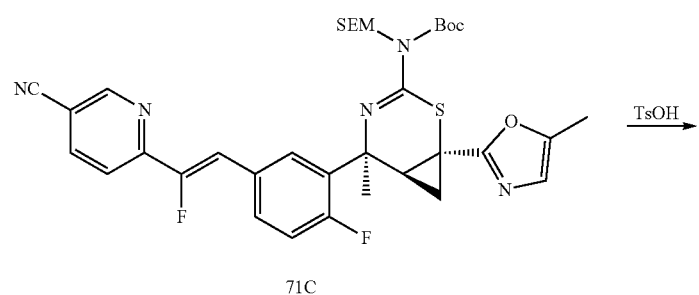
71C
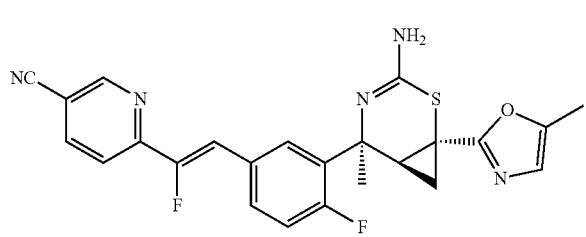
Example 344

Preparation of tert-butyl ((1S,5S,6S)-5-(5-((Z)-2-(5-cyanopyridin-2-yl)-2-fluorovinyl)-2-fluorophenyl)-1-((2-hydroxypropyl)carbamoyl)-5-methyl-2-thia-4-azabicyclo[4.1.0]hept-3-en-3-yl)((2-(trimethylsilyl)ethoxy)methyl)carbamate (71A)

To a solution of (1S,5S,6S)-3-((tert-butoxycarbonyl)((2-(trimethylsilyl)ethoxy)methyl)amino)-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxylic acid (18) (190 mg, 0.289 mmol) in MeCN (1.5 mL) was added 1-chloro-N,N,2-trimethyl-1-propenylamine (50 μL, 0.374 mmol). The resulting mixture was stirred at room temperature for 30 minutes. Triethylamine (100 μL, 0.719 mmol) and amino-2-propanol (40 mg, 0.53 mmol) were added. After 20 minutes, the mixture was purified by chromatography on silica using EtOAc in heptane (20-50%) as eluent to afford tert-butyl ((1S,5S,6S)-5-(5-((Z)-2-(5-cyanopyridin-2-yl)-2-fluorovinyl)-2-fluorophenyl)-1-((2-hydroxypropyl)carbamoyl)-5-methyl-2-thia-4-azabicyclo[4.1.0]hept-3-en-3-yl)((2-(trimethylsilyl)ethoxy)methyl)carbamate (71A) as a clear film. LCMS (ESI, pos.): calcd for $C_{35}H_{45}F_2N_5O_5SSi$: 713.3; found: 714.2 (M+1).

Preparation of tert-butyl ((1S,5S,6S)-5-(5-((Z)-2-(5-cyanopyridin-2-yl)-2-fluorovinyl)-2-fluorophenyl)-5-methyl-1-((2-oxopropyl)carbamoyl)-2-thia-4-azabicyclo[4.1.0]hept-3-en-3-yl)((2-(trimethylsilyl)ethoxy)methyl)carbamate (71B)

A mixture of tert-butyl ((1S,5S,6S)-5-(5-((Z)-2-(5-cyanopyridin-2-yl)-2-fluorovinyl)-2-fluorophenyl)-1-((2-hydroxypropyl)carbamoyl)-5-methyl-2-thia-4-azabicyclo[4.1.0]hept-3-en-3-yl)((2-(trimethylsilyl)ethoxy)methyl)carbamate (71A) (110 mg, 0.154 mmol) and Dess-Martin periodinane (80 mg, 0.19 mmol) in DCM (2 mL) was stirred at room temperature for 10 minutes. More of Dess-Martin periodinane (80 mg, 0.19 mmol) was added. After an additional 10 minutes, the mixture was filtered through a pad of Celite with DCM rinsing. The residue was purified by chromatography on silica using EtOAc in heptane (10-40%) as eluent to tert-butyl ((1S,5S,6S)-5-(5-((Z)-2-(5-cyanopyridin-2-yl)-2-fluorovinyl)-2-fluorophenyl)-5-methyl-1-((2-oxopropyl)carbamoyl)-2-thia-4-azabicyclo[4.1.0]hept-3-en-3-yl)((2-(trimethylsilyl)ethoxy)methyl)carbamate (71B) as a white solid (30 mg, 27% yield). LCMS (ESI, pos.): calcd for $C_{35}H_{43}F_2N_5O_5SSi$: 711.3; found: 712.2 (M+1). $^1$H NMR (400 MHz, CHLOROFORM-d) δ 8.82 (s, 1H), 8.02 (dd, J=2.05, 8.31 Hz, 1H), 7.80 (dd, J=2.05, 7.73 Hz, 1H), 7.64-7.75 (m, 2H), 7.31 (m, 1H), 7.27 (d, J=43.43 Hz, 1H), 7.13 (dd, J=8.51, 11.64 Hz, 1H), 5.39 (d, J=10.56 Hz, 1H), 5.17 (d, J=10.56 Hz, 1H), 4.19 (d, J=4.70 Hz, 2H), 3.64-3.78 (m, 2H), 2.28-2.38 (m, 1H), 2.23 (s, 3H), 1.79-1.89 (m, 4H), 1.57 (s, 9H), 1.28-1.33 (m, 1H), 0.96-1.02 (m, 2H), −0.02 (s, 9H).

Preparation of tert-butyl ((1S,5S,6S)-5-(5-((Z)-2-(5-cyanopyridin-2-yl)-2-fluorovinyl)-2-fluorophenyl)-5-methyl-1-(5-methyloxazol-2-yl)-2-thia-4-azabicyclo[4.1.0]hept-3-en-3-yl)((2-(trimethylsilyl)ethoxy)methyl)carbamate (71C)

A mixture of tert-butyl ((1S,5S,6S)-5-(5-((Z)-2-(5-cyanopyridin-2-yl)-2-fluorovinyl)-2-fluorophenyl)-5-methyl-1-((2-oxopropyl)carbamoyl)-2-thia-4-azabicyclo[4.1.0]hept-3-en-3-yl)((2-(trimethylsilyl)ethoxy)methyl)carbamate (71B) (30 mg, 0.042 mmol) and (methoxycarbonylsulfamoyl)triethyl-ammonium hydroxide, inner salt (40 mg, 0.17 mmol) in THF (2.0 mL) was stirred at room temperature for 30 minutes. The mixture was filtered through a pad of Celite, concentrated, and purified on silica gel using EtOAc-heptane (10-55%) as eluent to give first the desired product followed by the recovered starting material. The recovered starting material was dissolved in DCM (1 mL) and was treated with 4AMS beads (oven dried) and (methoxycarbonylsulfamoyl)triethyl-ammonium hydroxide, inner salt (40 mg, 0.17 mmol). After 10 minutes, dioxane (1 mL) was added and the mixture was heated at 80° C. for 5 minutes to boil off the DCM. The mixture was filtered through a pad of Celite, concentrated, and purified on silica gel using EtOAc-heptane (10-45%) as eluent to give the desired product as a white foam. The combined product was determined to be tert-butyl ((1S,5S,6S)-5-(5-((Z)-2-(5-cyanopyridin-2-yl)-2-fluorovinyl)-2-fluorophenyl)-5-methyl-1-(5-methyloxazol-2-yl)-2-thia-4-azabicyclo[4.1.0]hept-3-en-3-yl)((2-(trimethylsilyl)ethoxy)methyl)carbamate (71C) (10 mg, 34% yield). LCMS (ESI, pos.): calcd for $C_{35}H_{41}F_2N_5O_4SSi$: 693.3; found: 694.3 (M+1).

Preparation of 6-((Z)-2-(3-((1S,5S,6S)-3-amino-5-methyl-1-(5-methyloxazol-2-yl)-2-thia-4-azabicyclo[4.1.0]hept-3-en-5-yl)-4-fluorophenyl)-1-fluorovinyl)nicotinonitrile (Example 344)

A solution of tert-butyl ((1S,5S,6S)-5-(5-((Z)-2-(5-cyanopyridin-2-yl)-2-fluorovinyl)-2-fluorophenyl)-5-methyl-1-(5-methyloxazol-2-yl)-2-thia-4-azabicyclo[4.1.0]hept-3-en-3-yl)((2-(trimethylsilyl)ethoxy)methyl)carbamate (10 mg, 0.014 mmol) dissolved in dioxane (2 mL) was treated with p-toluenesulfonic acid monohydrate (30 mg, 0.16 mmol). The mixture was heated at 80° C. for 3 hours. The mixture was loaded to a Strata-X-C 33u resin (1 g) column and the TsOH was washed with MeOH (5 mL). The product was released with $NH_3$-MeOH (1N, 5 mL). The product was purified by chromatography on silica using $NH_3$-MeOH (1N) in DCM (0-5%) as eluent to give 6-((Z)-2-(3-((1S,5S,6S)-3-amino-5-methyl-1-(5-methyloxazol-2-yl)-2-thia-4-azabicyclo[4.1.0]hept-3-en-5-yl)-4-fluorophenyl)-1-fluorovinyl)nicotinonitrile (Example 344) (5.9 mg, 88% yield). LCMS (ESI, pos.): calcd for $C_{24}H_{19}F_2N_5OS$: 463.1; found: 464.1 (M+1). $^1$H NMR (400 MHz, CHLOROFORM-d) δ ppm 1.19-1.25 (m, 1H) 1.63 (dd, J=9.8, 5.7 Hz, 1H) 1.82 (s, 3H) 2.31 (d, J=1.0 Hz, 3H) 2.44-2.53 (m, 1H) 6.67 (d, J=1.0 Hz, 1H) 7.12 (dd, J=11.7, 8.4 Hz, 1H) 7.27 (d, J=40.5 Hz, 1H) 7.69-7.75 (m, 2H) 7.95-8.00 (m, 1H) 8.03 (dd, J=8.3, 2.1 Hz, 1H) 8.84 (s, 1H). $^{19}$F NMR (376 MHz, CHLOROFORM-d) δ ppm −125.70 (br s, 1F), −109.12 (br s, 1F).

Synthesis of Example 345

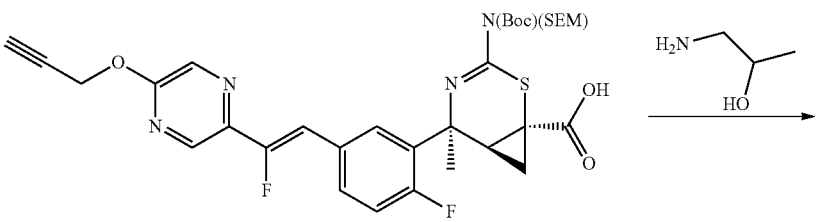

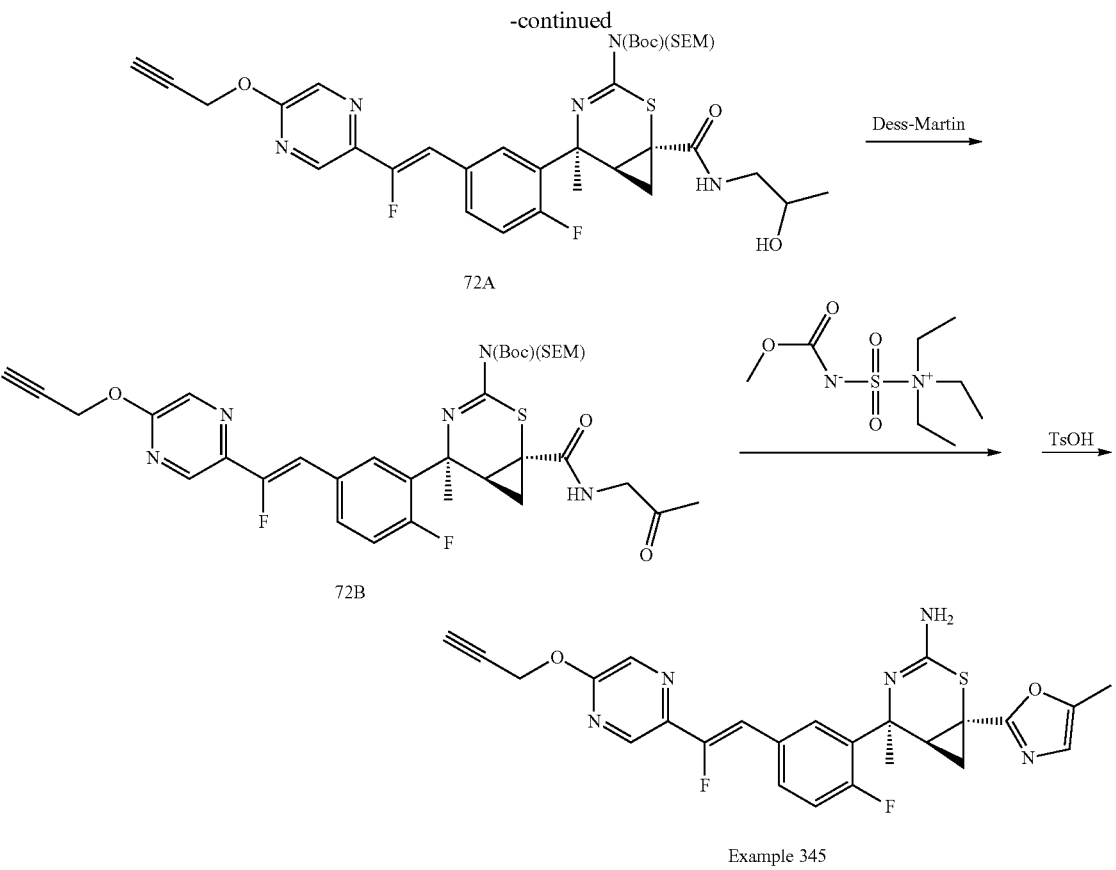

Example 345

Preparation of tert-butyl ((1S,5S,6S)-5-(2-fluoro-5-((Z)-2-fluoro-2-(5-(prop-2-yn-1-yloxy)pyrazin-2-yl)vinyl)phenyl)-1-((2-hydroxypropyl)carbamoyl)-5-methyl-2-thia-4-azabicyclo[4.1.0]hept-3-en-3-yl)((2-(trimethylsilyl)ethoxy)methyl)carbamate (Example 72A)

Using a procedure similar to that described for 71A starting from the acid 59 (230 mg, 0.335 mmol), triethylamine (100 µL, 0.719 mmol), and amino-2-propanol (50 µL, 0.648 mmol) were coupled to give tert-butyl ((1S,5S,6S)-5-(2-fluoro-5-((Z)-2-fluoro-2-(5-(prop-2-yn-1-yloxy)pyrazin-2-yl)vinyl)phenyl)-1-((2-hydroxypropyl)carbamoyl)-5-methyl-2-thia-4-azabicyclo[4.1.0]hept-3-en-3-yl)((2-(trimethylsilyl)ethoxy)methyl)carbamate (72A) (215 mg, 86% yield) as a clear film. LCMS (ESI, pos.): calcd for $C_{36}H_{47}F_2N_5O_6SSi$: 743.3; found: 744.3 (M+1).

Preparation of tert-butyl ((1S,5S,6S)-5-(2-fluoro-5-((Z)-2-fluoro-2-(5-(prop-2-yn-1-yloxy)pyrazin-2-yl)vinyl)phenyl)-5-methyl-1-((2-oxopropyl)carbamoyl)-2-thia-4-azabicyclo[4.1.0]hept-3-en-3-yl)((2-(trimethylsilyl)ethoxy)methyl)carbamate (Example 72B)

Following the procedure described for Example 71B, tert-butyl ((1S,5S,6S)-5-(2-fluoro-5-((Z)-2-fluoro-2-(5-(prop-2-yn-1-yloxy)pyrazin-2-yl)vinyl)phenyl)-1-((2-hydroxypropyl)carbamoyl)-5-methyl-2-thia-4-azabicyclo[4.1.0]hept-3-en-3-yl)((2-(trimethylsilyl)ethoxy)methyl)carbamate (72A) (215 mg, 0.289 mmol) was oxidized to tert-butyl ((1S,5S,6S)-5-(2-fluoro-5-((Z)-2-fluoro-2-(5-(prop-2-yn-1-yloxy)pyrazin-2-yl)vinyl)phenyl)-5-methyl-1-((2-oxopropyl)carbamoyl)-2-thia-4-azabicyclo[4.1.0]hept-3-en-3-yl)((2-(trimethylsilyl)ethoxy)methyl)carbamate (72B) (181 mg, 84% yield) as a white foam. LCMS (ESI, pos.): calcd for $C_{36}H_{45}F_2N_5O_6SSi$: 741.3; found: 742.3 (M+1). $^1$H NMR (400 MHz, CHLOROFORM-d) δ ppm 8.38 (s, 1H), 8.25 (s, 1H), 7.73 (dd, J=7.8, 2.0 Hz, 1H), 7.61-7.69 (m, 1H), 7.31 (t, J=4.5 Hz, 1H), 7.10 (dd, J=11.7, 8.4 Hz, 1H), 6.86 (d, J=40.1 Hz, 1H), 5.38 (d, J=10.6 Hz, 1H), 5.17 (d, J=10.6 Hz, 1H), 5.04 (d, J=2.3 Hz, 2H), 4.18 (d, J=4.7 Hz, 2H), 3.71 (ddd, J=9.6, 7.0, 3.1 Hz, 2H), 2.53 (t, J=2.3 Hz, 1H), 2.27-2.35 (m, 1H), 2.23 (s, 3H), 1.81-1.87 (m, 4H), 1.56 (s, 9H), 1.26-1.29 (m, 2H), 0.99-1.02 (m, 1H), −0.01 (s, 9H).

Preparation of (1S,5S,6S)-5-(2-fluoro-5-((Z)-2-fluoro-2-(5-(prop-2-yn-1-yloxy)pyrazin-2-yl)vinyl)phenyl)-5-methyl-1-(5-methyloxazol-2-yl)-2-thia-4-azabicyclo[4.1.0]hept-3-en-3-amine (Example 345)

To a solution of tert-butyl ((1S,5S,6S)-5-(2-fluoro-5-((Z)-2-fluoro-2-(5-(prop-2-yn-1-yloxy)pyrazin-2-yl)vinyl)phenyl)-5-methyl-1-((2-oxopropyl)carbamoyl)-2-thia-4-azabicyclo[4.1.0]hept-3-en-3-yl)((2-(trimethylsilyl)ethoxy)methyl)carbamate (181 mg, 0.244 mmol) in DCM (3 mL) was added 4AMS beads (50 mg, oven dried) and then (methoxycarbonylsulfamoyl)triethyl-ammonium hydroxide, inner salt (200 mg, 0.839 mmol). After 10 minutes dioxane (5 mL) was added. The mixture was heated at 90° C. for 40 minutes. The solvent was removed and the residue was purified by chromatography on silica using EtOAc in heptane (5-35%) as eluent to give a product that was treated with p-toluenesulfonic acid monohydrate (110 mg, 0.578 mmol) in dioxane and heated at 80° C. for 2 hours. The mixture was diluted with EtOAc (10 mL) and was washed with saturated NaHCO$_3$ (5 mL), water (5 mL), and brine (5 mL). The organic layer was dried over Na$_2$SO$_4$, filtered, and concentrated. The residue was purified by chromatography on silica using MeOH in EtOAc (0-5%) as eluent to give (1S,5S,6S)-5-(2-fluoro-5-((Z)-2-fluoro-2-(5-(prop-2-yn-1-yloxy)pyrazin-2-yl)vinyl)phenyl)-5-methyl-1-(5-methyloxazol-2-yl)-2-thia-4-azabicyclo[4.1.0]hept-3-en-3-amine (Example 345) (67 mg, 63% yield) as a white powder. LCMS (ESI, pos.): calcd for C$_{25}$H$_{21}$F$_2$N$_5$O$_2$S: 493.1; found: 494.1 (M+1). $^1$H NMR (400 MHz, CHLOROFORM-d) δ 8.40 (s, 1H), 8.27 (s, 1H), 7.87-7.95 (m, 1H), 7.62-7.71 (m, 1H), 7.09 (dd, J=8.41, 11.93 Hz, 1H), 6.89 (d, J=40.10 Hz, 1H), 6.66 (d, J=0.98 Hz, 1H), 5.04 (d, J=2.54 Hz, 2H), 2.54 (t, J=2.35 Hz, 1H), 2.47 (dd, J=8.02, 9.00 Hz, 1H), 2.30 (d, J=0.78 Hz, 3H), 1.81 (s, 3H), 1.62 (dd, J=5.67, 9.59 Hz, 1H), 1.18-1.25 (m, 1H). $^{19}$F NMR (376 MHz, CHLOROFORM-d) δ −110.97 (br s, 1F), −125.89 (s, 1F).

Synthesis of Example 346

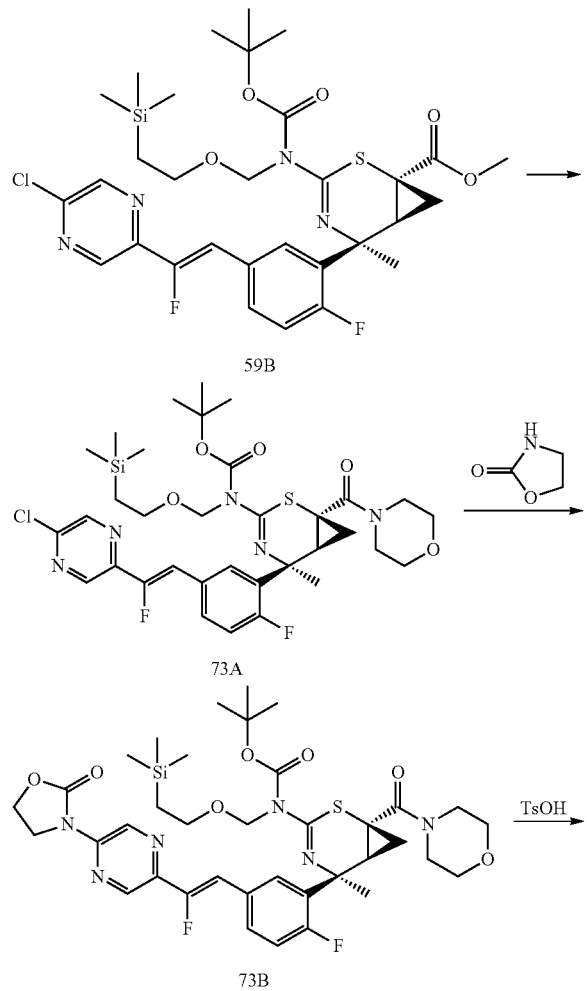

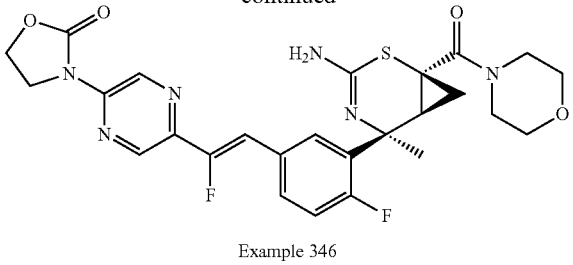

Example 346

Preparation of tert-butyl ((1S,5S,6S)-5-(5-((Z)-2-(5-chloropyrazin-2-yl)-2-fluorovinyl)-2-fluorophenyl)-5-methyl-1-(morpholine-4-carbonyl)-2-thia-4-azabicyclo[4.1.0]hept-3-en-3-yl)((2-(trimethylsilyl)ethoxy)methyl)carbamate (73A)

To a mixture of (1S,5S,6S)-methyl 3-((tert-butoxycarbonyl)((2-(trimethylsilyl)ethoxy)methyl)amino)-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate (370 mg, 0.543 mmol) in THF (5 mL)-water (2 mL) was added lithium hydroxide monohydrate (55 mg, 1.3 mmol). The mixture was stirred for 16 hours. EtOAc (15 mL) was added followed by HCl (1N, 3 mL). The organic layer was washed with water (3 mL), brine (5 mL), dried over Na$_2$SO$_4$, filtered, and concentrated to give the crude acid as a yellow foam. The acid was suspended in MeCN (5 mL) and was treated with 1-chloro-N,N,2-trimethyl-1-propenylamine (150 μL, 1.12 mmol). After 20 minutes, morpholine (100 μL, 1.15 mmol) was added. After an additional 20 minutes, EtOAc (15 mL) was added followed by water (5 mL). The organic layer was washed with HCl (1N, 2 mL)-water (3 mL), brine (5 mL), dried over Na$_2$SO$_4$, filtered, and concentrated. The residue was purified by chromatography on silica using EtOAc in heptane (10-50%) as eluent to give tert-butyl ((1S,5S,6S)-5-(5-((Z)-2-(5-chloropyrazin-2-yl)-2-fluorovinyl)-2-fluorophenyl)-5-methyl-1-(morpholine-4-carbonyl)-2-thia-4-azabicyclo[4.1.0]hept-3-en-3-yl)((2-(trimethylsilyl)ethoxy)methyl)carbamate (73A) (290 mg, 72% yield) as a white foam. LCMS (ESI, pos.): calcd for C$_{34}$H$_{44}$ClF$_2$N$_5$O$_5$SSi: 735; found: 736.2 (M+1). $^1$H NMR (400 MHz, CHLOROFORM-d) δ ppm 8.62 (s, 1H), 8.54 (s, 1H), 7.92 (dd, J=7.7, 2.1 Hz, 1H), 7.61-7.71 (m, 1H), 6.98-7.19 (m, 2H), 5.35 (d, J=10.4 Hz, 1H), 5.13 (d, J=10.6 Hz, 1H), 3.62-3.80 (m, 10H), 2.51 (t, J=8.1 Hz, 1H), 1.87 (s, 3H), 1.54 (s, 9H), 1.25 (dd, J=9.8, 5.9 Hz, 1H), 1.07 (t, J=6.4 Hz, 1H), 0.91-0.99 (m, 2H), −0.01 (s, 9H).

Preparation of tert-butyl ((1S,5S,6S)-5-(2-fluoro-5-((Z)-2-fluoro-2-(5-(2-oxooxazolidin-3-yl)pyrazin-2-yl)vinyl)phenyl)-5-methyl-1-(morpholine-4-carbonyl)-2-thia-4-azabicyclo[4.1.0]hept-3-en-3-yl)((2-(trimethylsilyl)ethoxy)methyl)carbamate (73B)

A mixture of tert-butyl ((1S,5S,6S)-5-(5-((Z)-2-(5-chloropyrazin-2-yl)-2-fluorovinyl)-2-fluorophenyl)-5-methyl-1-(morpholine-4-carbonyl)-2-thia-4-azabicyclo[4.1.0]hept-3-en-3-yl)((2-(trimethylsilyl)ethoxy)methyl)carbamate (160 mg, 0.217 mmol), 2-oxazolidone (60 mg, 0.689 mmol) and cesium carbonate (98 μL, 1.2 mmol) were heated at 60° C. for 2 hours. This reaction was repeated twice. The combined reaction mixtures were diluted with EtOAc (30 mL). The mixture was washed with water (10 mL). The organic layer was dried over Na$_2$SO$_4$, filtered, and concentrated. The residue was purified by chromatography on silica using EtOAc in heptane (5-40%) as eluent to give tert-butyl ((1S,5S,6S)-5-(2-fluoro-5-((Z)-2-fluoro-2-(5-(2-oxooxazolidin-3-yl)pyrazin-2-yl)vinyl)phenyl)-5-methyl-1-(morpholine-4-carbonyl)-2-thia-4-azabicyclo[4.1.0]hept-3-en-3-yl)((2-(trimethylsilyl)ethoxy)methyl)carbamate (73B) (75 mg, 22% yield) as a clear film. LCMS (ESI, pos.): calcd for C$_{37}$H$_{48}$F$_2$N$_6$O$_7$SSi: 786.3; found: 787.3 (M+1).

Preparation of 3-(5-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)pyrazin-2-yl)oxazolidin-2-one (Example 346)

A mixture of tert-butyl ((1S,5S,6S)-5-(2-fluoro-5-((Z)-2-fluoro-2-(5-(2-oxooxazolidin-3-yl)pyrazin-2-yl)vinyl)phenyl)-5-methyl-1-(morpholine-4-carbonyl)-2-thia-4-azabicyclo[4.1.0]hept-3-en-3-yl)((2-(trimethylsilyl)ethoxy)methyl) carbamate (73B) (75 mg, 0.095 mmol) and p-toluenesulfonic acid monohydrate (90 mg, 0.47 mmol) in dioxane (3 mL) was heated at 80° C. for 2 hours. The mixture was diluted with EtOAc (15 mL) and washed with saturated NaHCO$_3$ (2×5 mL), water (5 mL), brine (5 mL), dried over Na$_2$SO$_4$, filtered, and concentrated. The residue was purified by chromatography on silica using EtOH-EtOAc (1:3) in heptane (10-80%) as eluent to give 3-(5-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)pyrazin-2-yl)oxazolidin-2-one (Example 346) (50 mg, 94% yield) as a white foam after lyophilization. LCMS (ESI, pos.): calcd for C$_{26}$H$_{26}$F$_2$N$_6$O$_4$S: 556.2; found: 557.2 (M+1). $^1$H NMR (400 MHz, CHLOROFORM-d) δ ppm 9.53 (s, 1H), 8.52 (s, 1H), 7.77 (dd, J=7.8, 2.0 Hz, 1H), 7.64 (ddd, J=8.4, 4.6, 2.2 Hz, 1H), 7.07 (dd, J=11.7, 8.4 Hz, 1H), 6.87-7.02 (m, 1H), 4.54-4.63 (m, 2H), 4.23-4.32 (m, 2H), 3.60-3.75 (m, 8H), 2.31 (dd, J=9.0, 8.0 Hz, 1H), 1.85 (s, 3H), 1.36 (dd, J=9.8, 5.7 Hz, 1H), 0.84-0.92 (m, 1H). $^{19}$F NMR (376 MHz, CHLOROFORM-d) δ ppm −109.84 (s, 1F), −127.01 (s, 1F).

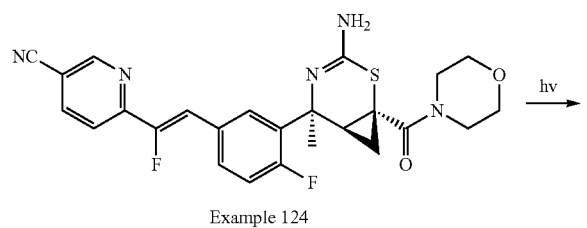

Example 124

6-((E)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)nicotinonitrile (Example 347)

A solution of 6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)nicotinonitrile (Example 124, 140 mg, 0.263 mmol) and (Ir[dF(CF$_3$)ppy]$_2$(dtbpy))PF$_6$ (1.0 mg, 0.89 μmol, Aldrich) in DMSO (2 mL) in a flat bottomed vial (d=2.8 cm) was briefly purged with nitrogen and irradiated (from the bottom) with an blue LED light. After 2 hours, the mixture was purified by reverse-phase preparative HPLC (Gilson GX-281) using a Agilent SB-C18 PrepHT column (30×150 mm) or Phenomenex (C18 13×150 mm), 0.1% TFA in CH$_3$CN/H$_2$O, gradient 15% to 80% over 10 minutes at 35 mL/min. The product fractions were concentrated to ~3 mL volume and neutralized with solid NaHCO$_3$. The slurry was filtered and the solid was washed with saturated NaHCO$_3$ (5 mL), water (5 mL), and air-dried to give 6-((E)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)nicotinonitrile (Example 347) (40 mg, 31% yield) as a white powder. LCMS (ESI, pos.): calcd for C$_{25}$H$_{23}$F$_2$N$_5$O$_2$S: 495.2; found: 496.1 (M+1). $^1$H NMR (400 MHz, DMSO-d$_6$) δ ppm 8.97 (s, 1H), 8.35 (dd, J=8.2, 1.8 Hz, 1H), 7.60 (d, J=8.2 Hz, 1H), 7.43-7.51 (m, 1H), 7.19-7.29 (m, 1H), 7.09 (dd, J=11.8, 8.5 Hz, 1H), 6.92 (d, J=23.1 Hz, 1H), 6.12 (br s, 2H), 3.47-3.64 (m, 8H), 2.02 (br t, J=8.1 Hz, 1H), 1.60 (s, 3H), 1.27 (dd, J=9.5, 5.4 Hz, 1H), 0.53 (t, J=6.3 Hz, 1H). $^{19}$F NMR (376 MHz, DMSO-d$_6$) δ ppm −106.42 (d, J=1.7 Hz, 1F), −111.56 (s, 1F).

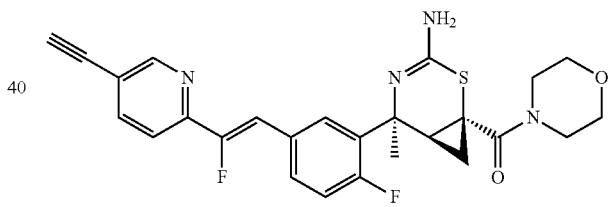

Example 348

Preparation of ((1S,5S,6S)-3-amino-5-(5-((Z)-2-(5-ethynylpyridin-2-yl)-2-fluorovinyl)-2-fluorophenyl)-5-methyl-2-thia-4-azabicyclo[4.1.0]hept-3-en-1-yl)(morpholino)methanone (Example 348)

The title compound was synthesized using a procedure similar to that described for Example 110 starting from ((1S,5S,6S)-3-amino-5-(5-((Z)-2-(5-bromopyridin-2-yl)-2-fluorovinyl)-2-fluorophenyl)-5-methyl-2-thia-4-azabicyclo[4.1.0]hept-3-en-1-yl)(morpholino)methanone (Example 338). ((1S,5S,6S)-3-amino-5-(5-((Z)-2-(5-ethynylpyridin-2-yl)-2-fluorovinyl)-2-fluorophenyl)-5-methyl-2-thia-4-azabicyclo[4.1.0]hept-3-en-1-yl)(morpholino)methanone (Example 348) was obtained as a white solid (29 mg, 70% yield). LCMS (ESI$^+$) m/z=495 (M+H). $^1$H NMR (400 MHz, CHLOROFORM-d) δ 8.68 (s, 1H), 7.83 (dd, J=1.86, 8.12 Hz, 1H), 7.76 (d, J=7.24 Hz, 1H), 7.68 (br. s., 1H), 7.57 (d, J=7.83 Hz, 1H), 7.00-7.16 (m, 2H), 3.60-3.72 (m, 8H), 3.30

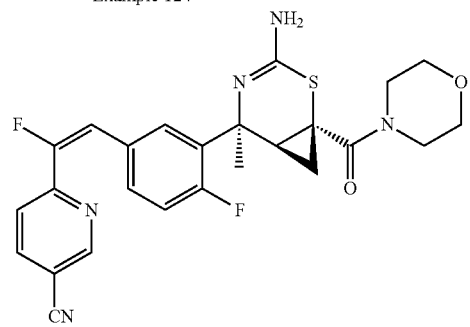

Example 347

(s, 1H), 2.31 (t, J=8.31 Hz, 1H), 1.87 (s, 3H), 1.38 (br. s., 1H), 0.89 (t, J=6.36 Hz, 1H).

Synthesis of Intermediate 74

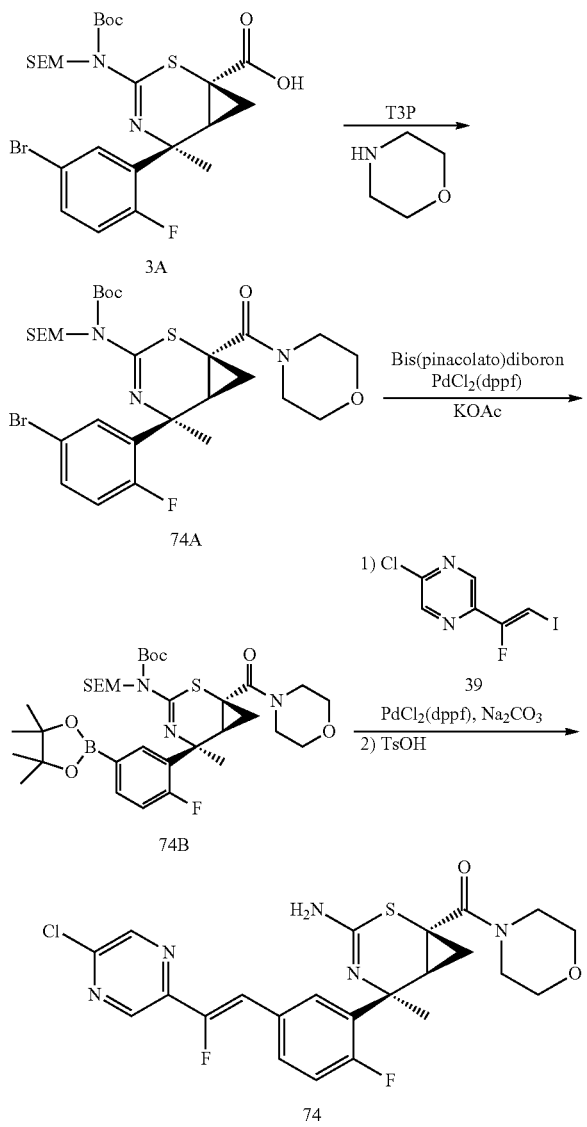

Preparation of tert-butyl ((1S,5S,6S)-5-(5-bromo-2-fluorophenyl)-5-methyl-1-(morpholine-4-carbonyl)-2-thia-4-azabicyclo[4.1.0]hept-3-en-3-yl)((2-(trimethylsilyl)ethoxy)methyl)carbamate (74A)

A mixture of (1S,5S,6S)-5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (3A) (1.04 g, 1.76 mmol), DCM (6 mL), propanephosphonic acid cyclic anhydride solution, 50 wt. % in ethyl acetate (2.80 mL, 4.40 mmol), and morpholine (0.31 mL, 3.5 mmol) was stirred at room temperature overnight. LCMS showed the reaction was complete. The mixture was diluted with saturated NaHCO₃, and extracted with EtOAc. The organic layer was dried over Na₂SO₄ and concentrated in vacuo. The crude product was purified by silica gel chromatography: 0-100% EtOAc in heptane to provide tert-butyl ((1S,5S,6S)-5-(5-bromo-2-fluorophenyl)-5-methyl-1-(morpholine-4-carbonyl)-2-thia-4-azabicyclo[4.1.0]hept-3-en-3-yl)((2-(trimethylsilyl)ethoxy)methyl)carbamate (74A) as a white solid (1.1 g, 91% yield). LCMS (ESI⁺) m/z=658, 660 (M+H).

Preparation of tert-butyl ((1S,5S,6S)-5-(2-fluoro-5-(4,4,5,5-tetramethyl-1,3,2-dioxaborolan-2-yl)phenyl)-5-methyl-1-(morpholine-4-carbonyl)-2-thia-4-azabicyclo[4.1.0]hept-3-en-3-yl)((2-(trimethylsilyl)ethoxy)methyl)carbamate (74B)

A mixture of tert-butyl ((1S,5S,6S)-5-(5-bromo-2-fluorophenyl)-5-methyl-1-(morpholine-4-carbonyl)-2-thia-4-azabicyclo[4.1.0]hept-3-en-3-yl)((2-(trimethylsilyl)ethoxy)methyl)carbamate (1.06 g, 1.61 mmol) (74A), bis(pinacolato)diboron (0.53 g, 2.1 mmol), potassium acetate (0.63 g, 6.4 mmol) and 1,4-dioxane (15 mL) was purged with Ar, then [1,1'-bis(diphenylphosphino)ferrocene]-dichloropalladium(II), complex with dichloromethane (0.079 g, 0.097 mmol) was added. The mixture was heated to 90° C. for 1 hour. The mixture was filtered through celite and the cake was washed with EtOAc. The filtrate was concentrated in vacuo to provide the crude product of tert-butyl ((1S,5S,6S)-5-(2-fluoro-5-(4,4,5,5-tetramethyl-1,3,2-dioxaborolan-2-yl)phenyl)-5-methyl-1-(morpholine-4-carbonyl)-2-thia-4-azabicyclo[4.1.0]hept-3-en-3-yl)((2-(trimethylsilyl)ethoxy)methyl)carbamate (74B), which was used without additional purification Preparation of ((1S,5S,6S)-3-amino-5-(5-((Z)-2-(5-chloropyrazin-2-yl)-2-fluorovinyl)-2-fluorophenyl)-5-methyl-2-thia-4-azabicyclo[4.1.0]hept-3-en-1-yl)(morpholino)methanone (74)

Using a procedure similar to that described for Example 222, tert-butyl ((1S,5S,6S)-5-(2-fluoro-5-(4,4,5,5-tetramethyl-1,3,2-dioxaborolan-2-yl)phenyl)-5-methyl-1-(morpholine-4-carbonyl)-2-thia-4-azabicyclo[4.1.0]hept-3-en-3-yl)((2-(trimethylsilyl)ethoxy)methyl)carbamate (74B) was coupled with 39, which followed by deprotection with TsOH afforded ((1S,5S,6S)-3-amino-5-(5-((Z)-2-(5-chloropyrazin-2-yl)-2-fluorovinyl)-2-fluorophenyl)-5-methyl-2-thia-4-azabicyclo[4.1.0]hept-3-en-1-yl)(morpholino)methanone (74) as yellow solid. LCMS (ESI⁺) m/z=506 (M+H).

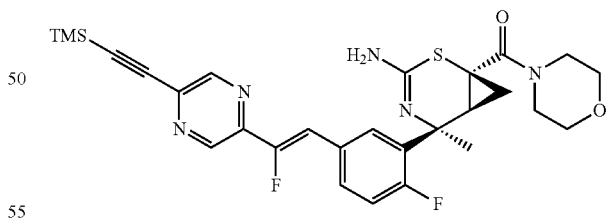

Example 349

Preparation of ((1S,5S,6S)-3-amino-5-(2-fluoro-5-((Z)-2-fluoro-2-(5-((trimethylsilyl)ethynyl)pyrazin-2-yl)vinyl)phenyl)-5-methyl-2-thia-4-azabicyclo[4.1.0]hept-3-en-1-yl)(morpholino)methanone (Example 349)

Using a procedure similar to that described for Example 116, ((1S,5S,6S)-3-amino-5-(5-((Z)-2-(5-chloropyrazin-2- yl)-2-fluorovinyl)-2-fluorophenyl)-5-methyl-2-thia-4-azabicyclo[4.1.0]hept-3-en-1-yl)(morpholino)methanone (74) (0.055 g, 0.109 mmol), trans-dichlorobis(triphenyl-phosphine)palladium (II) (7.63 mg, 10.87 µmol), copper (I) iodide (2.07 mg, 10.87 µmol), and (trimethylsilyl)acetylene (0.077 mL, 0.544 mmol) were combined to afford ((1S,5S,6S)-3-amino-5-(5-((Z)-2-(5-chloropyrazin-2-yl)-2-fluorovinyl)-2-fluorophenyl)-5-methyl-2-thia-4-azabicyclo[4.1.0]hept-3-en-1-yl)(morpholino)methanone (Example 349) (33 mg, 54% yield). LCMS (ESI+) m/z=568 (M+H). $^1$H NMR (400 MHz, CHLOROFORM-d) δ 8.79 (s, 1H), 8.60 (s, 1H), 7.80 (d, J=7.43 Hz, 1H), 7.60-7.71 (m, 1H), 6.96-7.15 (m, 2H), 3.59-3.73 (m, 8H), 2.26-2.36 (m, 1H), 1.85 (s, 3H), 1.36 (dd, J=5.67, 9.78 Hz, 1H), 0.88 (t, J=6.36 Hz, 1H), 0.31 (s, 9H).

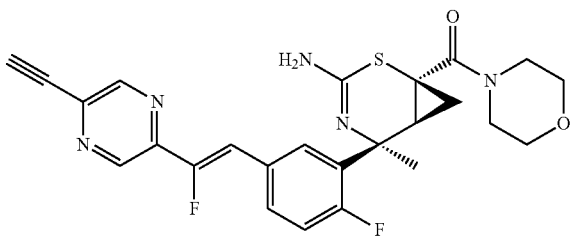 [SMILES: C#Cc1cnc(/C(F)=C/c2ccc(F)c([C@@]3(C)N=C(N)S[C@@]4(C(=O)N5CCOCC5)C[C@H]43)c2)cn1]

Example 350

Preparation of ((1S,5S,6S)-3-amino-5-(5-((Z)-2-(5-ethynylpyrazin-2-yl)-2-fluorovinyl)-2-fluorophenyl)-5-methyl-2-thia-4-azabicyclo[4.1.0]hept-3-en-1-yl)(morpholino)methanone (Example 350)

Using a procedure similar to that described for Example 167, ((1S,5S,6S)-3-amino-5-(2-fluoro-5-((Z)-2-fluoro-2-(5-((trimethylsilyl)ethynyl)pyrazin-2-yl)vinyl)phenyl)-5-methyl-2-thia-4-azabicyclo[4.1.0]hept-3-en-1-yl)(morpholino)methanone (0.031 g, 0.055 mmol), potassium carbonate (0.038 g, 0.27 mmol) and methanol (1 mL) were combined to afford ((1S,5S,6S)-3-amino-5-(5-((Z)-2-(5-ethynylpyrazin-2-yl)-2-fluorovinyl)-2-fluorophenyl)-5-methyl-2-thia-4-azabicyclo[4.1.0]hept-3-en-1-yl)(morpholino)methanone (Example 350) as a light brown solid (16 mg, 58% yield). LCMS (ESI+) m/z=496 (M+H). $^1$H NMR (400 MHz, CHLOROFORM-d) δ 8.82 (s, 1H), 8.64 (s, 1H), 7.81 (d, J=7.43 Hz, 1H), 7.65 (d, J=4.11 Hz, 1H), 7.00-7.17 (m, 2H), 4.48 (br. s., 2H), 3.62-3.74 (m, 8H), 3.43 (s, 1H), 2.31 (t, J=8.41 Hz, 1H), 1.85 (s, 3H), 1.35 (dd, J=5.77, 9.68 Hz, 1H), 0.88 (t, J=6.46 Hz, 1H).

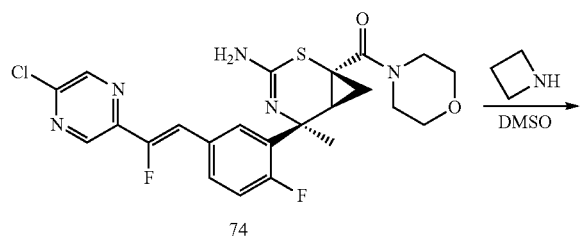

74

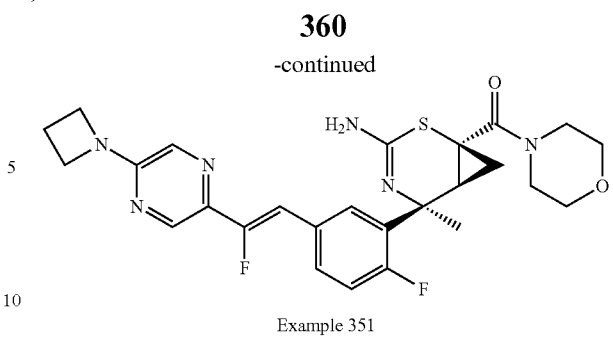

Example 351

((1S,5S,6S)-3-amino-5-(5-((Z)-2-(5-(azetidin-1-yl)pyrazin-2-yl)-2-fluorovinyl)-2-fluorophenyl)-5-methyl-2-thia-4-azabicyclo[4.1.0]hept-3-en-1-yl)(morpholino)methanone (Example 351)

A mixture of ((1S,5S,6S)-3-amino-5-(5-((Z)-2-(5-chloropyrazin-2-yl)-2-fluorovinyl)-2-fluorophenyl)-5-methyl-2-thia-4-azabicyclo[4.1.0]hept-3-en-1-yl)(morpholino)methanone (74) (0.050 g, 0.099 mmol), azetidine (0.028 g, 0.49 mmol) and DMSO (0.7 mL) was stirred at 45° C. for 1 hour, then diluted with water and EtOAc. The organic solution was washed with water and brine, dried over Na$_2$SO$_4$ and concentrated in vacuo. The crude was purified by silica gel chromatography: 0-100% EtOAc/EtOH (3/1) in heptane. The product was obtained as yellow solid (30 mg, 58% yield). ~10% of the E olefin isomer was present in the product. The product LCMS (ESI+) m/z=527 (M+H). $^1$H NMR for the major Z-isomer: (400 MHz, CHLOROFORM-d) δ 8.31 (s, 1H), 7.73 (s, 1H), 7.67 (d, J=6.65 Hz, 1H), 7.55-7.61 (m, 1H), 7.04 (dd, J=8.41, 11.74 Hz, 1H), 6.56-6.73 (m, 1H), 4.19 (t, J=7.53 Hz, 4H), 3.61-3.73 (m, 10H), 2.51 (m, 2H), 2.26-2.34 (m, 1H), 1.86 (s, 3H), 1.33-1.41 (m, 1H), 0.89 (t, J=6.36 Hz, 1H).

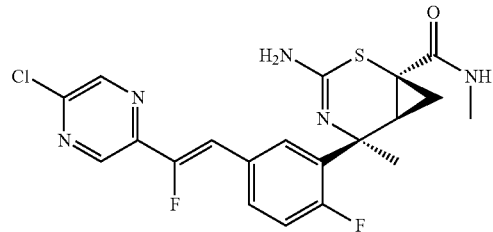 [SMILES: CNC(=O)[C@]12C[C@H]1[C@@](C)(c1cc(/C=C(\F)c3cnc(Cl)cn3)ccc1F)N=C(N)S2]

Example 352

Preparation of (1S,5S,6S)-3-amino-5-(5-((Z)-2-(5-chloropyrazin-2-yl)-2-fluorovinyl)-2-fluorophenyl)-N,5-dimethyl-2-thia-4-azabicyclo[4.1.0]hept-3-ene-1-carboxamide (Example 352)

Using a procedure similar to that described for Example 224 starting from intermediate 39 and 41, (1S,5S,6S)-3-amino-5-(5-((Z)-2-(5-chloropyrazin-2-yl)-2-fluorovinyl)-2-fluorophenyl)-N,5-dimethyl-2-thia-4-azabicyclo[4.1.0]hept-3-ene-1-carboxamide (Example 352) was obtained as off-white solid (39 mg, 64% yield). LCMS (ESI+) m/z=450 (M+H). $^1$H NMR (400 MHz, DMSO-d$_6$) δ 8.85 (s, 1H), 8.80 (s, 1H), 8.02 (d, J=6.06 Hz, 1H), 7.68 (d, J=4.50 Hz, 2H), 7.27 (dd, J=8.51, 12.03 Hz, 1H), 7.04-7.20 (m, 1H), 6.18 (br.

s., 2H), 2.62 (d, J=4.50 Hz, 3H), 2.16 (t, J=8.22 Hz, 1H), 1.62 (s, 3H), 1.41 (dd, J=5.18, 9.49 Hz, 1H), 0.76 (t, J=6.16 Hz, 1H).

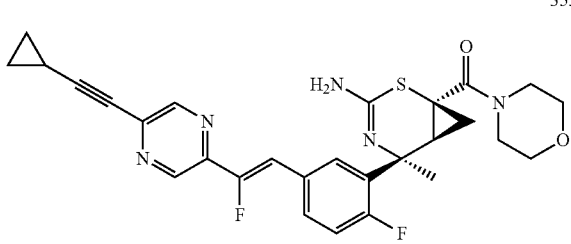

353

Preparation of ((1S,5S,6S)-3-amino-5-(5-((Z)-2-(5-(cyclopropylethynyl)pyrazin-2-yl)-2-fluorovinyl)-2-fluorophenyl)-5-methyl-2-thia-4-azabicyclo[4.1.0]hept-3-en-1-yl)(morpholino)methanone (Example 353)

Using a procedure similar to that described for Example 109 starting from ((1S,5S,6S)-3-amino-5-(5-((Z)-2-(5-chloropyrazin-2-yl)-2-fluorovinyl)-2-fluorophenyl)-5-methyl-2-thia-4-azabicyclo[4.1.0]hept-3-en-1-yl)(morpholino)methanone (74) (0.0506 g, 0.100 mmol), ((1S,5S,6S)-3-amino-5-(5-((Z)-2-(5-(cyclopropylethynyl)pyrazin-2-yl)-2-fluorovinyl)-2-fluorophenyl)-5-methyl-2-thia-4-azabicyclo[4.1.0]hept-3-en-1-yl)(morpholino)methanone (Example 353) was obtained as yellow solid (34 mg, 64% yield). LCMS (ESI$^+$) m/z=536 1H NMR (400 MHz, DMSO-d6) δ 8.85 (s, 1H), 8.69 (s, 1H), 7.95 (d, J=7.24 Hz, 1H), 7.66 (m, 1H), 7.26 (dd, J=8.41, 11.93 Hz, 1H), 7.10 (d, J=38.34 Hz, 1H), 6.30 (br. s., 2H), 3.49-3.64 (m, 8H), 2.12 (t, J=8.31 Hz, 1H), 1.61-1.76 (m, 4H), 1.33 (dd, J=5.48, 9.39 Hz, 1H), 0.95-1.05 (m, 2H), 0.83-0.92 (m, 2H), 0.71 (t, J=6.06 Hz, 1H).

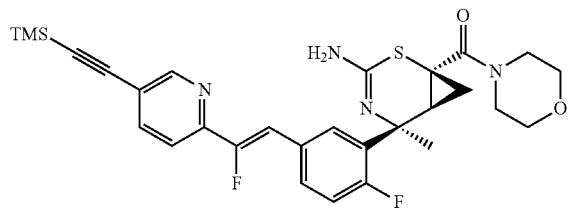 [SMILES: C[C@]1(c2cc(/C=C(\F)c3ccc(C#C[Si](C)(C)C)cn3)ccc2F)N=C(N)S[C@@]2(C(=O)N3CCOCC3)C[C@H]21]

Example 354

Preparation of ((1S,5S,6S)-3-amino-5-(2-fluoro-5-((Z)-2-fluoro-2-(5-(((trimethylsilyl)ethynyl)pyridin-2-yl)vinyl)phenyl)-5-methyl-2-thia-4-azabicyclo[4.1.0]hept-3-en-1-yl)(morpholino)methanone (Example 354)

Using a procedure similar to that described for Example 166, ((1S,5S,6S)-3-amino-5-(5-((Z)-2-(5-bromopyridin-2-yl)-2-fluorovinyl)-2-fluorophenyl)-5-methyl-2-thia-4-azabicyclo[4.1.0]hept-3-en-1-yl)(morpholino)methanone (Example 338) (0.048 g, 0.065 mmol) and trimethylsilylacetylene were combined to provide the di-Boc protected coupling product, which after deprotection with TFA gave ((1S,5S,6S)-3-amino-5-(2-fluoro-5-((Z)-2-fluoro-2-(5-(((trimethylsilyl)ethynyl)pyridin-2-yl)vinyl)phenyl)-5-methyl-2-thia-4-azabicyclo[4.1.0]hept-3-en-1-yl)(morpholino)methanone (Example 354) as a white solid (28 mg, 76% yield). LCMS (ESI$^+$) m/z=567 (M+H). $^1$H NMR (400 MHz, DMSO-d$_6$) δ 8.69 (s, 1H), 7.99 (dd, J=2.05, 8.31 Hz, 1H), 7.91 (d, J=7.83 Hz, 1H), 7.66 (d, J=7.83 Hz, 2H), 7.24 (dd, J=8.41, 11.93 Hz, 1H), 7.01-7.17 (m, 1H), 6.30 (br. s., 2H), 3.50-3.60 (m, 8H), 2.11 (t, J=8.41 Hz, 1H), 1.67 (s, 3H), 1.33 (dd, J=5.38, 9.49 Hz, 1H), 0.70 (t, J=6.26 Hz, 1H), 0.26 (s, 9H).

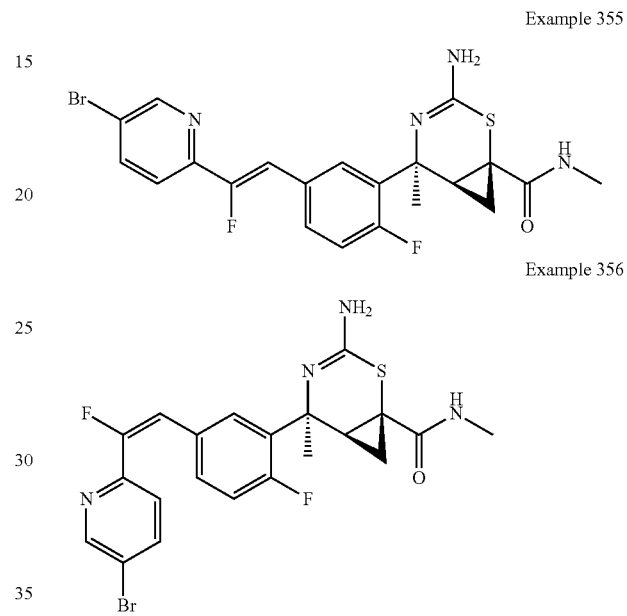

Example 355

Example 356

Preparation of (1S,5S,6S)-3-amino-5-(5-((Z)-2-(5-bromopyridin-2-yl)-2-fluorovinyl)-2-fluorophenyl)-N,5-dimethyl-2-thia-4-azabicyclo[4.1.0]hept-3-ene-1-carboxamide (Example 355) and (1S,5S,6S)-3-amino-5-(5-((E)-2-(5-bromopyridin-2-yl)-2-fluorovinyl)-2-fluorophenyl)-N,5-dimethyl-2-thia-4-azabicyclo[4.1.0]hept-3-ene-1-carboxamide (Example 356)

Using a procedure similar to that described for Example 108, starting from aldehyde intermediate 1, sulfone intermediate 8 and methylamine, a mixture of (1S,5S,6S)-3-amino-5-(5-((Z)-2-(5-bromopyridin-2-yl)-2-fluorovinyl)-2-fluorophenyl)-N,5-dimethyl-2-thia-4-azabicyclo[4.1.0]hept-3-ene-1-carboxamide (Example 355) and (1S,5S,6S)-3-amino-5-(5-((E)-2-(5-bromopyridin-2-yl)-2-fluorovinyl)-2-fluorophenyl)-N,5-dimethyl-2-thia-4-azabicyclo[4.1.0]hept-3-ene-1-carboxamide (Example 356) was obtained and separated into two compounds by preparative HPLC. LCMS (ESI$^+$) m/z=493, 495 (M+H).

$^1$H NMR for Example 355 (400 MHz, DMSO-d$_6$) δ 8.77 (s, 1H), 8.19 (d, J=8.22 Hz, 1H), 7.98 (br. s., 1H), 7.65 (d, J=8.41 Hz, 3H), 7.26 (br. s., 1H), 7.01-7.19 (m, 1H), 6.18 (br. s., 2H), 2.62 (d, J=4.30 Hz, 3H), 2.17 (br. s., 1H), 1.62 (br. s., 3H), 1.40 (br. s., 1H), 0.76 (br. s., 1H).

$^1$H NMR for Example 356 (400 MHz, DMSO-d$_6$) δ 8.71 (d, J=2.35 Hz, 1H), 8.11 (d, J=6.65 Hz, 1H), 7.58-7.71 (m, 1H), 7.47-7.58 (m, 1H), 7.40 (d, J=8.02 Hz, 1H), 7.00-7.22

(m, 2H), 6.71-6.86 (m, 1H), 5.98 (br. s., 2H), 2.61 (d, J=4.50 Hz, 3H), 2.01-2.11 (m, 1H), 1.54 (br. s., 3H), 1.33 (br. s., 1H), 0.61 (br. s., 1H).

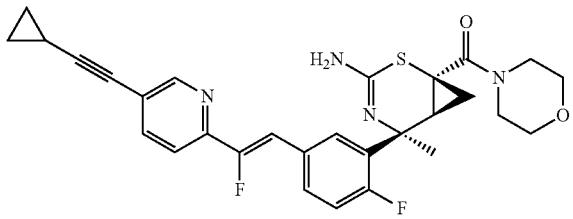 [SMILES: C[C@]1(c2cc(/C=C(\F)c3ccc(C#CC4CC4)cn3)ccc2F)N=C(N)S[C@@]2(C(=O)N3CCOCC3)C[C@H]21]

Example 357

Preparation of ((1S,5S,6S)-3-amino-5-(5-((Z)-2-(5-(cyclopropylethynyl)pyridin-2-yl)-2-fluorovinyl)-2-fluorophenyl)-5-methyl-2-thia-4-azabicyclo[4.1.0]hept-3-en-1-yl)(morpholino)methanone (Example 357)

Using a procedure similar to that described for Example 334, starting from ((1S,5S,6S)-3-amino-5-(5-((Z)-2-(5-bromopyridin-2-yl)-2-fluorovinyl)-2-fluorophenyl)-5-methyl-2-thia-4-azabicyclo[4.1.0]hept-3-en-1-yl)(morpholino)methanone (Example 338) (0.033 g, 0.044 mmol), N,N-dimethylacetamide (0.5 mL), and cyclopropylacetylene (0.019 mL, 0.220 mmol), ((1S,5S,6S)-3-amino-5-(5-((Z)-2-(5-(cyclopropylethynyl)pyridin-2-yl)-2-fluorovinyl)-2-fluorophenyl)-5-methyl-2-thia-4-azabicyclo[4.1.0]hept-3-en-1-yl)(morpholino)methanone (Example 357) was obtained as off-white solid (18 mg, 75% yield). LCMS (ESI⁺) m/z=535 (M+H). 1H NMR (400 MHz, DMSO-d6) δ 8.60 (s, 1H), 7.90 (m, 2H), 7.58-7.68 (m, 2H), 7.28-7.21 (m, 1H), 7.07 (d, J=39.32 Hz, 1H), 6.31 (br. s., 2H), 3.50-3.60 (m, 8H), 2.12 (t, J=8.12 Hz, 1H), 1.68 (s, 3H), 1.57-1.65 (m, 1H), 1.35 (br. s., 1H), 0.91-0.97 (m, 2H), 0.77-0.82 (m, 2H), 0.72 (br. s., 1H).

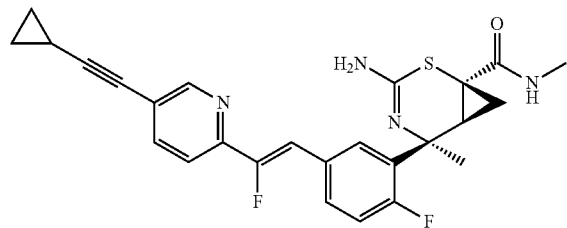 [SMILES: CNC(=O)[C@]12C[C@H]1[C@@](C)(c1cc(/C=C(\F)c3ccc(C#CC4CC4)cn3)ccc1F)N=C(N)S2]

Example 358

Preparation of (1S,5S,6S)-3-amino-5-(5-((Z)-2-(5-(cyclopropylethynyl)pyridin-2-yl)-2-fluorovinyl)-2-fluorophenyl)-N,5-dimethyl-2-thia-4-azabicyclo[4.1.0]hept-3-ene-1-carboxamide (Example 358)

Using a procedure similar to that described for Example 109, (1S,5S,6S)-3-amino-5-(5-((Z)-2-(5-bromopyridin-2-yl)-2-fluorovinyl)-2-fluorophenyl)-N,5-dimethyl-2-thia-4-azabicyclo[4.1.0]hept-3-ene-1-carboxamide (Example 355) (0.031 g, 0.063 mmol), trans-dichlorobis(triphenyl-phosphine)palladium (II) (4.41 mg, 6.28 μmol), copper (I) iodide (1.20 mg, 6.28 μmol), N,N-dimethylacetamide (0.7 mL), N,N-diisopropylethylamine (0.109 mL, 0.628 mmol) and cyclopropylacetylene (0.027 mL, 0.314 mmol) were combined to provide (1S,5S,6S)-3-amino-5-(5-((Z)-2-(5-(cyclopropylethynyl)pyridin-2-yl)-2-fluorovinyl)-2-fluorophenyl)-N,5-dimethyl-2-thia-4-azabicyclo[4.1.0]hept-3-ene-1-carboxamide (Example 358) (15 mg, 51% yield) as a white solid. LCMS (ESI⁺) m/z=479 (M+H). 1H NMR (400 MHz, DMSO-d6) δ 8.61 (s, 1H), 7.82-8.03 (m, 2H), 7.55-7.79 (m, 3H), 7.25 (br. s., 1H), 6.98-7.18 (m, 1H), 6.19 (br. s., 2H), 2.62 (d, J=4.50 Hz, 3H), 2.16 (br. s., 1H), 1.52-1.71 (m, 4H), 1.42 (br. s., 1H), 0.87-1.00 (m, 2H), 0.75-0.86 (m, 3H).

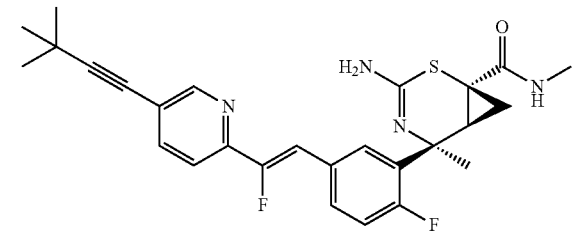 [SMILES: CNC(=O)[C@]12C[C@H]1[C@@](C)(c1cc(/C=C(\F)c3ccc(C#CC(C)(C)C)cn3)ccc1F)N=C(N)S2]

Example 359

Preparation of (1S,5S,6S)-3-amino-5-(5-((Z)-2-(5-(3,3-dimethylbut-1-yn-1-yl)pyridin-2-yl)-2-fluorovinyl)-2-fluorophenyl)-N,5-dimethyl-2-thia-4-azabicyclo[4.1.0]hept-3-ene-1-carboxamide (Example 359)

Using a procedure similar to that described for Example 109, (1S,5S,6S)-3-amino-5-(5-((Z)-2-(5-bromopyridin-2-yl)-2-fluorovinyl)-2-fluorophenyl)-N,5-dimethyl-2-thia-4-azabicyclo[4.1.0]hept-3-ene-1-carboxamide (Example 355) (0.033 g, 0.067 mmol) and 3,3-dimethylbut-1-yne (0.033 g, 0.40 mmol) were combined to provide (1S,5S,6S)-3-amino-5-(5-((Z)-2-(5-(3,3-dimethylbut-1-yn-1-yl)pyridin-2-yl)-2-fluorovinyl)-2-fluorophenyl)-N,5-dimethyl-2-thia-4-azabicyclo[4.1.0]hept-3-ene-1-carboxamide (Example 359) (9 mg, 28% yield) as a white solid. LCMS (ESI⁺) m/z=495 (M+H). 1H NMR (400 MHz, DMSO-d6) δ 8.60 (s, 1H), 7.96 (br d, J=7.24 Hz, 1H), 7.89 (dd, J=2.15, 8.22 Hz, 1H), 7.60-7.74 (m, 3H), 7.25 (dd, J=8.41, 11.74 Hz, 1H), 6.99-7.17 (m, 1H), 6.05-6.42 (m, 2H), 2.62 (d, J=4.50 Hz, 3H), 2.15 (br s, 1H), 1.62 (br s, 3H), 1.38-1.46 (m, 1H), 1.32 (s, 9H), 0.77 (br d, J=2.35 Hz, 1H).

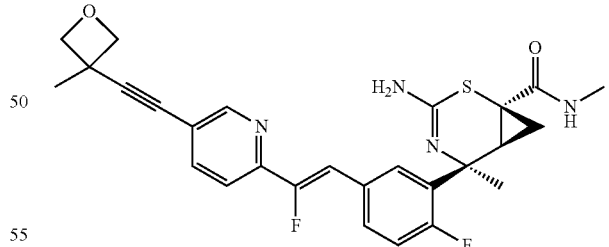

Example 360

Preparation of (1S,5S,6S)-3-amino-5-(2-fluoro-5-((Z)-2-fluoro-2-(5-((3-methyloxetan-3-yl)ethynyl)pyridin-2-yl)vinyl)phenyl)-N,5-dimethyl-2-thia-4-azabicyclo[4.1.0]hept-3-ene-1-carboxamide (Example 360)

Using a procedure similar to that described for Example 109, (1S,5S,6S)-3-amino-5-(5-((Z)-2-(5-bromopyridin-2- yl)-2-fluorovinyl)-2-fluorophenyl)-N,5-dimethyl-2-thia-4-azabicyclo[4.1.0]hept-3-ene-1-carboxamide (Example 355) (0.033 g, 0.067 mmol) and 3-ethynyl-3-methyloxetane (0.039 g, 0.40 mmol) were combined to provide (1S,5S,6S)-3-amino-5-(2-fluoro-5-((Z)-2-fluoro-2-(5-((3-methyloxetan-3-yl)ethynyl)pyridin-2-yl)vinyl)phenyl)-N,5-dimethyl-2-thia-4-azabicyclo[4.1.0]hept-3-ene-1-carboxamide (Example 360) (21 mg, 63% yield) as a white solid. LCMS (ESI⁺) m/z=509 (M+H). 1H NMR (400 MHz, DMSO-d6) δ 8.68 (s, 1H), 7.99 (m, 2H), 7.69 (m, 3H), 7.25 (m, 1H), 7.13 (d, J=40.30 Hz, 1H), 6.20 (br s, 2H), 4.78 (d, J=5.48 Hz, 2H), 4.46 (d, J=5.48 Hz, 2H), 2.62 (d, J=4.50 Hz, 3H), 2.16 (s, 1H), 1.66 (s, 3H), 1.62 (br s, 3H), 1.42 (m, 1H), 0.76 (m, 1H).

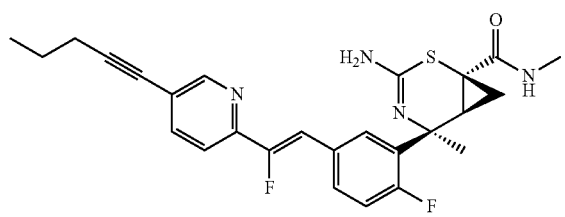 [SMILES: CCCC#Cc1ccc(/C(F)=C/c2ccc(F)c([C@@]3(C)N=C(N)S[C@@]4(C(=O)NC)C[C@H]43)c2)nc1]

Example 361

Preparation of (1S,5S,6S)-3-amino-5-(2-fluoro-5-((Z)-2-fluoro-2-(5-(pent-1-yn-1-yl)pyridin-2-yl)vinyl)phenyl)-N,5-dimethyl-2-thia-4-azabicyclo[4.1.0]hept-3-ene-1-carboxamide (Example 361)

Using a procedure similar to that described for Example 109, (1S,5S,6S)-3-amino-5-(5-((Z)-2-(5-bromopyridin-2-yl)-2-fluorovinyl)-2-fluorophenyl)-N,5-dimethyl-2-thia-4-azabicyclo[4.1.0]hept-3-ene-1-carboxamide (Example 355) (0.033 g, 0.067 mmol) and pent-1-yne (0.027 g, 0.401 mmol) were combined to provide (1S,5S,6S)-3-amino-5-(2-fluoro-5-((Z)-2-fluoro-2-(5-(pent-1-yn-1-yl)pyridin-2-yl)vinyl)phenyl)-N,5-dimethyl-2-thia-4-azabicyclo[4.1.0]hept-3-ene-1-carboxamide (Example 361) (20 mg, 61% yield) as a white solid. LCMS (ESI⁺) m/z=481 (M+H). ¹H NMR (400 MHz, DMSO-d₆) δ 8.63 (s, 1H), 7.92 (dd, J=2.15, 8.22 Hz, 2H), 7.62-7.76 (m, 3H), 7.19-7.34 (m, 1H), 6.99-7.17 (m, 1H), 6.08-6.34 (m, 2H), 2.62 (d, J=4.50 Hz, 3H), 2.44-2.48 (m, 2H), 2.09-2.25 (m, 1H), 1.53-1.67 (m, 5H), 1.36-1.51 (m, 1H), 1.01 (t, J=7.34 Hz, 3H), 0.69-0.82 (m, 1H).

Synthesis of Example 362

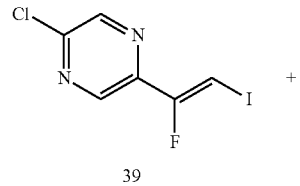

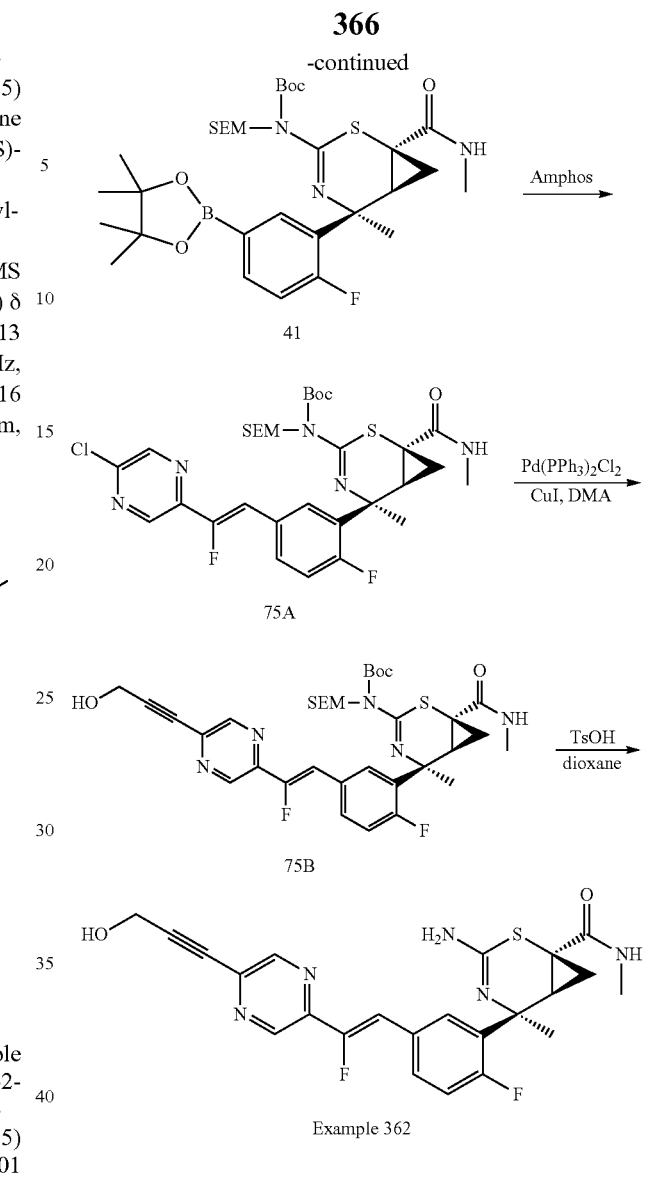

Example 362

Preparation of tert-butyl ((1S,5S,6S)-5-(5-((Z)-2-(5-chloropyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate was obtained as off-white solid (75A)

Step 1.

Using a procedure similar to that described for Example 222, starting from (Z)-2-chloro-5-(1-fluoro-2-iodovinyl)pyrazine (39) (1.06 g, 3.73 mmol), and tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (41) (1.86 g, 2.87 mmol), the coupling product tert-butyl ((1S,5S,6S)-5-(5-((Z)-2-(5-chloropyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (75A) was obtained as off-white solid (1.59 g, 81% yield). LCMS (ESI⁺) m/z=680 (M+H).

Preparation of tert-butyl ((1S,5S,6S)-5-(2-fluoro-5-((Z)-2-fluoro-2-(5-(3-hydroxyprop-1-yn-1-yl)pyrazin-2-yl)vinyl)phenyl)-5-methyl-1-(methylcarbamoyl)-2-thia-4-azabicyclo[4.1.0]hept-3-en-3-yl)((2-(trimethylsilyl)ethoxy)methyl)carbamate (75B)

Using a procedure similar to that described for Example 109, tert-butyl ((1S,5S,6S)-5-(5-((Z)-2-(5-chloropyrazin-2-yl)-2-fluorovinyl)-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (75A) (0.100 g, 0.147 mmol), trans-dichlorobis(triphenyl-phosphine)palladium (II) (10 mg, 0.015 mmol), copper(I) iodide (2.8 mg, 0.015 mmol), N,N-dimethylacetamide (1 mL), N,N-diisopropylethylamine (0.256 mL, 1.470 mmol) and prop-2-yn-1-ol (0.041 g, 0.74 mmol) were combined to afford tert-butyl ((1S,5S,6S)-5-(2-fluoro-5-((Z)-2-fluoro-2-(5-(3-hydroxyprop-1-yn-1-yl)pyrazin-2-yl)vinyl)phenyl)-5-methyl-1-(methylcarbamoyl)-2-thia-4-azabicyclo[4.1.0]hept-3-en-3-yl)((2-(trimethylsilyl)ethoxy)methyl)carbamate (75B) as yellow solid (73 mg, 71% yield). LCMS (ESI$^+$) m/z=700 (M+H).

Preparation of (1S,5S,6S)-3-amino-5-(2-fluoro-5-((Z)-2-fluoro-2-(5-(3-hydroxyprop-1-yn-1-yl)pyrazin-2-yl)vinyl)phenyl)-N,5-dimethyl-2-thia-4-azabicyclo[4.1.0]hept-3-ene-1-carboxamide (Example 362)

A mixture of tert-butyl ((1S,5S,6S)-5-(2-fluoro-5-((Z)-2-fluoro-2-(5-(3-hydroxyprop-1-yn-1-yl)pyrazin-2-yl)vinyl)phenyl)-5-methyl-1-(methylcarbamoyl)-2-thia-4-azabicyclo[4.1.0]hept-3-en-3-yl)((2-(trimethylsilyl)ethoxy)methyl)carbamate (75B) (0.021 g, 0.030 mmol), p-toluenesulfonic acid monohydrate (0.018 g, 0.095 mmol), and 1,4-dioxane (1 mL) was heated at 80° C. for 1.5 hours, then diluted with saturated Na$_2$CO$_3$ and extracted with EtOAc. The organic solution was dried over Na$_2$SO$_4$ and concentrated in vacuo. The crude was purified by silica gel chromatography to afford (1S,5S,6S)-3-amino-5-(2-fluoro-5-((Z)-2-fluoro-2-(5-(3-hydroxyprop-1-yn-1-yl)pyrazin-2-yl)vinyl)phenyl)-N,5-dimethyl-2-thia-4-azabicyclo[4.1.0]hept-3-ene-1-carboxamide (Example 362) (8 mg, 58% yield) as yellow solid. LCMS (ESI$^+$) m/z=470 (M+H). $^1$H NMR (400 MHz, DMSO-d$_6$) δ 8.89 (s, 1H), 8.73 (s, 1H), 7.89 (br d, J=7.04 Hz, 1H), 7.76 (br d, J=3.91 Hz, 1H), 7.62-7.71 (m, 1H), 7.26 (dd, J=8.61, 11.74 Hz, 1H), 7.04-7.18 (m, 1H), 6.10-6.37 (m, 2H), 5.63-5.71 (m, 1H), 4.39 (d, J=5.87 Hz, 2H), 2.61 (d, J=4.50 Hz, 3H), 2.08-2.18 (m, 1H), 1.63 (s, 3H), 1.44-1.52 (m, 1H), 0.71-0.79 (m, 1H).

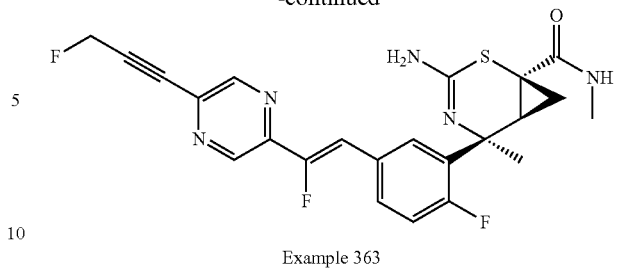

Example 363

Preparation of (1S,5S,6S)-3-amino-5-(2-fluoro-5-((Z)-2-fluoro-2-(5-(3-fluoroprop-1-yn-1-yl)pyrazin-2-yl)vinyl)phenyl)-N,5-dimethyl-2-thia-4-azabicyclo[4.1.0]hept-3-ene-1-carboxamide (Example 363)

To a mixture of tert-butyl ((1S,5S,6S)-5-(2-fluoro-5-((Z)-2-fluoro-2-(5-(3-hydroxyprop-1-yn-1-yl)pyrazin-2-yl)vinyl)phenyl)-5-methyl-1-(methylcarbamoyl)-2-thia-4-azabicyclo[4.1.0]hept-3-en-3-yl)((2-(trimethylsilyl)ethoxy)methyl)carbamate (75B) (0.050 g, 0.071 mmol) and DCM (1 mL) at 0° C. was added deoxofluor (0.052 mL, 0.29 mmol). The mixture was stirred at 0° C. for 1.5 hours, then diluted with EtOAc and saturated NaHCO$_3$. The organic solution was dried over Na$_2$SO$_4$, and concentrated in vacuo. The crude was purified by silica gel chromatography to provide the deoxofluorination product as yellow solid, which after deprotection with p-toluenesulfonic acid monohydrate gave (1S,5S,6S)-3-amino-5-(2-fluoro-5-((Z)-2-fluoro-2-(5-(3-fluoroprop-1-yn-1-yl)pyrazin-2-yl)vinyl)phenyl)-N,5-dimethyl-2-thia-4-azabicyclo[4.1.0]hept-3-ene-1-carboxamide (Example 363) (13 mg, 39% yield over two steps) as yellow solid. LCMS (ESI$^+$) m/z=472 (M+H). $^1$H NMR (400 MHz, DMSO-d$_6$) δ 8.94 (s, 1H), 8.83 (s, 1H), 7.91 (br d, J=7.63 Hz, 1H), 7.76 (br d, J=4.70 Hz, 1H), 7.68 (br dd, J=2.35, 5.67 Hz, 1H), 7.27 (dd, J=8.71, 11.84 Hz, 1H), 7.07-7.22 (m, 1H), 6.10-6.41 (m, 2H), 5.48 (s, 1H), 5.36 (s, 1H), 2.61 (d, J=4.50 Hz, 3H), 2.08-2.19 (m, 1H), 1.63 (s, 3H), 1.48 (br s, 1H), 0.75 (br s, 1H).

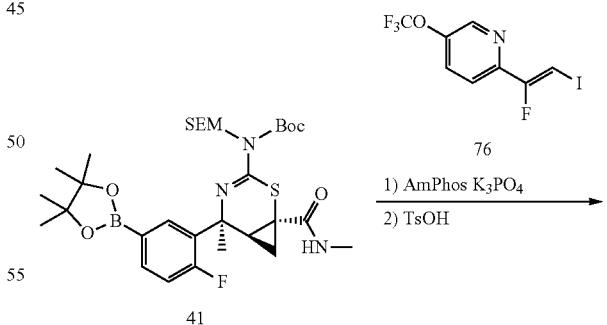

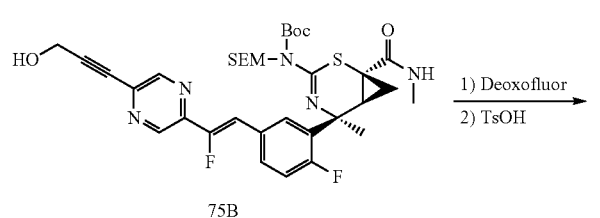

75B

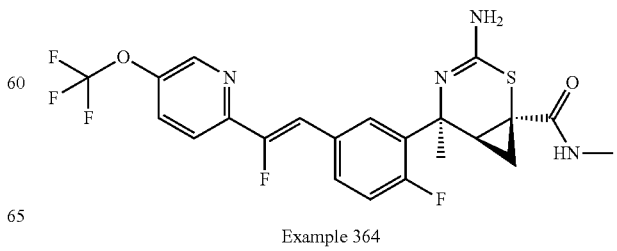

Example 364

Preparation of (1S,5S,6S)-3-Amino-5-(2-fluoro-5-((Z)-2-fluoro-2-(5-(trifluoromethoxy)pyridin-2-yl)vinyl)phenyl)-N,5-dimethyl-2-thia-4-azabicyclo[4.1.0]hept-3-ene-1-carboxamide (Example 364)

Preparation of (Z)-2-(1-fluoro-2-iodovinyl)-5-(trifluoromethoxy)pyridine (76)

Using a similar procedure described for 37, (Z)-6-(1-fluoro-2-iodovinyl)nicotinonitrile was prepared in a 5-step sequence starting from 2-bromo-5-(trifluoromethoxy)pyridine MS m/z=334 [M+H]$^+$. $^1$H NMR (400 MHz, DMSO-d$_6$) δ 8.71 (s, 1H), 8.02 (m, 1H), 7.78 (d, J=8.61 Hz, 1H), 7.16 (d, J=37.44 Hz, 1H). $^{19}$F NMR (376 MHz, DMSO-d$_6$) δ −57.16 (s, 3F), −99.23 (s, 1F).

Preparation of (1S,5S,6S)-3-amino-5-(2-fluoro-5-((Z)-2-fluoro-2-(5-(trifluoromethoxy)pyridin-2-yl)vinyl)phenyl)-N,5-dimethyl-2-thia-4-azabicyclo[4.1.0]hept-3-ene-1-carboxamide (Example 364)

Using a similar procedure described for Example 222, (Z)-2-(1-fluoro-2-iodovinyl)-5-(trifluoromethoxy)pyridine (76) (95 mg, 0.28 mmol), tert-butyl ((1S,5S,6S)-5-(2-fluoro-5-(4,4,5,5-tetramethyl-1,3,2-dioxaborolan-2-yl)phenyl)-5-methyl-1-(methylcarbamoyl)-2-thia-4-azabicyclo[4.1.0]hept-3-en-3-yl)((2-(trimethylsilyl)ethoxy)methyl)carbamate (41) (213 mg, 0.33 mmol), potassium phosphate tribasic (182 mg, 0.85 mmol), and bis-(di-tert-butyl(4-dimethylaminophenyl)phosphine)dichloropalladium(II) (Am-phos) (16 mg, 0.023 mmol) in dioxane/water=2:1 (3 mL) were reacted. The crude product was treated with 4-methylbenzenesulfonic acid hydrate (136 mg, 0.71 mmol) to afford (1S,5S,6S)-3-amino-5-(2-fluoro-5-((Z)-2-fluoro-2-(5-(trifluoromethoxy)pyridin-2-yl)vinyl)phenyl)-N,5-dimethyl-2-thia-4-azabicyclo[4.1.0]hept-3-ene-1-carboxamide (Example 364) (77 mg, 54% yield) as an off-white solid. MS m/z=499.2 [M+H]$^+$. $^1$H NMR (400 MHz, DMSO-d$_6$) δ 8.74 (d, J=2.35 Hz, 1H), 8.02 (m, 2H), 7.83 (d, J=8.22 Hz, 1H), 7.67 (m, 2H), 7.25 (m, 1H), 7.15 (s, 0.5H), 7.05 (s, 0.5H), 6.19 (br., 2H), 2.62 (d, J=4.50 Hz, 3H), 2.16 (m, 1H), 1.62 (s, 3H), 1.41 (dd, J=4.99, 9.68 Hz, 1H), 0.76 (dd, J=5.09, 7.04 Hz, 1H). $^{19}$F NMR (376 MHz, DMSO-d$_6$) δ −57.15 (s, 3F), −109.98 (s, 1F), −123.33 (s, 1F).

Table 1 contains biological activity data for the Example compounds. The data presented includes BACE1 enzyme assay, BACE1 cell assay, BACE2 enzyme assay and CatD assay, inhibitory data expressed as µM IC$_{50}$s. The assays procedures and data measurements are described hereinbelow.

TABLE 1

| Example No. | IC50 IP (µM) BACE1 Enzyme | IC50 IP (µM) BACE1 Cell | IC50 IP (µM) BACE2 Enzyme | IC50 IP (µM) CatD |
|---|---|---|---|---|
| 100 | 0.0228 | 0.26 | 0.0421 | 933.2 |
| 101 | 0.303 | 1.6 | 0.281 | 154 |
| 102 | 0.00483 | 0.0194 | 0.002 | 329 |
| 103 | 0.0012 | 0.00302 | 0.00597 | 246 |
| 104 | 0.0226 | 0.0221 | 0.144 | 185 |
| 105 | 0.0258 | 0.84 | 0.127 | 302 |
| 106 | 0.00253 | 0.00287 | 0.0143 | 147.8 |
| 107 | 0.000673 | 0.00384 | 0.0244 | 396 |
| 108 | 0.00199 | 0.00853 | 0.00292 | 518.8 |
| 109 | 0.00849 | 0.223 | 0.0615 | 138 |
| 110 | 0.00324 | 0.0127 | 0.0144 | 403.2 |
| 111 | 0.0959 | 1.57 | 0.102 | 734.3 |
| 112 | 0.00183 | 0.0236 | 0.00672 | 97.6 |
| 113 | 0.0285 | 4.23 | 0.0339 | 400 |
| 114 | 0.021 | 0.446 | 0.0555 | 667.8 |
| 115 | 0.00828 | 0.0414 | 0.00835 | 57.6 |
| 116 | 0.00623 | 0.00929 | 0.0119 | 107 |
| 117 | 0.00587 | 0.00623 | 0.0209 | 166 |
| 118 | 0.0299 | 0.291 | 0.047 | 13.4 |
| 119 | 0.0034 | 0.00406 | 0.00752 | 42.3 |
| 120 | 0.00275 | 0.0267 | 0.0108 | 132 |
| 121 | 0.00932 | 0.00728 | 0.164 | 52.9 |
| 122 | 0.00166 | 0.00502 | 0.0694 | 133 |
| 123 | 0.00136 | 0.00161 | 0.015 | 376.3 |
| 124 | 0.00173 | 0.00335 | 0.108 | 494.7 |
| 125 | 0.000592 | 0.000986 | 0.0364 | 592.3 |
| 126 | 0.000518 | 0.000789 | 0.0299 | 390.1 |
| 127 | 0.000509 | 0.00131 | 0.0519 | 131.2 |
| 128 | 0.00331 | 0.00198 | 0.0892 | 143.9 |
| 129 | 0.00117 | 0.0165 | 0.0311 | 133 |
| 130 | 0.0034 | 0.00747 | 0.121 | 120 |
| 131 | 0.00322 | 0.00884 | 0.015 | 96.9 |
| 132 | 0.00267 | 0.000655 | 0.0758 | 1687.9 |
| 133 | 0.00362 | 0.0035 | 0.099 | 146 |
| 134 | 0.0207 | 0.0011 | 0.8 | 400 |
| 135 | 0.000527 | 0.00388 | 0.00166 | 5.5 |
| 136 | 0.00582 | 0.0154 | 0.0363 | 4.18 |
| 137 | 0.00871 | 0.0196 | 0.21 | 43.2 |
| 138 | 0.00156 | 0.00117 | 0.0924 | 70.9 |
| 139 | 0.000744 | 0.000907 | 0.00257 | 81.5 |
| 140 | 0.000958 | 0.00916 | 0.0131 | 12.8 |
| 141 | 0.0575 | 0.00358 | 0.336 | 400 |
| 142 | 0.00178 | 0.00219 | 0.0173 | 400 |
| 143 | 0.00123 | 0.00159 | 0.0127 | 152 |
| 144 | 0.00177 | 0.00388 | 0.0282 | 400 |
| 145 | 0.000867 | 0.0096 | 0.0174 | 42.6 |
| 146 | 0.000863 | 0.0149 | 0.025 | 162 |
| 147 | 0.000793 | 0.003 | 0.00486 | 93.9 |
| 148 | 0.375 | 2.84 | 1.03 | 231 |
| 149 | 0.0352 | 0.883 | 0.206 | 259 |
| 150 | 0.0535 | 0.379 | 2.42 | 333 |
| 151 | 0.00577 | 0.0137 | 0.396 | 135 |
| 152 | 0.052 | 0.0846 | 1.51 | 71.8 |
| 153 | 0.00393 | 0.00237 | 0.0518 | 106 |
| 154 | 0.00798 | 0.0049 | 0.0455 | 107 |
| 155 | 0.0412 | 0.371 | 0.0823 | 167 |
| 156 | 0.0424 | 0.22 | 0.135 | 93.8 |
| 157 | 0.0127 | 0.079 | 0.0262 | 39.1 |
| 158 | 0.116 | 0.119 | 0.0927 | 400 |
| 159 | 0.000856 | 0.0166 | 0.0196 | 71.9 |
| 160 | 0.00734 | 0.0149 | 0.0891 | 311 |
| 161 | 0.0864 | 1.84 | 0.755 | 86.5 |
| 162 | 0.0173 | 0.0273 | 0.659 | 116 |
| 163 | 0.0249 | 0.291 | 0.266 | 69.7 |
| 164 | 0.0125 | 0.0497 | 0.229 | 156.3 |
| 165 | 0.00707 | 0.121 | 0.307 | 537.9 |
| 166 | 0.0171 | 0.185 | 1.72 | 146.5 |
| 167 | 0.00978 | 0.194 | 0.16 | 182.4 |
| 168 | 0.00496 | 0.0368 | 0.104 | 442.1 |
| 169 | 0.00115 | 0.00383 | 0.0174 | 95.5 |
| 170 | 0.00432 | 0.00397 | 0.00305 | 1704.9 |
| 171 | 0.102 | 0.159 | 0.642 | 823.9 |
| 172 | 0.0327 | — | 0.146 | 202 |
| 173 | 0.15 | 0.924 | 0.3 | 225 |
| 174 | 0.209 | 0.139 | 0.406 | 280 |
| 175 | 0.0121 | 0.0412 | 0.0364 | 204 |
| 176 | 0.142 | 1.76 | 0.214 | >400 |
| 177 | 0.291 | 5.44 | 2.904 | 527 |
| 178 | 0.0227 | 0.385 | 0.00574 | 609 |
| 179 | 0.112 | 4.01 | 0.041 | 168.5 |
| 180 | 0.00544 | 0.0023 | 0.023 | >400 |
| 181 | 0.0021 | 0.0073 | 0.033 | 653 |
| 182 | 0.0024 | 0.007 | 0.045 | 776 |
| 183 | 0.0165 | 0.041 | 0.241 | 2137 |
| 184 | — | 0.014 | 0.34 | 125 |
| 185 | 0.132 | 0.695 | 0.0764 | 172 |

TABLE 1-continued

| Example No. | IC50 IP (µM) BACE1 Enzyme | IC50 IP (µM) BACE1 Cell | IC50 IP (µM) BACE2 Enzyme | IC50 IP (µM) CatD |
|---|---|---|---|---|
| 186 | 0.128 | 0.575 | 0.302 | 48.7 |
| 200 | 0.001 | 0.004 | 0.118 | 89.800 |
| 201 | 0.001 | 0.009 | 0.074 | 16.700 |
| 202 | 0.001 | 0.001 | 0.040 | 47.300 |
| 203 | 0.001 | 0.001 | 0.045 | 47.700 |
| 204 | 0.001 | 0.003 | 0.048 | 38.150 |
| 205 | 0.002 | 0.569 | 0.010 | 112.910 |
| 206 | 0.010 | 0.093 | 0.008 | 12.200 |
| 207 | 0.005 | 0.335 | 0.018 | 14.600 |
| 208 | 0.309 | 0.228 | 0.117 | 9.280 |
| 209 | 0.094 | 0.324 | 0.010 | 56.000 |
| 210 | 0.011 | 0.007 | 0.072 | 159.000 |
| 211 | 0.022 | 0.247 | 0.044 | 67.750 |
| 212 | 0.076 | 0.065 | 0.077 | 202.000 |
| 213 | 0.021 | 0.039 | 0.065 | 102.550 |
| 214 | 0.014 | 0.024 | 0.072 | 133.500 |
| 215 | 0.037 | 0.262 | 0.051 | 121.000 |
| 216 | 0.007 | 0.005 | 0.072 | 390.990 |
| 217 | 0.002 | 0.002 | 0.070 | 438.420 |
| 218 | 0.010 | 0.040 | 0.033 | 156.000 |
| 219 | 0.004 | 0.005 | 0.007 | 110.000 |
| 220 | 0.011 | 0.022 | 0.002 | 26.400 |
| 221 | 0.128 | 0.575 | 0.302 | 48.650 |
| 222 | 0.0018 | 0.0017 | 0.091 | 429.3 |
| 223 | 0.0018 | 0.0022 | 0.08 | 234 |
| 224 | 0.015 | 0.031 | 0.564 | 396.280 |
| 225 | 0.027 | 0.033 | 0.621 | 197.630 |
| 226 | 0.126 | 0.608 | 0.285 | 18.500 |
| 227 | 0.0006 | 0.0105 | 0.058 | 55.1 |
| 228 | 0.0246 | 0.129 | 0.292 | 46.3 |
| 229 | 0.0147 | 0.1885 | 0.085 | 23 |
| 230 | 0.0057 | 0.231 | 0.011 | 121 |
| 231 | 0.0002 | 0.0029 | 0.03 | 47.8 |
| 232 | 0.001 | 0.0395 | 0.108 | 88.5 |
| 233 | 0.0016 | 0.0087 | 0.014 | 204 |
| 234 | 0.0059 | 0.0111 | 0.581 | 124.8 |
| 235 | 0.0022 | 0.0058 | 0.247 | 586.9 |
| 236 | 0.118 | 0.284 | 1.28 | 400 |
| 237 | 0.0032 | 0.0339 | 0.438 | 172 |
| 238 | 0.0121 | 0.0066 | 0.245 | 891.6 |
| 239 | 0.0013 | 0.0029 | 0.177 | 74.3 |
| 240 | 0.0012 | 0.0175 | 0.081 | 124 |
| 241 | 0.0004 | 0.0039 | 0.115 | 165 |
| 242 | 0.0164 | 0.0181 | 0.034 | 205 |
| 243 | 0.003 | 0.0022 | 0.043 | 412.4 |
| 244 | 0.0004 | 0.0147 | 0.055 | 150 |
| 245 | 0.005 | 0.0341 | 0.057 | 400 |
| 246 | 0.171 | 0.050 | 0.390 | 53.100 |
| 247 | 0.293 | 0.295 | 0.385 | 1192.900 |
| 248 | 0.0625 | 1.585 | 0.083 | 200 |
| 249 | 0.293 | 0.336 | 0.503 | 323 |
| 250 | 0.029 | 0.017 | 0.076 | 367.820 |
| 251 | 0.012 | 0.062 | 0.159 | 360.4 |
| 252 | 0.0509 | 0.6175 | 0.151 | 158.1 |
| 253 | 0.0054 | 0.0636 | 0.385 | 147 |
| 254 | 0.0075 | 0.0894 | 0.082 | 473.7 |
| 255 | 0.0477 | 0.5045 | 0.056 | 234.7 |
| 256 | 0.0285 | 3.575 | 0.252 | 760 |
| 257 | 0.0172 | 0.187 | 0.208 | 182 |
| 258 | 0.0119 | 0.256 | 0.118 | 90.7 |
| 259 | 0.0095 | 0.0309 | 0.113 | 1108.8 |
| 260 | 0.0289 | 0.1095 | 0.115 | 84.1 |
| 261 | 0.0248 | 0.0566 | 0.08 | 356.6 |
| 262 | 0.0114 | 0.0258 | 0.694 | 317.2 |
| 263 | 0.0179 | 0.126 | 1.84 | 492.3 |
| 264 | 0.003 | 0.026 | 0.917 | 362.8 |
| 265 | 0.503 | 1.905 | 3.86 | 1319.6 |
| 266 | 0.5905 | 1.51 | 1.58 | 408.9 |
| 267 | 0.1115 | 0.559 | 1.73 | 209 |
| 268 | 2.585 | 7.78 | 1.55 | 245 |
| 269 | 0.839 | 1.665 | 1.14 | 328.8 |
| 270 | 0.6595 | 5.125 | 1.22 | 211 |
| 271 | 0.716 | 8.925 | 1.84 | 120 |
| 272 | 3.045 | 2.53 | 4.02 | 864 |
| 273 | 1.31 | 1.375 | 5.11 | 646.6 |
| 274 | 1.9 | 4.255 | 2.19 | 181 |
| 275 | 0.2485 | 2 | 1.2 | 144 |
| 276 | 0.825 | 3.19 | 0.966 | 156 |
| 277 | 3.505 | 7.255 | 2.42 | 207 |
| 278 | 2.28 | 8.67 | 1.32 | 199 |
| 279 | 0.0012 | 0.001 | 0.176 | 42 |
| 280 | 0.0013 | 0.0016 | 0.119 | 115 |
| 281 | 0.0214 | 0.0542 | 0.164 | 269.1 |
| 282 | 0.0441 | 0.303 | 0.125 | 286.7 |
| 283 | 0.0017 | 0.0044 | 0.375 | 66.7 |
| 284 | 0.0039 | 0.0035 | 0.255 | 132.8 |
| 285 | 0.0695 | 26 | 6.35 | 316.3 |
| 286 | 0.0712 | 0.3465 | 0.069 | 570.8 |
| 287 | 0.0019 | 0.0022 | 0.04 | 205.8 |
| 288 | 0.365 | 0.133 | 0.294 | 175 |
| 289 | 0.0008 | 0.002 | 0.022 | 227 |
| 290 | 0.0158 | 0.0621 | 0.229 | 400 |
| 291 | 0.0406 | 0.3255 | 0.106 | 290.1 |
| 292 | 0.0004 | 0.0007 | 0.1 | 77 |
| 293 | 0.0165 | 0.0265 | 0.192 | 400 |
| 294 | 0.0089 | 0.0949 | 2.76 | 400 |
| 295 | 0.0008 | 0.0004 | 0.078 | 58.6 |
| 296 | 0.0119 | 0.0435 | 0.037 | 289.5 |
| 297 | 0.0009 | 0.0004 | 0.041 | 23.7 |
| 298 | 0.012 | 0.0173 | 0.108 | 400 |
| 299 | 0.0073 | 0.0063 | 0.259 | 490.7 |
| 300 | 0.0025 | 0.0066 | 0.411 | 20 |
| 301 | 0.0018 | 0.0045 | 0.309 | 177.2 |
| 302 | 0.0019 | 0.0047 | 0.109 | 8.5 |
| 303 | 0.0004 | 0.0005 | 0.093 | 34.6 |
| 304 | 0.0006 | 0.0015 | 0.29 | 48.2 |
| 305 | 1.755 | 0.793 | 0.373 | 595.220 |
| 306 | 0.002 | 0.001 | 0.111 | 16.250 |
| 307 | 0.002 | 0.002 | 0.100 | 11.000 |
| 308 | 0.0021 | 0.001 | 0.013 | 295.7 |
| 309 | 0.0006 | 0.0003 | 0.007 | 401.1 |
| 310 | 0.0009 | 0.0006 | 0.041 | 433.6 |
| 311 | 0.0018 | 0.0015 | 0.048 | 681.4 |
| 312 | 0.0012 | 0.0008 | 0.068 | 714 |
| 313 | 0.0019 | 0.0022 | 0.147 | 257 |
| 314 | 0.0047 | 0.0067 | 0.24 | 447 |
| 315 | 0.0016 | 0.0013 | 0.071 | 390.2 |
| 316 | 0.003 | 0.007 | 0.033 | 170 |
| 317 | 0.0018 | 0.007 | 0.007 | 115 |
| 318 | 0.0029 | 0.0033 | 0.051 | 108 |
| 319 | 0.0025 | 0.0017 | 0.097 | 318 |
| 320 | 0.0052 | 0.0024 | 0.039 | 292 |
| 321 | 0.0035 | 0.0027 | 0.111 | 577.5 |
| 322 | 0.0021 | 0.0026 | 0.03 | 27.8 |
| 323 | 0.0031 | 0.0026 | 0.192 | 410.8 |
| 324 | 0.0011 | 0.0031 | 0.019 | 57.3 |
| 325 | 0.0019 | 0.0042 | 0.089 | 445.5 |
| 326 | 0.0016 | 0.0022 | 0.045 | 648.4 |
| 327 | 0.0008 | 0.0003 | 0.028 | 143 |
| 328 | 0.0023 | 0.0019 | 0.085 | 40.3 |
| 329 | 0.0045 | 0.0035 | 0.124 | 73.9 |
| 330 | 0.0086 | 0.0177 | 0.239 | 138 |
| 331 | 0.0013 | 0.0032 | 0.061 | 8.9 |
| 332 | 0.0023 | 0.0026 | 0.109 | 117 |
| 333 | 0.0008 | 0.0007 | 0.053 | 434.2 |
| 334 | 0.0064 | 0.0041 | 0.146 | 19 |
| 335 | 0.0028 | 0.0026 | 0.186 | 148.2 |
| 336 | 0.0013 | 0.0005 | 0.055 | 151 |
| 337 | 0.0044 | 0.01 | 0.046 | 2.4 |
| 338 | 0.0011 | 0.0034 | 0.005 | 353.2 |
| 339 | 0.22 | 0.252 | 0.165 | 519.6 |
| 340 | 0.5448 | 0.4572 | 3.21 | 298.4 |
| 341 | 0.003 | 0.0011 | 0.024 | 6.8 |
| 342 | 0.1221 | 0.0073 | 0.7 | 400 |
| 343 | 0.0826 | 0.0031 | 0.692 | 883.5 |
| 344 | 0.0033 | 0.0285 | 0.18 | 227 |
| 345 | 0.0063 | 0.1565 | 0.52 | 88.9 |
| 346 | 1.400 | 2.195 | 0.942 | 25.500 |
| 347 | 0.006 | 0.007 | 0.165 | 62.400 |
| 348 | 0.007 | 0.008 | 0.097 | 161.550 |

TABLE 1-continued

| Example No. | IC50 IP (µM) BACE1 Enzyme | IC50 IP (µM) BACE1 Cell | IC50 IP (µM) BACE2 Enzyme | IC50 IP (µM) CatD |
|---|---|---|---|---|
| 349 | 0.003 | 0.034 | 0.253 | 78.100 |
| 350 | 0.004 | 0.040 | 0.046 | 193.000 |
| 351 | 0.306 | 0.286 | 1.560 | 52.600 |
| 352 | 0.007 | 0.006 | 0.029 | 101.000 |
| 354 | 0.013 | 0.058 | 0.412 | 26.000 |
| 353 | 0.002 | 0.014 | 0.145 | 61.044 |
| 355 | 0.010 | 0.023 | 0.069 | 141.000 |
| 356 | 0.023 | 0.154 | 0.137 | 64.050 |
| 357 | 0.015 | 0.155 | 0.430 | 29.100 |
| 358 | 0.018 | 0.256 | 0.415 | 39.800 |
| 359 | 0.233 | 1.665 | 0.794 | 26.000 |
| 360 | 0.150 | 0.636 | 0.756 | 72.500 |
| 361 | 0.058 | 1.410 | 0.490 | 34.000 |
| 362 | 0.004 | 0.104 | 0.365 | 348.510 |
| 363 | 0.010 | 1.345 | 0.152 | >400.0 |
| 364 | 0.008 | 0.025 | 0.285 | 256.000 |

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependent on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, iPrOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g., pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations, e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas IA, IB, IC, ID, and IE, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

Biological Evaluation

The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE1 and BACE2 FRET (Fluorescence Resonance Energy Transfer) Assays (Enzyme Assay Data in Table 1)

The cDNAs for both human recombinant BACE1 and 2 with C-terminal 6-His Tags were cloned into transient protein expression vectors, which were subsequently transfected into mammalian cell lines. These recombinant proteins were further purified using Ni-NTA affinity chromatography (Qiagen). The assay buffer used in these screens was 0.05M acetate, pH 4.5, 8% DMSO final, 100 uM genapol (which is a nonionic detergent, below its Critical Micelle Concentration). The Beta Secretase enzyme (0.02 nM for BACE1 and 0.64 nM for BACE2) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 590 nm).

Where available, the in-vitro BACE FRET enzyme data for each of the Examples is provided in Table 1.

In Vitro BACE1 Cell-Based Assay

The cell-based assay measures inhibition or reduction of Aβ40 in conditioned medium of test compound treated cells expressing amyloid precursor protein. Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 μg/mL in Superblock/TBS (Pierce) that was supplemented with 0.05% Tween 20 (Sigma). Optimal concentration for the detection antibody 6E10-biotinylated was 0.5 μg/mL in Superblock/TBS (Pierce) that had been supplemented with 2% normal goat serum and 2% normal mouse serum. Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin- Europium and Enhancement solutions (Perkin Elmer) and the Victor 2 multilabel counter (Perkin Elmer).

Where available, the in-vitro BACE cell based data for each of the Examples is provided in the above Table.

In Vitro Enzymatic Cathepsin D (Cat D) FRET (Fluorescence Resonance Energy Transfer) Assay Recombinant Cat D was expressed in CHO cells. The assay buffer for CatD is 0.05M citrate pH 3.5, 10% DMSO final, 5 mM CHAPS. The CatD enzyme (9 nM) is pre-incubated for one hour with inhibitors, typically in about 1 uL of DMSO according to a serial dilution, is added thereto. The assays are effectively started by the addition of different FRET substrates (20 nM for CatD) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. The CatD substrate peptide sequence is based on sequence #1 of Table 1 from Gulnik et al. FEBS Letters v413 p 379-384 1997. Proteolytic cleavage of the FRET substrate releases quenching of fluorescence (CatD excitation 500 nm and emission 580 nm).

Alternatively, a CatD assay may also be run according to the procedure described in the article, Characterization of new fluorgenic substrates for the rapid and sensitive assay of cathepsin E and cathepsin D, *J. Biochem.*, 125:1137, 1999. In addition, the CatD and cathepsin E assays are described in PCT publication WO2011069934. This WIPO publication describes BACE inhibitor compounds having an amide linker connecting two aromatic groups with extremely poor CatD and/or cathepsin E inhibitory activity (see Table 2).

Where available, the in-vitro CatD FRET assay data for each of the Examples, conducted by the first procedure, is provided in Table 1. As shown by the high micromolar CatD data (very poorly active or inactive against CatD), the compounds of the present invention possess the unexpected property of little to no ability to inhibit the activity of CatD. Thus, with this surprising selectivity profile, the compounds of the present invention are believed to minimize, reduce or completely eliminate any risk of retinal atrophy and abnormal development of the eye and of the retinal pigmented epithelium as it relates to the normal function and activity of CatD.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of Aβ levels and drug or test compound concentrations (Dovey et al., 2001, *Journal of Neurochemistry*, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of Aβ by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice. Actual vehicles used: Oral: 2% HPMC, 1% Tween80, pH 2.2

IV: 5% EtOH, 45% Propylene Glycol in 5% Dextrose

The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs. The following examples in Table 2 exhibited the following percent Aβ 40 reductions at 10 mpk (unless otherwise noted) in the CSF and brain of the rat, respectively.

TABLE 2

| Example | % Aβ 40 reduction in rat CSF at 10 mpk | % Aβ 40 reduction in rat brain at 10 mpk |
| --- | --- | --- |
| 102 | 55 | 20 |
| 103 | 62 | 33 |
| 106 | 78 | 71 |
| 122 | 67 | 44 |
| 123 | 81 | 73 |
| 124 | 77 | 71 |
| 126 | 73 | 73 |
| 127 | 73 | 76 |
| 151 | 64 | 45 |
| 222 | 70 | 62 |
| 223 | 64 | 48 |
| 227 | 60 | 75 |
| 231 | 37 | 26 |
| 234 | 53 | 48 |
| 239 | 62 | 58 |
| 241 | 45 | 47 |
| 284 | 14 | 4 |
| 292 | 70 | 75 |
| 299 | 71 | 64 |
| 301 | 48 | 41 |
| 302 | 62 | 55 |
| 307 | 67 | 59 |
| 312 | 66 | 56 |

Indications

According to the amyloid cascade hypothesis, cerebral deposition of amyloid-beta peptide (Aβ) is critical for Alzheimer's disease (AD) pathogenesis. Aβ generation is initiated when β-secretase (BACE1) cleaves the amyloid precursor protein. De Meyer et al re-affirm the believed role which the accumulation of Aβ in cerebral spinal fluid (CSF) in a subject plays in the progression of symptoms, initially revealed as mild cognitive impairment, which ultimately leads to AD. *Arch Neurol.* 67(8):949-956, 2010. Amyloid-b (Aβ) peptides generated from amyloid precursor protein (APP) by proteolytic cleavage, such as by aspartyl protease enzymes including beta-secretase (BACE) and gamma-secretase, likely play a causal role in AD pathogenesis (Tanzi and Bertram, *Cell*, (120): 545-555, 2005; Walsh and Selkoe, *Neuron*, (44): 181-193, 2004). Although the precise mechanisms of Aβ toxicity are unclear, oligomeric forms of Aβ may contribute to cognitive decline by altering synaptic structure and function (Palop and Mucke, *Nat. Neuroscience*, (13): 812-818, 2010; Selkoe, *Behavioral Brain Res.*, (192): 106-113, 2008; Shankar et al., *Nat. Medicine* (14): 837-842, 2008). Transgenic mouse models that overexpress mutant APP and produce high levels of Aβ show amyloid plaque deposition, synaptic deficits, learning and memory impairments, and other behavioral abnormalities (Games et al., *Nature*, (373): 523-527, 1995; Go tz et al., *Molecular Psychiatry* (9): 664-683, 2004; Hsia et al., *Proc. Natl. Academy of Science* USA (96): 3228-3233, 1999; Hsiao et al., *Science* (274): 99-102, 1996, citing Harris et al, *Neuron* (68): 428-441, 2010).

For more than a decade, BACE1 has been a prime target for designing drugs to prevent or treat AD. However, development of such agents has turned out to be extremely challenging, with major hurdles in cell penetration, oral bioavailability/metabolic clearance, and brain access.

MK-8931, a small molecule inhibitor of BACE (structure unknown) was tested in a two-part randomized, double-blind, placebo-controlled phase 1 clinical trial in 88 healthy individuals (18-45 years old). MK-8931 seemed to be generally well tolerated (66 patients), and no serious adverse events were reported. A major goal of the trial was to determine whether MK-8931 was able to enter the brain and block β secretase. To monitor this, biomarkers of BACE1 activity in the CSF were measured, including Aβ40 and Aβ42, as was soluble peptide APP (sAPPβ), a direct product of BACE1 cleavage of APP. MK-8931 significantly reduced CSF Aβ concentrations in a sustained and dose-dependent manner. At 36 h post-dose, a single dose of 100 mg reduced CSF Aβ40 concentrations by 75% and a single dose of 550 mg by 92%. Similar reductions of CSF concentrations of Aβ42 and sAPPβ, the BACE1-cleaved ectodomain of APP, were also observed. Vassar & Yan, *Lancet Neurology*, 13:319-329 (2014). Currently, MK-8931 is enrolling mild-to-moderate Alzheimer's Disease patients in a Ph ⅔ trial; and enrolling participants with prodromal Alzheimer's disease in a Phase III safety and efficacy trial. (US clinical trials; Merck Newsroom, 2014).

Bapineuzamab, a monoclonal amino-terminus specific anti-amyloid antibody was in Phase III clinical trials for the treatment of AD. *Alzheimer's Research & Therapy*, 1:2, 2009. Each of the known genetic causes of AD is linked to Aβ. Dementia, Down's Syndrome to APP over-production, are all believed to be linked to the deposition of Aβ on the brain. With methods for identifying brain amyloid deposition, positron emission scanning (PET) and CSF measurements of Ab42, identification of AD suffering individuals needing treatment is becoming easier and more common. It is believed that by reducing the formation of Aβ, one can begin to pre-treat AD. Vassar et al, *Journal of Neuroscience*, 29 (41): 12787-12794, 2009. One published pathway for treatment of AD is inhibition of beta-secretase. Tirrell, *Bloomberg News, The Boston Globe*, Jan. 7, 2010.

The US biotech company CoMentis has been developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma Aβ40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

Using a fragment-based chemistry strategy, Eli Lilly and company generated LY2811376 [S)-4-(2,4-difluoro-5-pyrimidin-5-yl-phenyl)-4-methyl-5,6-dihydro-4H-[1,3]thiazin-2-ylamine], an orally available non-peptidic BACE1 inhibitor that produces profound Aβ-lowering effects in animals. The biomarker changes obtained in preclinical animal models translate into man at doses of LY2811376 that were safe and well tolerated in healthy volunteers (US Ph I Clinical trial—www.clinicaltrials.gov). Prominent and long-lasting Aβ reductions in lumbar CSF were measured after oral dosing of 30 or 90 mg of LY2811376. This represents the first translation of BACE1-driven biomarker changes in CNS from preclinical animal models to man. Because of toxicology findings identified in longer-term preclinical studies, this compound is no longer progressing in clinical development. However, BACE1 remains a viable target because the adverse effects reported here were recapitulated in LY2811376-treated BACE1 KO mice and thus are unrelated to BACE1 inhibition. The magnitude and duration of central Aβ reduction obtainable with BACE1 inhibition positions this protease as a tractable small-molecule target through which to test the amyloid hypothesis in man. *Neuroscience,* 31(46):16507-16515, 2011

The compounds of the invention have been shown to modulate, and specifically inhibit the activity of the beta-secretase enzymes as shown in Table 1, thereby reducing the Aβ fragments. Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of Aβ and reducing the formation and deposition of Aβ in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject a therapeutically effective amount of a compound of the invention. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of the compounds or pharmaceutical formulation of any of the embodiments. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions in subjects.

In one embodiment, the compounds of the invention are provided for the manufacture of a medicament, or a pharmaceutical composition, for the therapeutic and/or prophylactic treatment of diseases and disorders characterized by elevated levels of β-amyloid and/or β-amyloid oligomers and/or b-amyloid plaques and further deposits, including Alzheimer's Disease (AD). In another embodiment, the invention provides compounds, in therapeutically effective amounts, for the therapeutic and/or prophylactic treatment of AD. The compounds of the invention are useful for treating various stages and degrees of AD, including without limitation, mild, moderate and severe AD. Additionally, the compounds of the invention may be used to treat prodromal patients, i.e., subjects exhibiting the biomarkers and/or hallmarks of developing AD, without exhibiting any symptoms of AD.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein.

Formulations and Method of Use

Treatment of diseases and disorders herein is intended to also include therapeutic administration of a compound of the invention, or stereoisomer, tautomer, hydrate, solvate or a pharmaceutical salt thereof, or a pharmaceutical composition of any of these to a subject (i.e., an animal such as a mammal, and in some embodiments, a human) which may be in need of preventative treatment. Treatment also encompasses prophylactic administration of a compound of the invention or stereoisomer, tautomer, hydrate, solvate or a pharmaceutical salt thereof, or a pharmaceutical composition of any of these to a subject (i.e., an animal such as mammal which ins some embodiments may be a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, or in some embodiments, between about 0.01 and about 50 mg/kg, and in still other embodiments between about 0.01 and about 30 mg/kg body weight may be appropriate. In yet other embodiments, a daily dose of between about 0.1 and about 10 mg/kg body weight may be appropriate and should be useful for all methods of use disclosed herein. The daily dose can be administered a number of times a day such as from one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise a therapeutically effective amount of a compound of the invention.

The compound(s) of the present invention may be administered by any suitable route such as in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly, intrasternally, and by infusion techniques, in dosage unit formulations containing conventional pharmaceutically acceptable excipients such as carriers, adjuvants, and vehicles.

For oral administration, the pharmaceutical composition may be in the form of, for example, a tablet, capsule, suspension or liquid. The pharmaceutical composition is typically made in the form of a dosage unit containing a particular amount of the active ingredient. Examples of such dosage units are tablets or capsules. For example, these may contain an amount of active ingredient from about 1 to 2000 mg, from about 1 to 500 mg, and from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more diluents or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other excipients and modes of administration are well and widely known in the pharmaceutical art. The active ingredient may also be administered by injection as a composition with suitable excipients including saline, dextrose, or water, and optionally comprising one or more of a cosolvent such as propylene glycol or emulsifier such as, for example, Tween 80. Such formulations may also include compounds such as a cyclodextrin (e.g. Captisol).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and in some embodiments may be from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional excipients, such as preservatives, stabilizers, wetting agents, emulsifiers, buffers etc. Tablets and pills can additionally be prepared with enteric coatings. Such compositions may also comprise excipients, such as wetting, sweetening, flavoring, and perfuming agents. Accordingly, in yet another embodiment of the present invention, there is provided a method of manufacturing a medicament, the method comprising combining an amount of a compound according to Formulas IA, IB, IC, ID, and IE with a pharmaceutically acceptable diluent to manufacture the medicament.

In yet another embodiment, the invention provides a method of manufacturing a medicament for the treatment of Alzheimer's disease, the method comprising combining an amount of a compound according to Formulas IA, IB, IC, ID, and IE with a pharmaceutically acceptable excipient to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas IA, IB, IC, ID, and IE may also be administered sequentially with other known medicinal agents. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I

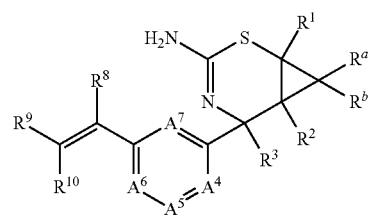

or a stereoisomer, tautomer, hydrate, solvate or a pharmaceutically acceptable salt thereof, wherein $A^4$ is $CR^4$ or N;
$A^5$ is $CR^5$ or N;
$A^6$ is $CR^6$ or N;
$A^7$ is $CR^7$ or N, provided that no more than two of $A^4$, $A^5$, $A^6$, and $A^7$ are N;
each of $R^a$ and $R^b$, independently, is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$-alkenyl, $C_{2-4}$-alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl, and —$C(O)C_{1-6}$-alkyl are optionally substituted with 1-4 substituents independently selected from F, oxo, or OH;
$R^1$ is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)NH_2$, —$CH$=$CHC(O)NH_2$, —$CH$=$CHC(O)NHC_{1-6}$-alkyl, —$CH$=$CHC(O)N(C_{1-6}$-alkyl$)_2$, —$CH$=$CHC(O)NHC_{1-6}$-alkyl-$OC_{1-6}$-alkyl, —$CH$=$CHC(O)$-heterocyclyl, —$CH$=$C(CH_3)C(O)$-heterocyclyl, —$CH$=$CHC(O)_2H$, —$CH$=$CHC(O)OC_{1-6}$-alkyl, —$CH$=$CHCH_2OH$, $C_{1-6}$-alkyl-$C(O)NHC_{1-6}$-alkyl, $C_{1-6}$-alkyl-$C(O)N(C_{1-6}$-alkyl$)_2$, —$C(O)C_{1-6}$-alkyl, —$C(O)C_{2-6}$-alkenyl, —$C(O)OH$, —$C(O)OC_{1-6}$-alkyl, —$C(O)NHC_{1-6}$-alkyl, —$C(O)N(C_{1-6}$-alkyl$)_2$, —$C(O)NHC_{3-6}$-cycloalkyl, —$C(O)NH$-aryl, —C(O)NH-heterocyclyl, —C(O)NHOC$_{1-6}$-alkyl, —C(O)N(C$_{1-6}$-alkyl)OC$_{1-6}$-alkyl, —C(O)-heterocyclyl, —CH$_2$-heteroaryl, or heteroaryl, wherein the heterocyclyl groups of the —CH=CHC(O)-heterocyclyl, —CH=C(CH$_3$)C(O)-heterocyclyl, —C(O)— heterocyclyl, and —C(O)NH-heterocyclyl groups are fully or partially saturated 3-, 4-, 5-, or 7-membered monocyclic rings or 6-, 7-, 8-, 9-, or 10-membered bicyclic rings that include 1 heteroatom selected from N, O, or S if the ring is a 3-membered ring, that include 1 or 2 heteroatoms independently selected from N, O, or S if the ring is a 4- or 5-membered ring, and include 1, 2, or 3 heteroatoms independently selected from N, O, or S if the ring is a 6-, 7-, 8-, 9-, or 10-membered ring, wherein the heteroaryl groups of the —CH$_2$-heteroaryl and heteroaryl groups is a 5- or 6-membered ring that includes 1, 2, 3, or 4 heteroatoms independently selected from N, O, or S, wherein the aryl group of the —C(O)NH-aryl group is a phenyl or naphthyl group, wherein each of the C$_{1-6}$-alkyl, C$_{2-4}$-alkenyl, C$_{2-4}$-alkynyl, and C$_{1-6}$-alkyl and C$_{2-6}$-alkenyl portions of —CH$_2$OC$_{1-6}$-alkyl, —OC$_{1-6}$-alkyl, —S(O)$_o$C$_{1-6}$-alkyl, —NHC$_{1-6}$-alkyl, C(O)C$_{1-6}$-alkyl, —C(O)C$_{2-6}$-alkenyl, —CH=CHC(O)NHC$_{1-6}$-alkyl, —C(O)NHC$_{1-6}$-alkyl, —C(O)N(C$_{1-6}$-alkyl)$_2$, and C$_{1-6}$-alkyl-C(O)NHC$_{1-6}$-alkyl groups is optionally substituted with 1-4 substituents independently selected from F, CN, oxo, or OH, and further wherein each of the heterocyclyl groups of the —CH=CHC(O)-heterocyclyl, —CH=C(CH$_3$)C(O)-heterocyclyl, —C(O)heterocyclyl, and —C(O)NH-heterocyclyl groups is optionally substituted with 1-4 substituents independently selected from methyl, F, OH, oxo, —CN, OCH$_3$, —CH$_2$OC$_{1-6}$-alkyl, —C(O)C$_{1-6}$-alkyl, —C(O)OC$_{1-6}$-alkyl, —CH$_2$OH, —NH$_2$, —NHC$_{1-6}$-alkyl, —N(C$_{1-6}$-alkyl)$_2$, —CF$_3$, phenyl, or —CH$_2$—C$_{3-6}$-cycloalkyl and further wherein each of the heteroaryl groups of the —CH$_2$-heteroaryl and heteroaryl groups and the aryl group of the —C(O)NH-aryl group is optionally substituted with 1-3 substituents independently selected from halo, methyl, or OH;

R$^2$ is H, F, Cl, C$_{1-6}$-alkyl, C$_{2-4}$-alkenyl, C$_{2-4}$-alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl, —C(O)NH$_2$, —CH=CHC(O)NHC$_{1-6}$-alkyl, —CH=CHC(O)$_2$H, —CH=CHCH$_2$OH, C$_{1-6}$-alkyl-C(O)NHC$_{1-6}$-alkyl, —C(O)C$_{1-6}$-alkyl, or —C(O)C$_{2-6}$-alkenyl, wherein each of the C$_{1-6}$-alkyl, C$_{2-4}$-alkenyl, C$_{2-4}$-alkynyl, and C$_{1-6}$-alkyl and C$_{2-6}$-alkenyl portion of —CH$_2$OC$_{1-6}$-alkyl, —OC$_{1-6}$-alkyl, —S(O)$_o$C$_{1-6}$-alkyl, —NHC$_{1-6}$-alkyl, C(O)C$_{1-6}$-alkyl, —C(O)C$_{2-6}$-alkenyl, —CH=CHC(O)NHC$_{1-6}$-alkyl, and C$_{1-6}$-alkyl-C(O)NHC$_{1-6}$-alkyl, is optionally substituted with 1-4 substituents independently selected from F, CN, oxo, or OH;

R$^3$ is C$_{1-4}$-alkyl, CH$_2$OC$_{1-4}$-alkyl, CH$_2$OH, C$_{1-4}$haloalkyl or cyclopropyl, wherein each of the C$_{1-4}$-alkyl, CH$_2$OC$_{1-4}$-alkyl, C$_{1-4}$-haloalkyl, and cyclopropyl is optionally substituted with 1-4 F atoms;

each of R$^4$, R$^5$, R$^6$ and R$^7$, independently, is H, halo, haloalkyl, haloalkoxyl, C$_{1-4}$-alkyl, CN, OH, OC$_{1-4}$-alkyl, S(O)$_o$C$_{1-4}$-alkyl, NHC$_{1-4}$-alkyl, C(O)C$_{1-4}$-alkyl, C(O)OC$_{1-4}$-alkyl, or CH$_2$OH;

R$^8$ is selected from H, F, Cl, or C$_{1-3}$-alkyl;

one of R$^9$ and R$^{10}$ is selected from F or H and the other of R$^9$ and R$^{10}$ is a fully or partially unsaturated 3-, 4-, 5-, 6-, or 7-membered monocyclic or 8-, 9-, or 10-membered bicyclic ring formed of carbon atoms, said ring optionally including 1-4 heteroatoms if monocyclic or 1-5 heteroatoms if bicyclic, said heteroatoms selected from O, N, or S, wherein the ring is optionally substituted, independently, with 1-5 substituents of R$^{11}$;

each R$^{11}$, independently, is H, halo, haloalkyl, CN, OH, NO$_2$, NH$_2$, SF$_5$, acetyl, —C(O)NHC$_{1-6}$-alkyl, —OCH$_2$C(O)NHC$_{1-6}$-alkyl, —OCH$_2$C(O)N(C$_{1-6}$-alkyl)$_2$, —OCH$_2$CH$_2$-pyrrolidinonyl, oxo, cyclopropylmethoxy, 2-propynyloxy, 2-butynyloxy, 2-pentyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, morpholinyl, pyrazolyl, isoxazolyl, dihydropyranyl, pyrrolyl, pyrrolidinyl, piperazinyl, oxetan-3-yl, imidazo-pyridinyl, dioxolyl, or —OCH$_2$-heteroaryl, wherein the heteroaryl group of the —OCH$_2$-heteroaryl group is a 5- or 6-membered ring that includes 1, 2, 3, or 4 heteroatoms selected from N, O, or S, and further wherein each of the cyclopropylmethoxy, 2-propynyloxy, 2-butynyloxy, 2-pentyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, morpholinyl, pyrazolyl, isoxazolyl, dihydropyranyl, pyrrolidinyl, oxetan-3-yl, dioxolyl, or —OCH$_2$-heteroaryl is optionally substituted independently with 1-5 substituents of F, Cl, Br, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, trimethylsilyl, cyclopentyl, cyclohexyl, C$_{1-3}$alkylamino-, C$_{1-3}$dialkylamino, C$_{1-3}$thioalkoxyl, oxazolyl, isoxazolyl, thiazolyl, isothiazolyl, thiadiazolyl, thienyl, furyl, pyrrolyl, tetrahydropyranyl, pyrrolidinyl, or oxetan-3yl; and the subscript o is selected from 0, 1, or 2.

2. The compound according to claim 1, or the stereoisomer, tautomer, hydrate, solvate or the pharmaceutically acceptable salt thereof, wherein the compound of Formula I is a compound of Formula IA

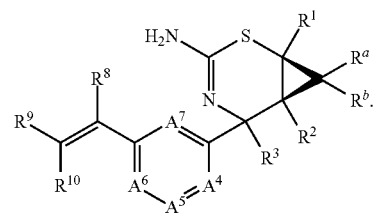

3. The compound according to claim 1, or the stereoisomer, tautomer, hydrate, solvate or the pharmaceutically acceptable salt thereof, wherein the compound of Formula I is a compound of Formula IB

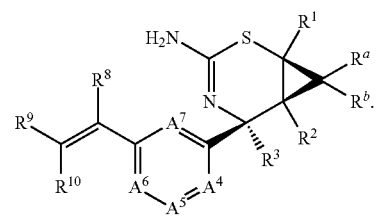

4. The compound according to claim 1, or the stereoisomer, tautomer, hydrate, solvate or the pharmaceutically acceptable salt thereof, wherein $R^a$ and $R^b$ are both —H.

5. The compound according to claim 1, or the stereoisomer, tautomer, hydrate, solvate or the pharmaceutically acceptable salt thereof, wherein $R^2$ is —H.

6. The compound according to claim 1, or the stereoisomer, tautomer, hydrate, solvate or the pharmaceutically acceptable salt thereof, wherein $A^6$ is $CR^6$ and $R^6$ is —H.

7. The compound according to claim 1, or the stereoisomer, tautomer, hydrate, solvate or the pharmaceutically acceptable salt thereof, wherein $A^7$ is $CR^7$ and $R^7$ is —H.

8. The compound according to claim 1, or the stereoisomer, tautomer, hydrate, solvate or the pharmaceutically acceptable salt thereof, wherein $A^4$ is $CR^4$.

9. The compound according to claim 8, or the stereoisomer, tautomer, hydrate, solvate or the pharmaceutically acceptable salt thereof, wherein $R^4$ is —H.

10. The compound according to claim 8, or the stereoisomer, tautomer, hydrate, solvate or the pharmaceutically acceptable salt thereof, wherein $R^4$ is —F.

11. The compound according to claim 8, or the stereoisomer, tautomer, hydrate, solvate or the pharmaceutically acceptable salt thereof, wherein $R^4$ is —$OCH_3$.

12. The compound according to claim 1, or the stereoisomer, tautomer, hydrate, solvate or the pharmaceutically acceptable salt thereof, wherein $R^8$ is —H.

13. The compound according to claim 1, or the stereoisomer, tautomer, hydrate, solvate or the pharmaceutically acceptable salt thereof, wherein $R^8$ is —F.

14. The compound according to claim 1, or the stereoisomer, tautomer, hydrate, solvate or the pharmaceutically acceptable salt thereof, wherein $R^3$ is selected from $C_{1-4}$-alkyl or $C_{1-4}$-haloalkyl.

15. The compound according to claim 1, or the stereoisomer, tautomer, hydrate, solvate or the pharmaceutically acceptable salt thereof, wherein $R^3$ is selected from —$CH_3$ or —$CH_2F$.

16. The compound according to claim 1, or the stereoisomer, tautomer, hydrate, solvate or the pharmaceutically acceptable salt thereof, wherein $A^5$ is $CR^5$.

17. The compound according to claim 16, or the stereoisomer, tautomer, hydrate, solvate or the pharmaceutically acceptable salt thereof, wherein $R^5$ is —H.

18. The compound according to claim 1, or the stereoisomer, tautomer, hydrate, solvate or the pharmaceutically acceptable salt thereof, wherein $A^5$ is N.

19. The compound according to claim 1, or the stereoisomer, tautomer, hydrate, solvate or the pharmaceutically acceptable salt thereof, wherein one of $R^9$ and $R^{10}$ is —F.

20. The compound according to claim 1, or the stereoisomer, tautomer, hydrate, solvate or the pharmaceutically acceptable salt thereof, wherein $R^1$ is selected from substituted or unsubstituted —$CH_2OC_{1-6}$-alkyl, substituted or unsubstituted —$S(O)_oC_{1-6}$-alkyl, —$C(O)NH_2$, substituted or unsubstituted —$C(O)C_{1-6}$-alkyl, substituted or unsubstituted —$C(=O)NHC_{1-6}$-alkyl, substituted or unsubstituted —$C(=O)N(C_{1-6}$-alkyl$)_2$, or substituted or unsubstituted —$C(O)$-heterocyclyl.

21. The compound according to claim 1, or the stereoisomer, tautomer, hydrate, solvate or the pharmaceutically acceptable salt thereof, wherein $R^1$ is selected from

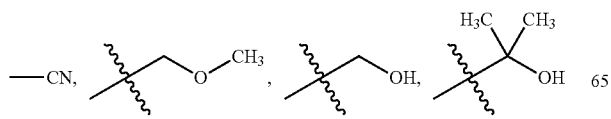

-continued

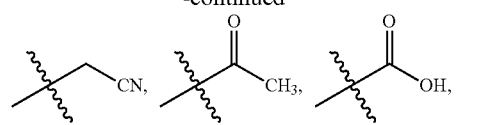

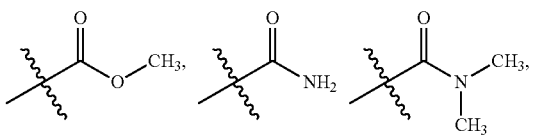

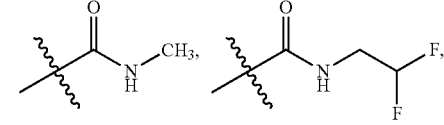

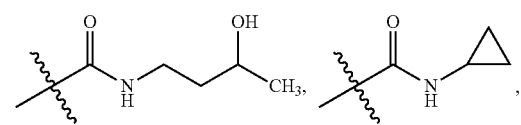

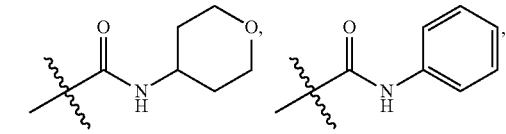

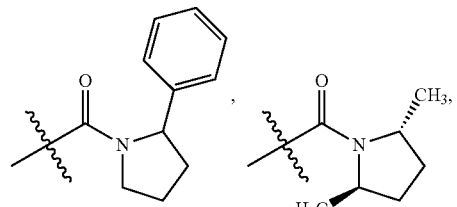

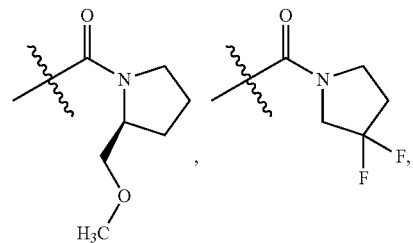

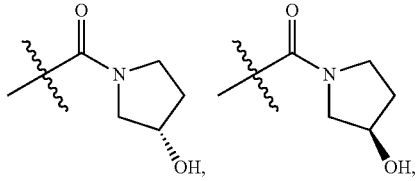

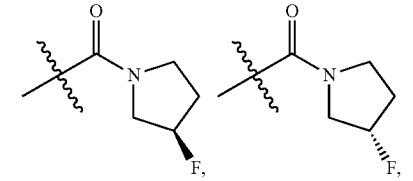

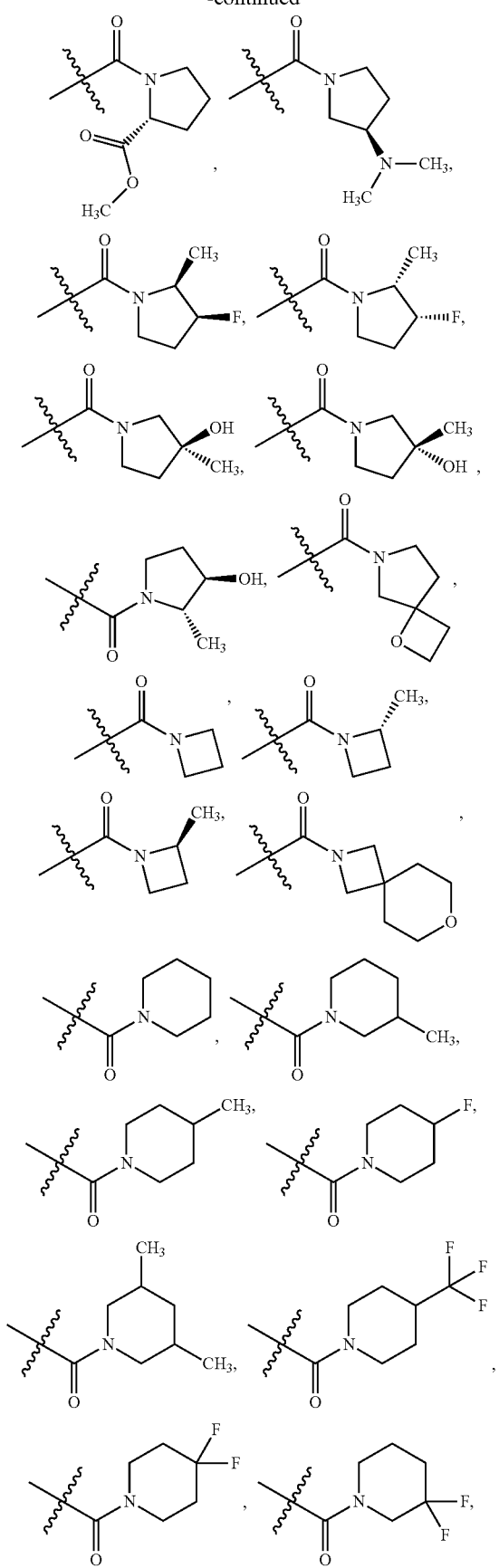
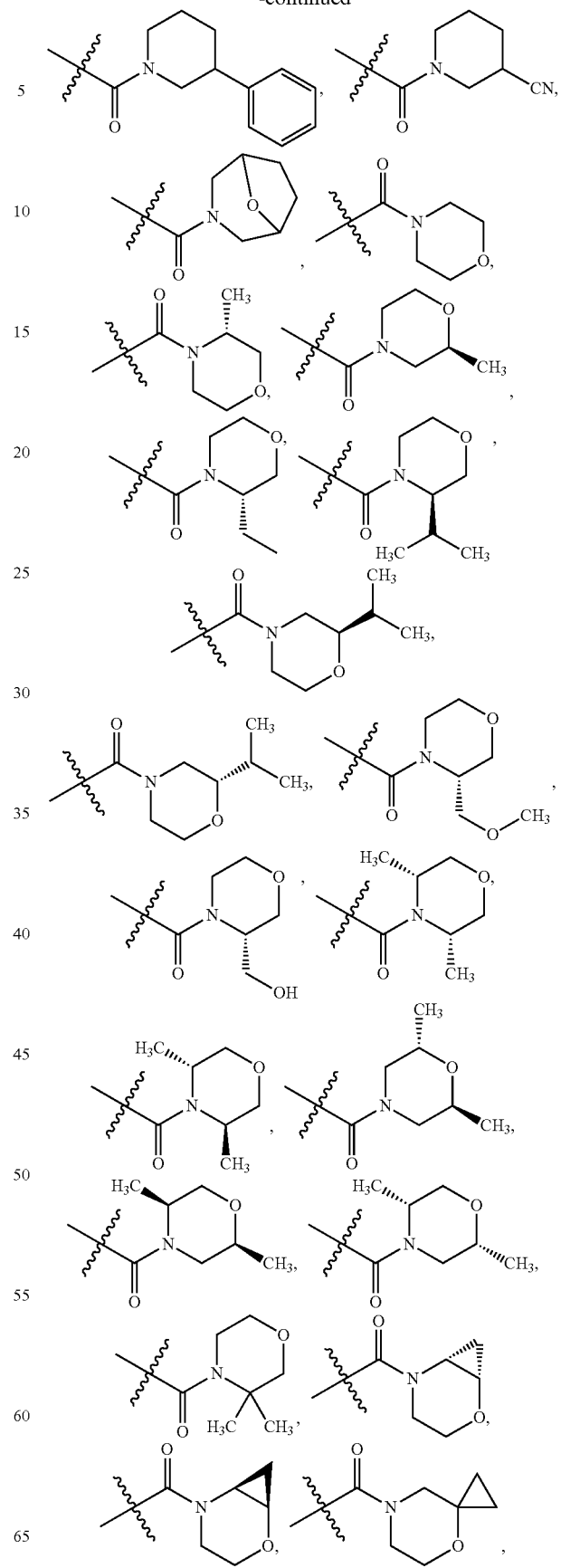

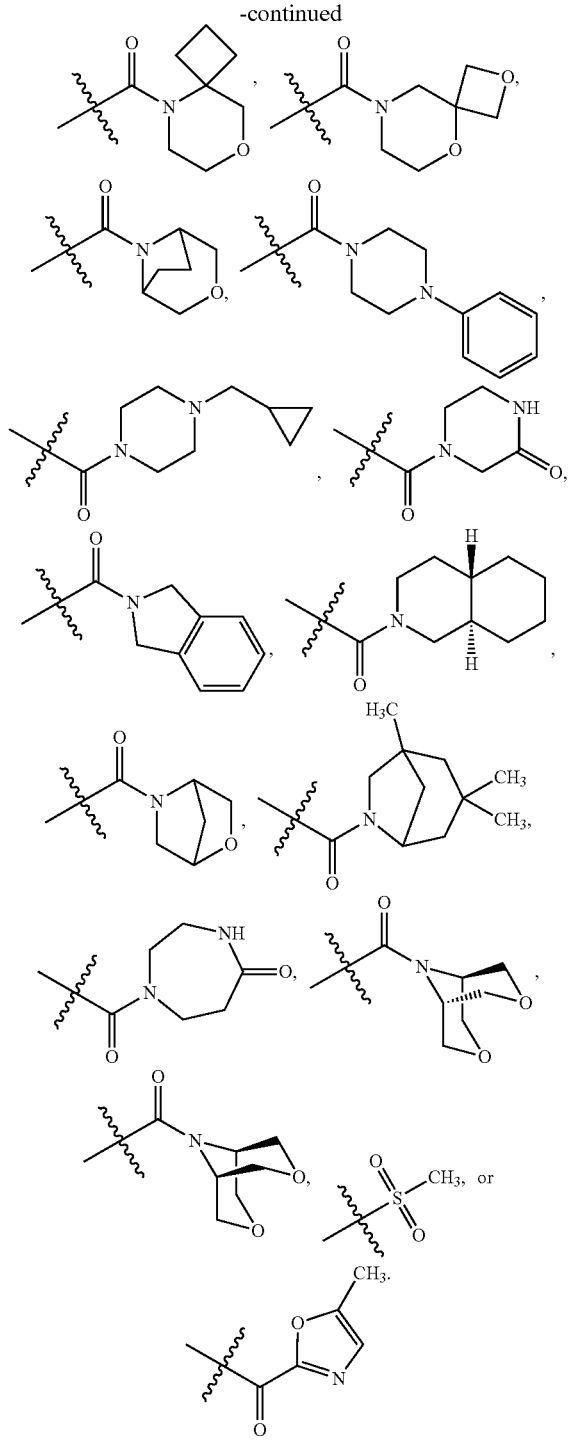
22. The compound according to claim 1, or the stereoisomer, tautomer, hydrate, solvate or the pharmaceutically acceptable salt thereof, wherein one of $R^9$ and $R^{10}$ is —F and the other of $R^9$ and $R^{10}$ is selected from
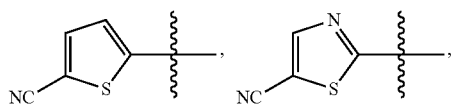
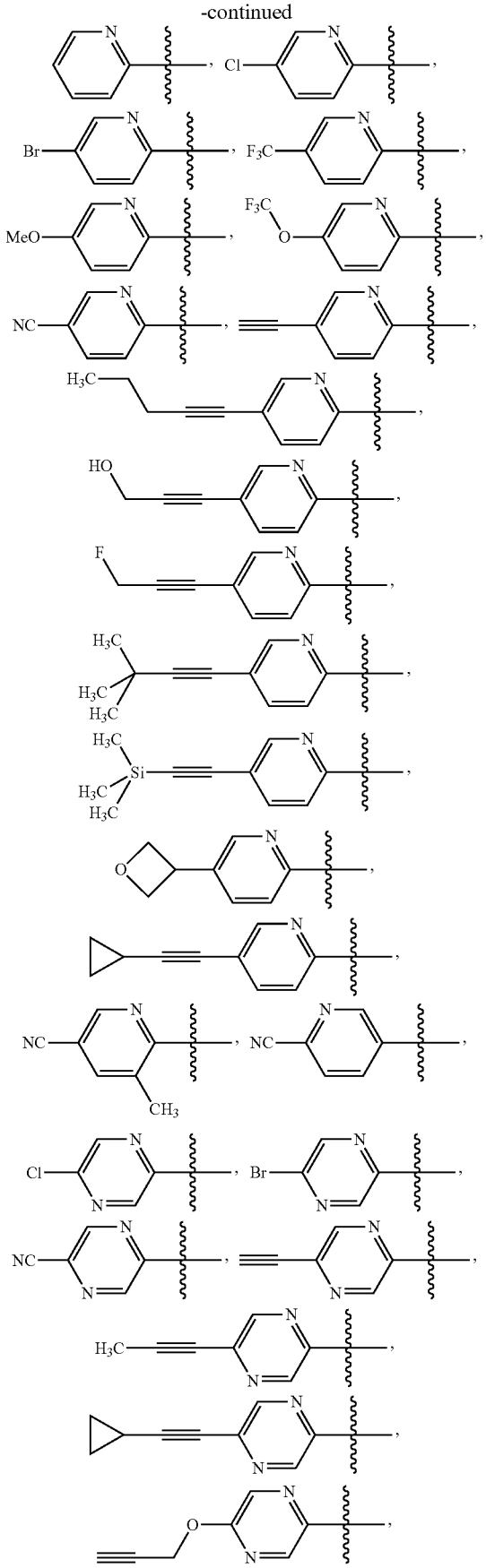

-continued
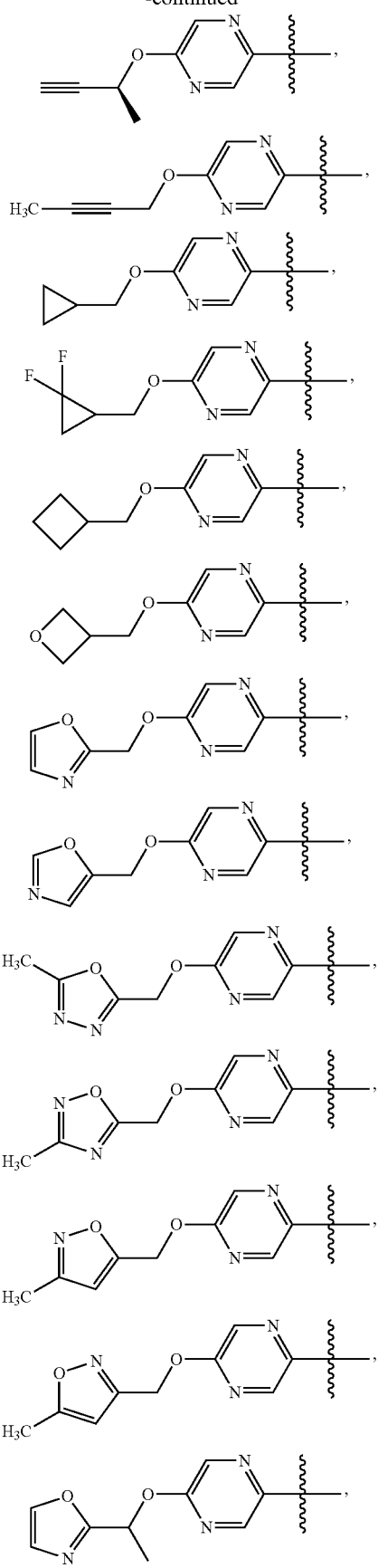
-continued
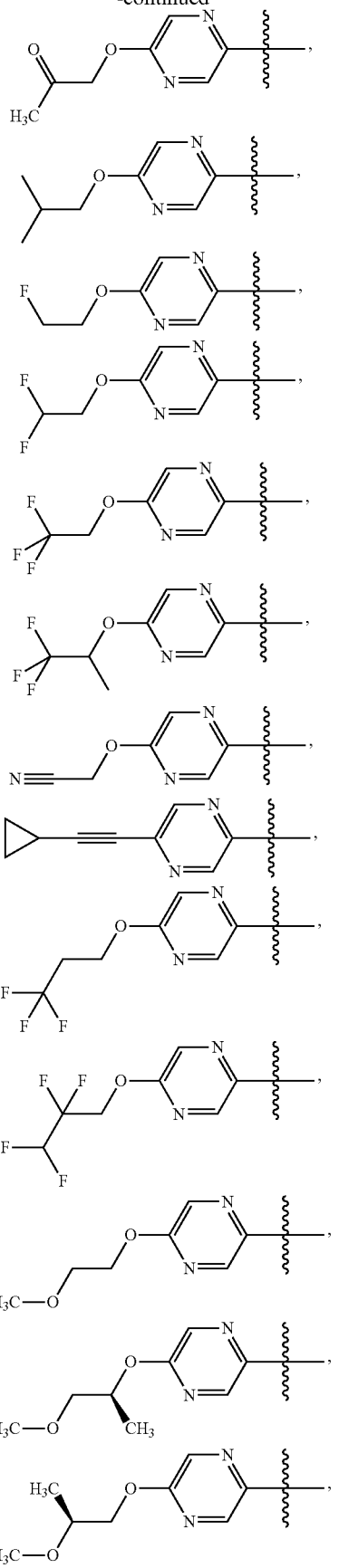

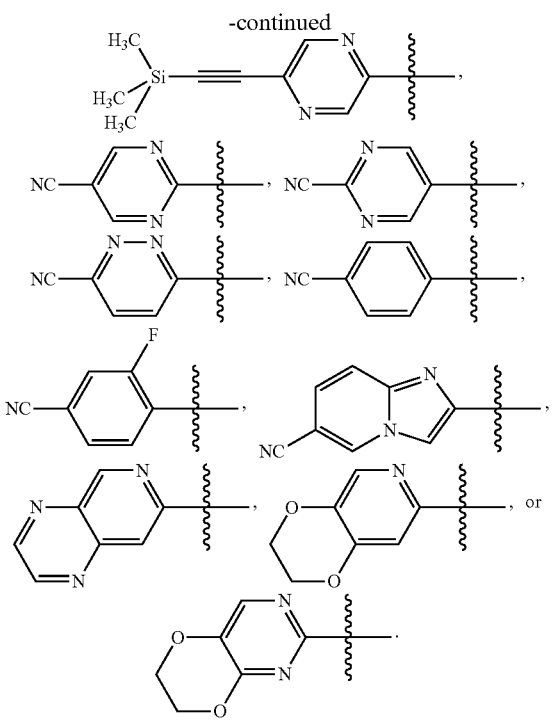

23. The compound according to claim 22, or the stereoisomer, tautomer, hydrate, solvate or the pharmaceutically acceptable salt thereof, wherein $R^{10}$ is —F.

24. The compound according to claim 1, or the stereoisomer, tautomer, hydrate, solvate or the pharmaceutically acceptable salt thereof, wherein one of $R^9$ and $R^{10}$ is —F and the other of $R^9$ and $R^{10}$ is selected from a substituted or unsubstituted thienyl, a substituted or unsubstituted thiazolyl, a substituted or unsubstituted pyridinyl, a substituted or unsubstituted pyrazinyl, a substituted or unsubstituted pyrimidinyl, a substituted or unsubstituted pyridazinyl, a substituted or unsubstituted phenyl, a substituted or unsubstituted imidazo[1,2-a]pyridinyl, a substituted or unsubstituted pyrido[3,4-b]pyrazinyl, a substituted or unsubstituted 2,3-dihydro-[1,4]dioxino[2,3-c]pyridinyl, or a substituted or unsubstituted 6,7-dihydro-[1,4]dioxino[2,3-d]pyrimidinyl group.

25. The compound according to claim 24, or the stereoisomer, tautomer, hydrate, solvate or the pharmaceutically acceptable salt thereof, wherein the substituted or unsubstituted thienyl, substituted or unsubstituted thiazolyl, substituted or unsubstituted pyridinyl, substituted or unsubstituted pyrazinyl, substituted or unsubstituted pyrimidinyl, substituted or unsubstituted pyridazinyl, substituted or unsubstituted phenyl, substituted or unsubstituted imidazo[1,2-a]pyridinyl, substituted or unsubstituted pyrido[3,4-b]pyrazinyl, substituted or unsubstituted 2,3-dihydro-[1,4]dioxino[2,3-c]pyridinyl, or substituted or unsubstituted 6,7-dihydro-[1,4]dioxino[2,3-d]pyrimidinyl of the $R^9$ or $R^{10}$ groups are independently substituted with 1-3 substituents selected from —Cl, —Br, —F, —CN, cyclopropylmethoxy, 2-propynyloxy, 2-butynyloxy, $C_{1-6}$-alkyl, $C_{2-6}$-alkynyl, $C_{1-6}$-alkoxy, oxetan-3-yl, or —O—$CH_2$-heteroaryl, and further wherein each of the 2-propynyloxy, $C_{1-6}$-alkyl, $C_{2-6}$-alkynyl, $C_{1-6}$-alkoxy, or —O—$CH_2$-heteroaryl is optionally substituted independently with 1-5 substituents of F, CN, OH, oxo, methyl, cyclopropyl, cyclobutyl, trimethylsilyl, or oxetanyl.

26. The compound according to claim 24, or the stereoisomer, tautomer, hydrate, solvate or the pharmaceutically acceptable salt thereof, wherein $R^{10}$ is —F.

27. The compound according to claim 1, or the stereoisomer, tautomer, hydrate, solvate or the pharmaceutically acceptable salt thereof, wherein the compound of Formula I is a compound of Formula IC

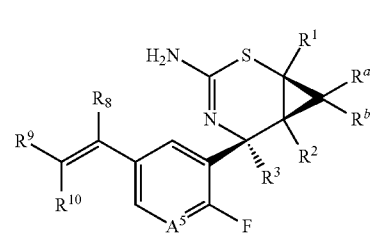

IC wherein
$A^5$ is $CR^5$ or N;
$R^a$ is —H;
$R^b$ is —H;
$R^2$ is —H;
$R^3$ is selected from $C_{1-4}$-alkyl or $C_{1-4}$-haloalkyl; and
$R^8$ is —H.

28. The compound according to claim 1, or the stereoisomer, tautomer, hydrate, solvate or the pharmaceutically acceptable salt thereof, wherein the compound of Formula I is a compound of Formula ID

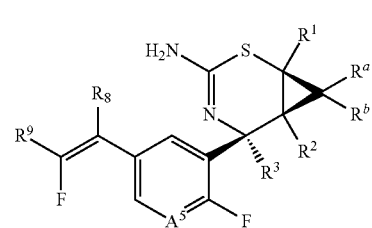

ID wherein
$A^5$ is $CR^5$ or N;
$R^a$ is —H;
$R^b$ is —H;
$R^2$ is —H;
$R^3$ is selected from $C_{1-4}$-alkyl or $C_{1-4}$-haloalkyl; and
$R^8$ is —H.

29. The compound according to claim 1, or the stereoisomer, tautomer, hydrate, solvate or the pharmaceutically acceptable salt thereof, wherein the compound of Formula I is a compound of Formula IE

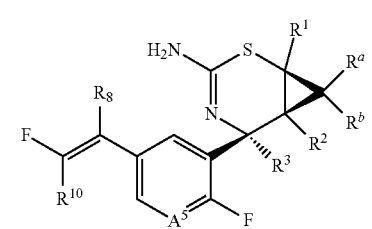

IE wherein
$A^5$ is $CR^5$ or N;
$R^a$ is —H;

R$^b$ is —H;
R$^2$ is —H;
R$^3$ is selected from C$_{1-4}$-alkyl or C$_{1-4}$-haloalkyl; and
R$^8$ is —H.

30. The compound of claim 1, or a pharmaceutically acceptable salt thereof, selected from
(1S,5S,6S)-5-(5-((Z)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine;
(1S,5S,6S)-5-(5-((E)-2-(5-chloropyridin-2-yl)-2-fluorovinyl)-2-fluorophenyl)-5-(fluoromethyl)-1-(methoxymethyl)-2-thia-4-azabicyclo[4.1.0]hept-3-en-3-amine;
(1S,5S,6S)-3-amino-5-(5-((Z)-2-(5-chloropyridin-2-yl)-2-fluorovinyl)-2-fluorophenyl)-N,N,5-trimethyl-2-thia-4-azabicyclo[4.1.0]hept-3-ene-1-carboxamide;
((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(pyrrolidin-1-yl)methanone;
((1S,5S,6S)-3-amino-5-(2-fluoro-5-((Z)-2-fluoro-2-(5-methoxypyridin-2-yl)vinyl)phenyl)-5-methyl-2-thia-4-azabicyclo[4.1.0]hept-3-en-1-yl)(pyrrolidin-1-yl)methanone;
(1S,5S,6S)-methyl 3-amino-5-(5-((Z)-2-(5-bromopyridin-2-yl)-2-fluorovinyl)-2-fluorophenyl)-5-methyl-2-thia-4-azabicyclo[4.1.0]hept-3-ene-1-carboxylate;
(1S,5S,6S)-3-amino-5-(5-((Z)-2-(5-cyanopyridin-2-yl)-2-fluorovinyl)-2-fluorophenyl)-N,N,5-trimethyl-2-thia-4-azabicyclo[4.1.0]hept-3-ene-1-carboxamide;
6-((Z)-2-(3-((1S,5S,6S)-3-amino-5-methyl-1-(pyrrolidine-1-carbonyl)-2-thia-4-azabicyclo[4.1.0]hept-3-en-5-yl)-4-fluorophenyl)-1-fluorovinyl)nicotinonitrile;
(1S,5S,6S)-3-amino-5-(5-((Z)-2-(5-bromopyridin-2-yl)-2-fluorovinyl)-2-fluorophenyl)-N,N,5-trimethyl-2-thia-4-azabicyclo[4.1.0]hept-3-ene-1-carboxamide;
(1S,5S,6S)-3-amino-5-(5-((Z)-2-(5-(cyclopropylethynyl)pyridin-2-yl)-2-fluorovinyl)-2-fluorophenyl)-N,N,-trimethyl-2-thia-4-azabicyclo[4.1.0]hept-3-ene-1-carboxamide;
(1S,5S,6S)-3-amino-5-(5-((Z)-2-(5-ethynylpyridin-2-yl)-2-fluorovinyl)-2-fluorophenyl)-N,N,5-trimethyl-2-thia-4-azabicyclo[4.1.0]hept-3-ene-1-carboxamide;
(1S,5S,6S)-methyl 3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxylate;
((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(azetidin-1-yl)methanone;
((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)methanol;
2-((1R,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)acetonitrile;
(1S,5S,6S)-3-amino-5-(5-((Z)-2-(5-chloropyridin-2-yl)-2-fluorovinyl)-2-fluorophenyl)-N-(3-hydroxybutyl)-5-methyl-2-thia-4-azabicyclo[4.1.0]hept-3-ene-1-carboxamide;
((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)(2-methylazetidin-1-yl)methanone;
((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((S)-2-(methoxymethyl)pyrrolidin-1-yl)methanone;
(1S,5S,6S)-3-amino-5-(5-((Z)-2-(5-chloropyridin-2-yl)-2-fluorovinyl)-2-fluorophenyl)-5-methyl-N-phenyl-2-thia-4-azabicyclo[4.1.0]hept-3-ene-1-carboxamide;
((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((S)-2-methylazetidin-1-yl)methanone;
((1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-en-1-yl)((R)-2-methylazetidin-1-yl)methanone;
(1S,5S,6S)-3-amino-5-(5-((Z)-2-(5-cyanopyridin-2-yl)-2-fluorovinyl)-2-fluorophenyl)-N-cyclopropyl-5-methyl-2-thia-4-azabicyclo[4.1.0]hept-3-ene-1-carboxamide;
6-((Z)-2-(3-((1S,5S,6S)-3-amino-1-(3,3-difluoropyrrolidine-1-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-(azetidine-1-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-((S)-3-hydroxypyrrolidine-1-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-((R)-3-fluoropyrrolidine-1-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-((S)-3-fluoropyrrolidine-1-carbonyl)-5-methyl-2-thia-4-azabicyclo[4.1.0]hept-3-en-5-yl)-4-fluorophenyl)-1-fluorovinyl)nicotinonitrile;
(1S,5S,6S)-3-amino-5-(5-((Z)-2-(5-cyanopyridin-2-yl)-2-fluorovinyl)-2-fluorophenyl)-5-methyl-N-(tetrahydro-2H-pyran-4-yl)-2-thia-4-azabicyclo[4.1.0]hept-3-ene-1-carboxamide;
6-((Z)-2-(3-((1S,5S,6S)-3-amino-1-(isoindoline-2-carbonyl)-5-methyl-2-thia-4-azabicyclo[4.1.0]hept-3-en-5-yl)-4-fluorophenyl)-1-fluorovinyl)nicotinonitrile;
(R)-methyl 1-((1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carbonyl)pyrrolidine-2-carboxylate;
6-((Z)-2-(3-((1S,5S,6S)-3-amino-5-methyl-1-(4-phenylpiperazine-1-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-(2-oxa-5-azabicyclo[2.2.1]heptane-5-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-((2R,5R)-2,5-dimethylpyrrolidine-1-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-((R)-3-(dimethylamino)pyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((4aS,8aR)-decahydroisoquinoline-2-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(1,3,3-trimethyl-6-azabicyclo[3.2.1]octane-6-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-(3,5-dimethylpiperidine-1-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(2-methylpyrrolidine-1-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(4-(trifluoromethyl)piperidine-1-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(3-phenylpiperidine-1-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-(4-(cyclopropylmethyl)piperazine-1-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(5-oxo-1,4-diazepane-1-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-1-(3-cyanopiperidine-1-carbonyl)-5-methyl-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(3-oxopiperazine-1-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(3-methylpiperidine-1-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(piperidine-1-carbonyl)-2-thia-4-azabicyclo[4.1.0]hept-3-en-5-yl)-4-fluorophenyl)-1-fluorovinyl)nicotinonitrile;
6-((Z)-2-(3-((1S,5S,6S)-3-amino-5-methyl-1-(4-methylpiperidine-1-carbonyl)-2-thia-4-azabicyclo[4.1.0]hept-3-en-5-yl)-4-fluorophenyl)-1-fluorovinyl)nicotinonitrile;
(1S,5S,6S)-methyl 3-amino-5-(5-((Z)-2-(5-bromopyrazin-2-yl)-2-fluorovinyl)-2-fluorophenyl)-5-methyl-2-thia-4-azabicyclo[4.1.0]hept-3-ene-1-carboxylate;
(1S,5S,6S)-methyl 3-amino-5-(5-((Z)-2-(5-chloropyrazin-2-yl)-2-fluorovinyl)-2-fluorophenyl)-5-methyl-2-thia-4-azabicyclo[4.1.0]hept-3-ene-1-carboxylate;
(1S,5S,6S)-methyl 3-amino-5-(2-fluoro-5-((Z)-2-fluoro-2-(5-(oxazol-2-ylmethoxy)pyrazin-2-yl)vinyl)phenyl)-5-methyl-2-thia-4-azabicyclo[4.1.0]hept-3-ene-1-carboxylate;
(1S,5S,6S)-3-amino-5-(2-fluoro-5-((Z)-2-fluoro-2-(5-(prop-2-yn-1-yloxy)pyrazin-2-yl)vinyl)phenyl)-N,5-dimethyl-2-thia-4-azabicyclo[4.1.0]hept-3-ene-1-carboxamide;
(1S,5S,6S)-3-amino-5-(2-fluoro-5-((Z)-2-fluoro-2-(5-(2-oxopropoxy)pyrazin-2-yl)vinyl)phenyl)-N,5-dimethyl-2-thia-4-azabicyclo[4.1.0]hept-3-ene-1-carboxamide;
(1S,5S,6S)-3-amino-5-(2-fluoro-5-((Z)-2-fluoro-2-(5-(prop-2-yn-1-yloxy)pyrazin-2-yl)vinyl)phenyl)-N,N,5-trimethyl-2-thia-4-azabicyclo[4.1.0]hept-3-ene-1-carboxamide;
(1S,5S,6S)-3-amino-5-(2-fluoro-5-((Z)-2-fluoro-2-(5-(oxazol-2-ylmethoxy)pyrazin-2-yl)vinyl)phenyl)-N,N,-trimethyl-2-thia-4-azabicyclo[4.1.0]hept-3-ene-1-carboxamide;
(1S,5S,6S)-3-amino-5-(2-fluoro-5-((Z)-2-fluoro-2-(5-(2,2,2-trifluoroethoxy)pyrazin-2-yl)vinyl)phenyl)-N,N,-trimethyl-2-thia-4-azabicyclo[4.1.0]hept-3-ene-1-carboxamide;
(1S,5S,6S)-3-amino-5-(2-fluoro-5-((Z)-2-fluoro-2-(5-(-1-(oxazol-2-yl)ethoxy)pyrazin-2-yl)vinyl)phenyl)-N,N,-trimethyl-2-thia-4-azabicyclo[4.1.0]hept-3-ene-1-carboxamide;
(1S,5S,6S)-3-amino-5-(5-((Z)-2-(5-bromopyrazin-2-yl)-2-fluorovinyl)-2-fluorophenyl)-N,N,5-trimethyl-2-thia-4-azabicyclo[4.1.0]hept-3-ene-1-carboxamide;
(1S,5S,6S)-3-amino-5-(5-((Z)-2-(5-(cyanomethoxy)pyrazin-2-yl)-2-fluorovinyl)-2-fluorophenyl)-N,N,-trimethyl-2-thia-4-azabicyclo[4.1.0]hept-3-ene-1-carboxamide;
(1S,5S,6S)-3-amino-5-(5-((Z)-2-(5-(cyclopropylethynyl)pyrazin-2-yl)-2-fluorovinyl)-2-fluorophenyl)-N,N,-trimethyl-2-thia-4-azabicyclo[4.1.0]hept-3-ene-1-carboxamide;
6-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)-5-methylnicotinonitrile;
(1S,5S,6S)-3-amino-5-(2-fluoro-5-((Z)-2-fluoro-2-(5-(2,2,3,3-tetrafluoropropoxy)pyrazin-2-yl)vinyl)phenyl)-N,5-dimethyl-2-thia-4-azabicyclo[4.1.0]hept-3-ene-1-carboxamide;
(1S,5S,6S)-3-amino-5-(2-fluoro-5-((Z)-2-fluoro-2-(5-(oxazol-2-ylmethoxy)pyrazin-2-yl)vinyl)phenyl)-N,5-dimethyl-2-thia-4-azabicyclo[4.1.0]hept-3-ene-1-carboxamide;
(1S,5S,6S)-3-amino-5-(5-((Z)-2-(5-bromopyrazin-2-yl)-2-fluorovinyl)-2-fluorophenyl)-N,5-dimethyl-2-thia-4-azabicyclo[4.1.0]hept-3-ene-1-carboxamide;
(1S,5S,6S)-3-amino-5-(2-fluoro-5-((Z)-2-fluoro-2-(5-(prop-1-yn-1-yl)pyrazin-2-yl)vinyl)phenyl)-N,5-dimethyl-2-thia-4-azabicyclo[4.1.0]hept-3-ene-1-carboxamide;
(1S,5S,6S)-3-amino-5-(5-((Z)-2-(5-(cyclopropylethynyl)pyrazin-2-yl)-2-fluorovinyl)-2-fluorophenyl)-N,5-dimethyl-2-thia-4-azabicyclo[4.1.0]hept-3-ene-1-carboxamide;
(1S,5S,6S)-3-amino-5-(2-fluoro-5-((Z)-2-fluoro-2-(5-((trimethyl silyl)ethynyl)pyrazin-2-yl)vinyl)phenyl)-N,5-dimethyl-2-thia-4-azabicyclo[4.1.0]hept-3-ene-1-carboxamide;
(1S,5S,6S)-3-amino-5-(5-((Z)-2-(5-ethynylpyrazin-2-yl)-2-fluorovinyl)-2-fluorophenyl)-N,5-dimethyl-2-thia-4-azabicyclo[4.1.0]hept-3-ene-1-carboxamide;
(1S,5S,6S)-3-amino-5-(5-((Z)-2-(4-cyanophenyl)-2-fluorovinyl)-2-fluorophenyl)-N,N,5-trimethyl-2-thia-4-azabicyclo[4.1.0]hept-3-ene-1-carboxamide;
(1S,5S,6S)-3-amino-5-(5-((Z)-2-(5-cyanopyrazin-2-yl)-2-fluorovinyl)-2-fluorophenyl)-N,N,5-trimethyl-2-thia-4-azabicyclo[4.1.0]hept-3-ene-1-carboxamide;
(1S,5S,6S)-3-amino-5-(5-((Z)-2-(5-cyanopyrimidin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(6-cyanopyridin-3-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(4-cyano-2-fluorophenyl)-2-fluorovinyl)-2-fluorophenyl)-N,N,-trimethyl-2-thia-4-azabicyclo[4.1.0]hept-3-ene-1-carboxamide;

(1S,5S,6S)-3-amino-5-(5-((Z)-2-(2-cyanopyrimidin-5-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(6-cyanopyridazin-3-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-chloropyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-methyl 3-amino-5-(5-((Z)-2-(5-chloropyridin-2-yl)-2-fluorovinyl)-2-fluoropyridin-3-yl)-5-methyl-2-thia-4-azabicyclo[4.1.0]hept-3-ene-1-carboxylate;

(1S,5S,6S)-methyl 3-amino-5-(5-((E)-2-(5-chloropyridin-2-yl)-2-fluorovinyl)-2-fluoropyridin-3-yl)-5-methyl-2-thia-4-azabicyclo[4.1.0]hept-3-ene-1-carboxylate;

(1S,5S,6S)-3-amino-5-(5-((Z)-2-(5-chloropyridin-2-yl)-2-fluorovinyl)-2-fluoropyridin-3-yl)-N,N,5-trimethyl-2-thia-4-azabicyclo[4.1.0]hept-3-ene-1-carboxamide;

(1S,5S,6S)-3-amino-5-(5-((E)-2-(5-chloropyridin-2-yl)-2-fluorovinyl)-2-fluoropyridin-3-yl)-N,N,5-trimethyl-2-thia-4-azabicyclo[4.1.0]hept-3-ene-1-carboxamide;

(1S,5S,6S)-3-amino-5-(5-((Z)-2-(5-cyanopyridin-2-yl)-2-fluorovinyl)-2-fluoropyridin-3-yl)-N,N,5-trimethyl-2-thia-4-azabicyclo[4.1.0]hept-3-ene-1-carboxamide;

6-((Z)-2-(5-((1S,5S,6S)-3-amino-1-((R)-3-fluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile;

6-((Z)-2-(5-((1S,5S,6S)-3-amino-1-((S)-3-fluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile;

6-((Z)-2-(5-((1S,5S,6S)-3-amino-5-methyl-1-(morpholine-4-carbonyl)-2-thia-4-azabicyclo[4.1.0]hept-3-en-5-yl)-6-fluoropyridin-3-yl)-1-fluorovinyl)nicotinonitrile;

6-((Z)-2-(5-((1S,5S,6S)-3-amino-1-((R)-3-fluoropyrrolidine-1-carbonyl)-5-methyl-2-thia-4-azabicyclo[4.1.0]hept-3-en-5-yl)-6-methoxypyridin-3-yl)-1-fluorovinyl)nicotinonitrile;

(1S,5S,6S)-3-amino-5-(5-((Z)-2-(5-chloropyridin-2-yl)-1-fluorovinyl)-2-fluorophenyl)-N,N,5-trimethyl-2-thia-4-azabicyclo[4.1.0]hept-3-ene-1-carboxamide; or (1S,5S,6S)-3-amino-5-(5-((Z)-2-(4-cyanophenyl)-1-fluorovinyl)-2-fluorophenyl)-N,N,5-trimethyl-2-thia-4-azabicyclo[4.1.0]hept-3-ene-1-carboxamide.

31. The compound of claim 1, or a pharmaceutically acceptable salt thereof, selected from 5-((Z)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)pyrazine-2-carbonitrile;

5-((Z)-2-(3-((1S,5S,6S)-3-amino-5-methyl-1-(piperidine-1-carbonyl)-2-thia-4-azabicyclo[4.1.0]hept-3-en-5-yl)-4-fluorophenyl)-1-fluorovinyl)pyrazine-2-carbonitrile;

5-((Z)-2-(3-((1S,5S,6S)-3-amino-1-((S)-3-fluoropyrrolidine-1-carbonyl)-5-methyl-2-thia-4-azabicyclo[4.1.0]hept-3-en-5-yl)-4-fluorophenyl)-1-fluorovinyl)pyrazine-2-carbonitrile;

5-((Z)-2-(3-((1S,5S,6S)-3-amino-1-((R)-3-fluoropyrrolidine-1-carbonyl)-5-methyl-2-thia-4-azabicyclo[4.1.0]hept-3-en-5-yl)-4-fluorophenyl)-1-fluorovinyl)pyrazine-2-carbonitrile;

5-((Z)-2-(3-((1S,5S,6S)-3-amino-5-methyl-1-(pyrrolidine-1-carbonyl)-2-thia-4-azabicyclo[4.1.0]hept-3-en-5-yl)-4-fluorophenyl)-1-fluorovinyl)pyrazine-2-carbonitrile;

(1S,5S,6S)-3-amino-5-(5-((Z)-2-(5-ethynylpyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(2-methoxyethoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(5-((Z)-2-(5-(cyclopropylmethoxy)pyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(oxetan-3-ylmethoxy)pyrazin-2-yl)vinyl)phenyl)-N,N,-trimethyl-2-thia-4-azabicyclo[4.1.0]hept-3-ene-1-carboxamide;

(1S,5S,6S)-3-amino-5-(5-((Z)-2-(5-(2,2-difluoroethoxy)pyrazin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(54(S)-1-methoxypropan-2-yl)oxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(5-((Z)-2-(5-(2,2-difluorocyclopropyl)methoxy)pyrazin-2-yl)-2-fluorovinyl)-2-fluorophenyl)-N,N,-trimethyl-2-thia-4-azabicyclo[4.1.0]hept-3-ene-1-carboxamide;

(1S,5S,6S)-3-amino-5-(2-fluoro-5-((Z)-2-fluoro-2-(54(5-methyl-1,3,4-oxadiazol-2-yl)methoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-((3-methyl-1,2,4-oxadiazol-5-yl)methoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-((3-methylisoxazol-5-yl)methoxy)pyrazin-2-yl)vinyl)phenyl)-N,N,5-trimethyl-2-thia-4-azabicyclo[4.1.0]hept-3-ene-1-carboxamide;

(1S,5S,6S)-3-amino-5-(5-((Z)-2-(5-cyanothiazol-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-cyanothiophen-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(4-cyanophenyl)-1-fluorovinyl)-2-fluorophenyl)-N,N,5-trimethyl-2-thia-4-azabicyclo[4.1.0]hept-3-ene-1-carboxamide;

(1S,5S,6S)-3-amino-5-(5-((Z)-2-(5-cyanopyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(5-((Z)-2-(5-cyanopyrazin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(trifluoromethyl)pyridin-2-yl)vinyl)phenyl)-N,5-dimethyl-2-thia-4-azabicyclo[4.1.0]hept-3-ene-1-carboxamide;

(1S,5S,6S)-3-amino-5-(5-((Z)-2-(5-cyano-3-methylpyridin-2-yl)-2-fluorovinyl)-2-fluorophenyl)-N,-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(oxazol-5-ylmethoxy)pyrazin-2-yl)vinyl)phenyl)-N,5-dimethyl-2-thia-4-azabicyclo[4.1.0]hept-3-ene-1-carboxamide;

(1R,5S,6S)-5-(2-fluoro-5-((Z)-2-fluoro-2-(5-(prop-2-yn-1-yloxy)pyrazin-2-yl)vinyl)phenyl)-5-methyl-1-(methyl sulfonyl)-2-thia-4-azabicyclo[4.1.0]hept-3-en-3-amine;

(1R,5S,6S)-5-(2-fluoro-5-((Z)-2-fluoro-2-(5-((5-methyl-1,3,4-oxadiazol-2-yl)methoxy)pyrazin-2-yl)vinyl)phenyl)-5-methyl-1-(methyl sulfonyl)-2-thia-4-azabicyclo[4.1.0]hept-3-en-3-amine;

(1R,5S,6S)-5-(2-fluoro-5-((Z)-2-fluoro-2-(5-(2,2,2-trifluoroethoxy)pyrazin-2-yl)vinyl)phenyl)-5-methyl-1-(methylsulfonyl)-2-thia-4-azabicyclo[4.1.0]hept-3-en-3-amine;

(1R,5S,6S)-5-(5-((Z)-2-(5-chloropyrazin-2-yl)-2-fluorovinyl)-2-fluorophenyl)-5-methyl-1-(methylsulfonyl)-2-thia-4-azabicyclo[4.1.0]hept-3-en-3-amine;

(1R,5S,6S)-5-(5-((Z)-2-(5-(but-2-yn-1-yloxy)pyrazin-2-yl)-2-fluorovinyl)-2-fluorophenyl)-5-methyl-1-(methylsulfonyl)-2-thia-4-azabicyclo[4.1.0]hept-3-en-3-amine;

(1R,5S,6S)-5-(5-((Z)-2-(5-((S)-but-3-yn-2-yloxy)pyrazin-2-yl)-2-fluorovinyl)-2-fluorophenyl)-5-methyl-1-(methylsulfonyl)-2-thia-4-azabicyclo[4.1.0]hept-3-en-3-amine;

6-((Z)-2-(3-((1R,5S,6S)-3-amino-5-methyl-1-(methylsulfonyl)-2-thia-4-azabicyclo[4.1.0]hept-3-en-5-yl)-4-fluorophenyl)-1-fluorovinyl)nicotinonitrile;

1-((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)ethanone;

1-((1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-en-1-yl)ethanone;

1-((1S,5S,6S)-3-amino-5-(2-fluoro-5-((Z)-2-fluoro-2-(5-(2,2,2-trifluoroethoxy)pyrazin-2-yl)vinyl)phenyl)-5-methyl-2-thia-4-azabicyclo[4.1.0]hept-3-en-1-yl)ethanone;

1-((1S,5S,6S)-3-amino-5-(5-((Z)-2-(5-((S)-but-3-yn-2-yloxy)pyrazin-2-yl)-2-fluorovinyl)-2-fluorophenyl)-5-methyl-2-thia-4-azabicyclo[4.1.0]hept-3-en-1-yl)ethanone;

6-((Z)-2-(3-((1S,5S,6S)-1-acetyl-3-amino-5-methyl-2-thia-4-azabicyclo[4.1.0]hept-3-en-5-yl)-4-fluorophenyl)-1-fluorovinyl)nicotinonitrile;

(1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxamide;

(1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carbonitrile;

(1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-ene-1-carboxamide;

(1S,5S,6S)-3-amino-5-(5-((Z)-2-(5-chloropyridin-2-yl)-2-fluorovinyl)-2-fluorophenyl)-5-methyl-2-thia-4-azabicyclo[4.1.0]hept-3-ene-1-carboxamide;

(1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carboxamide;

(1S,5S,6S)-3-amino-5-(5-((Z)-2-(5-(but-2-yn-1-yloxy)pyrazin-2-yl)-2-fluorovinyl)-2-fluorophenyl)-5-methyl-2-thia-4-azabicyclo[4.1.0]hept-3-ene-1-carbonitrile;

(1S,5S,6S)-3-amino-5-(5-((Z)-2-(5-cyanopyridin-2-yl)-2-fluorovinyl)-2-fluorophenyl)-5-methyl-2-thia-4-azabicyclo[4.1.0]hept-3-ene-1-carbonitrile;

(1S,5S,6S)-3-amino-5-(5-((Z)-2-(6-cyanoimidazo[1,2-a]pyridin-2-yl)-2-fluorovinyl)-2-fluorophenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(pyrido[3,4-b]pyrazin-7-yl)vinyl)phenyl)-N,N,5-trimethyl-2-thia-4-azabicyclo[4.1.0]hept-3-ene-1-carboxamide;

(1S,5S,6S)-methyl 3-amino-5-(5-((Z)-2-(5-chloropyridin-2-yl)-2-fluorovinyl)-2,3-difluorophenyl)-5-methyl-2-thia-4-azabicyclo[4.1.0]hept-3-ene-1-carboxylate;

(1S,5S,6S)-3-amino-5-(5-((Z)-2-(2,3-dihydro-[1,4]dioxino[2,3-c]pyridin-7-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(5-((Z)-2-(6,7-dihydro-[1,4]dioxino[2,3-d]pyrimidin-2-yl)-2-fluorovinyl)-2-fluorophenyl)-N,N,5-trimethyl-2-thia-4-azabicyclo[4.1.0]hept-3-ene-1-carboxamide;

6-((Z)-2-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-1-fluorovinyl)nicotinonitrile;

((1S,5S,6R)-3-amino-5-(5-((Z)-2-(5-chloropyrazin-2-yl)-2-fluorovinyl)-2-fluorophenyl)-7,7-difluoro-5-methyl-2-thia-4-azabicyclo[4.1.0]hept-3-en-1-yl)methanol;

((1S,5S,6R)-3-amino-7,7-difluoro-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)methanol;

5-((Z)-2-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-1-fluorovinyl)pyrazine-2-carbonitrile;

((1S,5S,6R)-3-amino-5-(5-((Z)-2-(5-chloropyridin-2-yl)-2-fluorovinyl)-2-fluorophenyl)-7,7-difluoro-5-methyl-2-thia-4-azabicyclo[4.1.0]hept-3-en-1-yl)methanol;

(1S,5S,6R)-methyl 3-amino-5-(5-((Z)-2-(5-cyanopyridin-2-yl)-2-fluorovinyl)-2-fluorophenyl)-7,7-difluoro-5-methyl-2-thia-4-azabicyclo[4.1.0]hept-3-ene-1-carboxylate;

6-((Z)-2-(3-((1S,5S,6R)-3-amino-7,7-difluoro-1-(2-hydroxypropan-2-yl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6R)-3-amino-7,7-difluoro-1-(methoxymethyl)-5-methyl-2-thia-4-azabicyclo[4.1.0]hept-3-en-5-yl)-4-fluorophenyl)-1-fluorovinyl)nicotinonitrile;

6-((Z)-2-(5-((1S,5S,6S)-3-amino-1-(3,3-difluoropyrrolidine-1-carbonyl)-5-methyl-2-thia-4-azabicyclo[4.1.0]hept-3-en-5-yl)-6-fluoropyridin-3-yl)-1-fluorovinyl)nicotinonitrile;

6-((Z)-2-(5-((1S,5S,6S)-3-amino-1-(4,4-difluoropiperidine-1-carbonyl)-5-methyl-2-thia-4-azabicyclo[4.1.0]hept-3-en-5-yl)-6-fluoropyridin-3-yl)-1-fluorovinyl)nicotinonitrile;

(1S,5S,6S)-5-(5-((Z)-2-(5-chloropyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(prop-2-yn-1-yloxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(5-((Z)-2-(5-(but-2-yn-1-yloxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(5-((Z)-2-(5-((S)-but-3-yn-2-yloxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-((S)-2-methoxypropoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(5-((Z)-2-(5-(2,2-difluoroethoxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(2,2,2-trifluoroethoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(3,3,3-trifluoropropoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(2-fluoroethoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(5-((Z)-2-(5-(cyclopropylmethoxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(5-((Z)-2-(5-(cyclobutylmethoxy)pyrazin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-(oxetan-3-ylmethoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-isobutoxypyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-((5-methylisoxazol-3-yl)methoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-((3-methylisoxazol-5-yl)methoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(2-fluoro-5-((Z)-2-fluoro-2-(5-((1,1,1-trifluoropropan-2-yl)oxy)pyrazin-2-yl)vinyl)phenyl)-1-(methoxymethyl)-5-methyl-2-thia-4-azabicyclo[4.1.0]hept-3-en-3-amine;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((1R,5R)-3,7-dioxa-9-azabicyclo[3.3.1]nonan-9-yl)methanone;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((S)-3-fluoropyrrolidin-1-yl)methanone;

(1S,5S,6S)-3-amino-5-(5-((Z)-2-(5-cyanopyridin-2-yl)-2-fluorovinyl)-2-fluoropyridin-3-yl)-N-(2,2-difluoroethyl)-5-methyl-2-thia-4-azabicyclo[4.1.0]hept-3-ene-1-carboxamide;

(1S,5S,6S)-3-amino-5-(2-fluoro-5-((Z)-2-fluoro-2-(5-(2,2,2-trifluoroethoxy)pyrazin-2-yl)vinyl)pyridin-3-yl)-N,N,5-trimethyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((R)-3-methylmorpholino)methanone;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((1R,5R)-3,7-dioxa-9-azabicyclo[3.3.1]nonan-9-yl)methanone;

(1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylic acid;

(1S,5S,6S)-5-(54Z)-2-(5-chloropyridin-2-yl)-2-fluorovinyl)-2-fluorophenyl)-1-(methoxymethyl)-5-methyl-2-thia-4-azabicyclo[4.1.0]hept-3-en-3-amine;

(1S,5S,6S)-3-amino-5-(2-fluoro-5-((Z)-2-fluoro-2-(5-(prop-2-yn-1-yloxy)pyrazin-2-yl)vinyl)pyridin-3-yl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-2-(5-(2-oxopropoxy)pyrazin-2-yl)vinyl)pyridin-3-yl)-N,N,5-trimethyl-2-thia-4-azabicyclo[4.1.0]hept-3-ene-1-carboxamide;

(1S,5S,6S)-3-amino-5-(5-((Z)-2-(5-(but-2-yn-1-yloxy)pyrazin-2-yl)-2-fluorovinyl)-2-fluoropyridin-3-yl)-N,N,5-trimethyl-2-thia-4-azabicyclo[4.1.0]hept-3-ene-1-carboxamide;

6-((Z)-2-(5-((1S,5S,6S)-3-amino-5-methyl-1-((R)-3-methylmorpholine-4-carbonyl)-2-thia-4-azabicyclo[4.1.0]hept-3-en-5-yl)-6-fluoropyridin-3-yl)-1-fluorovinyl)nicotinonitrile;

(1S,5S,6S)-3-amino-5-(2-fluoro-5-((Z)-2-fluoro-2-(5-(2,2,3,3-tetrafluoropropoxy)pyrazin-2-yl)vinyl)pyridin-3-yl)-N,N,5-trimethyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)(morpholino)methanone;

6-((Z)-2-(3-((1S,5S,6S)-3-amino-1-(methoxymethyl)-5-methyl-2-thia-4-azabicyclo[4.1.0]hept-3-en-5-yl)-4-fluorophenyl)-1-fluorovinyl)nicotinonitrile;

(1S,5S,6S)-methyl 3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxylate methanone;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)((R)-3-fluoropyrrolidin-1-yl)methanone;

(1S,5S,6S)-3-amino-5-(5-((Z)-2-(5-cyanopyrazin-2-yl)-2-fluorovinyl)-2-fluoropyridin-3-yl)-N,N,5-trimethyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((R)-3-fluoropyrrolidin-1-yl)methanone;

6-((Z)-2-(5-((1S,5S,6S)-3-amino-1-((1R,5R)-3,7-dioxa-9-azabicyclo[3.3.1]nonane-9-carbonyl)-5-methyl-2-thia-4-azabicyclo[4.1.0]hept-3-en-5-yl)-6-fluoropyridin-3-yl)-1-fluorovinyl)nicotinonitrile;

5-((Z)-2-(3-((1S,5S,6S)-3-amino-1-(methoxymethyl)-5-methyl-2-thia-4-azabicyclo[4.1.0]hept-3-en-5-yl)-4-fluorophenyl)-1-fluorovinyl)pyrazine-2-carbonitrile;

(1S,5S,6S)-3-amino-N-(2,2-difluoroethyl)-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)pyridin-3-yl)-5-methyl-2-thia-4-azabicyclo[4.1.0]hept-3-en-1-yl)(morpholino)methanone;

(1S,5S,6S)-3-amino-N-(2,2-difluoroethyl)-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-ene-1-carboxamide;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((S)-3-fluoropyrrolidin-1-yl)methanone;

((1S,5S,6S)-3-amino-5-(2-fluoro-5-((Z)-2-fluoro-2-(5-(prop-2-yn-1-yloxy)pyrazin-2-yl)vinyl)phenyl)-5-methyl-2-thia-4-azabicyclo[4.1.0]hept-3-en-1-yl)((R)-3-methylmorpholino)methanone;

(1S,5S,6S)-5-(5-((Z)-2-(2,3-dihydro-[1,4]dioxino[2,3-c]pyridin-7-yl)-2-fluorovinyl)-2-fluorophenyl)-1-(methoxymethyl)-5-methyl-2-thia-4-azabicyclo[4.1.0]hept-3-en-3-amine;

6-((Z)-2-(3-((1S,5S,6S)-3-amino-1-((2 S,3 S)-3-fluoro-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2R,3R)-3-fluoro-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(2,5-dioxa-8-azaspiro[3.5]nonane-8-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-hydroxy-3-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-3-hydroxy-3-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((1S,6R)-2-oxa-5-azabicyclo[4.1.0]heptane-5-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((1R,6S)-2-oxa-5-azabicyclo[4.1.0]heptane-5-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((3 S,5R)-3,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((3R,5R)-3,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(3-oxa-8-azabicyclo[3.2.1]octane-8-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-2-isopropylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-2-isopropylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(4-oxa-7-azaspiro[2.5]octane-7-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(4-oxa-7-azaspiro[2.5]octane-7-6-((Z)-2-(3-((1S,5S,6S)-3-amino-1-(8-oxa-3-azabicyclo[3.2.1]octane-3-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(7-oxa-2-azaspiro[3.5]nonane-2-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-((S)-2-methylmorpholine-4-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-3-isopropylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2 S,6S)-2,6-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(3,3-difluoropiperidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(4,4-difluoropiperidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(4-fluoropiperidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(1-oxa-6-azaspiro[3.4]octane-6-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-(methoxymethyl)morpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2 S,5S)-2,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2R,5R)-2,5-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(8-oxa-5-azaspiro[3.5]nonane-5-carbonyl)-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-(3,3-dimethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((R)-3-hydroxypyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-ethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((S)-3-ethylmorpholine-4-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-1-((2S,3R)-3-hydroxy-2-methylpyrrolidine-1-carbonyl)-5-methyl-2-thia-4-azabicyclo[4.1.0]hept-3-en-5-yl)-4-fluorophenyl)-1-fluorovinyl)nicotinonitrile;

6-((Z)-2-(3-((1S,5S,6S)-3-amino-5-methyl-1-(2-phenylpyrrolidine-1-carbonyl)-2-thia-4-azabicyclo[4.1.0]hept-3-en-5-yl)-4-fluorophenyl)-1-fluorovinyl)nicotinonitrile;

((1S,5S,6S)-3-amino-5-(5-((Z)-2-(5-bromopyridin-2-yl)-2-fluorovinyl)-2-fluorophenyl)-5-methyl-2-thia-4-azabicyclo[4.1.0]hept-3-en-1-yl)(morpholino)methanone;

((1S,5S,6S)-3-amino-5-(2-fluoro-5-((Z)-2-fluoro-2-(pyridin-2-yl)vinyl)phenyl)-5-methyl-2-thia-4-azabicyclo[4.1.0]hept-3-en-1-yl)(morpholino)methanone;

((1S,5S,6S)-3-amino-5-(2-fluoro-5-((Z)-2-fluoro-2-(5-(oxetan-3-yl)pyridin-2-yl)vinyl)phenyl)-5-methyl-2-thia-4-azabicyclo[4.1.0]hept-3-en-1-yl)(morpholino)methanone;

6-((Z)-2-(3-((1S,5S,6S)-3-amino-5-methyl-1-(5-methyloxazol-2-yl)-2-thia-4-azabicyclo[4.1.0]hept-3-en-5-yl)-4-fluorophenyl)-1-fluorovinyl)nicotinonitrile;

(1S,5S,6S)-5-(2-fluoro-5-((Z)-2-fluoro-2-(5-(prop-2-yn-1-yloxy)pyrazin-2-yl)vinyl)phenyl)-5-methyl-1-(5-methyloxazol-2-yl)-2-thia-4-azabicyclo[4.1.0]hept-en-3-amine;

6-((E)-2-(3-((1S,5S,6S)-3-amino-5-methyl-1-(morpholine-4-carbonyl)-2-thia-4-azabicyclo[4.1.0]hept-3-en-5-yl)-4-fluorophenyl)-1-fluorovinyl)nicotinonitrile;

((1S,5S,6S)-3-amino-5-(5-((Z)-2-(5-ethynylpyridin-2-yl)-2-fluorovinyl)-2-fluorophenyl)-5-methyl-2-thia-4-azabicyclo[4.1.0]hept-3-en-1-yl)(morpholino)methanone;

((1S,5S,6S)-3-amino-5-(2-fluoro-5-((Z)-2-fluoro-2-(5-((trimethyl silyl)ethynyl)pyrazin-2-yl)vinyl)phenyl)-5-methyl-2-thia-4-azabicyclo[4.1.0]hept-3-en-1-yl)(morpholino)methanone;

((1S,5S,6S)-3-amino-5-(5-((Z)-2-(5-ethynylpyrazin-2-yl)-2-fluorovinyl)-2-fluorophenyl)-5-methyl-2-thia-4-azabicyclo[4.1.0]hept-3-en-1-yl)(morpholino)methanone;

(1S,5S,6S)-3-amino-5-(5-((Z)-2-(5-chloropyrazin-2-yl)-2-fluorovinyl)-2-fluorophenyl)-N,5-dimethyl-2-thia-4-azabicyclo[4.1.0]hept-3-ene-1-carboxamide;

((1S,5S,6S)-3-amino-5-(5-((Z)-2-(5-(cyclopropylethynyl)pyrazin-2-yl)-2-fluorovinyl)-2-fluorophenyl)-5-methyl-2-thia-4-azabicyclo[4.1.0]hept-3-en-1-yl)(morpholino)methanone;

((1S,5S,6S)-3-amino-5-(2-fluoro-5-((Z)-2-fluoro-2-(5-((trimethyl silyl)ethynyl)pyridin-2-yl)vinyl)phenyl)-5-methyl-2-thia-4-azabicyclo[4.1.0]hept-3-en-1-yl)(morpholino)methanone;

(1S,5S,6S)-3-amino-5-(5-((Z)-2-(5-bromopyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(5-((E)-2-(5-bromopyridin-2-yl)-2-fluorovinyl)-2-fluorophenyl)-N,5-dimethyl-2-thia-4-azabicyclo[4.1.0]hept-3-ene-1-carboxamide;

((1S,5S,6S)-3-amino-5-(5-((Z)-2-(5-(cyclopropylethynyl)pyridin-2-yl)-2-fluorovinyl)-2-fluorophenyl)-5-methyl-2-thia-4-azabicyclo[4.1.0]hept-3-en-1-yl)(morpholino)methanone;

(1S,5S,6S)-3-amino-5-(5-((Z)-2-(5-(cyclopropylethynyl)pyridin-2-yl)-2-fluorovinyl)-2-fluorophenyl)-N,-dimethyl-2-thia-4-azabicyclo[4.1.0]hept-3-ene-1-carboxamide;

(1S,5S,6S)-3-amino-5-(5-((Z)-2-(5-(3,3-dimethylbut-1-yn-1-yl)pyridin-2-yl)-2-fluorovinyl)-2-fluorophenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(pent-1-yn-1-yl)pyridin-2-yl)vinyl)phenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(3-hydroxyprop-1-yn-1-yl)pyrazin-2-yl)vinyl)phenyl)-N,5-dimethyl-2-thia-4-azabicyclo[4.1.0]hept-3-ene-1-carboxamide;

(1S,5S,6S)-3-amino-5-(2-fluoro-5-((Z)-2-fluoro-2-(5-(3-fluoroprop-1-yn-1-yl)pyrazin-2-yl)vinyl)phenyl)-N,5-dimethyl-2-thia-4-azabicyclo[4.1.0]hept-3-ene-1-carboxamide; or (1S,5S,6S)-3-Amino-5-(2-fluoro-5-((Z)-2-fluoro-2-(5-(trifluoromethoxy)pyridin-2-yl)vinyl)phenyl)-N,5-dimethyl-2-thia-4-azabicyclo[4.1.0]hept-3-ene-1-carboxamide.

32. A compound, or a pharmaceutically acceptable salt thereof, selected from (1S,5S,6S)-3-amino-5-(2-fluoro-5-((E)-2-fluoro-2-iodovinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoro-4-phenylbut-1-en-3-yn-1-yl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluorovinyl)phenyl)-N,N,5-trimethyl-2-thia-4-azabicyclo[4.1.0]hept-3-ene-1-carboxamide;

(1S,5S,6S)-3-amino-5-(2-fluoro-5-((Z)-2-fluoropent-1-en-3-yn-1-yl)phenyl)-N,N,5-trimethyl-2-thia-4-azabicyclo[4.1.0]hept-3-ene-1-carboxamide;

(1S,5S,6S)-5-(2-fluoro-5-((Z)-2-fluoro-2-(5-(oxetan-2-ylmethoxy)pyrazin-2-yl)vinyl)phenyl)-1-(methoxymethyl)-5-methyl-2-thia-4-azabicyclo[4.1.0]hept-3-en-3-amine;

(1S,5S,6S)-5-(5-((Z)-2-(5-((3,3-difluorocyclobutyl)
methoxy)pyrazin-2-yl)-2-fluorovinyl)-2-fluorophe-
nyl)-1-(methoxymethyl)-5-methyl-2-thia-4-azabicyclo
[4.1.0]hept-3-en-3-amine;

6-((Z)-2-(3-((1S,5S,6S)-3-amino-5-methyl-1-(4-methyl-
4,5-dihydrooxazol-2-yl)-2-thia-4-azabicyclo[4.1.0]
hept-3-en-5-yl)-4-fluorophenyl)-1-fluorovinyl)nicoti-
nonitrile;

6-((Z)-2-(3-((1S,5S,6S)-3-amino-5-methyl-1-((R)-5-
methyl-4,5-dihydrooxazol-2-yl)-2-thia-4-azabicyclo
[4.1.0]hept-3-en-5-yl)-4-fluorophenyl)-1-fluorovinyl)
nicotinonitrile;

3-(5-((Z)-2-(3-((1S,5S,6S)-3-amino-5-methyl-1-(mor-
pholine-4-carbonyl)-2-thia-4-azabicyclo[4.1.0]hept-3-
en-5-yl)-4-fluorophenyl)-1-fluorovinyl)pyrazin-2-yl)
oxazolidin-2-one;

((1S,5S,6S)-3-amino-5-(5-((Z)-2-(5-(azetidin-1-yl)
pyrazin-2-yl)-2-fluorovinyl)-2-fluorophenyl)-5-
methyl-2-thia-4-azabicyclo[4.1.0]hept-3-en-1-yl)(mor-
pholino)methanone;

(1S,5S,6S)-3-amino-5-(5-((Z)-2-(5-cyanopyridin-2-yl)-2-
fluorovinyl)-2-fluorophenyl)-N-(2,2-dimethoxyethyl)-
5-methyl-2-thia-4-azabicyclo[4.1.0]hept-3-ene-1-car-
boxamide; or (1S,5S,6S)-3-amino-5-(2-fluoro-5-((Z)-2-fluoro-2-(5-((3-
methyloxetan-3-yl)ethynyl)pyridin-2-yl)vinyl)phenyl)-
N,5-dimethyl-2-thia-4-azabicyclo[4.1.0]hept-3-ene-1-
carboxamide.

33. The compound of claim 1, or a pharmaceutically acceptable salt thereof, selected from

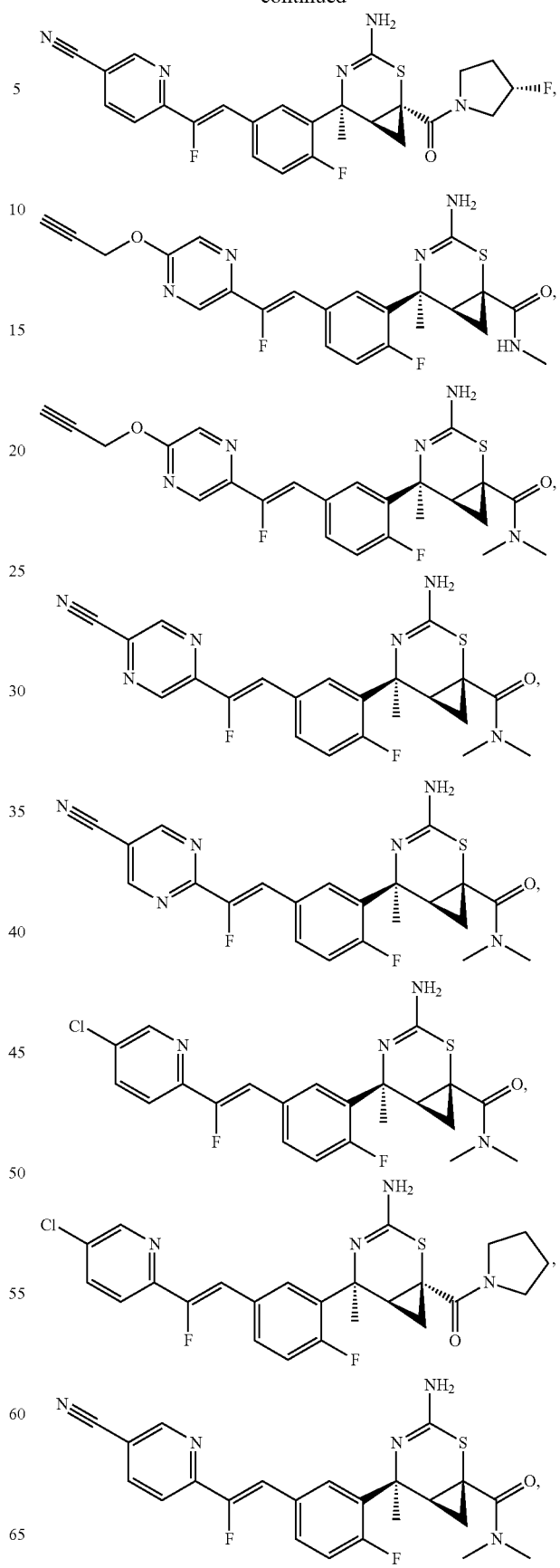

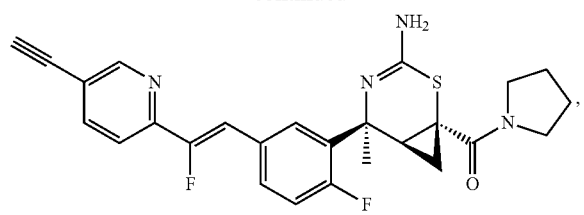
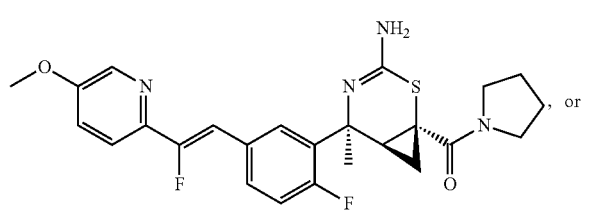, or
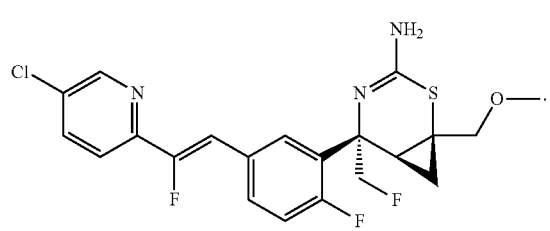
34. The compound of claim 1, or a pharmaceutically acceptable salt thereof, selected from
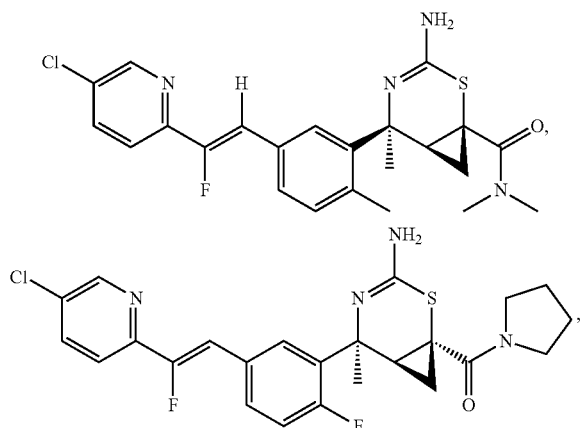
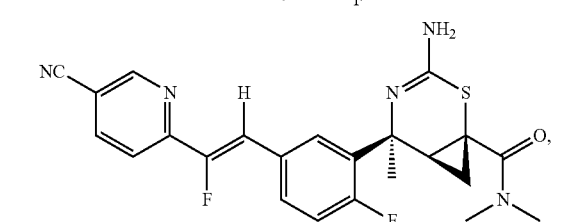
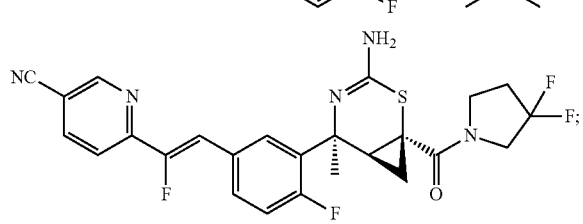
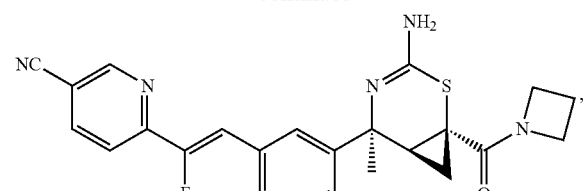
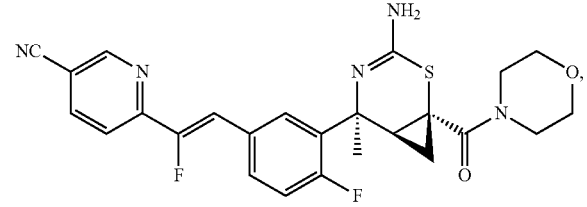
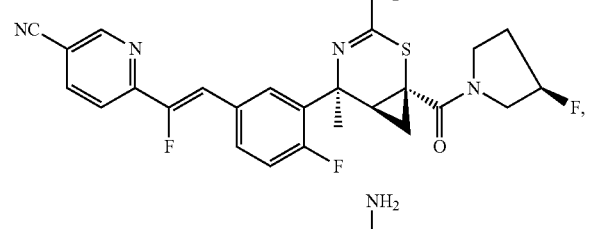
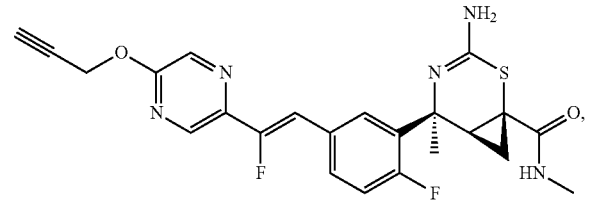
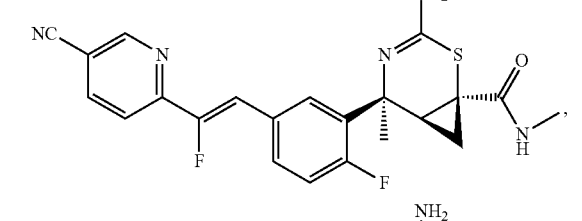
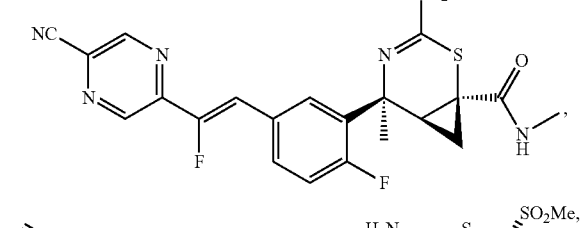
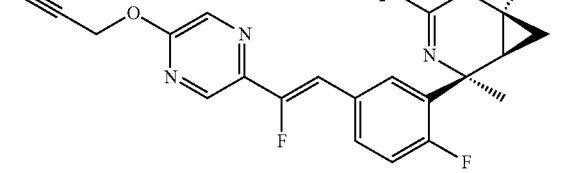

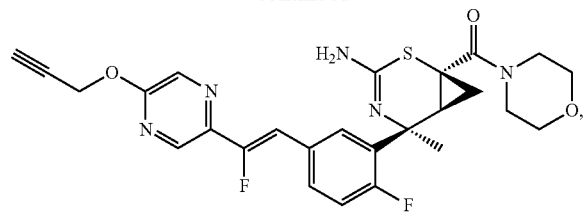
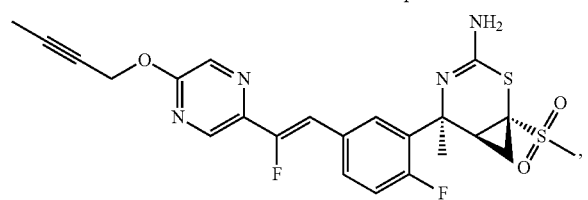
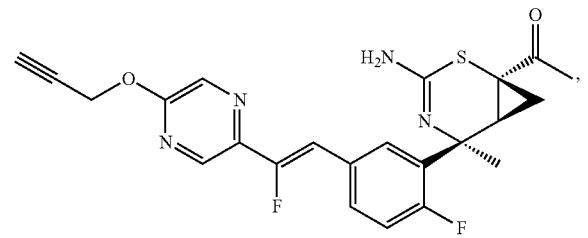
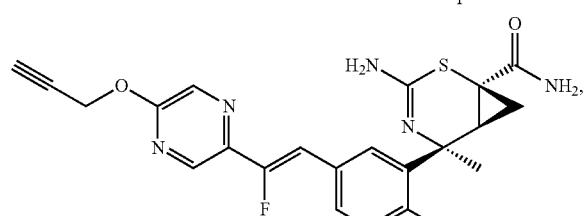
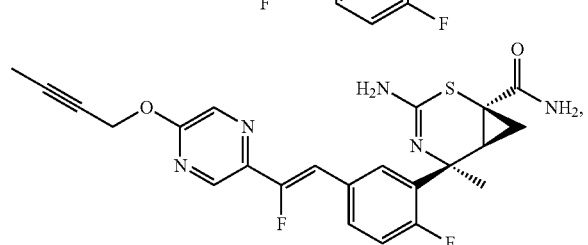
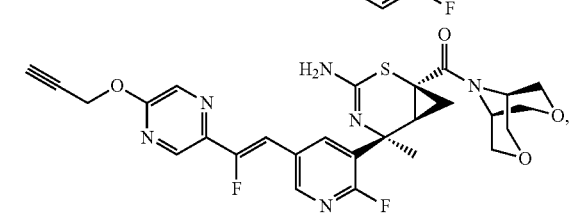
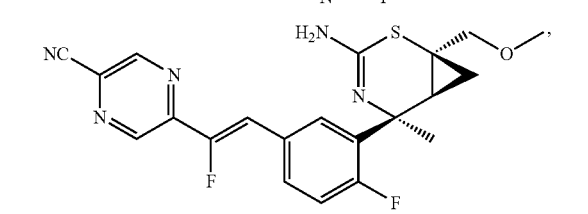
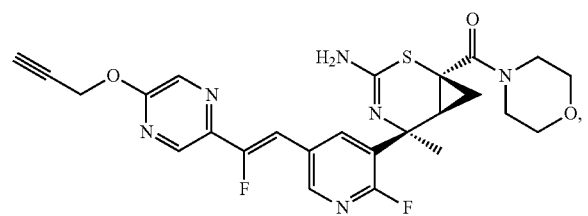

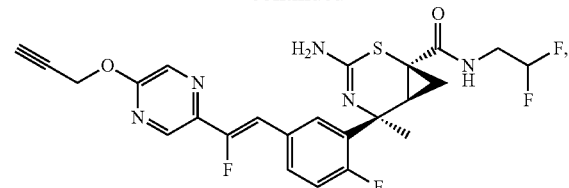
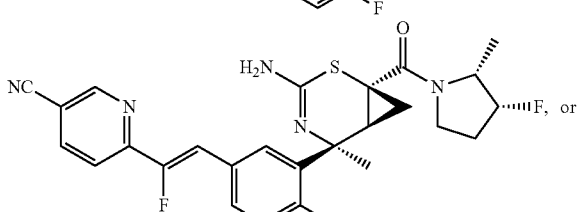
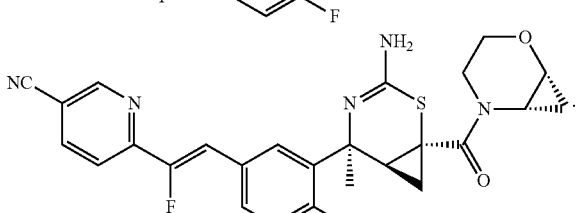

35. A pharmaceutical composition comprising the compound according to claim 1 and a pharmaceutically acceptable excipient.

36. A method of reducing beta amyloid peptide levels in the cerebral spinal fluid of a subject, the method comprising administering to the subject a therapeutically effective amount of a compound according to claim 1.

37. A method of treating Alzheimer's disease, cognitive impairment or a combination thereof in a subject, the method comprising administering to the subject a therapeutically effective amount of a compound according to claim 1.

38. A method of treating a neurological disorder selected from mild cognitive impairment, Down's syndrome, Hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease or a combination thereof in a subject, the method comprising administering to the subject a therapeutically effective amount of a compound according to claim 1.

39. A method of reducing the formation of plaque on the brain of a subject, the method comprising administering to the subject a therapeutically effective amount of a compound according to claim 1.

40. A pharmaceutical composition comprising the compound according to claim 30 and a pharmaceutically acceptable excipient.

41. A method of reducing beta amyloid peptide levels in the cerebral spinal fluid of a subject, the method comprising administering to the subject a therapeutically effective amount of a compound according to claim 30.

42. A method of treating Alzheimer's disease, cognitive impairment or a combination thereof in a subject, the method comprising administering to the subject a therapeutically effective amount of a compound according to claim 30.

43. A method of treating a neurological disorder selected from mild cognitive impairment, Down's syndrome, Hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease or a combination thereof in a subject, the method comprising administering to the subject a therapeutically effective amount of a compound according to claim 30.

44. A method of reducing the formation of plaque on the brain of a subject, the method comprising administering to the subject a therapeutically effective amount of a compound according to claim 30.

45. A pharmaceutical composition comprising the compound according to claim 31 and a pharmaceutically acceptable excipient.

46. A method of reducing beta amyloid peptide levels in the cerebral spinal fluid of a subject, the method comprising administering to the subject a therapeutically effective amount of a compound according to claim 31.

47. A method of treating Alzheimer's disease, cognitive impairment or a combination thereof in a subject, the method comprising administering to the subject a therapeutically effective amount of a compound according to claim 31.

48. A method of treating a neurological disorder selected from mild cognitive impairment, Down's syndrome, Hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease or a combination thereof in a subject, the method comprising administering to the subject a therapeutically effective amount of a compound according to claim 31.

49. A method of reducing the formation of plaque on the brain of a subject, the method comprising administering to the subject a therapeutically effective amount of a compound according to claim 31.

50. A pharmaceutical composition comprising the compound according to claim 32 and a pharmaceutically acceptable excipient.

51. A method of reducing beta amyloid peptide levels in the cerebral spinal fluid of a subject, the method comprising administering to the subject a therapeutically effective amount of a compound according to claim 32.

52. A method of treating Alzheimer's disease, cognitive impairment or a combination thereof in a subject, the method comprising administering to the subject a therapeutically effective amount of a compound according to claim 32.

53. A method of treating a neurological disorder selected from mild cognitive impairment, Down's syndrome, Hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease or a combination thereof in a subject, the method comprising administering to the subject a therapeutically effective amount of a compound according to claim 32.

54. A method of reducing the formation of plaque on the brain of a subject, the method comprising administering to the subject a therapeutically effective amount of a compound according to claim 32.

* * * * *